(12) United States Patent
Tao et al.

(10) Patent No.: US 9,499,539 B2
(45) Date of Patent: Nov. 22, 2016

(54) CYCLIC SULFONAMIDE CONTAINING DERIVATIVES AS INHIBITORS OF HEDGEHOG SIGNALING PATHWAY

(71) Applicant: NantBioScience, Inc., Culver City, CA (US)

(72) Inventors: Chunlin Tao, Newport Coast, CA (US); Chengzhi Yu, San Diego, CA (US); Forrest Arp, Irvine, CA (US); Paul Weingarten, Anaheim, CA (US); Patrick Soon-Shiong, Los Angeles, CA (US)

(73) Assignee: NantBioScience, Inc., Culver City, CA (US)

( * ) Notice: Subject to any disclaimer, the term of this patent is extended or adjusted under 35 U.S.C. 154(b) by 0 days.

(21) Appl. No.: 14/440,796

(22) PCT Filed: Nov. 4, 2013

(86) PCT No.: PCT/US2013/068287
§ 371 (c)(1),
(2) Date: May 5, 2015

(87) PCT Pub. No.: WO2014/071298
PCT Pub. Date: May 8, 2014

(65) Prior Publication Data
US 2015/0299190 A1    Oct. 22, 2015

Related U.S. Application Data

(60) Provisional application No. 61/852,112, filed on Mar. 15, 2013, provisional application No. 61/722,490, filed on Nov. 5, 2012.

(51) Int. Cl.
| | |
|---|---|
| *C07D 275/00* | (2006.01) |
| *C07D 471/04* | (2006.01) |
| *C07D 417/12* | (2006.01) |
| *C07D 419/12* | (2006.01) |
| *C07D 275/02* | (2006.01) |
| *C07D 279/02* | (2006.01) |
| *C07D 291/06* | (2006.01) |

(52) U.S. Cl.
CPC ........... *C07D 471/04* (2013.01); *C07D 275/02* (2013.01); *C07D 279/02* (2013.01); *C07D 291/06* (2013.01); *C07D 417/12* (2013.01); *C07D 419/12* (2013.01)

(58) Field of Classification Search
USPC ...................... 514/226.5, 252.06, 222, 222.2
See application file for complete search history.

(56) References Cited

U.S. PATENT DOCUMENTS

| | | | |
|---|---|---|---|
| 3,202,657 A | 8/1965 | Kühne et al. | |
| 5,916,596 A | 6/1999 | Desai et al. | |
| 6,506,405 B1 | 1/2003 | Desai et al. | |
| 6,537,579 B1 | 3/2003 | Desai et al. | |
| 2005/0267097 A1 | 12/2005 | Pinto et al. | |
| 2007/0027126 A1 | 2/2007 | McComas et al. | |
| 2007/0135428 A1 | 6/2007 | Qiao et al. | |
| 2012/0238539 A1* | 9/2012 | Cianci ................ | C07D 207/327 514/210.2 |

FOREIGN PATENT DOCUMENTS

| | | |
|---|---|---|
| EP | 1 571 154 A1 | 9/2005 |
| WO | WO 02/057240 A1 | 7/2002 |
| WO | WO 2004/072025 A2 | 8/2004 |
| WO | WO 2004/082687 A1 | 9/2004 |
| WO | WO 2005/058837 A1 | 6/2005 |
| WO | WO 2006/019831 A1 | 2/2006 |
| WO | WO 2006/044497 A2 | 4/2006 |
| WO | WO 2007/054453 A2 | 5/2007 |
| WO | WO 2008/094602 A2 | 8/2008 |
| WO | WO 2008/111299 A1 | 9/2008 |
| WO | WO 2009/016088 A1 | 2/2009 |
| WO | WO 2011/062939 A1 | 5/2011 |
| WO | WO 2011/093352 A1 | 8/2011 |

OTHER PUBLICATIONS

Dormer et al., *J. Org. Chem.*, 68, 467-477 (2003).
Echelard et al., *Cell*, 75, 1417-1430 (Dec. 31, 1993).
Heretsch et al., *Bioorganic & Med. Chem.*, 18, 6613-6624 (2010).
Lee et al., *Science*, 266, 1528-1537 (Dec. 2, 1994).
Mas et al., *Biochem. Pharmacol.*, 80, 712-723 (2010).
Mongin et al., *J. Org. Chem.*, 69, 6766-6771 (2004).
Nüsslein-Volhard et al., *Nature*, 287, 795-801 (Oct. 30, 1980).
Peukert, et al., "Hedgehog Signaling Pathway Inhibitors as Cancer Therapeutics," *Annual Resorts in Medicinal Chemistry*, v. 44, Chapter 16, Elsevier, Inc. (2009).
Porter et al., *Science*, 274, 255-259 (Oct. 11, 1996).
Stone et al., *Nature*, 384, 129-134 (Nov. 14, 1996).
Teglund et al., *Biochimica Biophysica Acta*, 1805, 181-208 (2010).
Xie et al., *Nature*, 391, 90-92 (Jan. 1998).
Xing et al., *J. Receptor & Signal Transduction Res.*, 20 (4), 189-210 (2000).
Berge et al., *J. Pharmaceutical Sciences*, 66 (1), 1-19 (Jan. 1977).
Bhatia et al., *J. Biol. Chem.*, 281 (28), 19320-19326 (Jul. 14, 2006).
Borcard et al., *Bioorg. & Med. Chem. Lett.*, 20, 5353-5356 (2010).
Chapoulaud et al., *Tetrahedron*, 56, 5499-5507 (2000).
Evangelista et al., *Clin. Cancer Res.*, 12 (20) 5924-5928 (Oct. 15, 2006).
Fan et al., *Chinese J. Cancer*, 30 (7), 472-481 (2011).
Fang et al., *J. Biol. Chem.*, 282 (19), 14048-14055 (May 11, 2007).
Fortin et al., *J. Med. Chem.*, 54, 4559-4580 (2011).
Gould, Philip L., *Intl. J. Pharmaceutics*, 33, 201-217 (1986).
Hudlicky, Milos, *Reductions in Organic Chemistry*, $2^{nd}$ ed., ACS Monograph 188, 19-30, American Chemical Society, Washington, D.C. (1996).
Hunter, Tony, *Cell*, 88, 333-346 (Feb. 7, 1997).

(Continued)

*Primary Examiner* — Pancham Bakshi
(74) *Attorney, Agent, or Firm* — Leydig, Voit & Mayer, Ltd.

(57) ABSTRACT

The invention relates generally to the creation and use of cyclic sulfonamide containing derivatives to inhibit the hedgehog signaling pathway and to the use of those compounds for the treatment of hyperproliferative diseases and angiogenesis mediated diseases.

1 Claim, 15 Drawing Sheets

(56) References Cited

OTHER PUBLICATIONS

Kunapuli et al., *Analytical Biochemistry*, 314, 16-29 (2003).
Morton et al., *PNAS*, 104 (12), 5103-5108 (Mar. 20, 2007).
Pepinsky et al., *J. Biol. Chem.*, 273 (22), 14037-14045 (1998).
Sausville et al., *Cancer Res.*, 66 (7), 3351-3354 (Apr. 1, 2006).
Sheng et al., *Mol. Cancer*, 3 (29) (2004).
Steinhuebel et al., *Tetrahedron Lett.*, 45, 3305-3307 (2004).
Thayer et al., *Nature*, 425, 851-856 (Oct. 23, 2003).
Zlokarnik et al., *Science*, 279, 84-88 (Jan. 2, 1998).
Aikin et al., *EMBO Reports*, 9(4), 330-336 (2008).
Chemical Abstracts Service, Accession No. 1995:955864 (1994).
Golub et al., *European J. Med. Chem.*, 58, 258-264 (2012).
Imai et al., *Makromol. Chem.*, 180, 1413-1418 (1979).
Whitlock et al., *Bioorganic & Med. Chem. Lett.*, 18, 596-599 (2008).
European Patent Application No. 13851306.4, Search Report (Mar. 29, 2016).

* cited by examiner

Activity Comparison of NTW-3729 and GDC-0449 in Subcutaneous *Ptch$^{+/-}$P53$^{-/-}$* Murine Medulloblastoma Allograft

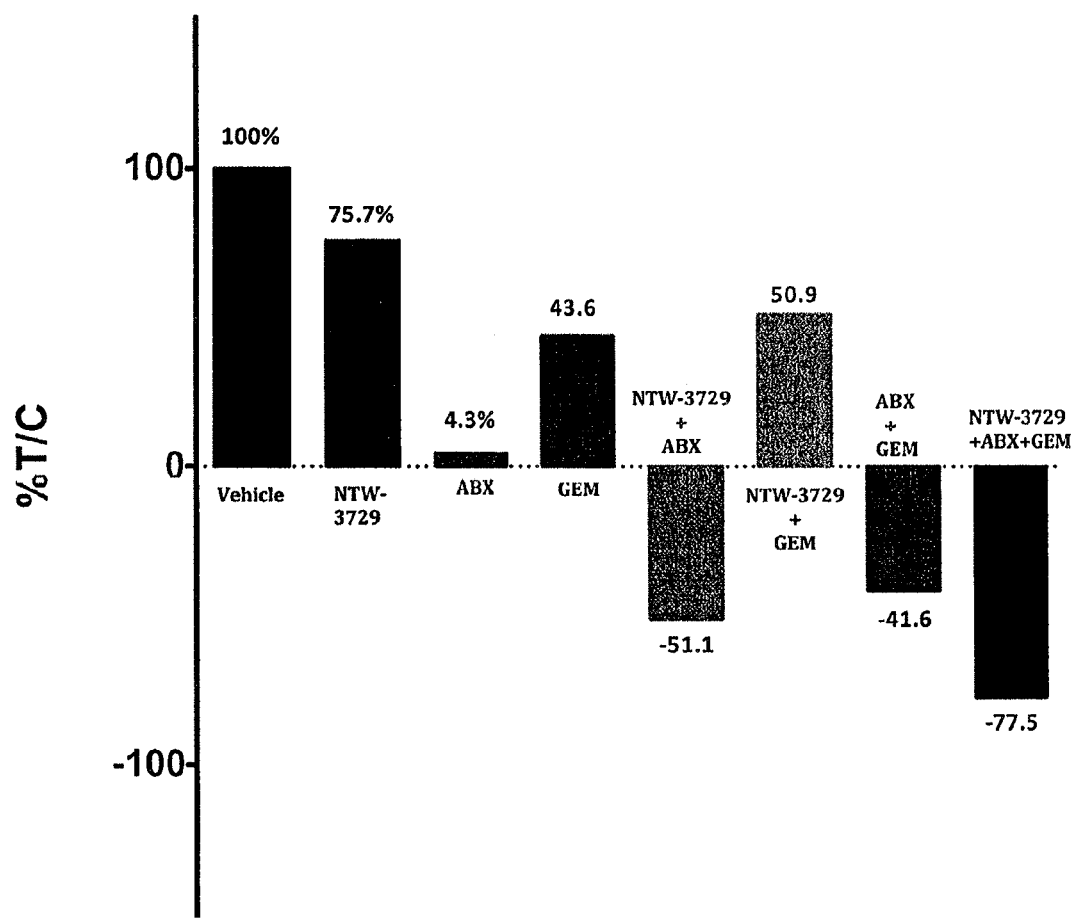

CYCLIC SULFONAMIDE CONTAINING DERIVATIVES AS INHIBITORS OF HEDGEHOG SIGNALING PATHWAY

CROSS-REFERENCE TO RELATED APPLICATIONS AND PRIORITY CLAIMS

This patent application is the national phase entry of International Application No. PCT/US2013/068287. This application claims the benefit of U.S. Provisional Patent Applications 61/722,490 (Filed on Nov. 5, 2012) and 61/852,112 (Filed on Mar. 15, 2013), both of which are hereby incorporated by reference in their entireties.

STATEMENT REGARDING FEDERALLY SPONSORED RESEARCH OR DEVELOPMENT

None

THE NAMES OF THE PARTIES TO A JOINT RESEARCH AGREEMENT

No Joint Research Agreement.

SEQUENCE LISTING

No sequences to list.

STATEMENT REGARDING PRIOR DISCLOSURES BY THE INVENTOR OR A JOINT INVENTOR

None

FIELD OF THE INVENTION

The present invention relates generally to the use of cyclic sulfonamide group containing derivatives to treat a variety of disorders, diseases and pathologic conditions, and more specifically to the use of cyclic sulfonamide containing derivatives to inhibit the hedgehog signaling pathway and to the use of those compounds for the treatment of hyperproliferative diseases and angiogenesis mediated diseases.

BACKGROUND OF THE INVENTION

The hedgehog (Hh) gene was first identified during a search for embryonic lethal mutants of *Drosophila melanogaster*, which found that mutation of Hh resulted in altered segment patterning of the larva (Nusslein-Volhard, C.; Wieschaus, E. *Nature* 1980, 287, 795-801). Subsequently the gene was identified in many other invertebrates and vertebrates, including humans. Three mammalian counterparts of the Hh gene, termed Sonic hedgehog (Shh), Dessert hedgehog (Dhh), and Indian hedgehog (Ihh), were identified by combined screening of mouse genomic and cDNA libraries (Echelard, Y.; Epstein, D. J.; et al., *Cell* 1993, 75, 1417-1430). Hh undergoes multiple processing events, including autocatalytic cleavage of the C-terminal domain combined with addition of a cholesterol moiety at the cleavage site, and an N-terminal palmitoylation, to generate the active ligand (Lee, J. J.; Ekker, S. C.; et al., *Science* 1994, 266, 1528-1537; Porter, J. A.; Young, K. E.; et al., *Science* 1996, 274, 255-259; Pepinsky, R. B.; Zeng, C. et al., *J. Biol. Chem.* 1998, 273, 14037-14045).

The receptor of secreted Hh protein is a 12-transmembrane protein Patched (Ptch). Of the two vertebrate homologues of Ptch (Ptch1 and Ptch2), the role of Ptch1 is better understood. In the absence of Hh ligand, Ptch inhibits the activity of the downstream effector Smoothened (Smo). The binding of Hh inactivates Ptch, resulting in activation of Smo (Stone, D. M.; Hynes, M.; et al., *Nature* 1996, 684, 129-134). These proteins modulate the function of Gli (Ci in *Drosophila*), the only transcription factor identified to date that operates directly downstream of Hh and translocates into the nucleus where they control transcription of target genes. Gli has been shown to affect transcription of Hh pathway inhibitors such as Ptc and Hip1 in a negative feedback loop indicating that a tight control of the Hh pathway activity is required for proper cellular differentiation and organ formation.

Hh genes have the ability to induce tissue proliferation. This function is important in embryogenesis and tissue maintenance, but inappropriate activation of the pathway can result in tumorigenesis (Hunter, T. *Cell* 1997, 88, 333-346). Tumors in about 25% of all cancer deaths are estimated to involve aberrant Hh pathway activation. Tumorigenesis or tumor growth can result from abnormal up-regulation of Hh ligand or from deregulation of the expression or function of downstream components by, for example, loss of Ptch, activating mutations of Smo (Xie, J.; Murone, M.; et al., *Nature* 1998, 391, 90-92), loss of SuFu, amplification or chromosomal translocation of Gli1 or Gli2 gene amplification or stabilization of Gli2 protein (Bhatia, N.; Thiyagarajan, S.; *J. Biol. Chem.* 2006, 281, 19320-19326).

Critical roles of HH-GLi signaling have been implicated in a large number of human cancers (reviewed in Teglund S and Toftgard R. *Biochimica et Biophysica acta* 2010, 1805, 181-208): from familial basal-cell carcinomas to sporadic basal-cell carcinomas, medulloblastomas, prostate, lung, pancreas, breast and colon cancers, as well as gliomas, leukemias, lymphomas and melanomas. HH-GLi not only controls the growth of the bulk of the tumor by promoting cell survival and proliferation, but it is also required for cancer stem cell self-renewal in gliomas, leukemias and colon cancers. For example, inhibition of HH-GLI activity in epithelial cells through RNA interference (RNAi) in human carcinomas in vitro and in mouse xenografts leads to tumor disappearance, inhibition of metastatic growth and tumor recurrence.

For example, Hh has also been shown to be an early and late mediator of pancreatic cancer tumorigenesis. Shh was not detected in normal adult human pancreata but was aberrantly expressed in 70% of pancreatic adenocarcinoma specimens (Thayer, S. P.; di Magliano, M. P.; et al., *Nature* 2003, 425, 851-856). Participation of Shh signaling has been indicated at multiple stages of pancreatic carcinogenesis and is accompanied by multiple oncogenic factors, including K-Ras, one of the most frequently mutated genes in pancreatic cancer (Morton, J. P.; Mongeau, M. E.; et al., *Proc. Natl. Acad. Sci. U.S.A.* 2007, 104, 5103-5108; Ji, Z.; Mei, F. C.; et al., *J. Biol. Chem.* 2007, 282, 14048-14055). Activated Hh signaling was detected in cell lines established from primary and metastatic pancreatic adenocarcinomas, and the Smo inhibitor cyclopamine induced apoptosis in a subset of the pancreatic cancer cell lines both in culture and in mice (Sheng, T.; Li, C.; et al., *Mol. Cancer* 2004, 3, 29).

The aberrant activation of Hh-Gli signaling in several cancers has made it an attractive target for anticancer drug discovery. A variety of small molecule inhibitors of hedgehog signaling pathway have been reported (Peukert S.; Miller-Moslin K. *Annual Rep. Med. Chem.* 2009, 44, 323-337; Heretsch P.; Tzgkaroulaki L.; Giannis A. *Bioorg. Med. Chem.* 2010, 18, 6613-6624). Among them, a few candidates have been advanced into clinical trials at various stages (Mas C.; Altaba, R. I. *Biochem. Pharm.* 2010, 80, 712-723). Despite with these ongoing exciting efforts, there still remains a need for potent and safe inhibitors of the hedgehog signaling pathway given of the emerging drug resistance being identified as well as the critical role of Hh pathway in embryonic development.

GENERAL SUMMARY OF THE INVENTION

It is an objective of the present invention to provide an antitumor agent comprising a cyclic sulfonamide containing compound as described in Formula (I), pharmaceutically-acceptable formulations thereof, methods for making novel compounds and methods and compositions for using the compounds.

BRIEF DESCRIPTION OF THE DRAWINGS

FIG. 3 depicts the tumor size time course for Ptch$^{+/-}$p53$^{-/-}$ mice treated with NTW-3729, Vehicle (negative control), and GDC-0449 (positive control) in.

FIG. 15 depicts the relative tumor size in pancreatic carcinoma xenografts (Panc-1 cells) treated with NTW-3729 alone or in combination with Abraxane® and/or Gemcitabine (Vehicle is a negative control).

DETAILED SUMMARY OF THE INVENTION

Figure 1:
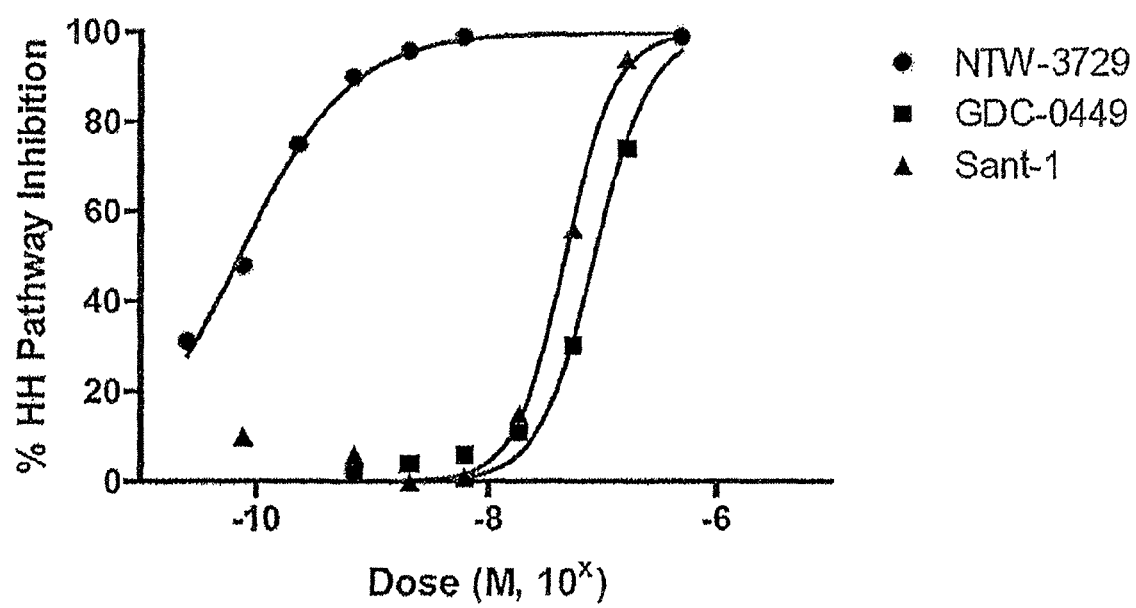
FIG. 1 depicts a dose response curve for NTW-3729 and positive control inhibitors (GDC-0449, Sant-1) in the Gli-Bla reporter assay.

The present invention is related to compounds of Formula (I) inhibiting hedgehop signaling:

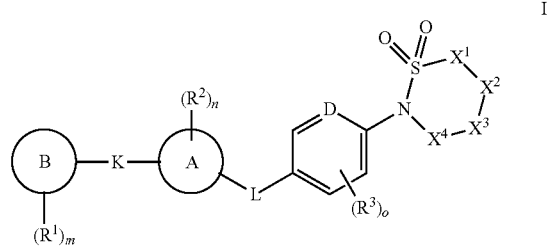

wherein ring A is aryl, heterocycle or heteroaryl;

$R^1$ and $R^3$ each independently is acyl, alkoxy, alkoxycarbonyl, alkyl, alkylthio, alkynyl, amino, aminocarbonyl, cyano, cycloalkyl, carbamoyl, hydrogen, hydroxyl, halogen, nitro, sulfamoyl, sulfinyl, sulfonamide or sulfonyl;

$R^2$ is acyl, alkoxy, alkyl, alkylthio, cycloalkyl, cyano, halogen or hydrogen;

ring B is selected from i) absence;

ii) aryl, heterocycle or heteroaryl;

K is selected from iii) absence;

iv) (C=O)NR$^4$ or (C=S)NR$^4$; wherein R$^4$ is alkyl, acyl, cycloalkyl or hydrogen;

L is O, S, S=O, SO$_2$, (C=O)O, NR$^4$, NR$^4$C=O, NR$^4$SO$_2$, SO$_2$NR$^4$, NR$^4$(C=O)NH, NR$^4$(C=S)NH, (C=O)NR$^4$ or (C=S)NR$^4$;

D is CR$^3$ or N;

$X^1$ is selected from v) absence;

vi) CHR$^5$ or CR$^5$R$^6$; wherein R$^5$ or R$^6$ is acyl, alkyl, cycloalkyl or hydrogen;

vii) O or NR$^5$; wherein $X^2$, $X^3$ and $X^4$ are CHR$^5$ or CR$^5$R$^6$;

$X^2$ is selected from i) absence;

ii) CHR$^5$ or CR$^5$R$^6$;

iii) O or NR$^5$; wherein $X^1$, $X^3$ and $X^4$ are CHR$^5$ or CR$^5$R$^6$;

$X^3$ is selected from i) CHR$^5$ or CR$^5$R$^6$;

ii) O or NR$^5$; wherein $X^1$, $X^2$ and $X^4$ are CHR$^5$ or CR$^5$R$^6$;

$X^4$ is selected from i) CHR$^5$ or CR$^5$R$^6$;

ii) C=O; wherein $X^1$, $X^2$ and $X^3$ are CHR$^5$ or CR$^5$R$^6$;

m is 0-3;

n is 0-3;

o is 0-3;

and pharmaceutically acceptable salts and solvates thereof.

In a particular embodiment, compounds of the invention have the general formular (Ia)

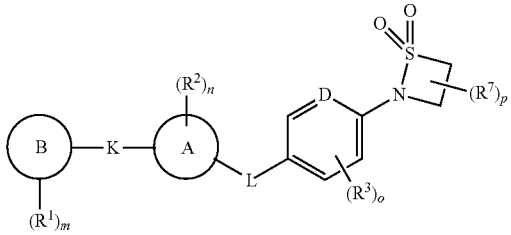

(Ia)

or a pharmaceutically acceptable salt thereof, wherein:
ring A is aryl, heterocycle or heteroaryl;
$R^1$ and $R^3$ each independently is acyl, alkoxy, alkoxycarbonyl, $C_{1-4}$ alkyl, alkylthio, alkynyl, amino, aminocarbonyl, cyano, $C_{3-6}$ cycloalkyl, carbamoyl, hydrogen, hydroxyl, halogen, nitro, sulfamoyl, sulfinyl, sulfonamide or sulfonyl;
$R^2$ is $C_{1-4}$ alkyl, $C_{3-6}$ cycloalkyl, halogen or hydrogen;
ring B is aryl, heterocycle or heteroaryl;
K is selected from
i) absence;
ii) (C=O)$NR^4$ or (C=S)$NR^4$; wherein $R^4$ is alkyl, acyl, cycloalkyl or hydrogen;
L is O, S, S=O, $SO_2$, (C=O)O, $NR^4$, $NR^4$C=O, $NR^4SO_2$, $SO_2NR^4$, $NR^4$(C=O)NH, $NR^4$(C=S)NH, (C=O)$NR^4$ or (C=S)$NR^4$;
D is $CR^3$ or N;
$R^7$ is $C_{1-3}$ alkyl, $C_{3-6}$ cycloalkyl or hydrogen;
m is 0-3;
n is 0-3;
o is 0-3;
p is 0-2;

In another particular embodiment, compounds of the invention have the general Formular (Ib)

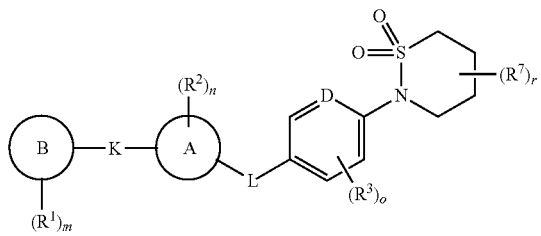

(Ib)

or a pharmaceutically acceptable salt thereof, wherein:
ring A is aryl, heterocycle or heteroaryl;
$R^1$ and $R^3$ each independently is acyl, acylamine, alkoxy, alkoxycarbonyl, $C_{1-4}$ alkyl, alkylthio, alkynyl, amino, aminocarbonyl, cyano, $C_{3-6}$ cycloalkyl, carbamoyl, hydrogen, hydroxyl, halogen, nitro, sulfamoyl, sulfinyl, sulfonamide or sulfonyl;
$R^2$ is $C_{1-4}$ alkyl, $C_{3-6}$ cycloalkyl, cyano, halogen or hydrogen;
ring B is aryl, heterocycle or heteroaryl;
K is selected from
i) absence;
ii) (C=O)$NR^4$ or (C=S)$NR^4$; wherein $R^4$ is alkyl, acyl, cycloalkyl or hydrogen;
L is O, S, S=O, $SO_2$, (C=O)O, $NR^4$, $NR^4$C=O, $NR^4SO_2$, $SO_2NR^4$, $NR^4$(C=O)NH, $NR^4$(C=S)NH, (C=O)$NR^4$ or (C=S)$NR^4$;
D is $CR^3$ or N;
$R^7$ is $C_{1-3}$ alkyl, $C_{3-6}$ cycloalkyl or hydrogen;
m is 0-3;
n is 0-3;
o is 0-3;
q is 0-3;

In another particular embodiment, compounds of the invention have the general Formular (Ic)

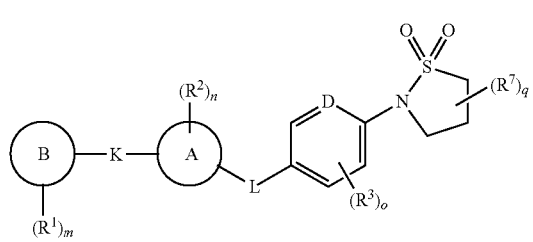

(Ic)

or a pharmaceutically acceptable salt thereof, wherein:
ring A is aryl, heterocycle or heteroaryl;
$R^1$ and $R^3$ each independently is acyl, alkoxy, alkoxycarbonyl, $C_{1-4}$ alkyl, alkylthio, alkynyl, amino, aminocarbonyl, cyano, $C_{3-6}$ cycloalkyl, carbamoyl, hydrogen, hydroxyl, halogen, nitro, sulfamoyl, sulfinyl, sulfonamide or sulfonyl;
$R^2$ is $C_{1-4}$ alkyl, $C_{3-6}$ cycloalkyl, cyano, halogen or hydrogen;
ring B is aryl, heterocycle or heteroaryl;
K is selected from
i) absence;
ii) (C=O)$NR^4$ or (C=S)$NR^4$; wherein $R^4$ is alkyl, acyl, cycloalkyl or hydrogen;
L is O, S, S=O, $SO_2$, (C=O)O, $NR^4$, $NR^4$C=O, $NR^4SO_2$, $SO_2NR^4$, $NR^4$(C=O)NH, $NR^4$(C=S)NH, (C=O)$NR^4$ or (C=S)$NR^4$;
D is $CR^3$ or N;
$R^7$ is $C_{1-3}$ alkyl, $C_{3-6}$ cycloalkyl or hydrogen;
m is 0-3;
n is 0-3;
o is 0-3;
r is 0-4;

In another particular embodiment, compounds of the invention have the general Formular (Id)

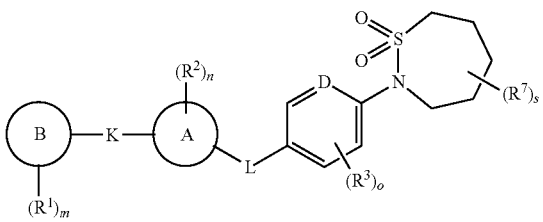

(Id)

or a pharmaceutically acceptable salt thereof, wherein:
ring A is aryl, heterocycle or heteroaryl;
$R^1$ and $R^3$ each independently is acyl, alkoxy, alkoxycarbonyl, $C_{1-4}$ alkyl, alkylthio, alkynyl, amino, aminocarbonyl, cyano, $C_{3-6}$ cycloalkyl, carbamoyl, hydrogen, hydroxyl, halogen, nitro, sulfamoyl, sulfinyl, sulfonamide or sulfonyl;

$R^2$ is $C_{1-4}$ alkyl, $C_{3-6}$ cycloalkyl, cyano, halogen or hydrogen;

ring B is aryl, heterocycle or heteroaryl;

K is selected from i) absence;

ii) (C=O)NR$^4$ or (C=S)NR$^4$; wherein R$^4$ is alkyl, acyl, cycloalkyl or hydrogen;

L is O, S, S=O, SO$_2$, (C=O)O, NR$^4$, NR$^4$C=O, NR$^4$SO$_2$, SO$_2$NR$^4$, NR$^4$(C=O)NH, NR$^4$(C=S)NH, (C=O)NR$^4$ or (C=S)NR$^4$;

D is CR$^3$ or N;

R$^7$ is $C_{1-3}$ alkyl, $C_{3-6}$ cycloalkyl or hydrogen;

m is 0-3;

n is 0-3;

o is 0-3;

s is 0-5;

In another particular embodiment, compounds of the invention have the general Formular (Ie)

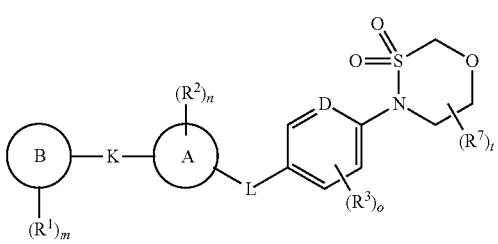

(Ie)

or a pharmaceutically acceptable salt thereof, wherein:

ring A is aryl, heterocycle or heteroaryl;

R$^1$ and R$^3$ each independently is acyl, alkoxy, alkoxycarbonyl, $C_{1-4}$ alkyl, alkylthio, alkynyl, amino, aminocarbonyl, cyano, $C_{3-6}$ cycloalkyl, carbamoyl, hydrogen, hydroxyl, halogen, nitro, sulfamoyl, sulfinyl, sulfonamide or sulfonyl;

R$^2$ is $C_{1-4}$ alkyl, $C_{3-6}$ cycloalkyl, cyano, halogen or hydrogen;

ring B is aryl, heterocycle or heteroaryl;

K is selected from i) absence;

ii) (C=O)NR$^4$ or (C=S)NR$^4$; wherein R$^4$ is alkyl, acyl, cycloalkyl or hydrogen;

L is O, S, S=O, SO$_2$, (C=O)O, NR$^4$, NR$^4$C=O, NR$^4$SO$_2$, SO$_2$NR$^4$, NR$^4$(C=O)NH, NR$^4$(C=S)NH, (C=O)NR$^4$ or (C=S)NR$^4$;

D is CR$^3$ or N;

R$^7$ is $C_{1-3}$ alkyl, $C_{3-6}$ cycloalkyl or hydrogen;

m is 0-3;

n is 0-3;

o is 0-3;

t is 0-3;

In another particular embodiment, compounds of the invention have the general Formular (If)

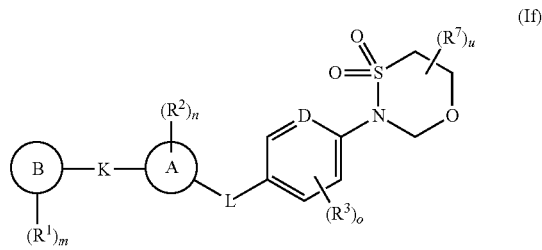

(If)

or a pharmaceutically acceptable salt thereof, wherein:

ring A is aryl, heterocycle or heteroaryl;

R$^1$ and R$^3$ each independently is acyl, alkoxy, alkoxycarbonyl, $C_{1-4}$ alkyl, alkylthio, alkynyl, amino, aminocarbonyl, cyano, $C_{3-6}$ cycloalkyl, carbamoyl, hydrogen, hydroxyl, halogen, nitro, sulfamoyl, sulfinyl, sulfonamide or sulfonyl;

R$^2$ is $C_{1-4}$ alkyl, $C_{3-6}$ cycloalkyl, cyano, halogen or hydrogen;

ring B is aryl, heterocycle or heteroaryl;

K is selected from i) absence;

ii) (C=O)NR$^4$ or (C=S)NR$^4$; wherein R$^4$ is alkyl, acyl, cycloalkyl or hydrogen;

L is O, S, S=O, SO$_2$, (C=O)O, NR$^4$, NR$^4$C=O, NR$^4$SO$_2$, SO$_2$NR$^4$, NR$^4$(C=O)NH, NR$^4$(C=S)NH, (C=O)NR$^4$ or (C=S)NR$^4$;

D is CR$^3$ or N;

R$^7$ is $C_{1-3}$ alkyl, $C_{3-6}$ cycloalkyl or hydrogen;

m is 0-3;

n is 0-3;

o is 0-3;

u is 0-3;

In another particular embodiment, compounds of the invention have the general Formular (Ig)

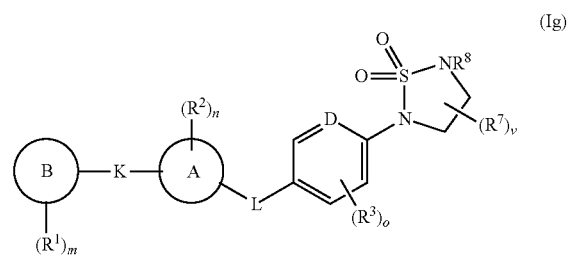

(Ig)

or a pharmaceutically acceptable salt thereof, wherein:

ring A is aryl, heterocycle or heteroaryl;

R$^1$ and R$^3$ each independently is acyl, alkoxy, alkoxycarbonyl, $C_{1-4}$ alkyl, alkylthio, alkynyl, amino, aminocarbonyl, cyano, $C_{3-6}$ cycloalkyl, carbamoyl, hydrogen, hydroxyl, halogen, nitro, sulfamoyl, sulfinyl, sulfonamide or sulfonyl;

R$^2$ is $C_{1-4}$ alkyl, $C_{3-6}$ cycloalkyl, cyano, halogen or hydrogen;

ring B is aryl, heterocycle or heteroaryl;

K is selected from i) absence;

ii) (C=O)NR$^4$ or (C=S)NR$^4$; wherein R$^4$ is alkyl, acyl, cycloalkyl or hydrogen;

L is O, S, S=O, SO$_2$, (C=O)O, NR$^4$, NR$^4$C=O, NR$^4$SO$_2$, SO$_2$NR$^4$, NR$^4$(C=O)NH, NR$^4$(C=S)NH, (C=O)NR$^4$ or (C=S)NR$^4$;

D is CR³ or N;
R⁷ is $C_{1-3}$ alkyl, $C_{3-6}$ cycloalkyl or hydrogen;
R⁸ is $C_{1-3}$ alkyl or hydrogen;
m is 0-3;
n is 0-3;
o is 0-3;
v is 0-2;

In another particular embodiment, compounds of the invention have the general Formular (Ih)

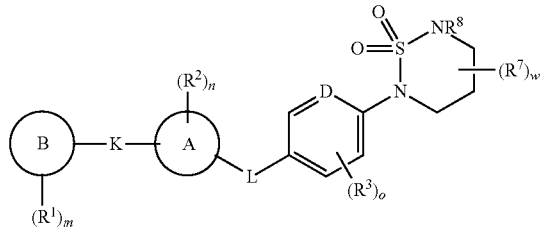

(Ih)

or a pharmaceutically acceptable salt thereof, wherein:
ring A is aryl, heterocycle or heteroaryl;
R¹ and R³ each independently is acyl, alkoxy, alkoxycarbonyl, $C_{1-4}$ alkyl, alkylthio, alkynyl, amino, aminocarbonyl, cyano, $C_{3-6}$ cycloalkyl, carbamoyl, hydrogen, hydroxyl, halogen, nitro, sulfamoyl, sulfinyl, sulfonamide or sulfonyl;
R² is $C_{1-4}$ alkyl, $C_{3-6}$ cycloalkyl, cyano, halogen or hydrogen;
ring B is aryl, heterocycle or heteroaryl;
K is selected from
i) absence;
ii) (C=O)NR⁴ or (C=S)NR⁴; wherein R⁴ is alkyl, acyl, cycloalkyl or hydrogen;
L is O, S, S=O, SO₂, (C=O)O, NR⁴, NR⁴C=O, NR⁴SO₂, SO₂NR⁴, NR⁴(C=O)NH, NR⁴(C=S)NH, (C=O)NR⁴ or (C=S)NR⁴;
D is CR³ or N;
R⁷ is $C_{1-3}$ alkyl, $C_{3-5}$ cycloalkyl or hydrogen;
R⁸ is $C_{1-3}$ alkyl or hydrogen;
m is 0-3;
n is 0-3;
o is 0-3;
w is 0-3;

In another particular embodiment, A is a ring preferably selected from the below groups:

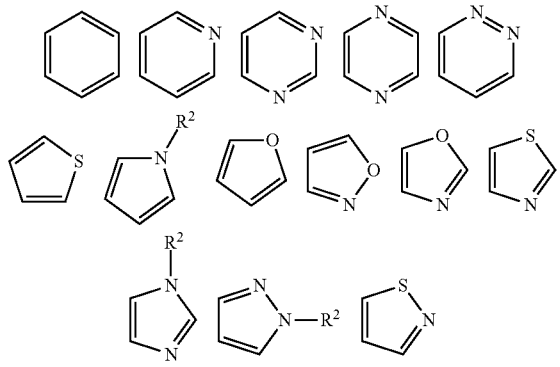

In another particular embodiment, B is a ring preferably selected from the below groups:

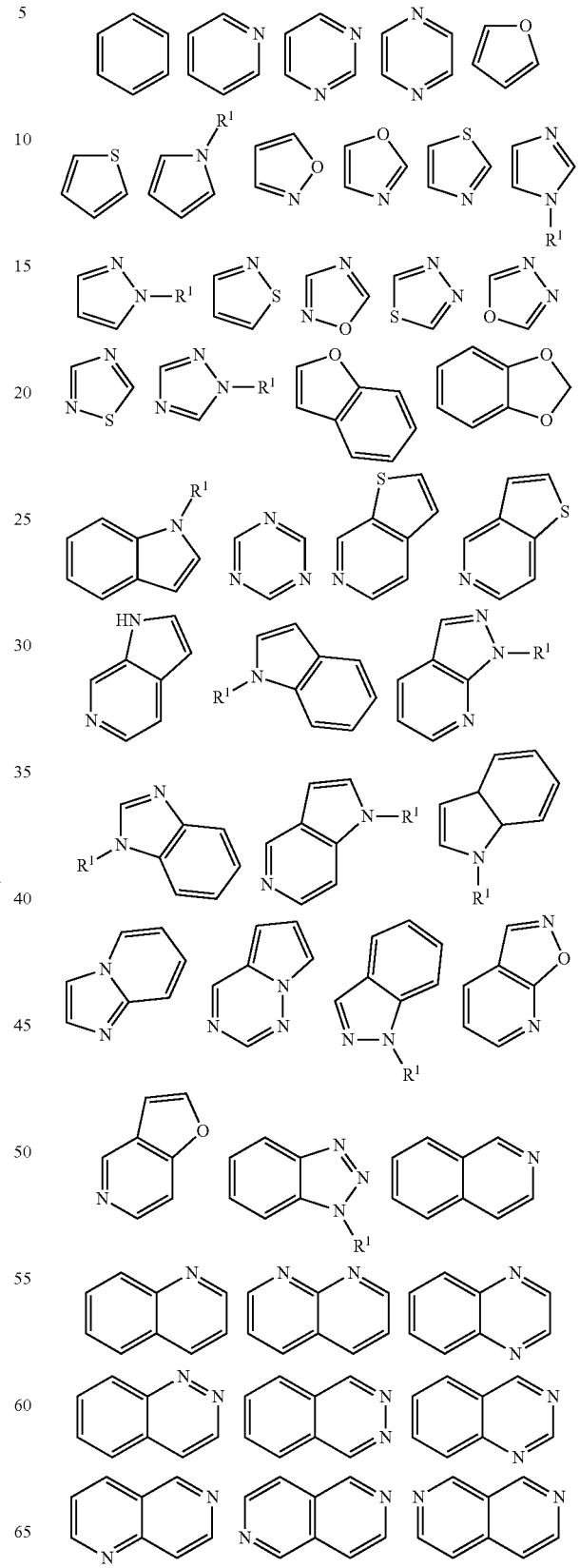

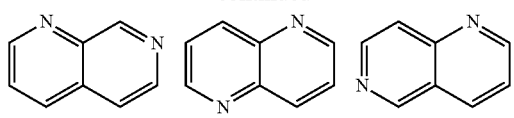
In another particular embodiment, the fragment of $(R^1)_m$—B-K-A$[(R^2)_n]$-L (wherein K is absence and L is $NH_2$) in compounds of this invention having the general Formular (I) is represented as ArNH$_2$ (II) and preferably selected from the following group (IIa-IIt):
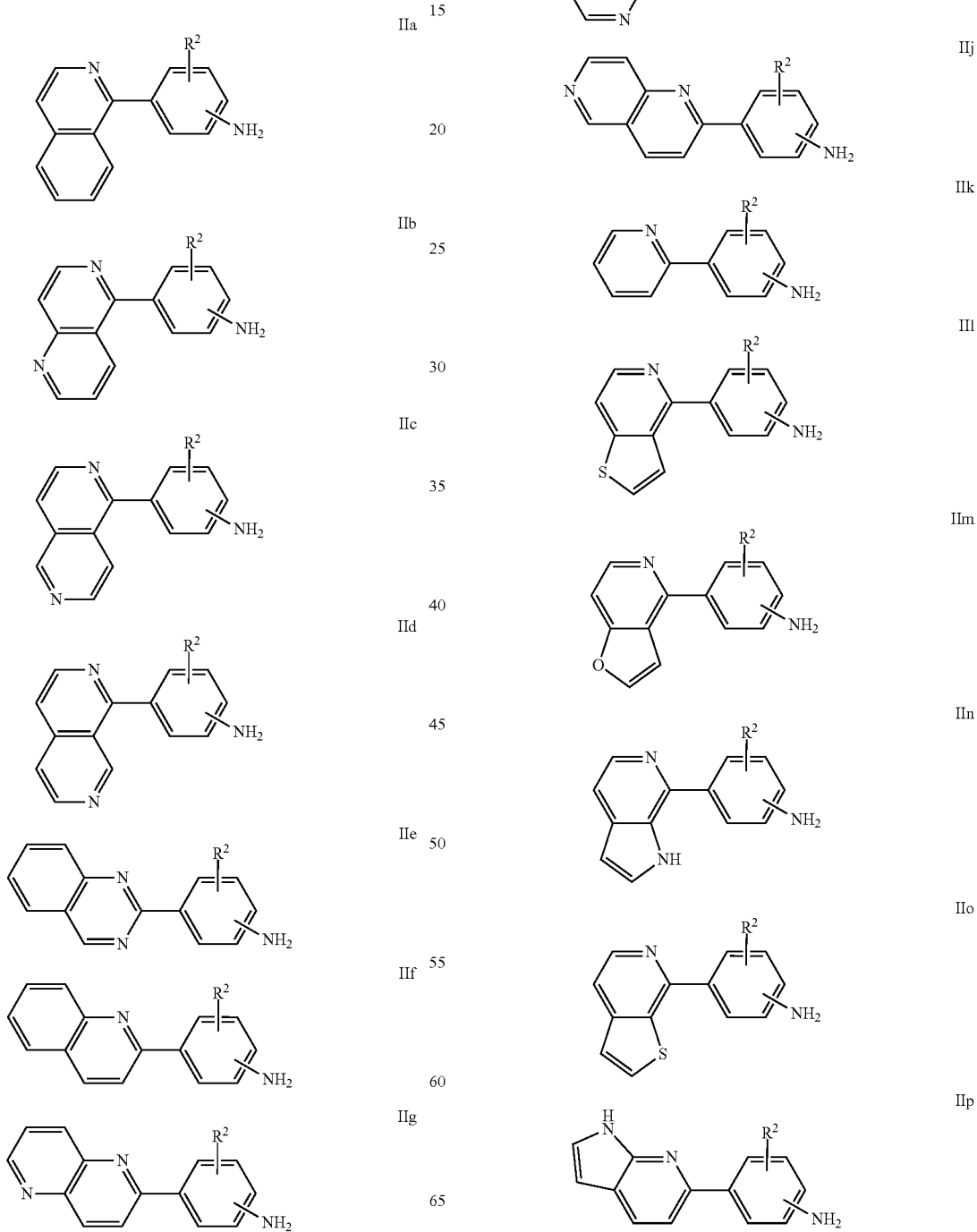

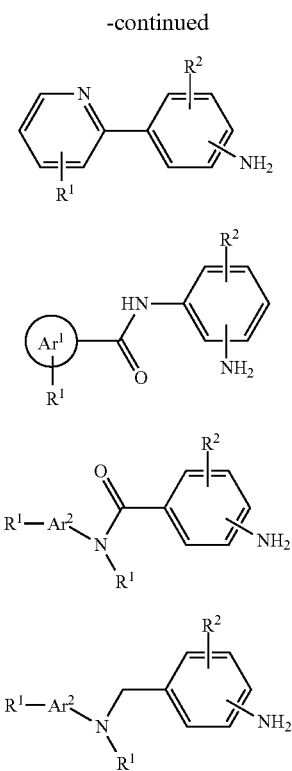

The following definitions refer to the various terms used above and throughout the disclosure.

Compounds are generally described herein using standard nomenclature. For compounds having asymmetric centers, it should be understood that (unless otherwise specified) all of the optical isomers and mixtures thereof are encompassed. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. Certain compounds are described herein using a general formula that include, variables (e.g. X, Ar.). Unless otherwise specified, each variable within such a formula is defined independently of any other variable, and any variable that occurs more than one time in a formula is defined independently at each occurrence.

The term "halo" or "halogen" refers to fluorine, chlorine, bromine or iodine.

The term "alkyl" herein alone or as part of another group refers to a monovalent alkane (hydrocarbon) derived radical containing from 1 to 12 carbon atoms unless otherwise defined. Alkyl groups may be substituted at any available point of attachment. An alkyl group substituted with another alkyl group is also referred to as a "branched alkyl group". Exemplary alkyl groups include methyl, ethyl, propyl, isopropyl, n-butyl, t-butyl, isobutyl, pentyl, hexyl, isohexyl, heptyl, dimethylpentyl, octyl, 2,2,4-trimethylpentyl, nonyl, decyl, undecyl, dodecyl, and the like. Exemplary substituents include but are not limited to one or more of the following groups: alkyl, aryl, halo (such as F, Cl, Br, I), haloalkyl (such as $CCl_3$ or $CF_3$), alkoxy, alkylthio, hydroxy, carboxy (—COOH), alkyloxycarbonyl (—C(O)R), alkylcarbonyloxy (—OCOR), amino (—$NH_2$), carbamoyl (—NHCOOR— or —OCONHR—), urea (—NHCONHR—) or thiol (—SH). In some preferred embodiments of the present invention, alkyl groups are substituted with, for example, amino, heterocycloalkyl, such as morpholine, piperazine, piperidine, azetidine, hydroxyl, methoxy.

The term 'cycloalkyl' herein alone or as part of another group refers to fully saturated and partially unsaturated hydrocarbon rings of 3 to 9, preferably 3 to 6 carbon atoms. The examples include cyclopropyl, cyclobutyl, cyclopentyl and cyclohexyl, and like. Further, a cycloalkyl may be substituted. A substituted cycloalkyl refers to such rings having one, two, or three substituents, selected from the group consisting of halo, alkyl, substituted alkyl, alkenyl, alkynyl, nitro, cyano, oxo (=O), hydroxy, alkoxy, thioalkyl, —$CO_2H$, —C(=O)H, $CO_2$-alkyl, —C(=O)alkyl, keto, =N—OH, =N—O-alkyl, aryl, heteroaryl, heterocyclo, —NR'R", —C(=O)NR'R", —$CO_2$NR'R", —C(=O)NR'R", —NR'$CO_2$R", —NR'C(=O)R", —$SO_2$NR'R", and —NR'$SO_2$R", wherein each of R' and R" are independently selected from hydrogen, alkyl, substituted alkyl, and cycloalkyl, or R' and R" together form a heterocyclo or heteroaryl ring.

The term "alkynyl" refers to straight or branched chain alkyne groups, which have one or more unsaturated carbon-carbon bonds, at least one of which is a triple bond. Alkynyl groups include C2-C8 alkynyl, C2-C6 alkynyl and C2-C4 alkynyl groups, which have from 2 to 8, 2 to 6 or 2 to 4 carbon atoms, respectively. Illustrative of the alkynyl group include ethenyl, propenyl, isopropenyl, butenyl, isobutenyl, pentenyl, and hexenyl. Alkynyl groups may also be substituted at any available point of attachment. Exemplary substituents for alkynyl groups include those listed above for alkyl groups such as amino, alkylamino, etc. The numbers in the subscript after the symbol "C" define the number of carbon atoms a particular group can contain.

The term "alkoxy" alone or as part of another group denotes an alkyl group as described above bonded through an oxygen linkage (—O—). Preferred alkoxy groups have from 1 to 8 carbon atoms. Examples of such groups include the methoxy, ethoxy, n-propoxy, isopropoxy, n-butoxy, isobutoxy, sec-butoxy, tert-butoxy, n-pentyloxy, isopentyloxy, n-hexyloxy, cyclohexyloxy, n-heptyloxy, n-octyloxy and 2-ethylhexyloxy.

The term "alkylthio" refers to an alkyl group as described above attached via a sulfur bridge. Preferred alkoxy and alkylthio groups are those in which an alkyl group is attached via the heteroatom bridge. Preferred alkylthio groups have from 1 to 8 carbon atoms. Examples of such groups include the methylthio, ethylthio, n-propythiol, n-butylthiol, and like.

The term "alkanoyl" refers to groups of the formula: —C(O)R, where the R group is a straight or branched C1-C6 alkyl group, cycloalkyl, aryl, or heteroaryl.

The term "alkoxycarbonyl" herein alone or as part of another group denotes an alkoxy group bonded through a carbonyl group. An alkoxycarbonyl radical is represented by the formula: —C(O)OR, where the R group is a straight or branched C1-C6 alkyl group, cycloalkyl, aryl, or heteroaryl.

The term "aryl" herein alone or as part of another group refers to monocyclic or bicyclic aromatic rings, e.g. phenyl, substituted phenyl and the like, as well as groups which are fused, e.g., napthyl, phenanthrenyl and the like. An aryl group thus contains at least one ring having at least 6 atoms, with up to five such rings being present, containing up to 20 atoms therein, with alternating (resonating) double bonds between adjacent carbon atoms or suitable heteroatoms. Aryl groups may optionally be substituted with one or more groups including, but not limited to halogen such as I, Br, F, or Cl; alkyl, such as methyl, ethyl, propyl, alkoxy, such as methoxy or ethoxy, hydroxy, carboxy, carbamoyl, alkyloxycarbonyl, nitro, alkenyloxy, trifluoromethyl, amino, cycloalkyl, aryl, heteroaryl, cyano, alkyl S(O)m (m=O, 1, 2), or thiol.

The term "amino" herein alone or as part of another group refers to —NH2, an "amino" may optionally be substituted with one or two substituents, which may be the same or different, such as acyl, alkyl, aryl, arylalkyl, alkenyl, alkynyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl, carbonyl or carboxyl. These substituents may be further substituted with a carboxylic acid, any of the alkyl or aryl substituents set out herein. In some embodiments, the amino groups are substituted with carboxyl or carbonyl to form N-acyl or N-carbamoyl derivatives.

The term "heteroatom" refers to any atom other than carbon, for example, N, O, or S.

The term "heteroaryl" herein alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is 4 or less and each ring has at least one carbon atom.

The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halo, alkyl, substituted alkyl, alkenyl, alkynyl, aryl, nitro, cyano, hydroxy, alkoxy, thioalkyl, —CO2H, —C(=O)H, —CO2-alkyl, —C(=O)alkyl, phenyl, benzyl, phenylethyl, phenyloxy, phenylthio, cycloalkyl, substituted cycloalkyl, heterocyclo, heteroaryl, —NR'R", —C(=O)NR'R", —CO2NR'R", —C(=O)NR'R", —NR'CO2R", —NR'C(=O)R", —SO2NR'R", and —NR'SO2R", wherein each of R' and R" is independently selected from hydrogen, alkyl, substituted alkyl, and cycloalkyl, or R' and R" together form a heterocyclo or heteroaryl ring.

Preferably monocyclic heteroaryl groups include pyrrolyl, pyrazolyl, pyrazolinyl, imidazolyl, oxazolyl, diazolyl, isoxazolyl, thiazolyl, thiadiazolyl, S isothiazolyl, furanyl, thienyl, oxadiazolyl, pyridyl, pyrazinyl, pyrimidinyl, pyridazinyl, triazinyl and the like.

Preferably bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, dihydroisoindolyl, tetrahydroquinolinyl and the like.

Preferably tricyclic heteroaryl groups include carbazolyl, benzidolyl, phenanthrollinyl, acridinyl, phenanthridinyl, xanthenyl and the like.

The term "heterocycle" or "heterocycloalkyl" herein alone or as part of another group refers to a cycloalkyl group (nonaromatic) in which one of the carbon atoms in the ring is replaced by a heteroatom selected from O, S or N. The "heterocycle" has from 1 to 3 fused, pendant or spiro rings, at least one of which is a heterocyclic ring (i.e., one or more ring atoms is a heteroatom, with the remaining ring atoms being carbon). The heterocyclic ring may be optionally substituted which means that the heterocyclic ring may be substituted at one or more substitutable ring positions by one or more groups independently selected from alkyl (preferably lower alkyl), heterocycloalkyl, heteroaryl, alkoxy (preferably lower alkoxy), nitro, monoalkylamino (preferably a lower alkylamino), dialkylamino (preferably a alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy; lower alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. A heterocyclic group may generally be linked via any ring or substituent atom, provided that a stable compound results. N-linked heterocyclic groups are linked via a component nitrogen atom.

Typically, a heterocyclic ring comprises 1 to 4 heteroatoms; within certain embodiments each heterocyclic ring has 1 or 2 heteroatoms per ring. Each heterocyclic ring generally contains from 3 to 8 ring members (rings having from to 7 ring members are recited in certain embodiments), and heterocycles comprising fused, pendant or spiro rings typically contain from 9 to 14 ring members which consists of carbon atoms and contains one, two, or three heteroatoms selected from nitrogen, oxygen and/or sulfur.

Examples of "heterocycle" include piperazine, piperidine, morpholine, thiomorpholine, pyrrolidine, imidazolidine and thiazolide.

The term "carbamoyl" herein refers to aminocarbonyl containing substituent represented by the formular C(O)N(R)2 in which R is H, hydroxyl, alkyl, a carbocycle, a heterocycle, carbocycle-substituted alkyl or alkoxy, or heterocycle-substituted alkyl or alkoxy wherein the alkyl, alkoxy, carbocycle and heterocycles are as herein defined. Carbamoyl groups include alkylaminocarbonyl (e.g. ethylaminocarbonyl, Et-NH—CO—), arylaminocarbonyl (e.g. phenylaminocarbonyl), aralkylaminocarbonyl (e. g. benzoylaminocarbonyl), heterocycleaminocarbonyl (e. g. piperizinylaminocarbonyl), and in particular a heteroarylaminocarbonyl (e. g. pyridylaminocarbonyl).

The term "sulfamoyl" herein refers to —SO2-N(R)2 wherein each R is independently H, alkyl, carbocycle, heterocycle, carbocycloalkyl or heterocycloalkyl. Particular sulfamoyl groups are alkylsulfamoyl, for example methylsulfamoyl (—SO2-NHMe); arylsulfamoyl, for example phenylsulfamoyl; aralkylsulfamoyl, for example benzylsulfamoyl.

The term "sulfinyl" herein refers to —SOR wherein R is alkyl, carbocycle, heterocycle, carbocycloalkyl or heterocycloalkyl. Particular sulfinyl groups are alkylsulfinyl (i. e. —SO-alkyl), for example methylsulfinyl; arylsulfinyl (i. e. —SO-aryl) for example phenylsulfinyl; arakylsulfinyl, for example benzylsulfinyl.

The term "sulfoamide" herein refers to —NR—SO2-R wherein each R is independently H, alkyl, carbocycle, hetercycle, carbocycloalkyl or heterocycloalkyl), a carbocycle or a heterocycle. Particular sulfonamide groups are alkylsulfonamide (e. g. —NH—SO2-alkyl), for example methylsulfonamide; arylsulfonamide (e.g. —NH—SO2-aryl), for example phenylsulfonamide; aralkylsulfonamide, for example benzylsulfonamide.

The term "sulfonyl" herein refers to —SO2-R group wherein R is alkyl, carbocycle, heterocycle, carbocycloalkyl or heterocycloalkyl. Particular sulfonyl groups are alkylsulfonyl (e. G. —SO2-alkyl), for example methylsulfonyl; arylsulfonyl, for example phenylsulfonyl; aralkylsulfonyl, for example benzylsulfonyl.

A dash ("-") that is not between two letters or symbols is used to indicate a point of t attachment for a substituent. For example, —CONH2 is attached through the carbon atom.

The term "substituent," as used herein, refers to a molecular moiety that is covalently bonded to an atom within a molecule of interest. For example, a "ring substituent" may be a moiety such as a halogen, alkyl group, haloalkyl group or other group discussed herein that is covalently bonded to an atom (preferably a carbon or nitrogen atom) that is a ring member.

The term "optionally substituted" as it refers that the aryl or heterocyclyl or other group may be substituted at one or more substitutable positions by one or more groups independently selected from alkyl (preferably lower alkyl), alkoxy (preferably lower alkoxy), nitro, monoalkylamino (preferably with 1 to 6 carbons), dialkylamino (preferably with one to six carbons), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy and lower alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

Optional substitution is also indicated by the phrase "substituted with from 0 to X substituents," where X is the maximum number of possible substituents. Certain optionally substituted groups are substituted with from 0 to 2, 3 or 4 independently selected substituents.

Groups that are "optionally substituted" are unsubstituted or are substituted by other than hydrogen at one or more available positions. Such optional substituents include, for example, hydroxy, halogen, cyano, nitro, C1-C6 alkyl, C2-C6 alkenyl, C2-C6 alkynyl, C1-C6 alkoxy, C2-C6 alkyl ether, C3-C6 alkanone, C2-C6 alkylthio, amino, mono- or di-(C1-C6 alkyl)amino, C1-C6 haloalkyl, —COOH, —CONH2, mono- or di-(C1-C6 alkyl)aminocarbonyl, —SO2NH2, and/or mono or di(C1-C6 alkyl) sulfonamido, as well as carbocyclic and heterocyclic groups.

The term "pharmaceutically acceptable salt" of a compound recited herein is an acid or base salt that is suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—(CH2)n-COOH where n is 0-4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein. In general, a pharmaceutically acceptable acid or base salt can be synthesized from a parent compound that contains a basic or acidic moiety by any conventional chemical method. Briefly, such salts can be prepared by reaction of the free acid or base forms of these compounds with a stoichiometric amount of the appropriate base or acid in water or in an organic solvent, or in a mixture of the two; generally, the use of nonaqueous media, such as ether, ethyl acetate, ethanol, isopropanol or acetonitrile, is preferred. It will be apparent that each compound of Formula I may, but need not, be formulated as a hydrate, solvate or non-covalent complex. In addition, the various crystal forms and polymorphs are within the scope of the present invention. Also provided herein are prodrugs of the compounds of Formula I.

Examples of specific compounds of the present invention are those compounds defined in the following:

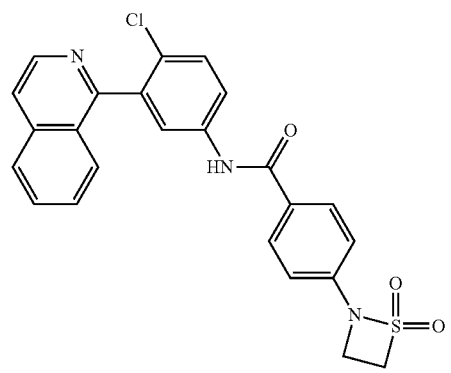

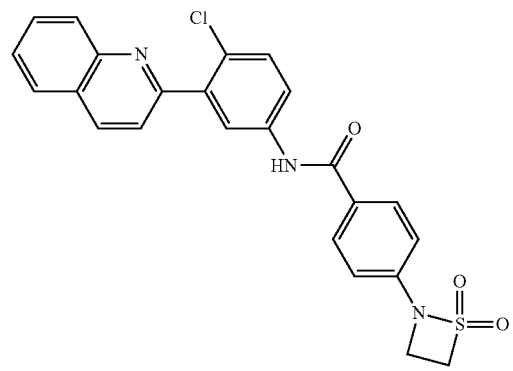

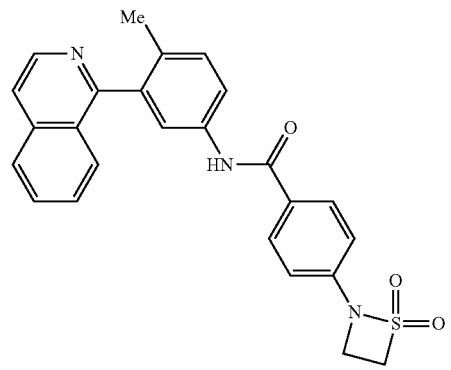

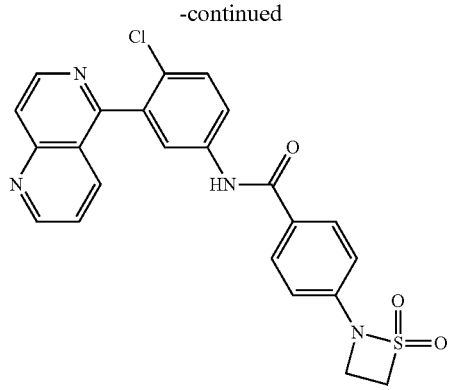
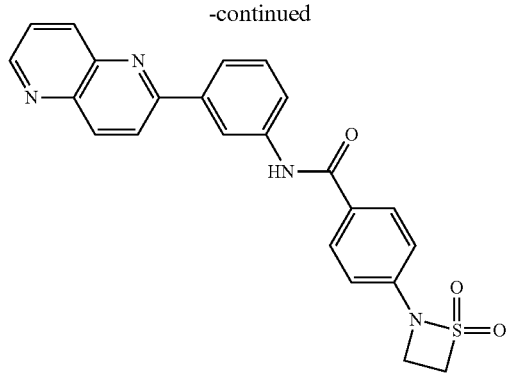
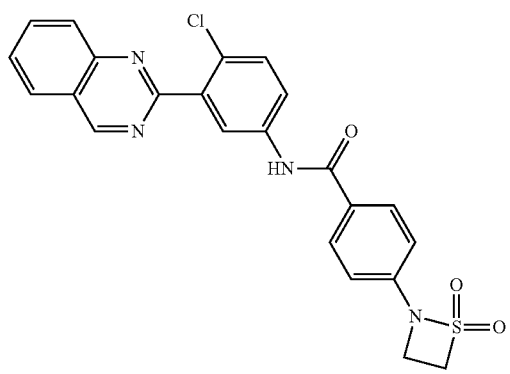
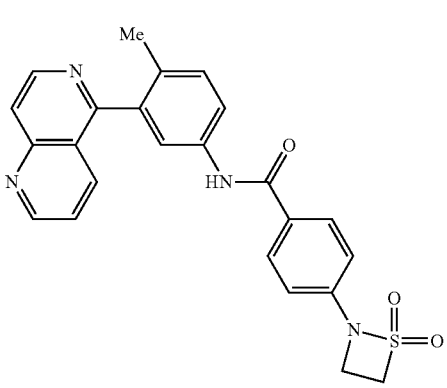
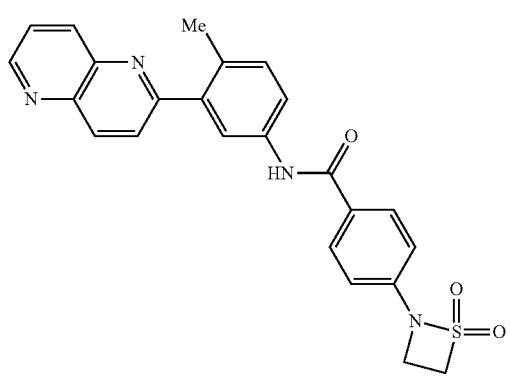
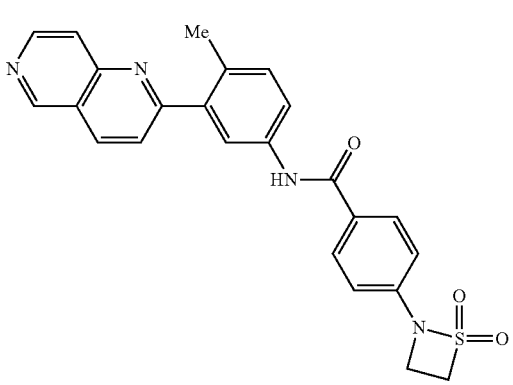
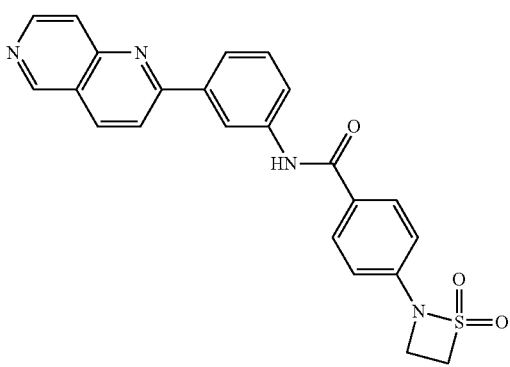
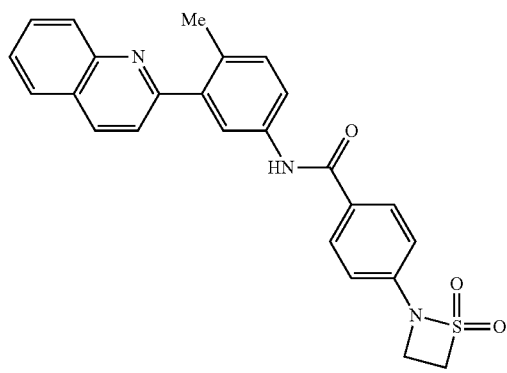

-continued
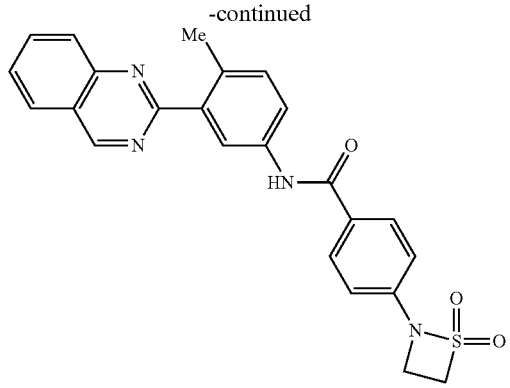
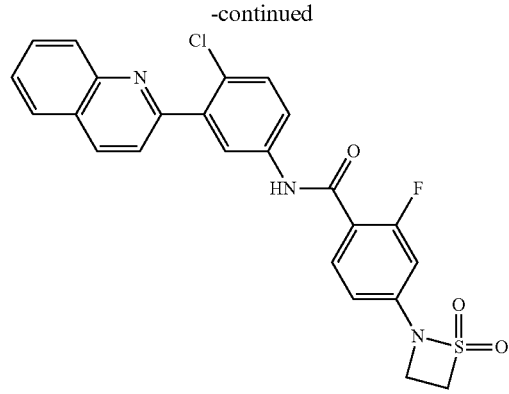
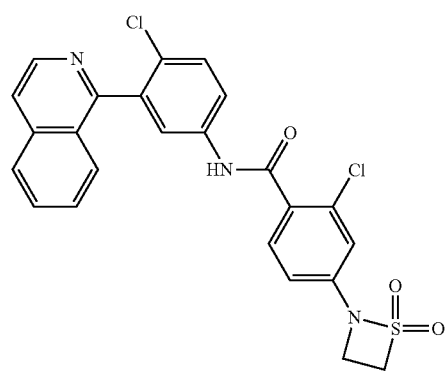
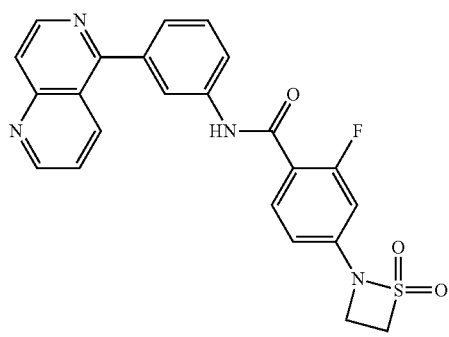
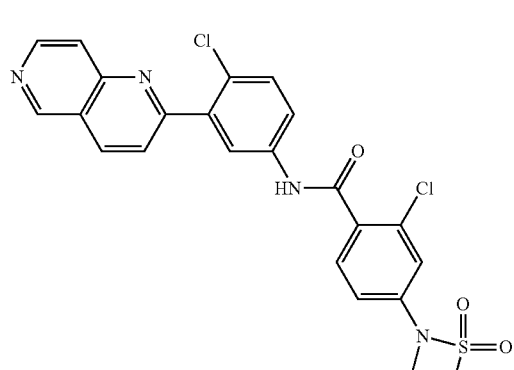
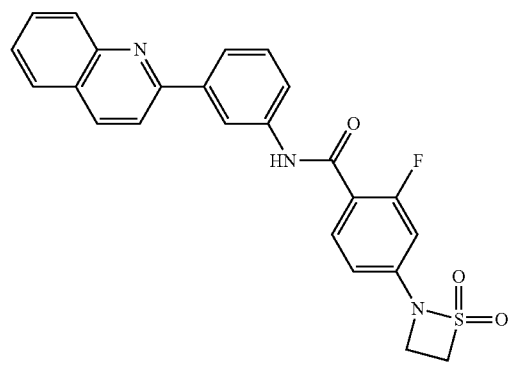
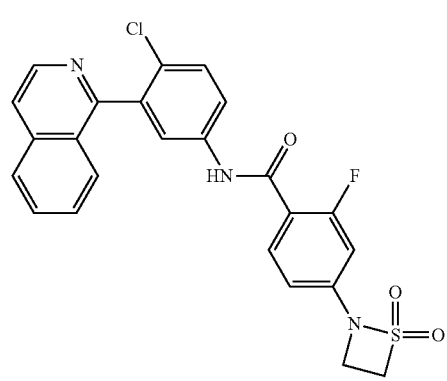
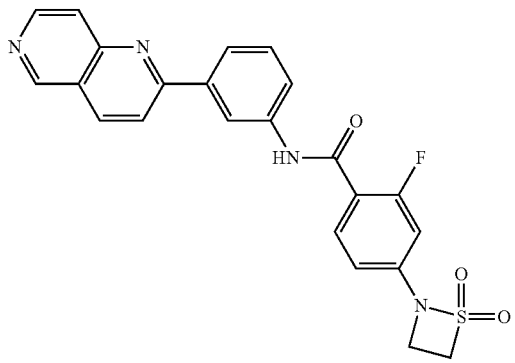

23
-continued
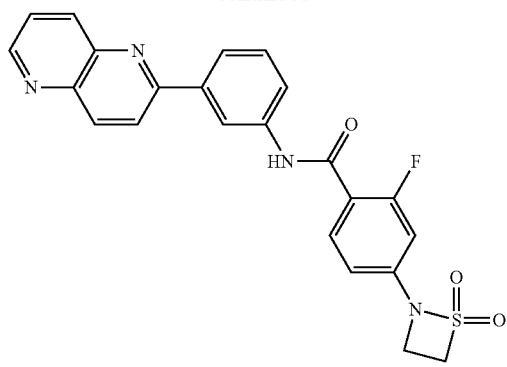
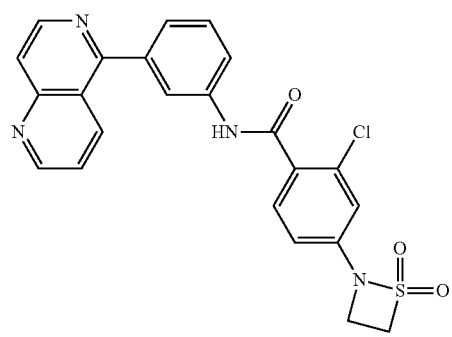
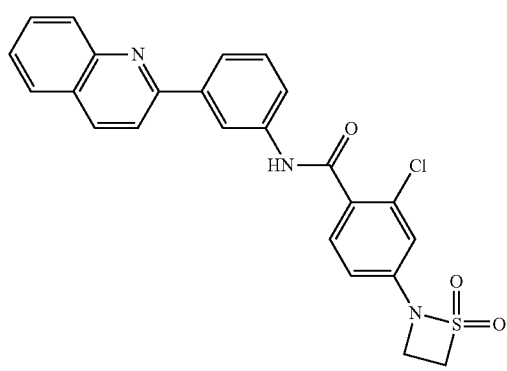
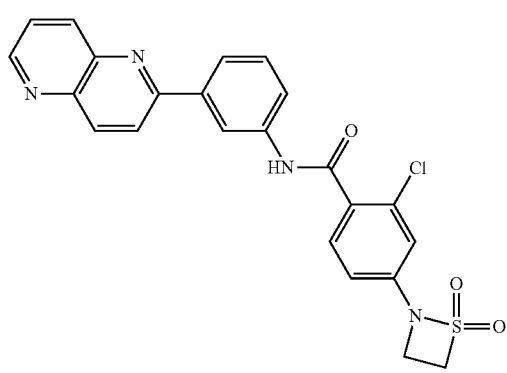
24
-continued
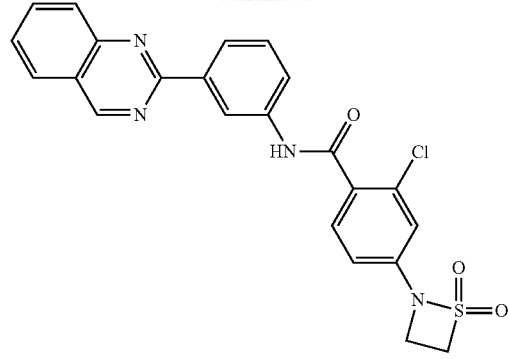
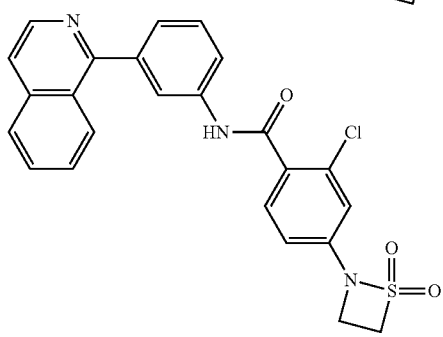
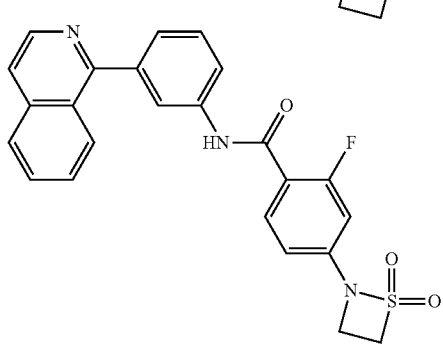

-continued
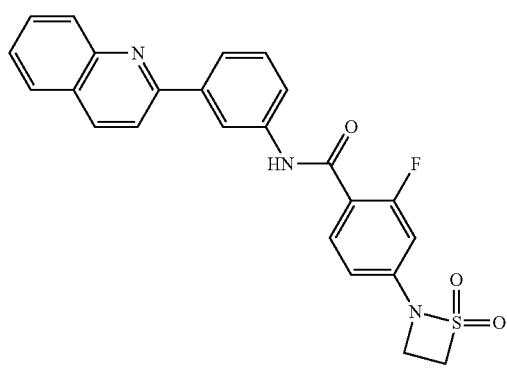
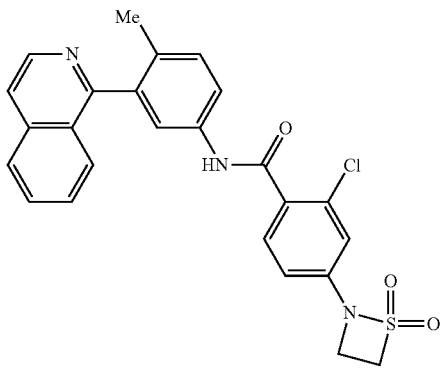
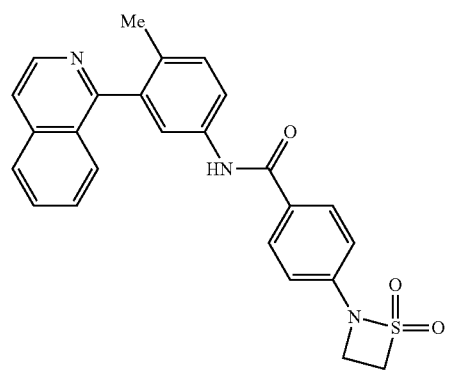
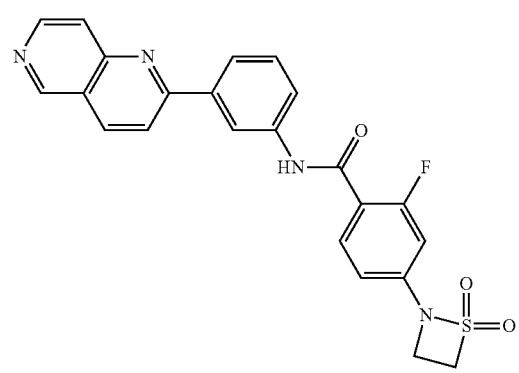
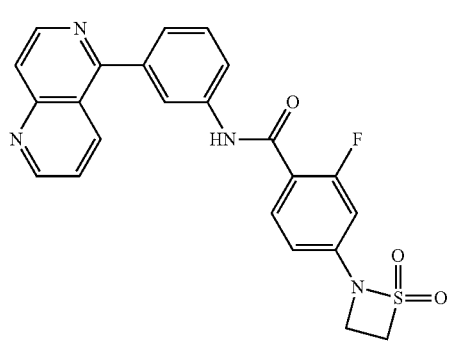
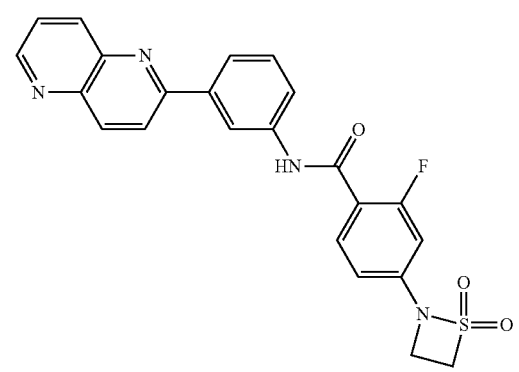
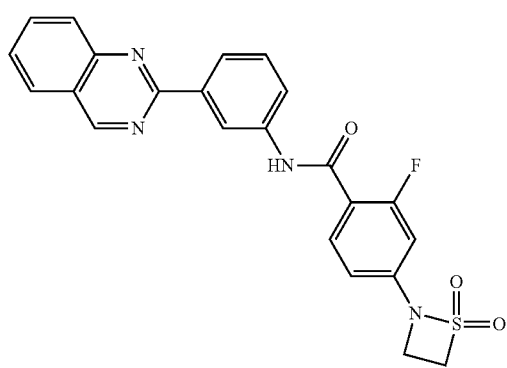
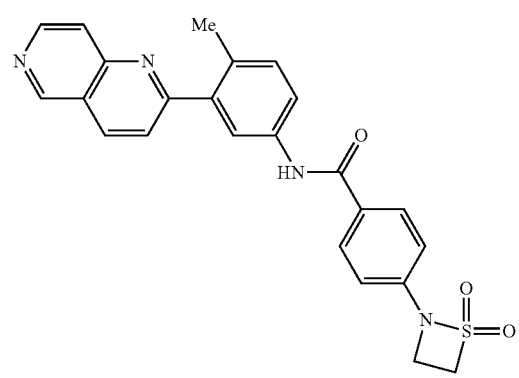

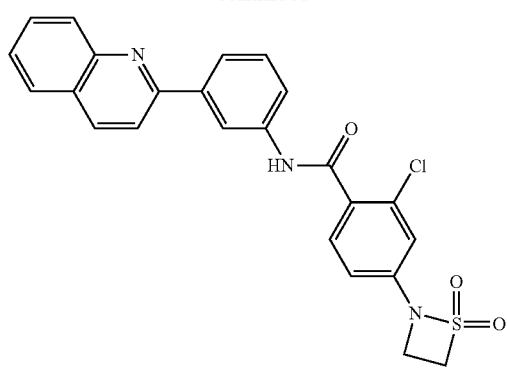
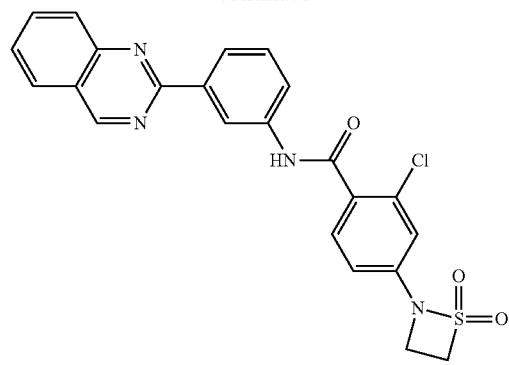
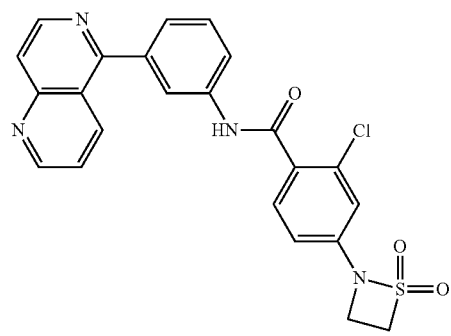
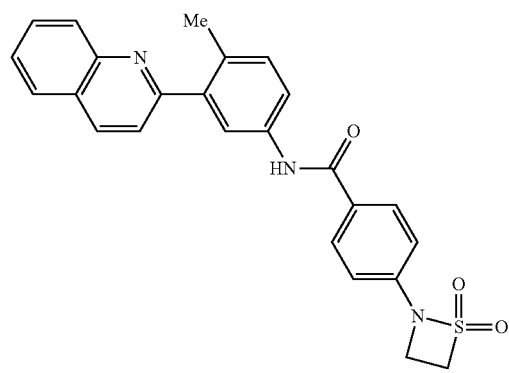
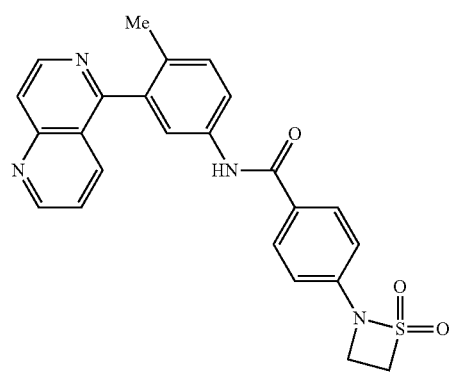
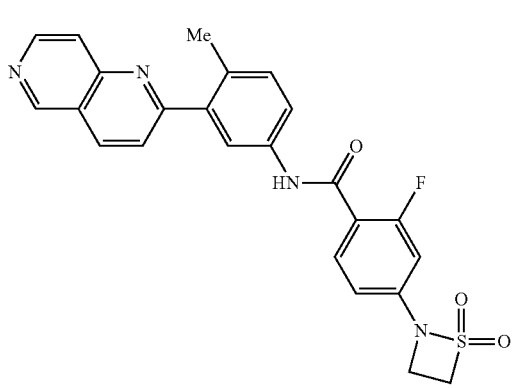
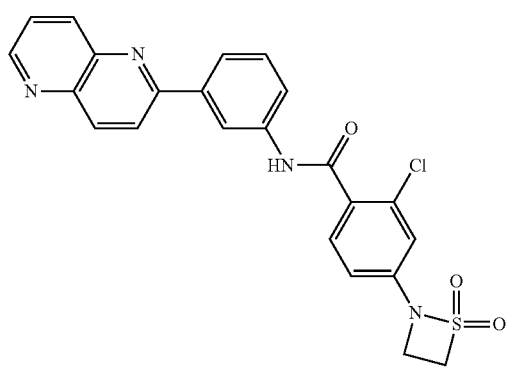
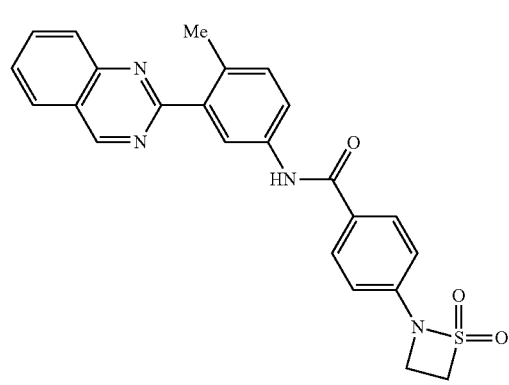

-continued
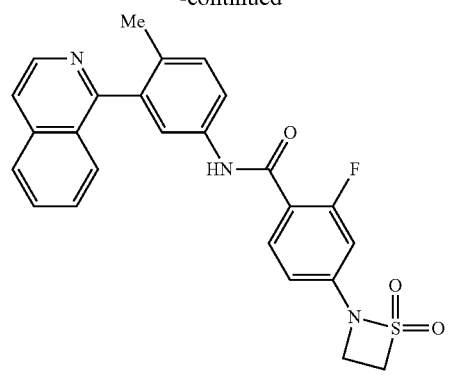
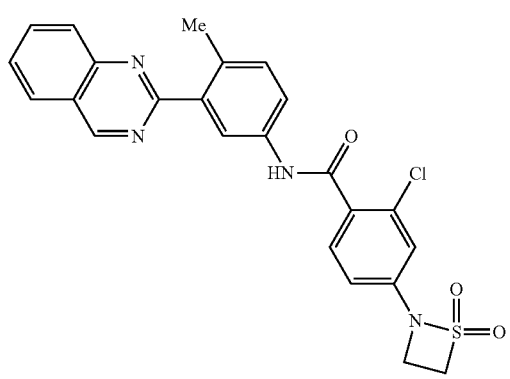
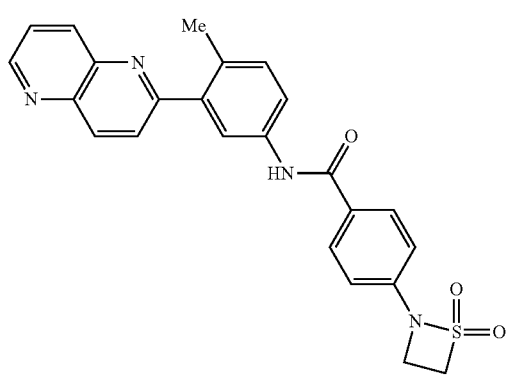
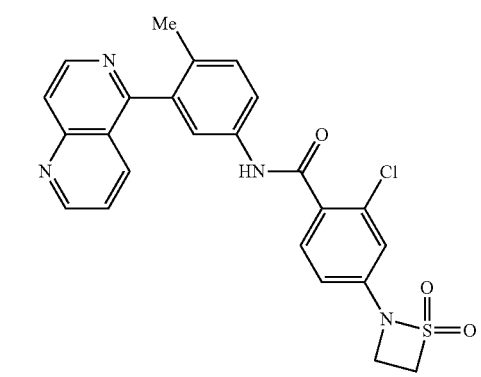
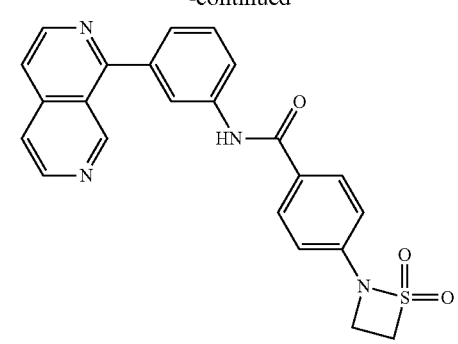
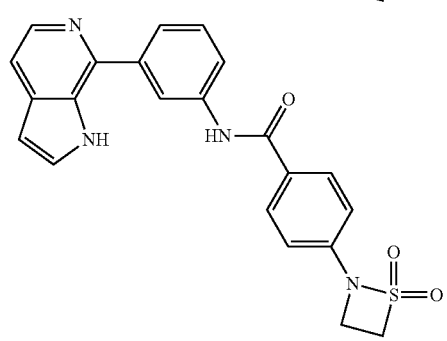
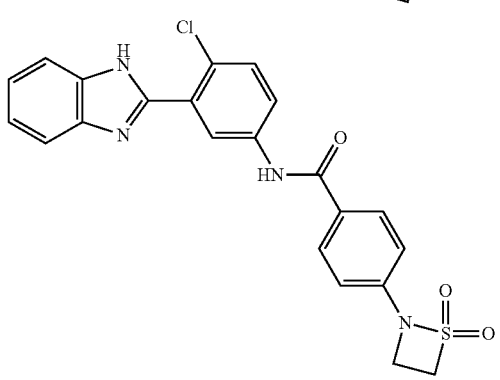
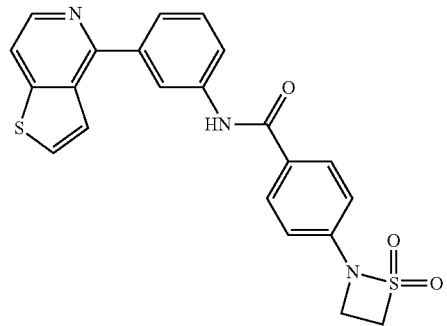
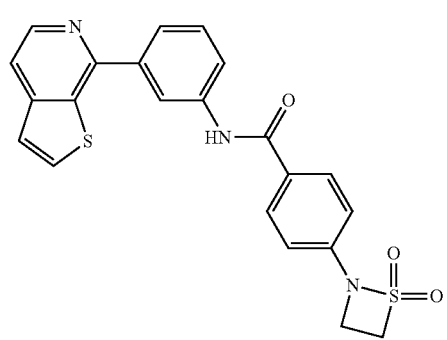

31
-continued
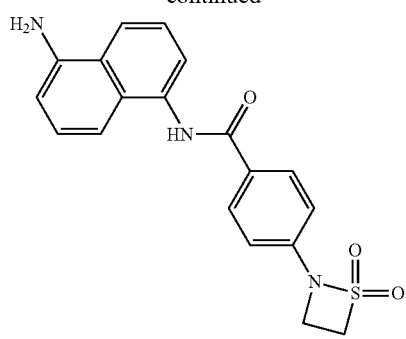
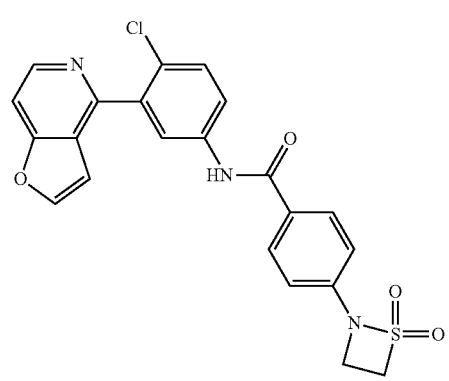
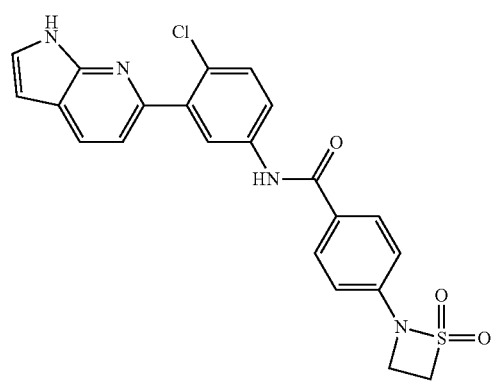
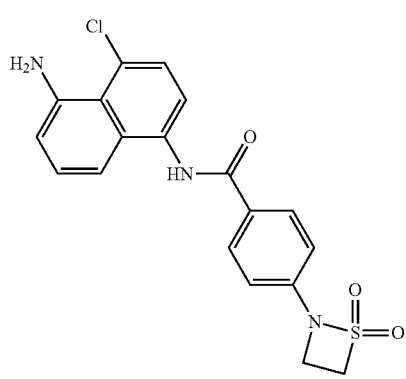
32
-continued
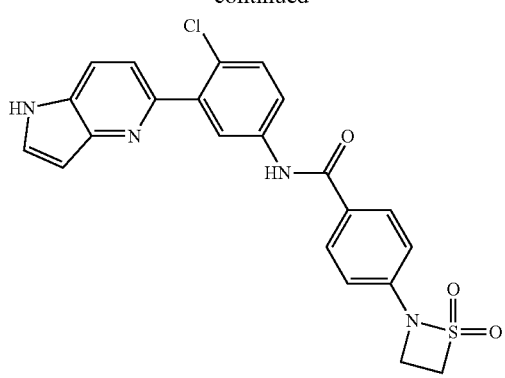
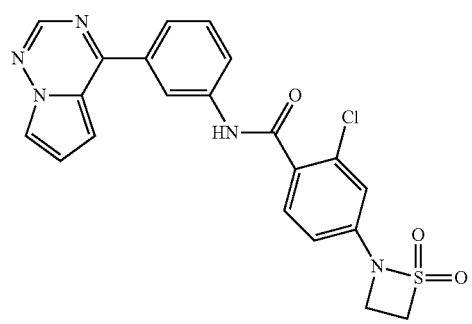
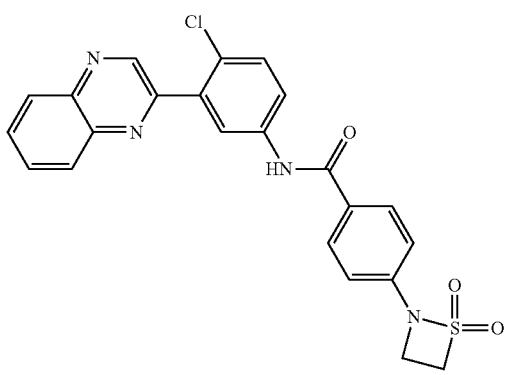

33
-continued
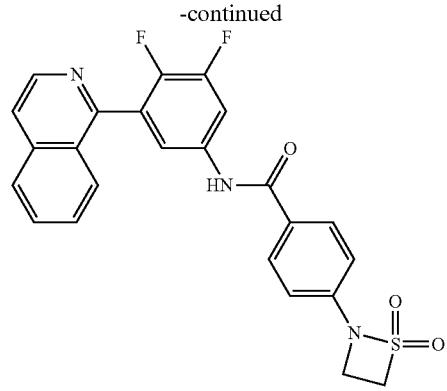
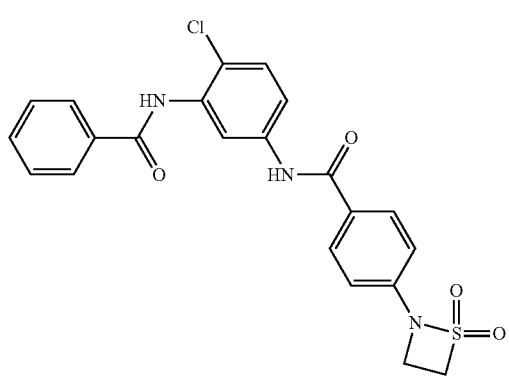
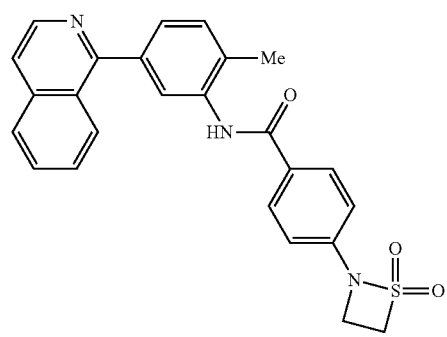
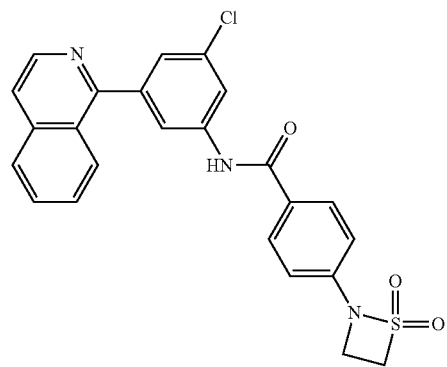
34
-continued
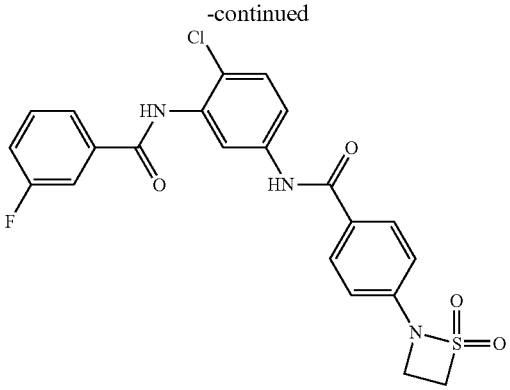
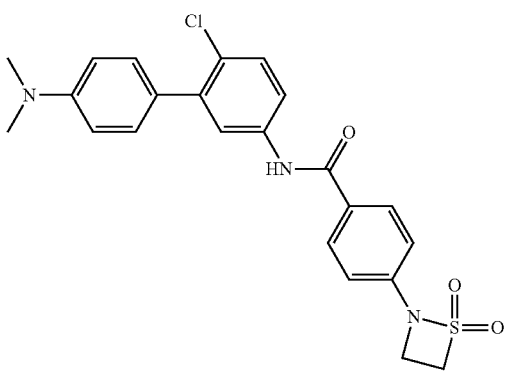
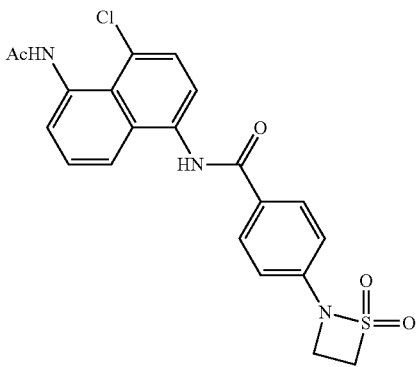
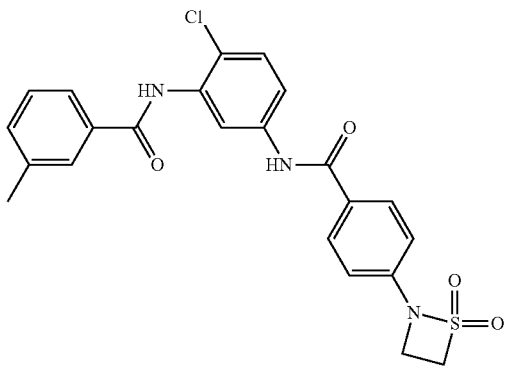

35
-continued
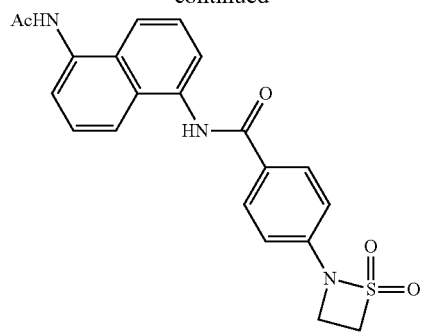
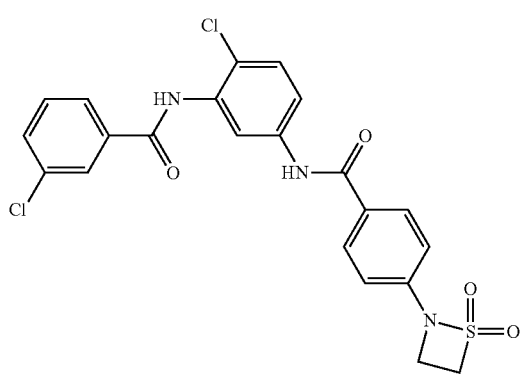
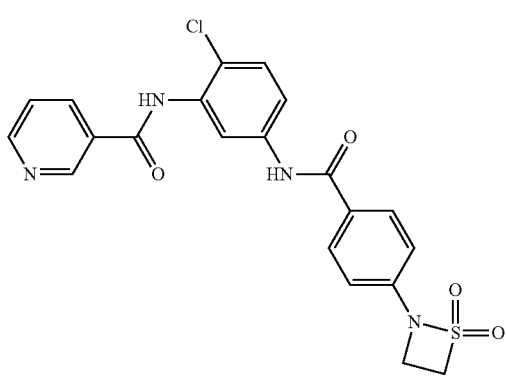
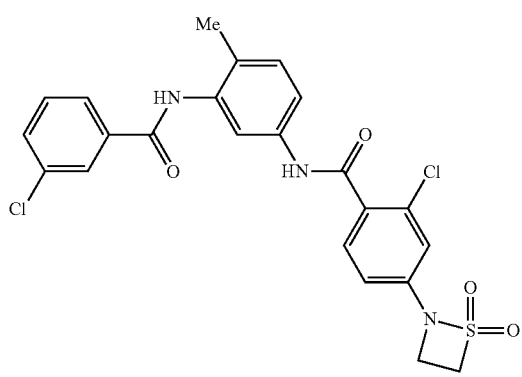
36
-continued
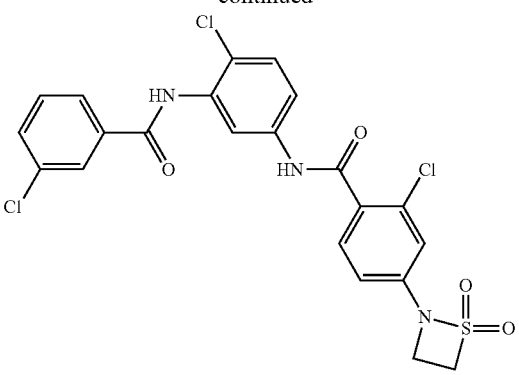
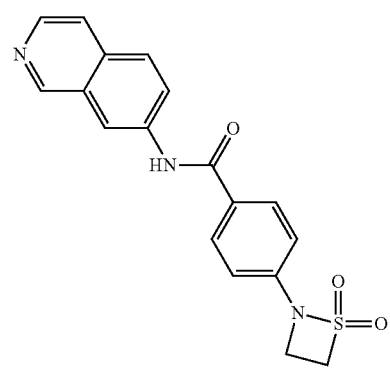
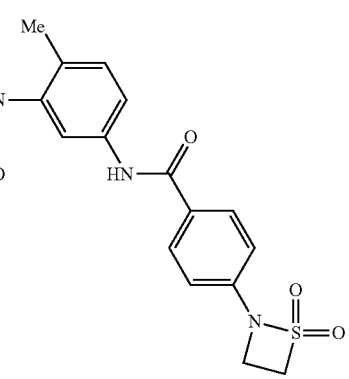
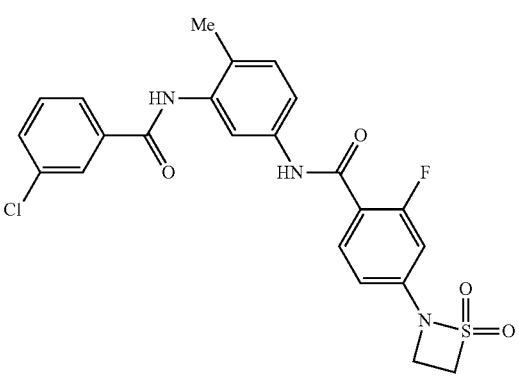

37
-continued
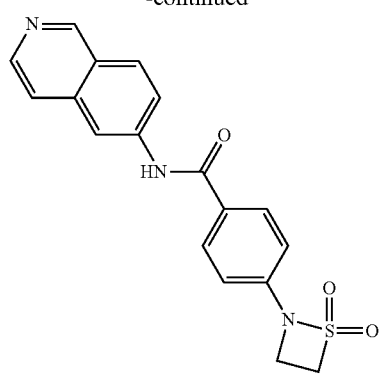
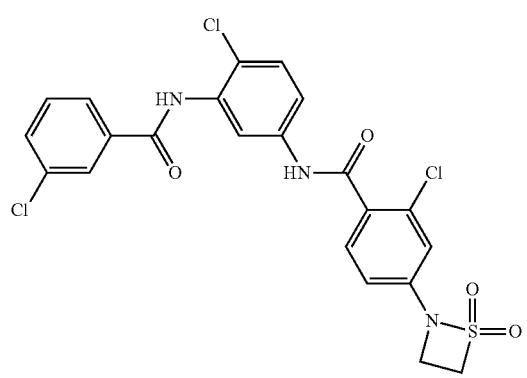
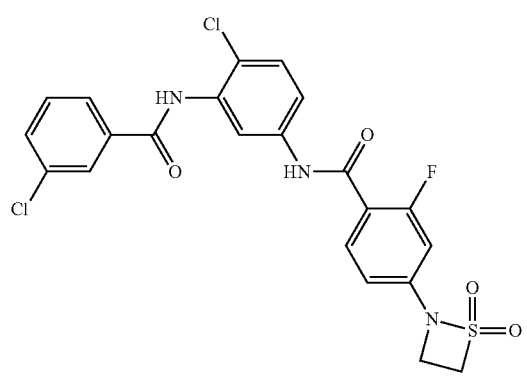
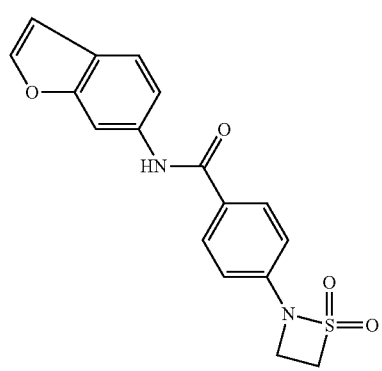
38
-continued
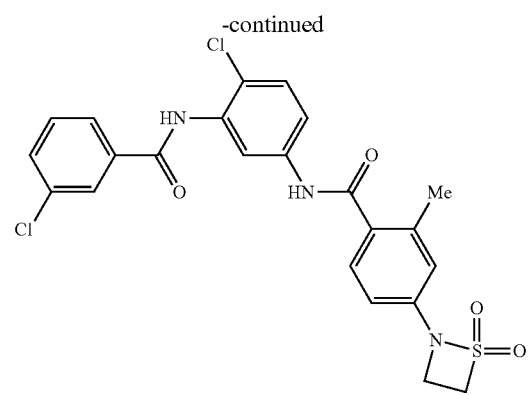
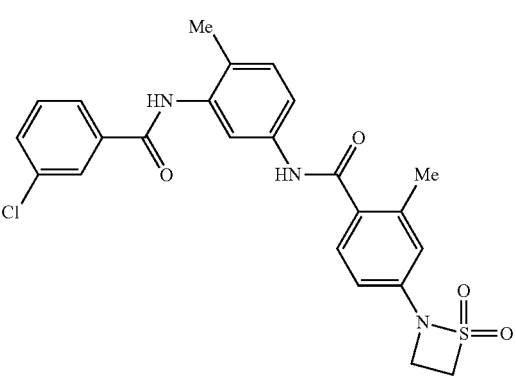
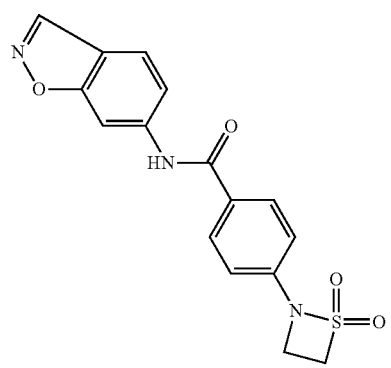
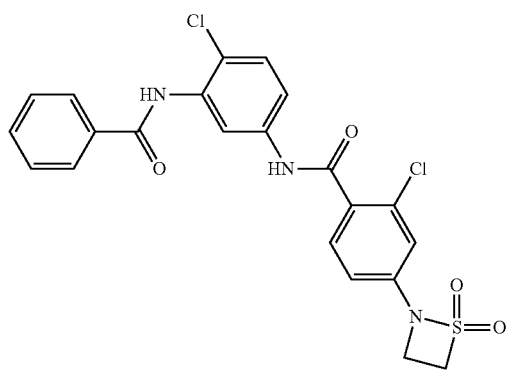

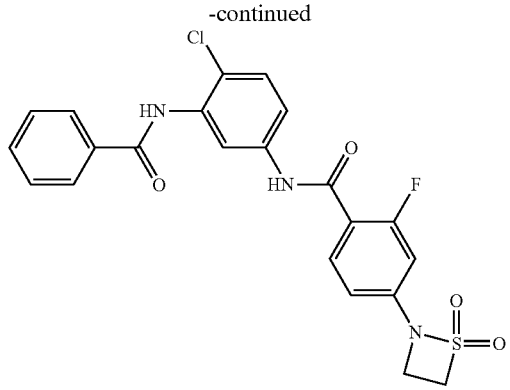
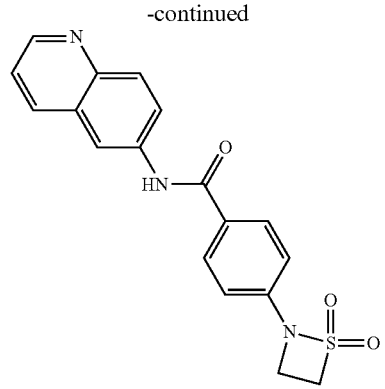
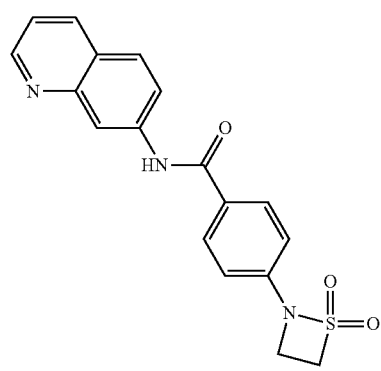
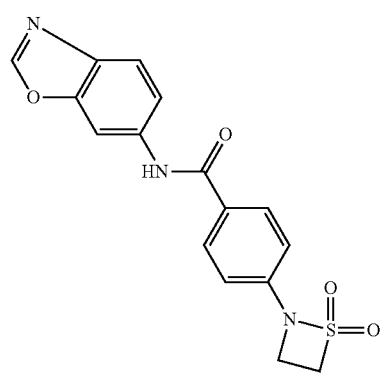
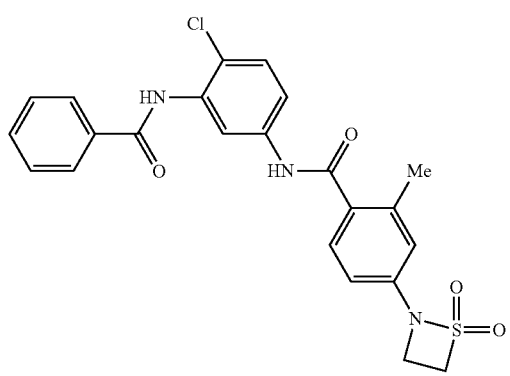
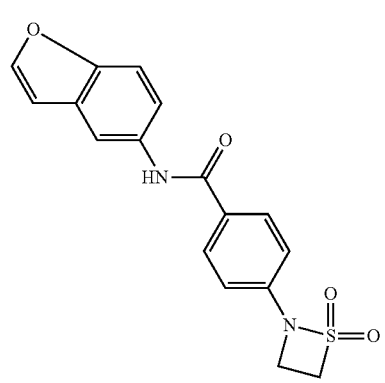
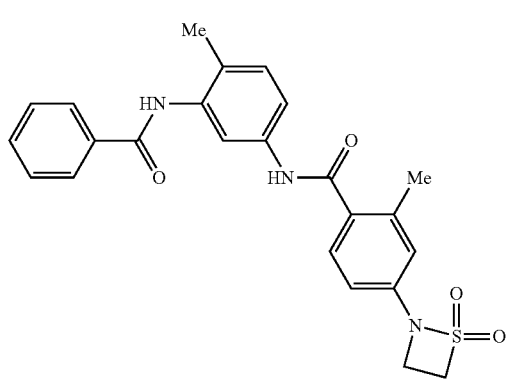
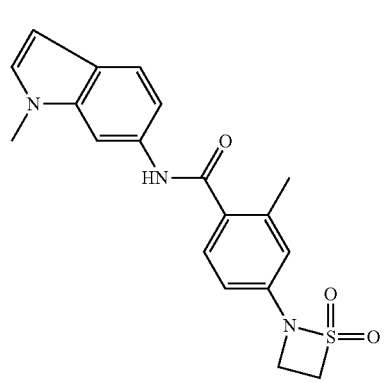

41
-continued
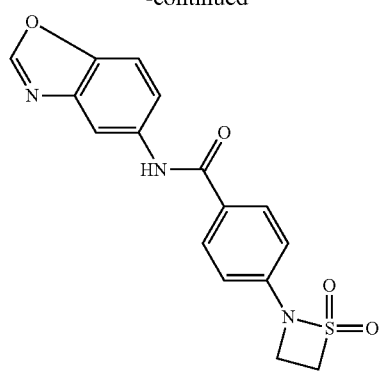
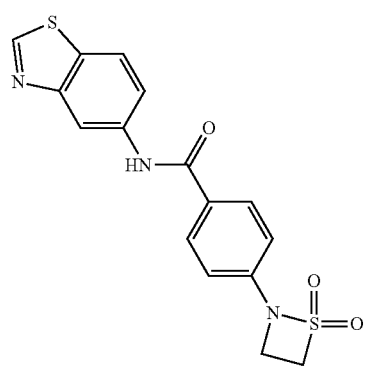
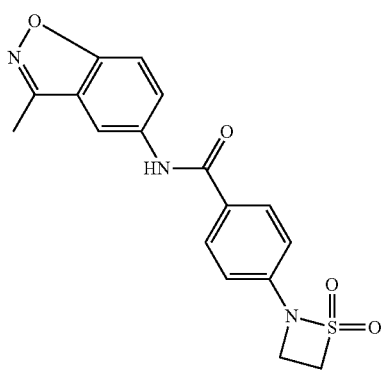
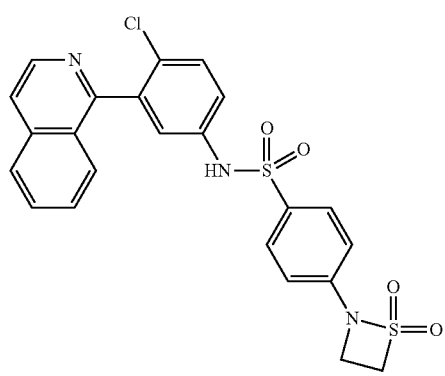
42
-continued
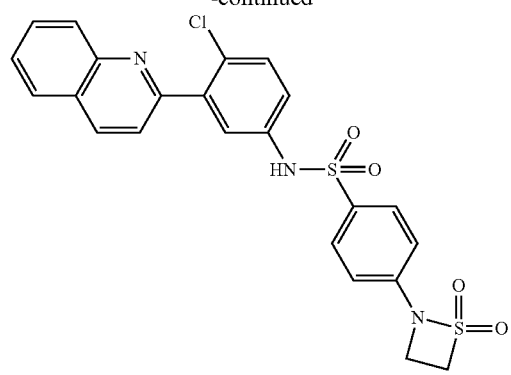
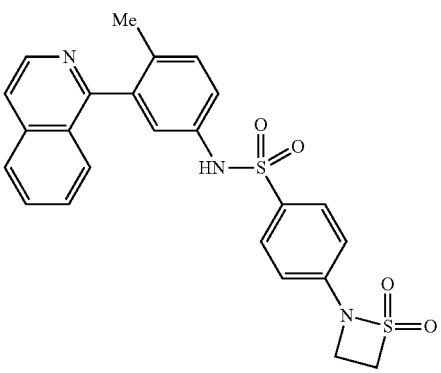
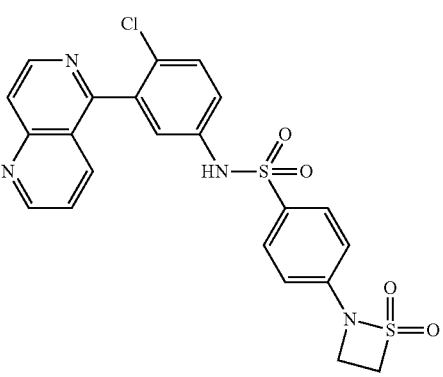
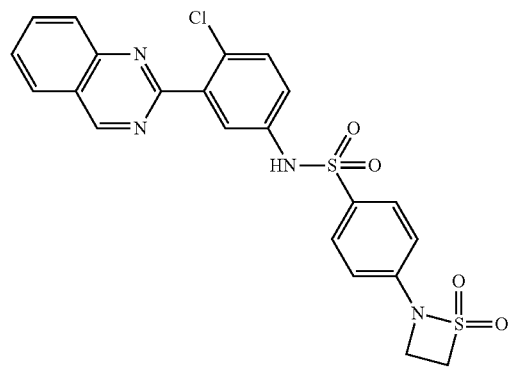

43
-continued
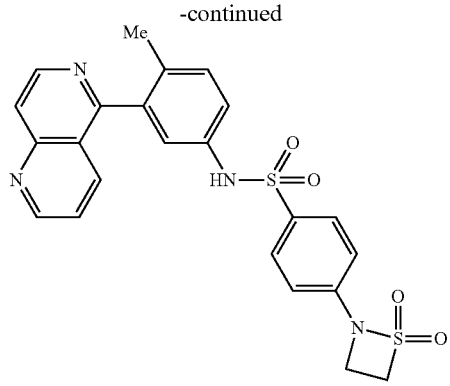
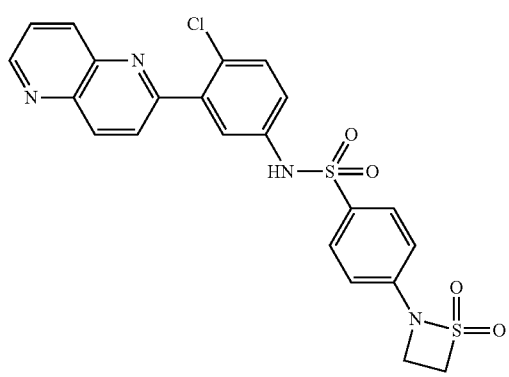
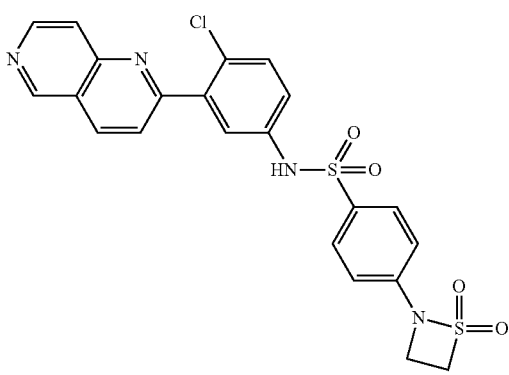
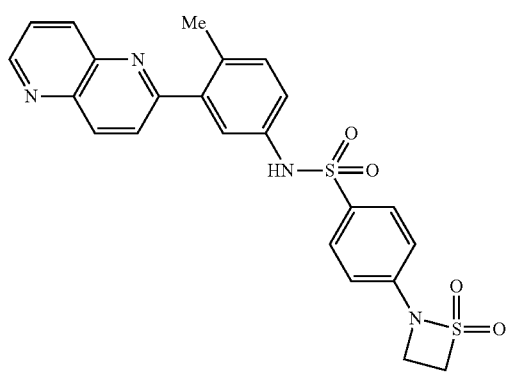
44
-continued
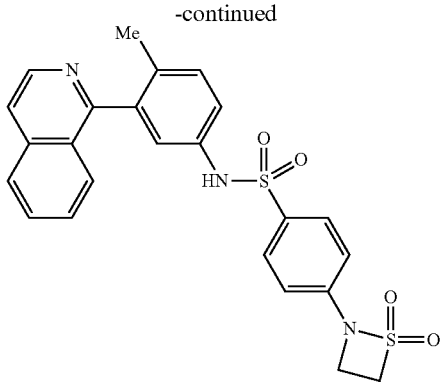
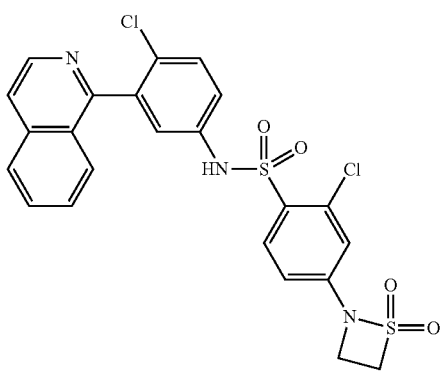
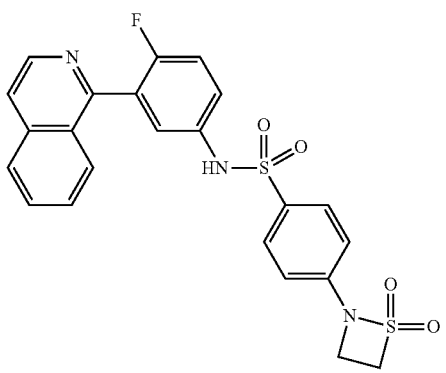
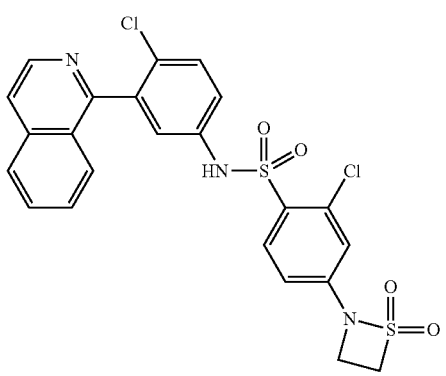

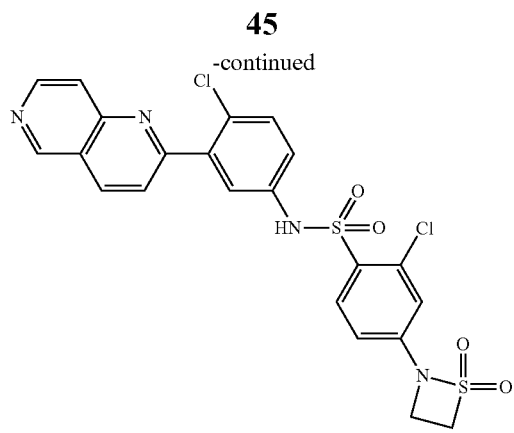
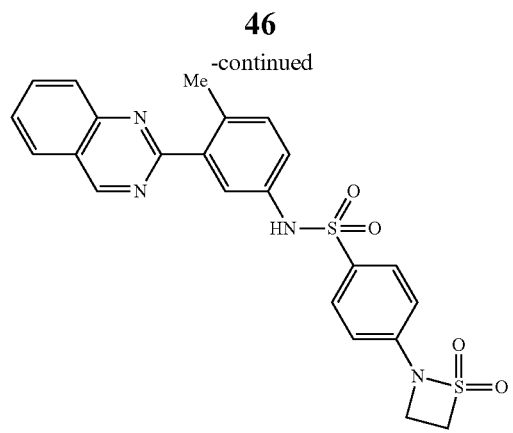
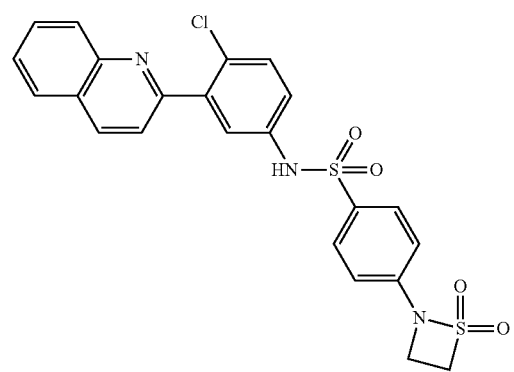
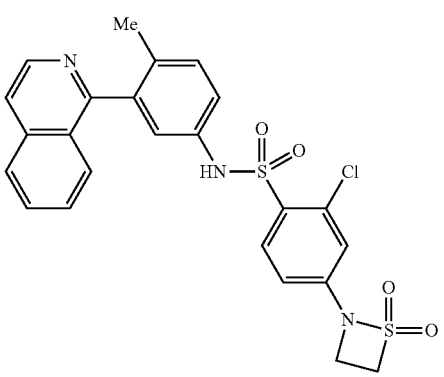
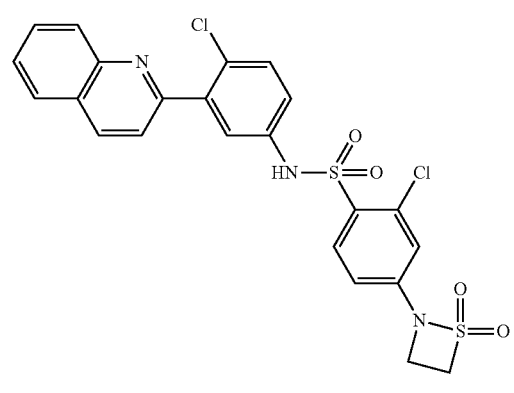
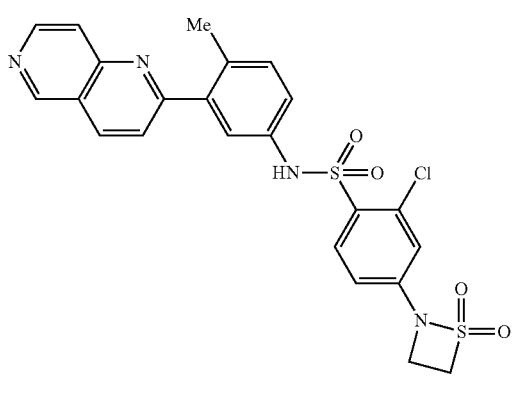
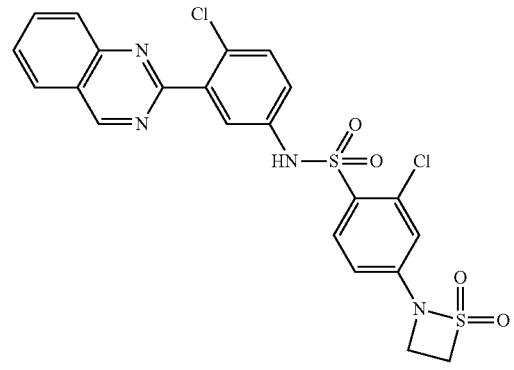
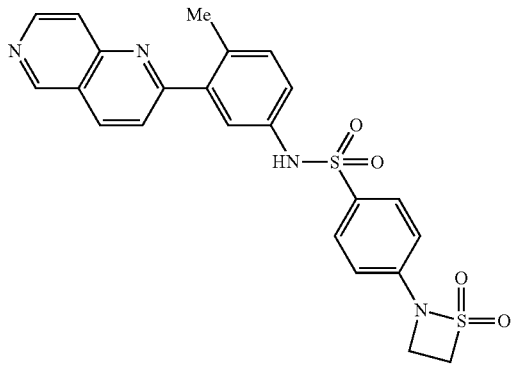

47
-continued
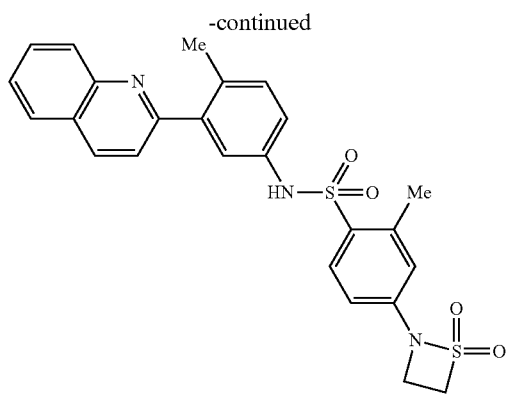
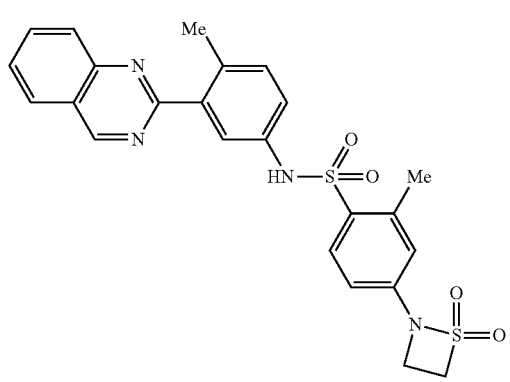
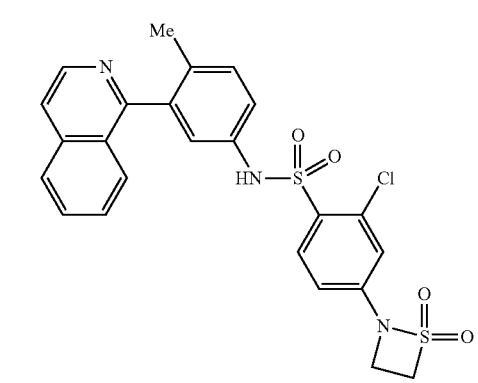
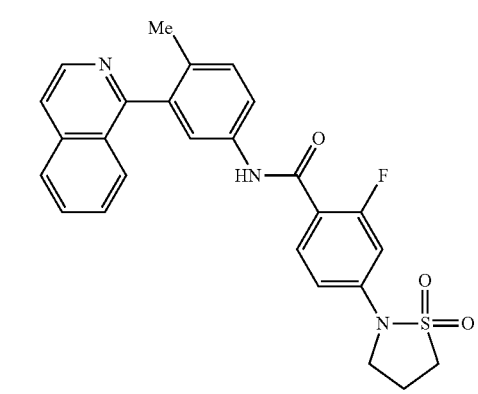
48
-continued
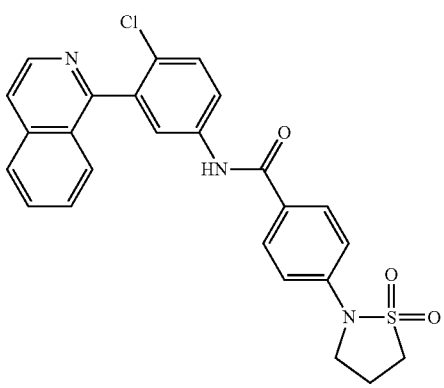
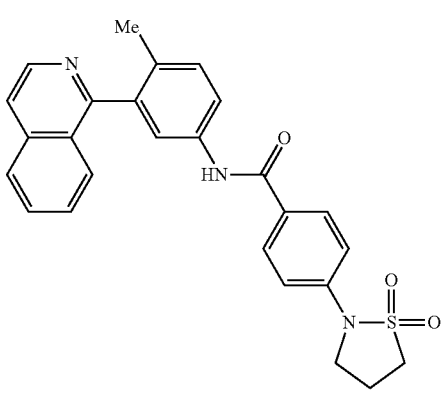
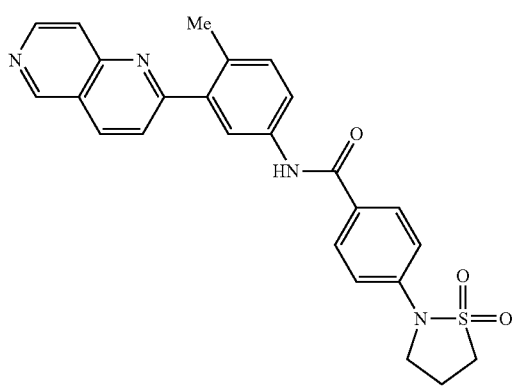

49
-continued
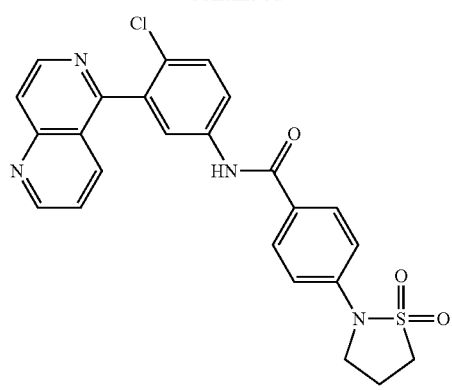
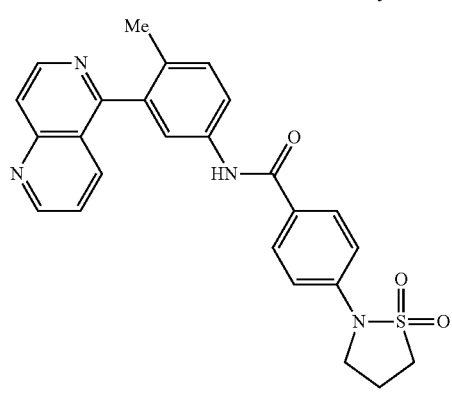
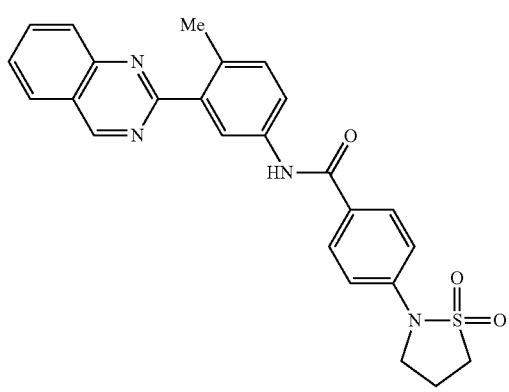
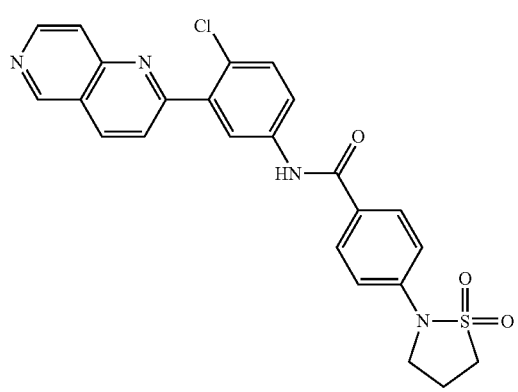
50
-continued
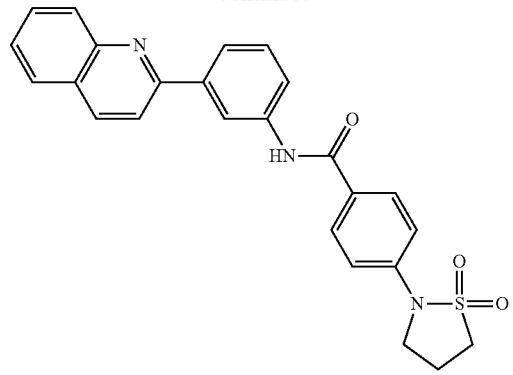
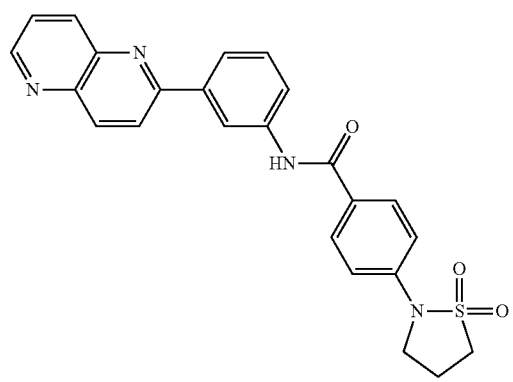
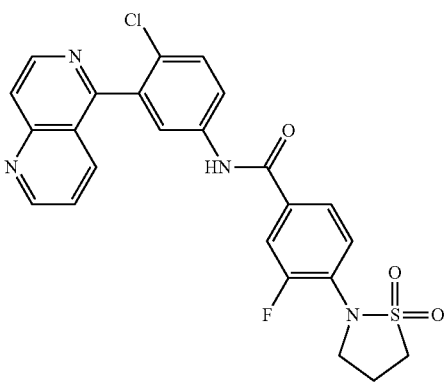
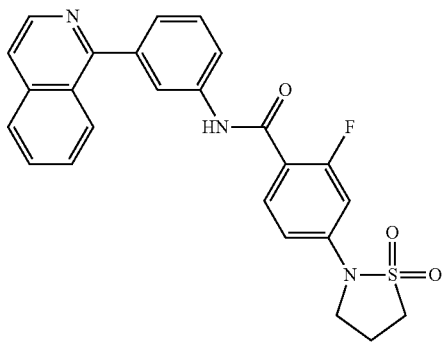

51
-continued
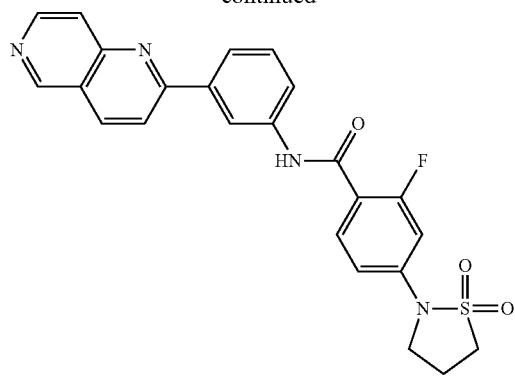
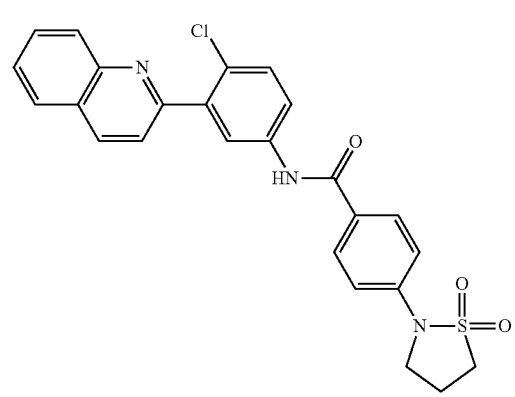
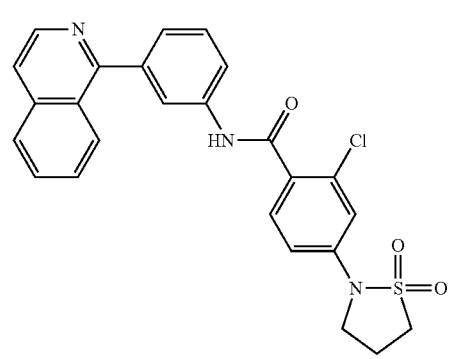
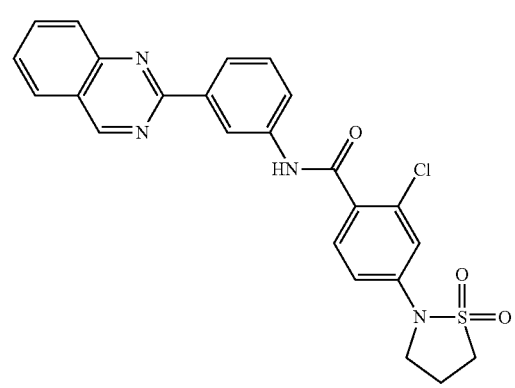
52
-continued
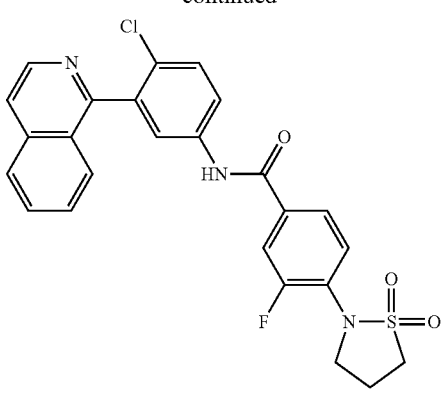
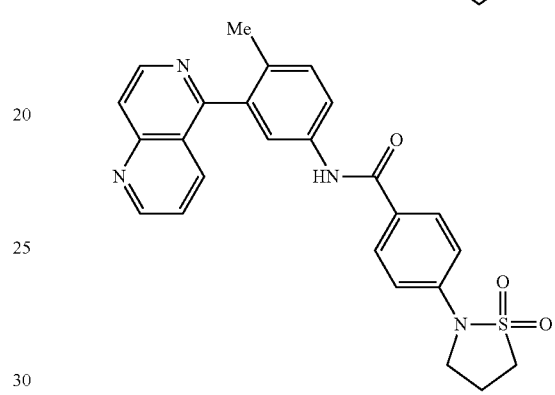
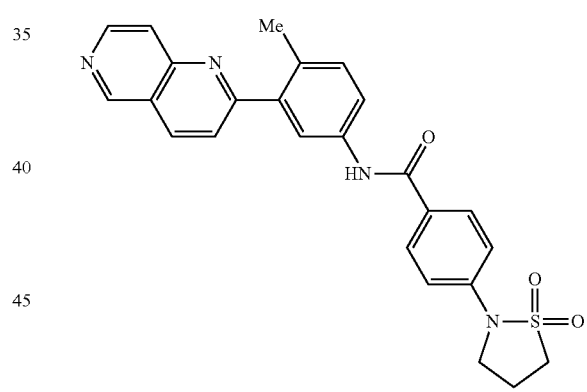
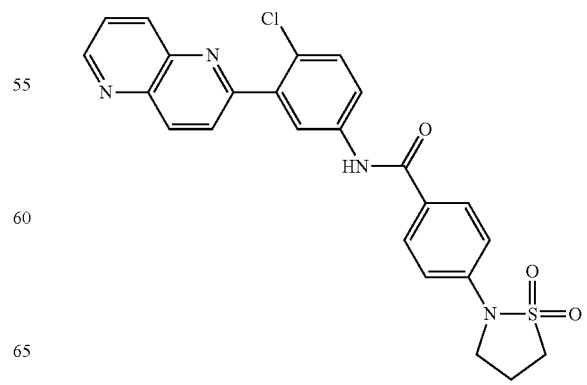

53
-continued
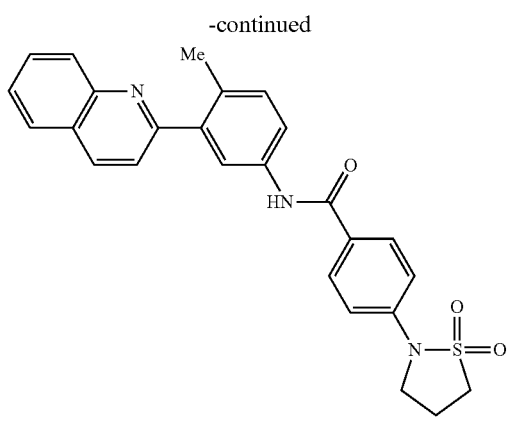
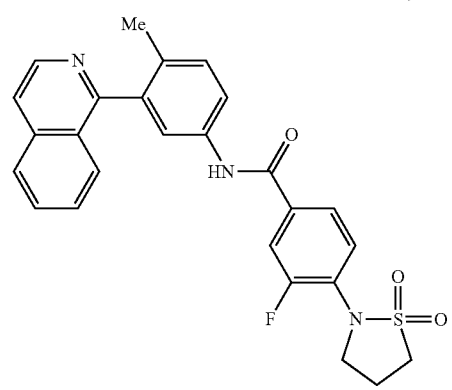
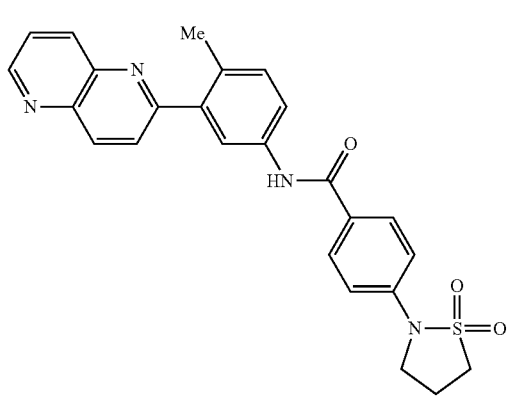
54
-continued
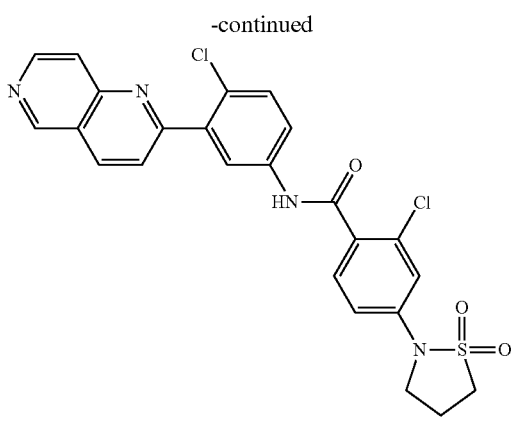
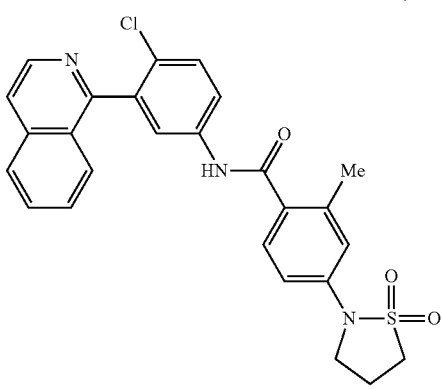
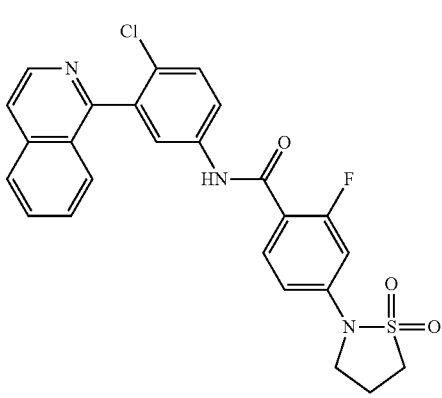
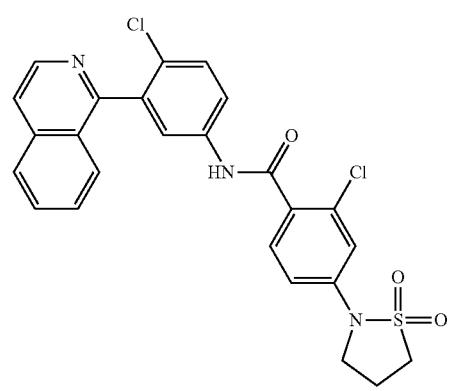
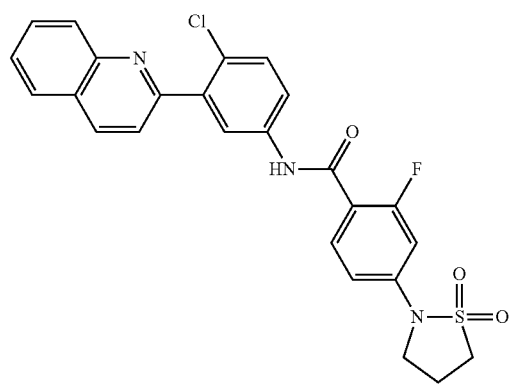

55
-continued
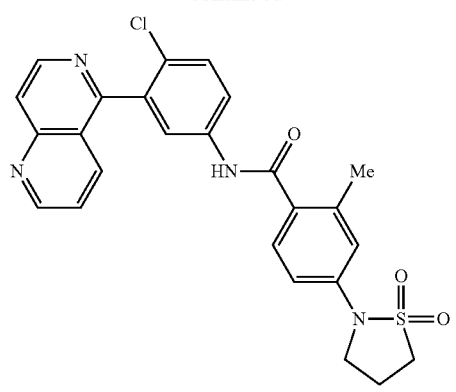
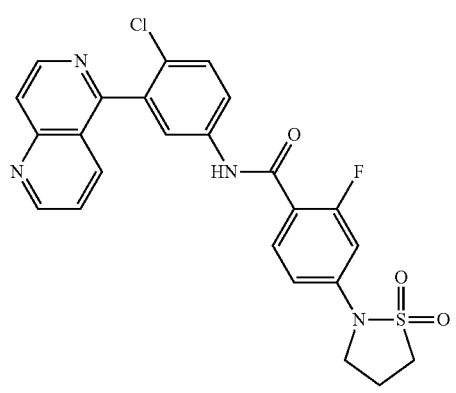
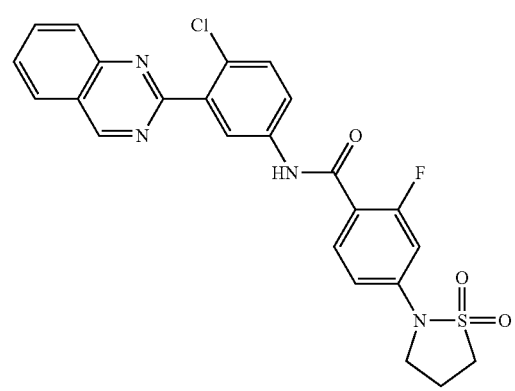
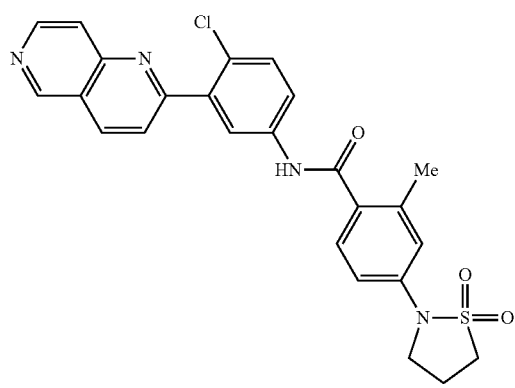
56
-continued
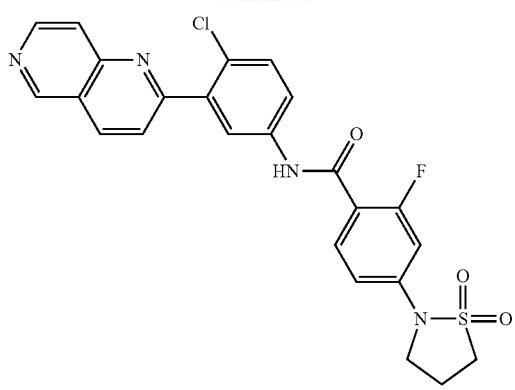
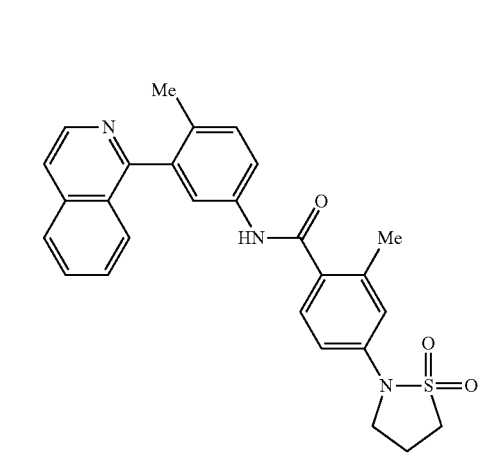
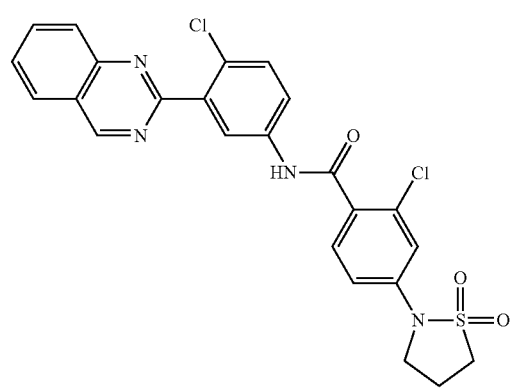

57
-continued
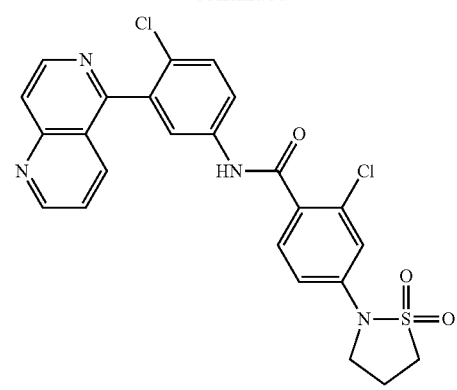
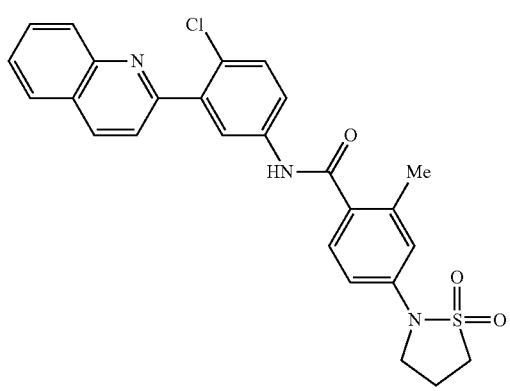
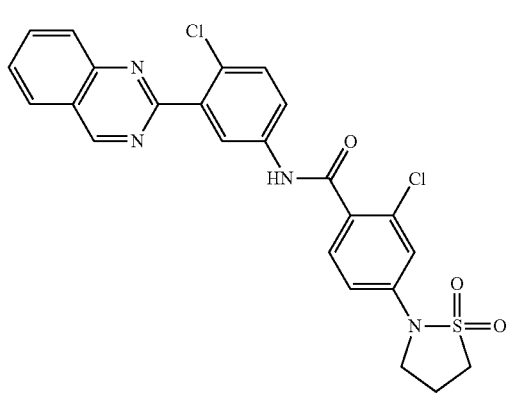
58
-continued
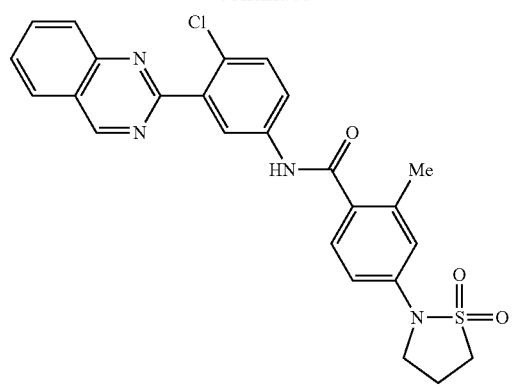
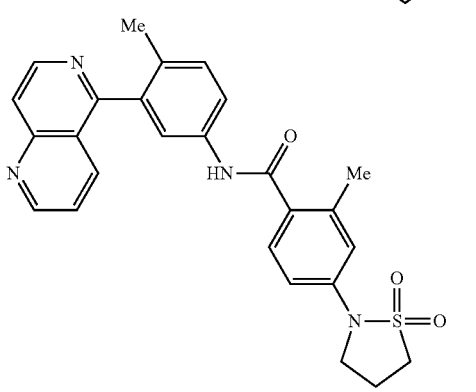
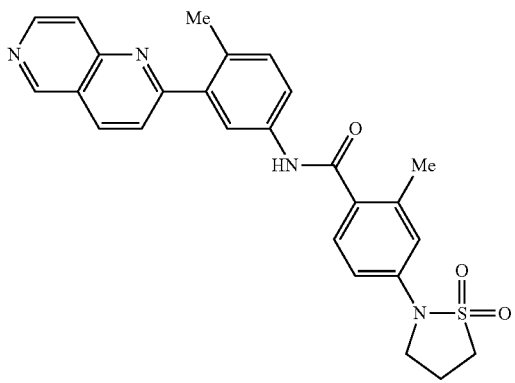
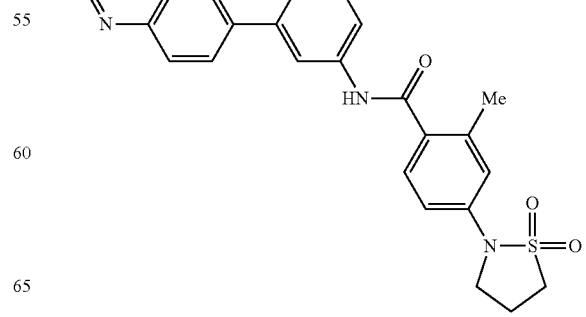

59
-continued
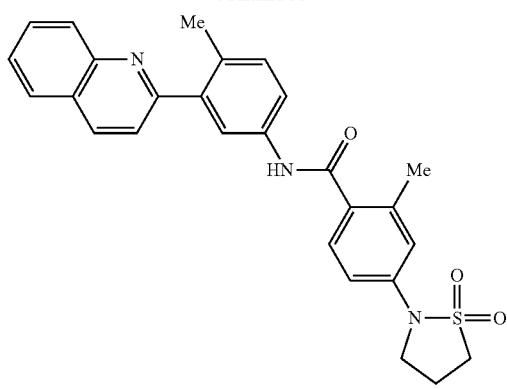
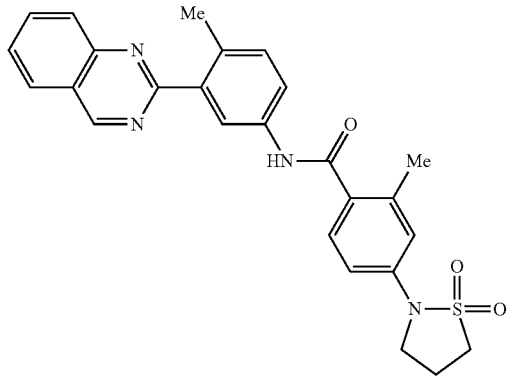
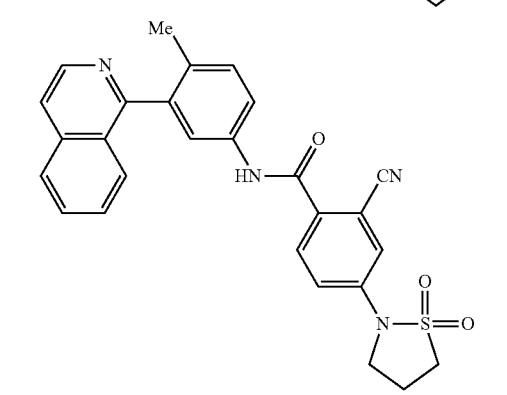
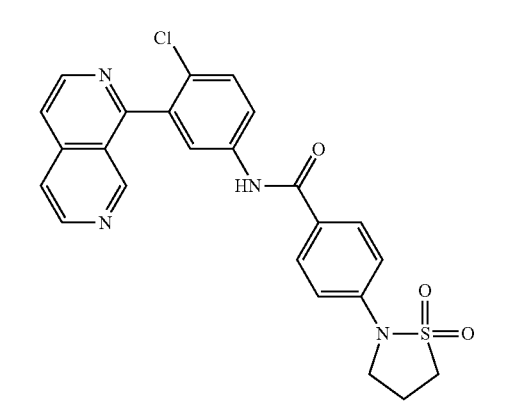
60
-continued
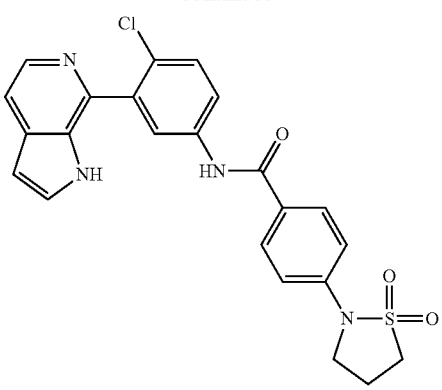
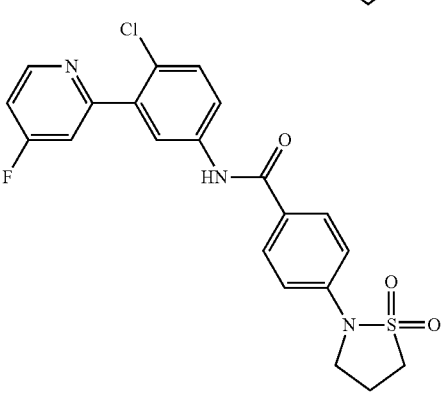
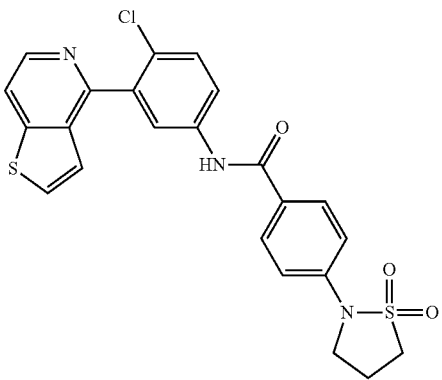
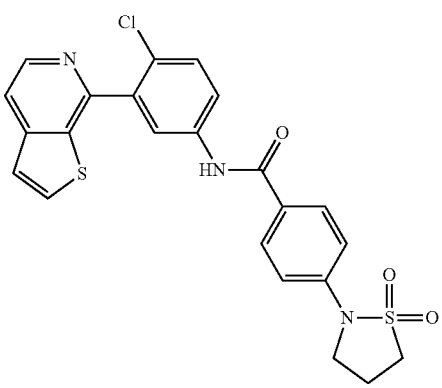

61
-continued
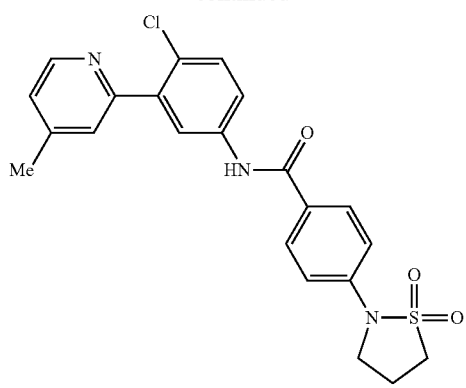
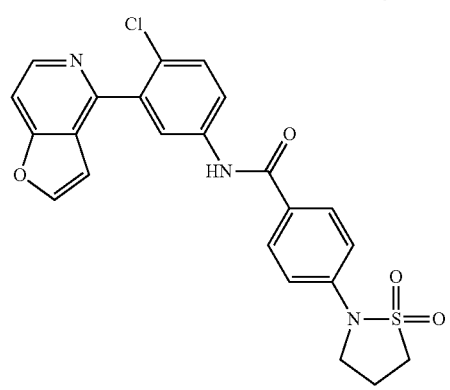
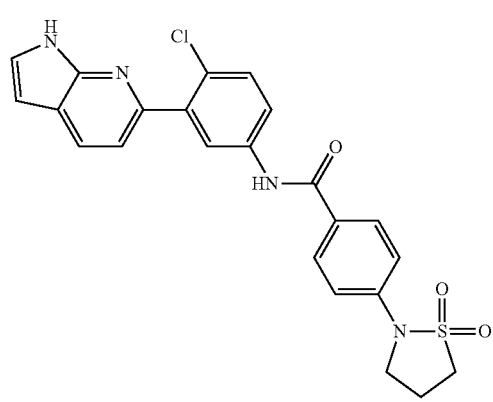
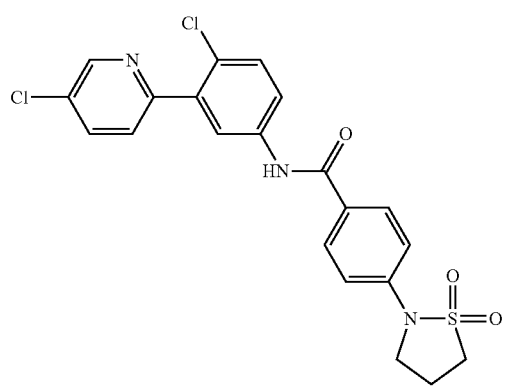
62
-continued
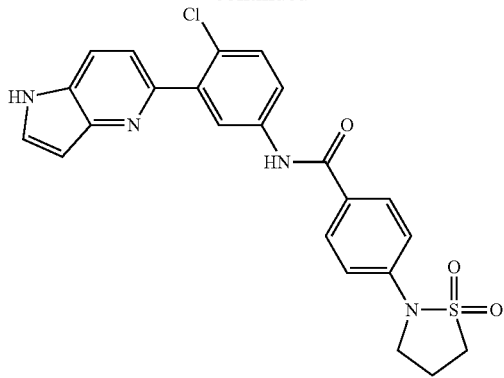
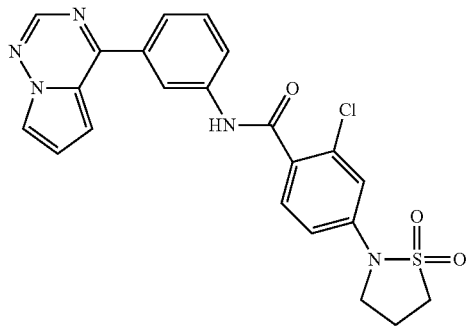
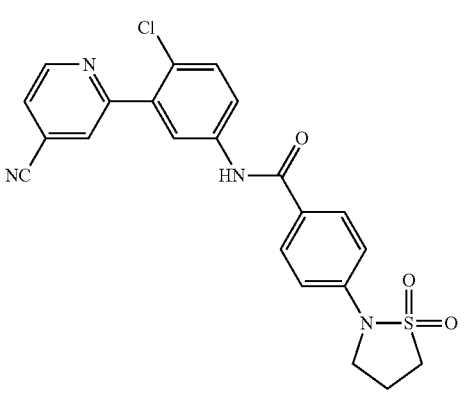
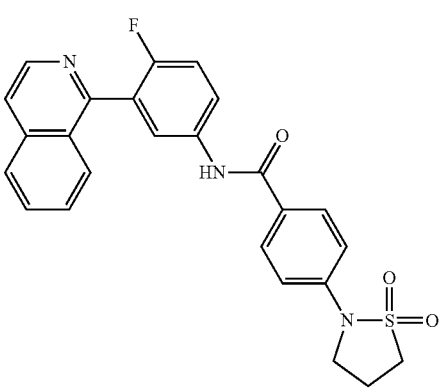

63
-continued
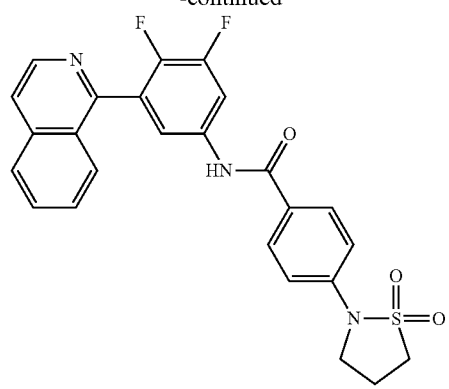
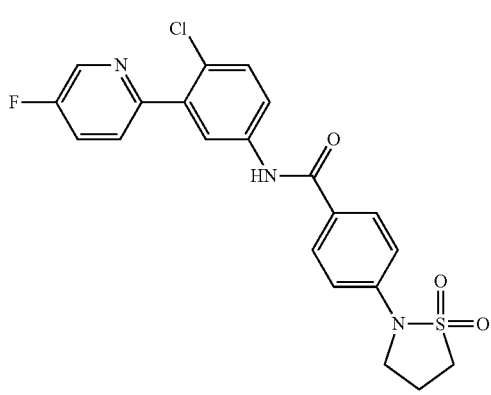
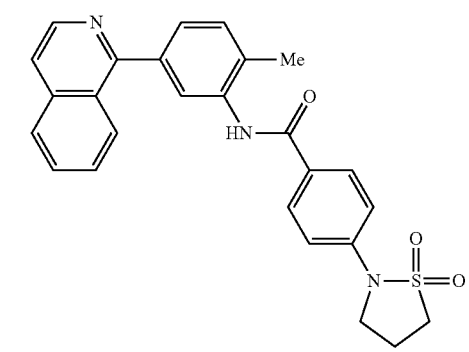
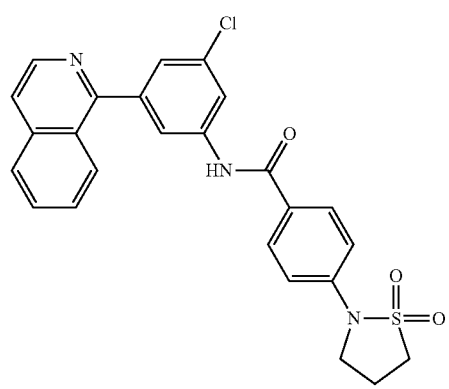
64
-continued
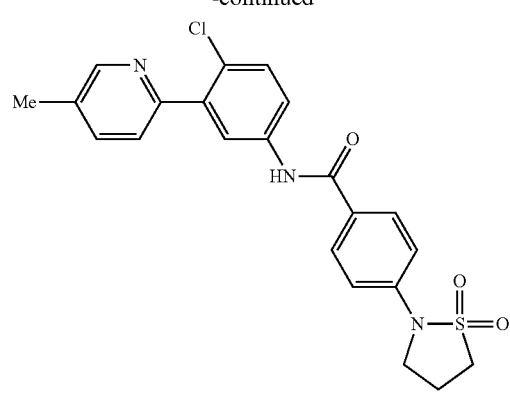
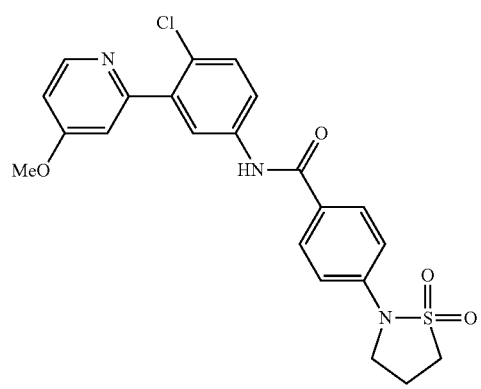
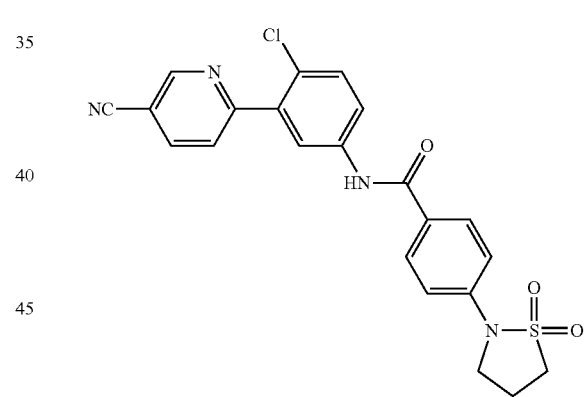

-continued
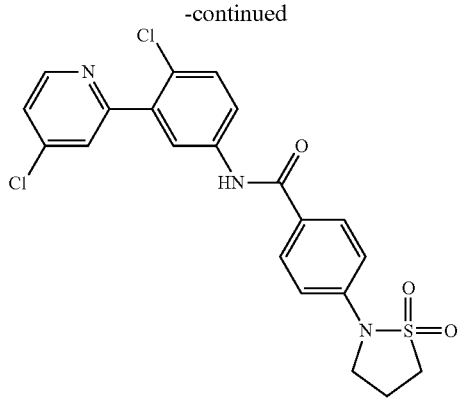
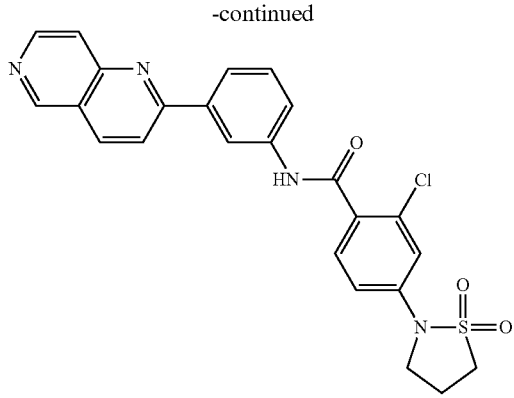
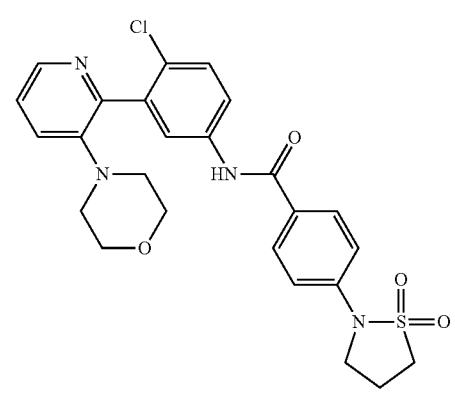
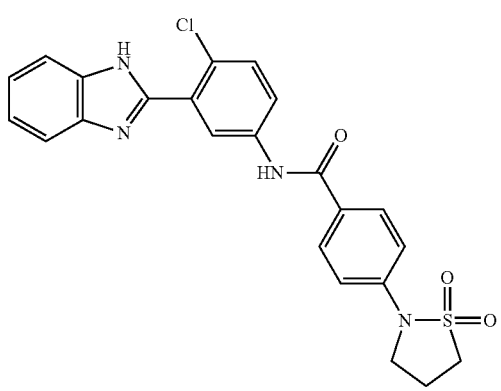
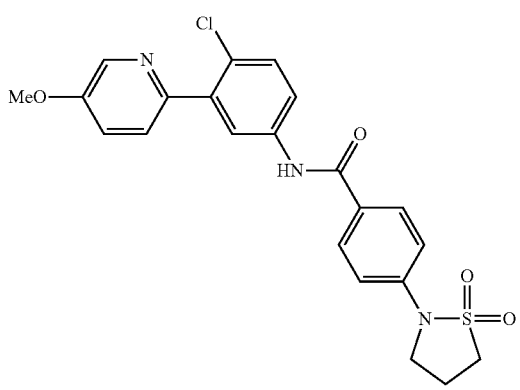
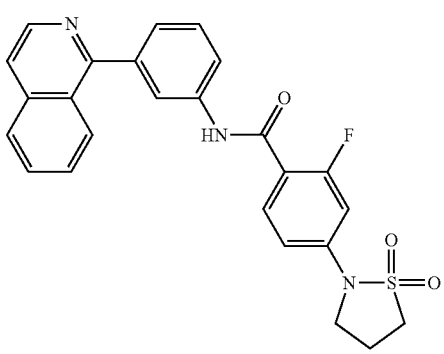
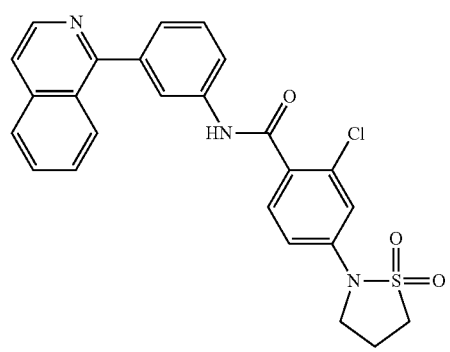
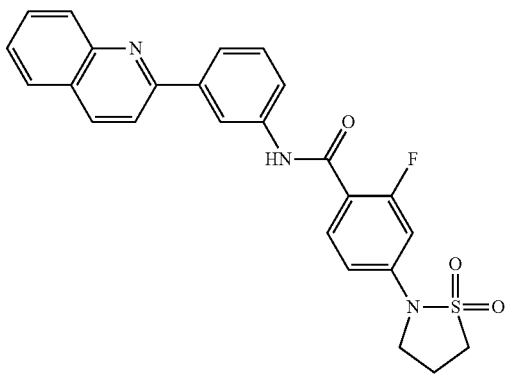

67
-continued
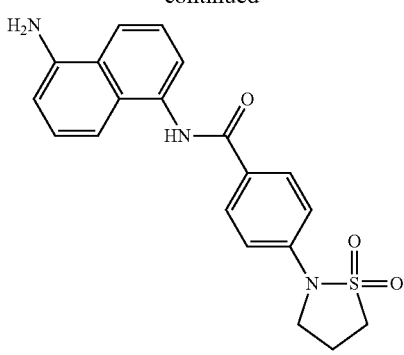
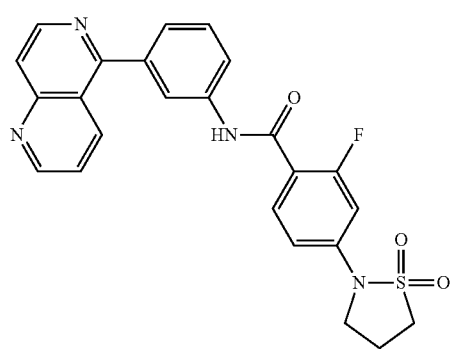
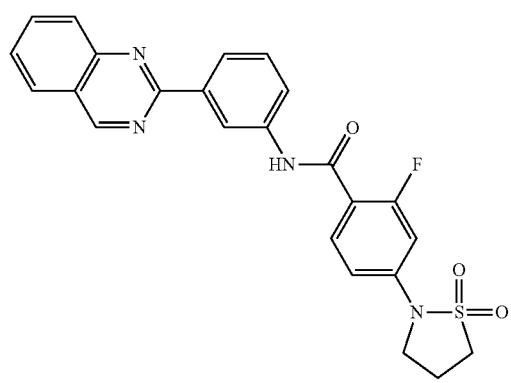
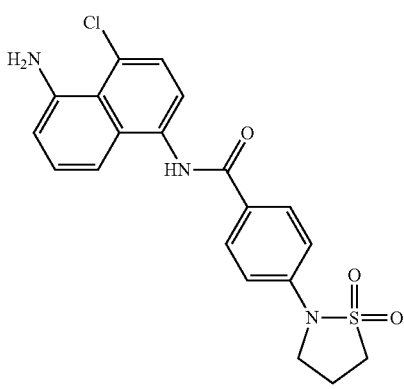
68
-continued
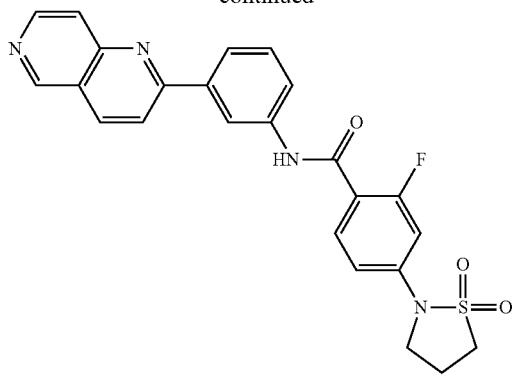
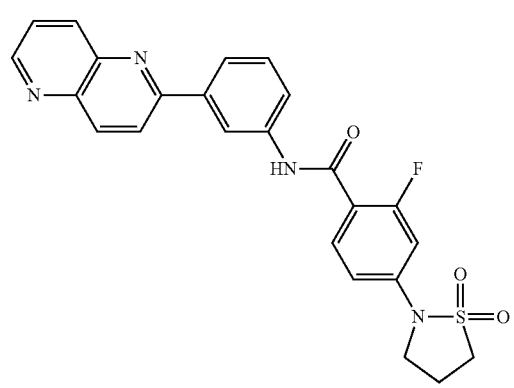
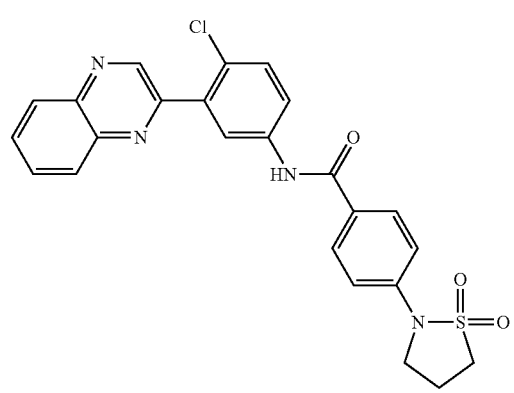
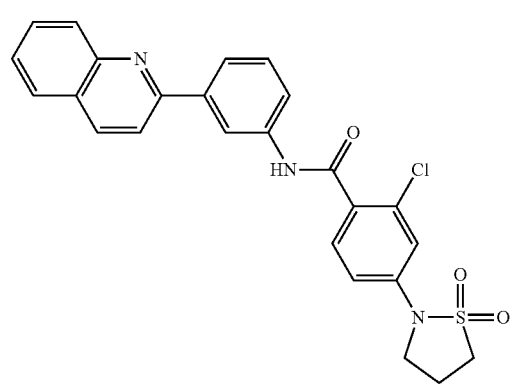

69
-continued
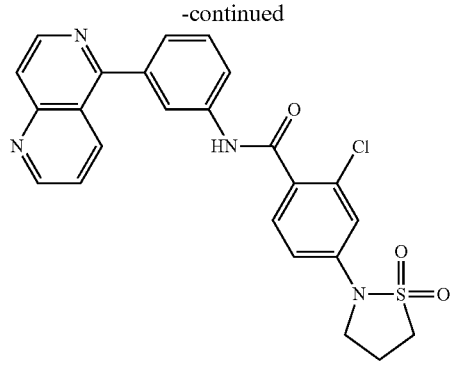
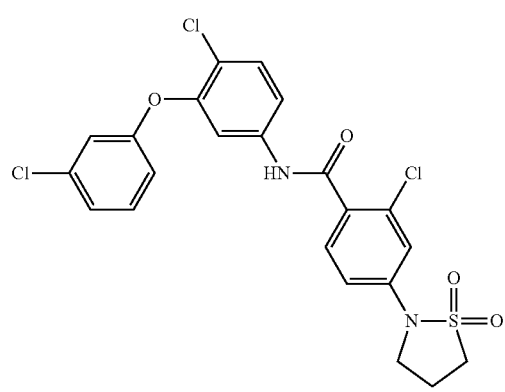
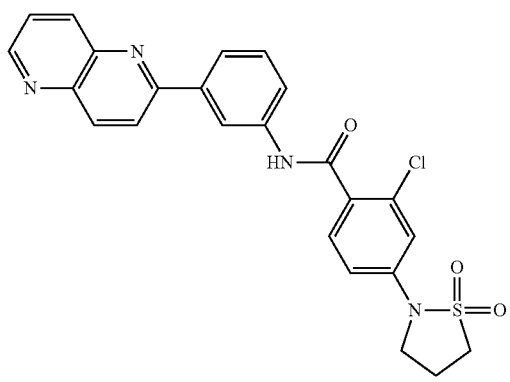
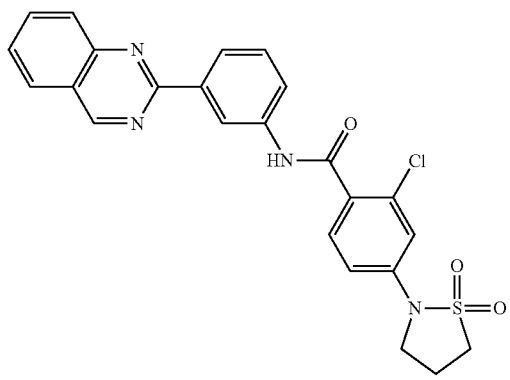
70
-continued
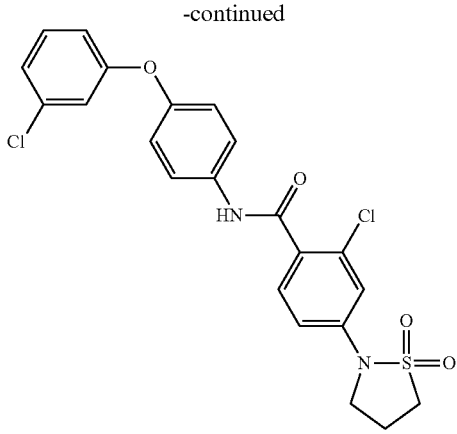
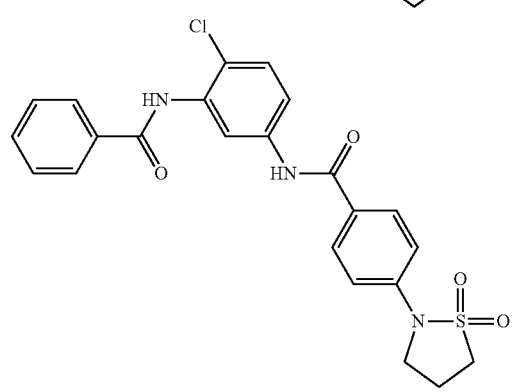
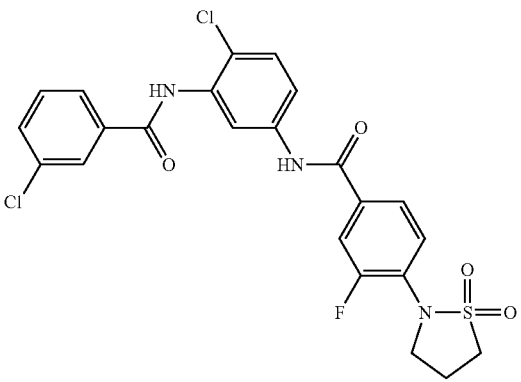
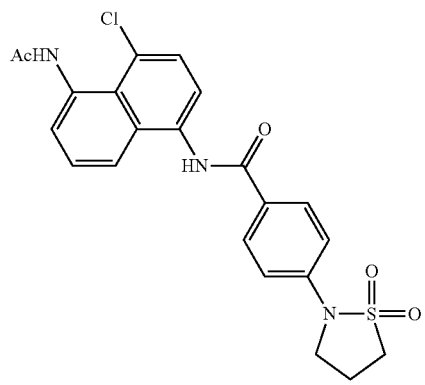

71
-continued
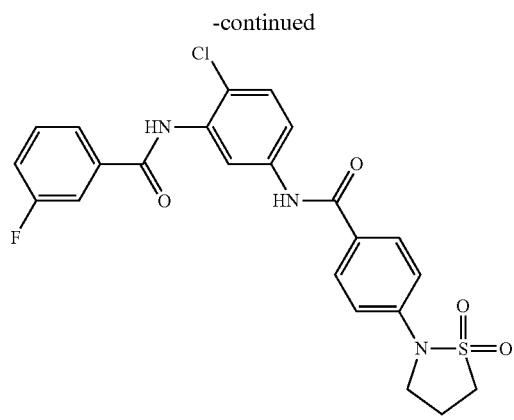
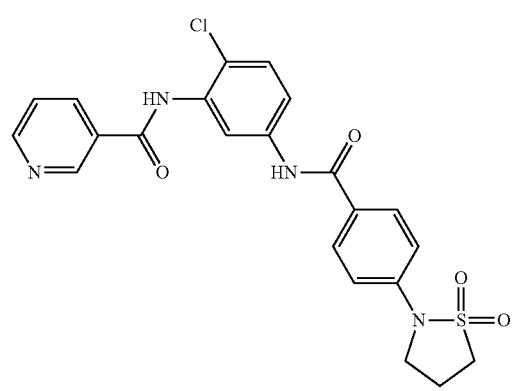
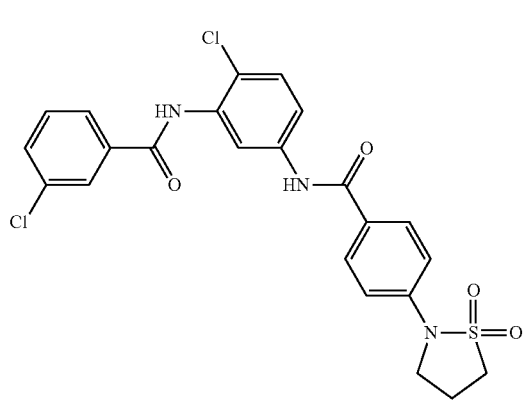
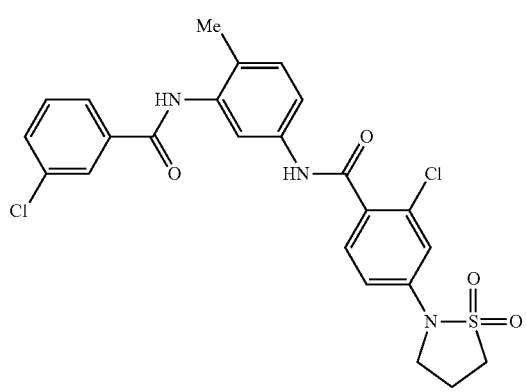
72
-continued
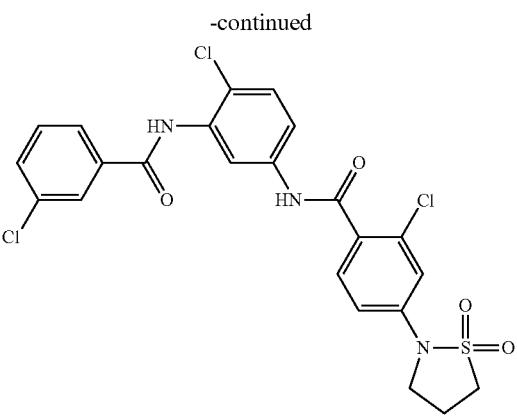
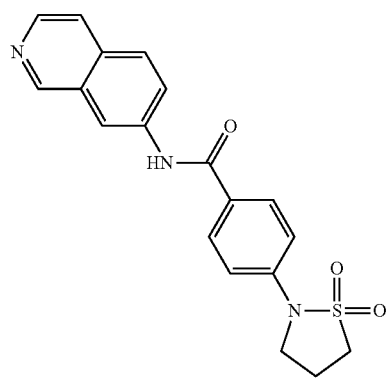
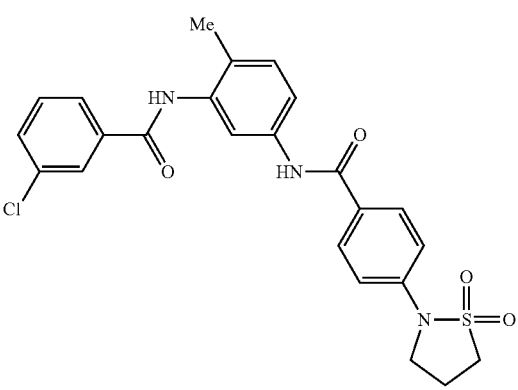
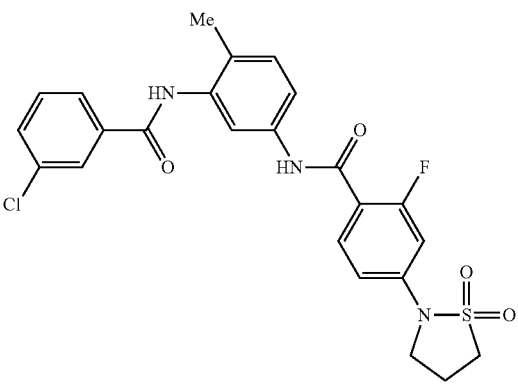

73
-continued
74
-continued
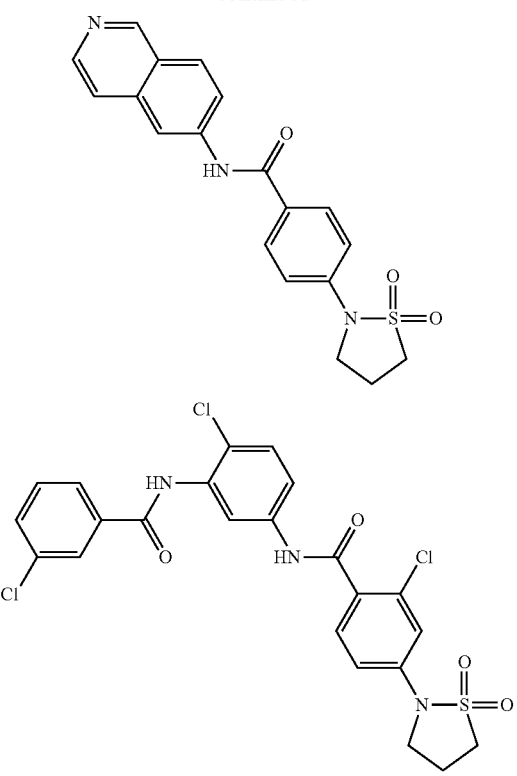
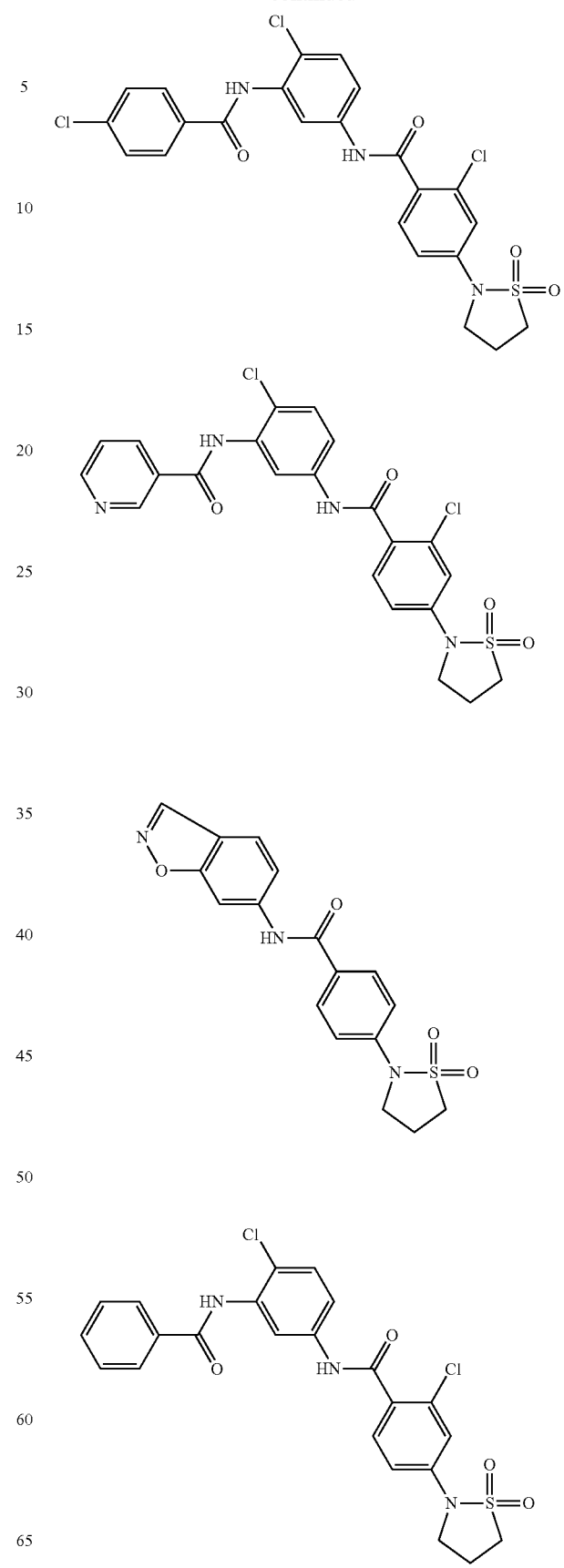

-continued
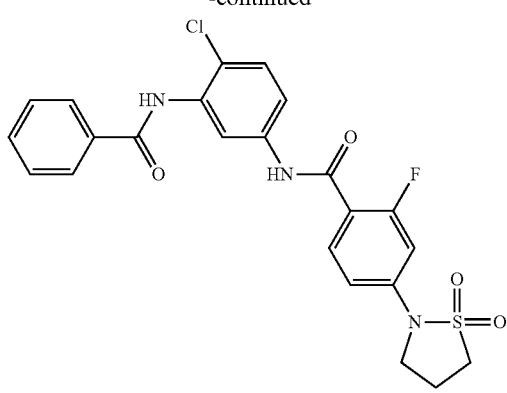
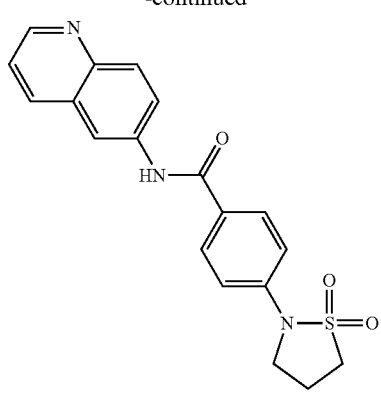
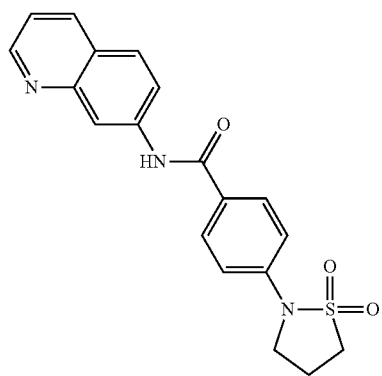
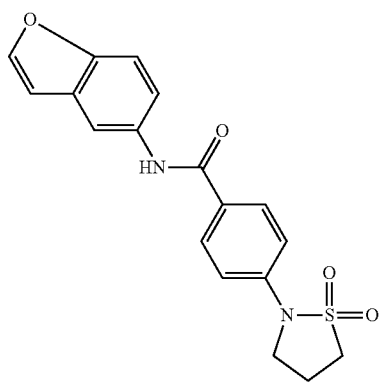
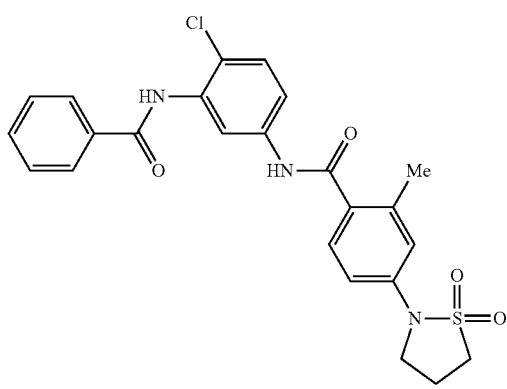
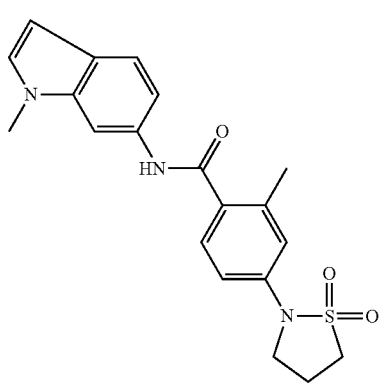
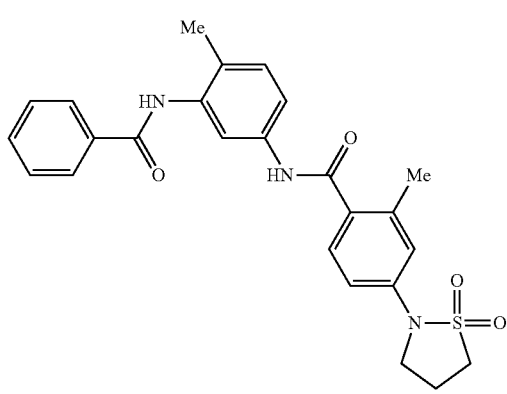
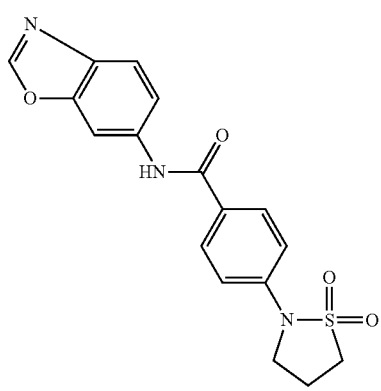

77
-continued
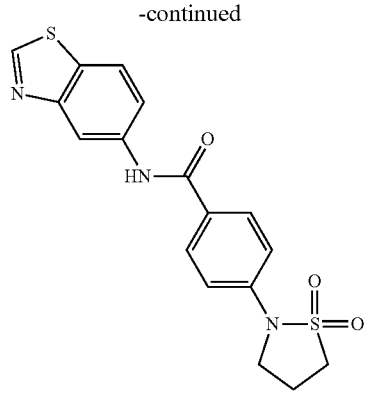
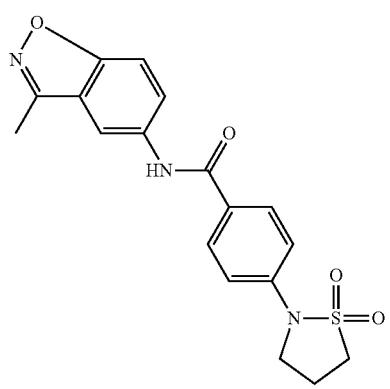
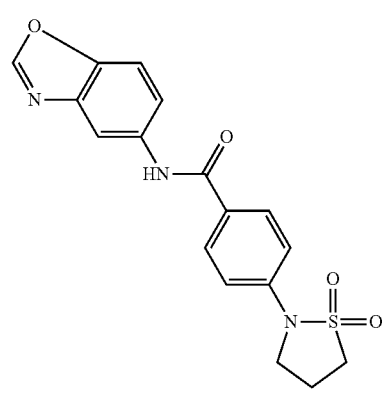
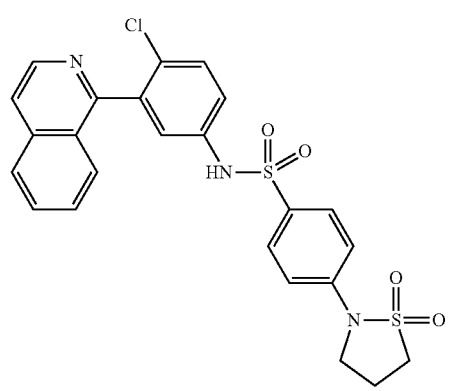
78
-continued
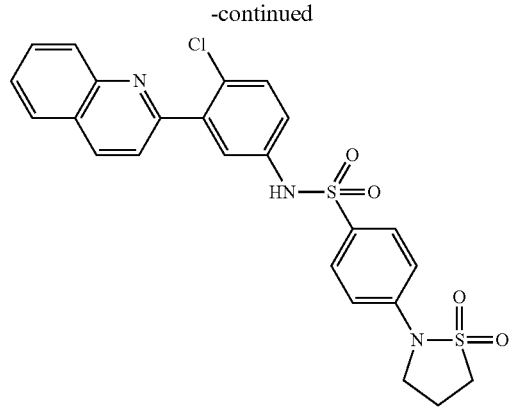
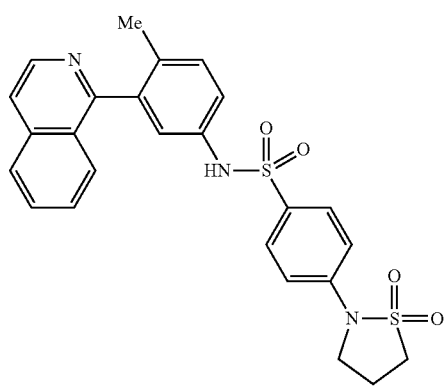
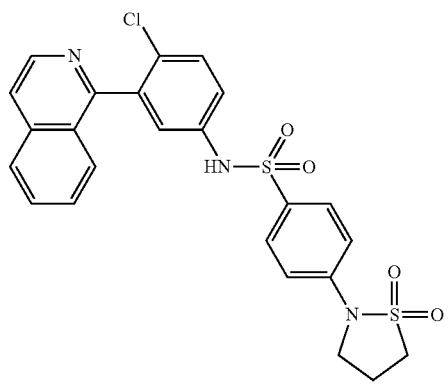
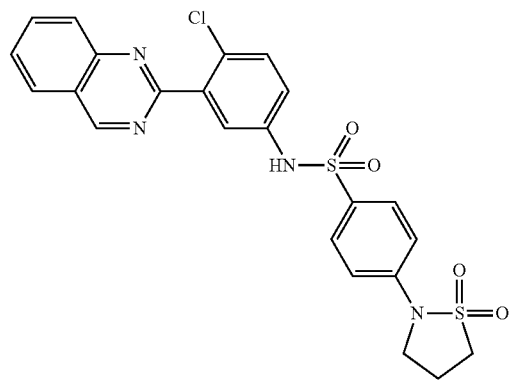

79
-continued
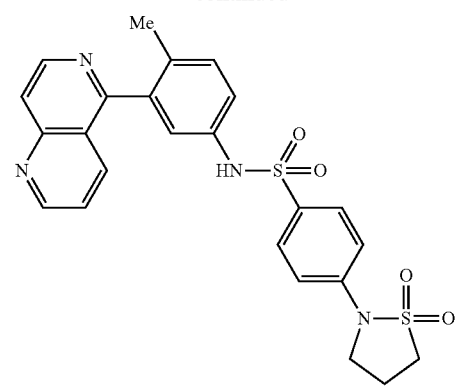
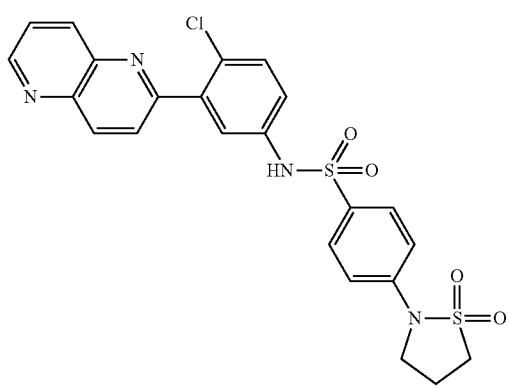
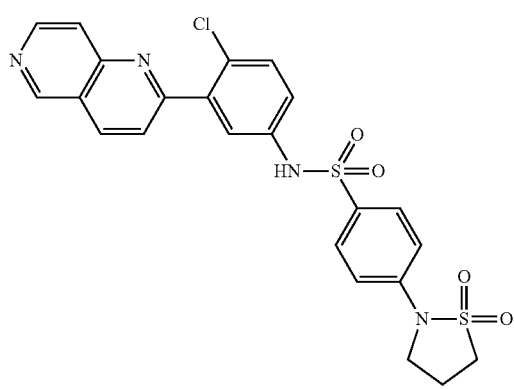
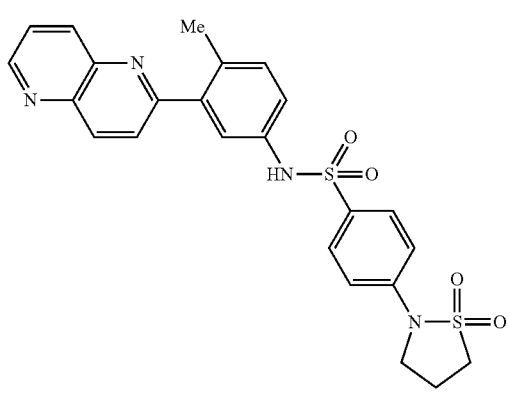
80
-continued
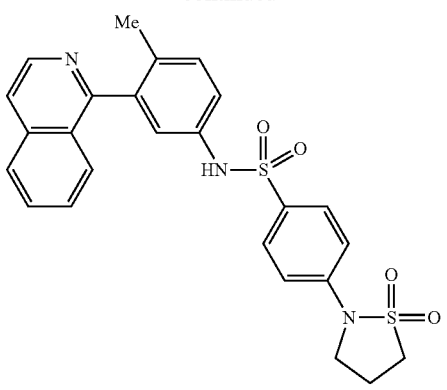
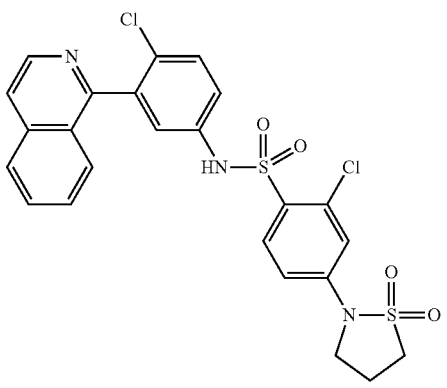
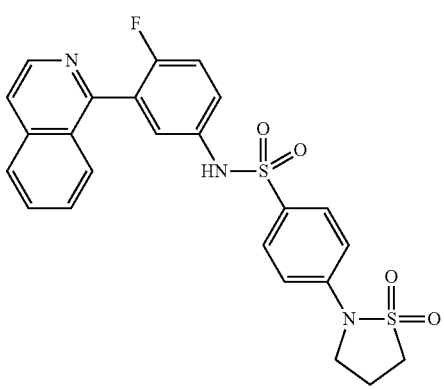
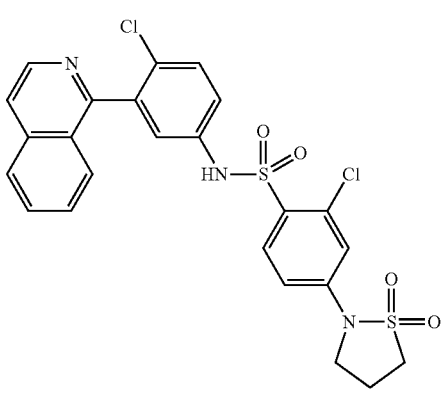

81
-continued
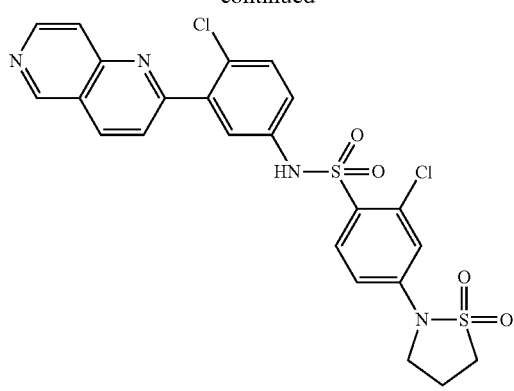
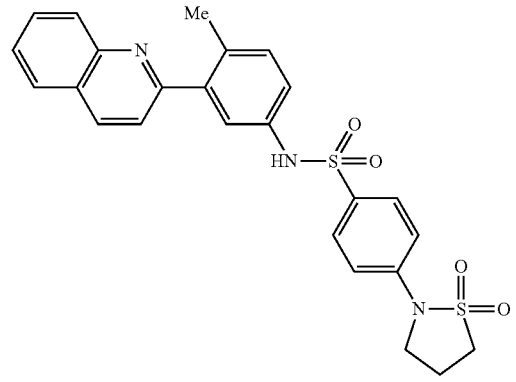
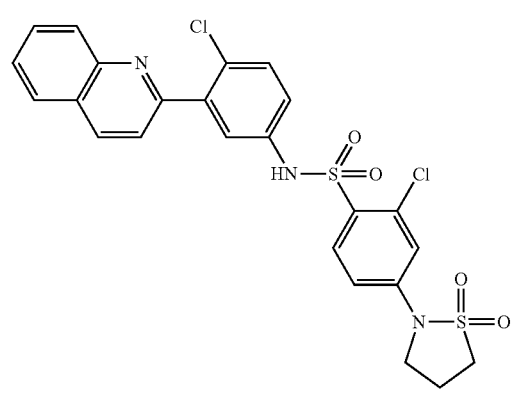
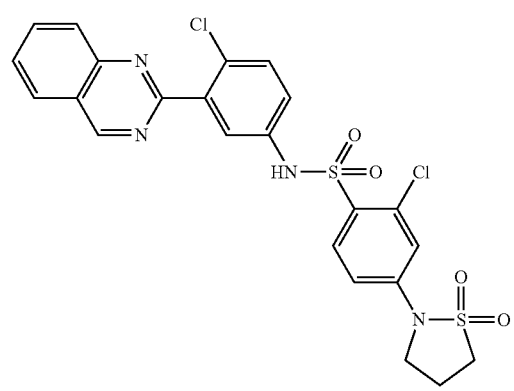
82
-continued
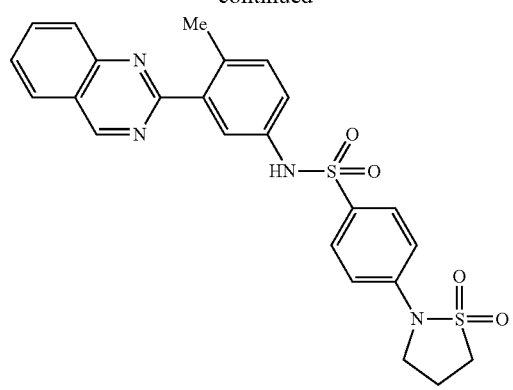
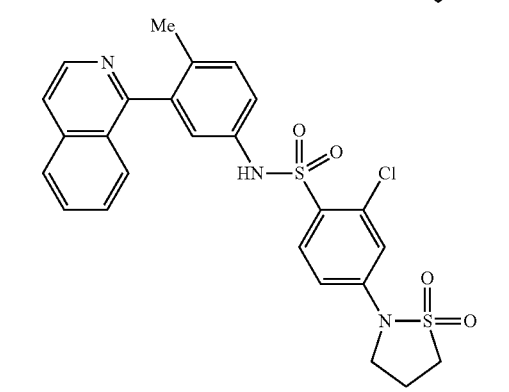
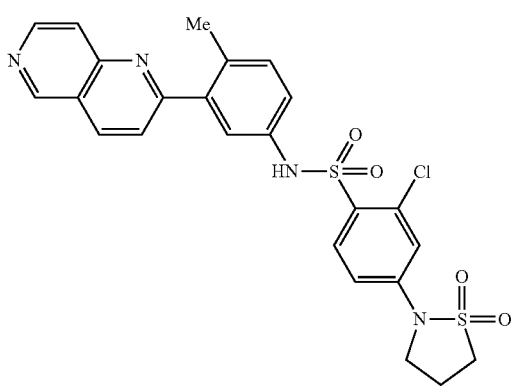
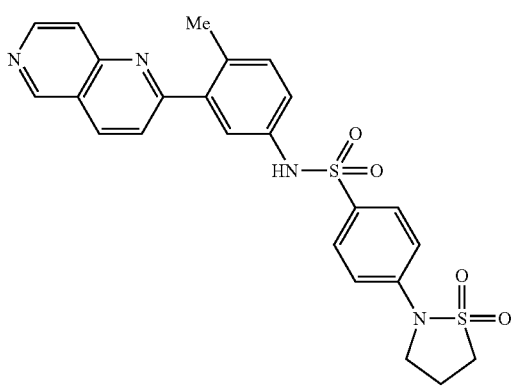

83
-continued
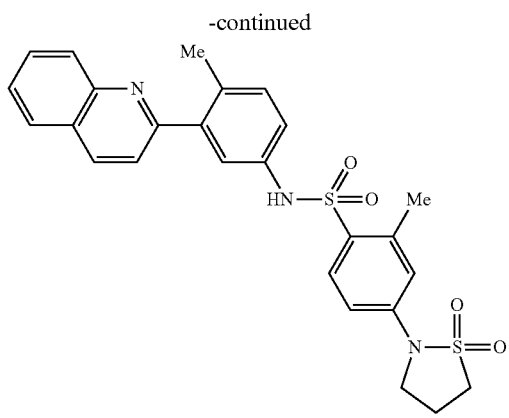
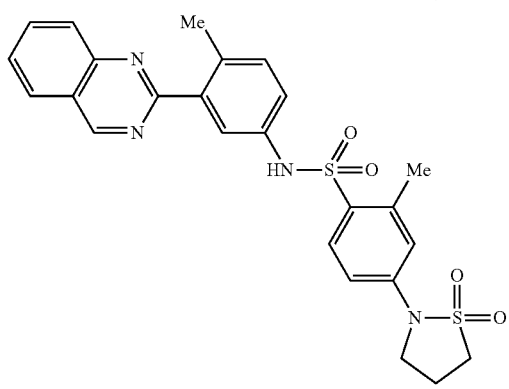
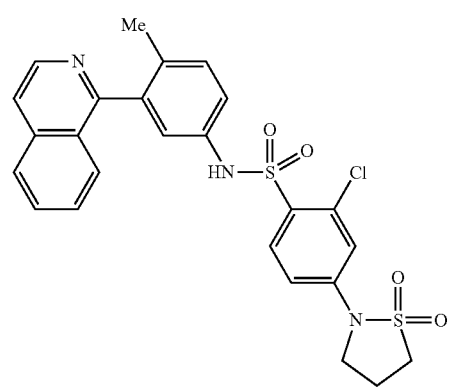
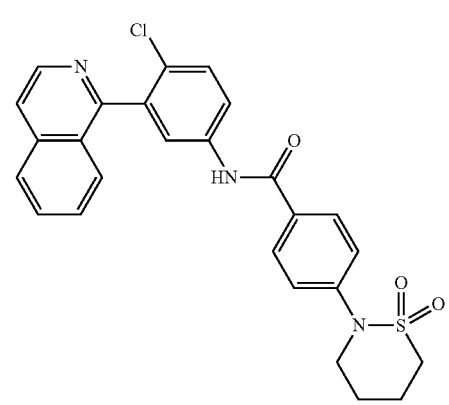
84
-continued
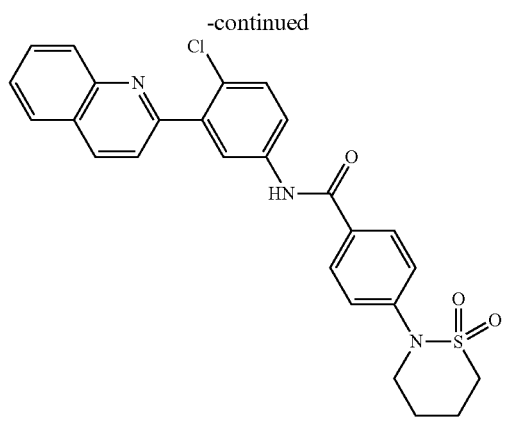
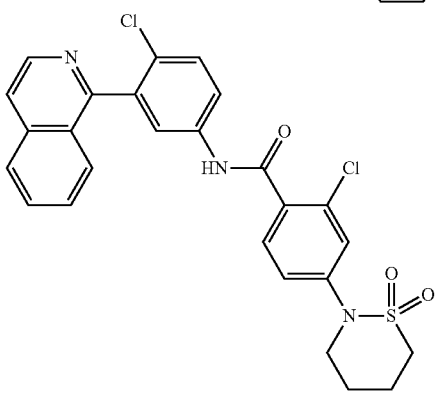
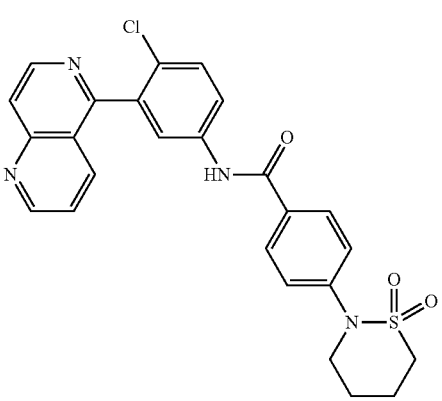
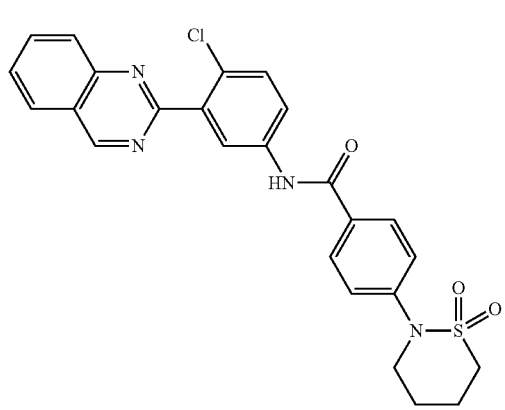

85
-continued
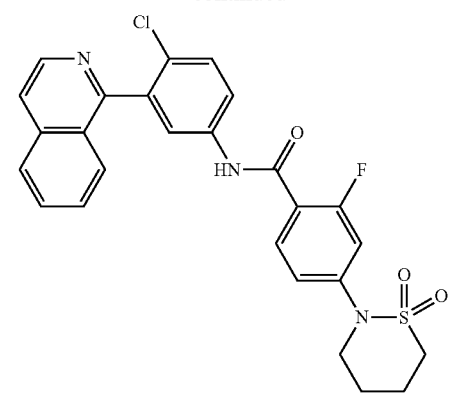
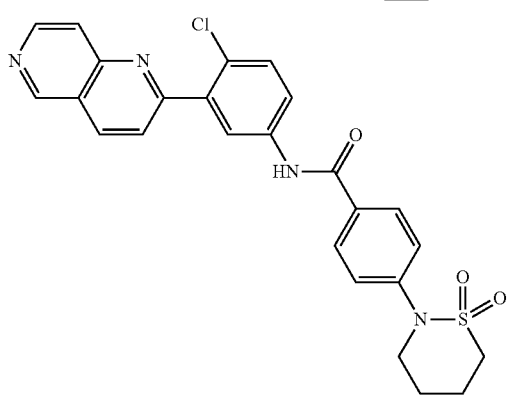
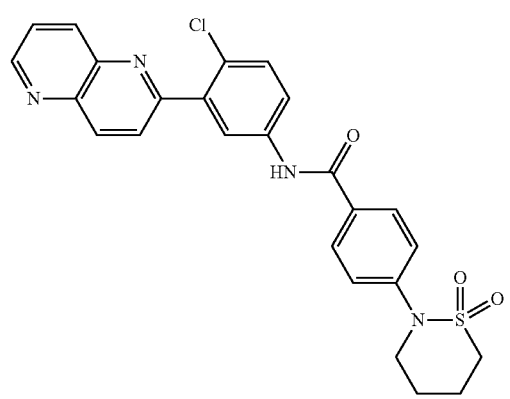
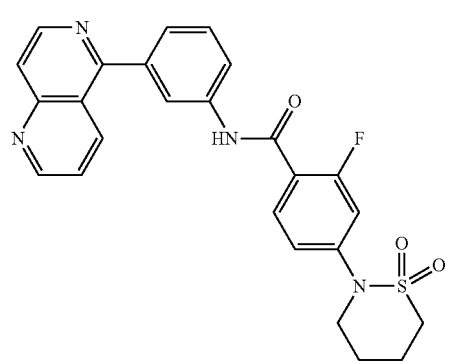
86
-continued
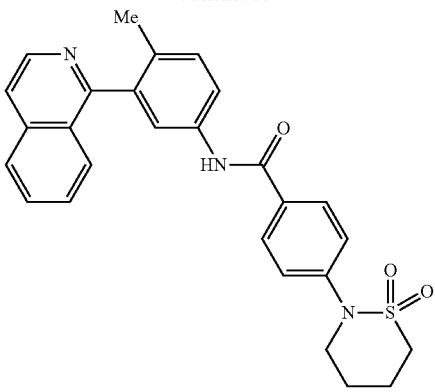
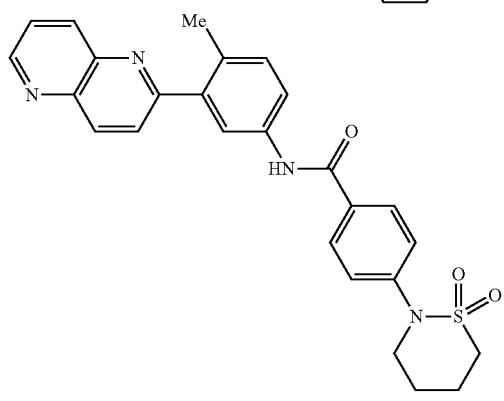
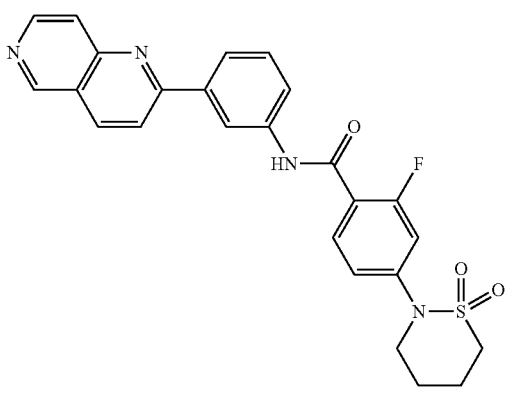
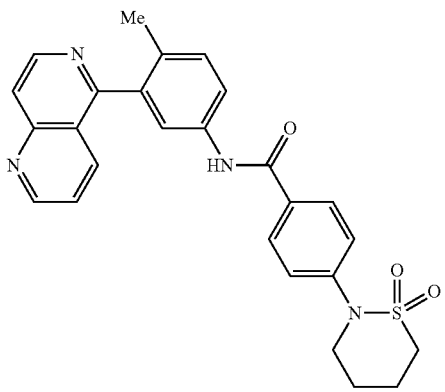

-continued
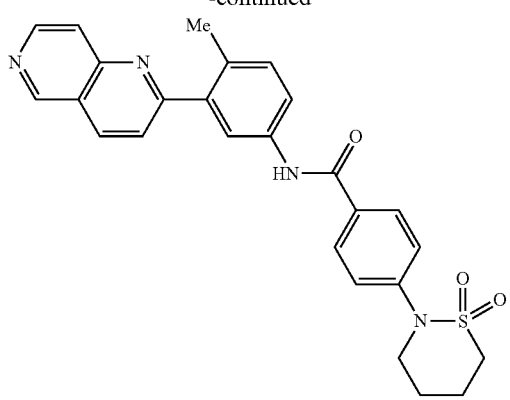
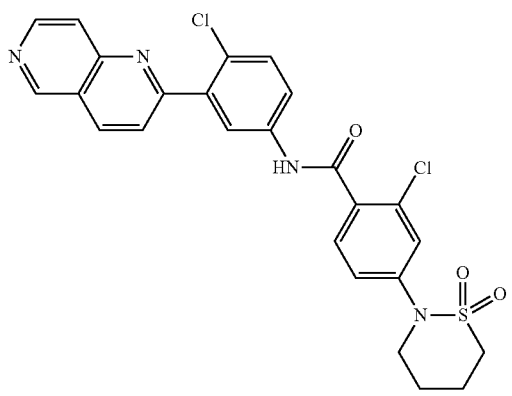
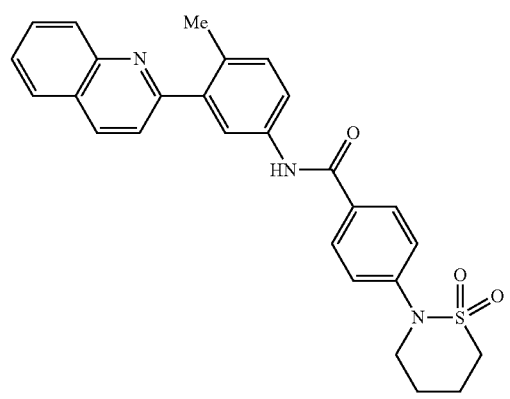
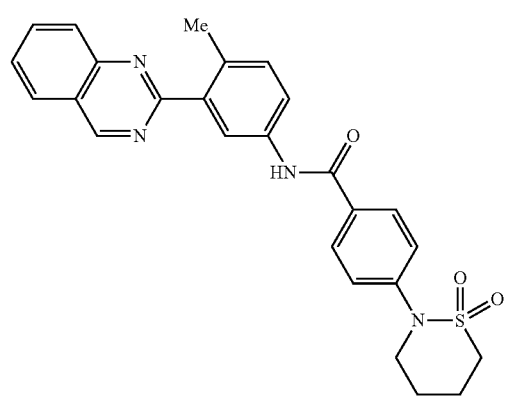
-continued
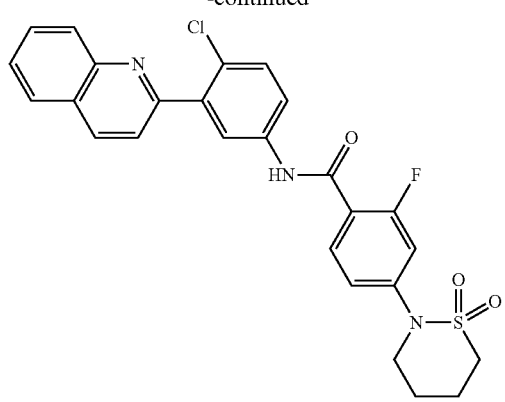
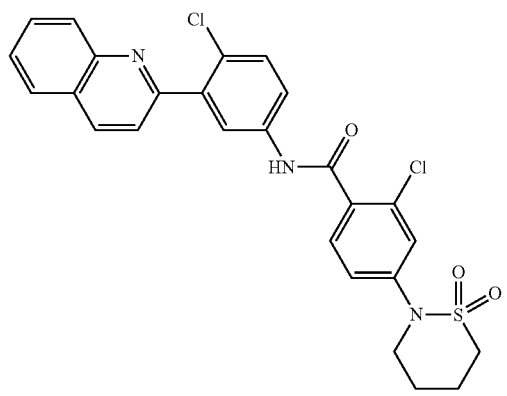
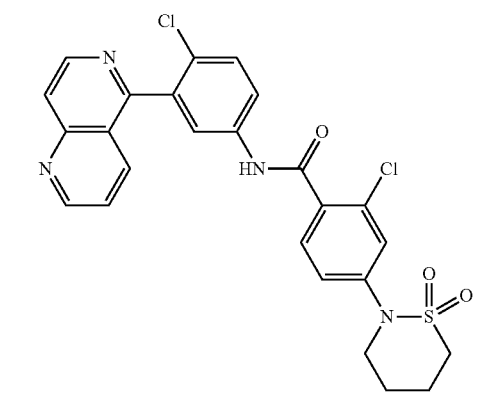
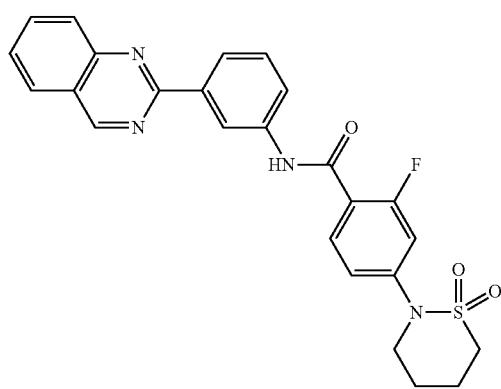

89
-continued
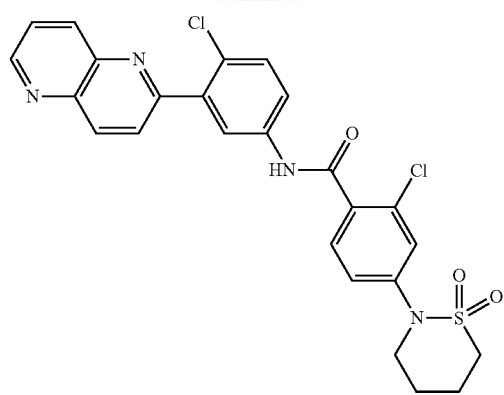
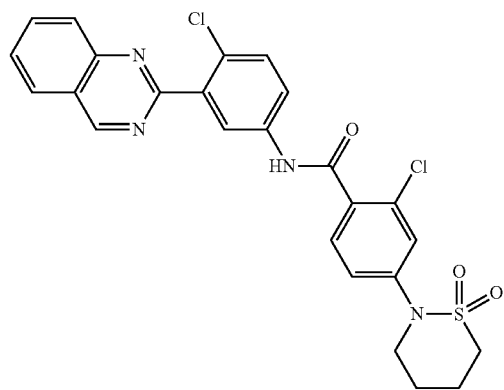
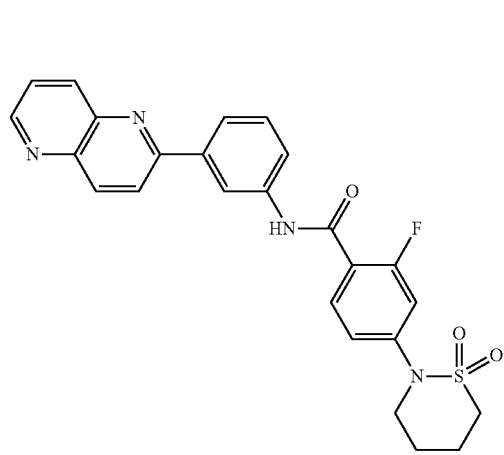
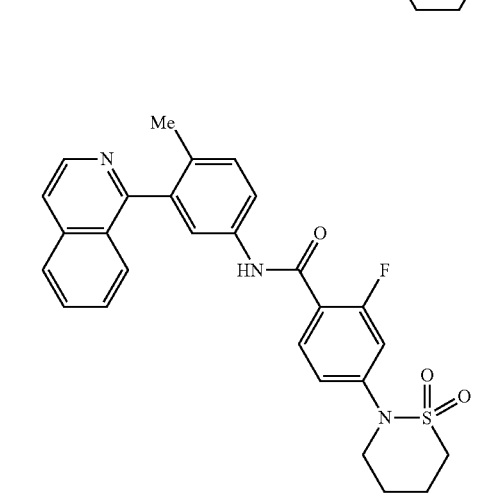
90
-continued
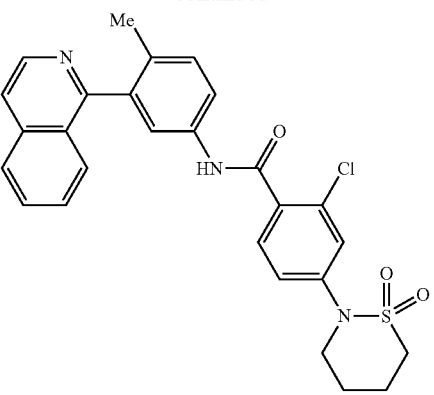

91
-continued
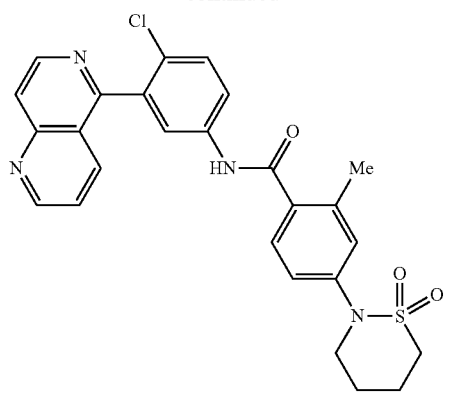
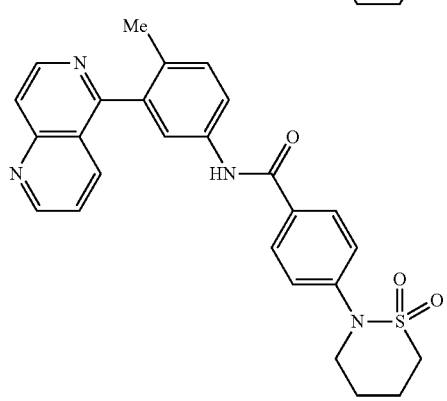
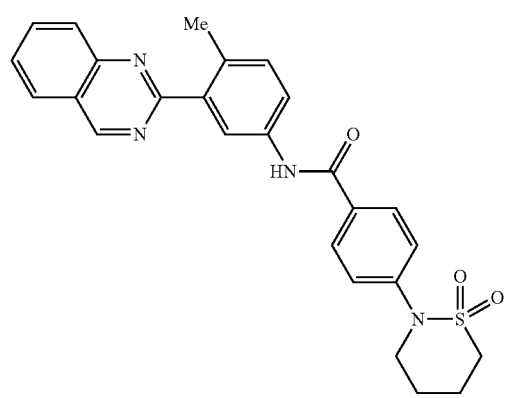
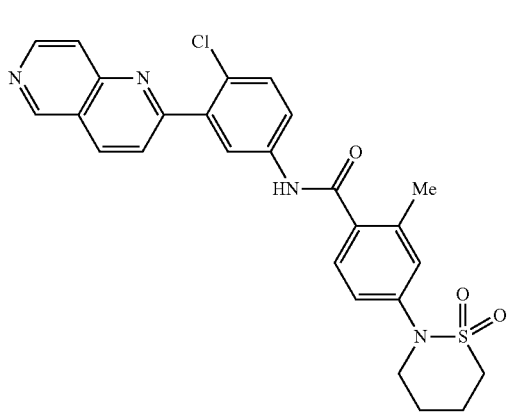
92
-continued
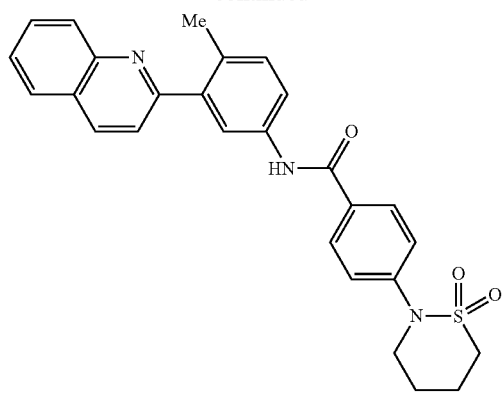
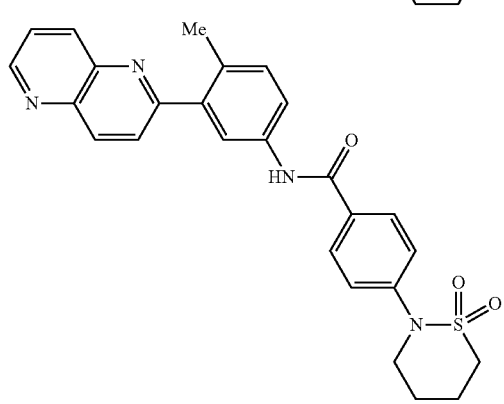
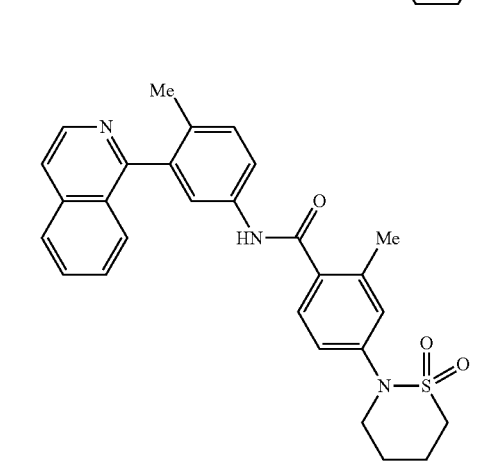
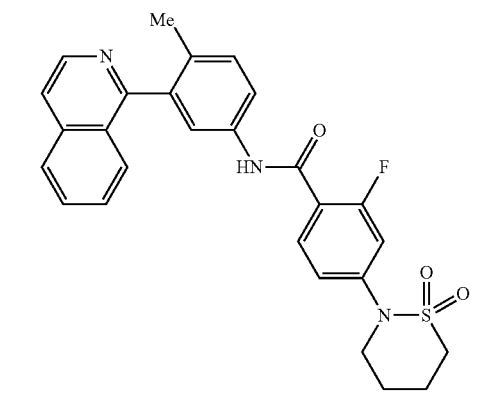

93
-continued
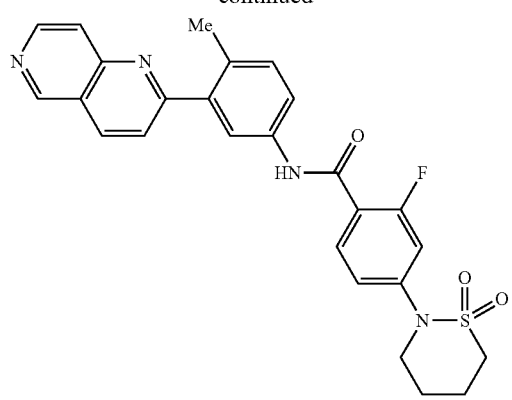
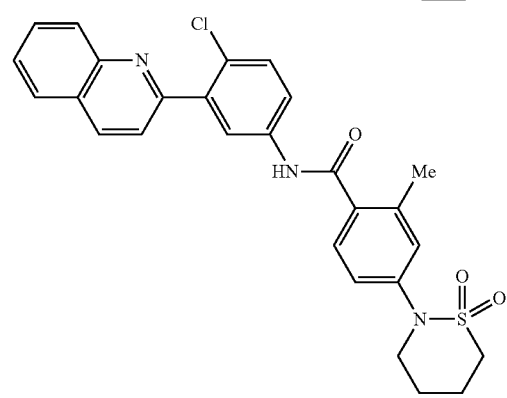
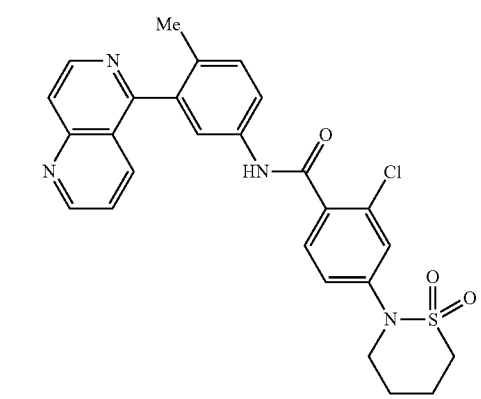
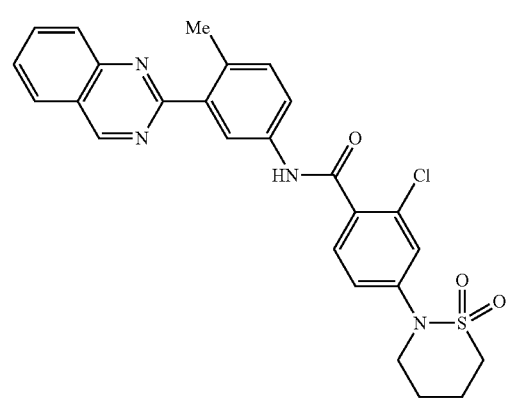
94
-continued
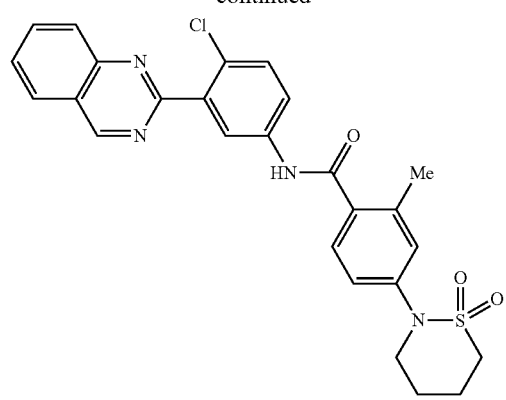
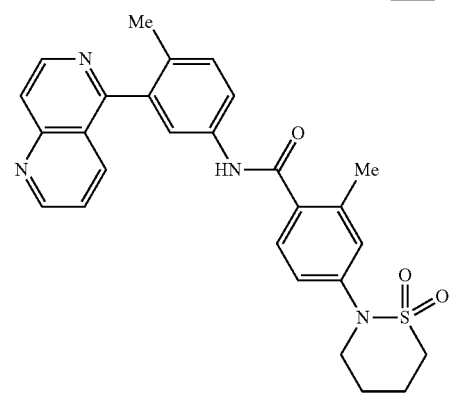
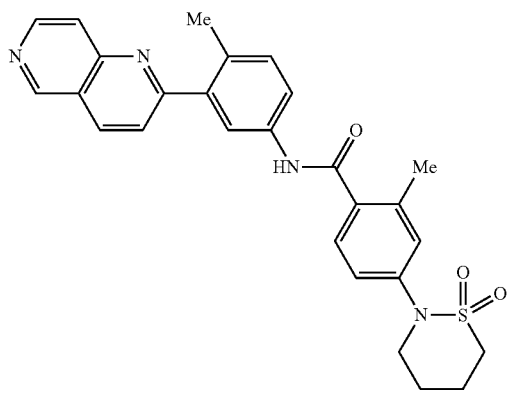
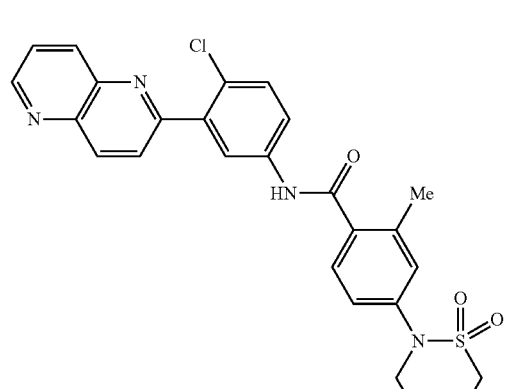

95
-continued
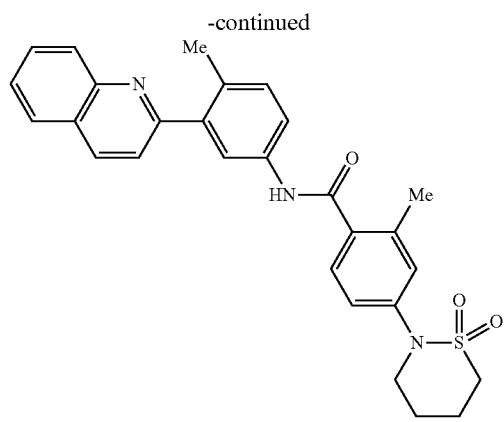
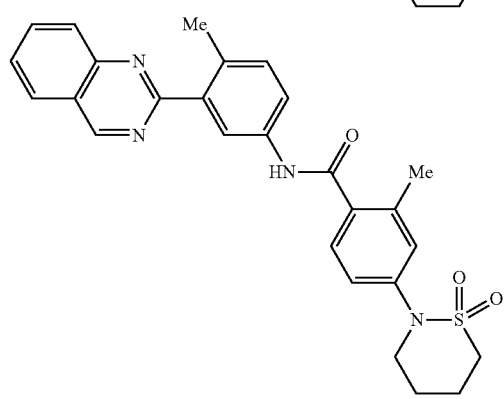
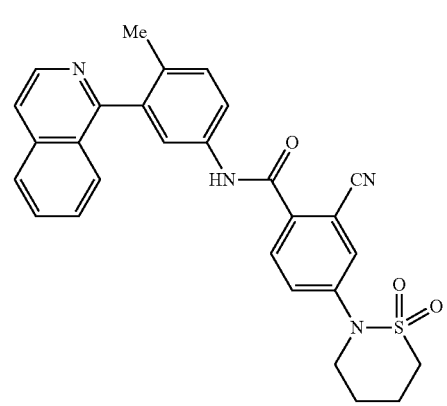
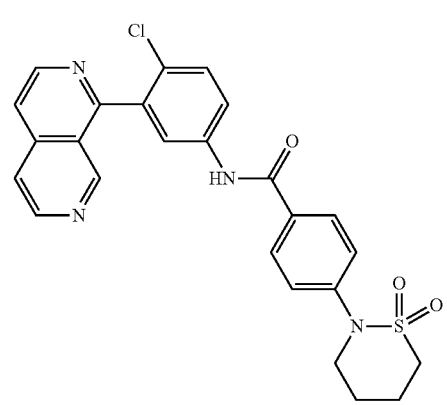
96
-continued
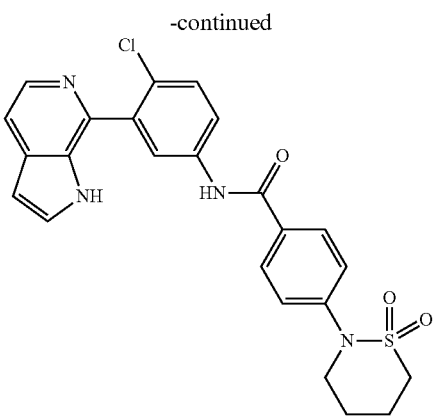
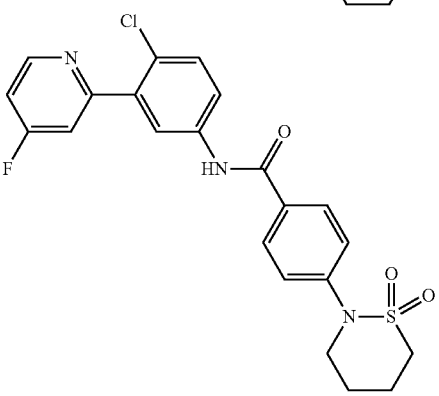
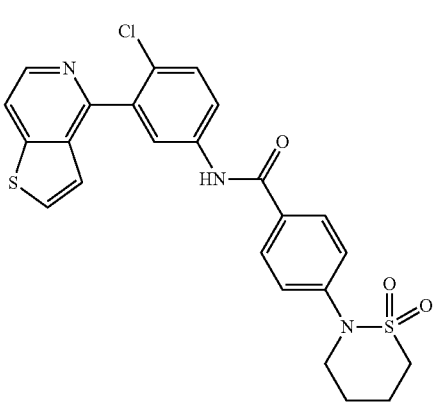
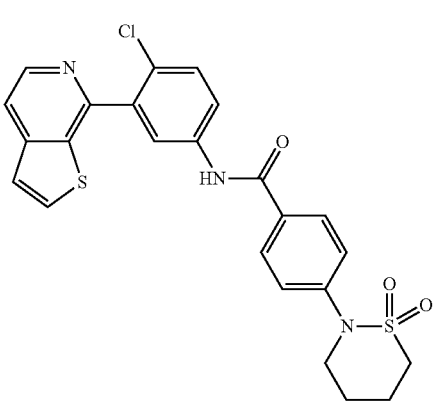

-continued
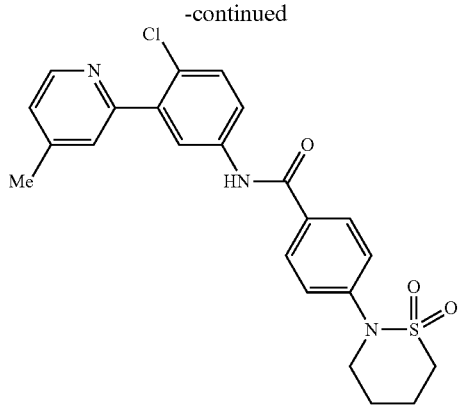
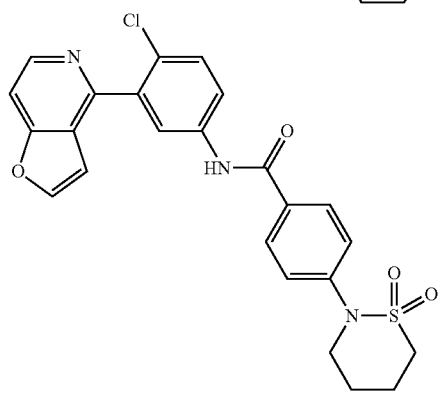
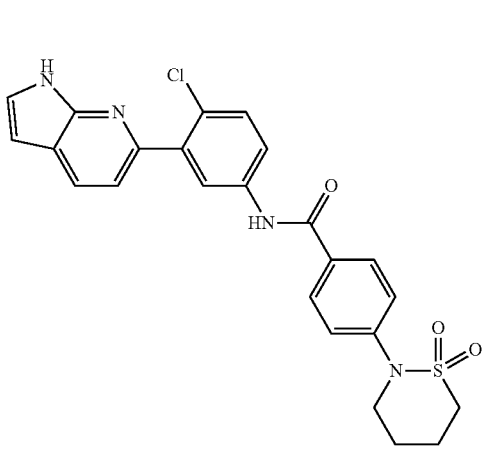
-continued
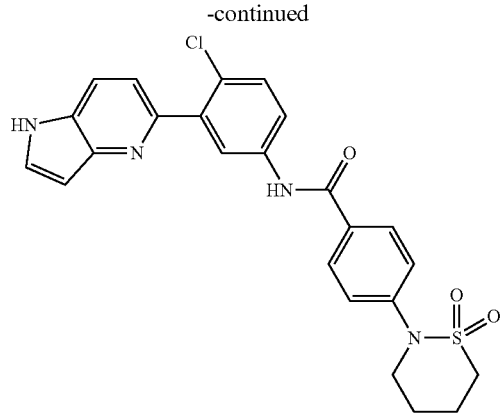
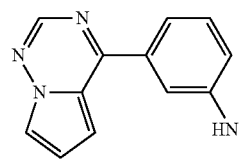
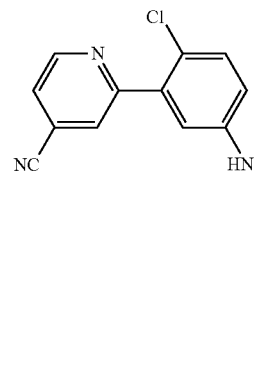
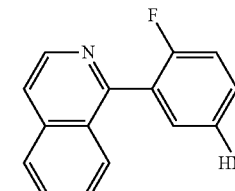
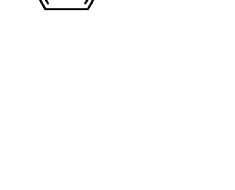

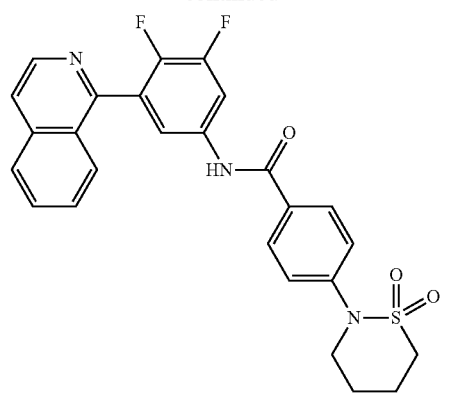
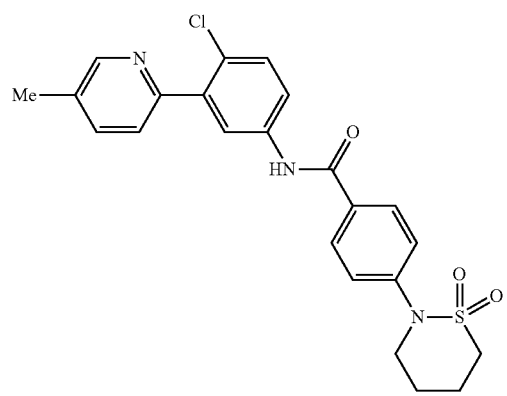
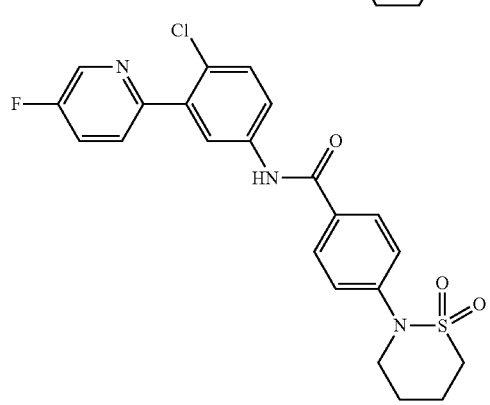
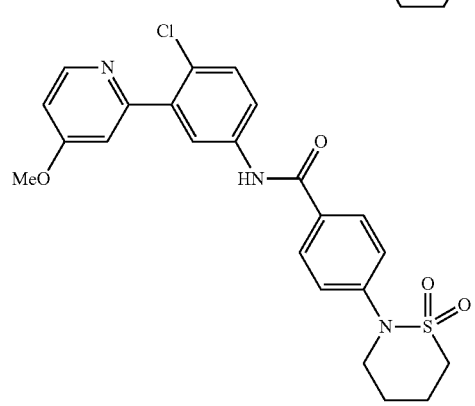
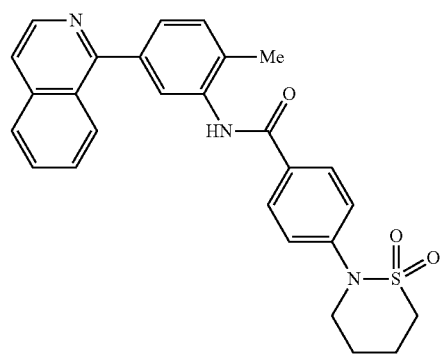
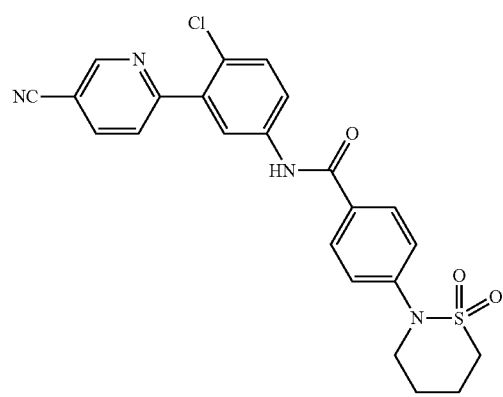
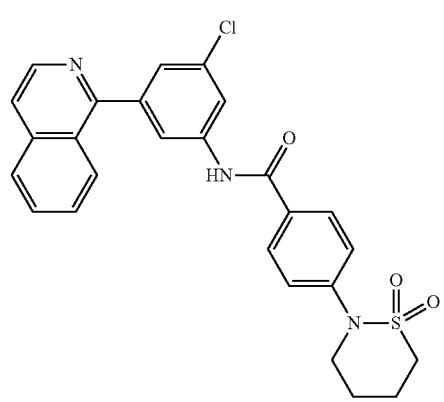
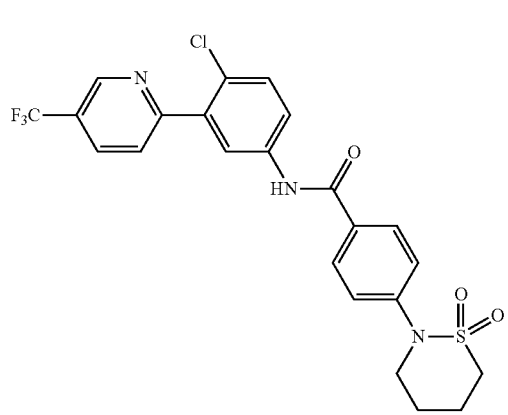

101
-continued
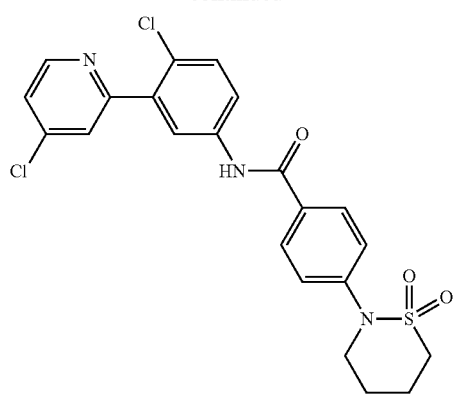
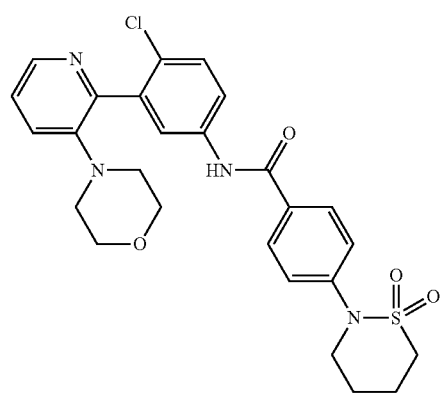
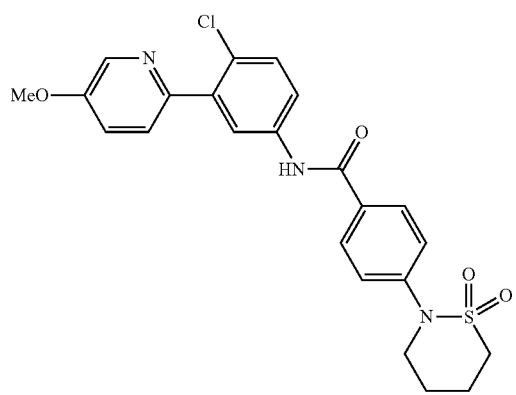
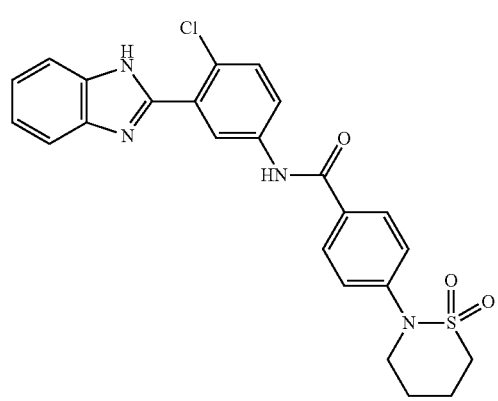
102
-continued
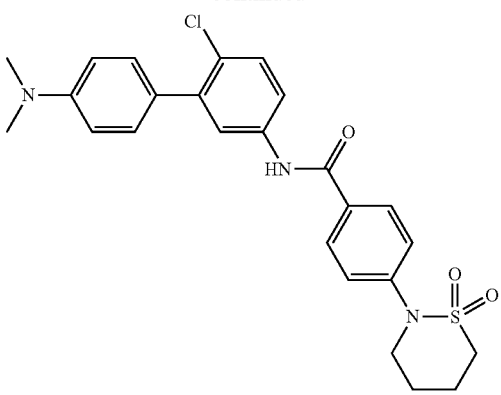
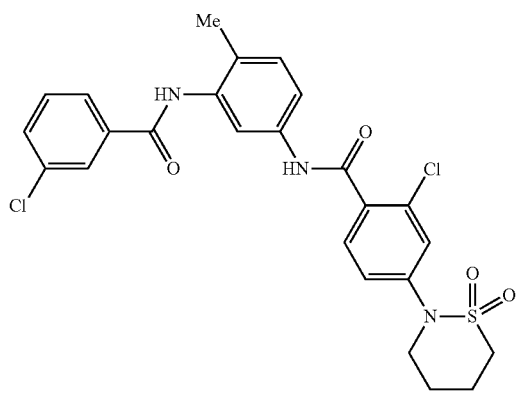
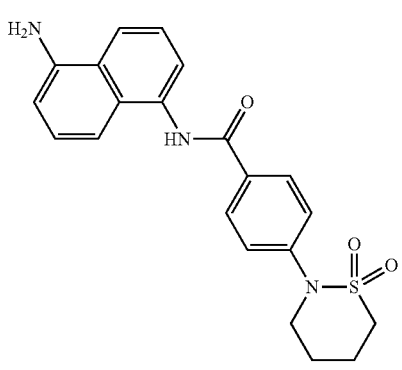
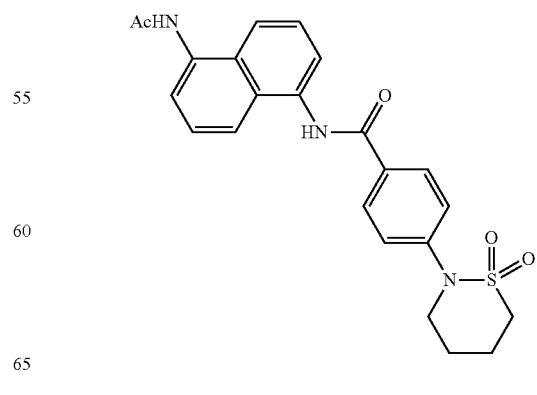

103
-continued
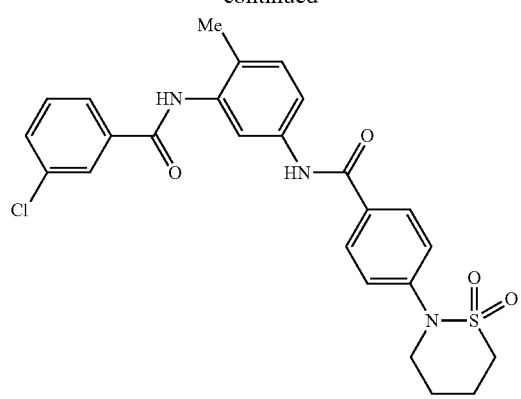
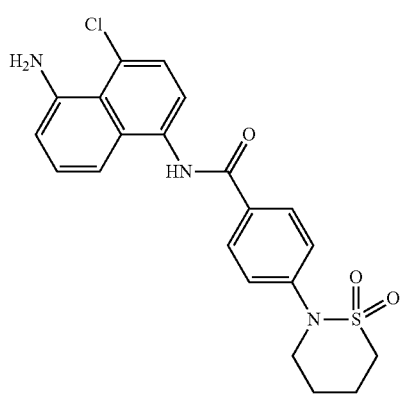
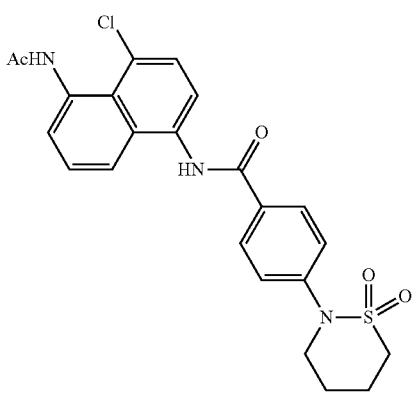
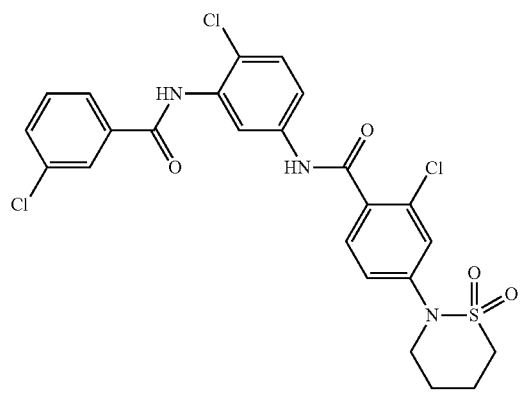
104
-continued
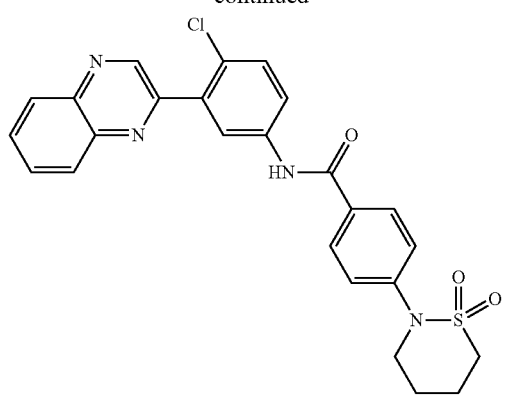
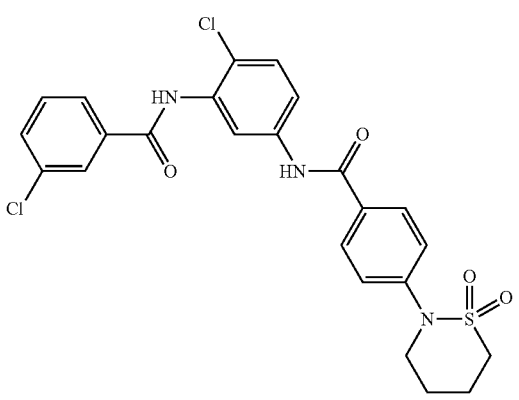
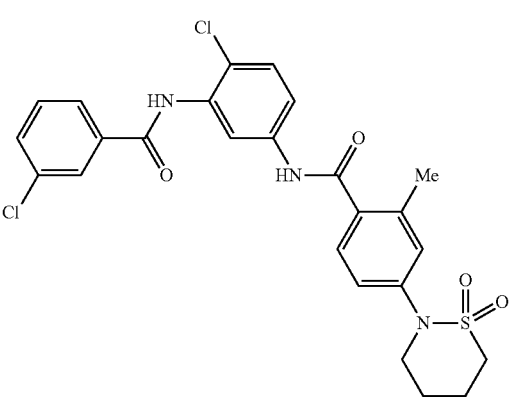
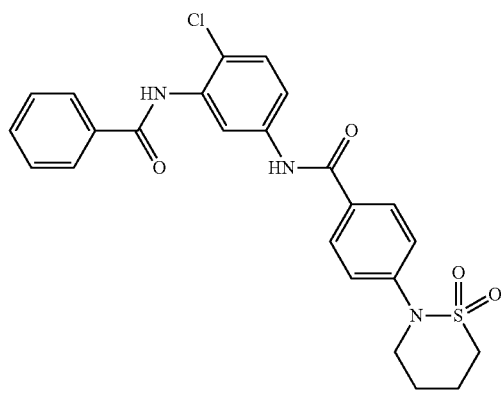

105
-continued
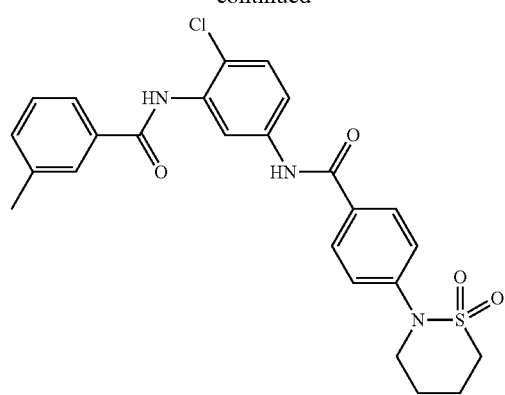
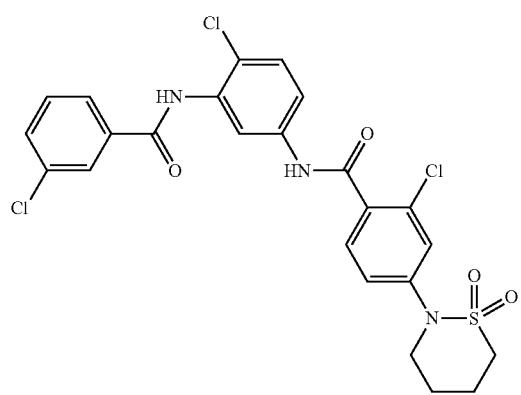
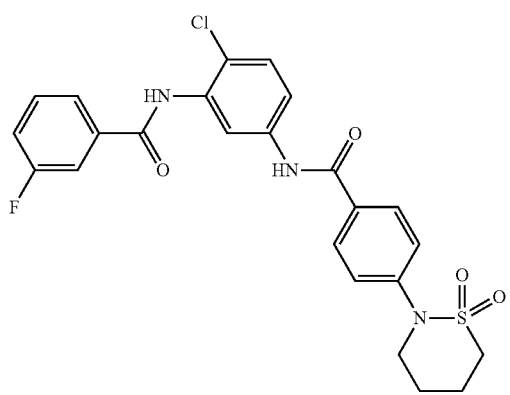
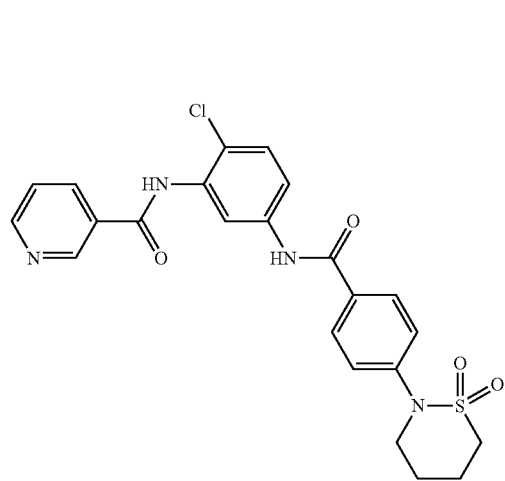
106
-continued
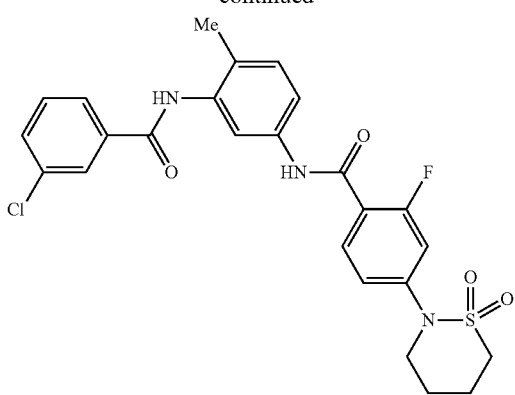
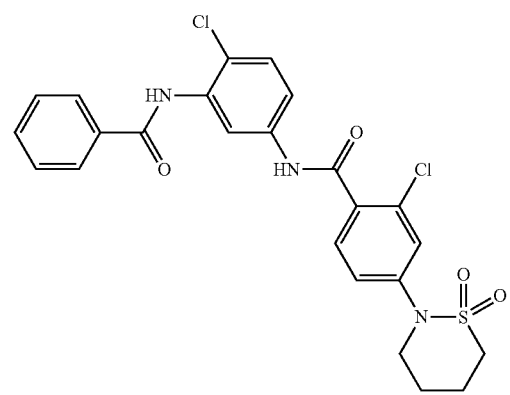
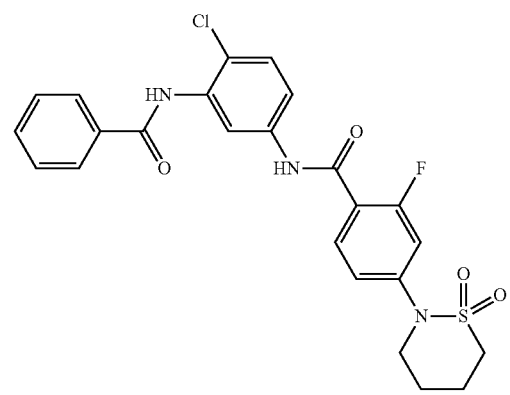
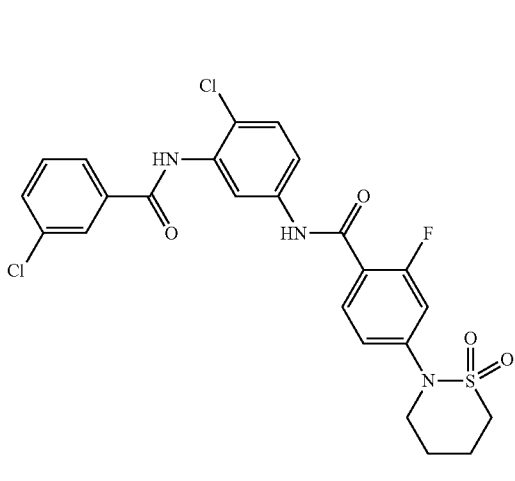

-continued
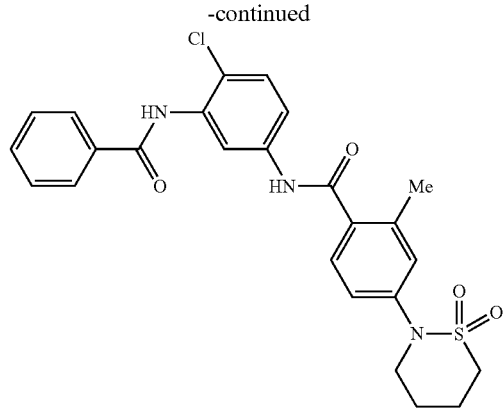
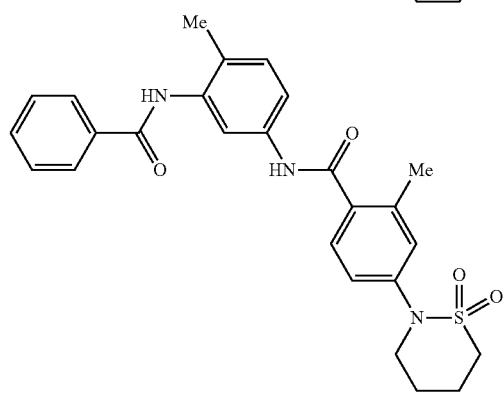
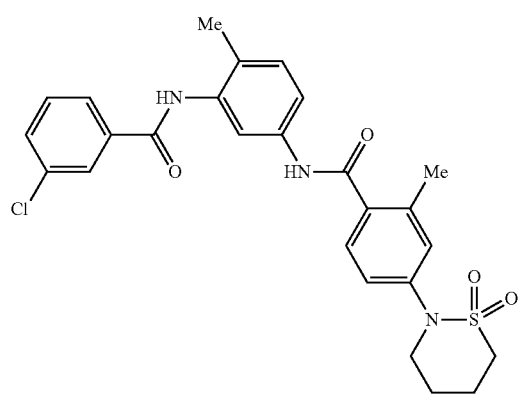
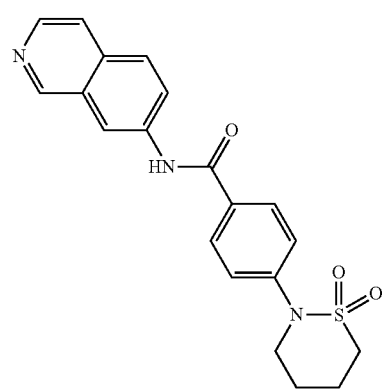
-continued
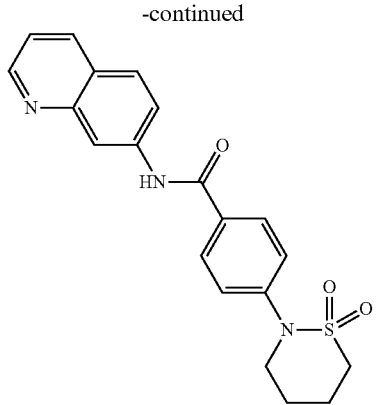
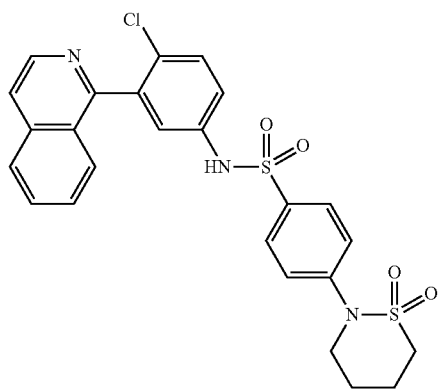
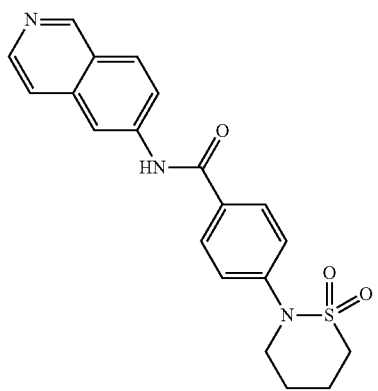
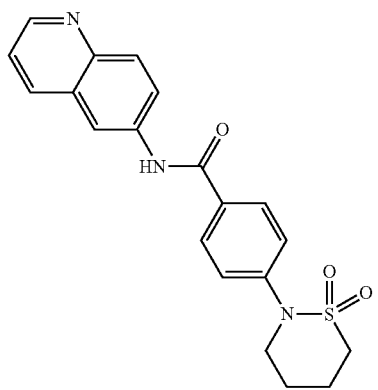

109
-continued
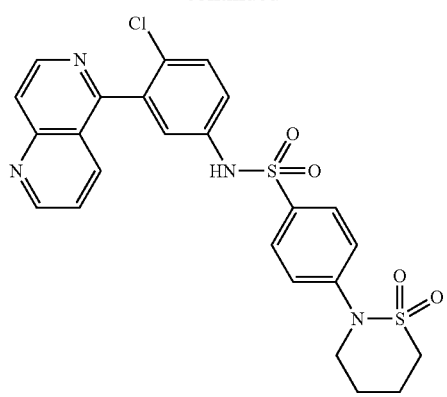
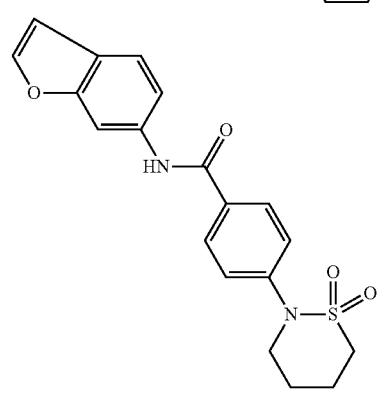
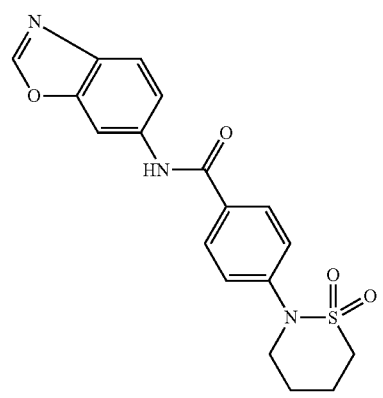
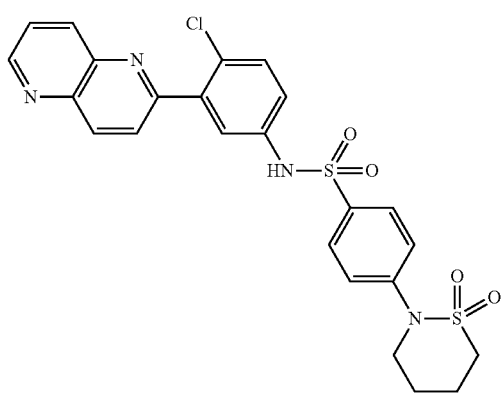
110
-continued
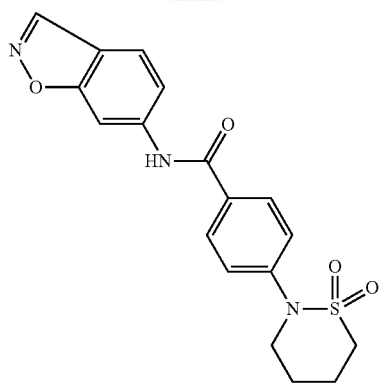
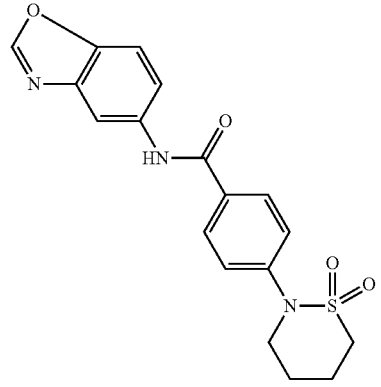
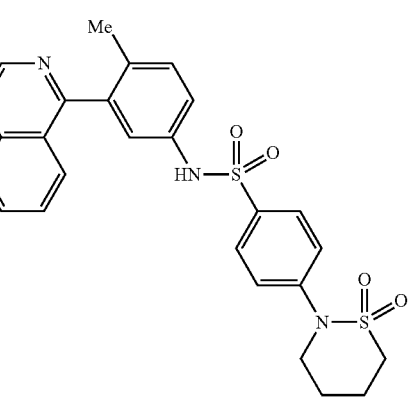
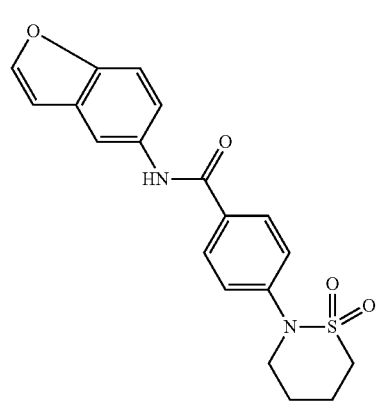

111
-continued
112
-continued
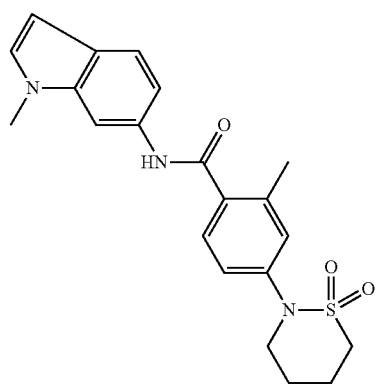
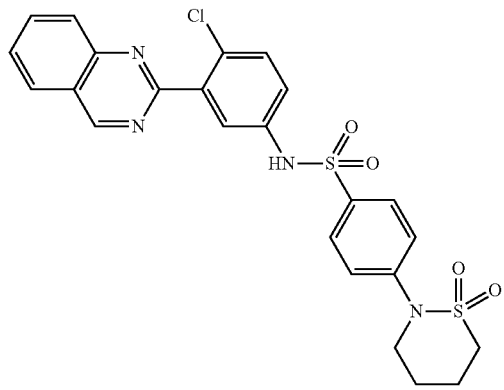
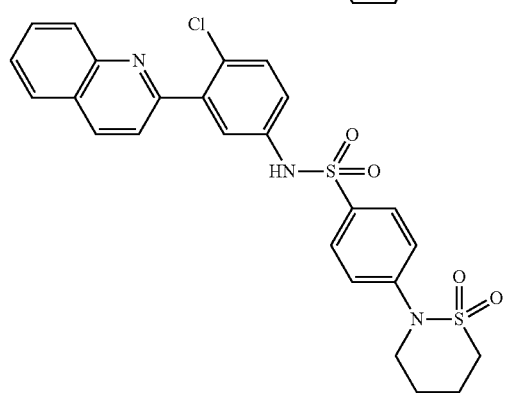
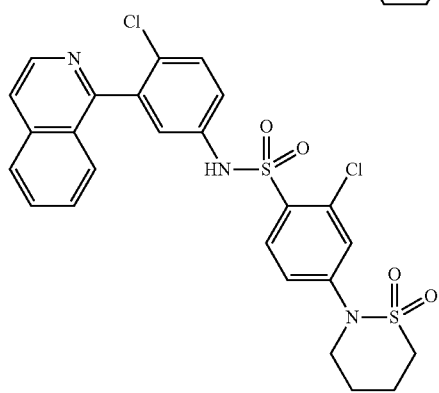
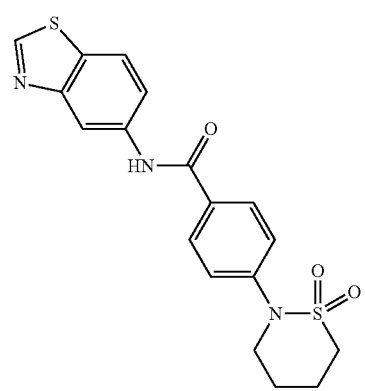
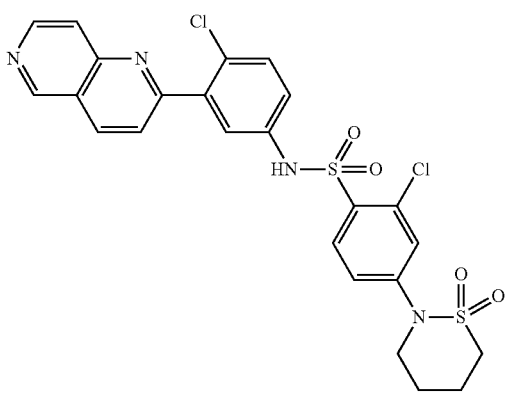
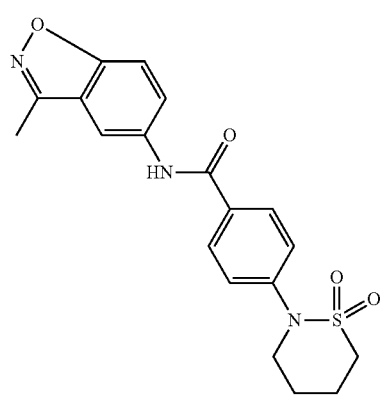
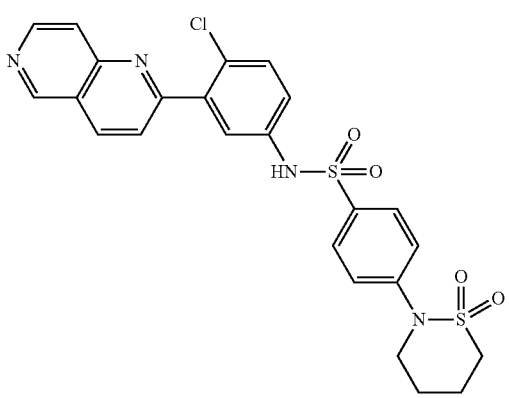

113
-continued
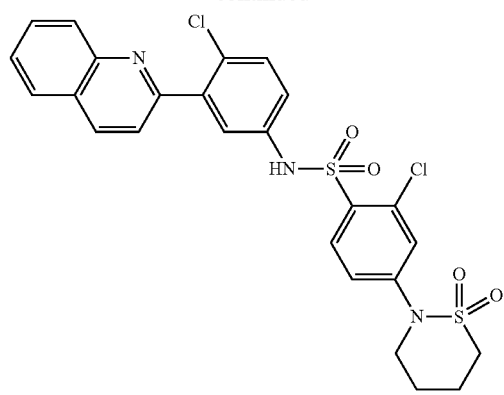
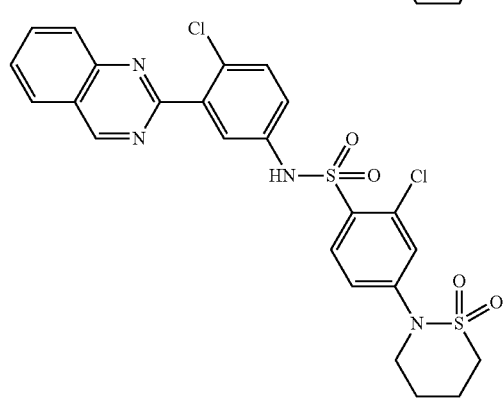
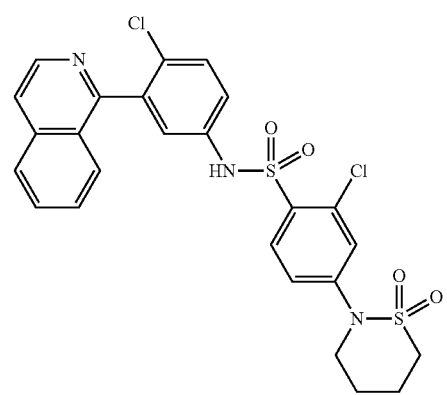
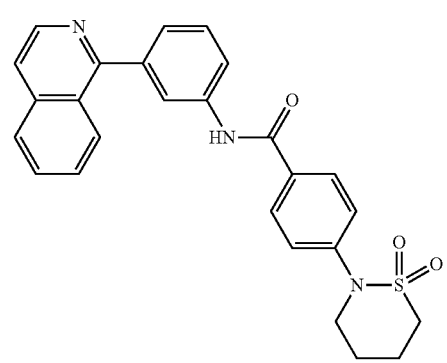
114
-continued
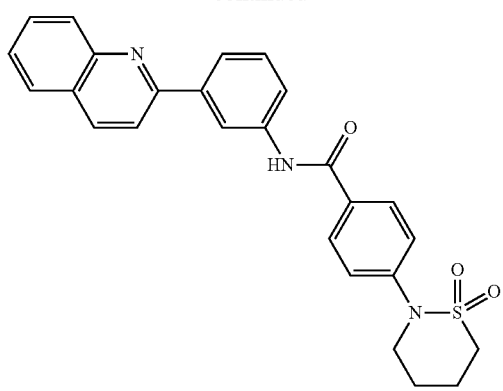
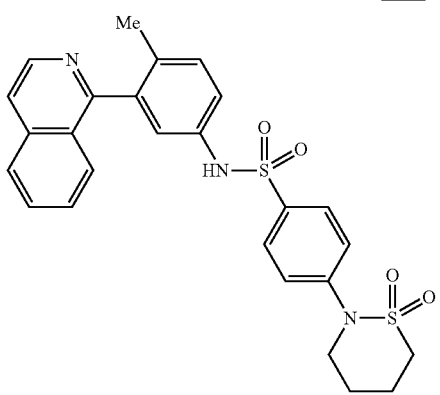
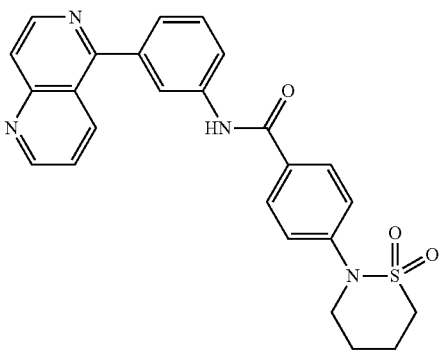
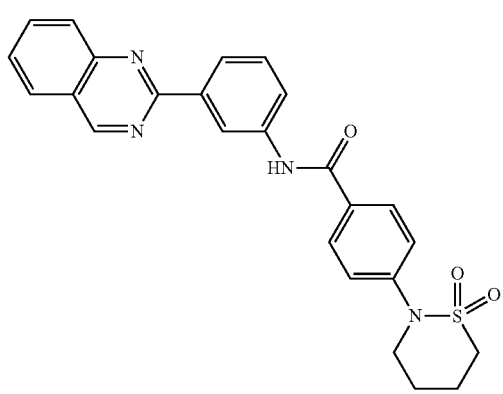

115
-continued
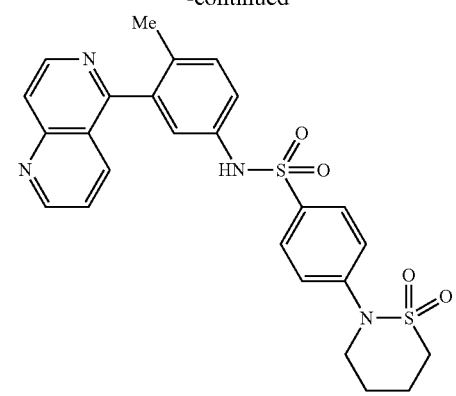
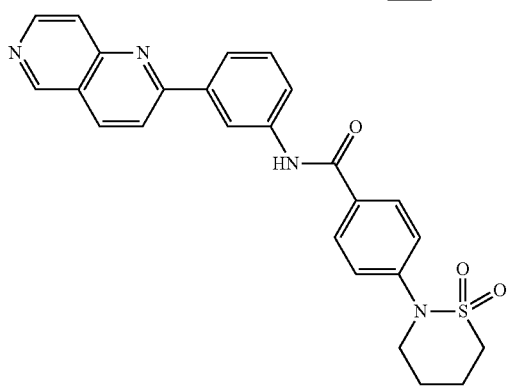
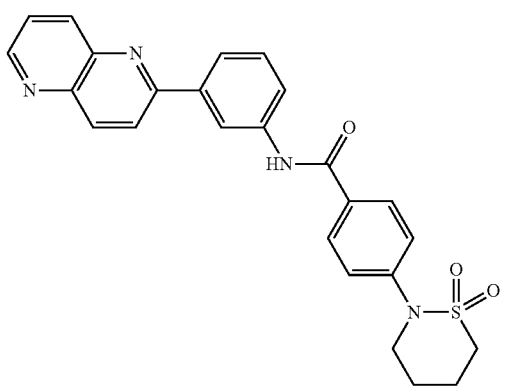
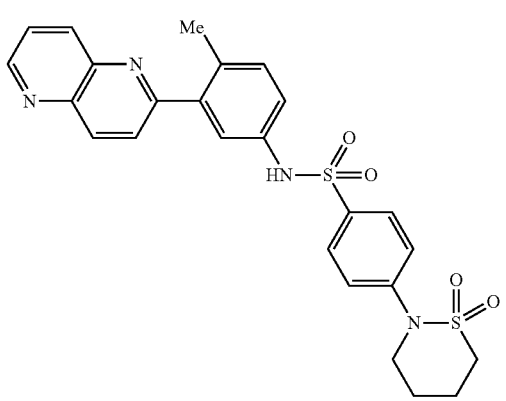
116
-continued
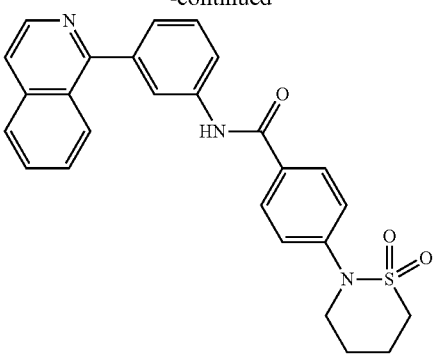
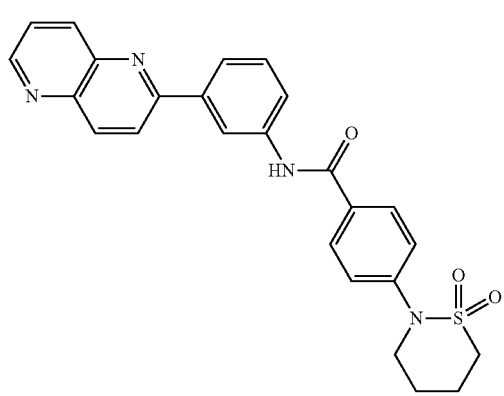
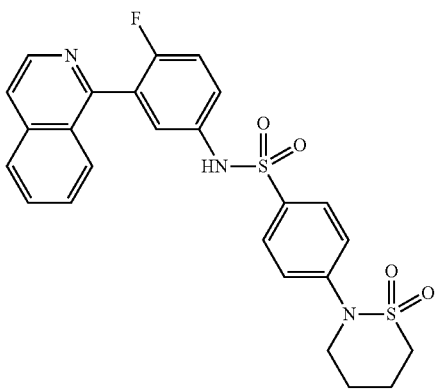
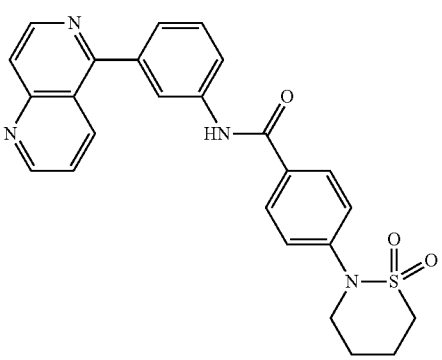

117
-continued
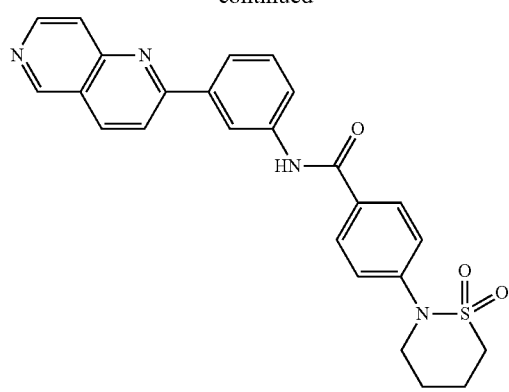
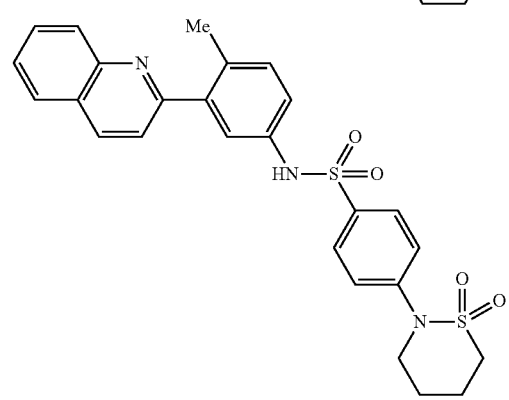
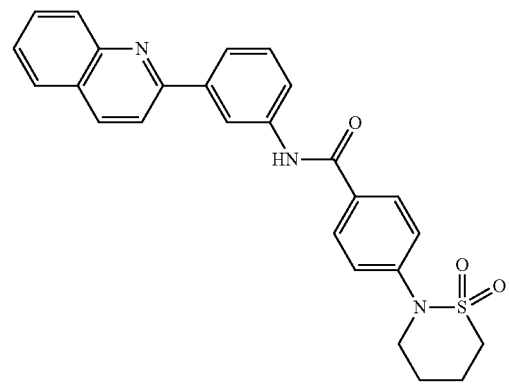
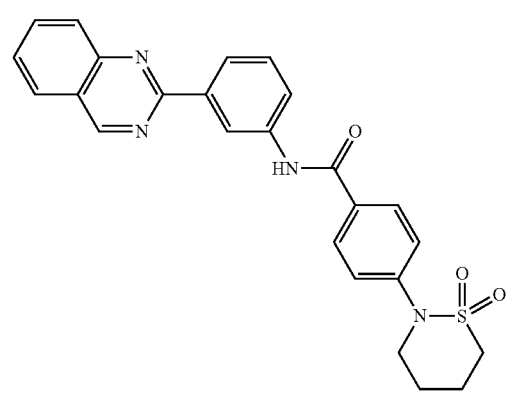
118
-continued
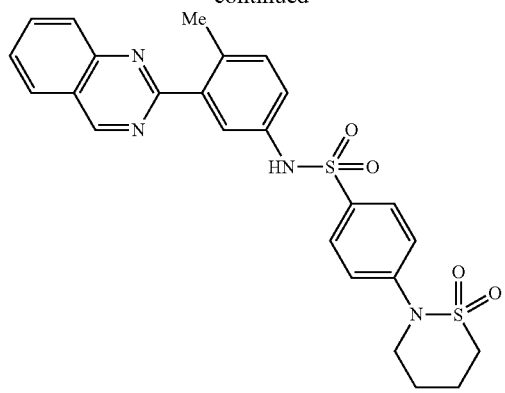
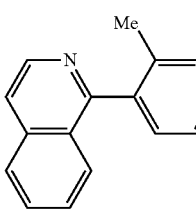
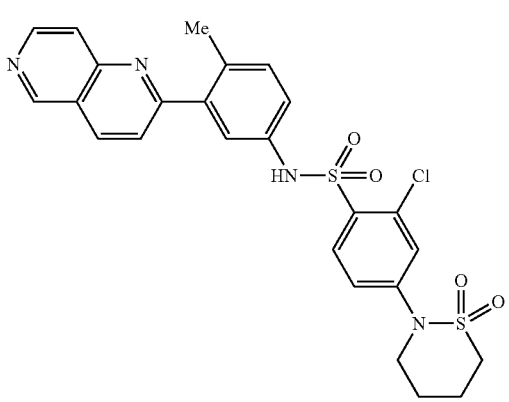
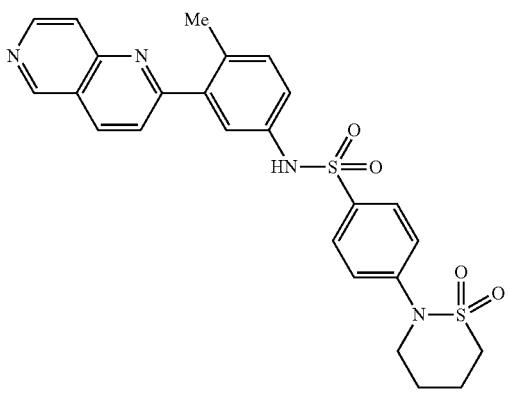

119
-continued
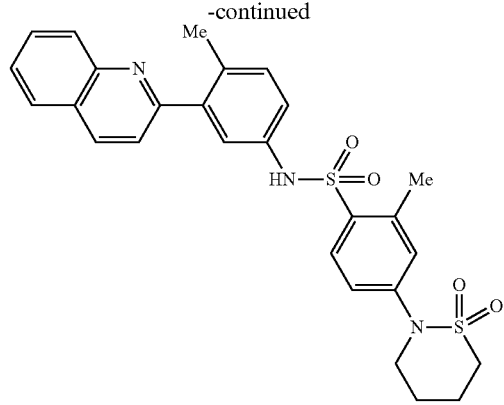
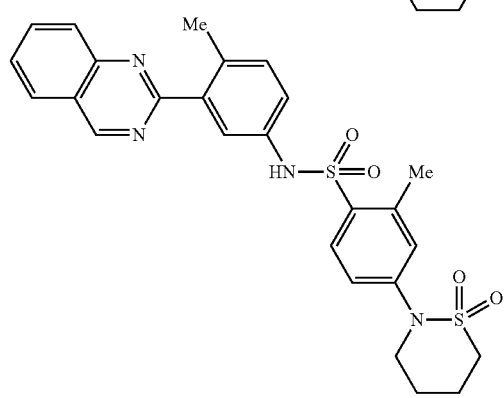
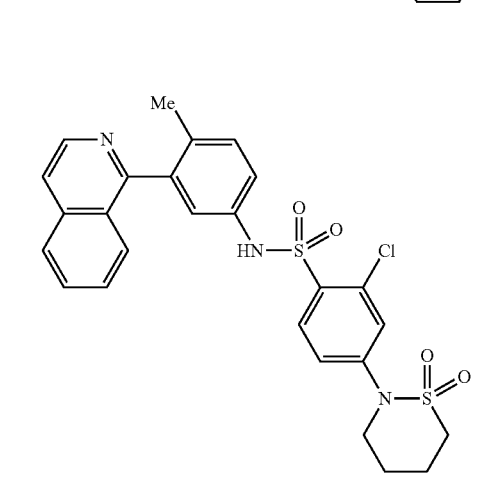
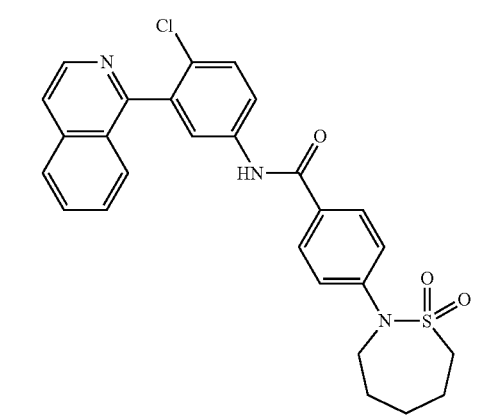
120
-continued
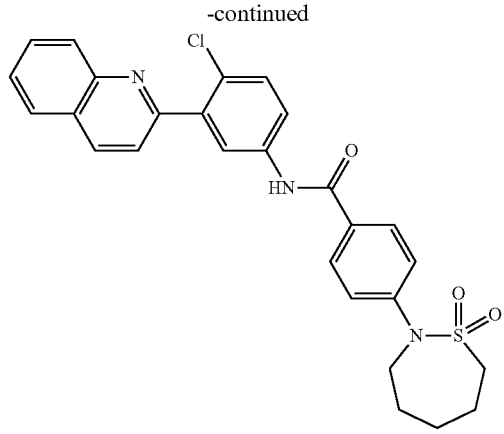
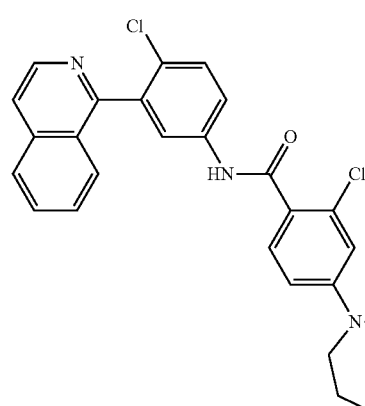
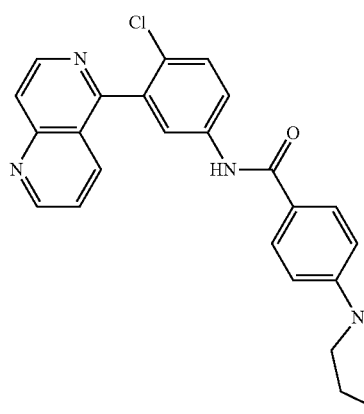
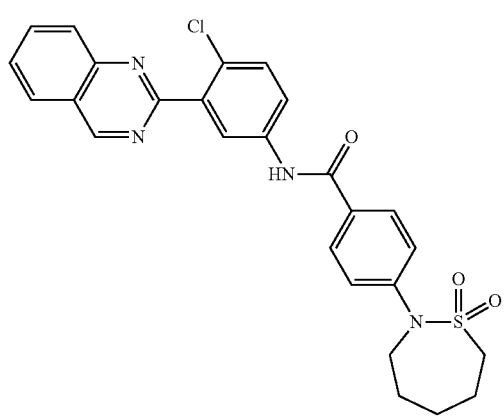

121
-continued
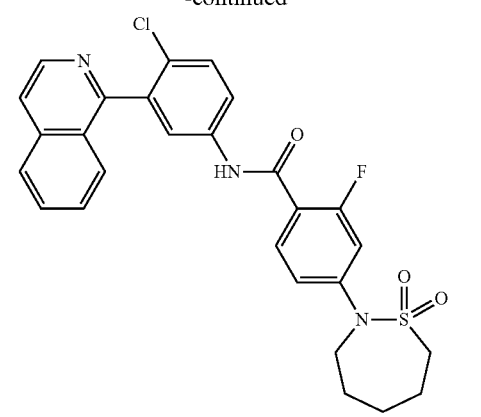
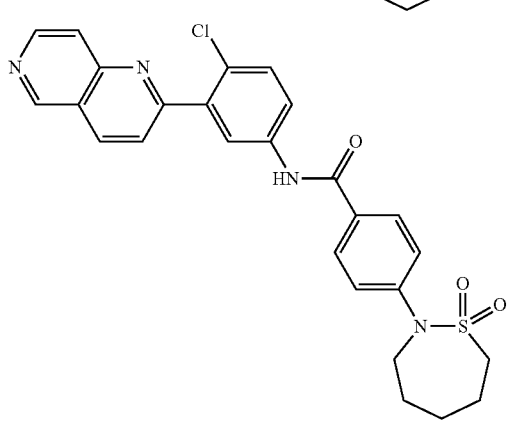
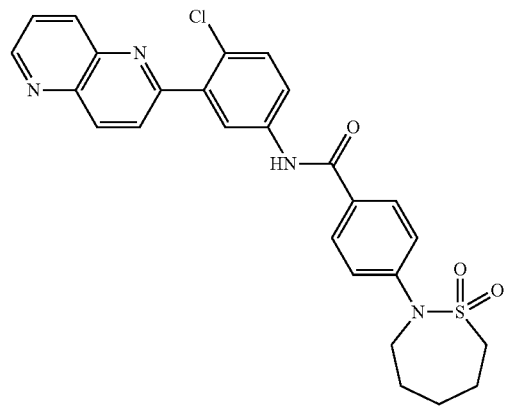
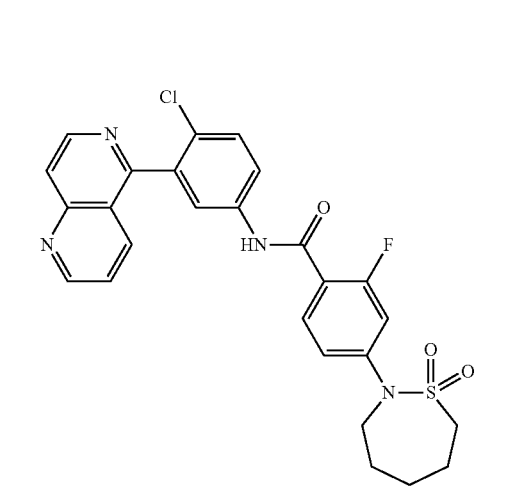
122
-continued
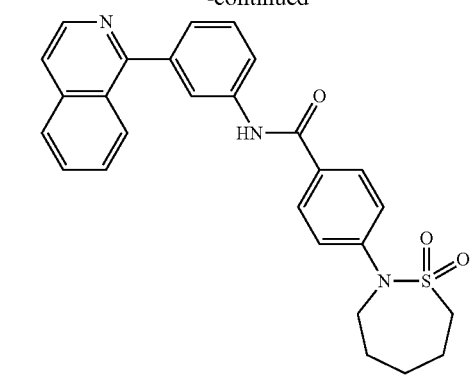
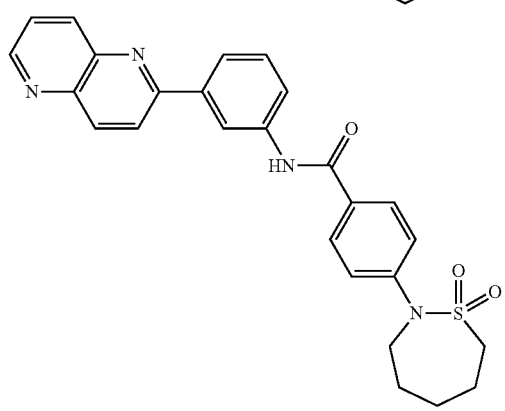
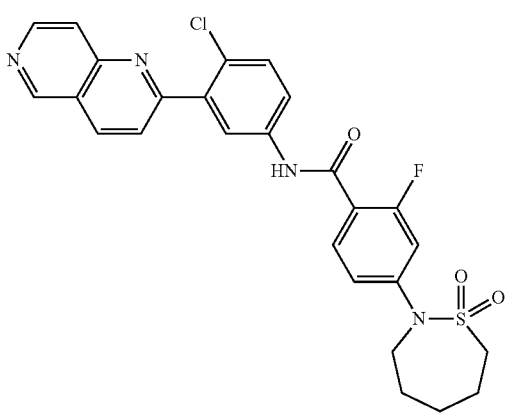

123
-continued
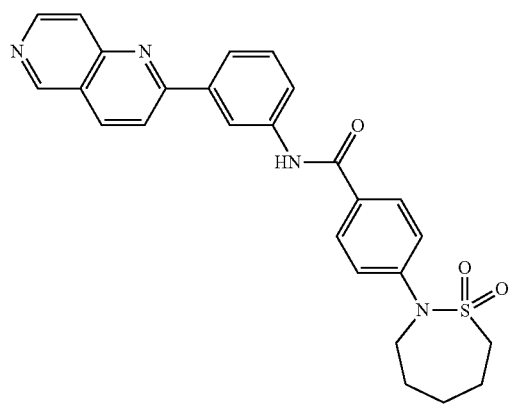
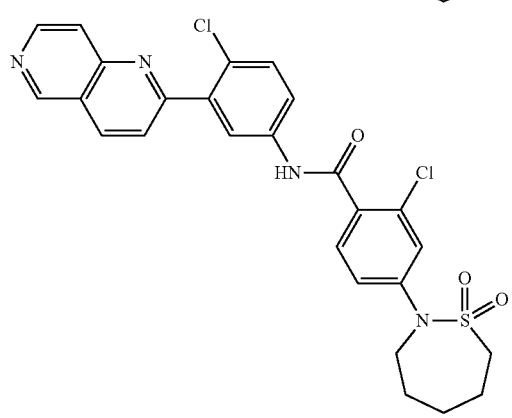
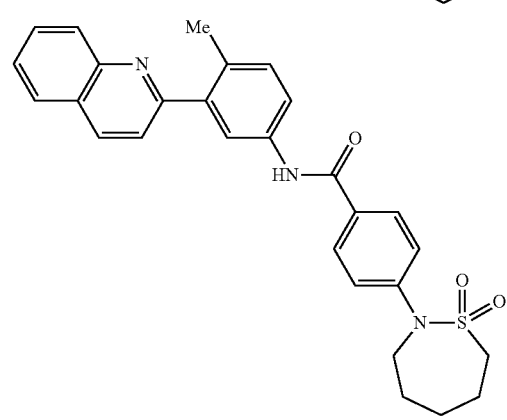
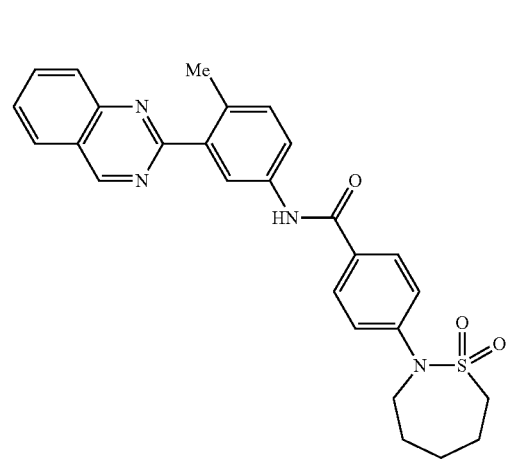
124
-continued
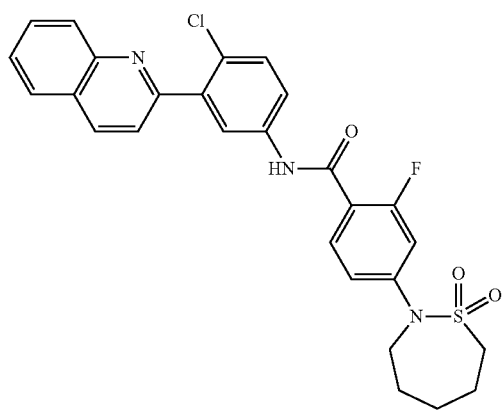
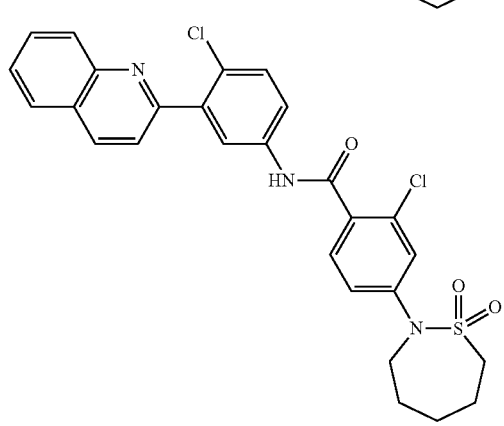
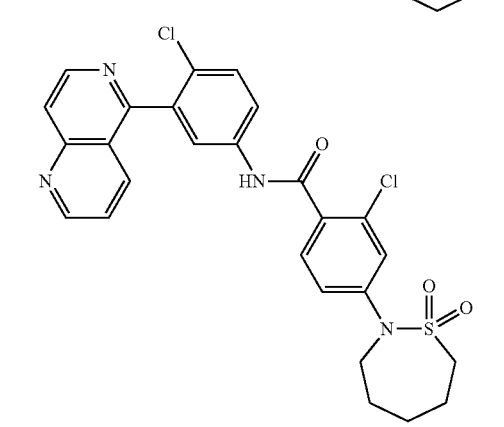
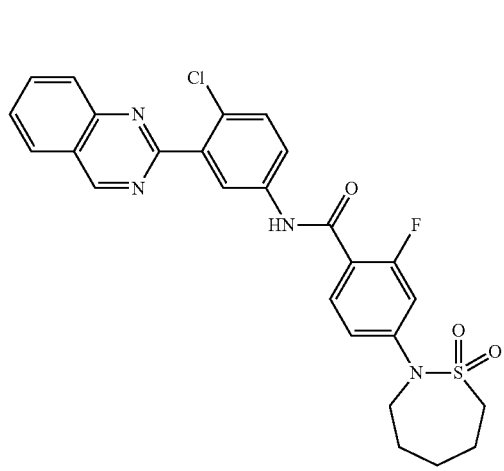

125
-continued
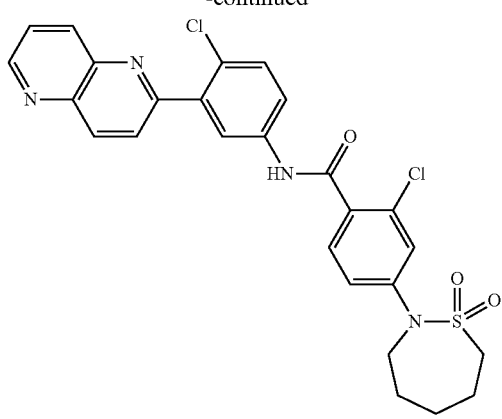
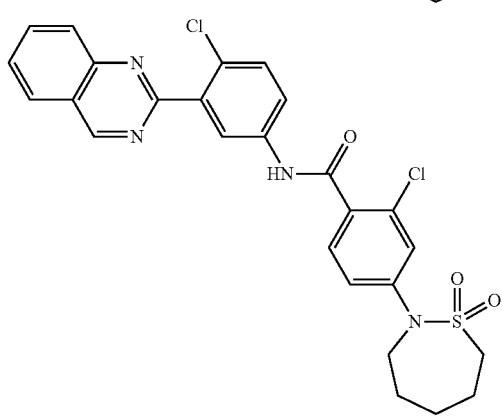

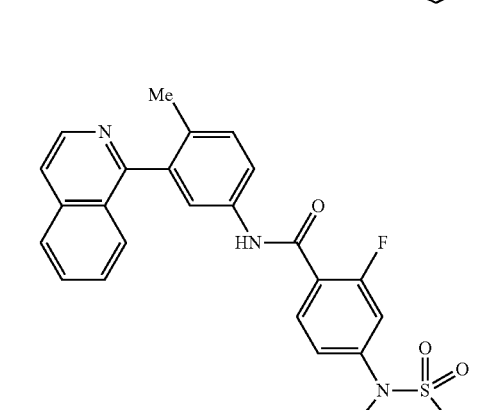
126
-continued
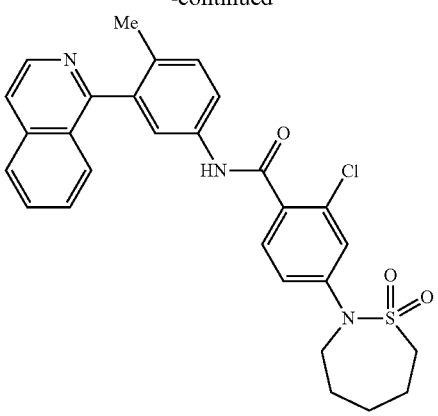
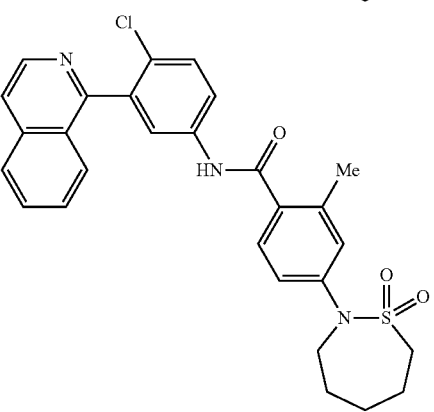
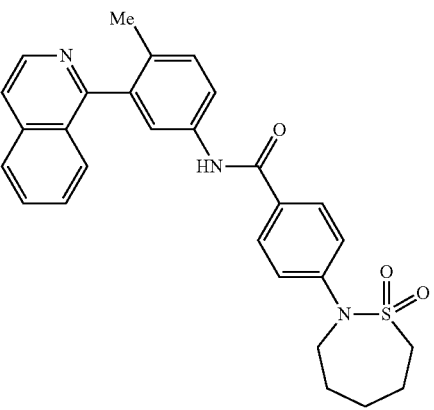
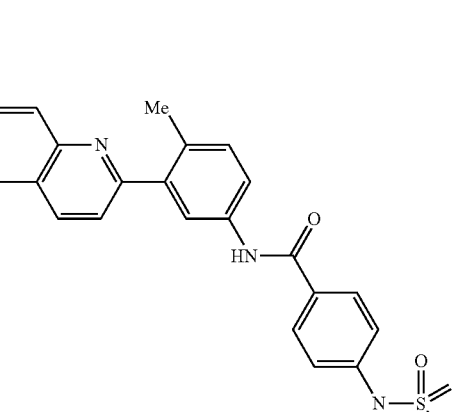

127
-continued
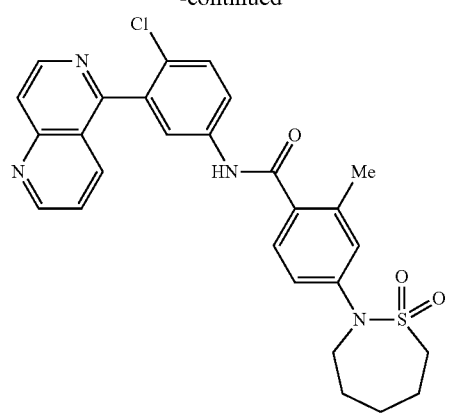
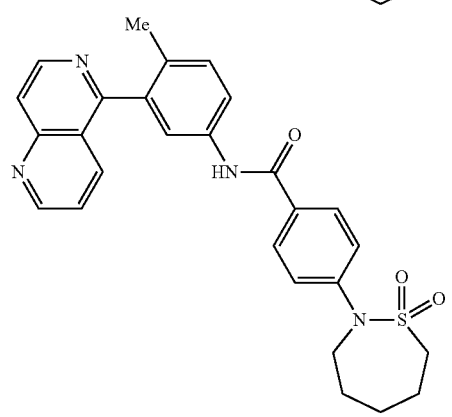
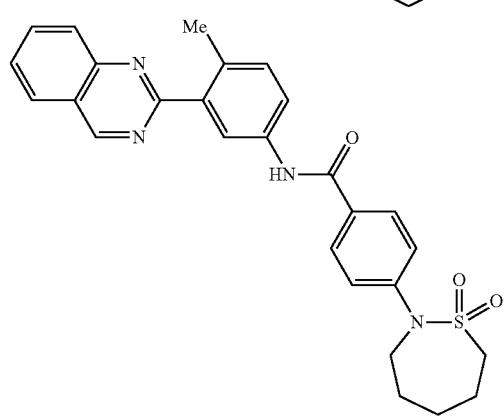
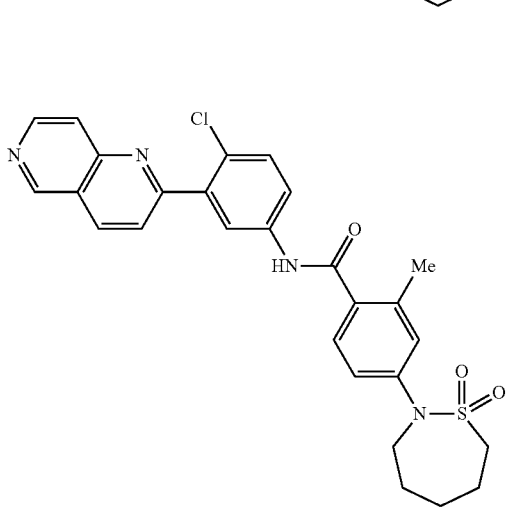
128
-continued
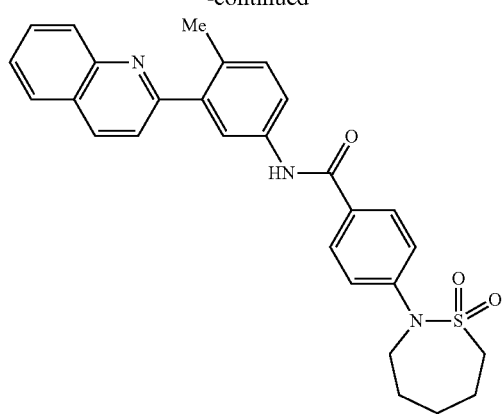
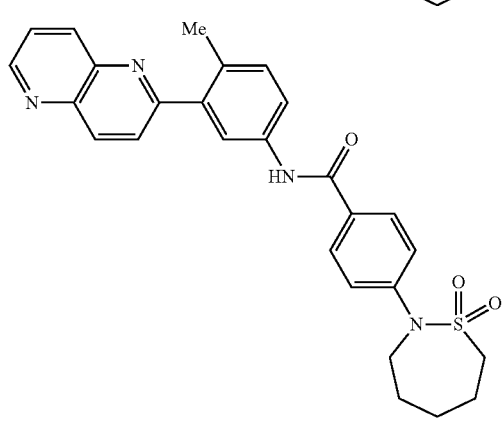
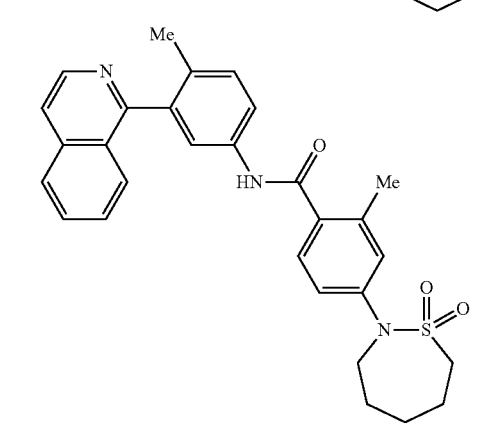
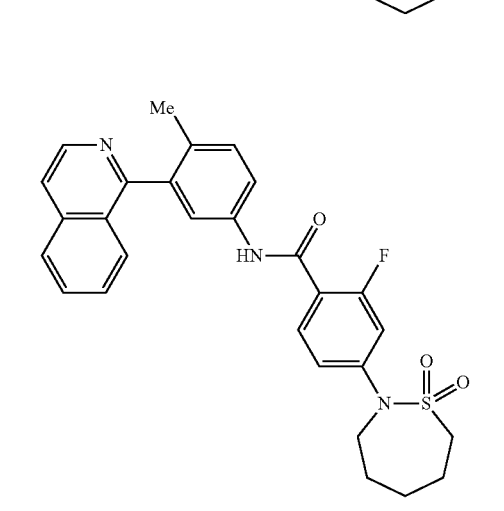

129
-continued
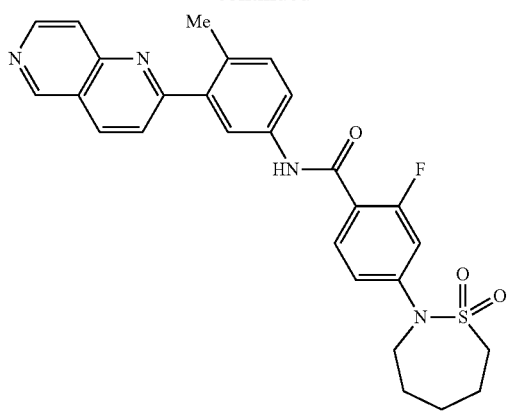
130
-continued
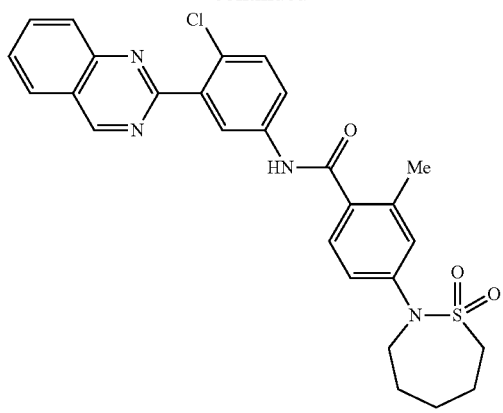
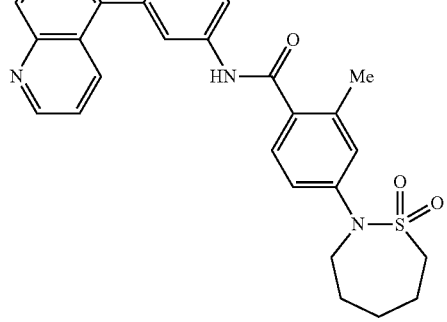
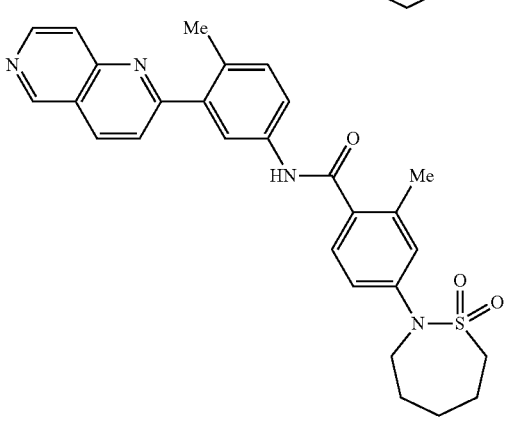
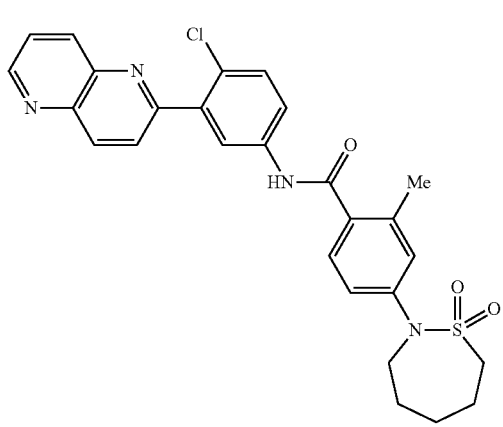

131
-continued
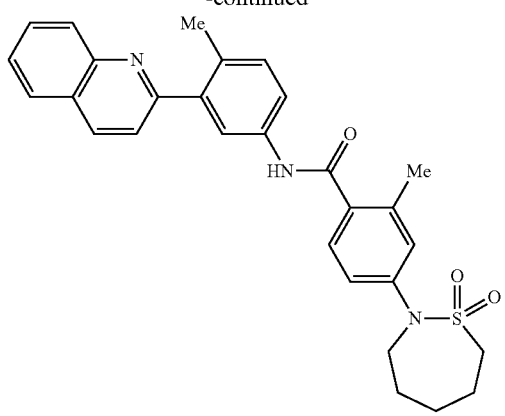
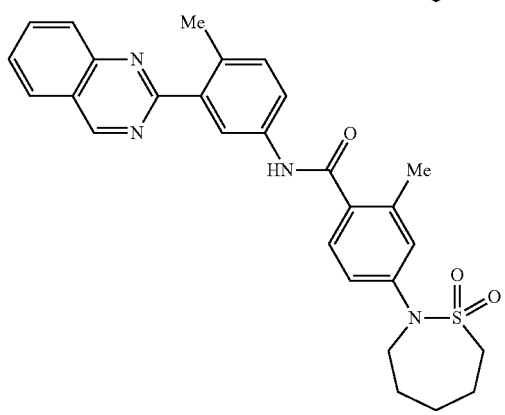
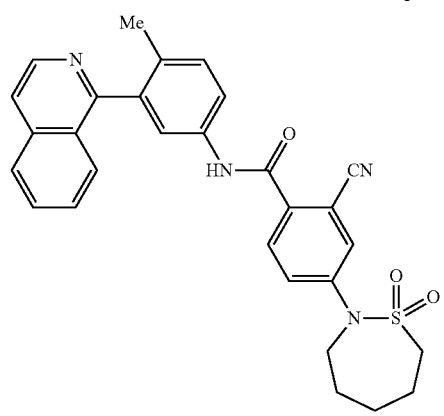
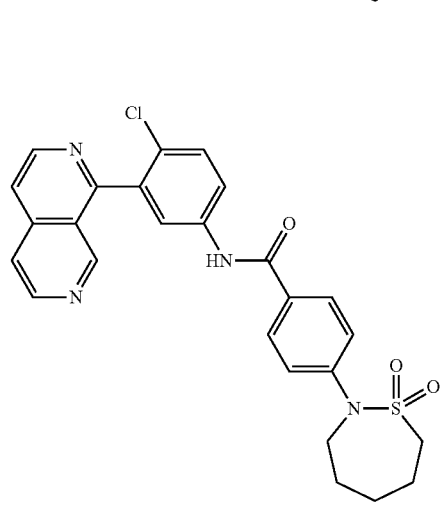
132
-continued
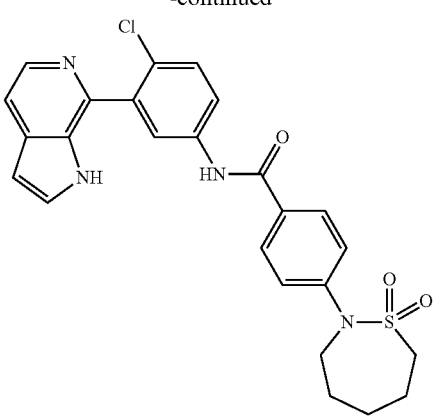
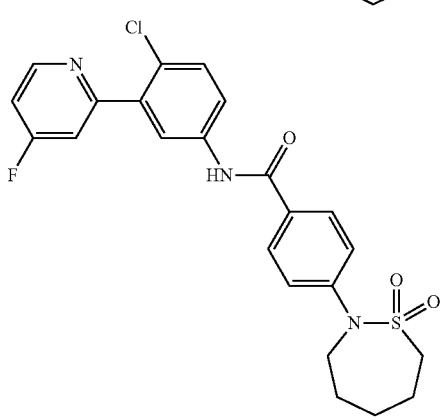
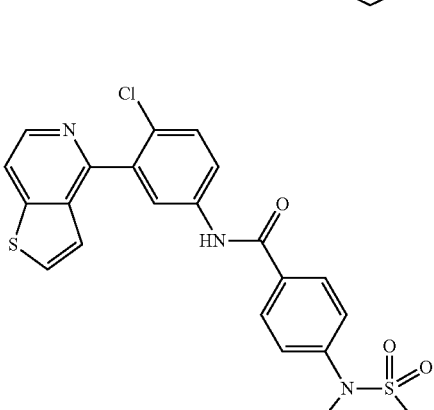
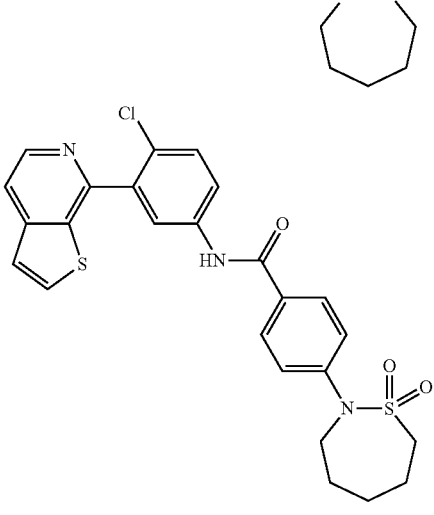

133
-continued
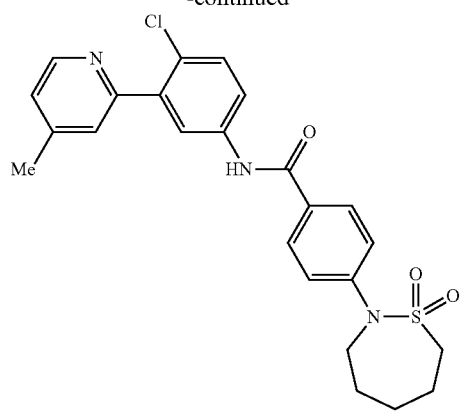
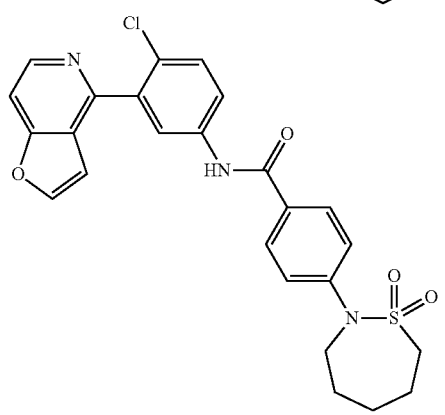
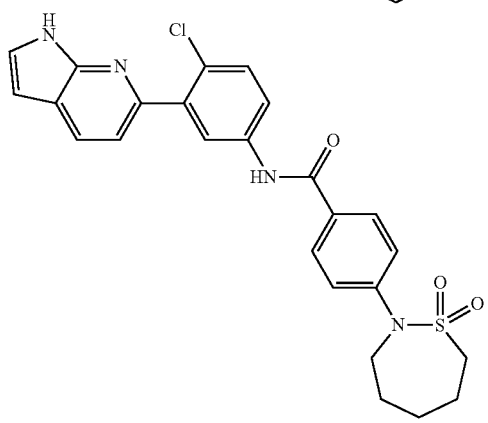
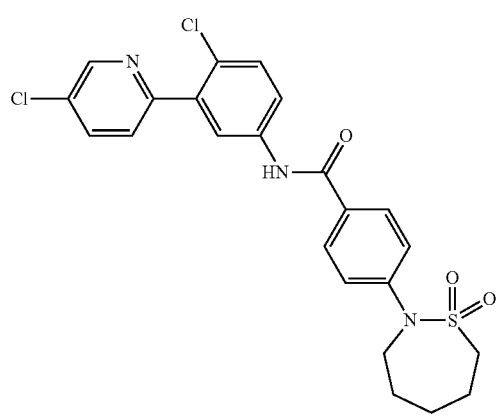
134
-continued
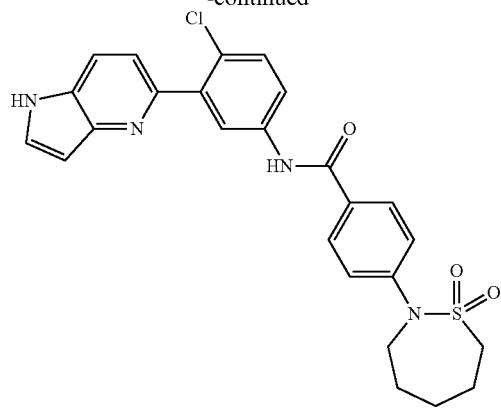
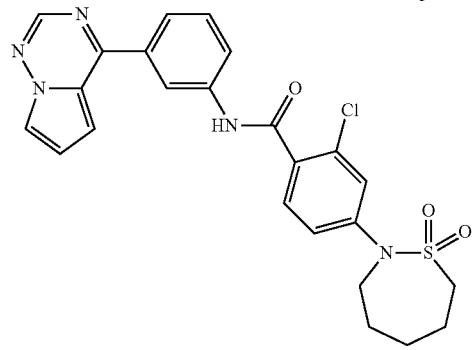
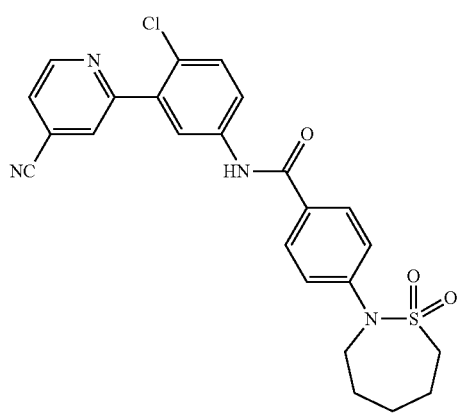
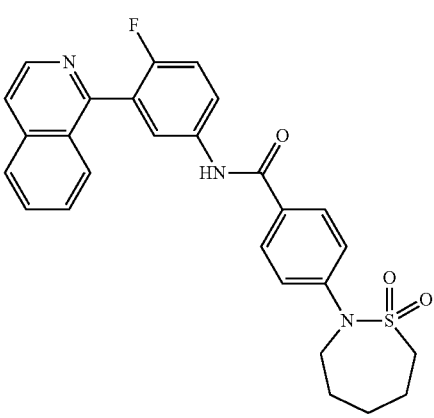

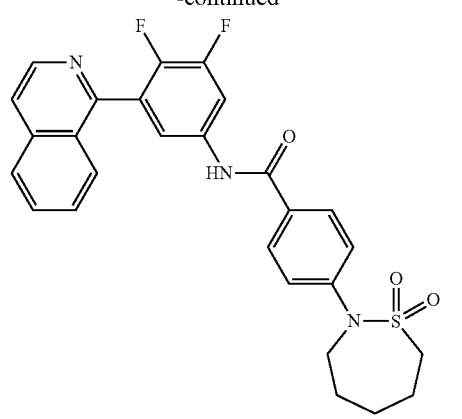
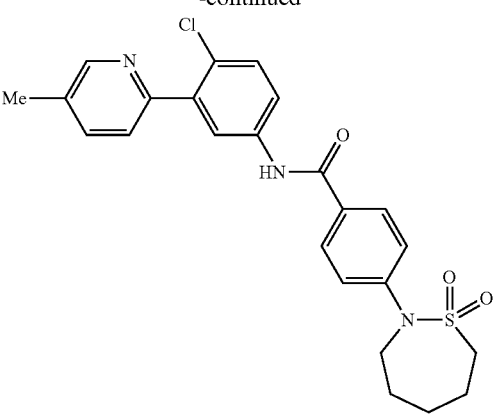
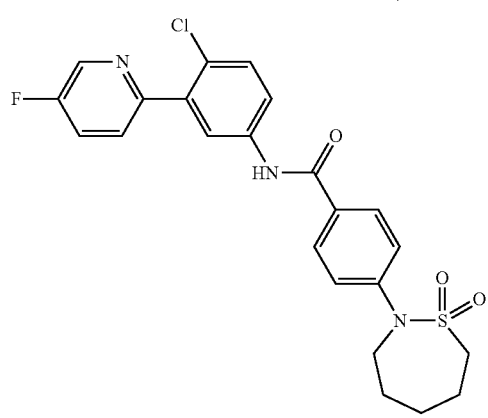
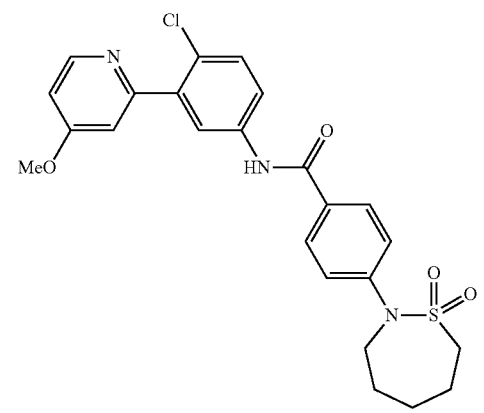
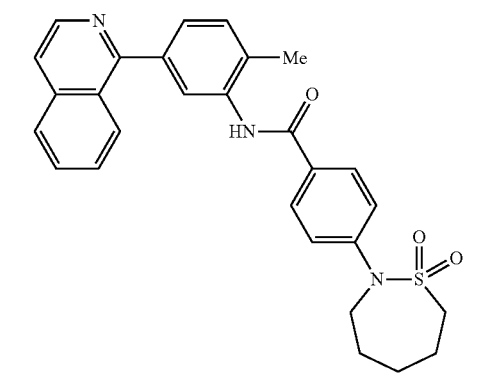
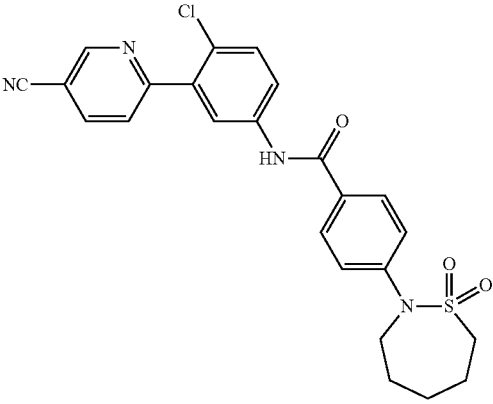
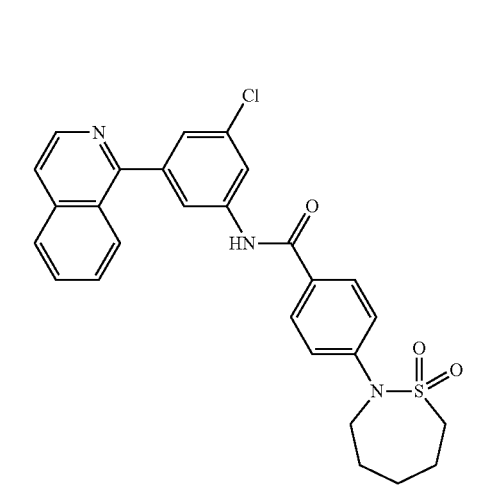
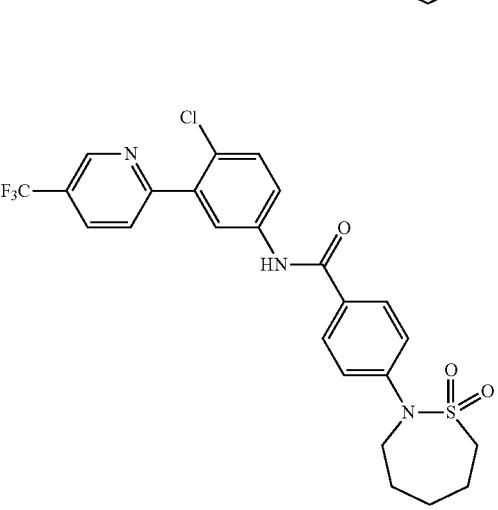

137
-continued
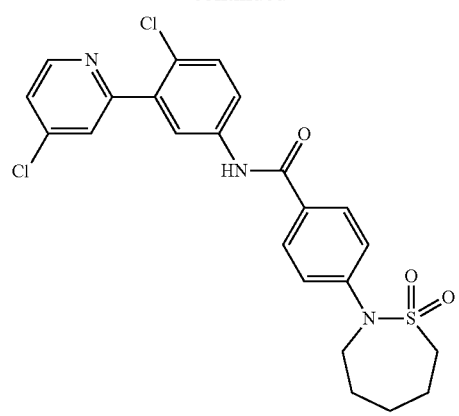
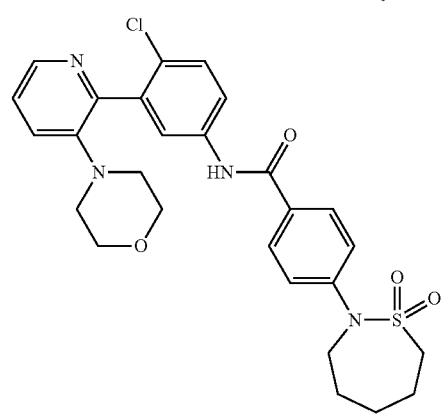
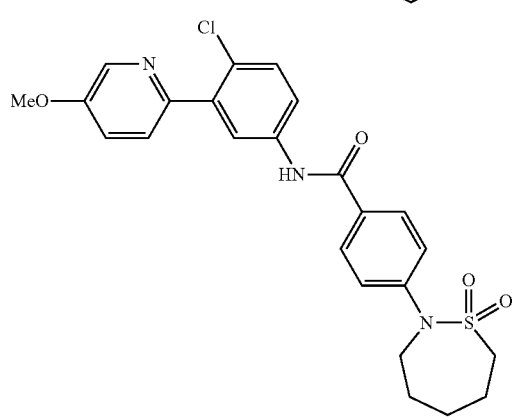
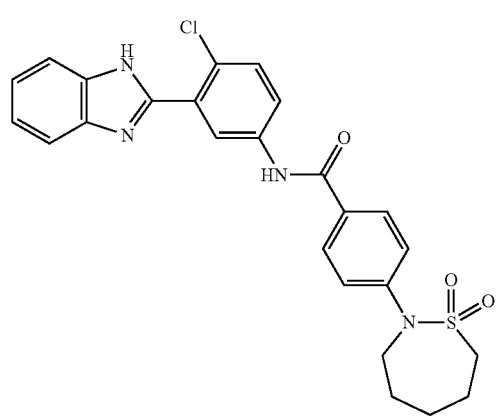
138
-continued
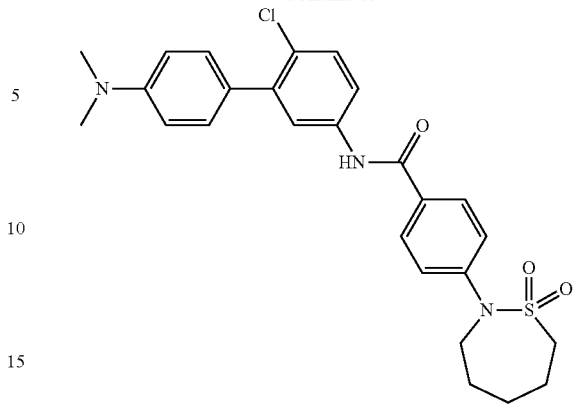
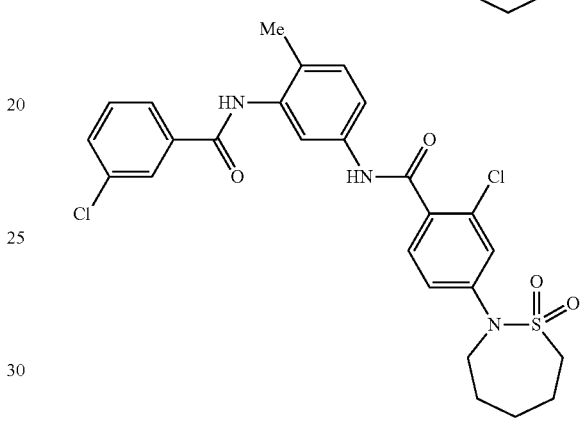
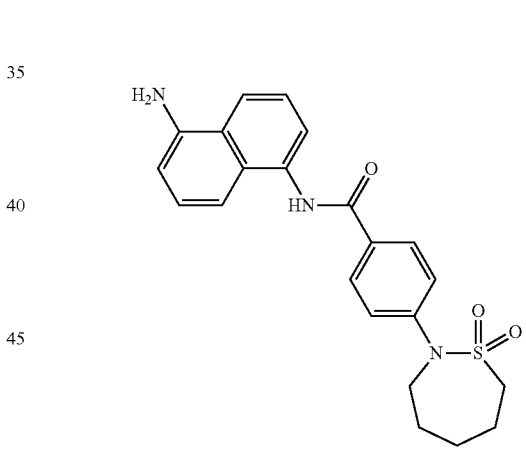
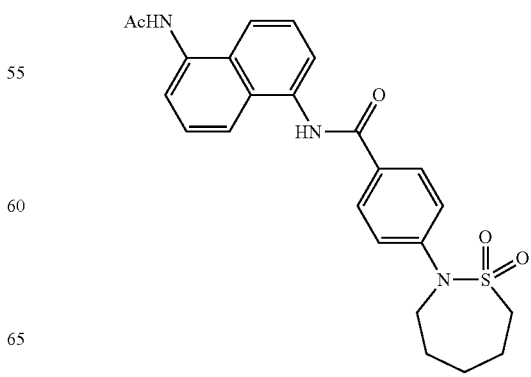

139
-continued
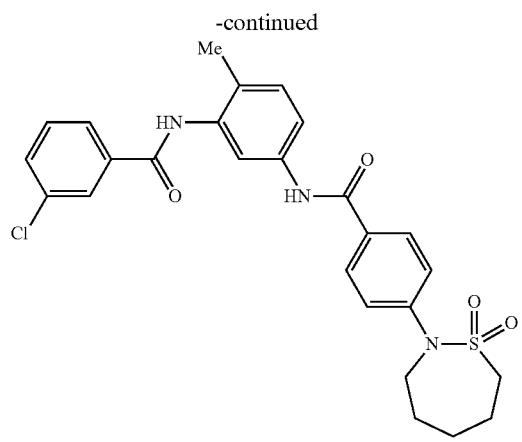
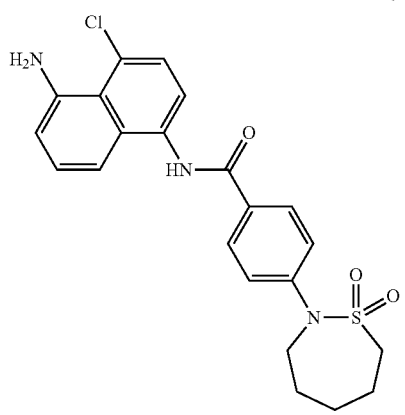
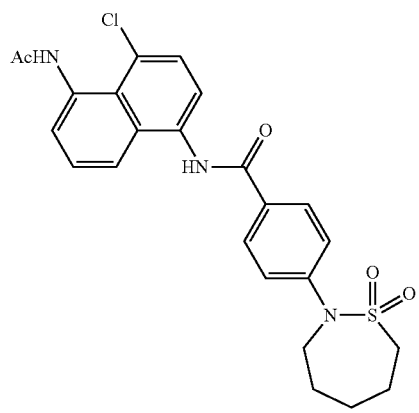
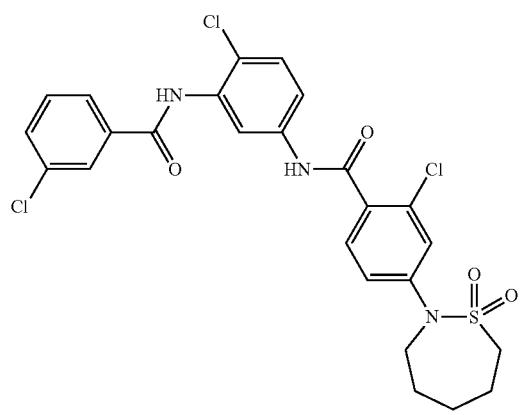
140
-continued
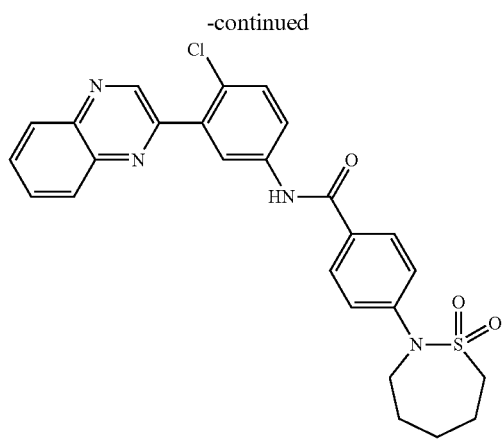
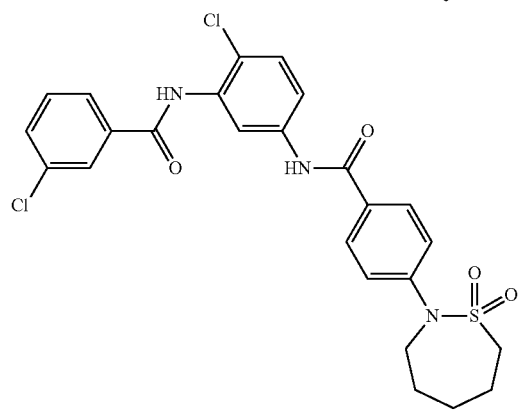
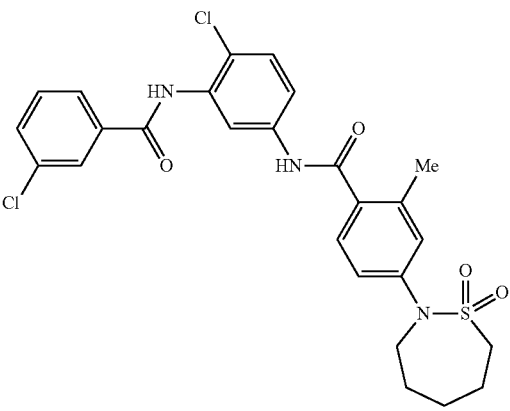
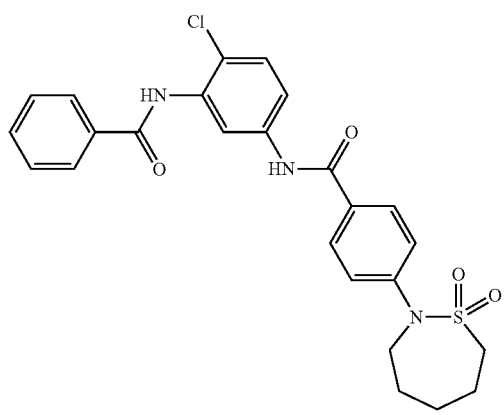

141
-continued
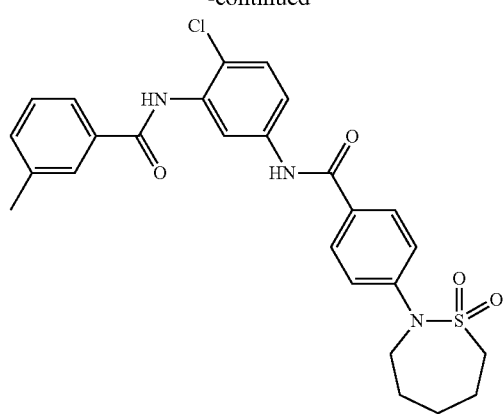
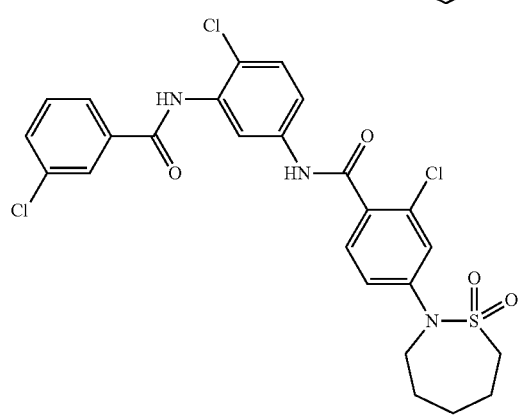
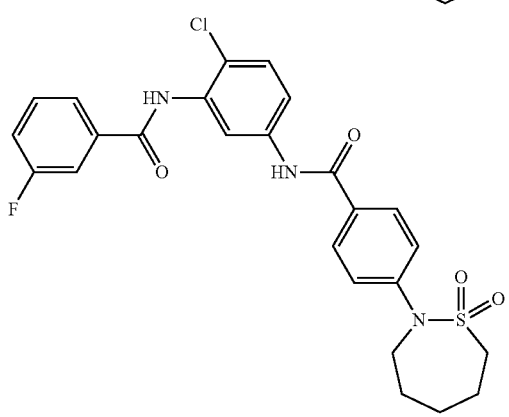
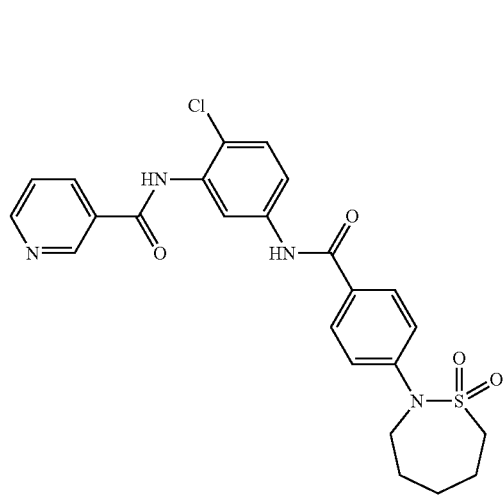
142
-continued
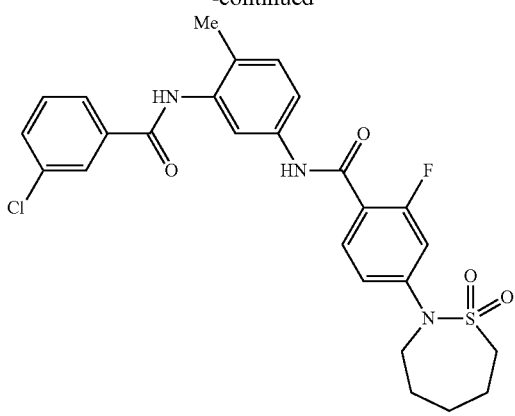
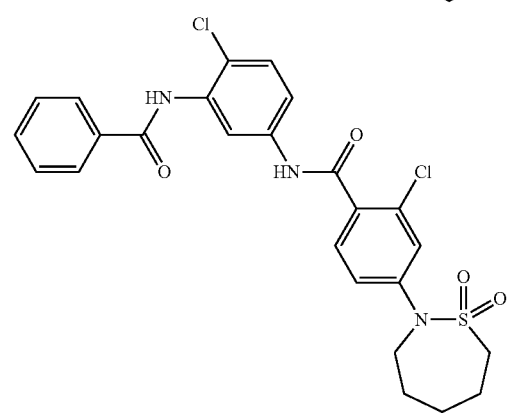
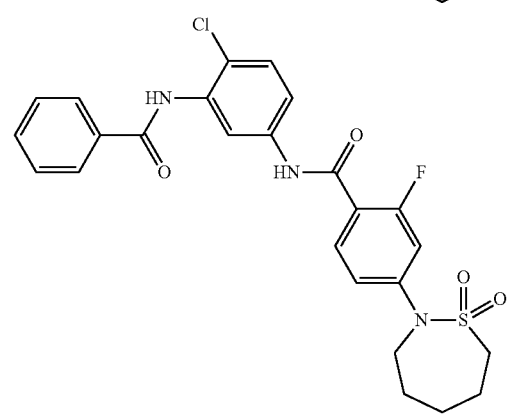
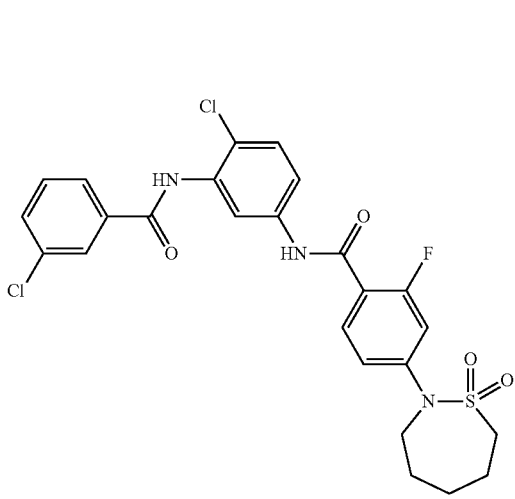

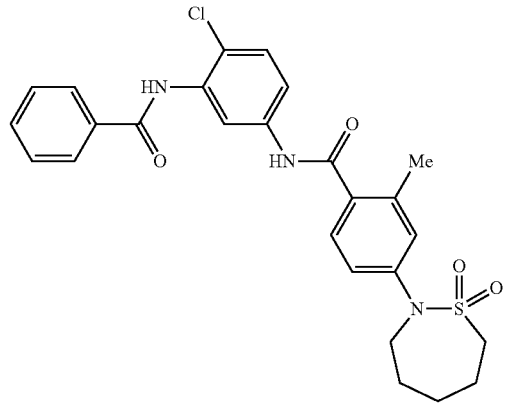
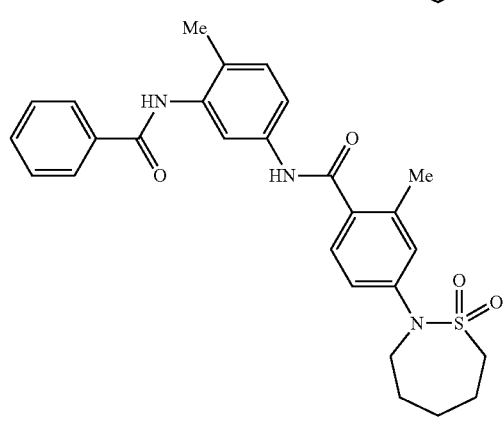
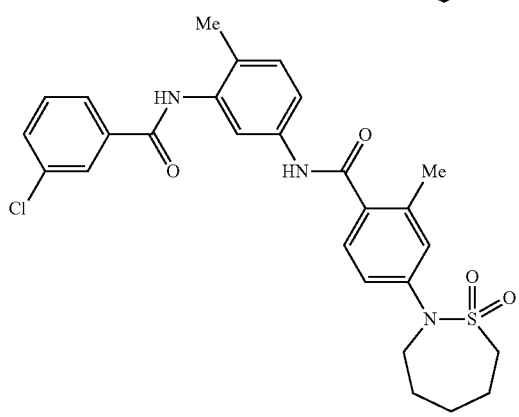
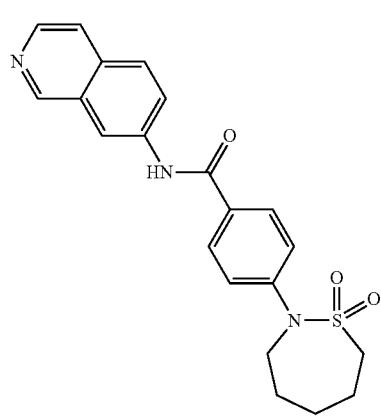
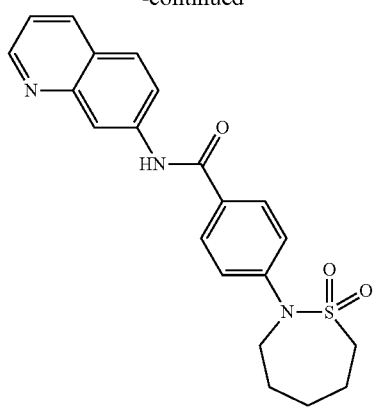
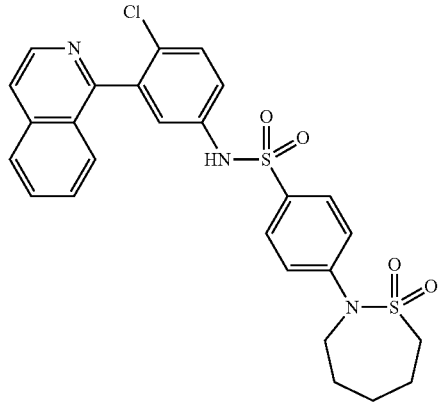
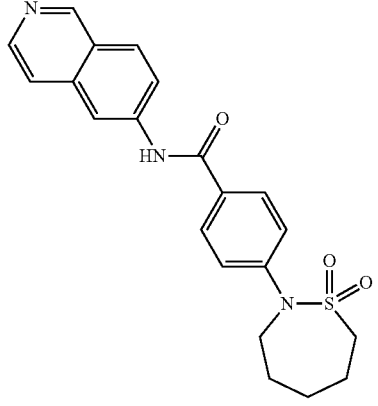
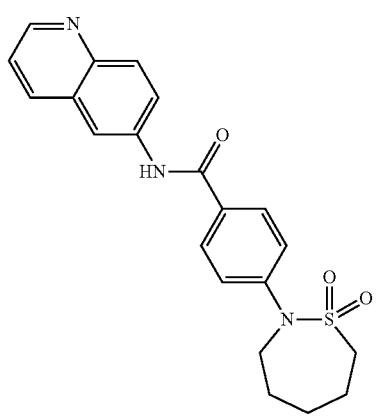

145
-continued
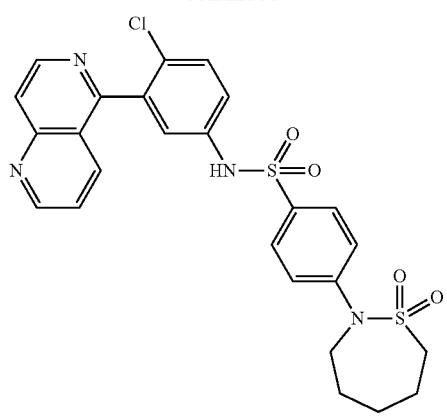
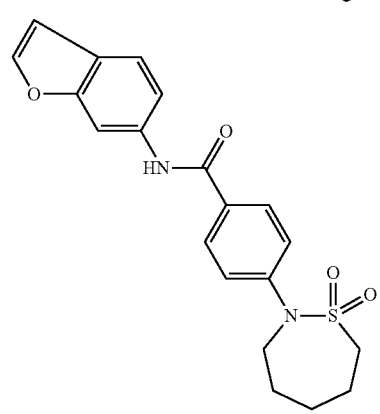
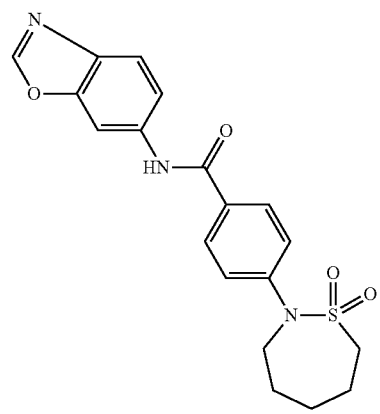
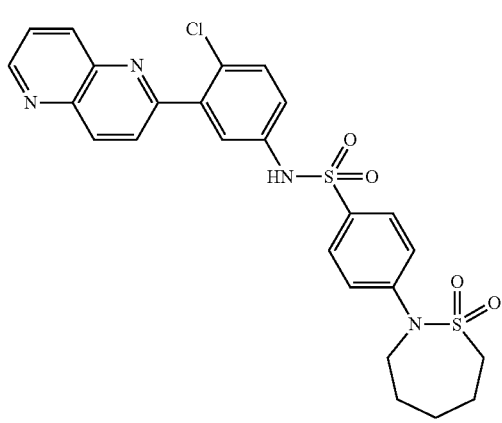
146
-continued
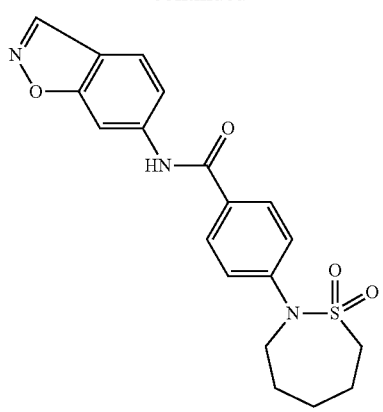
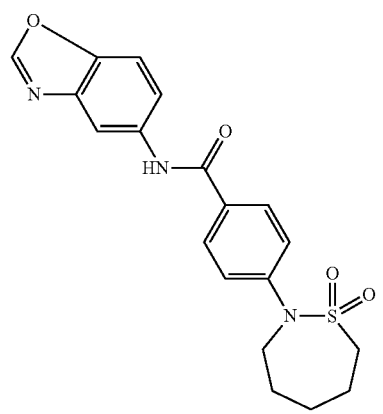
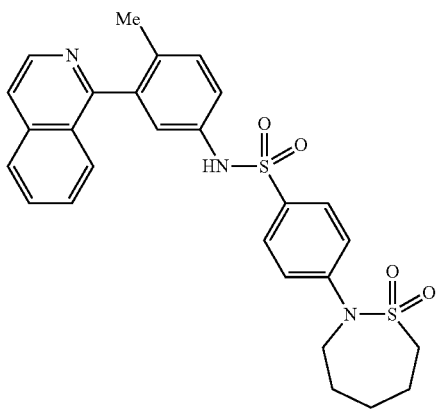
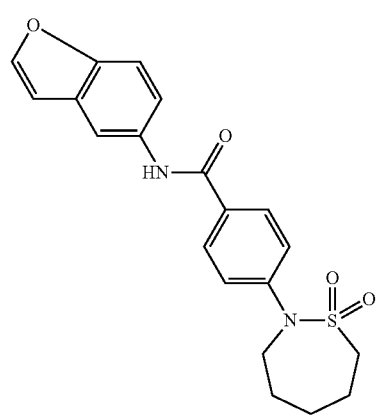

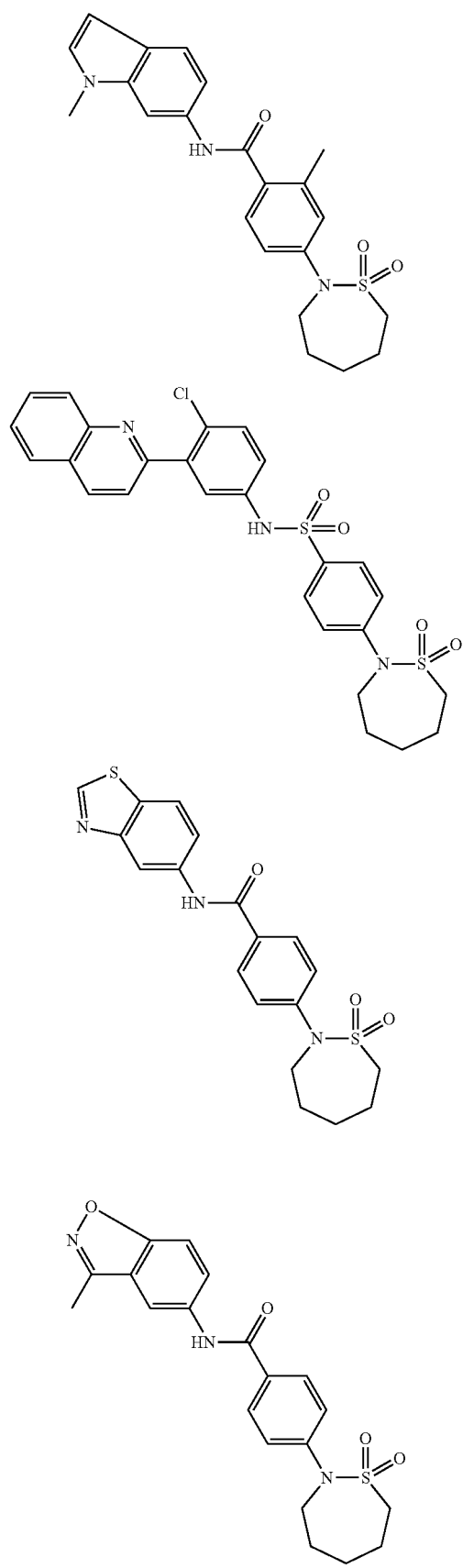

149
-continued
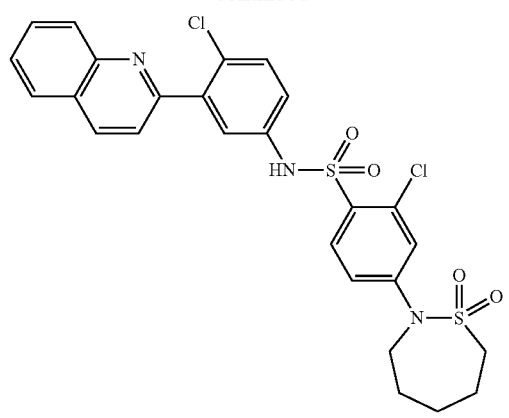
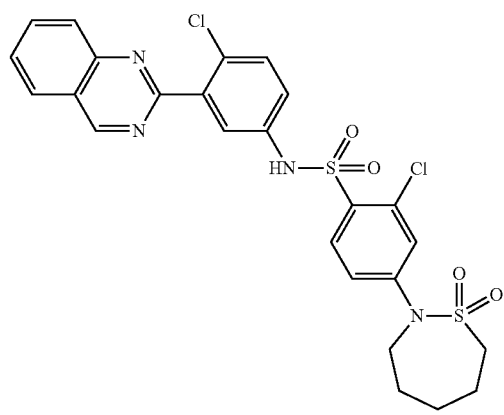
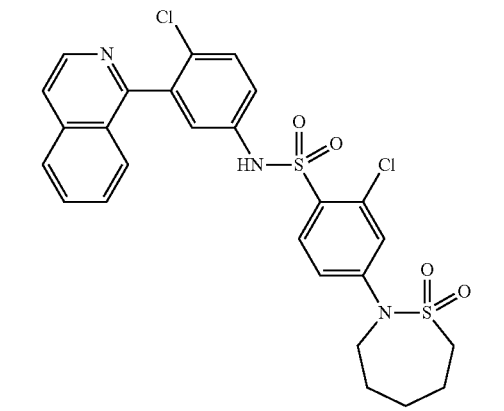
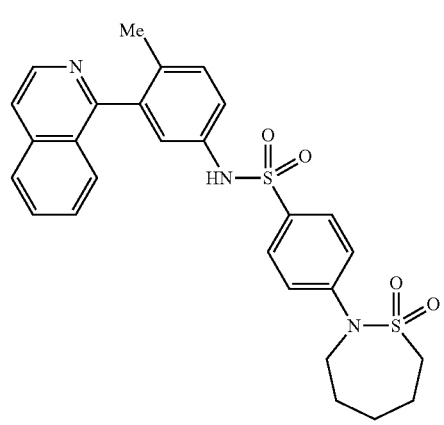
150
-continued
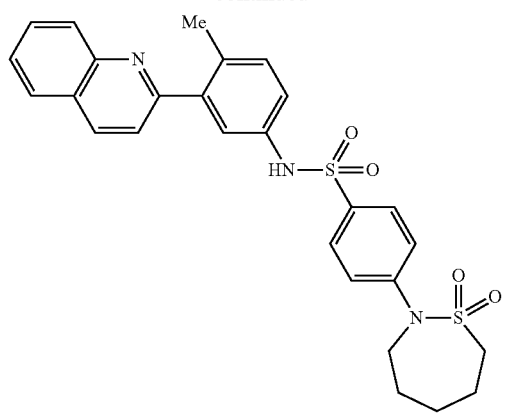
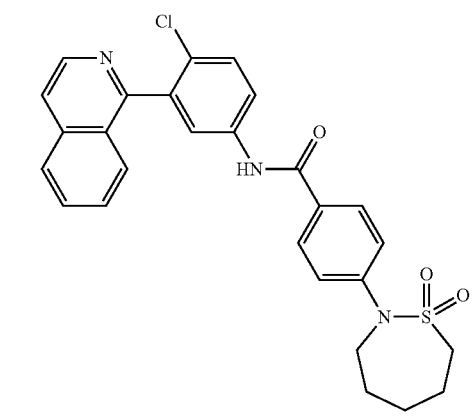
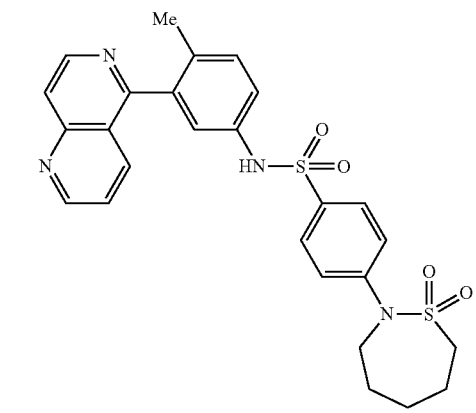
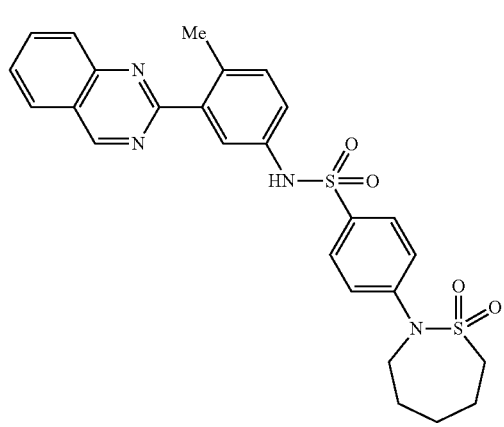

151
-continued
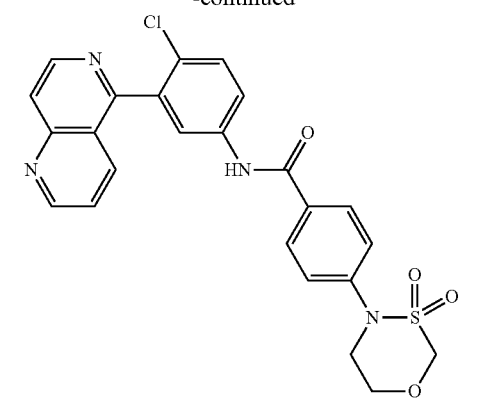
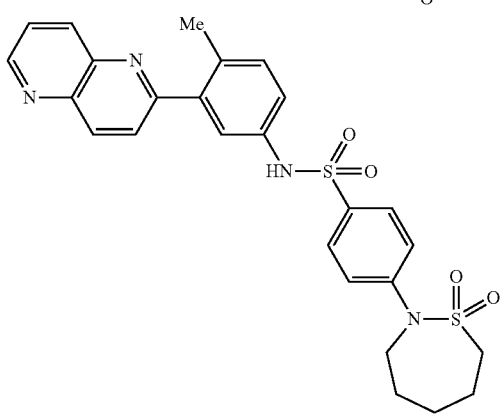
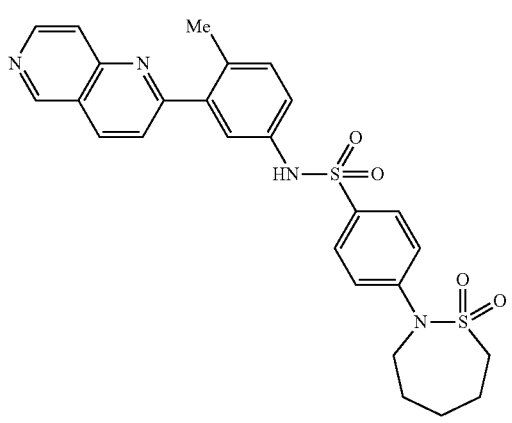
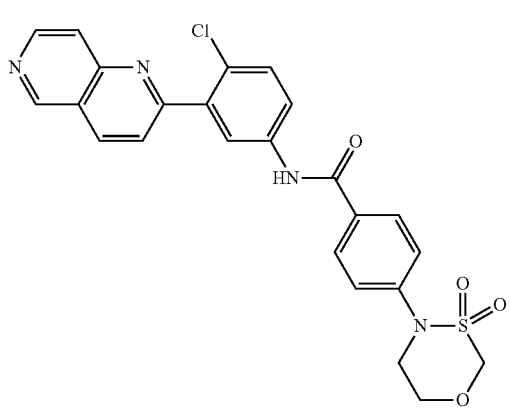
152
-continued
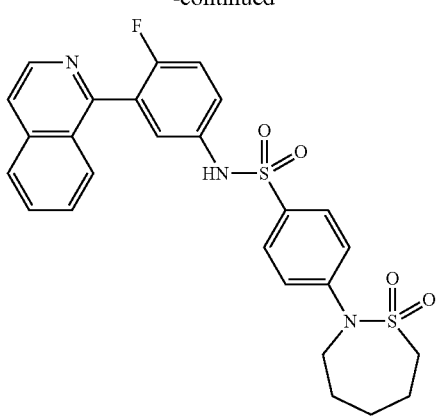
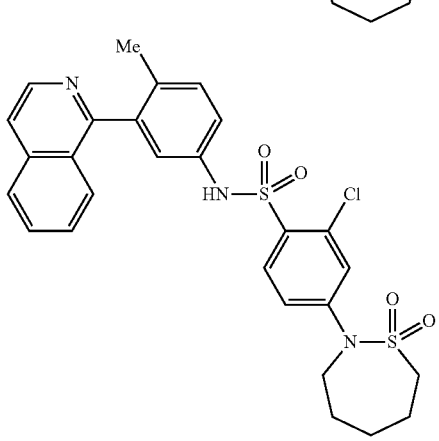
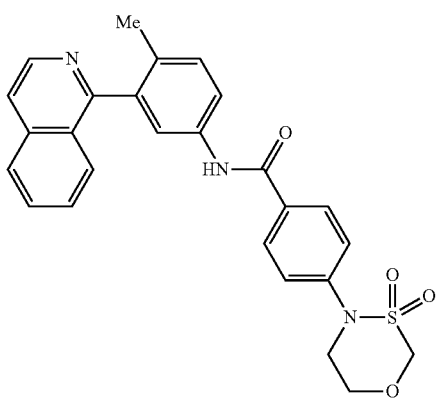
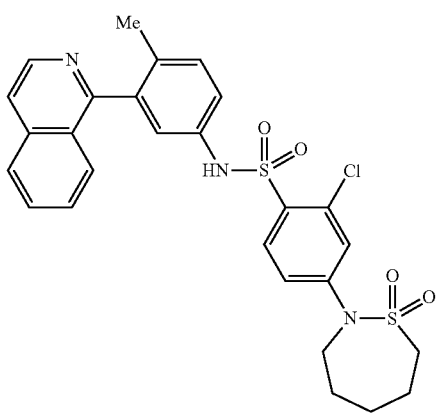

153
-continued
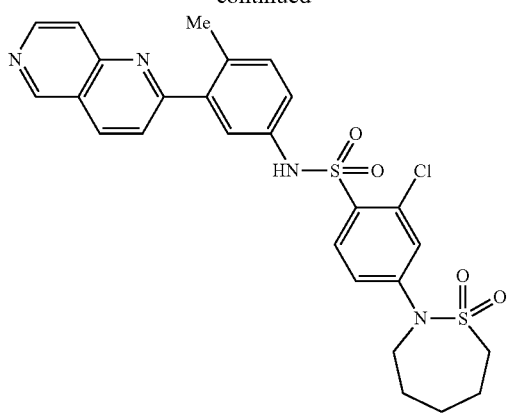
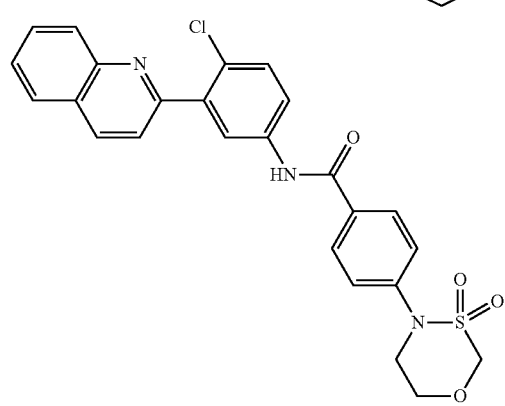
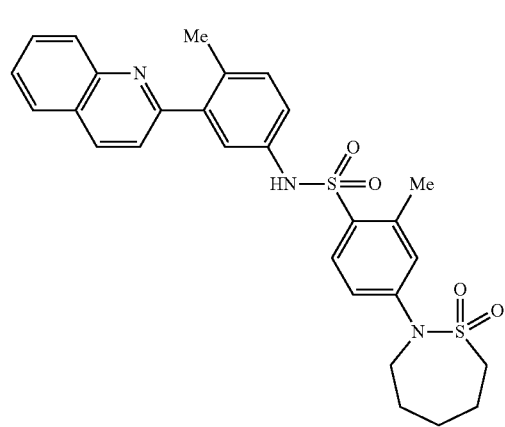
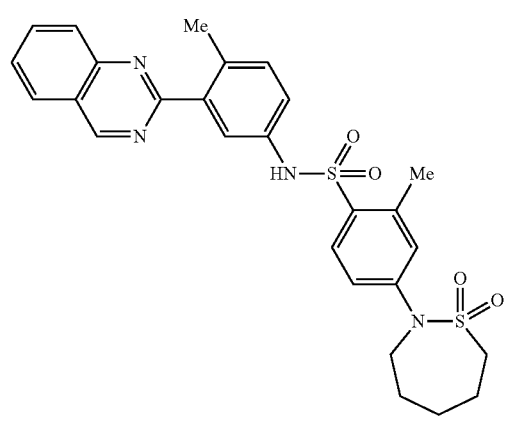
154
-continued
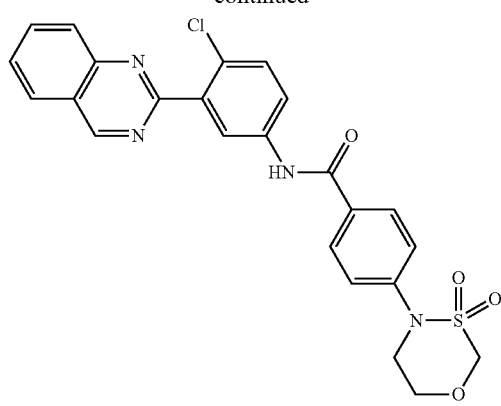
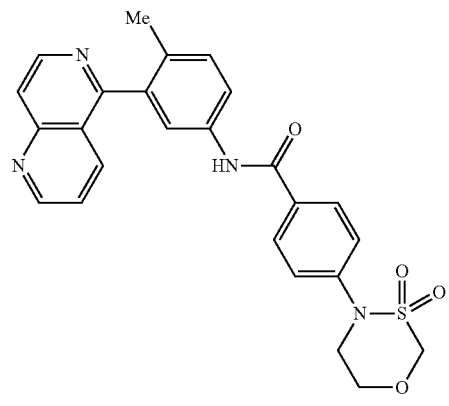
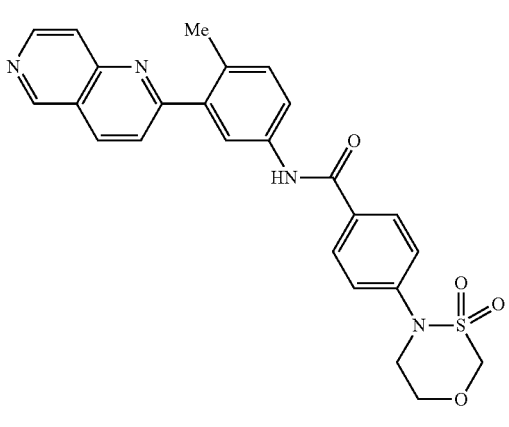
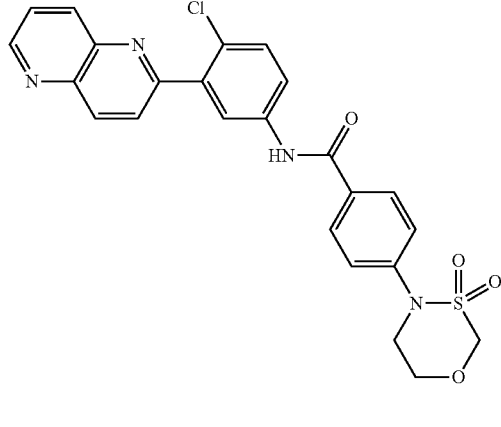

155
-continued
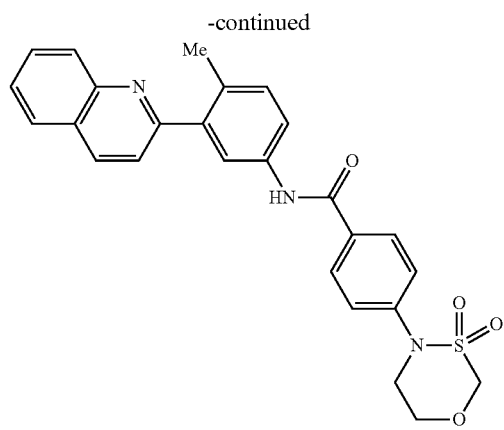
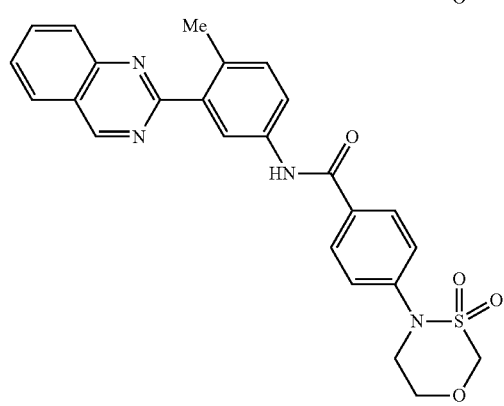
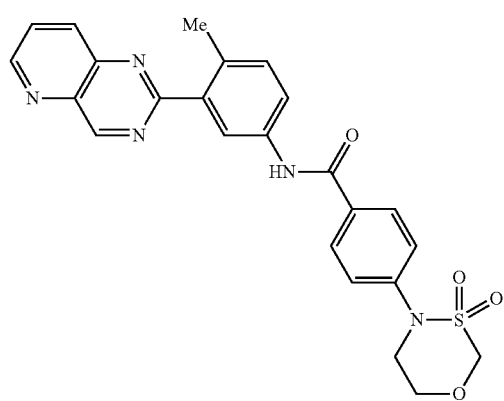
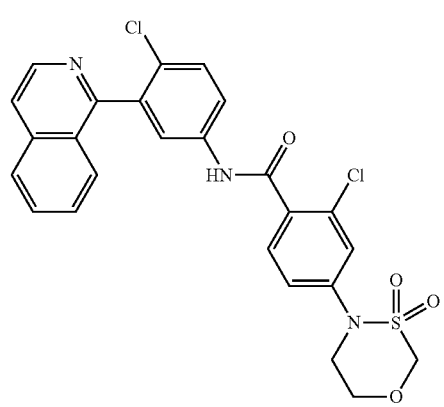
156
-continued
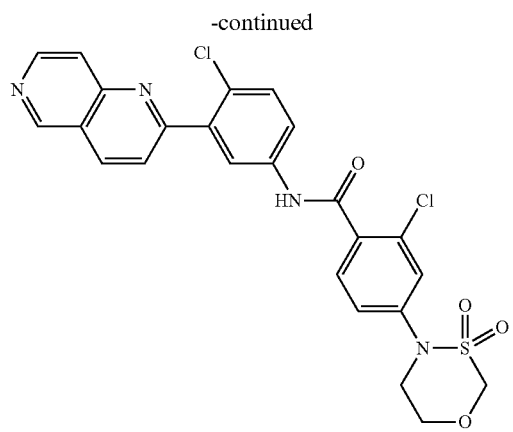
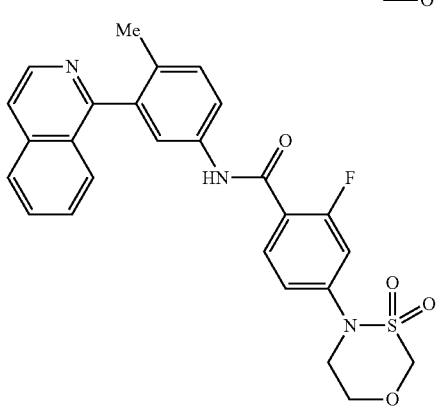
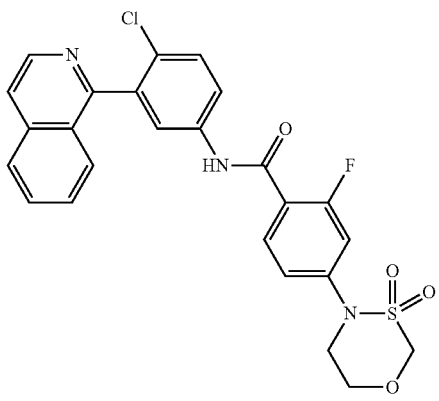
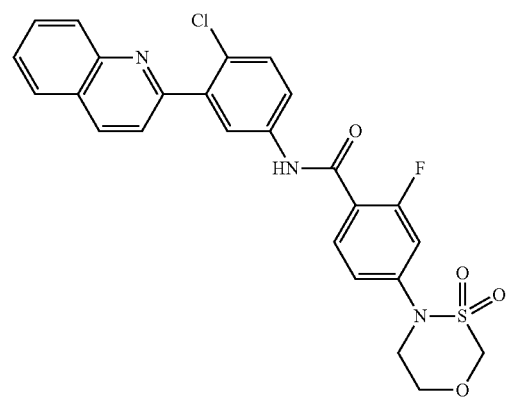

157
-continued
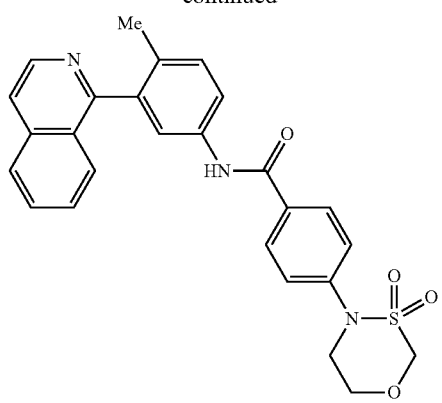
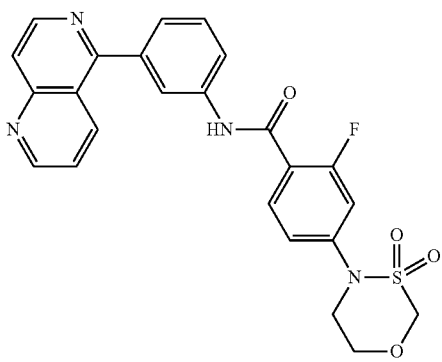
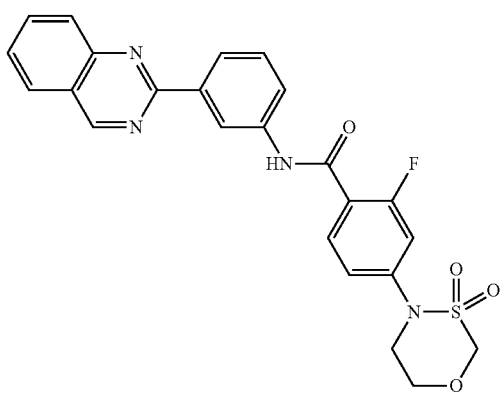
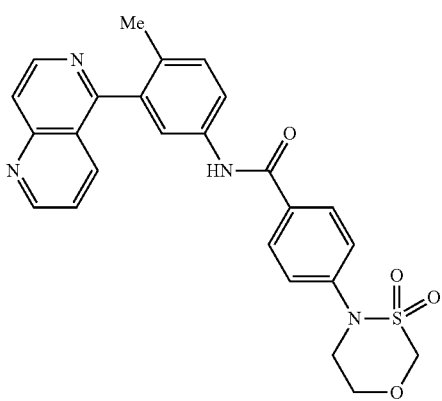
158
-continued
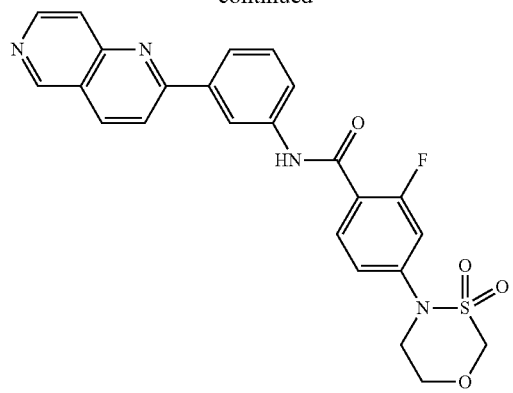
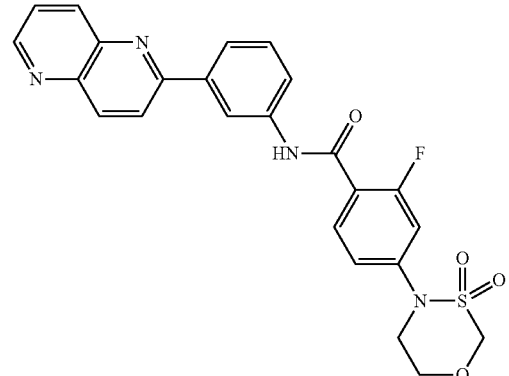
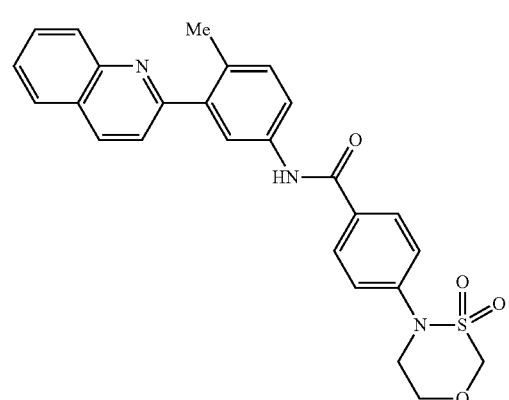
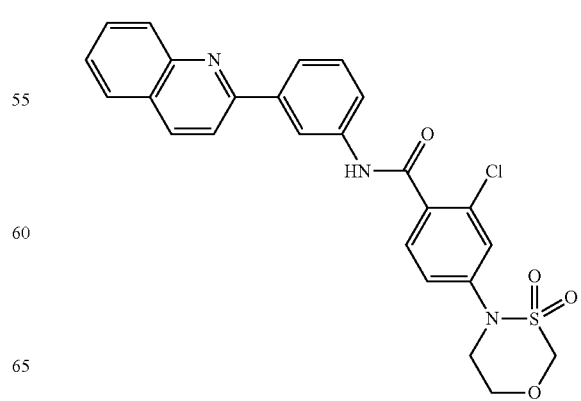

159
-continued
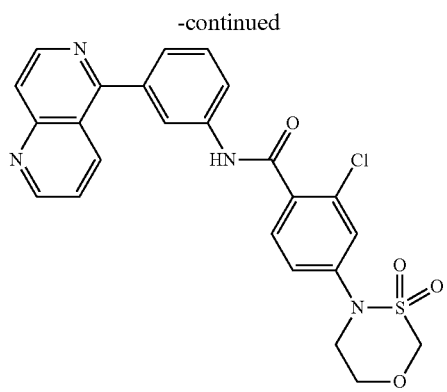
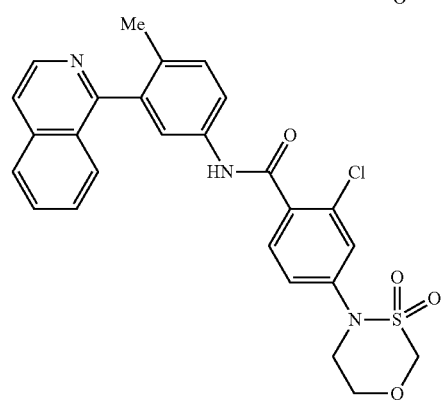
160
-continued
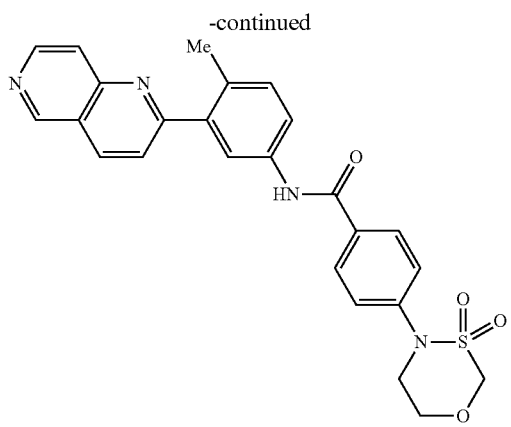
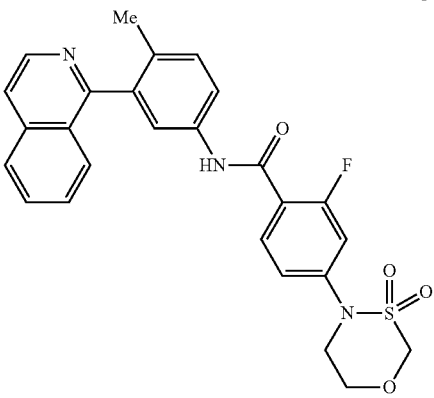
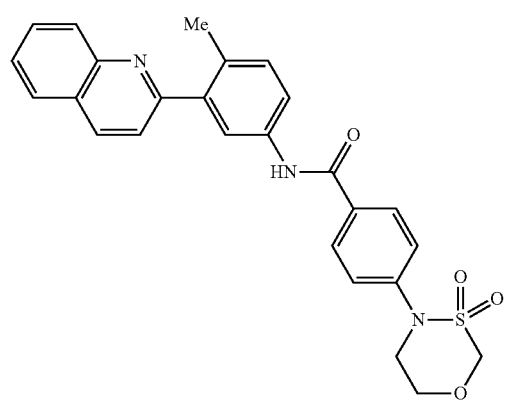

161
-continued
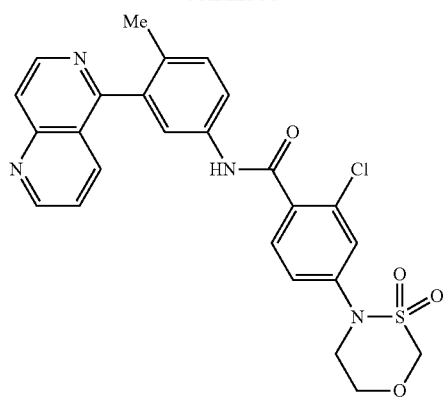
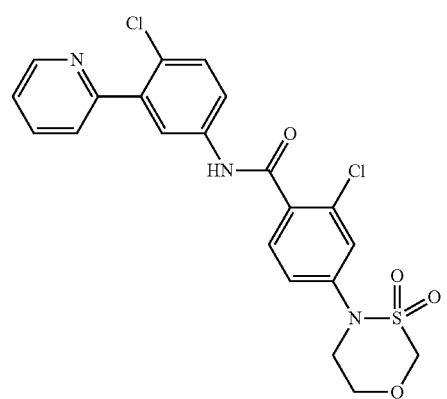
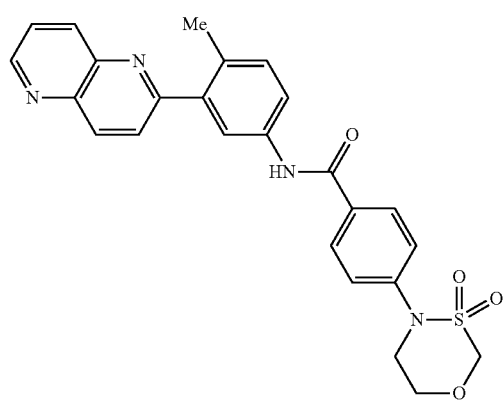
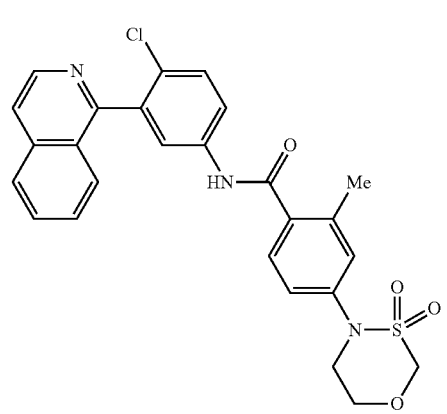
162
-continued
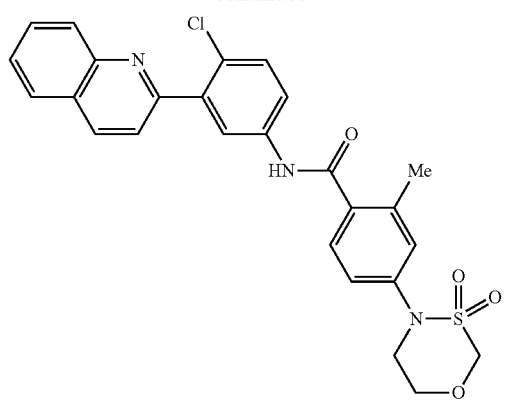
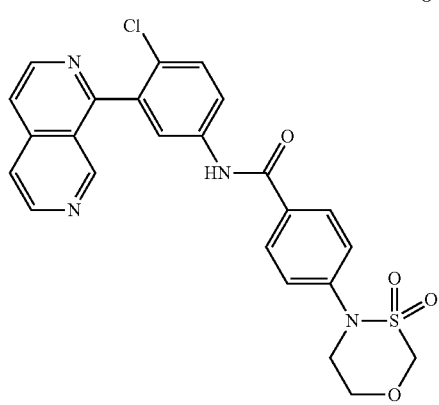

163
-continued
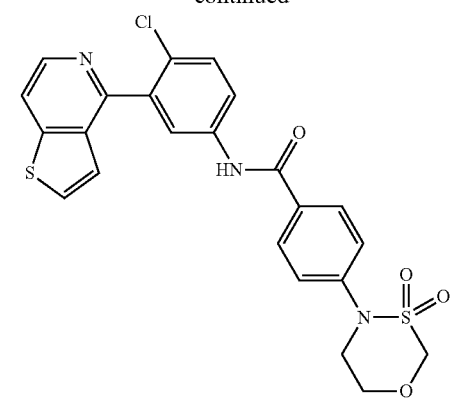
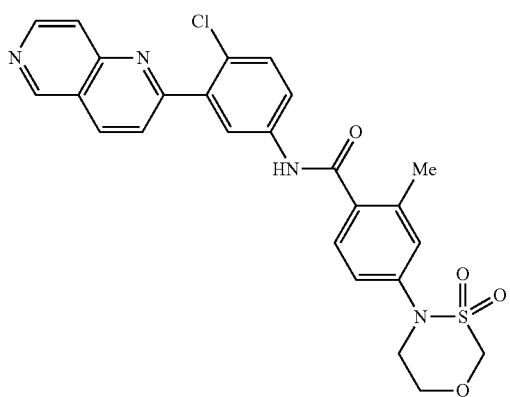
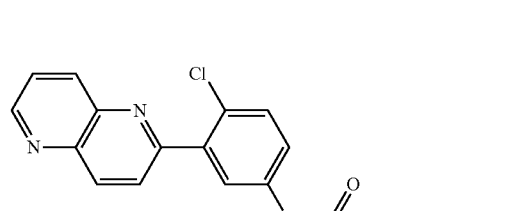
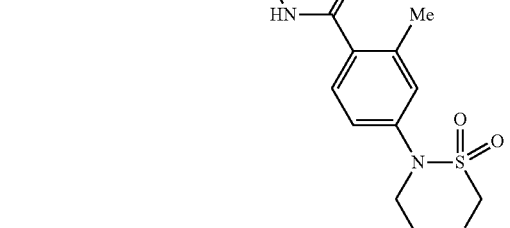
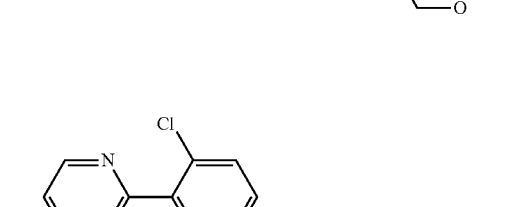
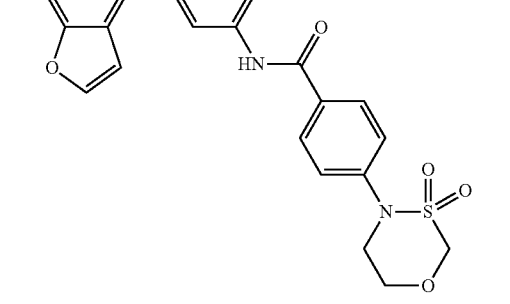
164
-continued
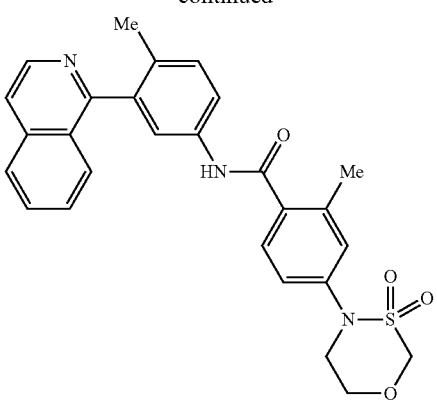
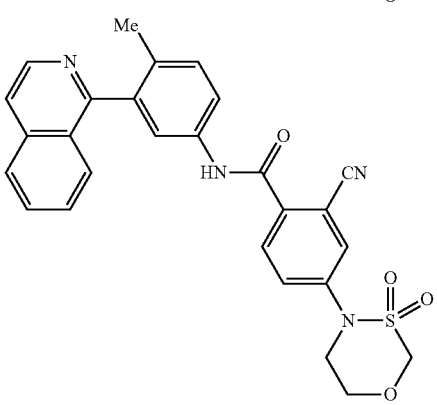
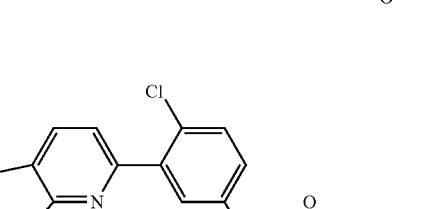
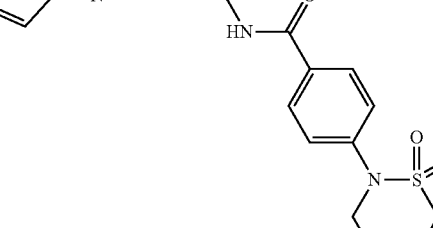
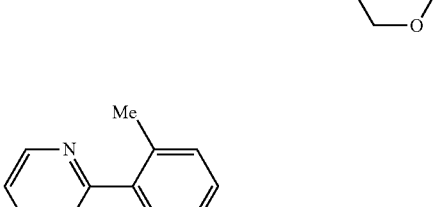
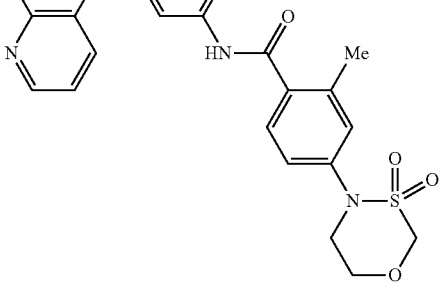

165
-continued
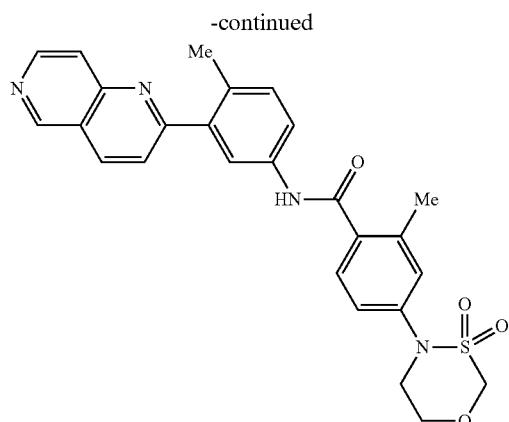
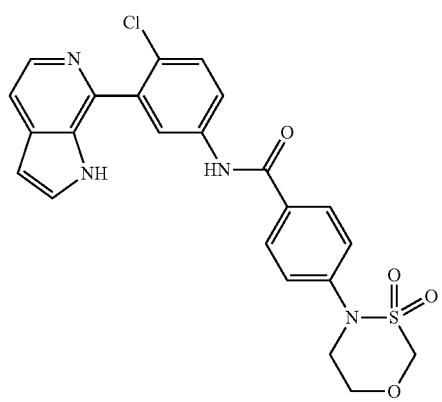
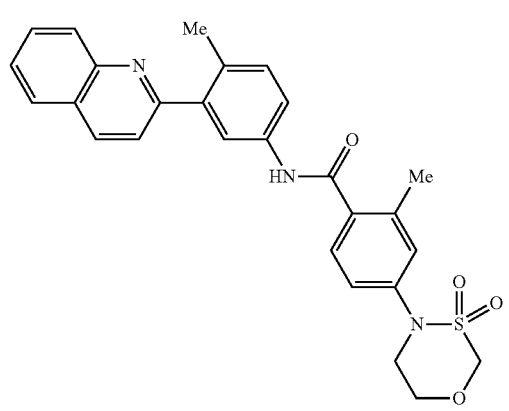
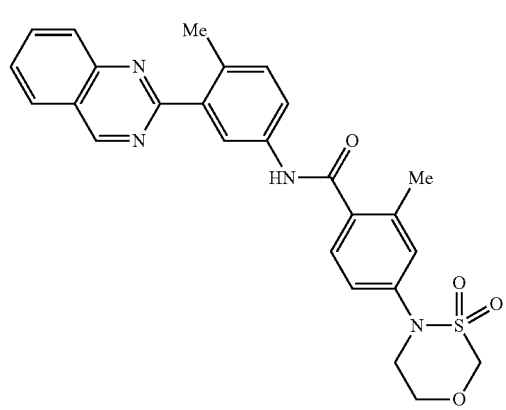
166
-continued
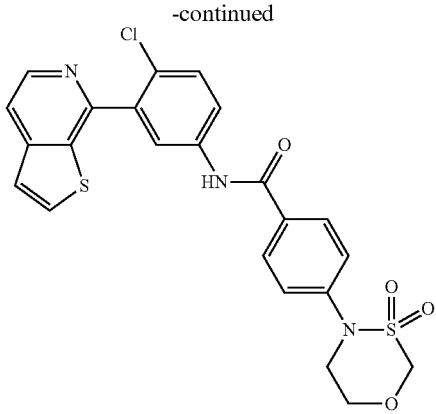
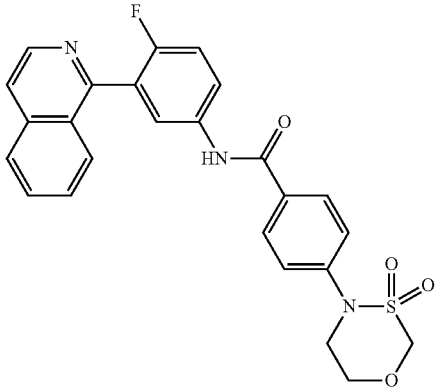
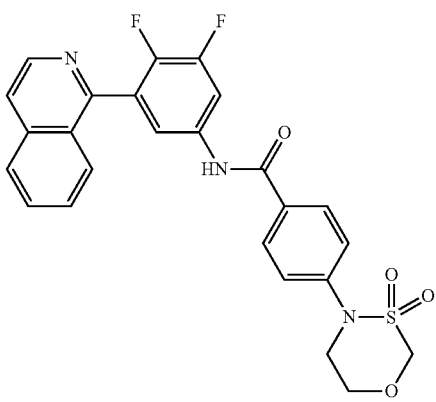
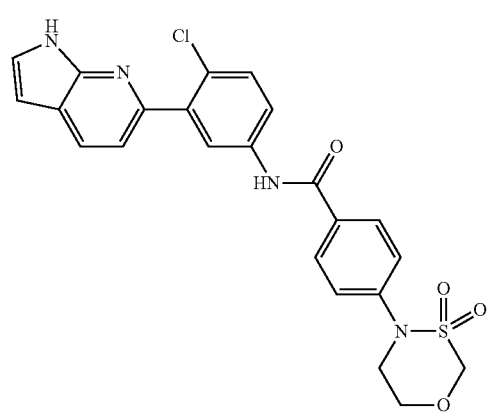

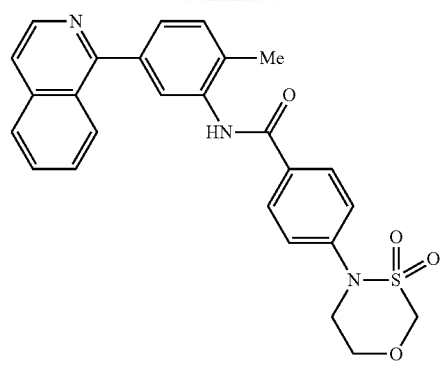
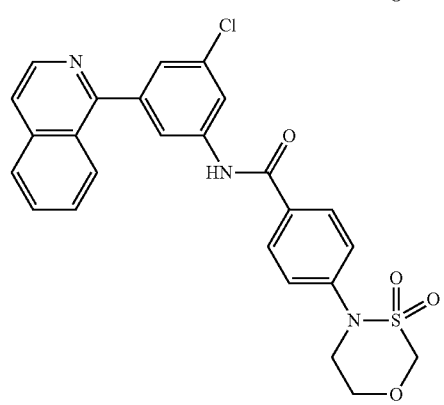
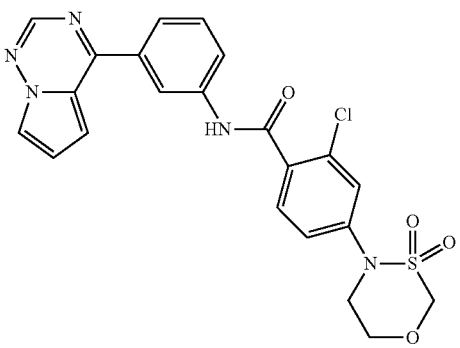
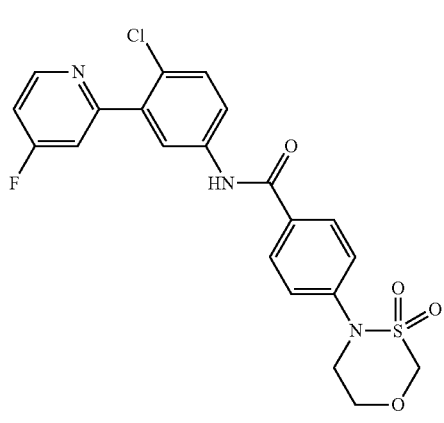
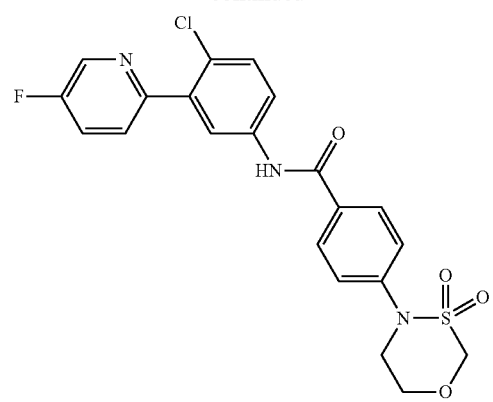
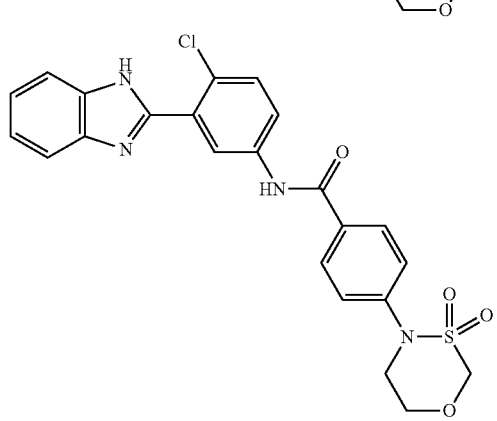
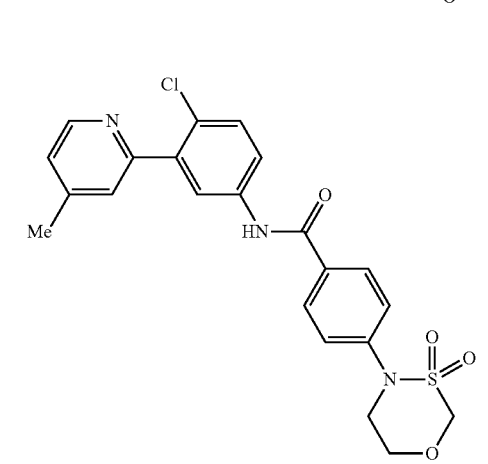
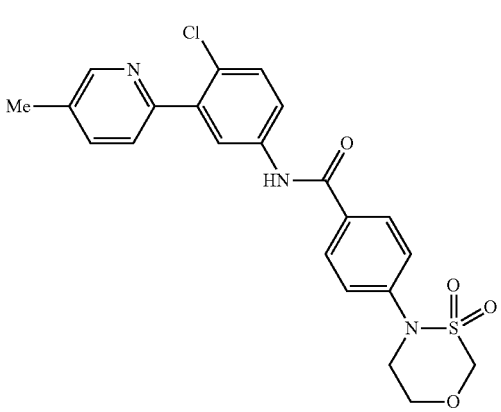

169
-continued
170
-continued
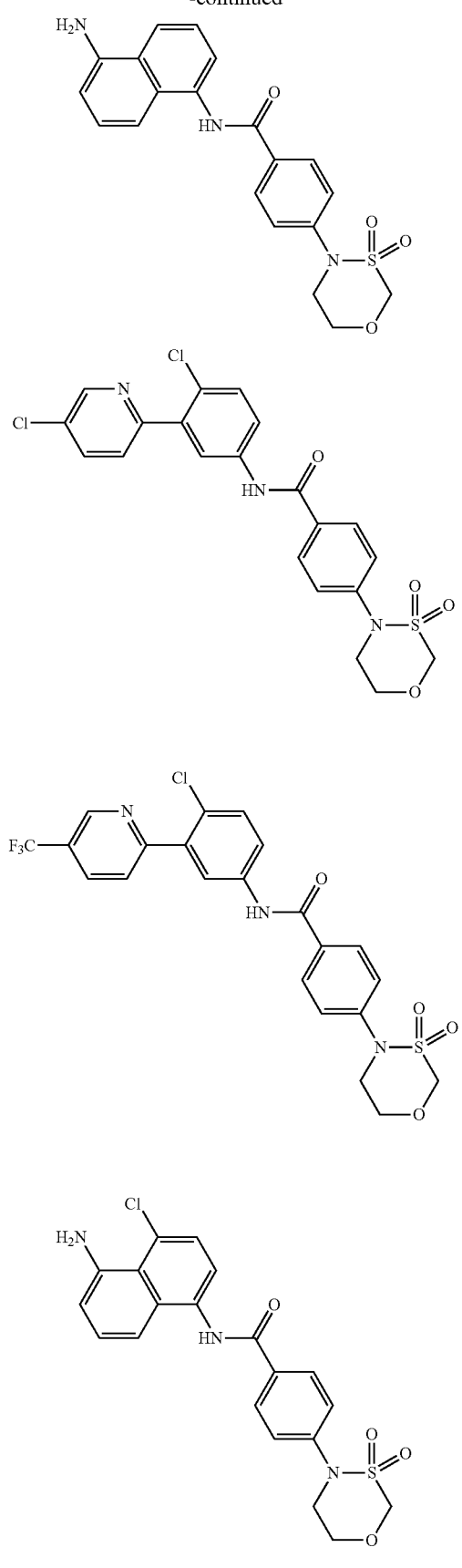

171
-continued
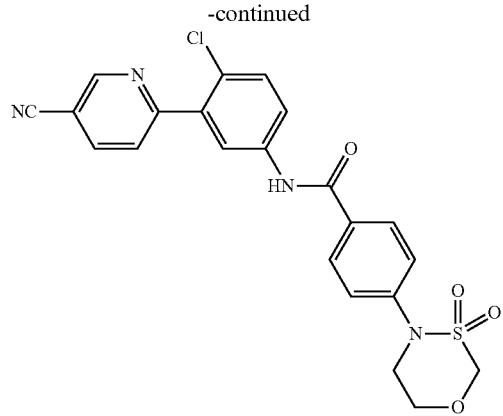
172
-continued
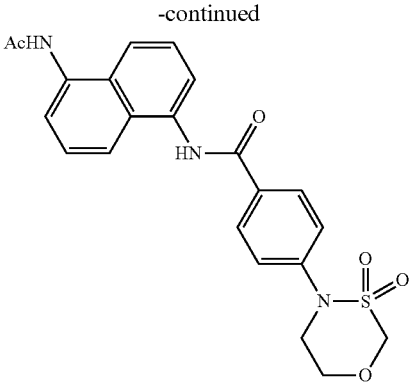
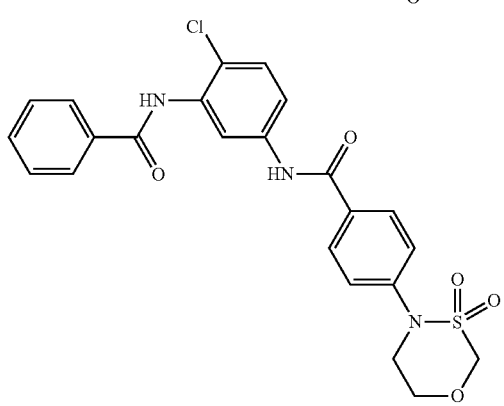
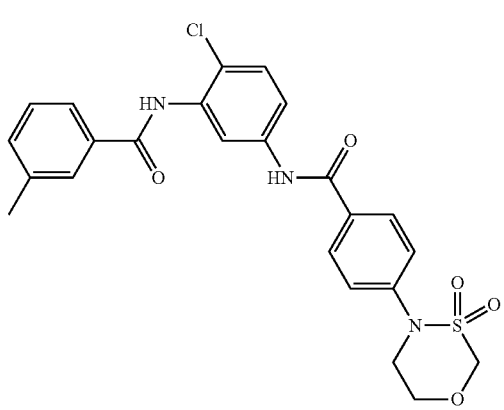
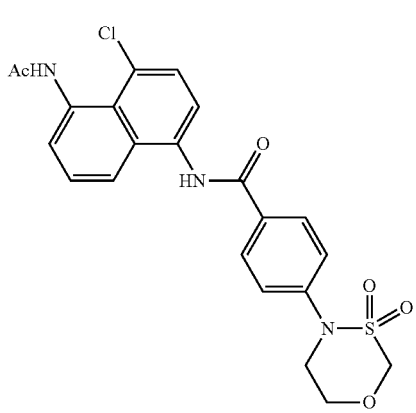

173
-continued
174
-continued
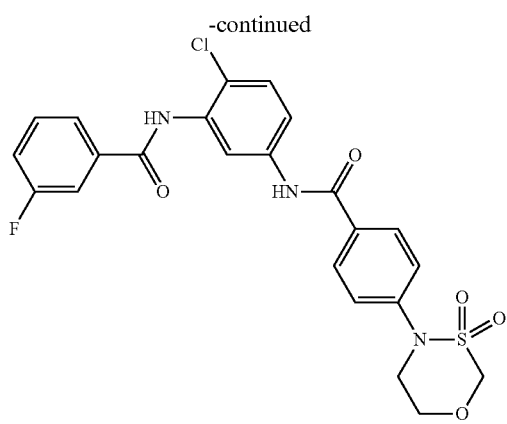
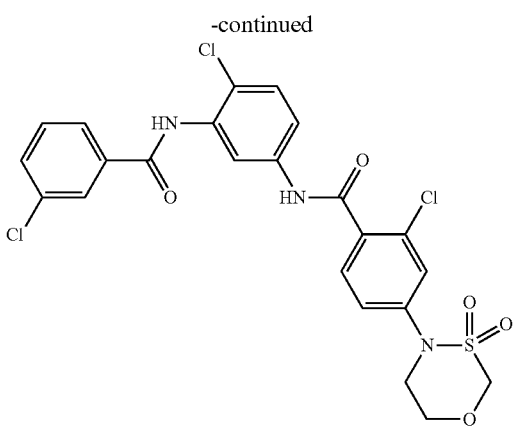
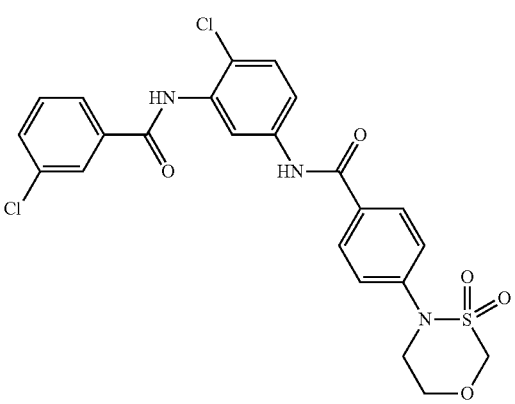
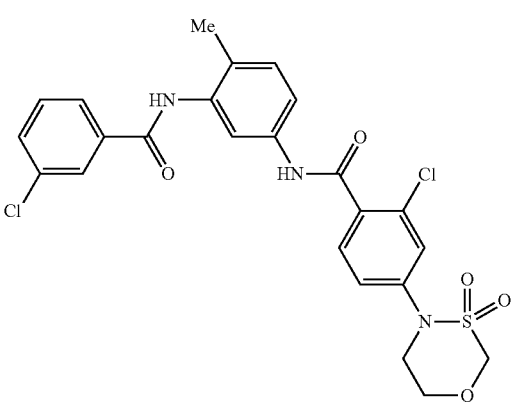

175
-continued
176
-continued
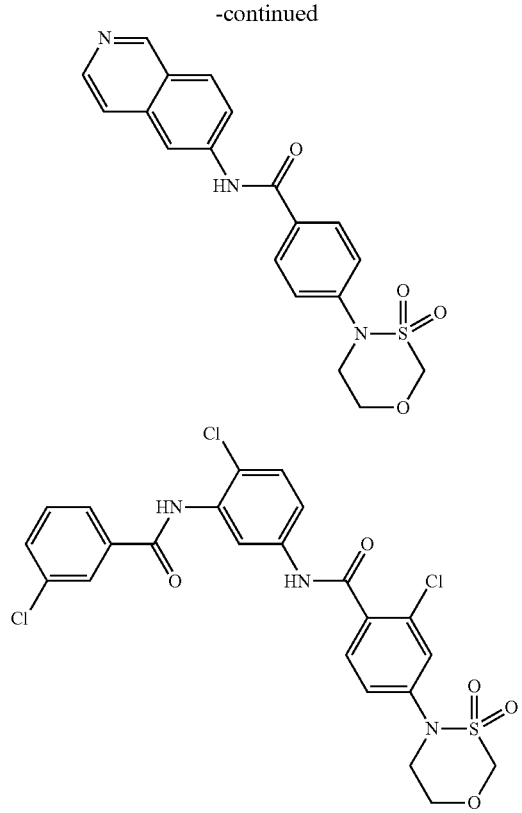
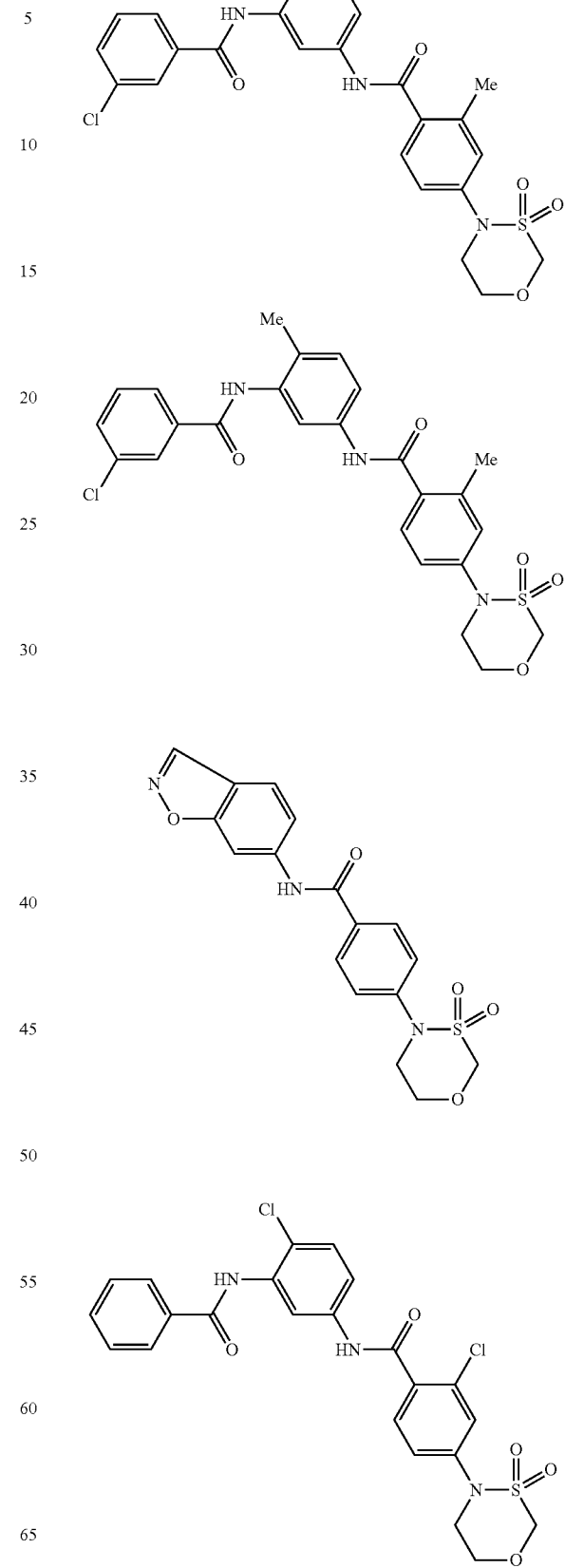

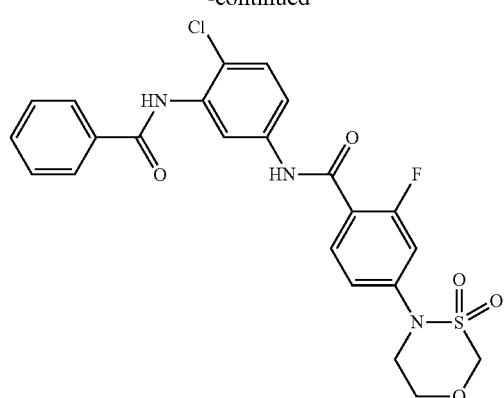
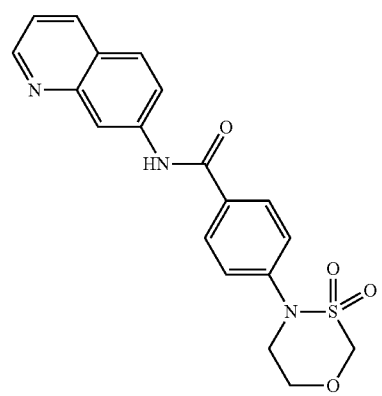
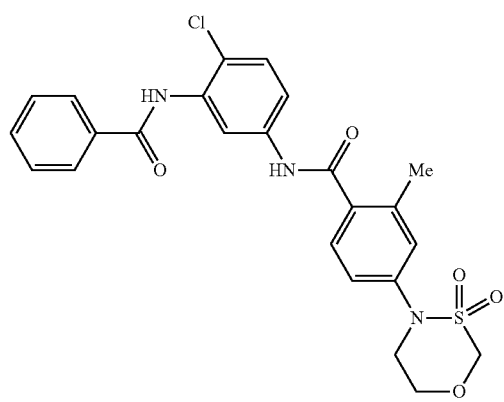
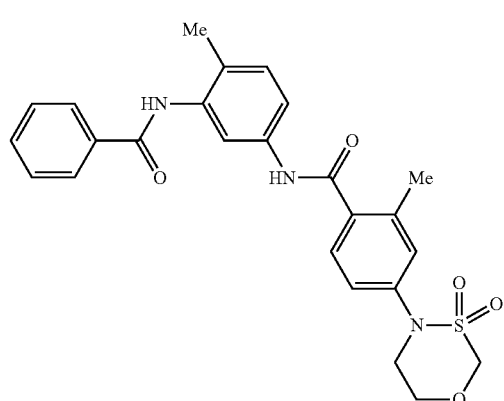
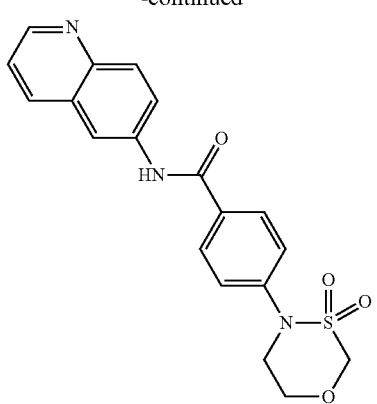
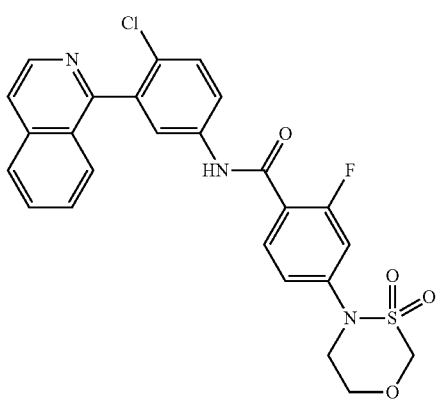
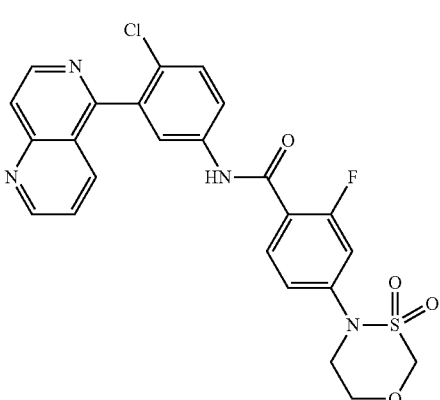
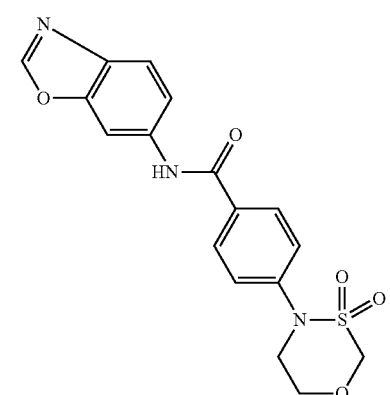

179
-continued
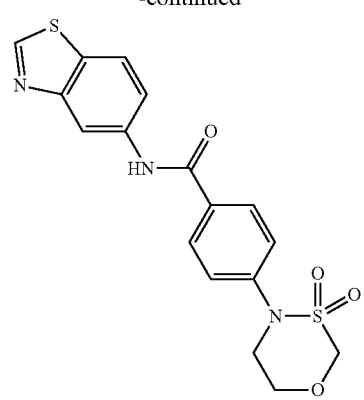
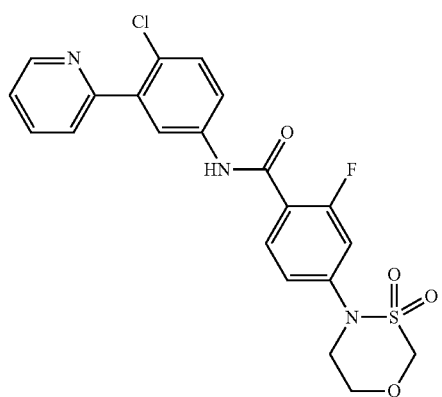
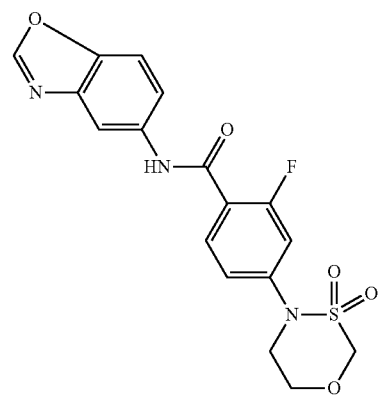
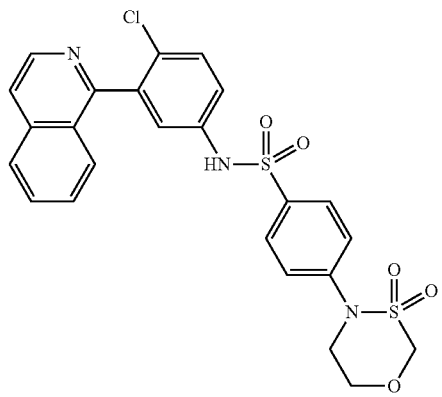
180
-continued
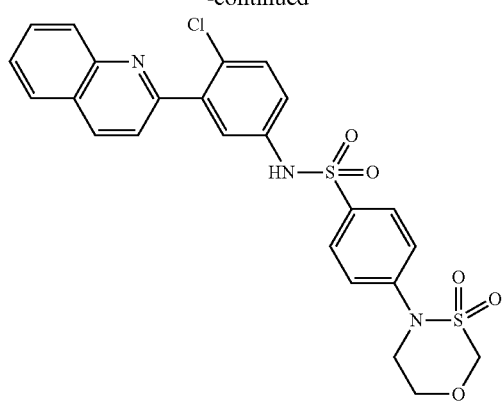
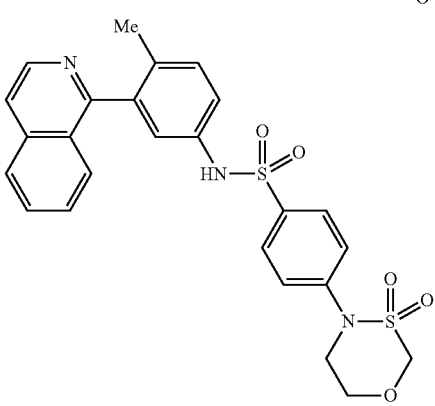
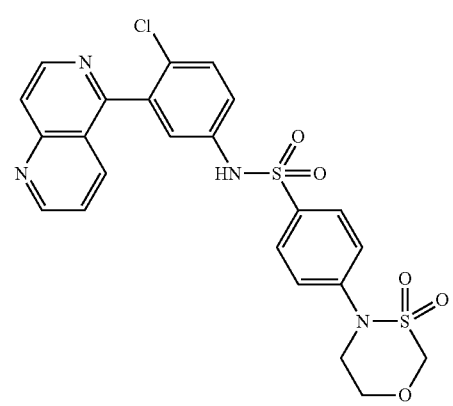
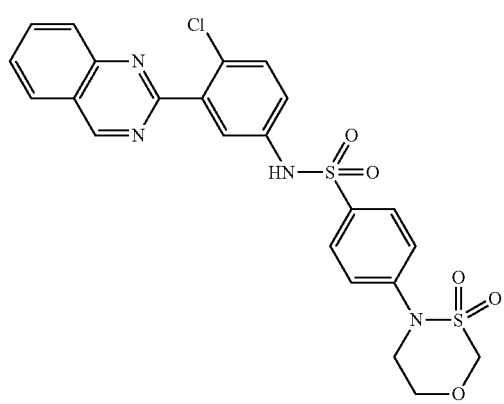

181
-continued
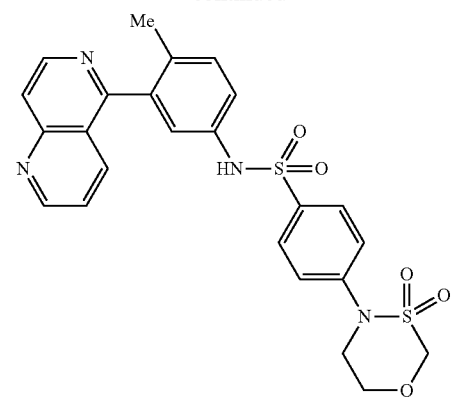
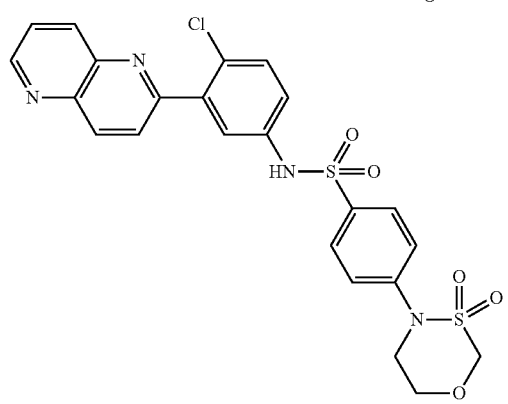
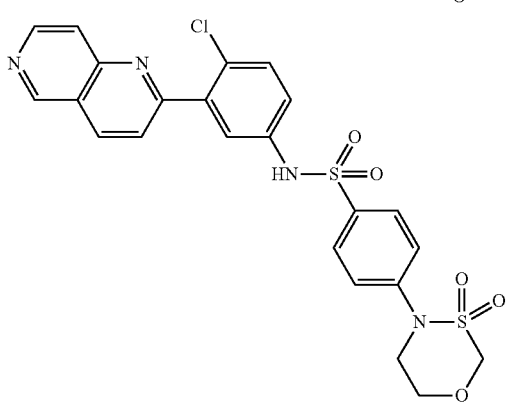
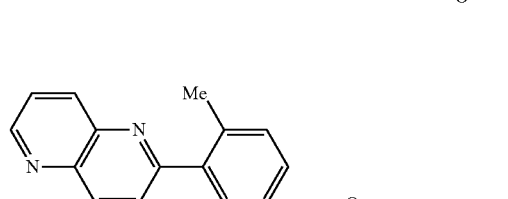
182
-continued
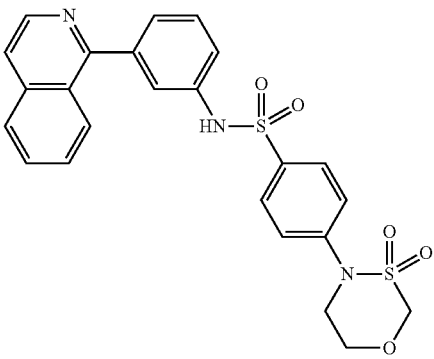
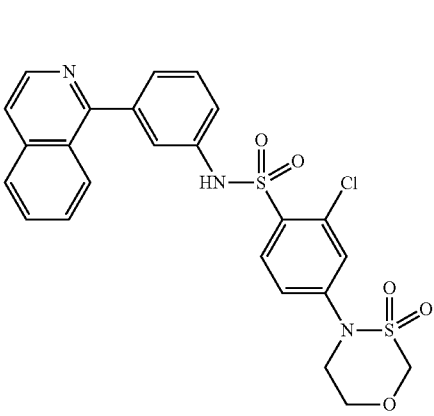
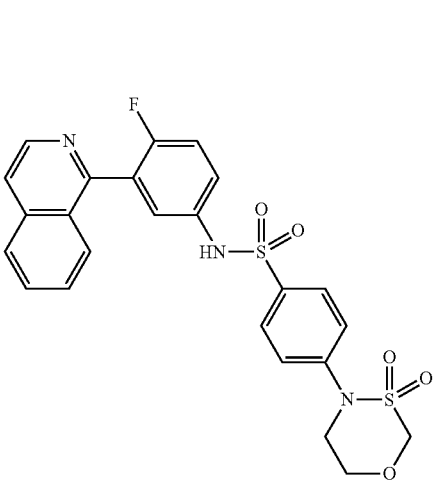
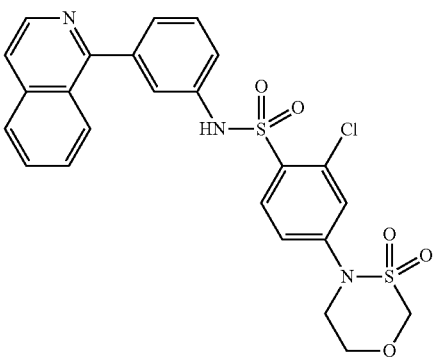

183
-continued
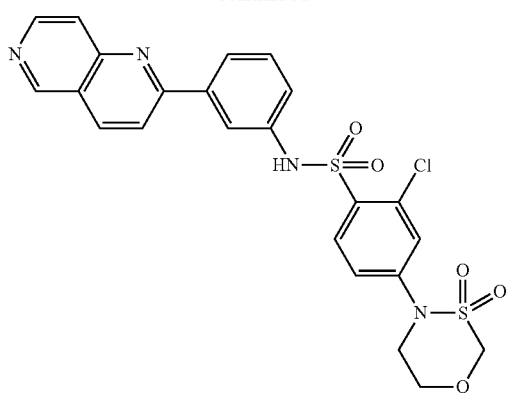
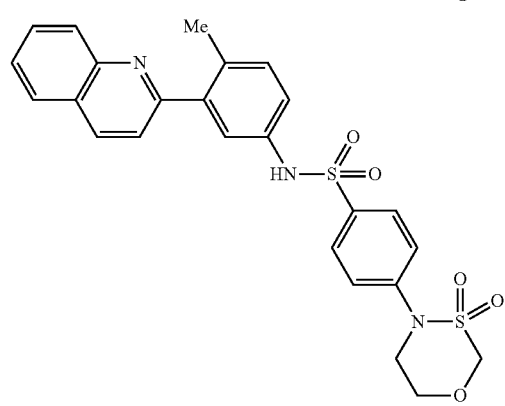
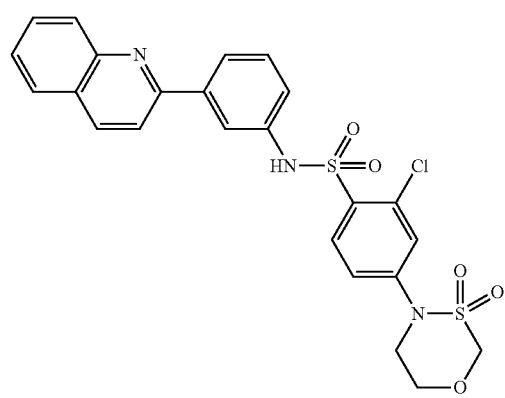
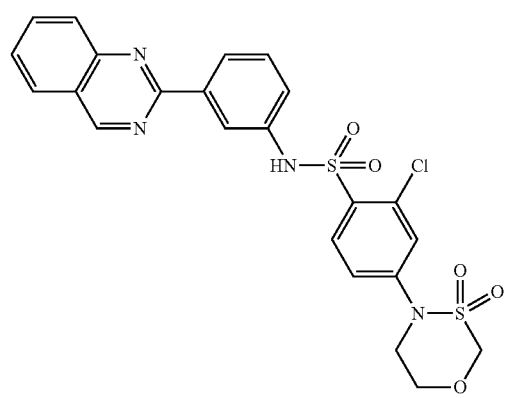
184
-continued
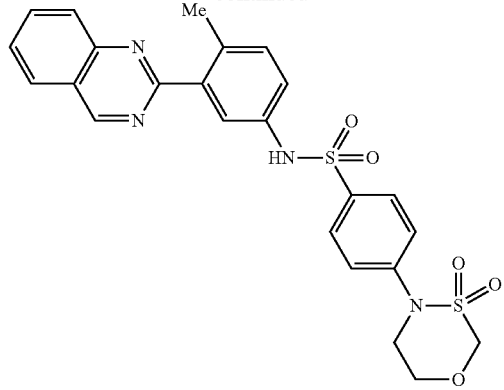
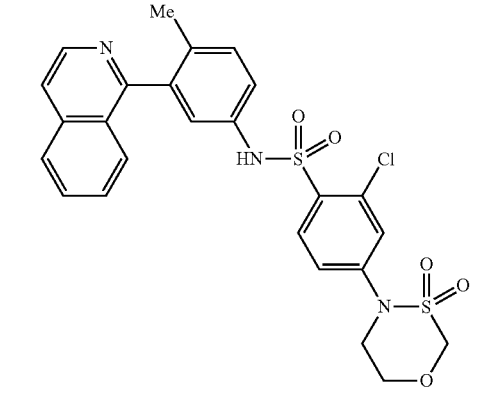
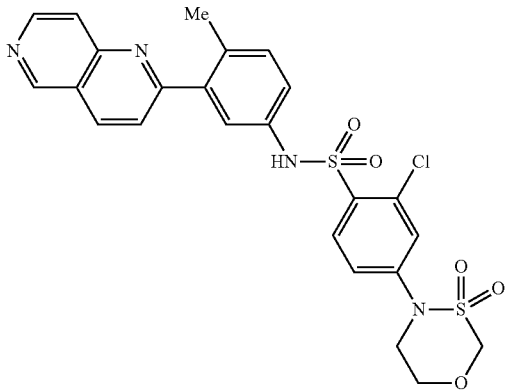
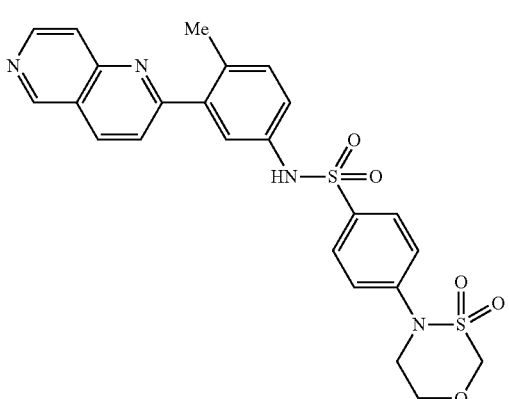

185
-continued
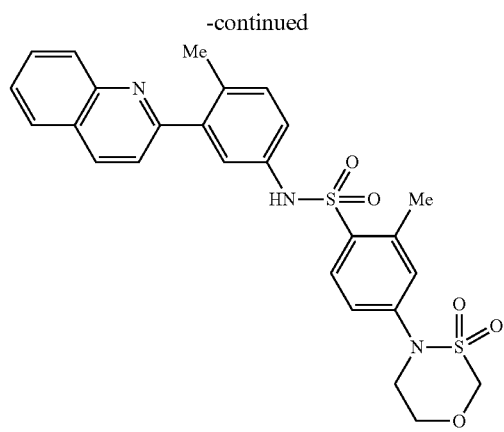
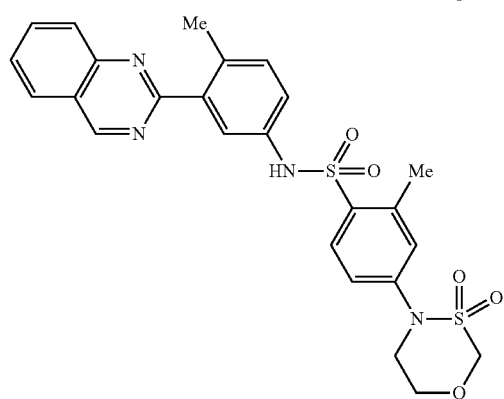
186
-continued
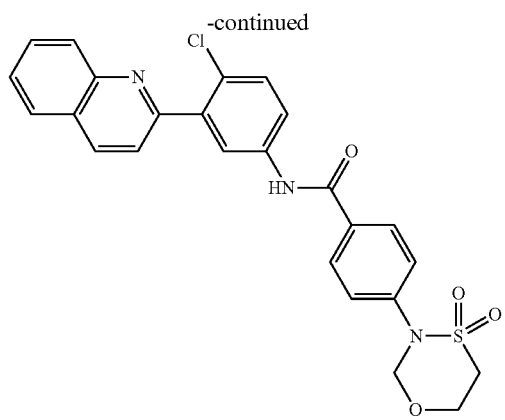
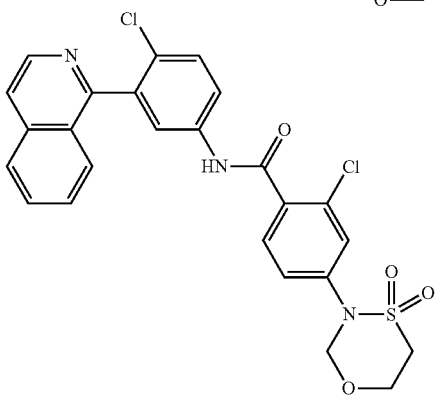
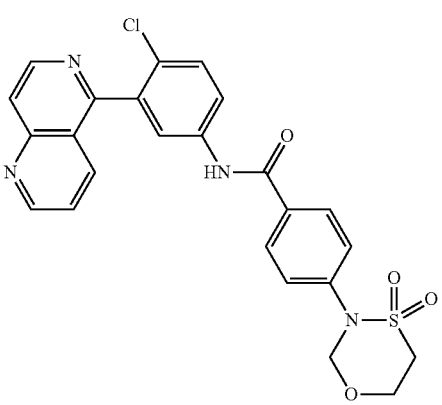
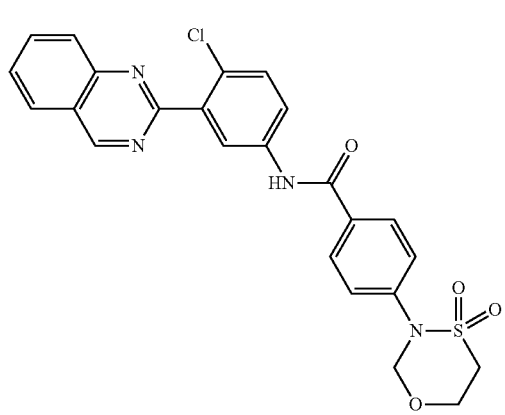

187
-continued

188
-continued

189
-continued
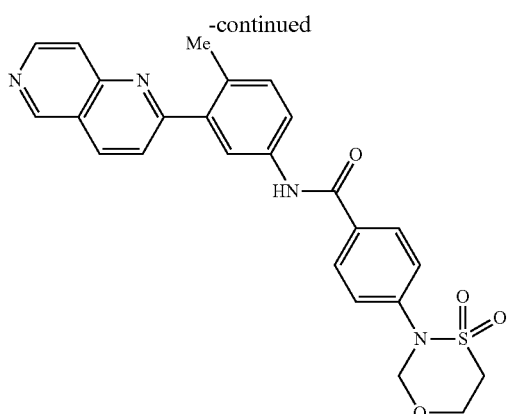
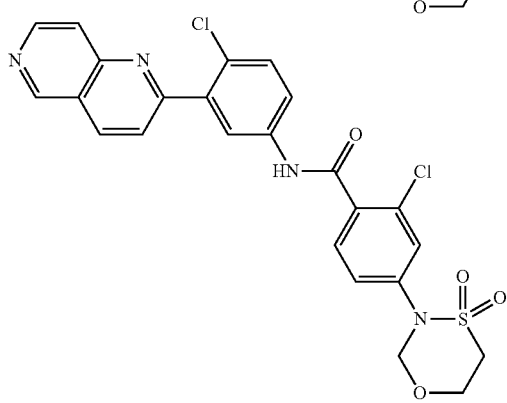
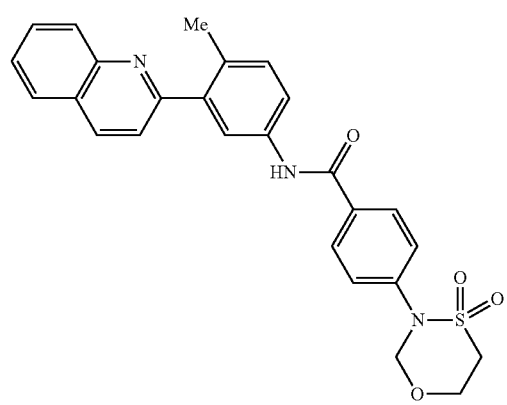
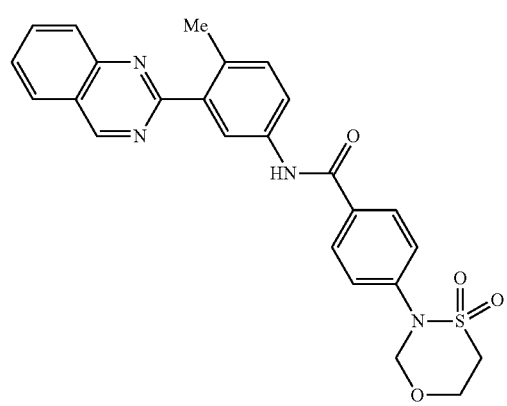
190
-continued
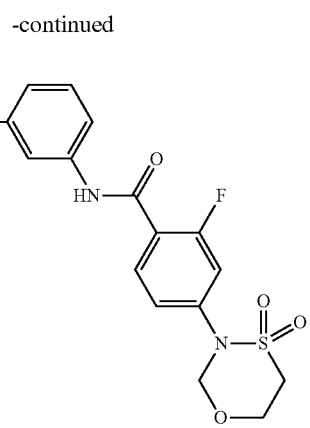
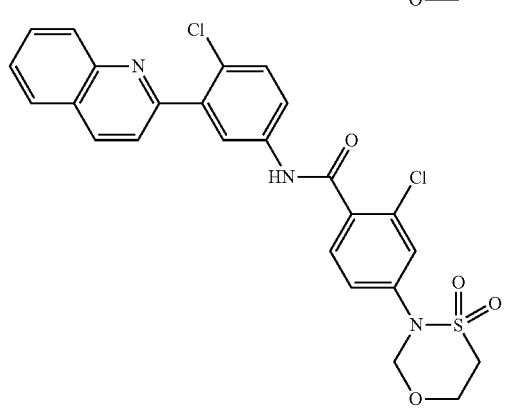
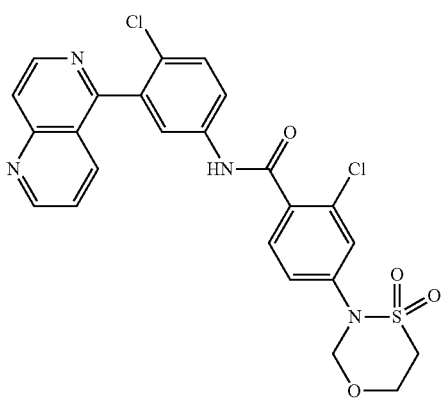
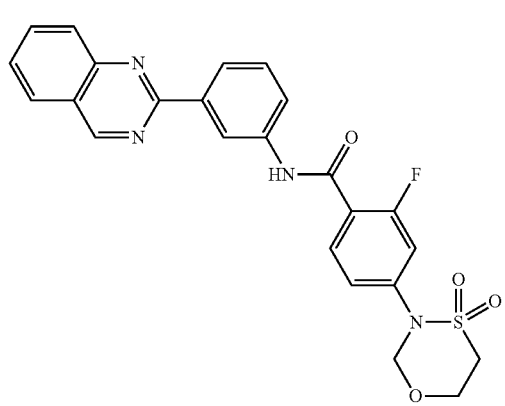

191
-continued

192
-continued

193
-continued
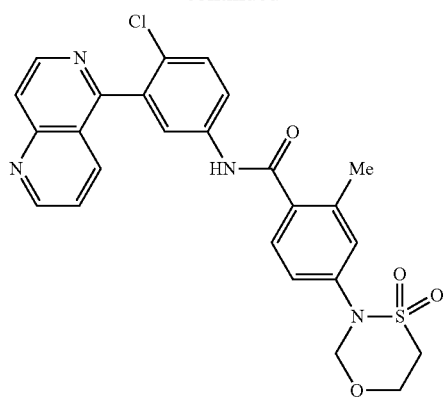
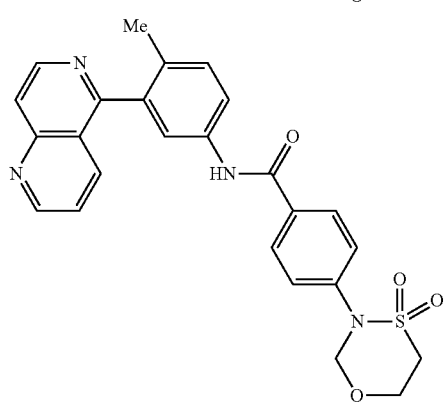
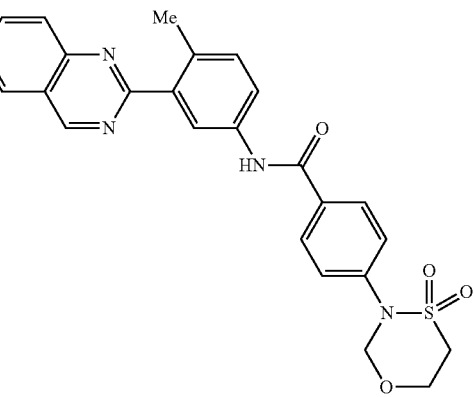
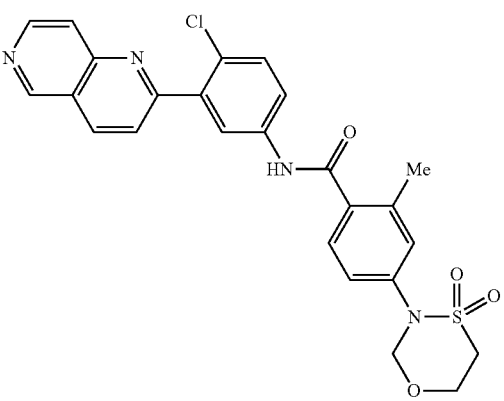
194
-continued
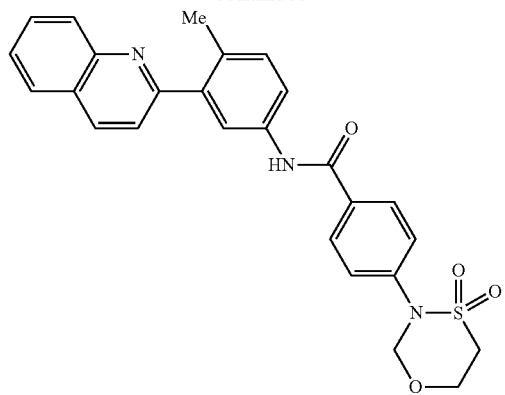
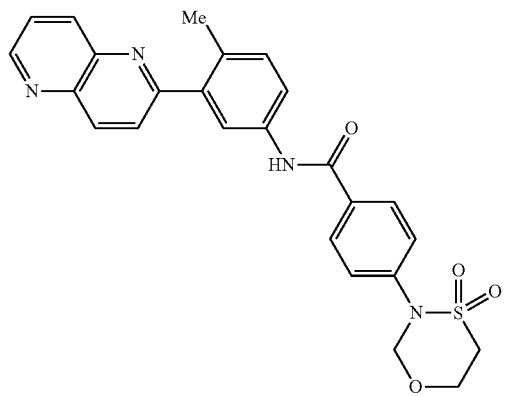
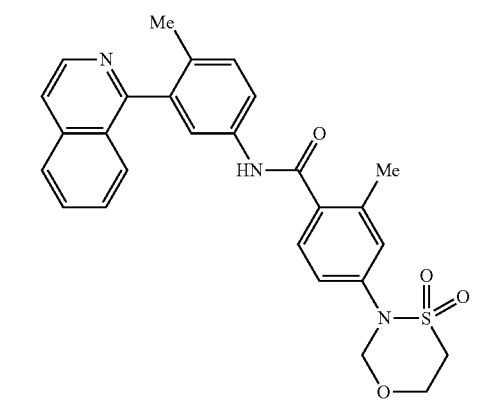
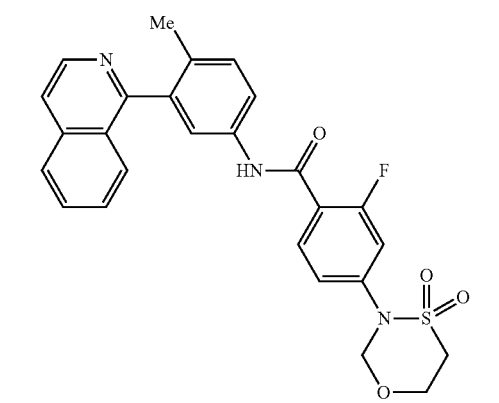

195
-continued
196
-continued
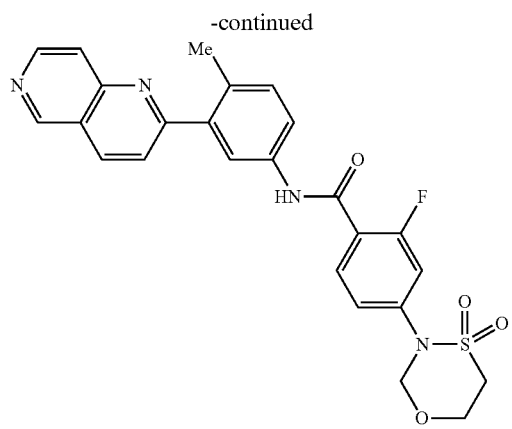
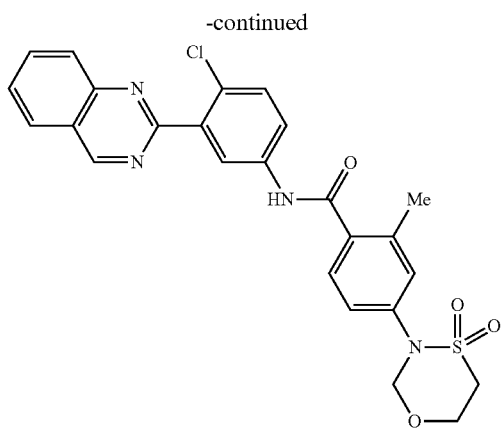
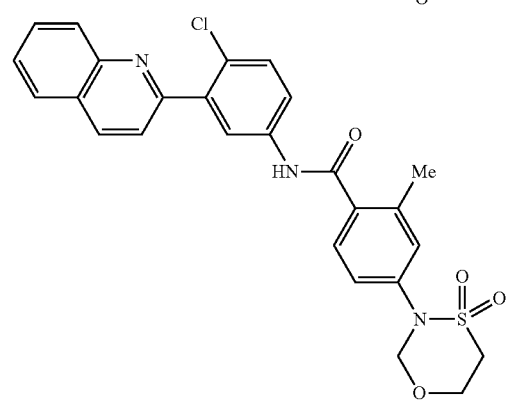
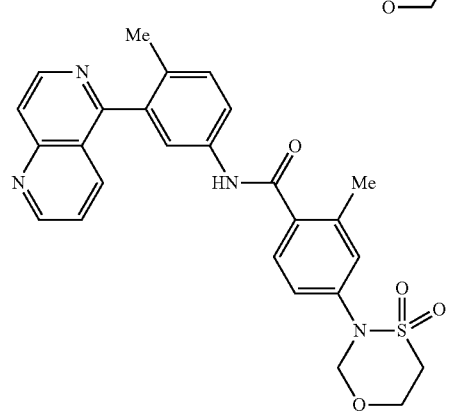
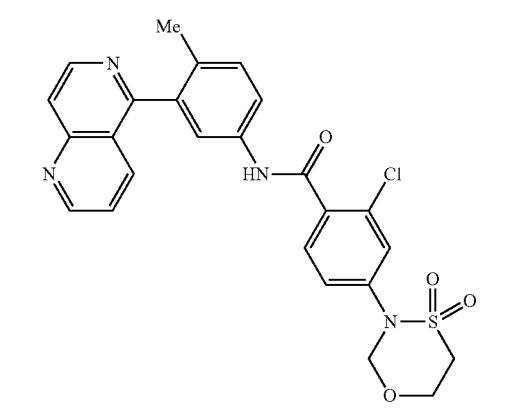
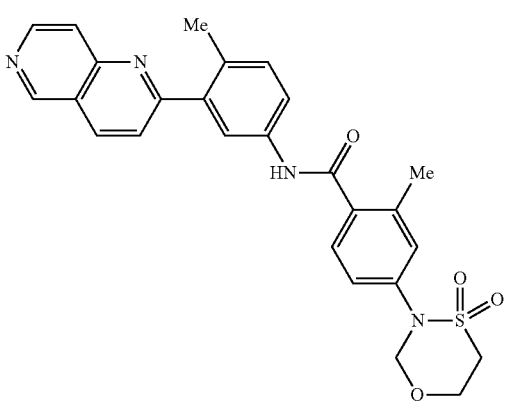
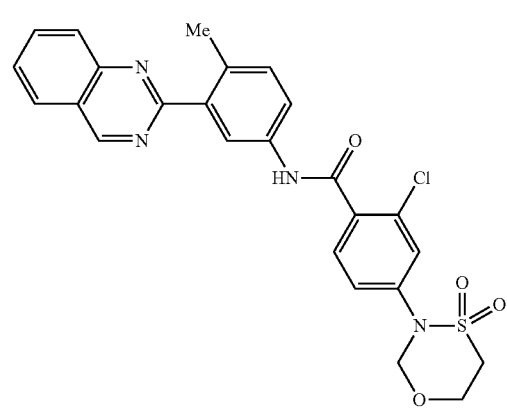
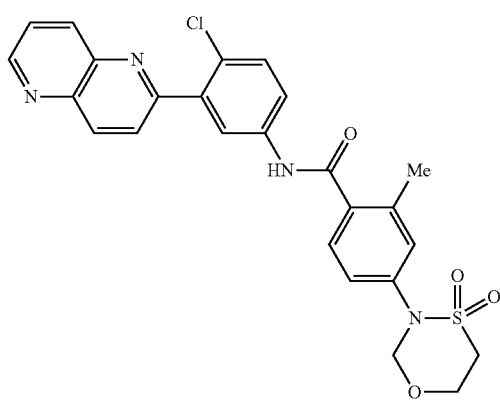

197
-continued
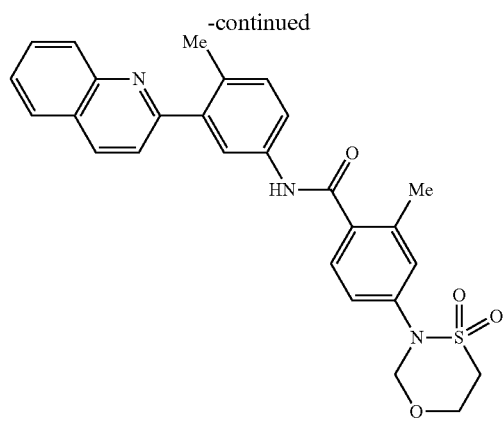
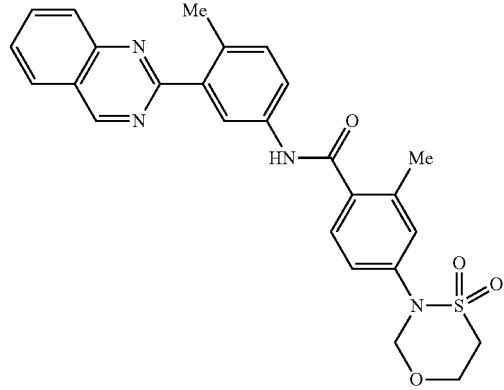
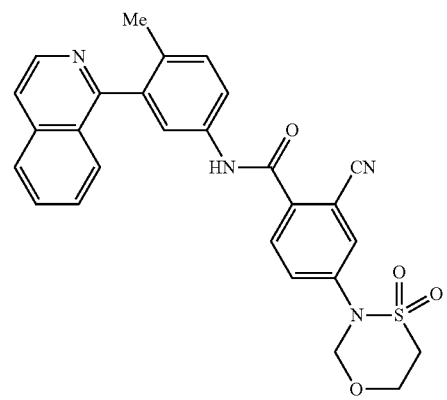
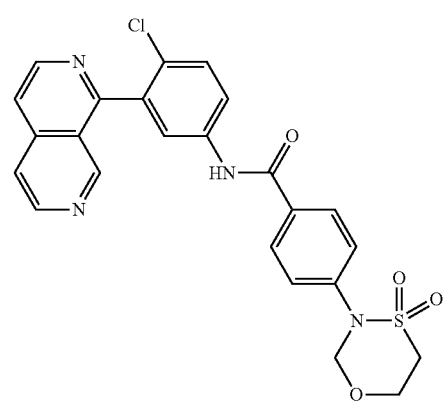
198
-continued
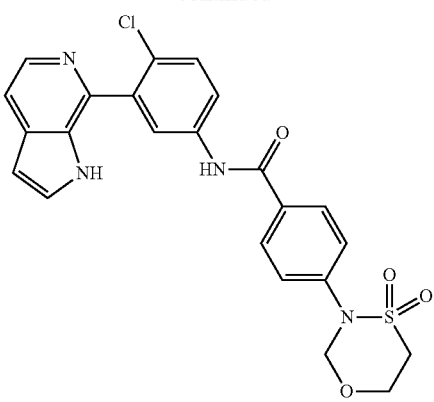
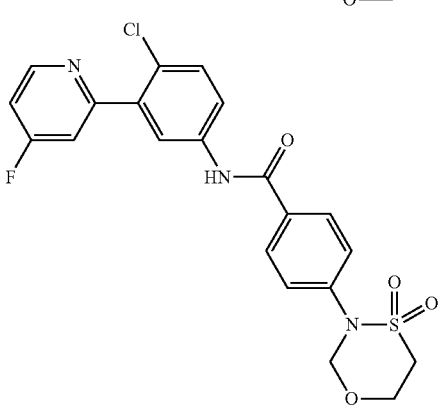
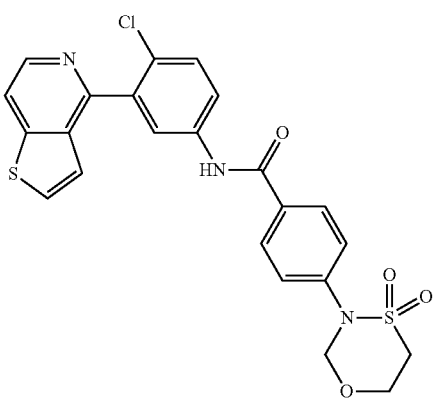

199
-continued
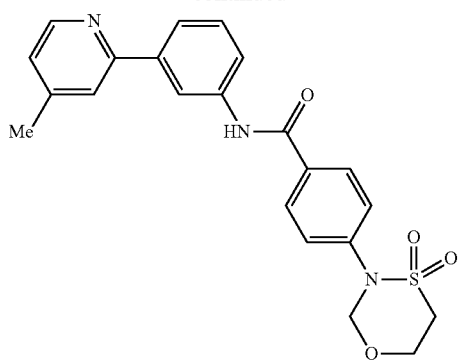
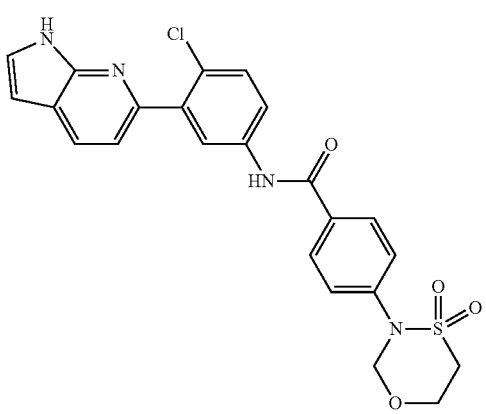
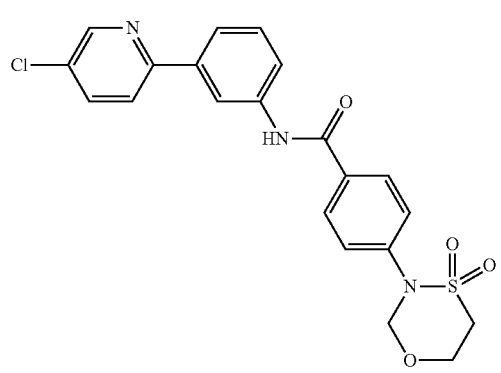
200
-continued
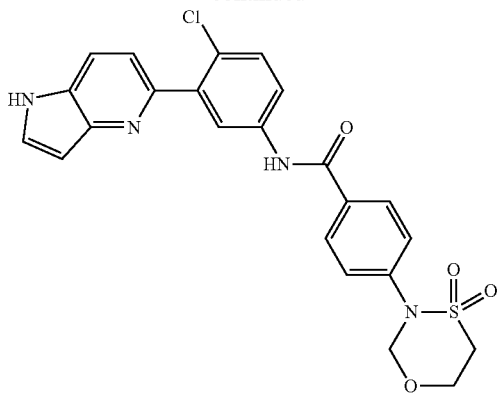
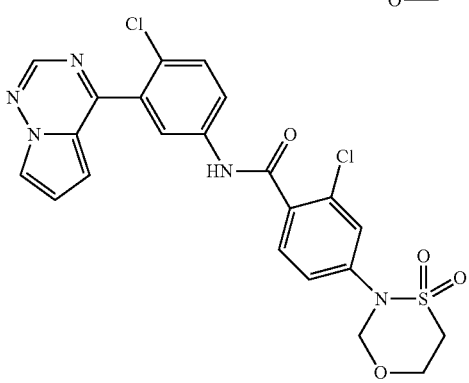
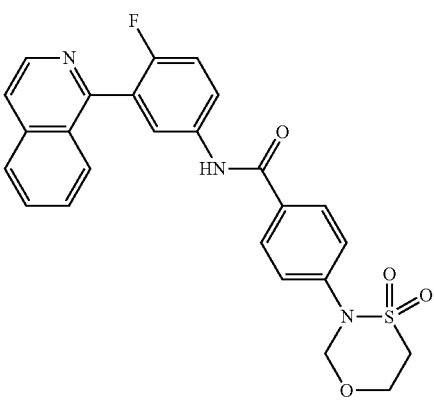

201
-continued
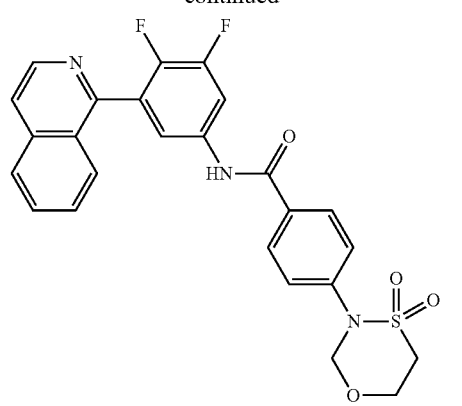
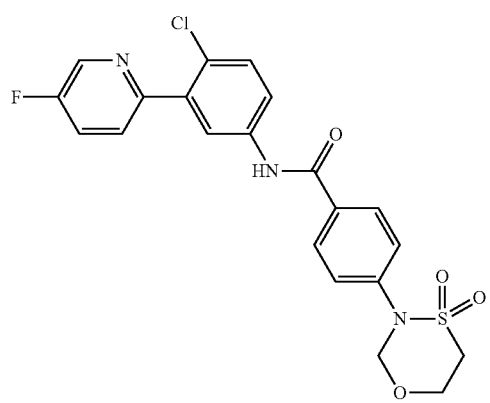
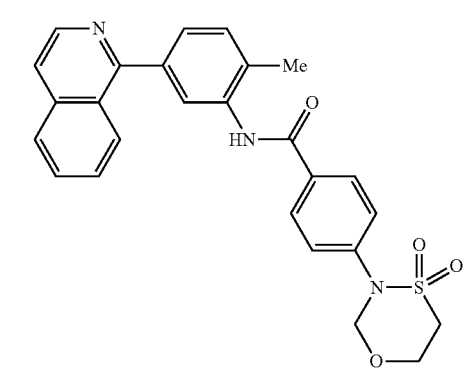
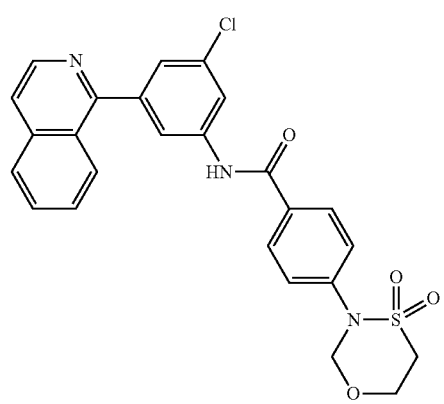
202
-continued
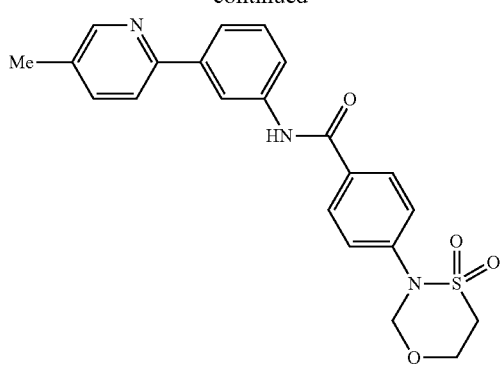
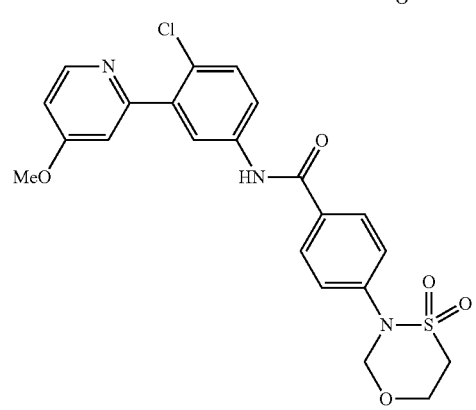
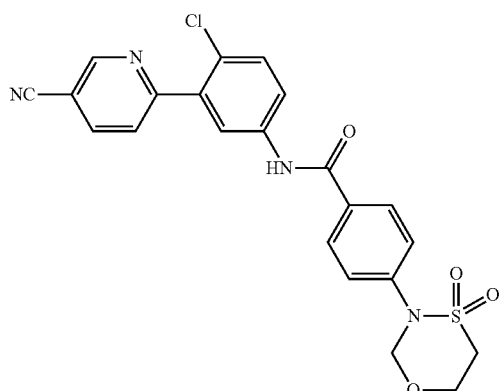
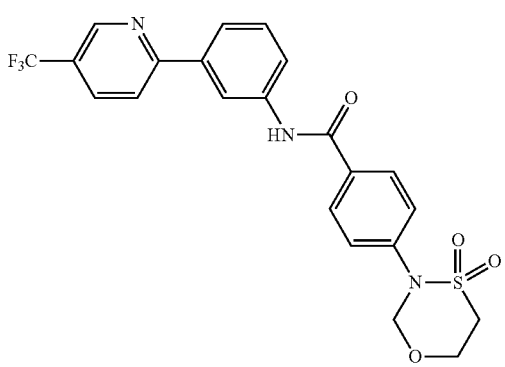

203
-continued
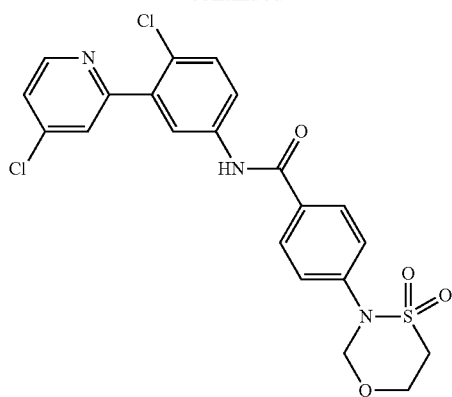
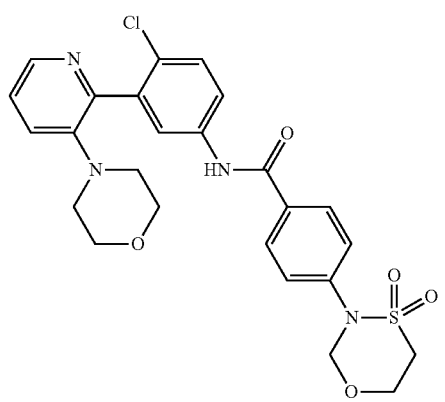
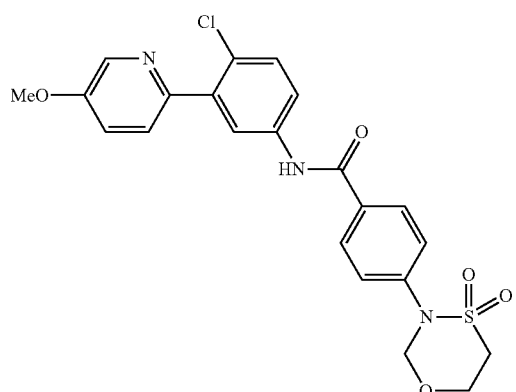
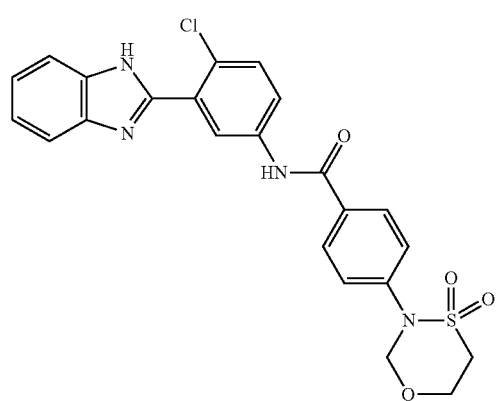
204
-continued
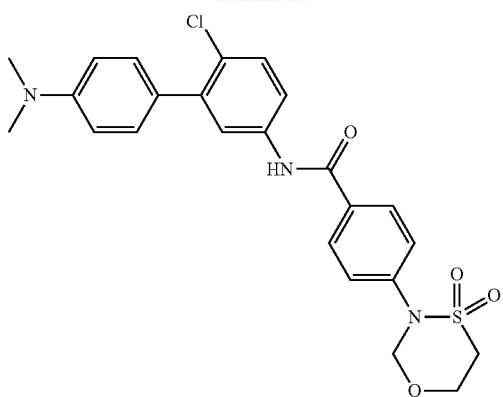
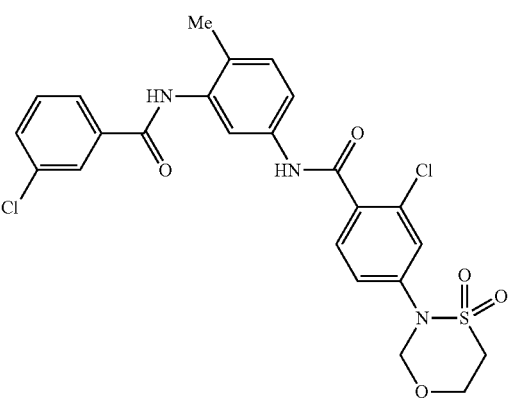
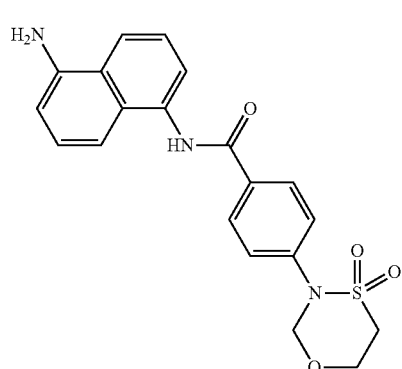
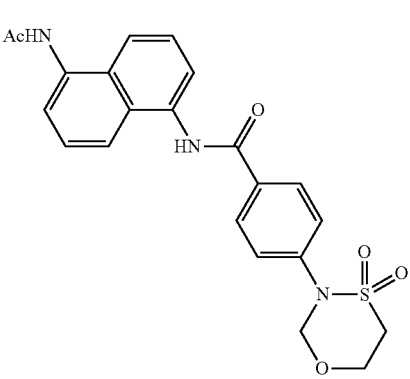

205
-continued
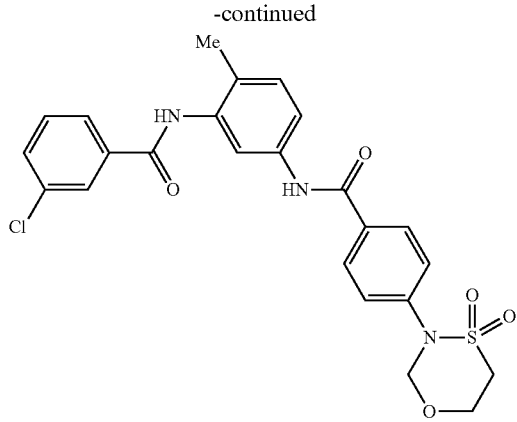
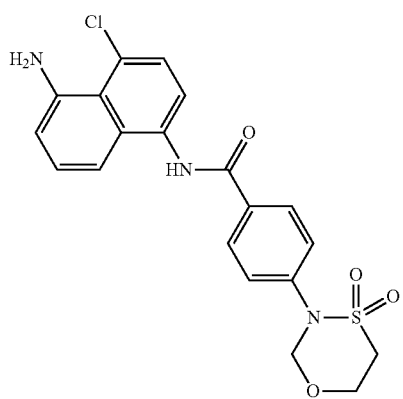
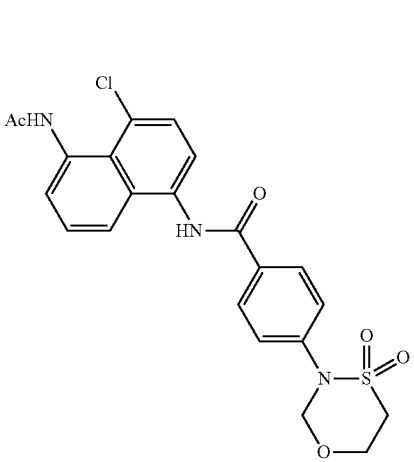
206
-continued
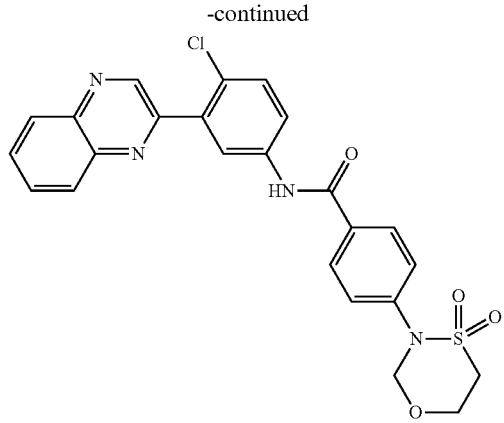
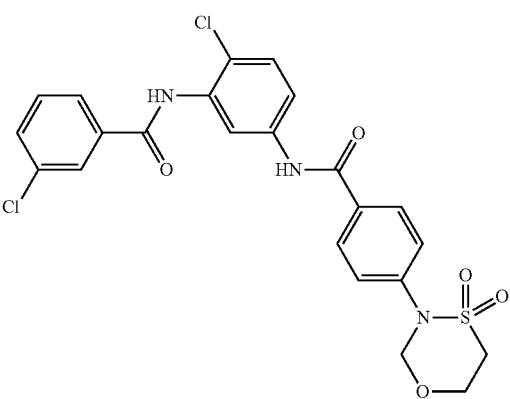
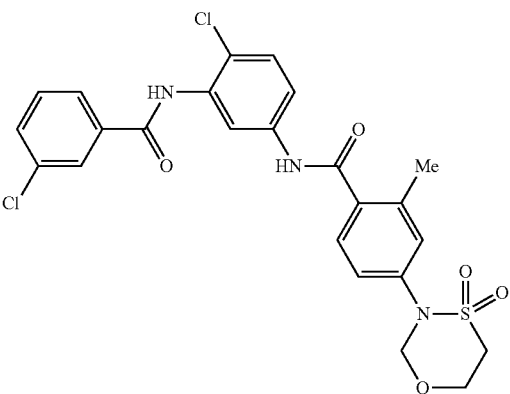
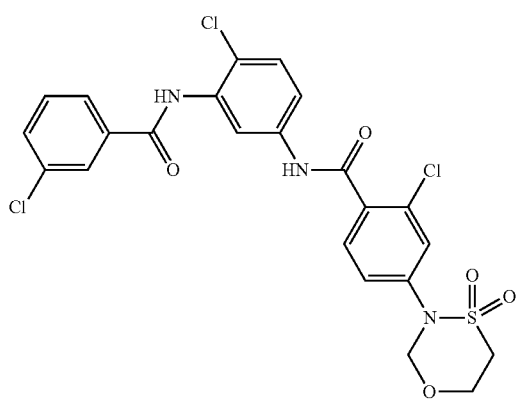
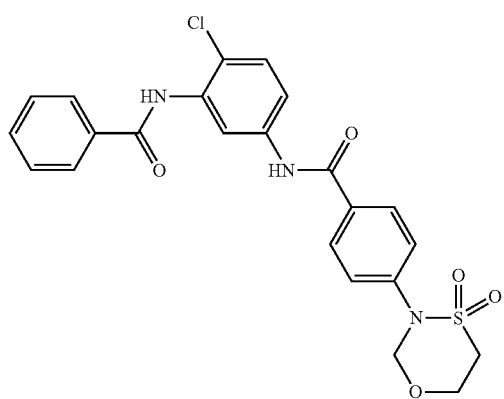

207
-continued
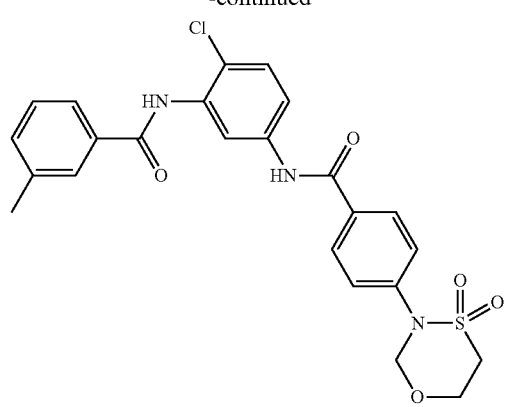
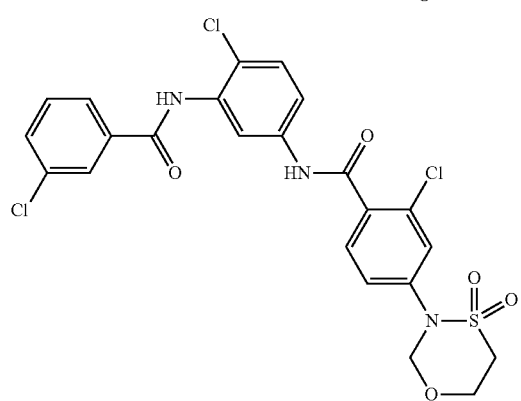
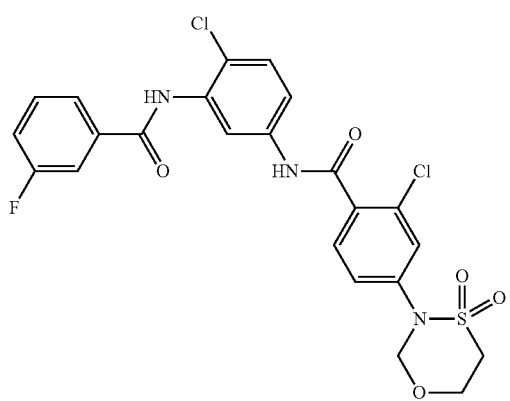
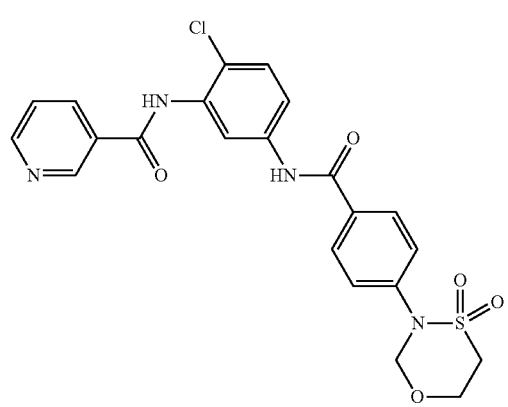
208
-continued
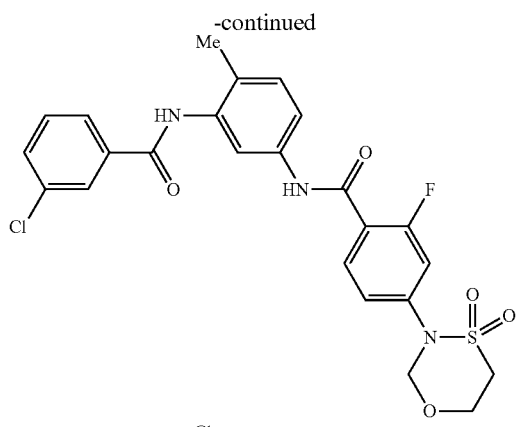
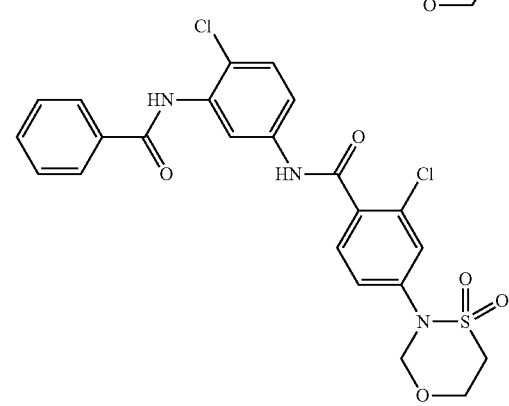
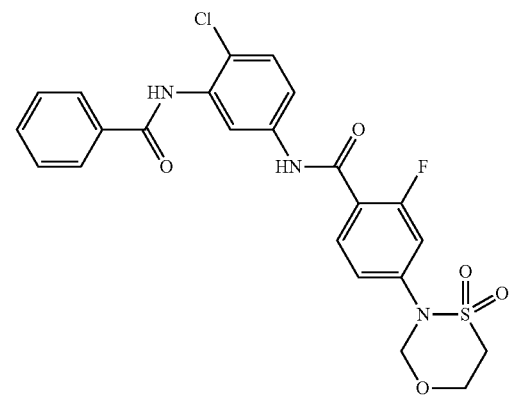
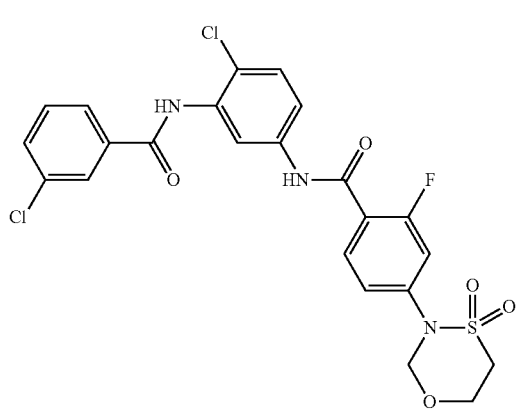

-continued
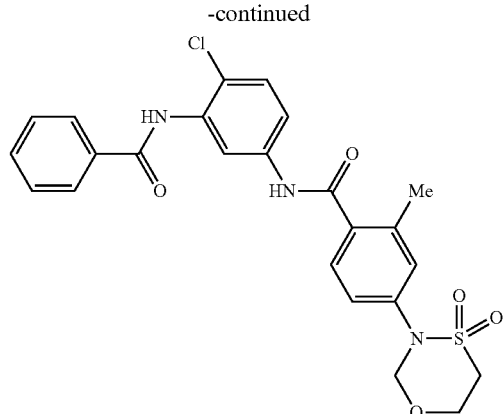
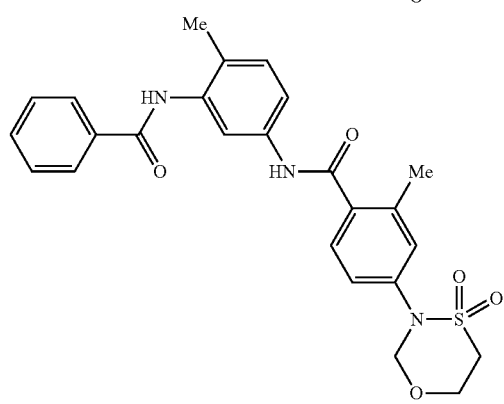
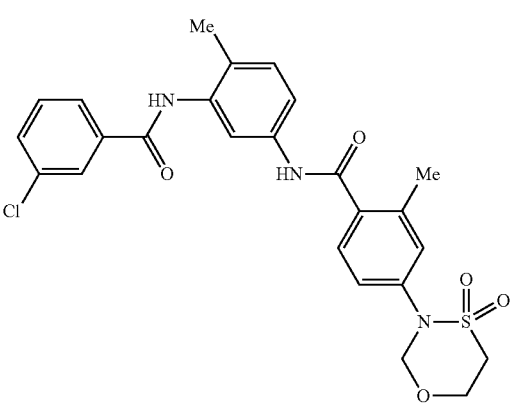
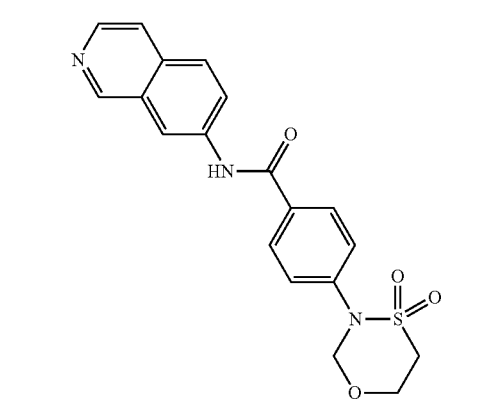
-continued
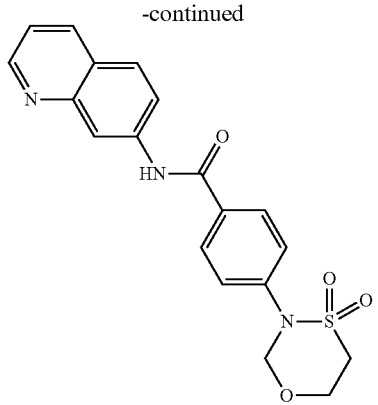
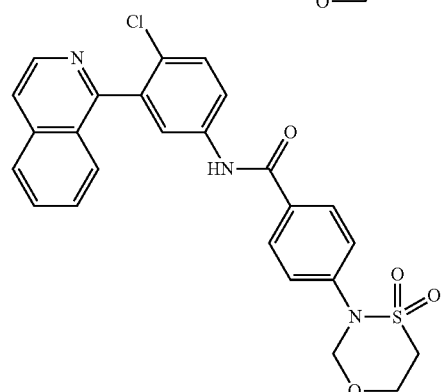
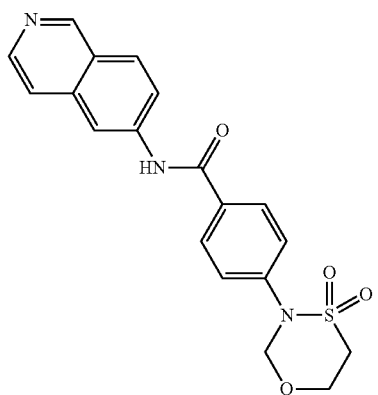
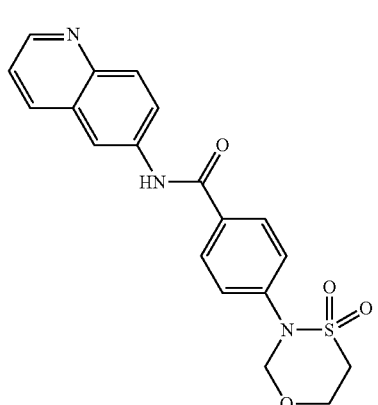

211
-continued
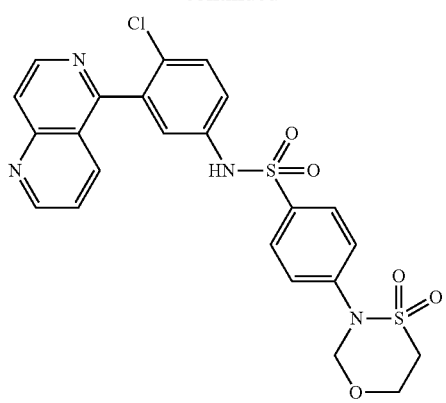
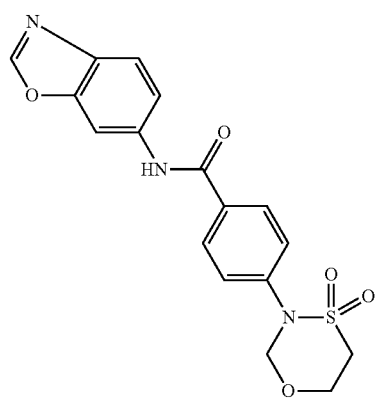
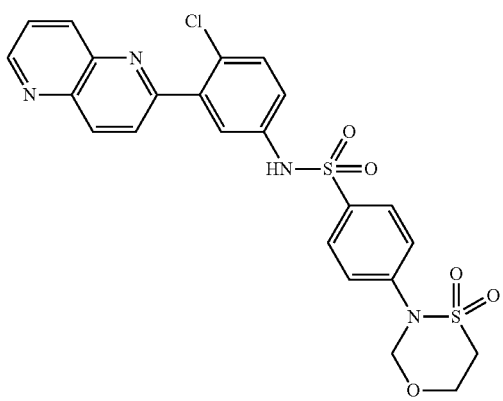
212
-continued
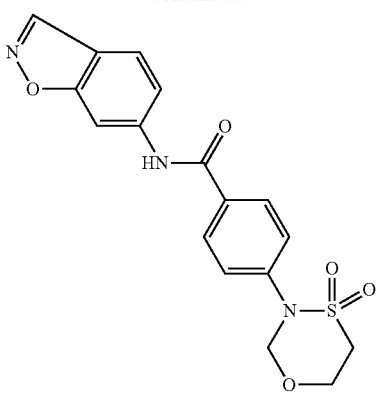
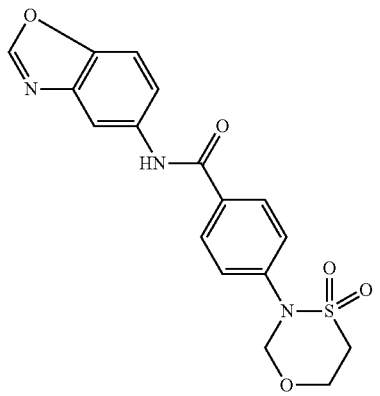
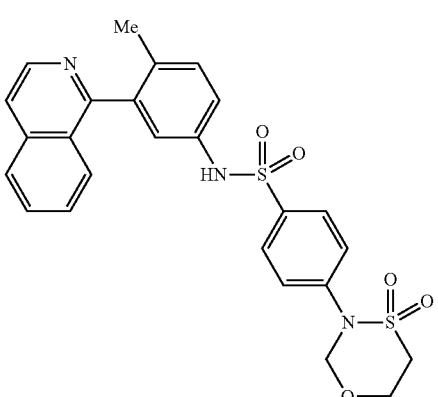
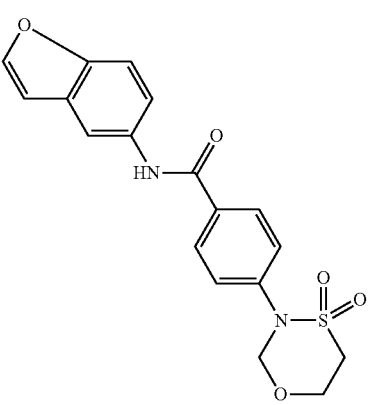

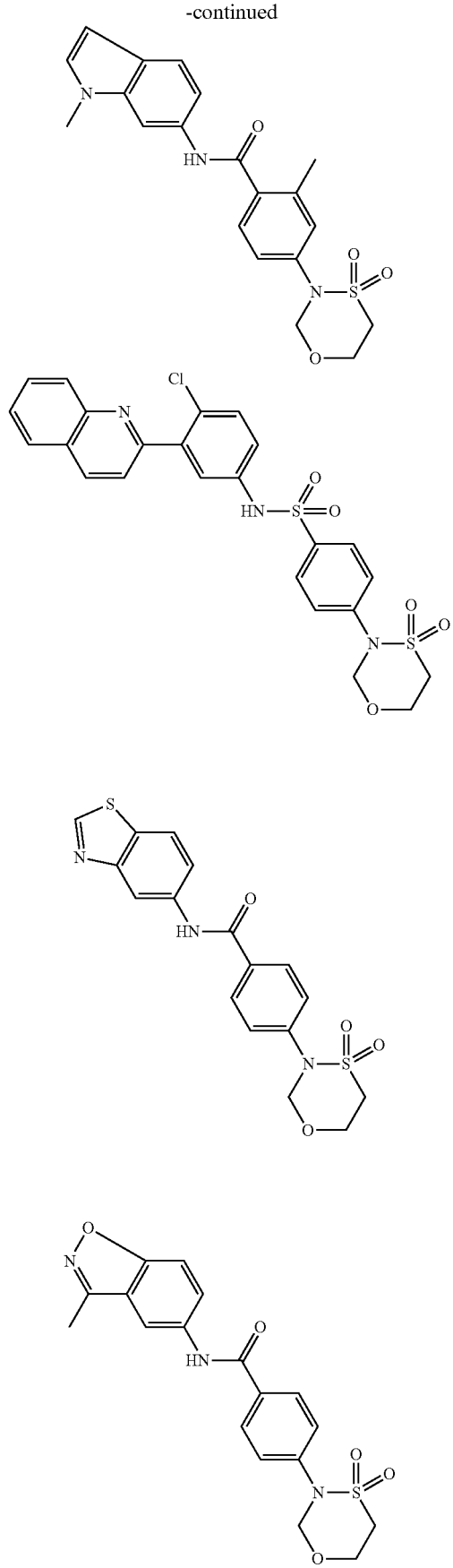

215
-continued
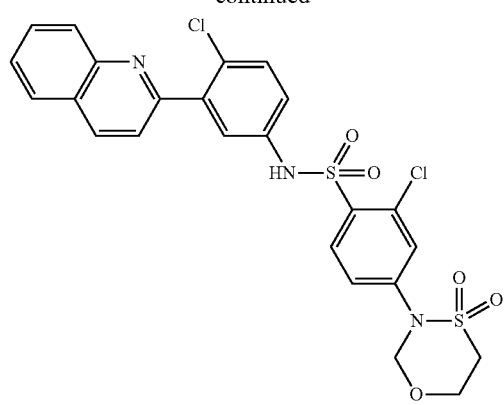
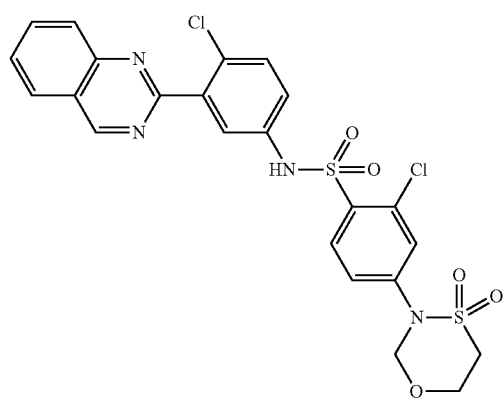
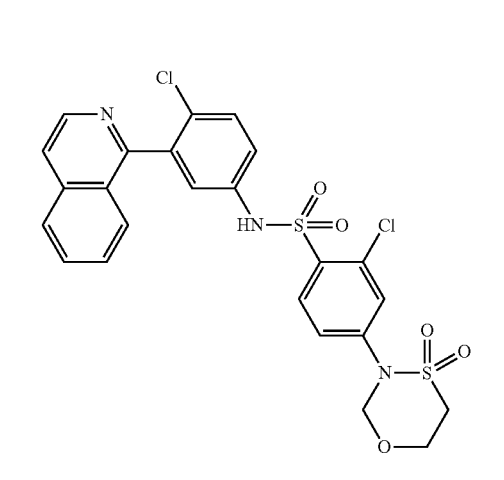
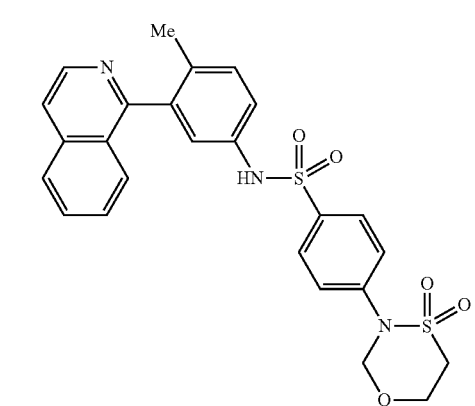
216
-continued
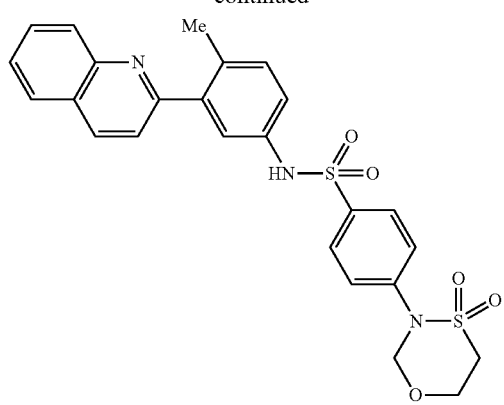
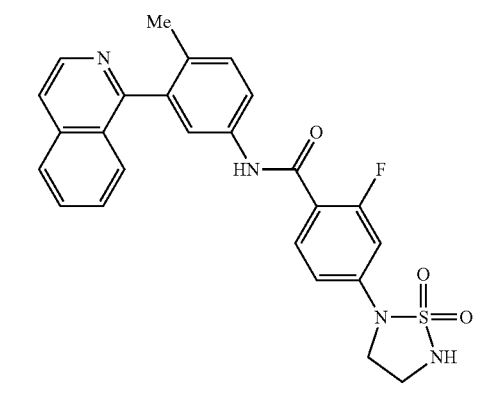
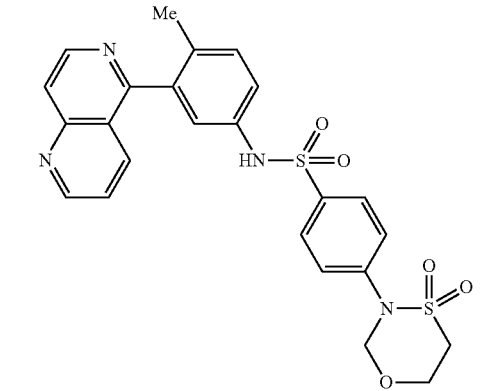
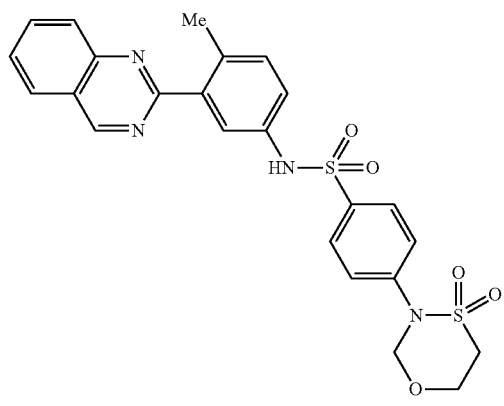

217
-continued
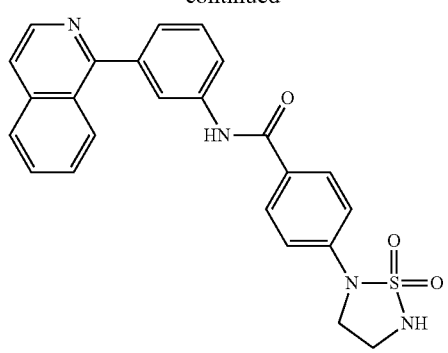
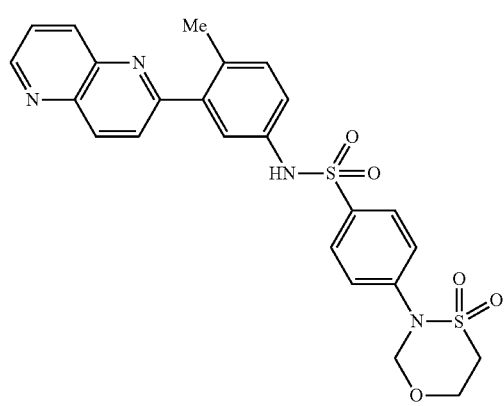
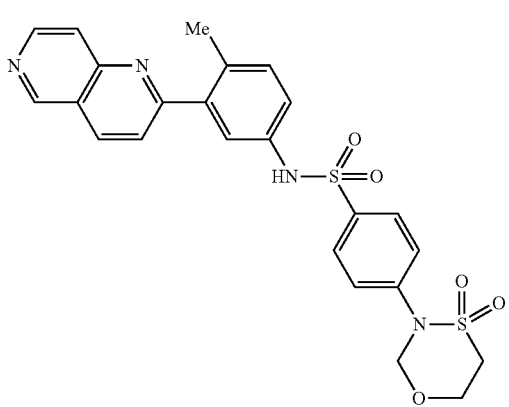
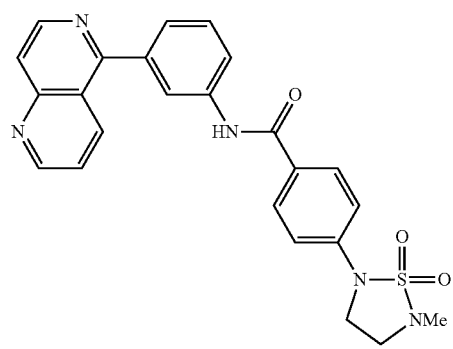
218
-continued
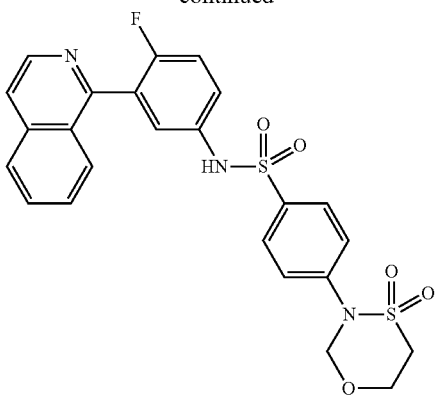
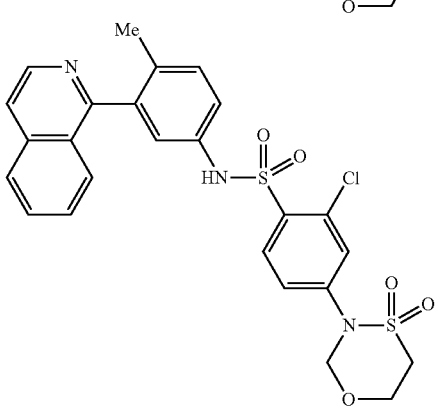
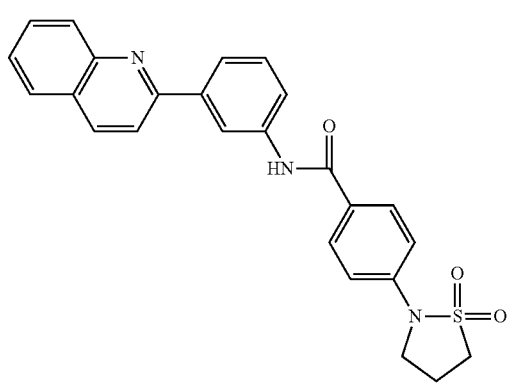
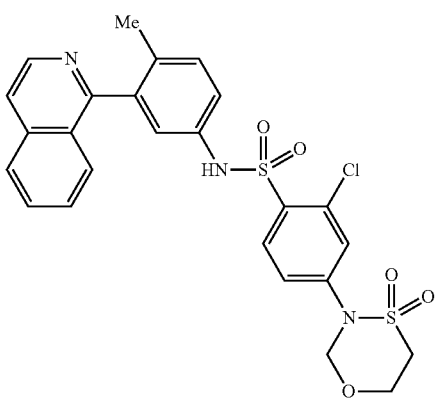

219
-continued
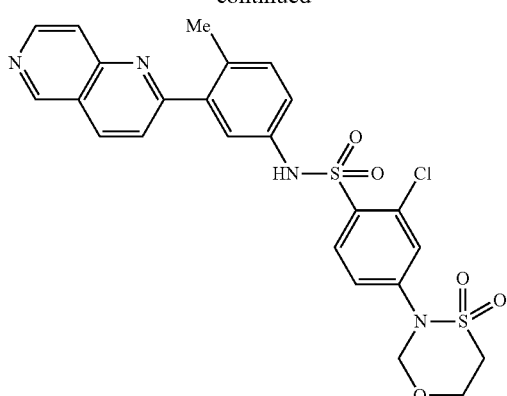
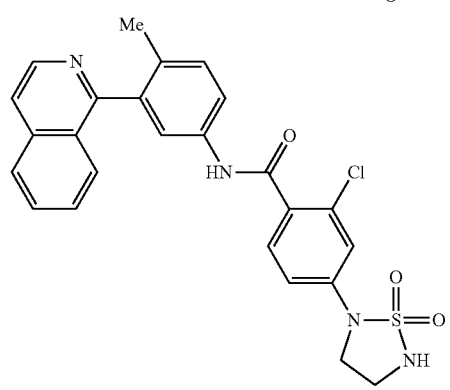
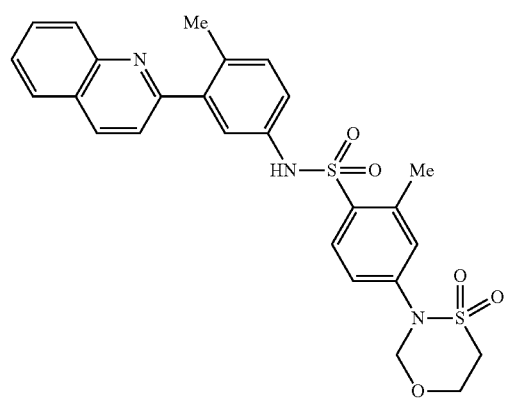
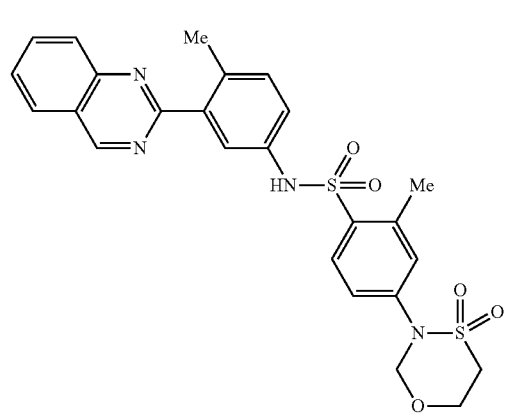
220
-continued
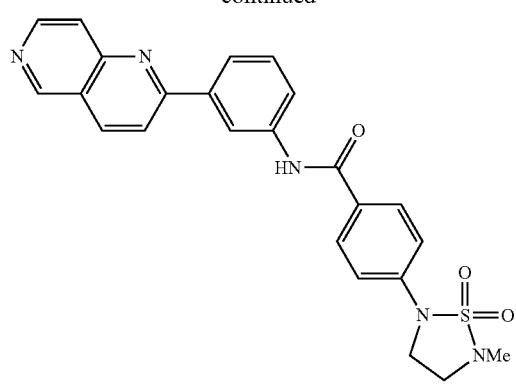
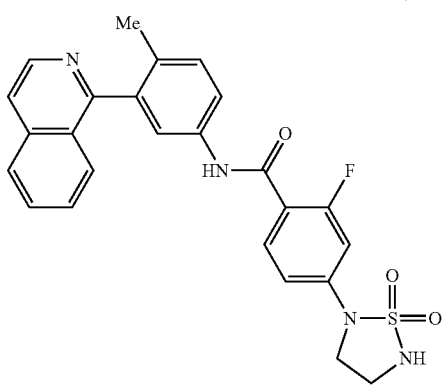
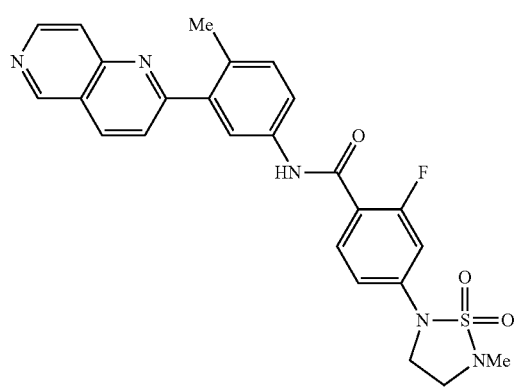
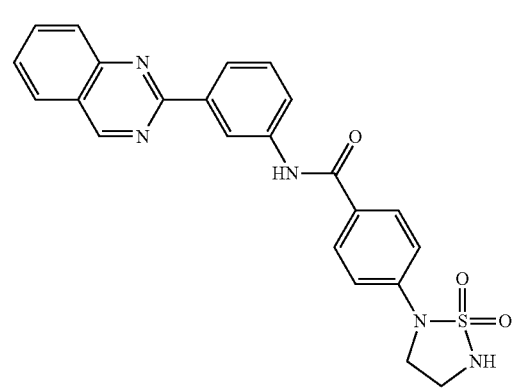

221
-continued
222
-continued
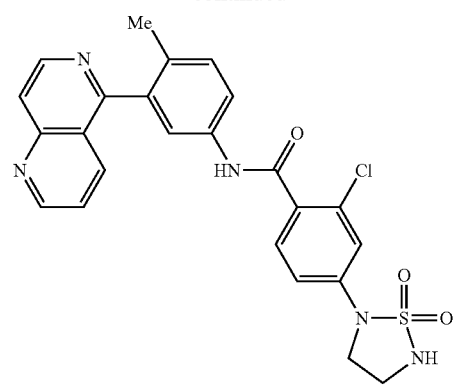
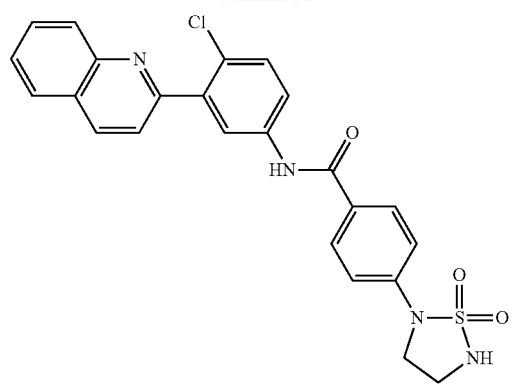
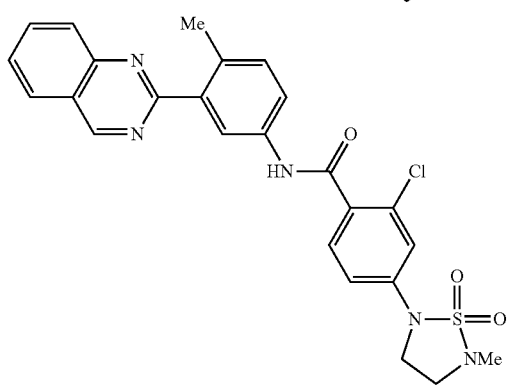
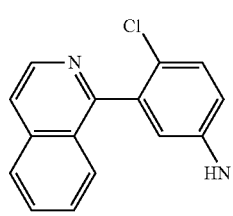
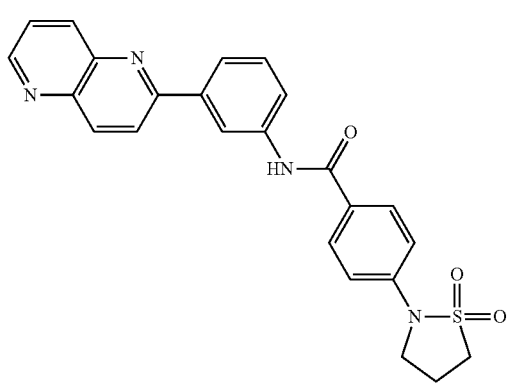
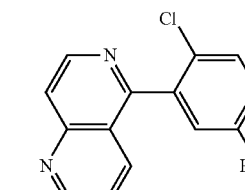
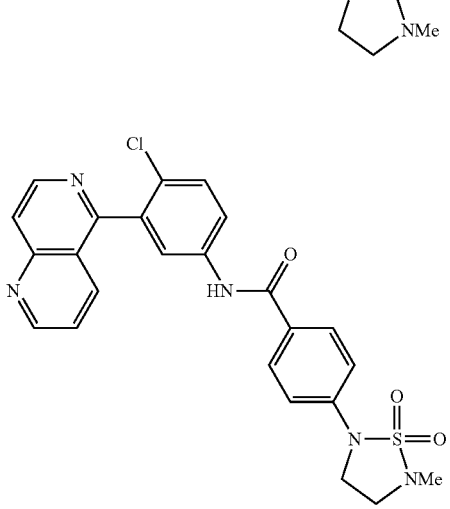
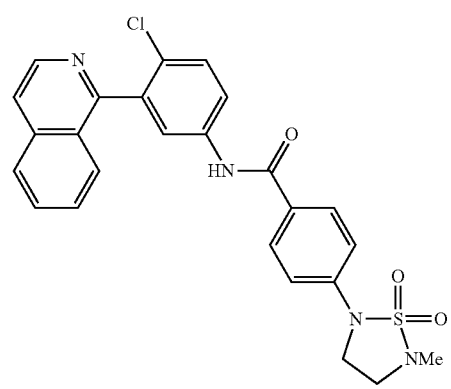
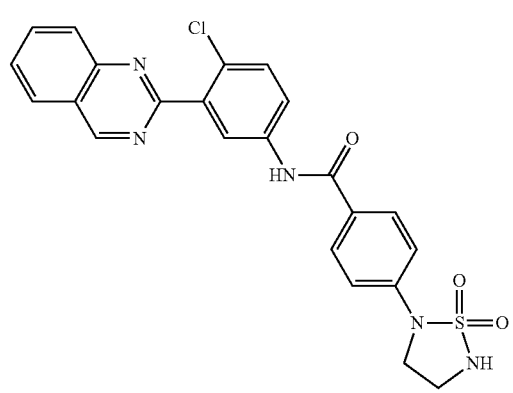

223
-continued
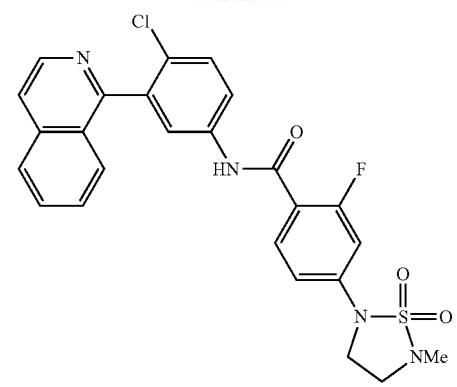
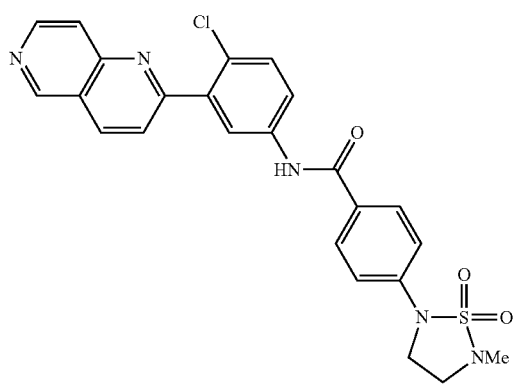
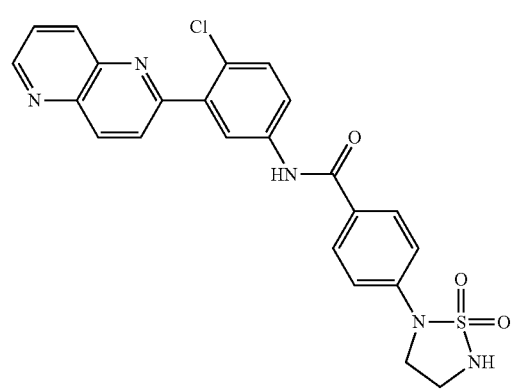
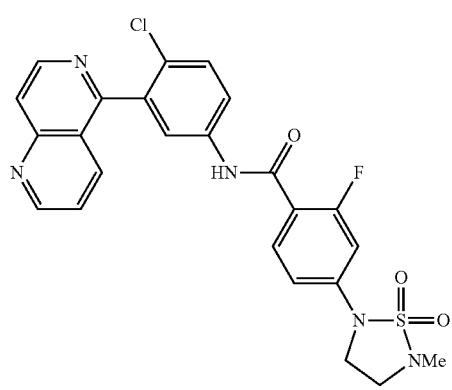
224
-continued
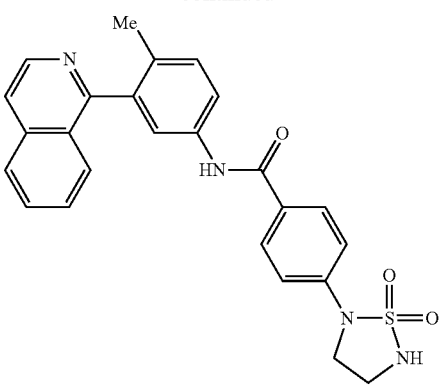
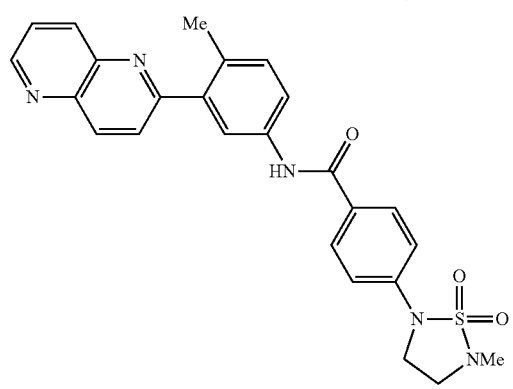
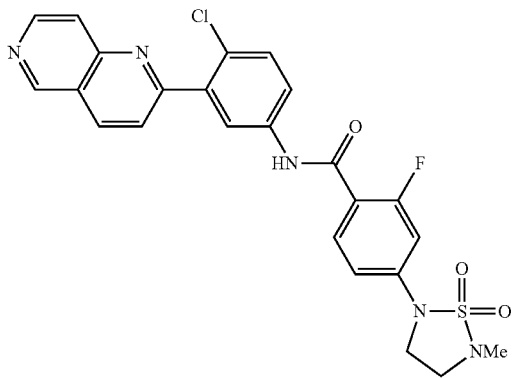
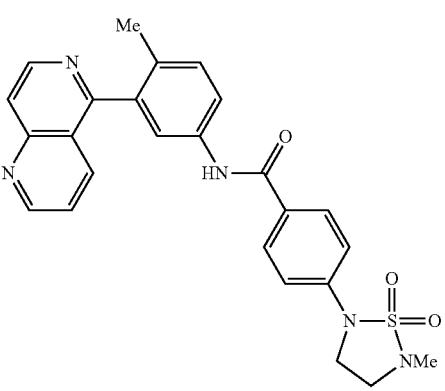

225
-continued
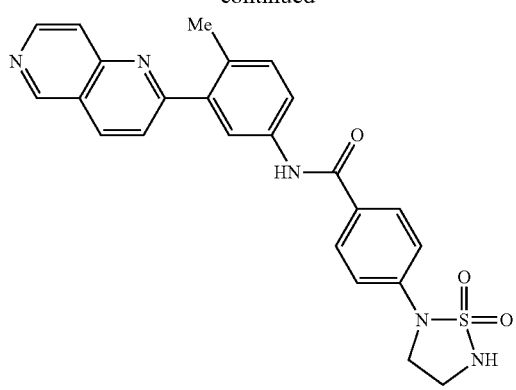
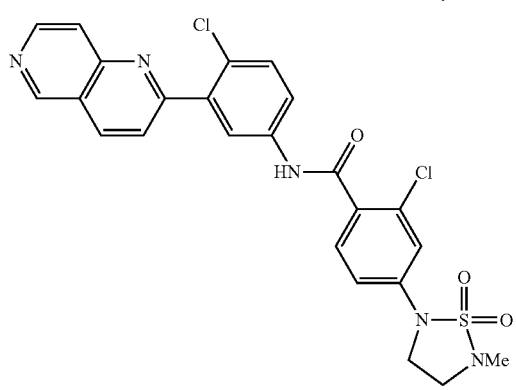
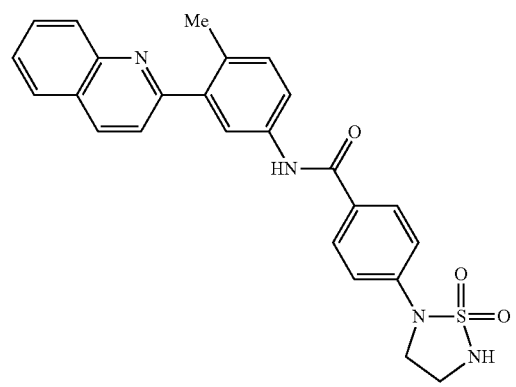
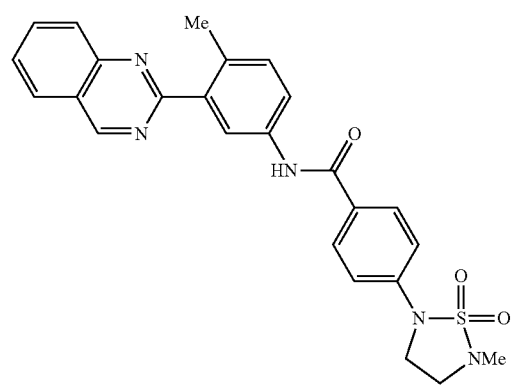
226
-continued
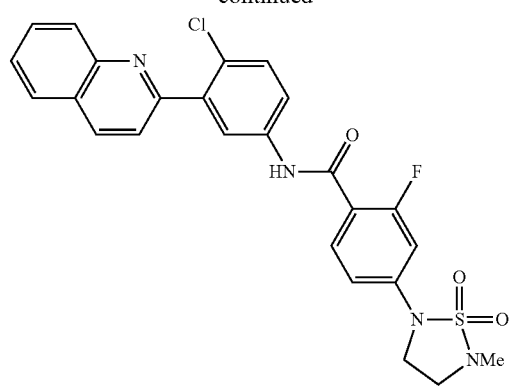
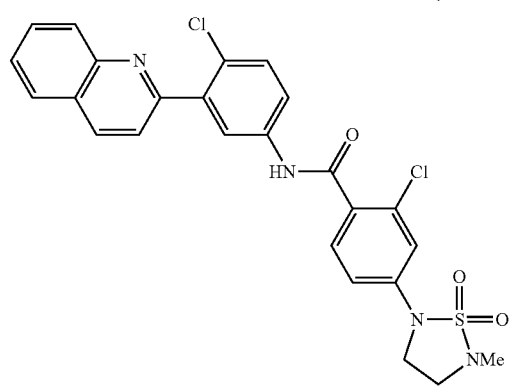
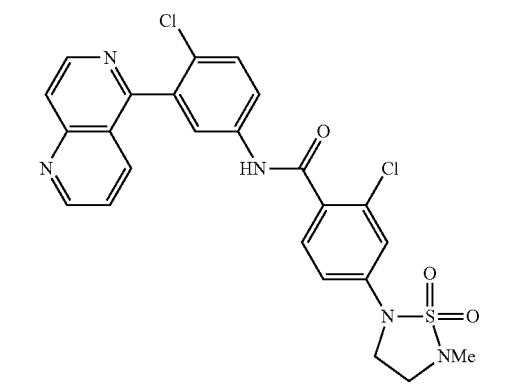
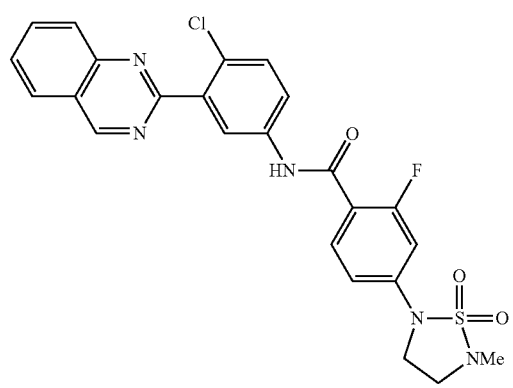

227
-continued
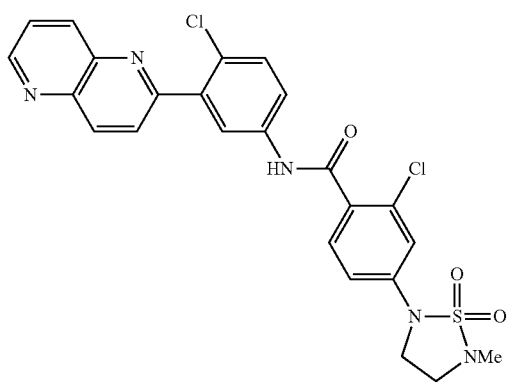
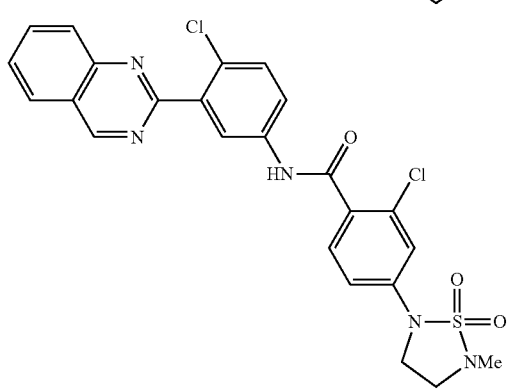
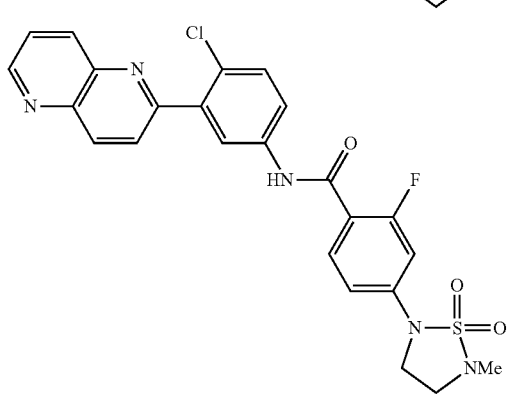
228
-continued
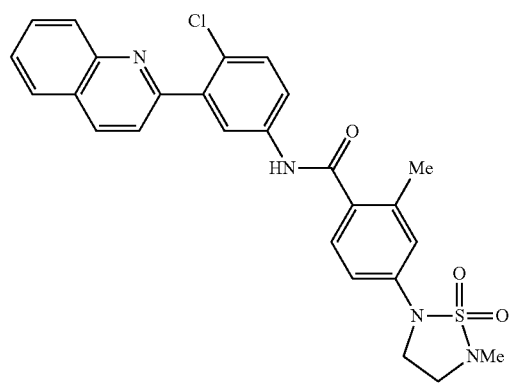
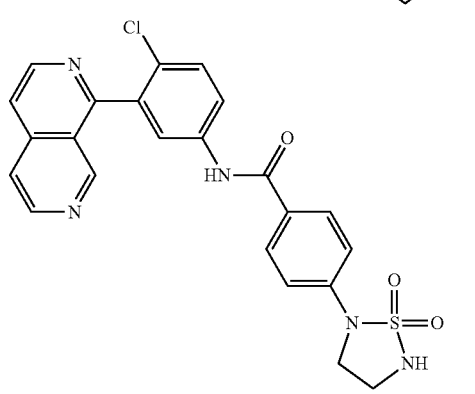
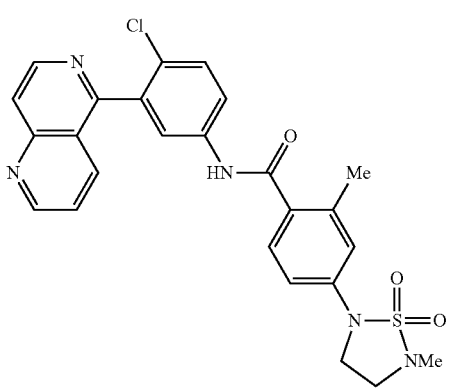
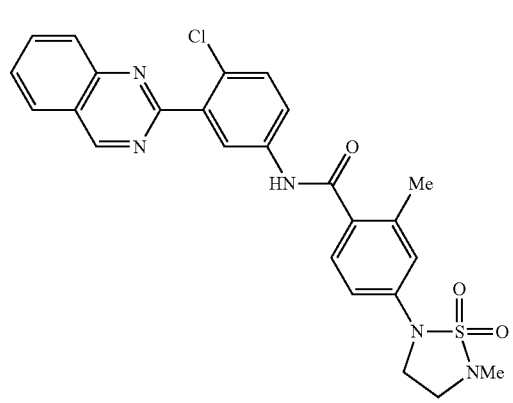

229
-continued
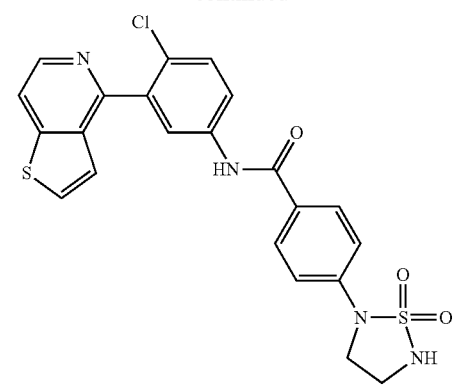
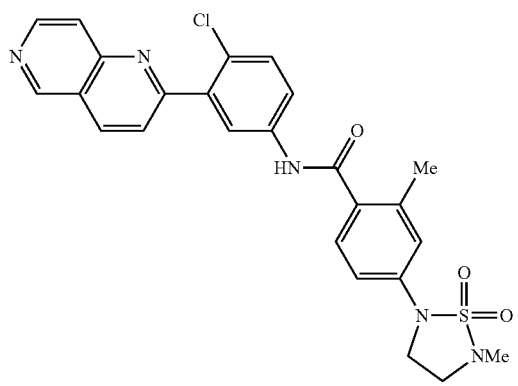
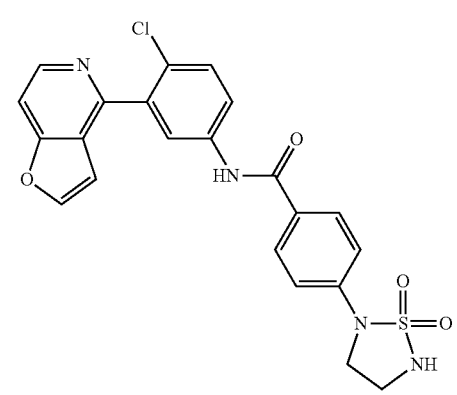
230
-continued
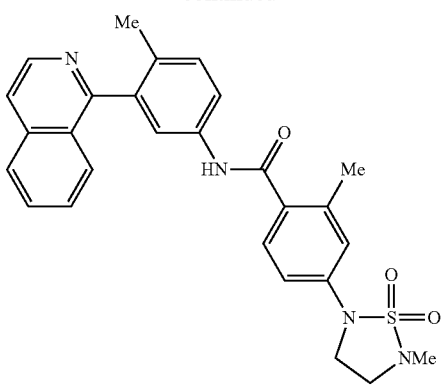
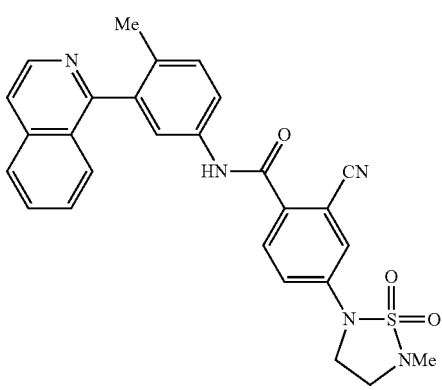
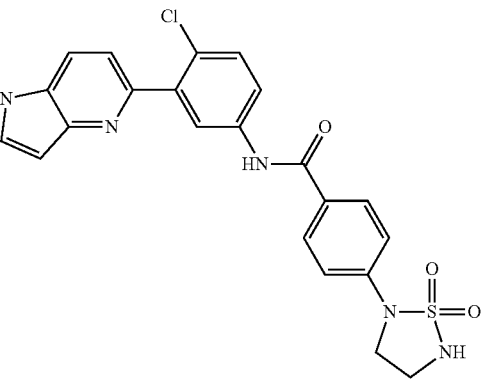
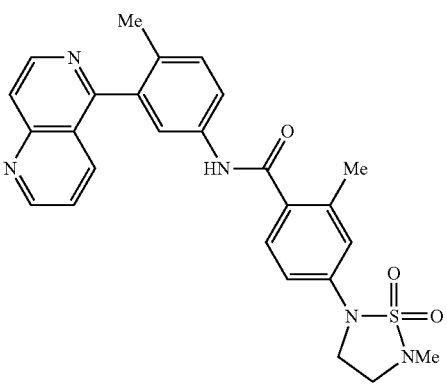

231
-continued
232
-continued
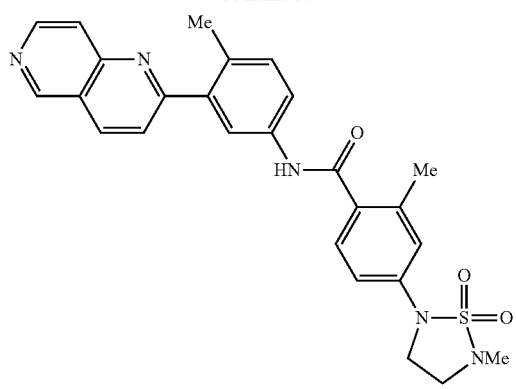
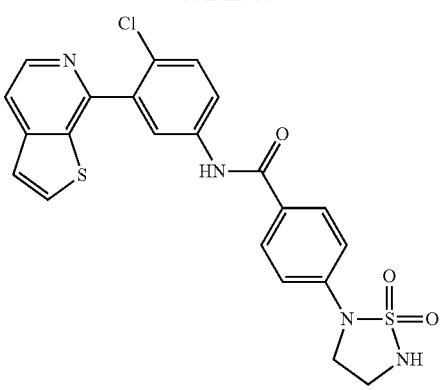
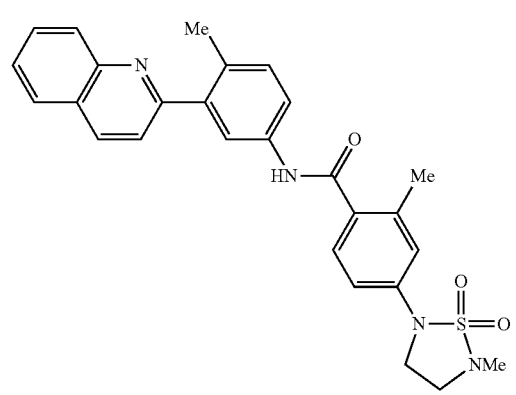
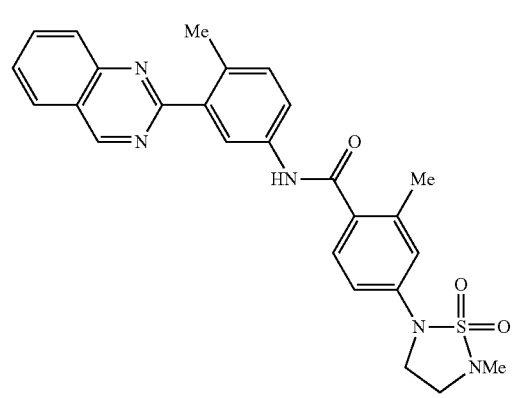

233
-continued
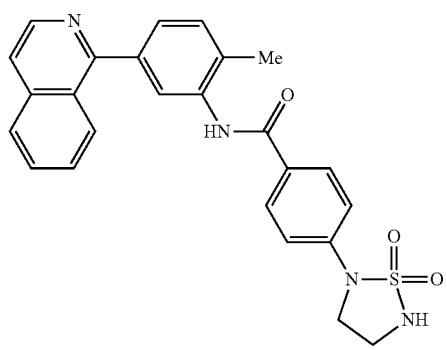
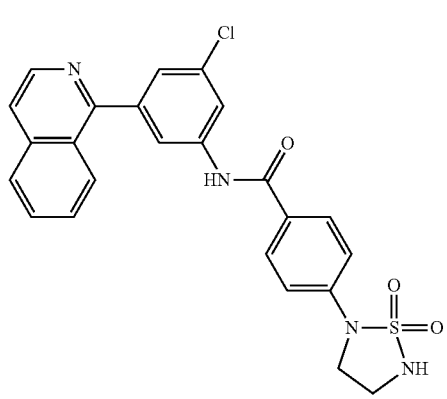
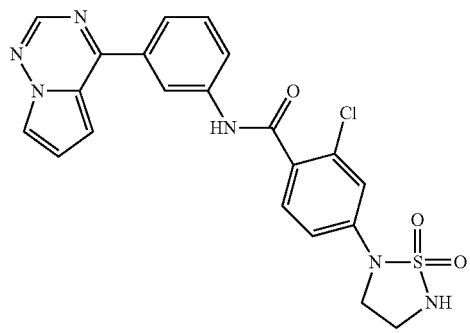
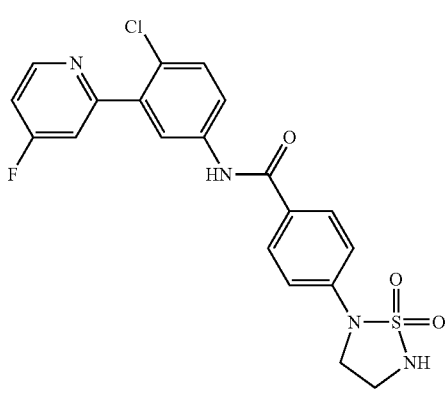
234
-continued
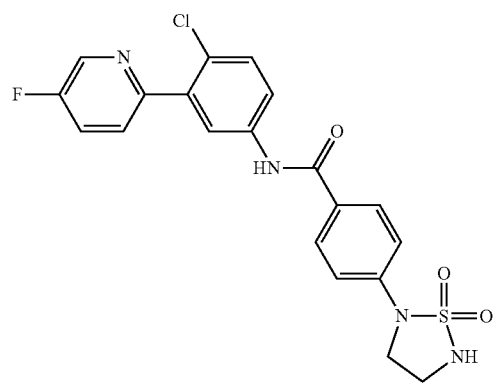
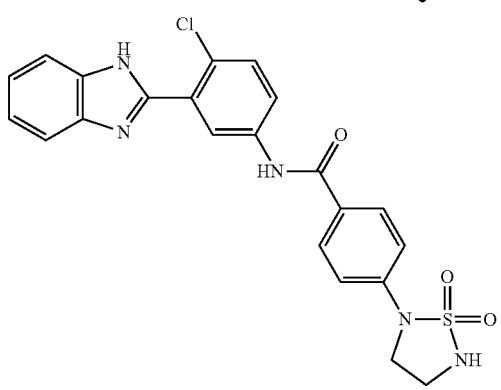
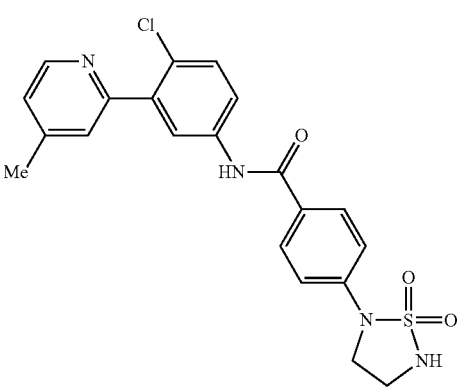
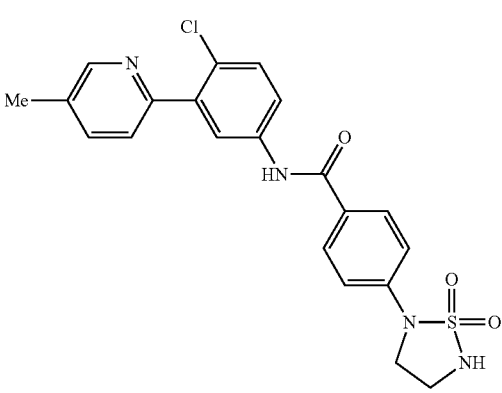

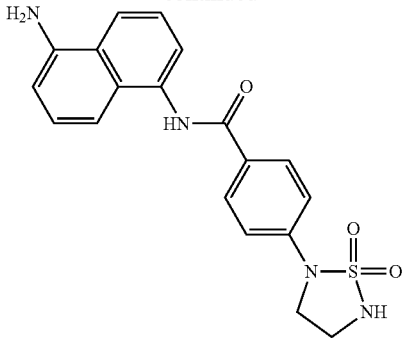
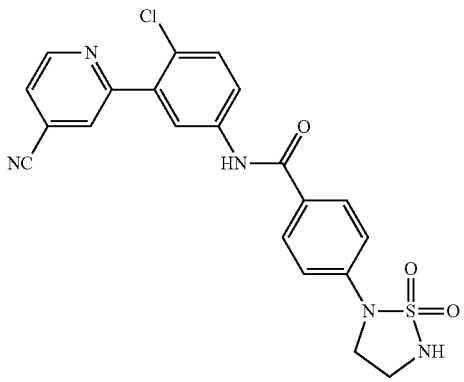
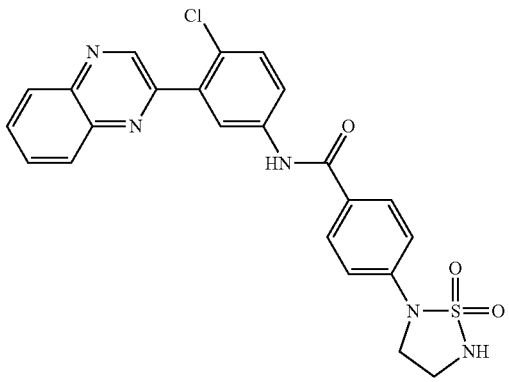
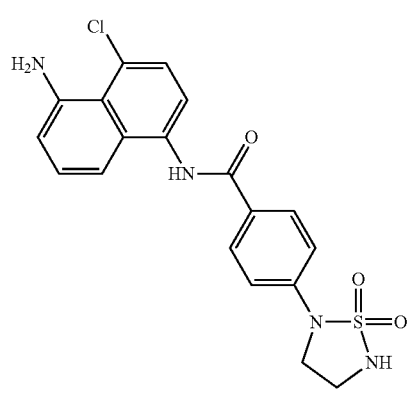

237
-continued
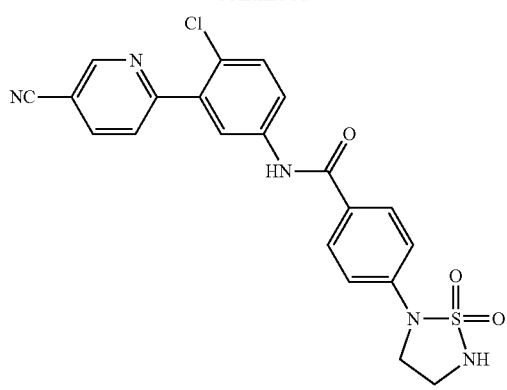
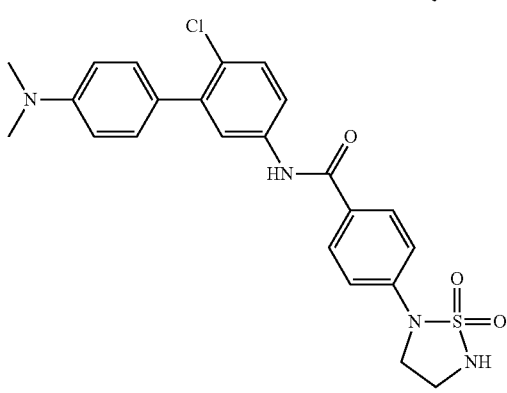
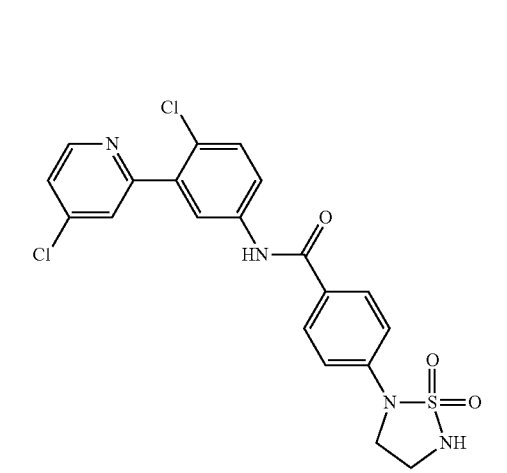
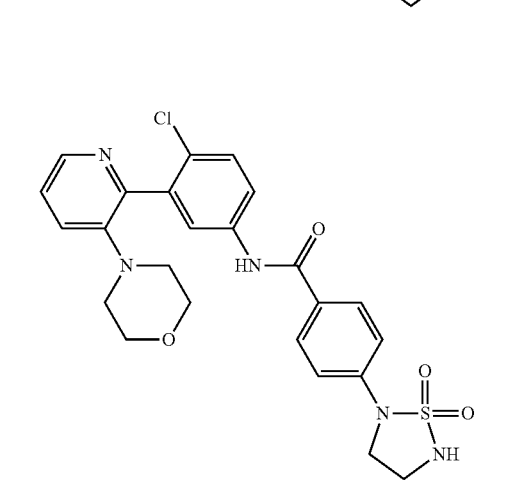
238
-continued
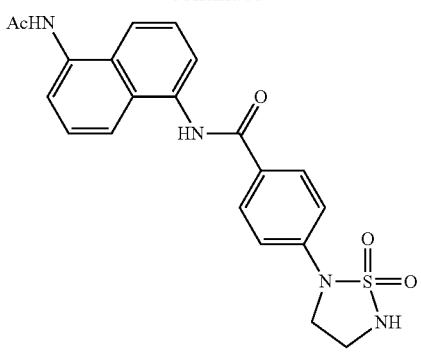
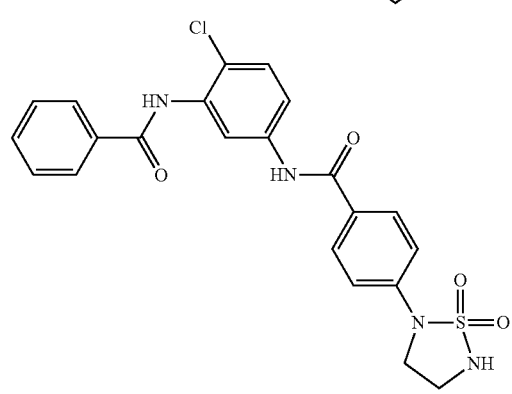
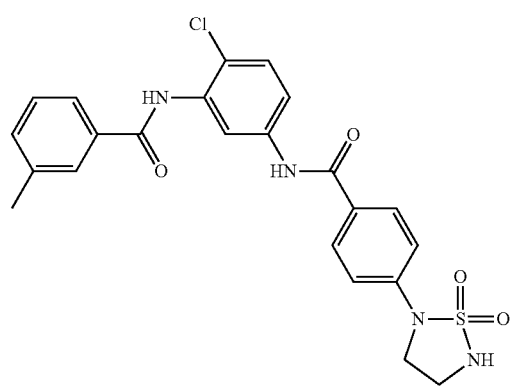
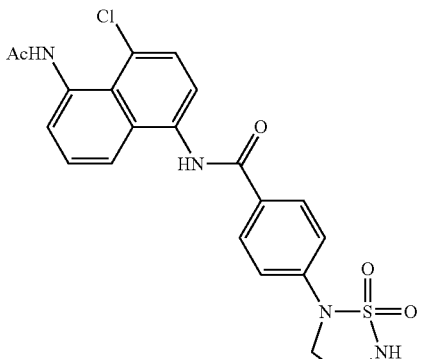

239
-continued

240
-continued

241
-continued
242
-continued
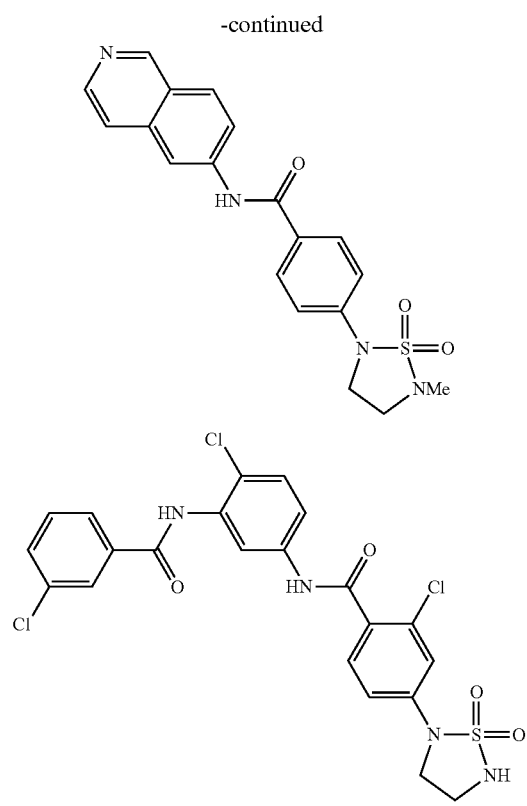
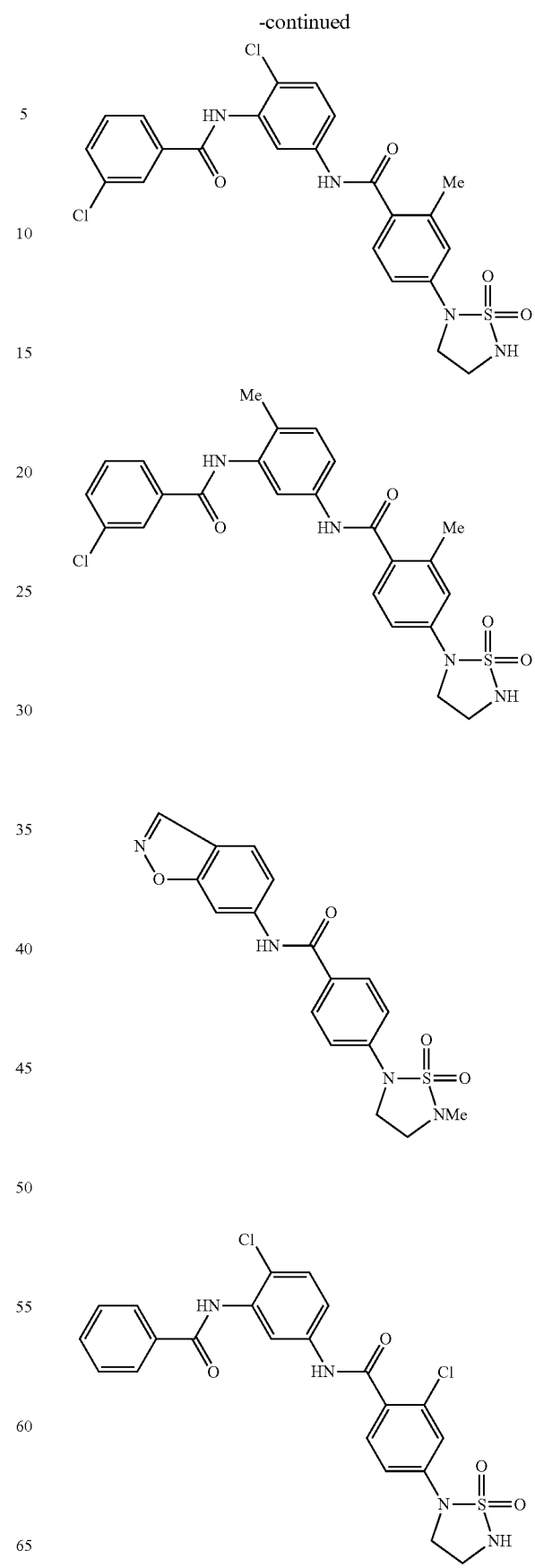

243
-continued
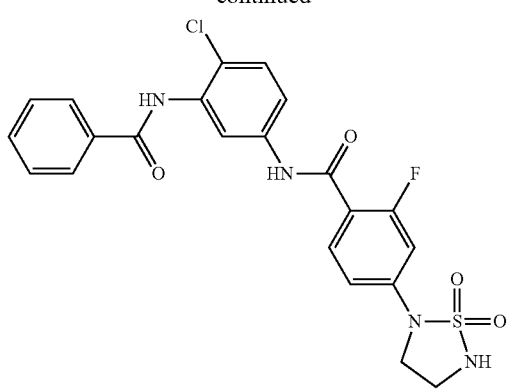
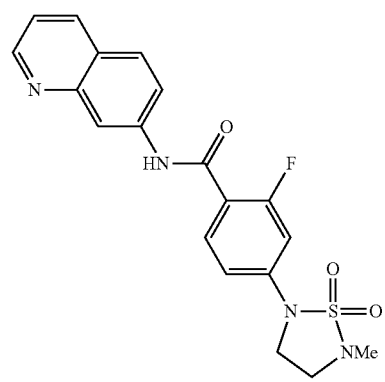
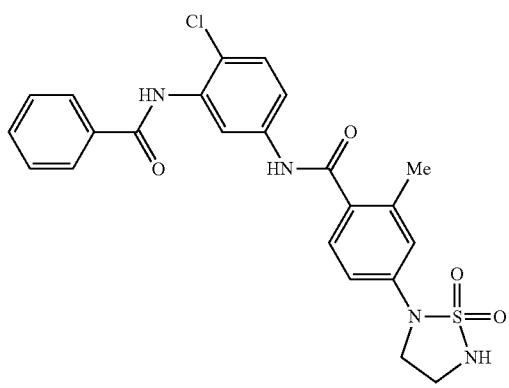
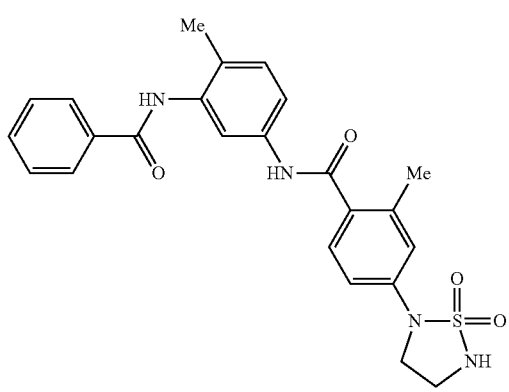
244
-continued
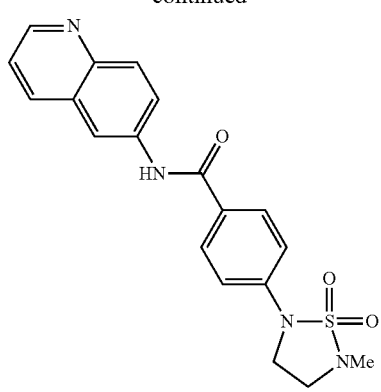
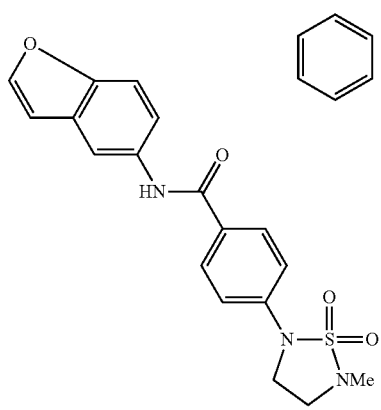
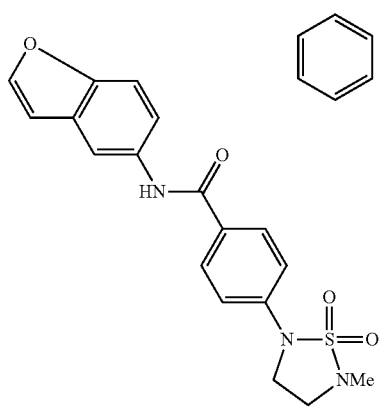
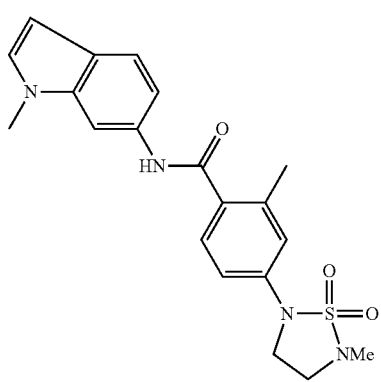
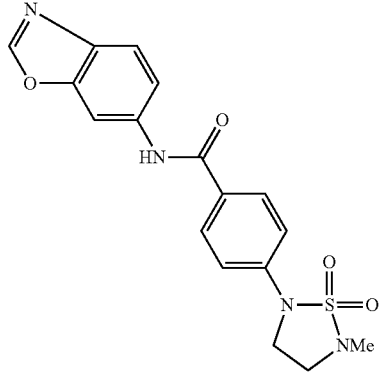

245
-continued
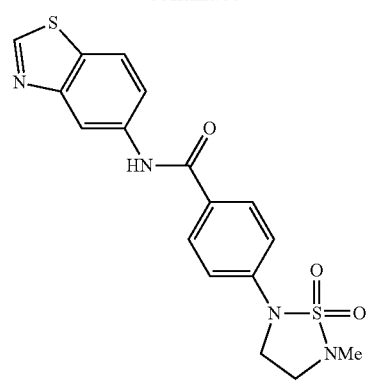
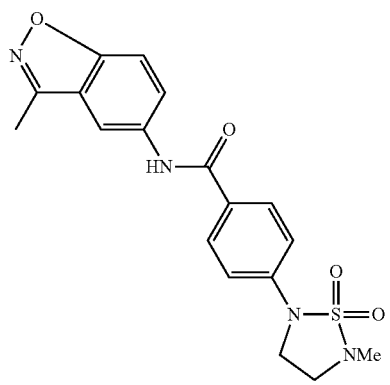
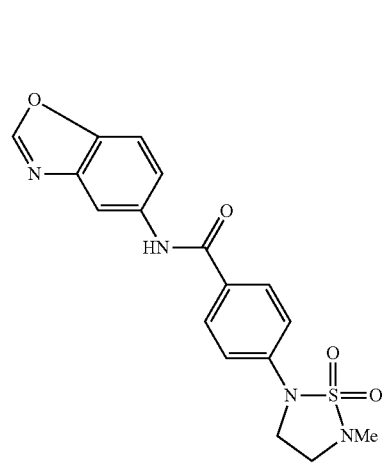
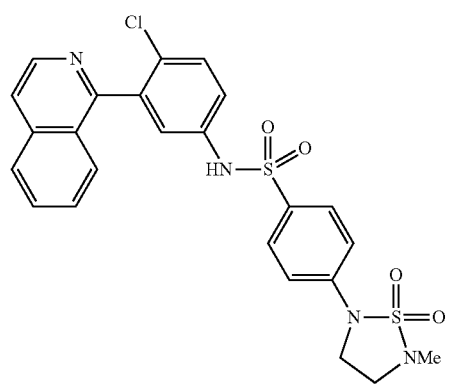
246
-continued
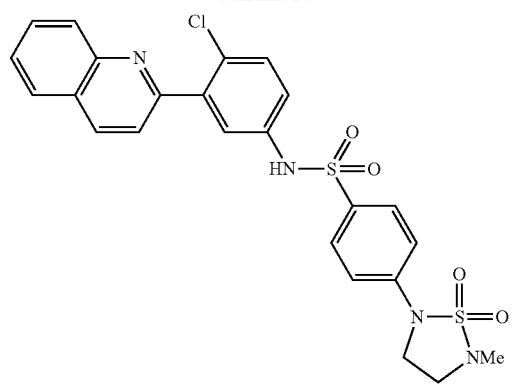
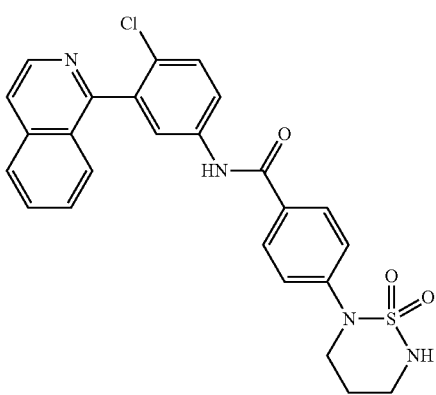
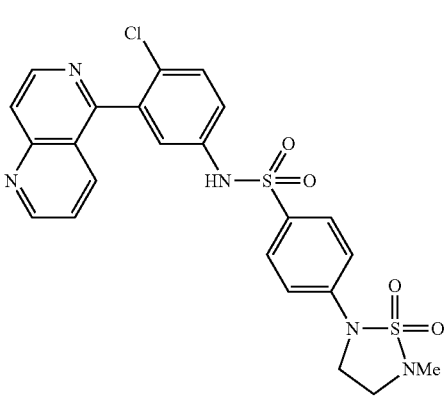
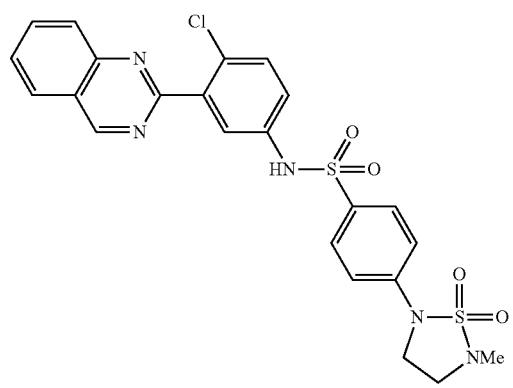

247
-continued
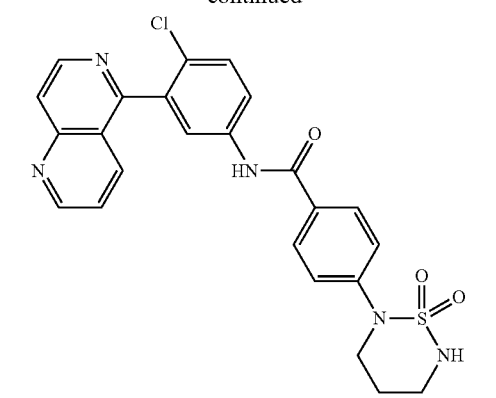
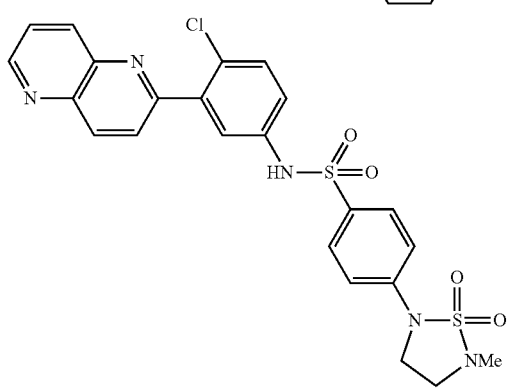
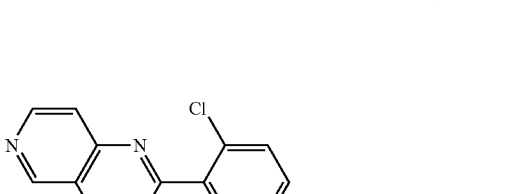
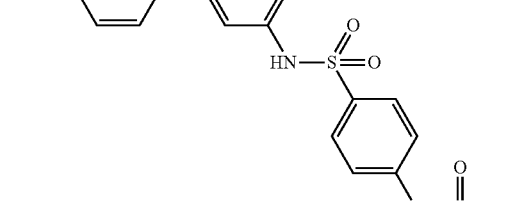
248
-continued
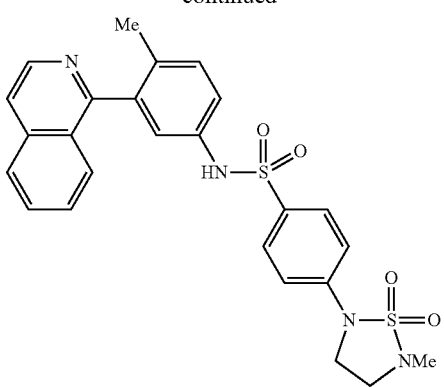
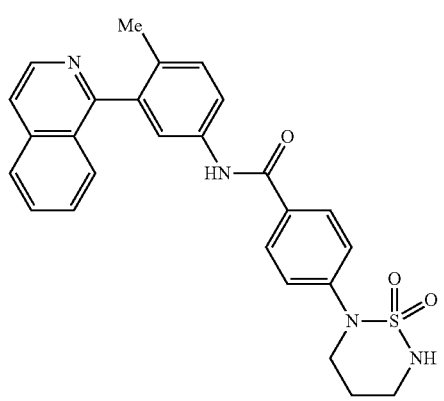
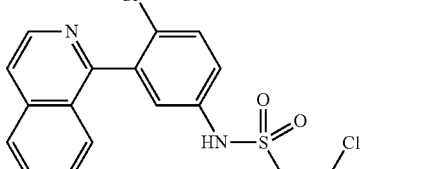
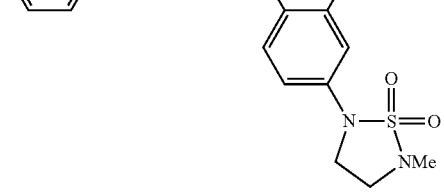

249
-continued
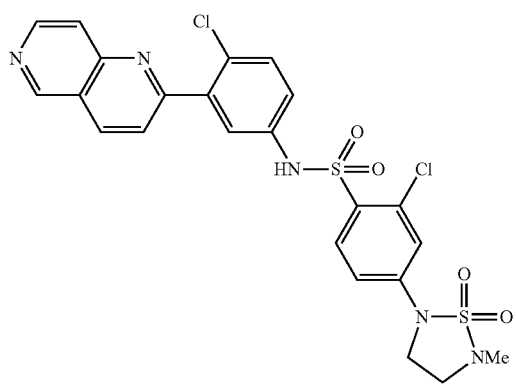
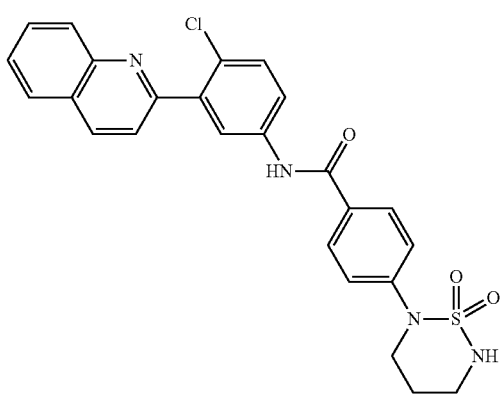
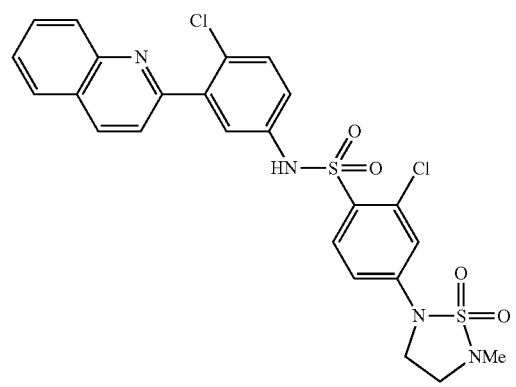
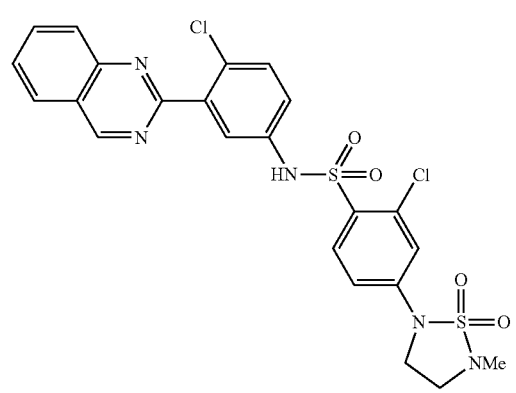
250
-continued
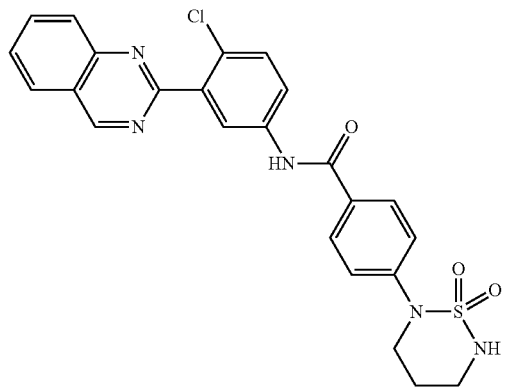
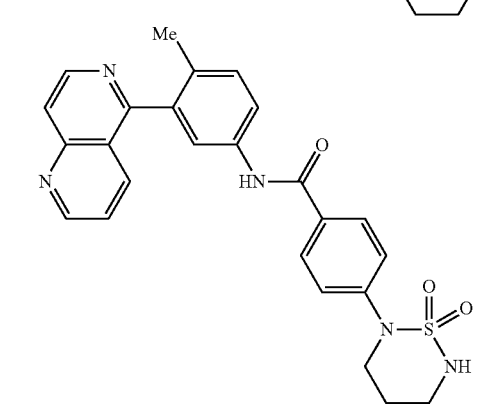
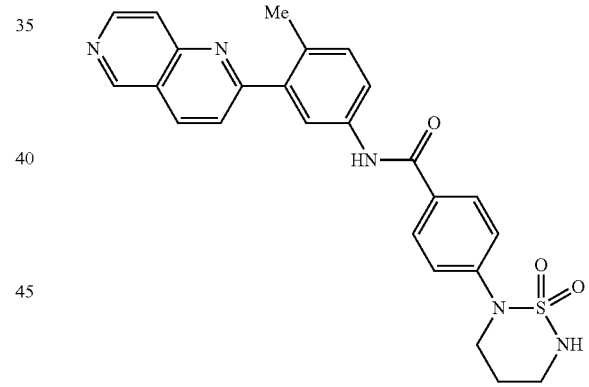
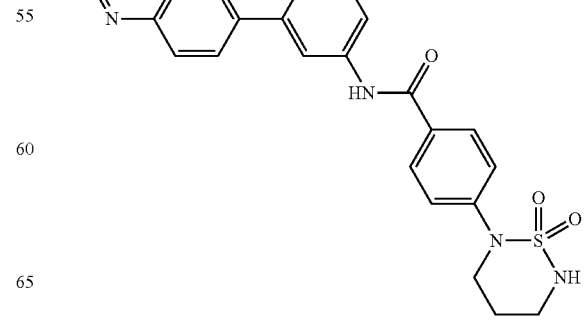

251
-continued
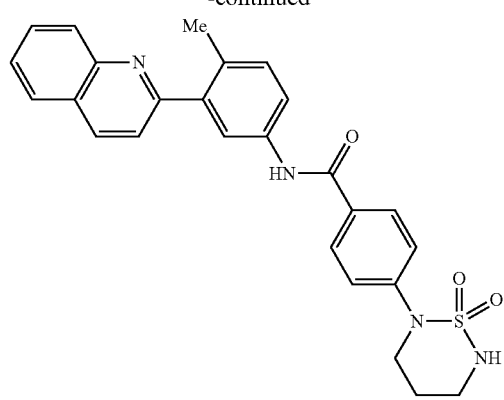
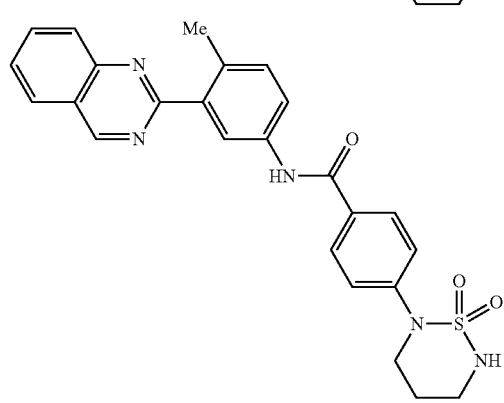
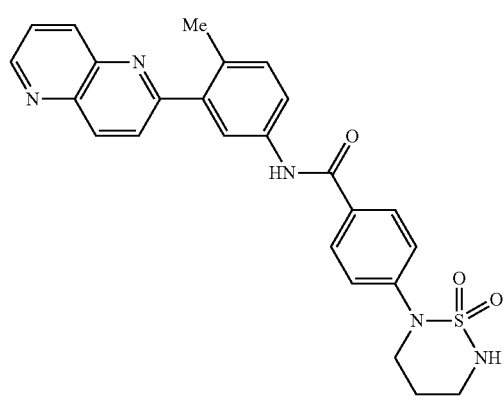
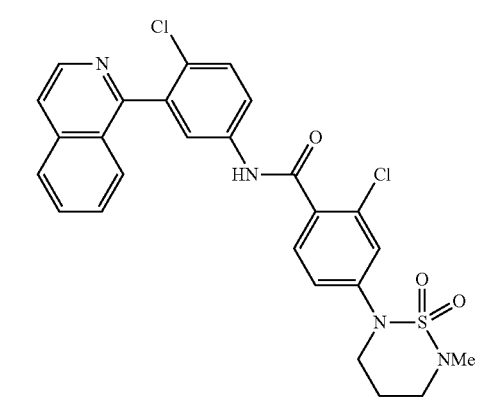
252
-continued
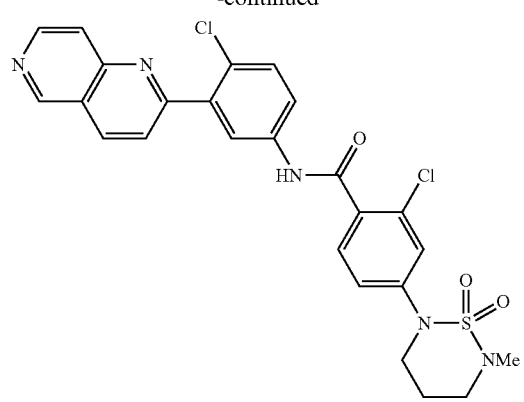
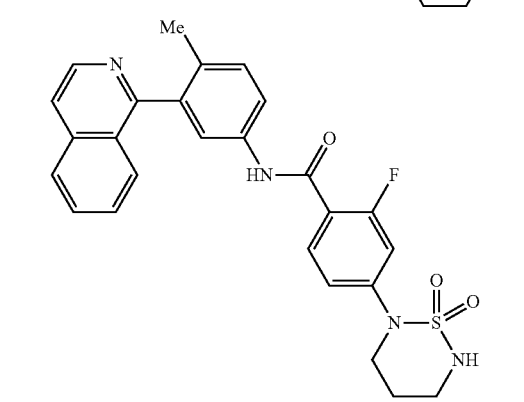
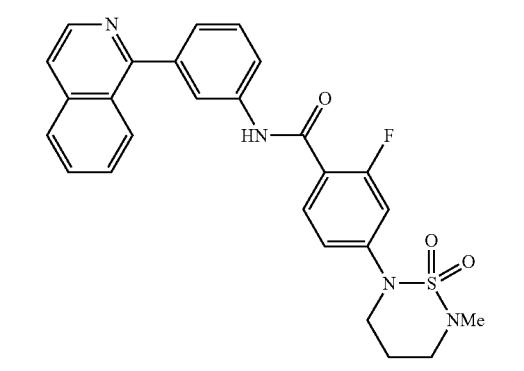
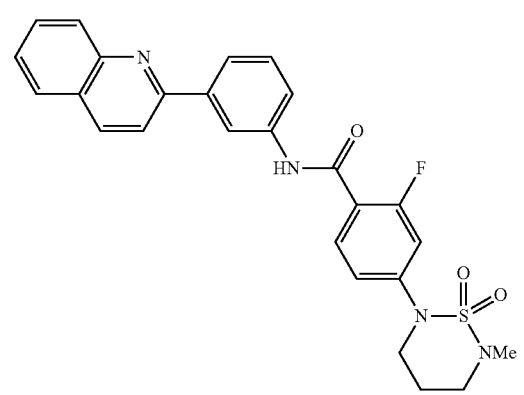

253
-continued
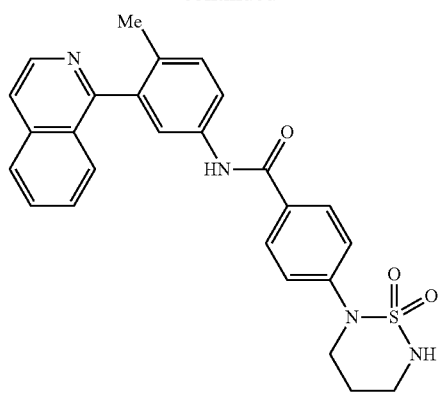
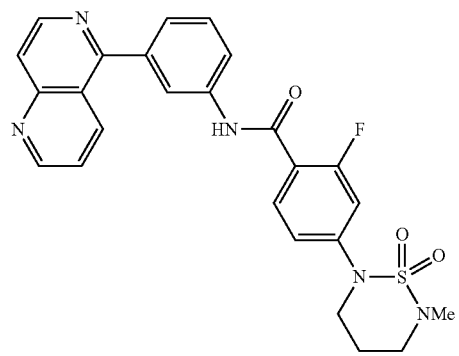
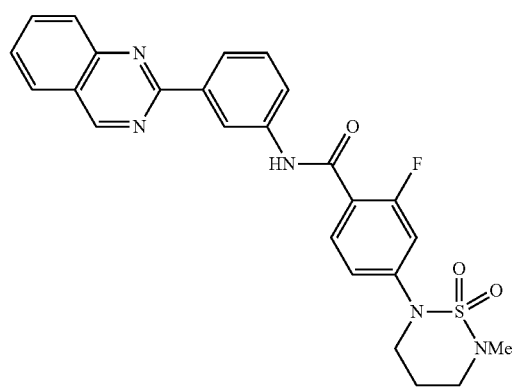
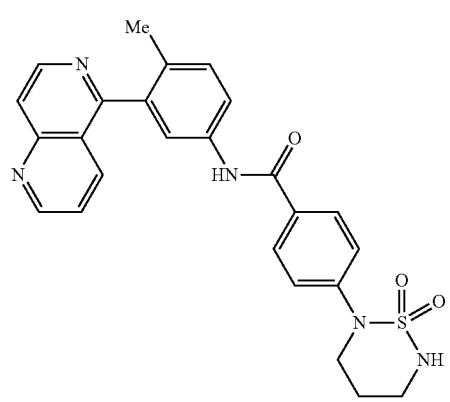
254
-continued
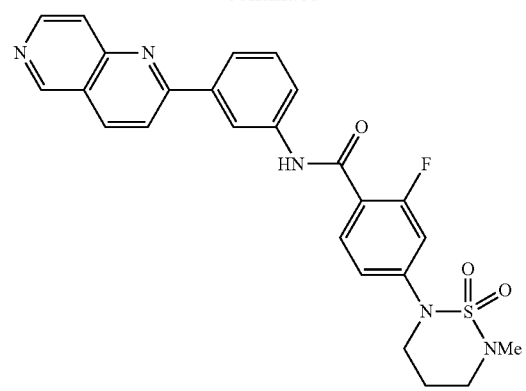
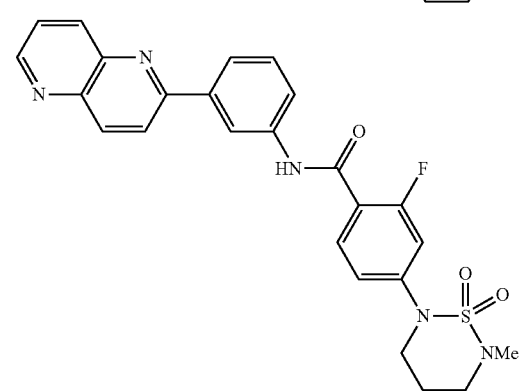
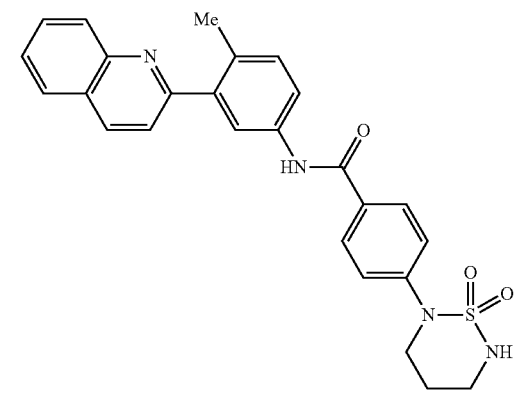
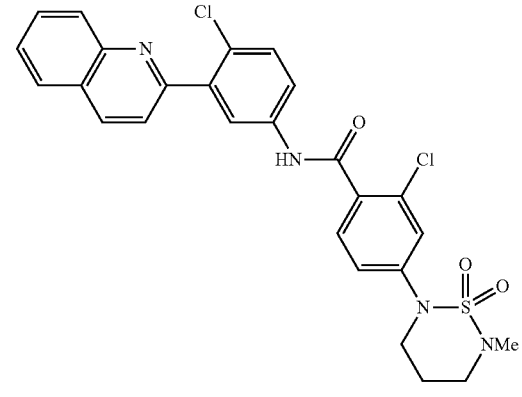

255
-continued
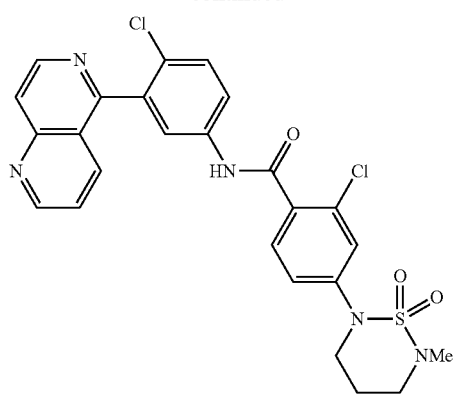
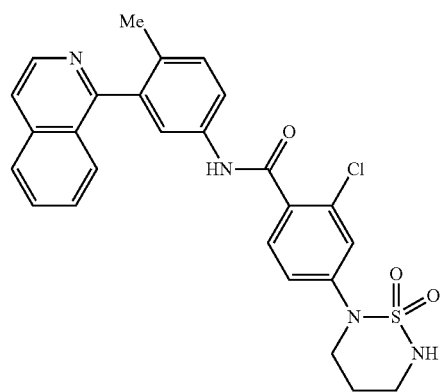
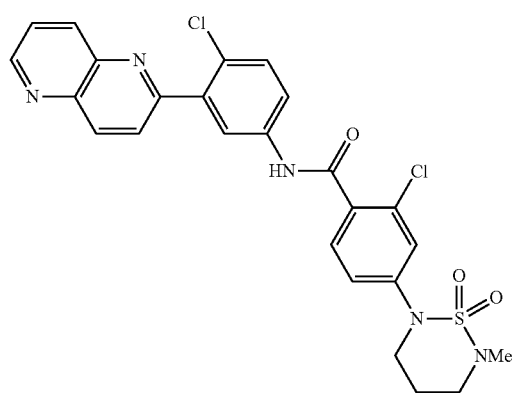
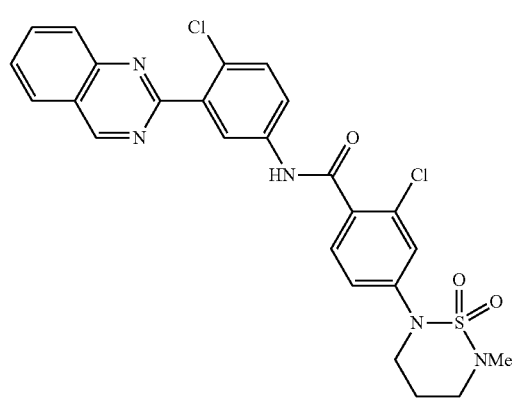
256
-continued
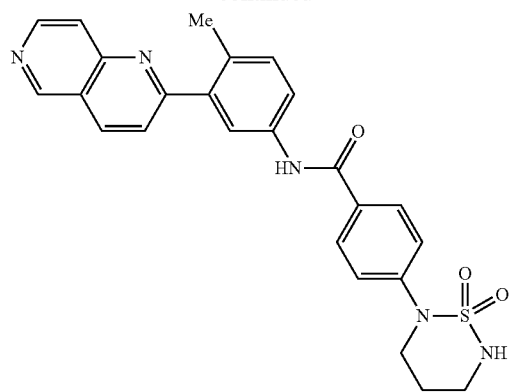
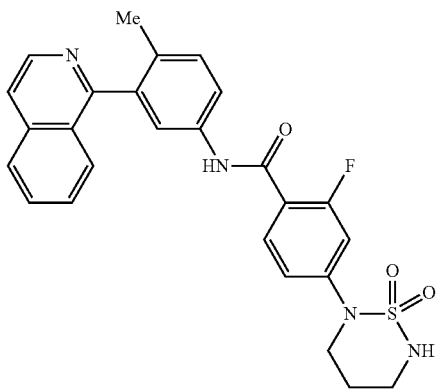
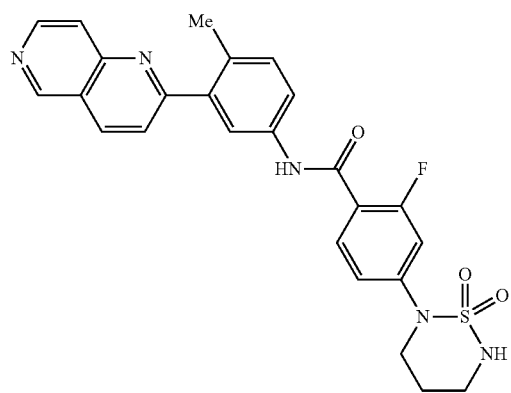
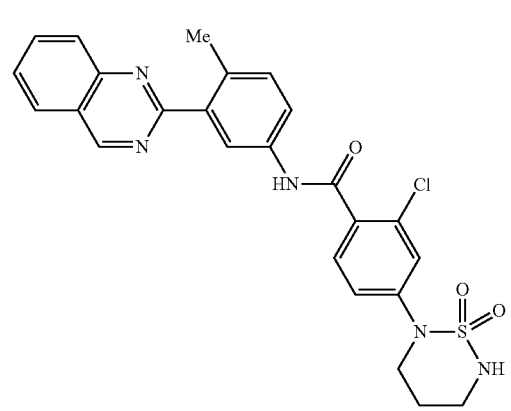

257
-continued
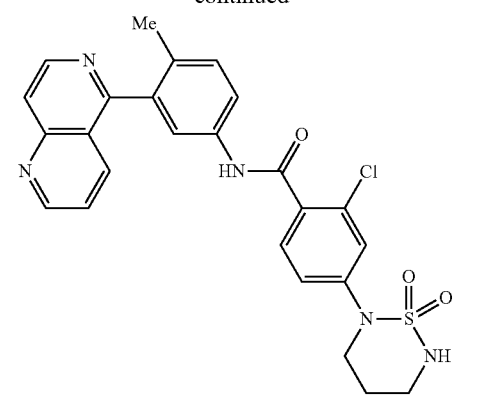
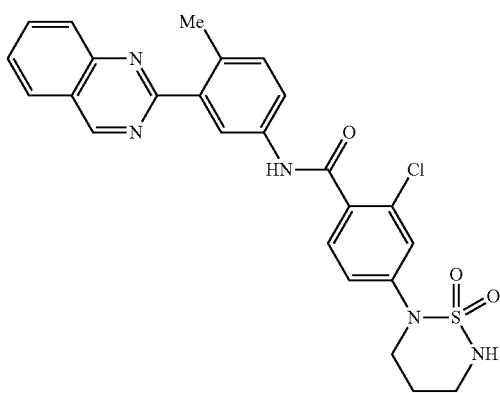
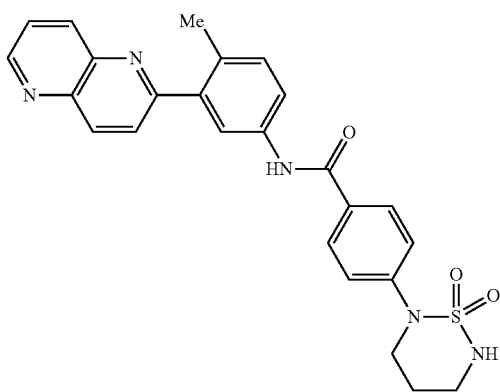
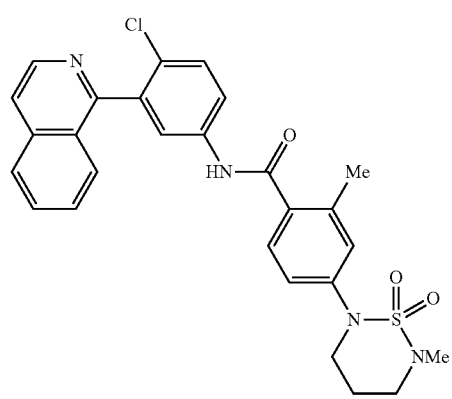
258
-continued
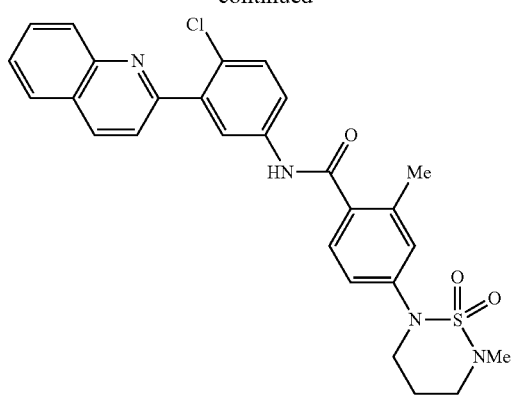
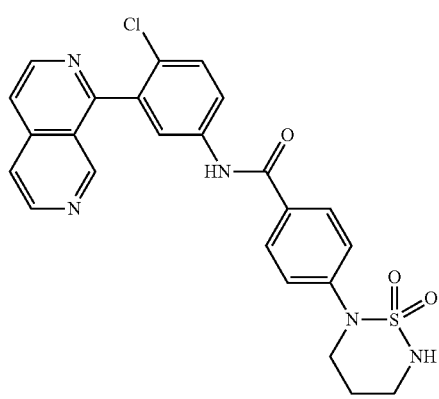
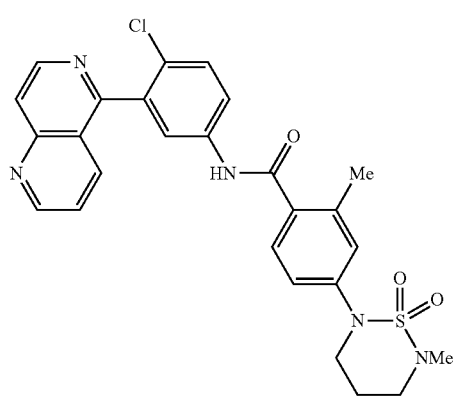
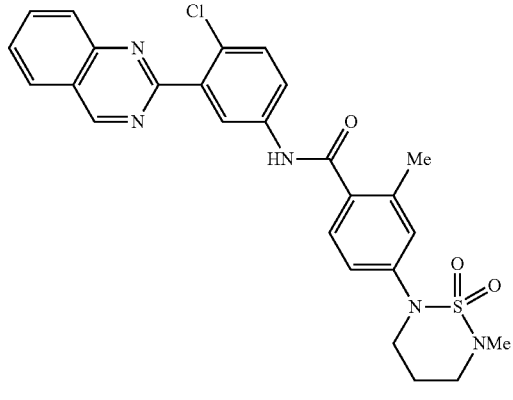

259
-continued
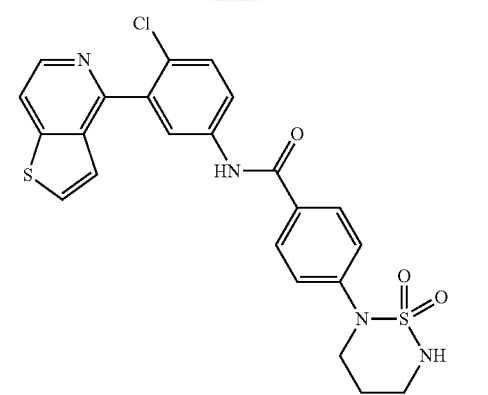
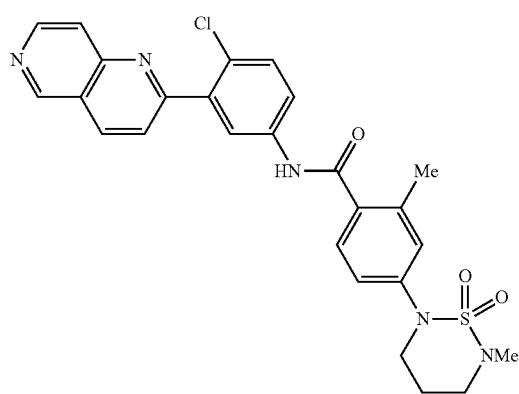
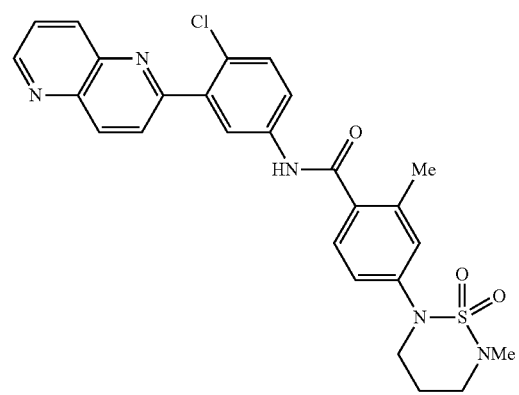
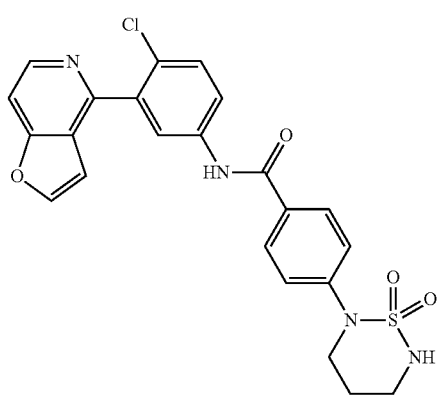
260
-continued
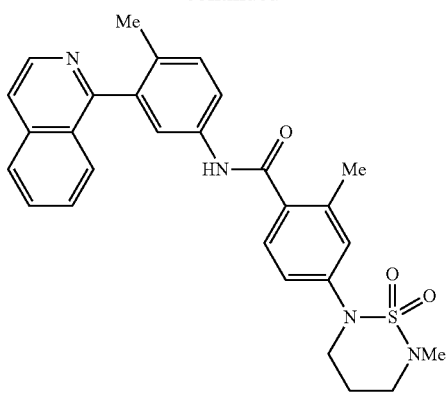
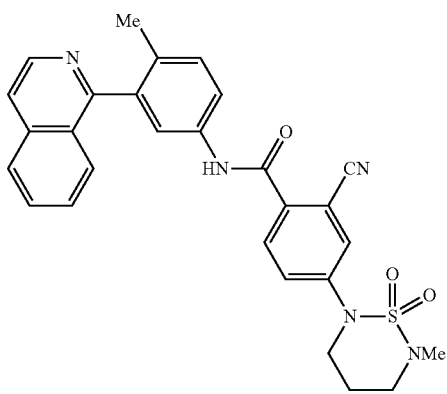
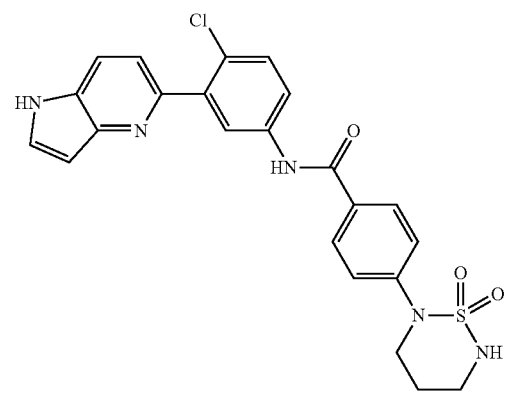
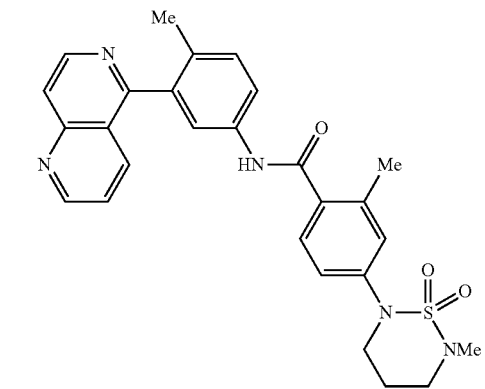

261
-continued
262
-continued
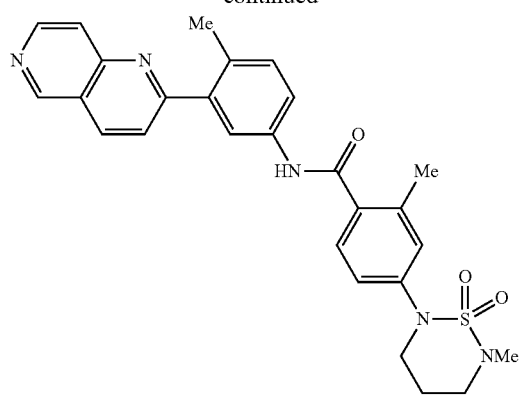
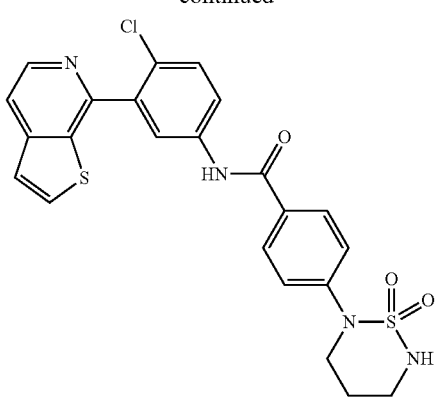

263
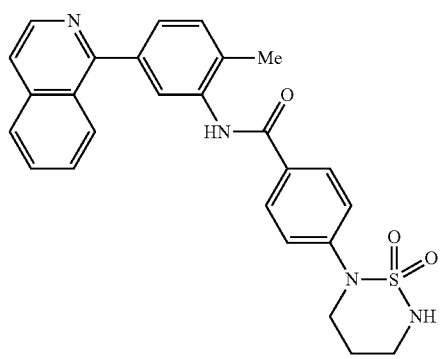
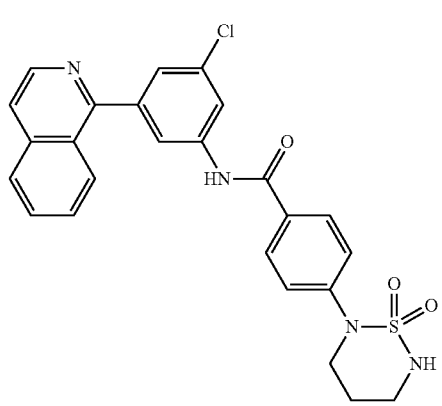
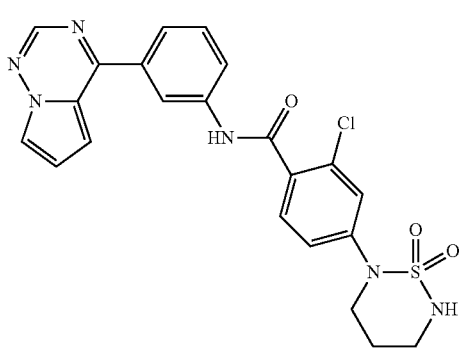
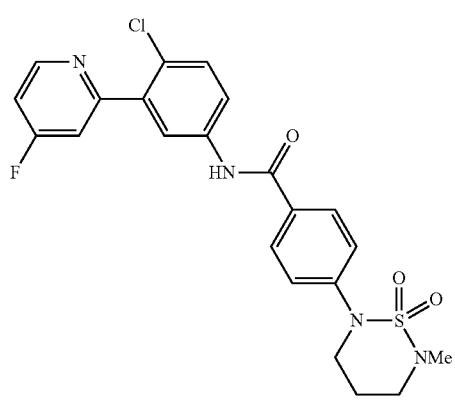
264
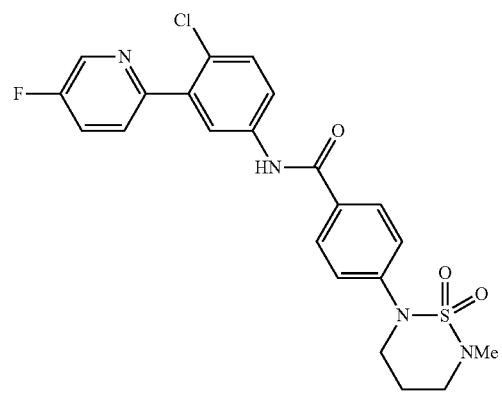
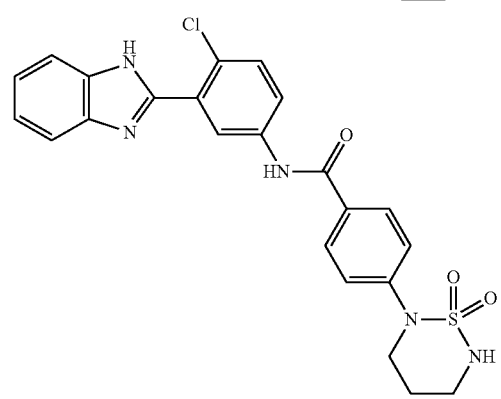
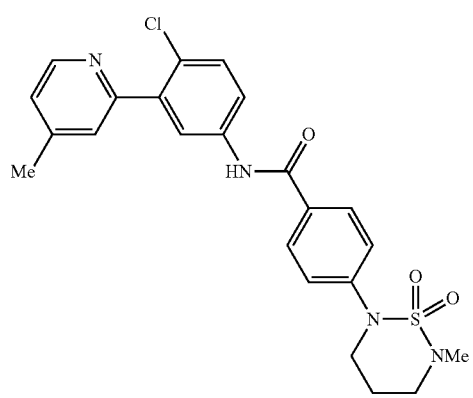
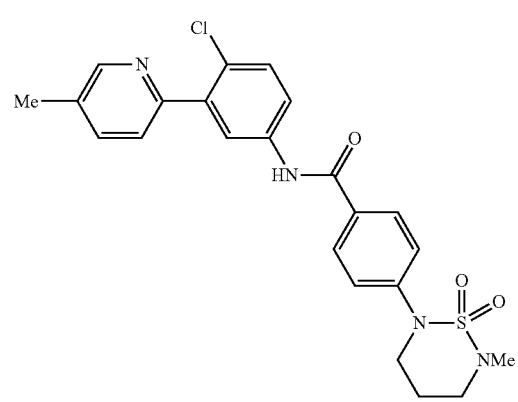

265
-continued
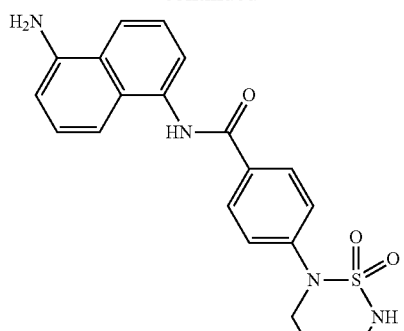
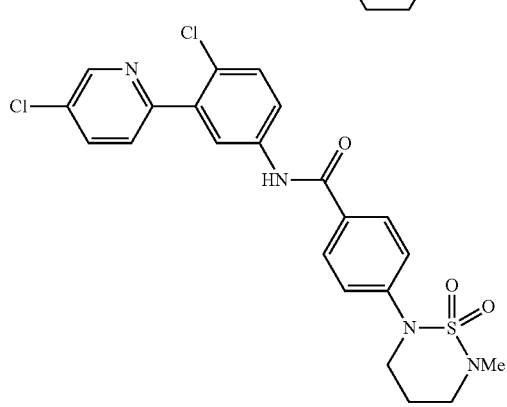
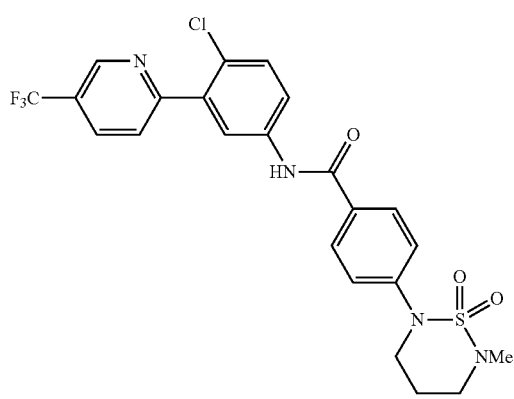
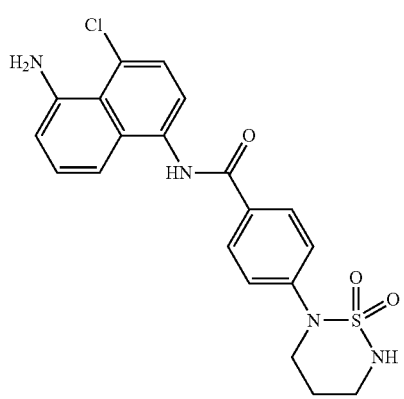
266
-continued
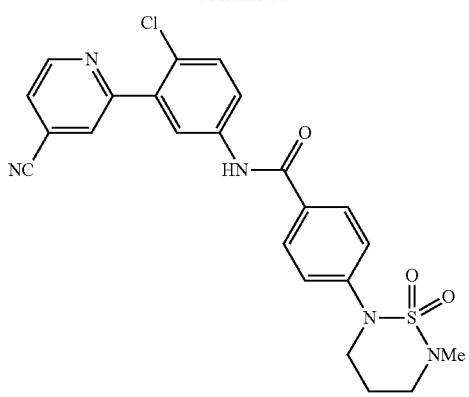
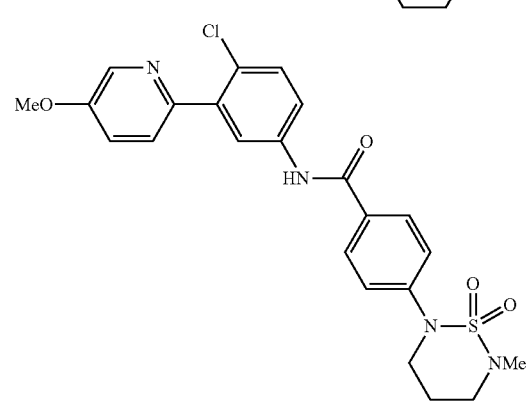
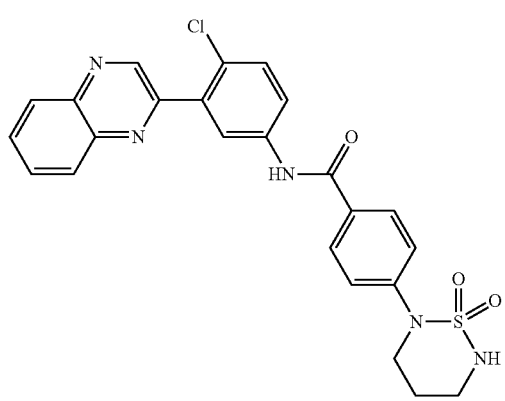
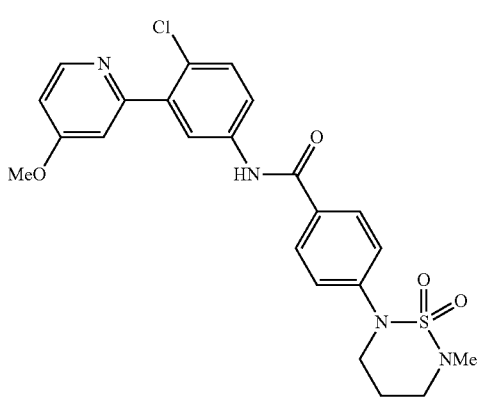

267
-continued
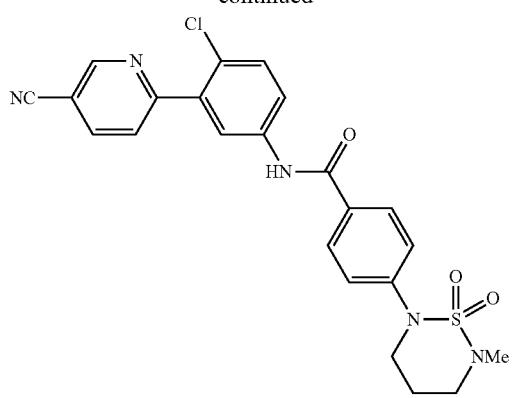
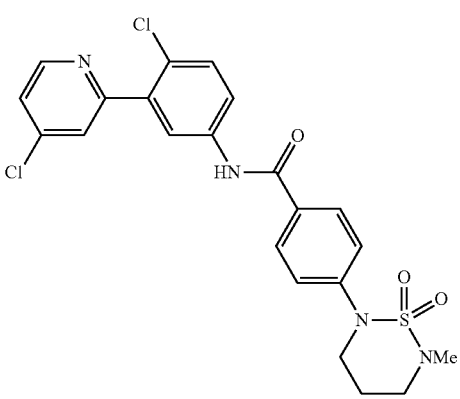
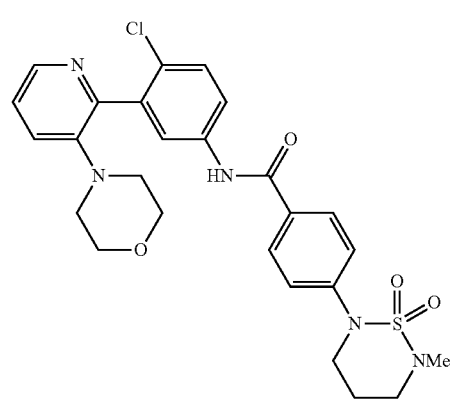
268
-continued
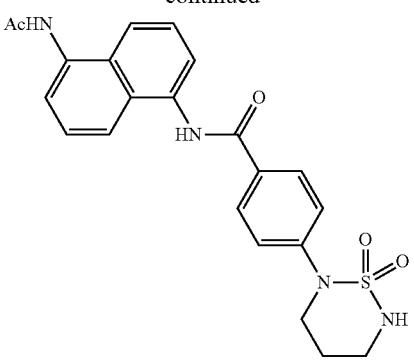
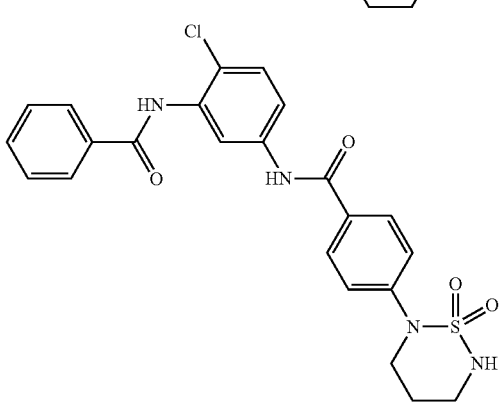
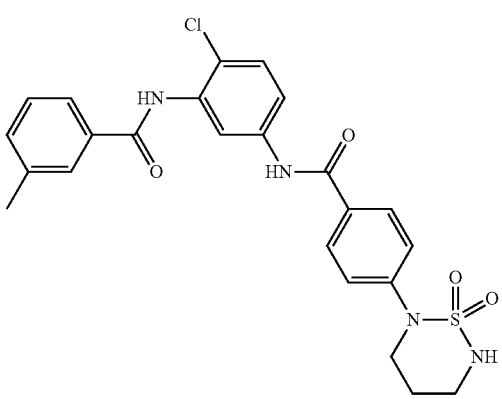
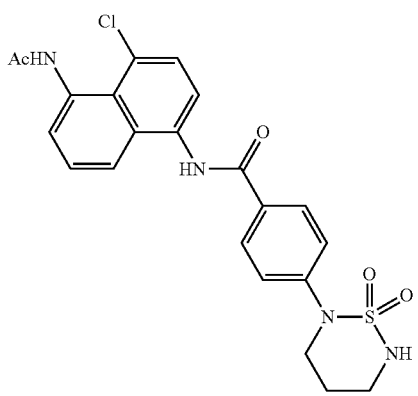

269
-continued
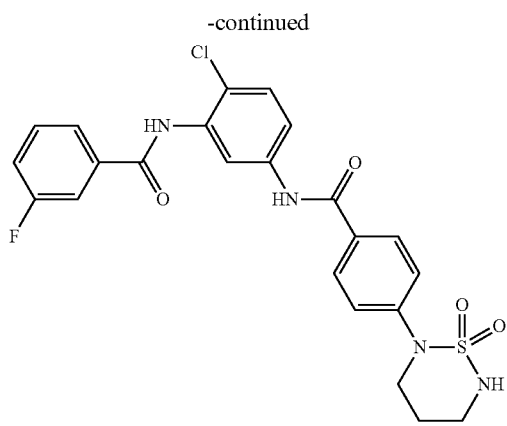
270
-continued
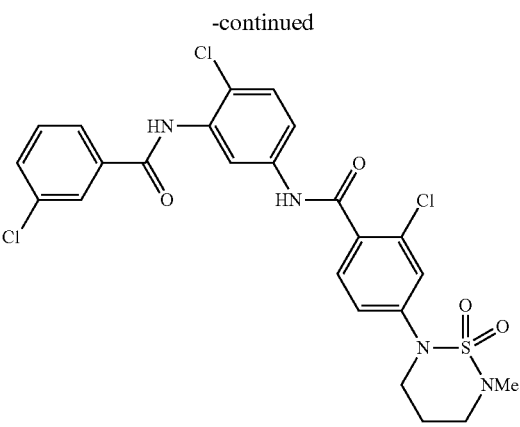
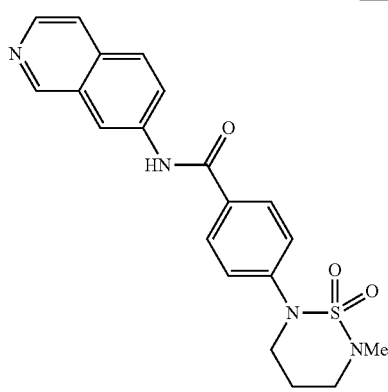
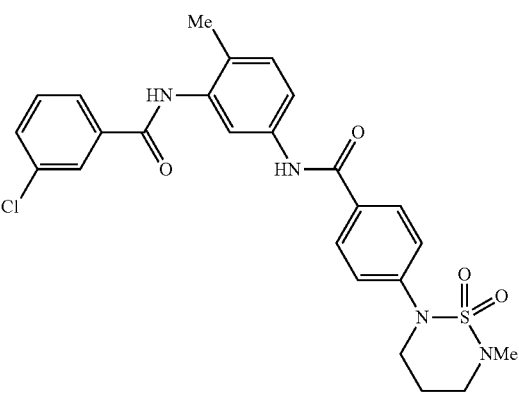
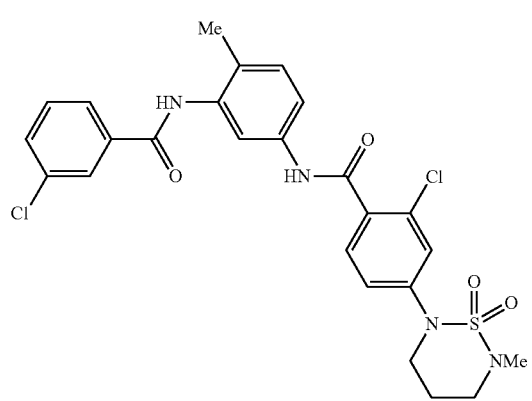

271
-continued
272
-continued
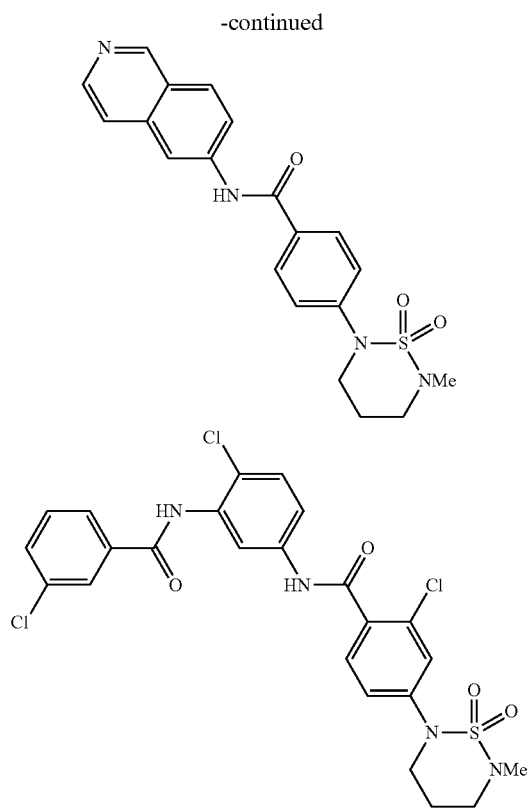
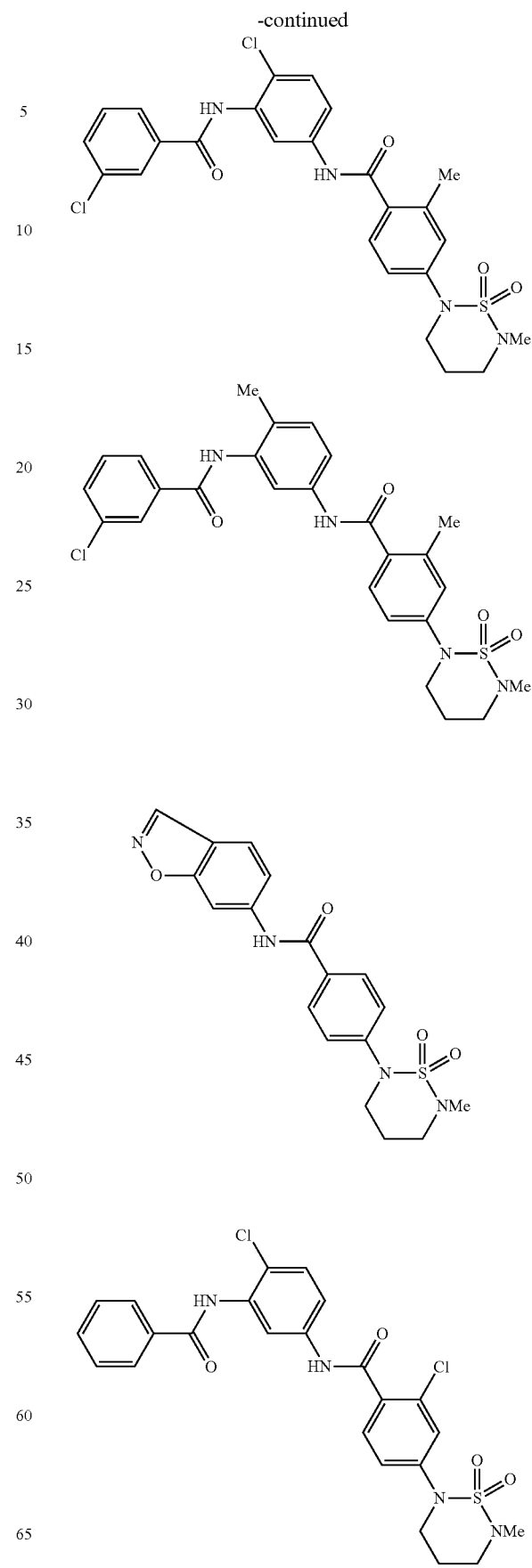

-continued
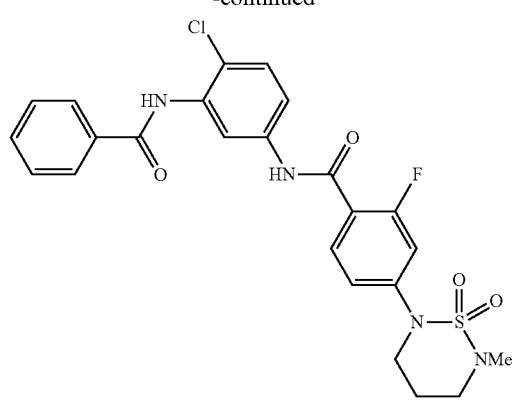
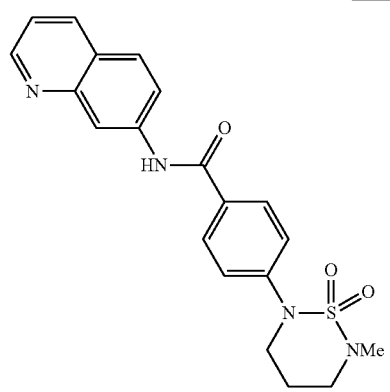
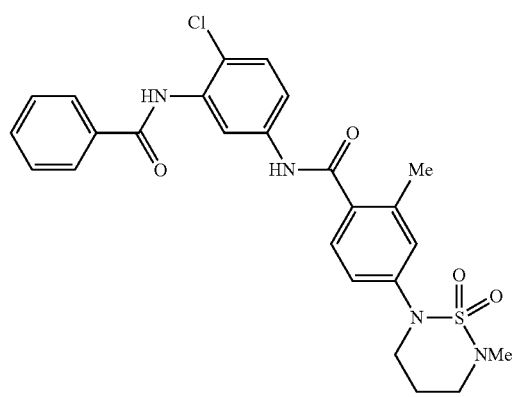
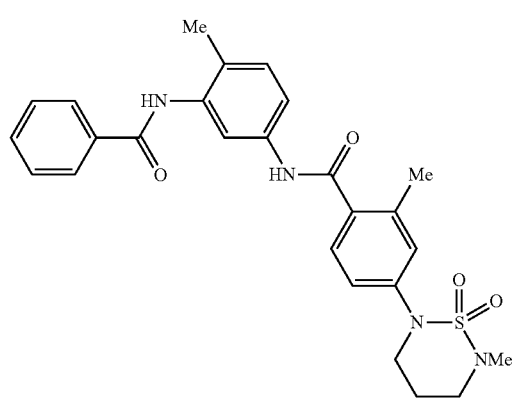
-continued
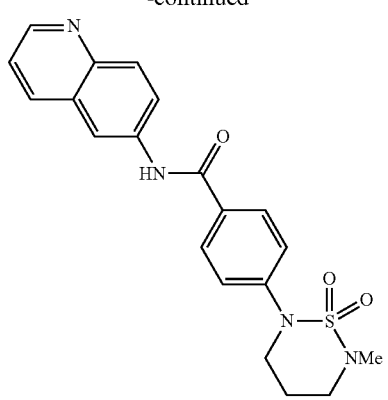
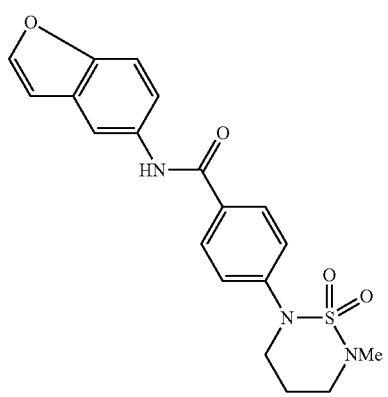
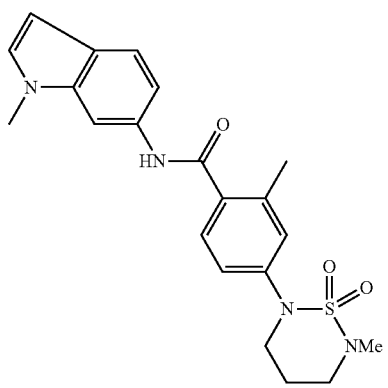
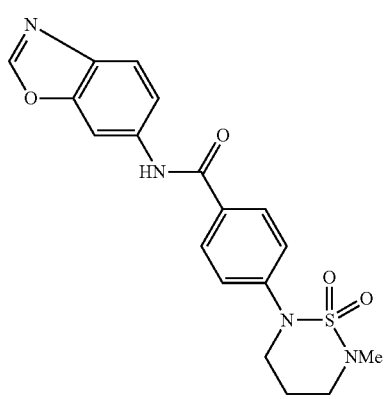

275
-continued
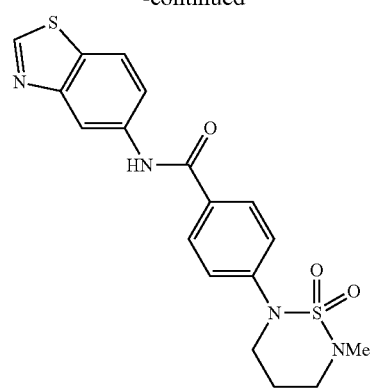
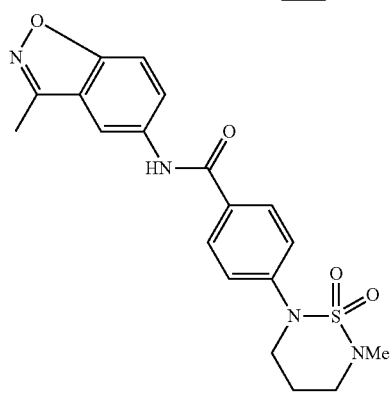
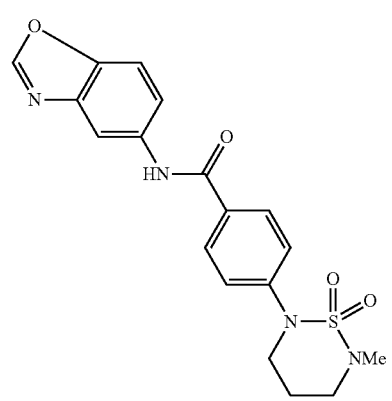
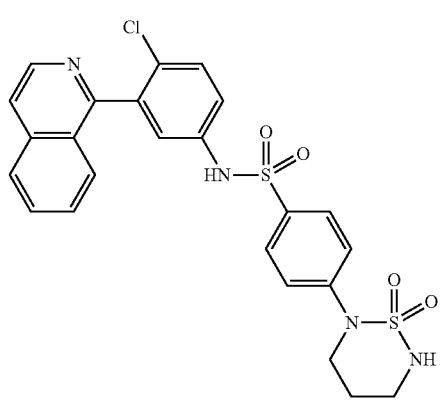
276
-continued
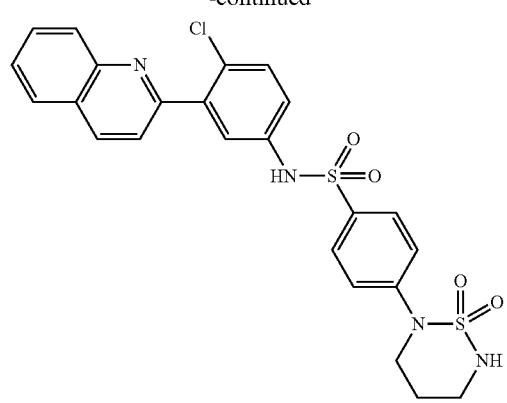
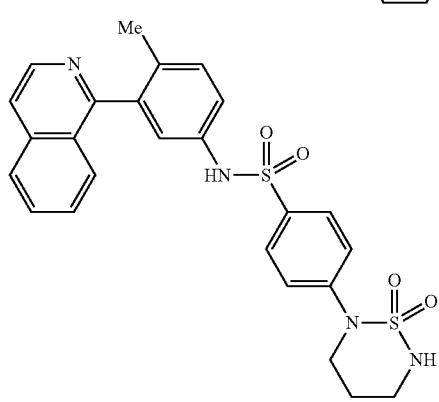
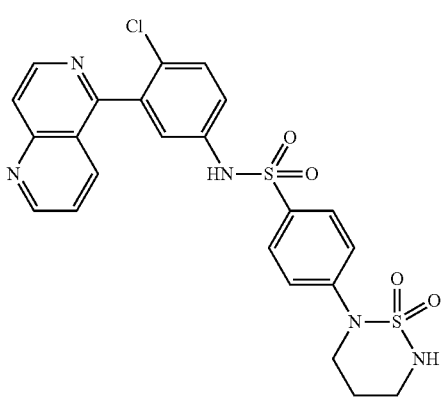
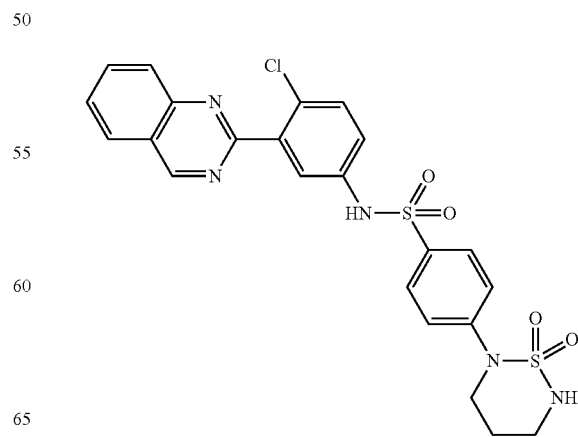

277
-continued
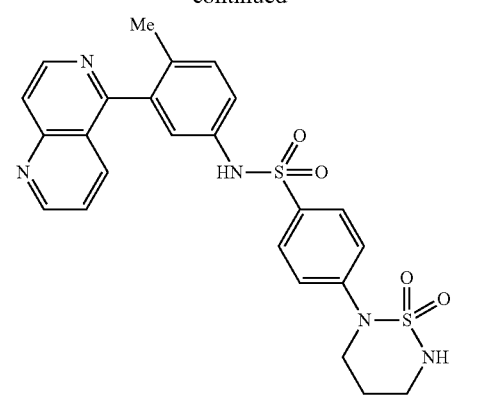
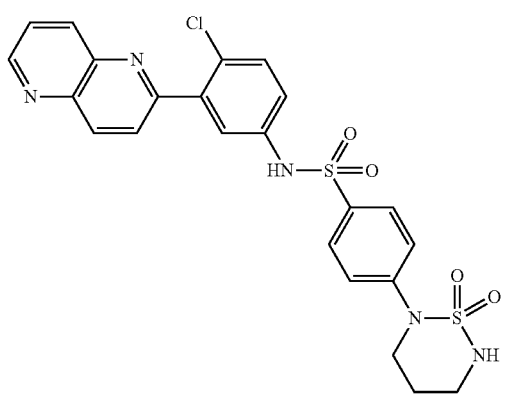
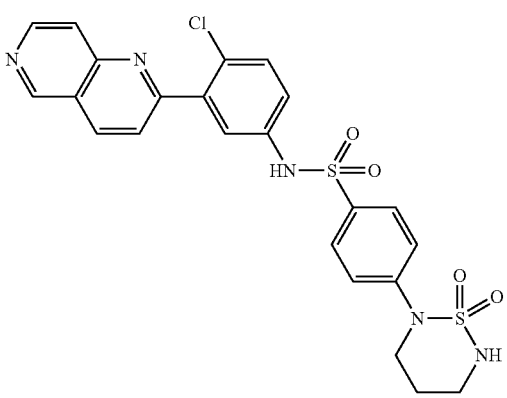
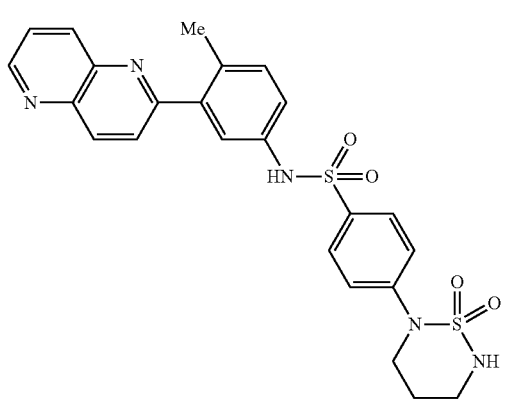
278
-continued
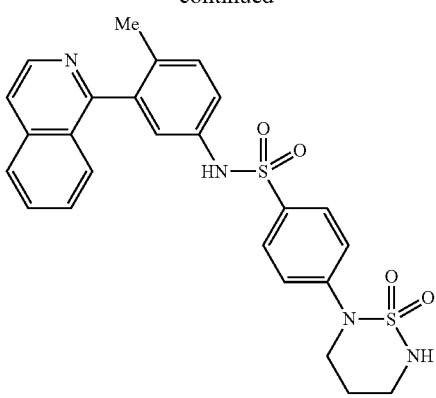
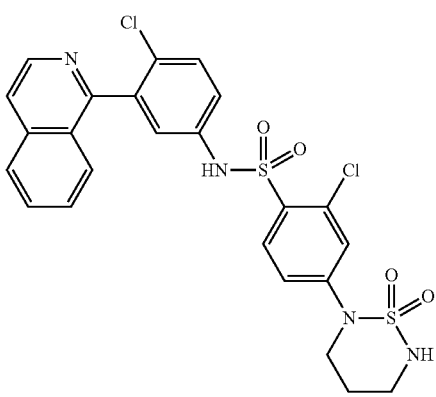
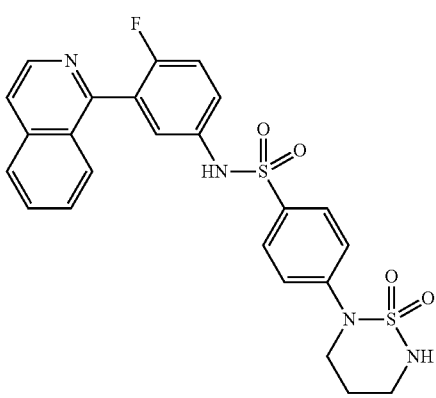
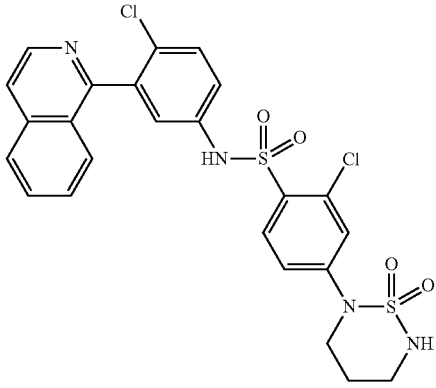

279
-continued
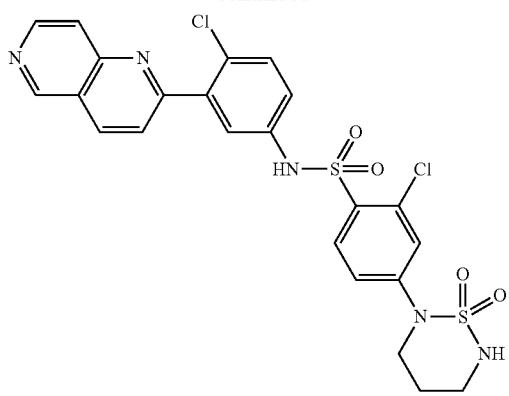
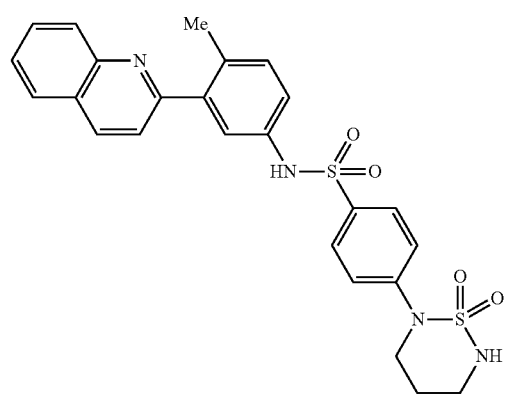
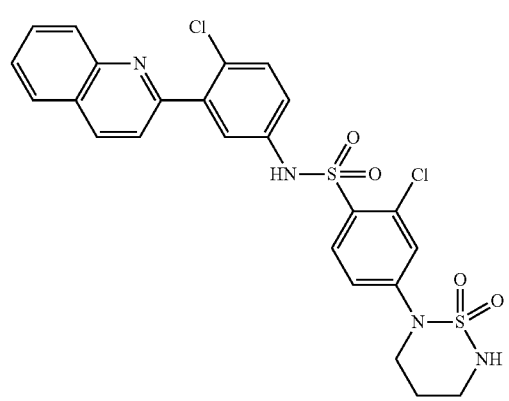
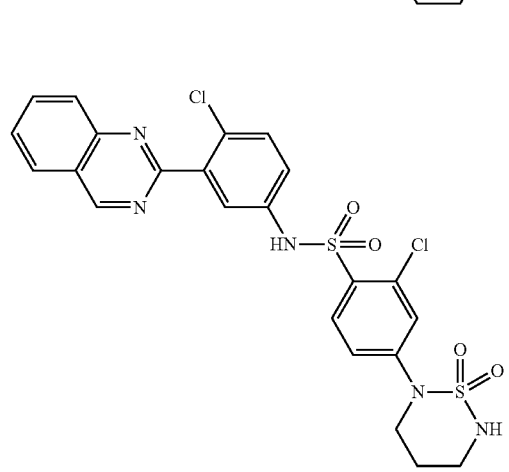
280
-continued
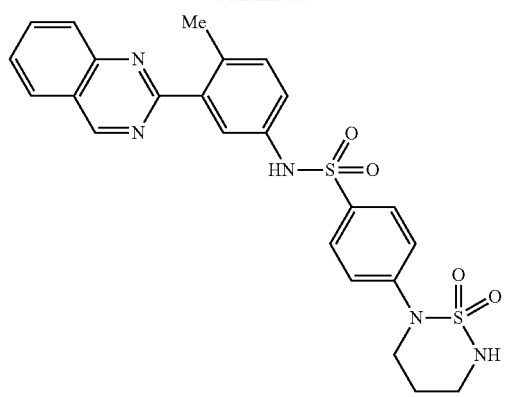
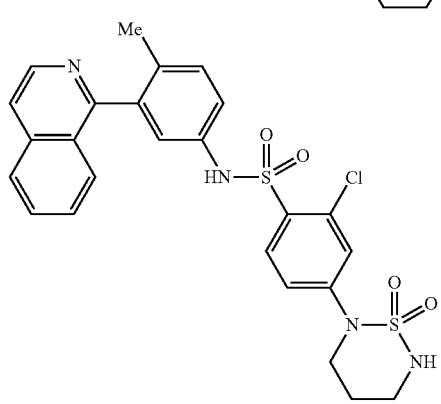
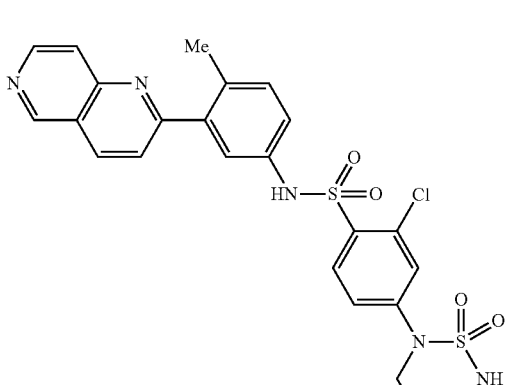
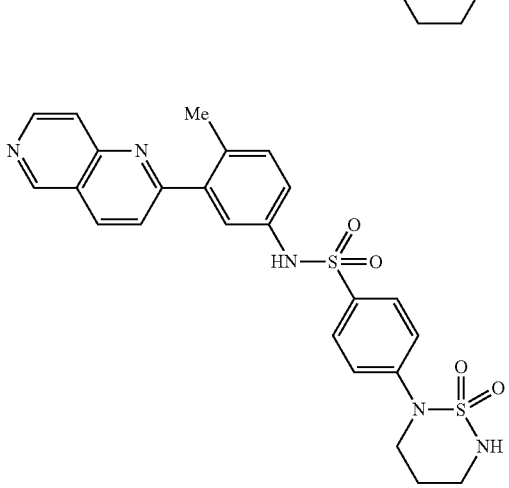

281
-continued

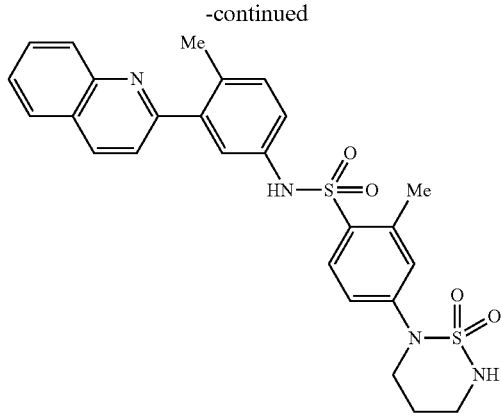

282
-continued

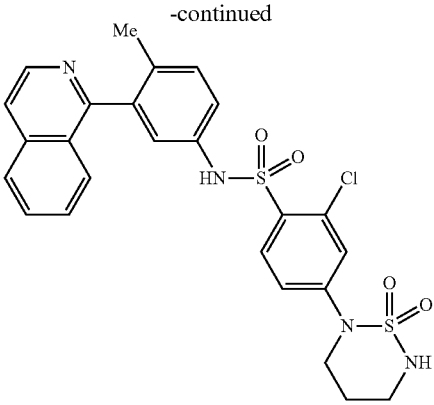

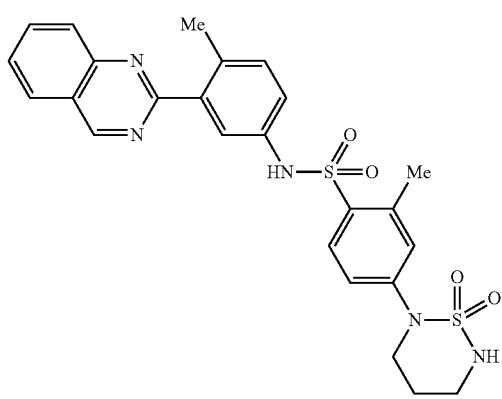

In another embodiment, a method is provided for preparing the invented compounds. The compounds of the present invention can be generally prepared by coupling the central rings and A ring intermediates via established condensation procedures. Compound (I) may contain various stereoisomers, geometric isomers, tautomeric isomers, and the like. All of possible isomers and their mixtures are included in the present invention, and the mixing ratio is not particularly limited.

Synthesis of the cyclic sulfonamide containing compounds of general formula (Ii) (wherein R3 is preferably H, Cl, F or Me and D is preferably H) was preferably carried out via two general strategies described in Scheme 1. Condensation of anilines II with acids III using HATU-mediated coupling in the presence of DIEA in DMF at room temperature could directly afford the desired product. Alternatively, the acids III could be converted to acyl chlorides IV using thionyl chloride in THF at room temperature or under reflux. Further treatment of IV with aniline II in anhydrous pyridine at room temperature afforded the desired Ii.

Scheme 1

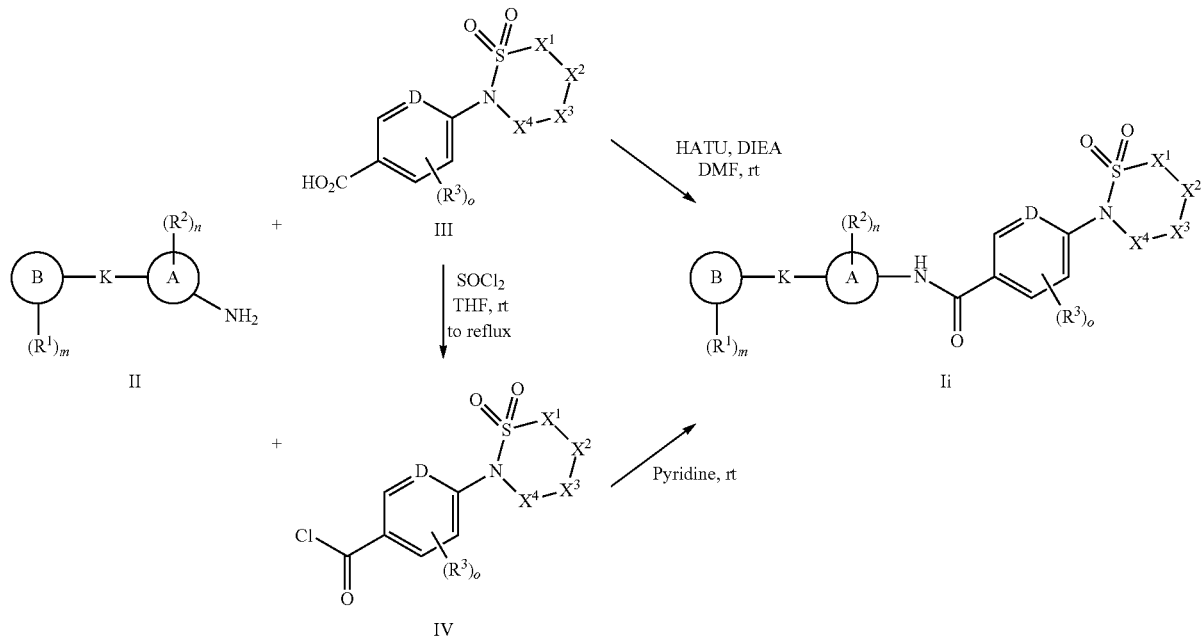

General methods to make heterocyclic anilines IIa-IIq are described in Scheme 2. Under Suzuki-Miyaura cross-coupling reaction conditions (Chapoulaud, V. G. et al., *Tetrahedron*, 2000, 56, 5499-5507; Mongin, F., Rebstock, A., et al., *J. Org. Chem.*, 2004, 69, 6766-6771), the coupling of various heteroaryl boronic acids 1 or the relevant pinacol boronates with bromides 2 (PG represents acetyl, Boc or other protecting groups) affords the compounds II in the presence of an appropriate palladium catalyst, such as palladium(II) acetate triphenylphosphine, dichlorobis(triphenylphosphine)palladium(0), or tetrakis(triphenylphosphine)palladium(0). The reaction also works with pseudohalides such as triflates (OTf), instead of halides, and also with boron-esters instead of boronic acids. A variety of base agent may be used, but not limited to, KOAC, $K_2CO_3$, $K_3PO_4$, KOH, NaOH, $Ba(OH)_2$, KF, CsF, NaOAc, $Na_2CO_3$, $Cs_2CO_3$, $NaHCO_3$ and the like. A suitable solvent may be used, but not limited to, dioxane, acetonitrile, THF, DMF, DMA, DMSO, toluene, water and the like, may be used alone or as a mixture thereof, conveniently at a temperature within the range room temperature to reflux.

Scheme 2

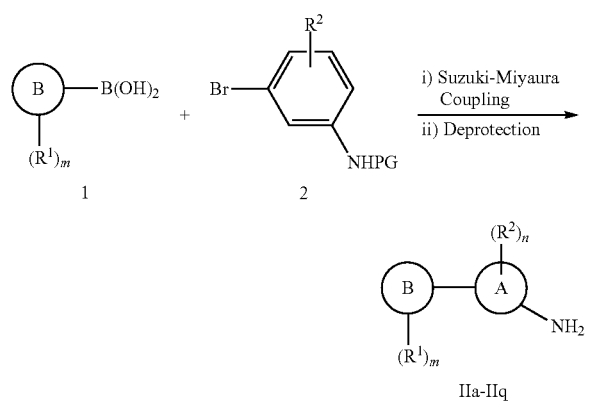

Alternatively, synthesis of the naphthyridine of general formula (5) is preferably carried out via Friedländer reaction as described in scheme 3 and 4.

Scheme 3

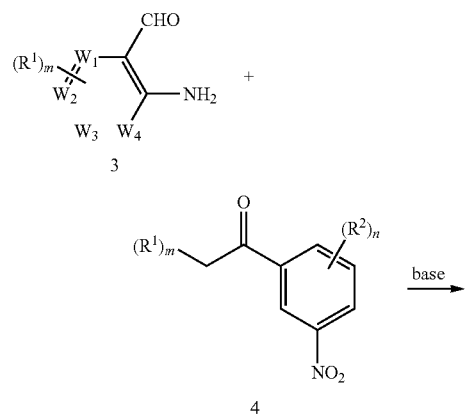

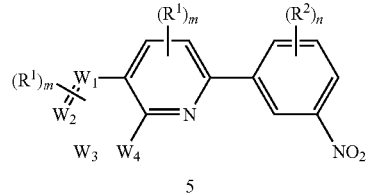

The condensation of 2-amino-aryl-aldehydes or amino-heterocycle-aldehyde 3 (wherein W1, W2, W3, W4, R1 is CH, CR1 or N) with aryl ketones 4 formed quinoline, naphthyuridine or pyrido-pyrimidine derivatives 5 (Peter G. D., Kan K. E., Roger N. F., et al., J. Org. Chem., 2003, 68, 467-477).

This reaction has been catalyzed by trifluoroacetic acid, toluenesulfonic acid, iodine, acetic acid, and Lewis acids, such as ZnCl2 or SnCl2 with solvent in the temperature starting from room temperature to 150° C. or can be promoted by thermolysis to 150° C.-200° C. in the absence of solvents. The alternative reaction condition is catalyzed by alkali alcohol, such as LiOH, NaOH and KOH, in the the solvent of alcohol, such as methanol, ethanol, Isopropanol, t-butyl alcohol, preferably is the ethanol.

Compound 5 was converted in the presence of a reducing reagent to intermediate 6 as shown in Scheme 4. The reduction of a nitro group can be carried out under a number of conditions well known to those skilled in the art of organic synthesis including, but not limited to, catalytic hydrogenolysis, phase-transfer hydrogenolysis, or reduction with ferric(0) powder, tin(II) chloride or titanium(II) chloride. Herein the preferred reducing reagent is SnCl2. In a particular embodiment, the reduction reaction was performed at about 60° C. For an overview of reduction methods see: Hudlicky, M. Reductions in Organic Chemistry, ACS Monograph 188, 1996.

Scheme 4

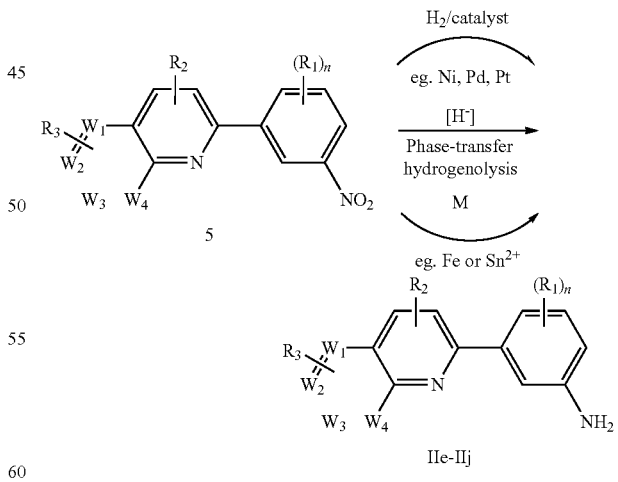

As described in Scheme 5, aniline intermediates IIr-IIt could be prepared by using either HATU-mediated condensation of commercially available or readily accessible carboxylic acids 7 or 10 and anilines 8 or 9, respectively, and or sodium triacetoxyborohydride mediated reductive aminations of aryl aldehydes 11 in the presence of anilines 9.

Scheme 5

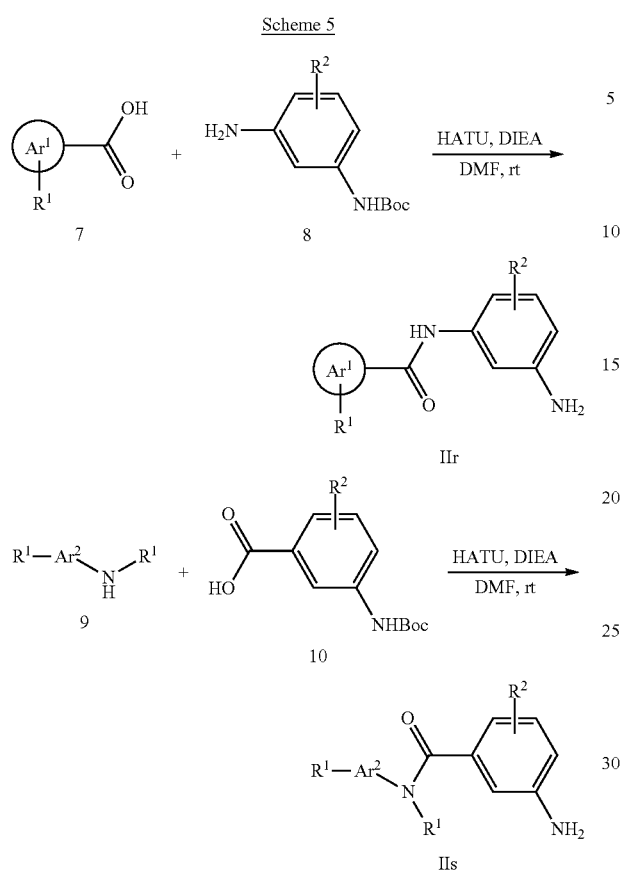

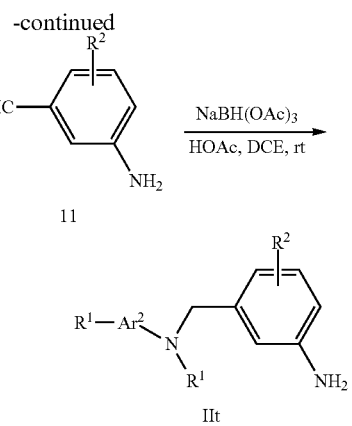

Synthesis of acid intermediates in the formula of IIIa is described in Scheme 6. Commercially available aniline 12A (FG=CO$_2$Et) was reacted with 3-chloropropane-1-sulfonyl chloride 13 in the presence of TEA in methylene chloride to form a sulfonamide-containing intermediate 14, which underwent intramolecular cyclization in the presence of NaH and catalytic amount of 15-c-5 or w-Bu$_4$NI in DMF (details see in WO2006/44497) or in the presence of cesium carbonate in DMF (details see in US2007/27126 and WO2006/19831) to afford the sulfonamide-containing intermediate 15. Alkaline hydrolysis of compound 15 in alcohol furnished compound IIIa (details see in WO2004/82687). Alternatively, compound 12 was reacted with 1,2-oxathiolane 2,2-dioxide to form intermediate alcohol intermediate 16, which was treated with oxyphosphoryl chloride to form sulfonyl chloride 17. Under alkaline conditions compound 17 underwent intramolecular cyclization and thermal hydrolysis to afford compound IIIa. Detailed procedures were referred to patent publication WO2004/82687.

Scheme 6

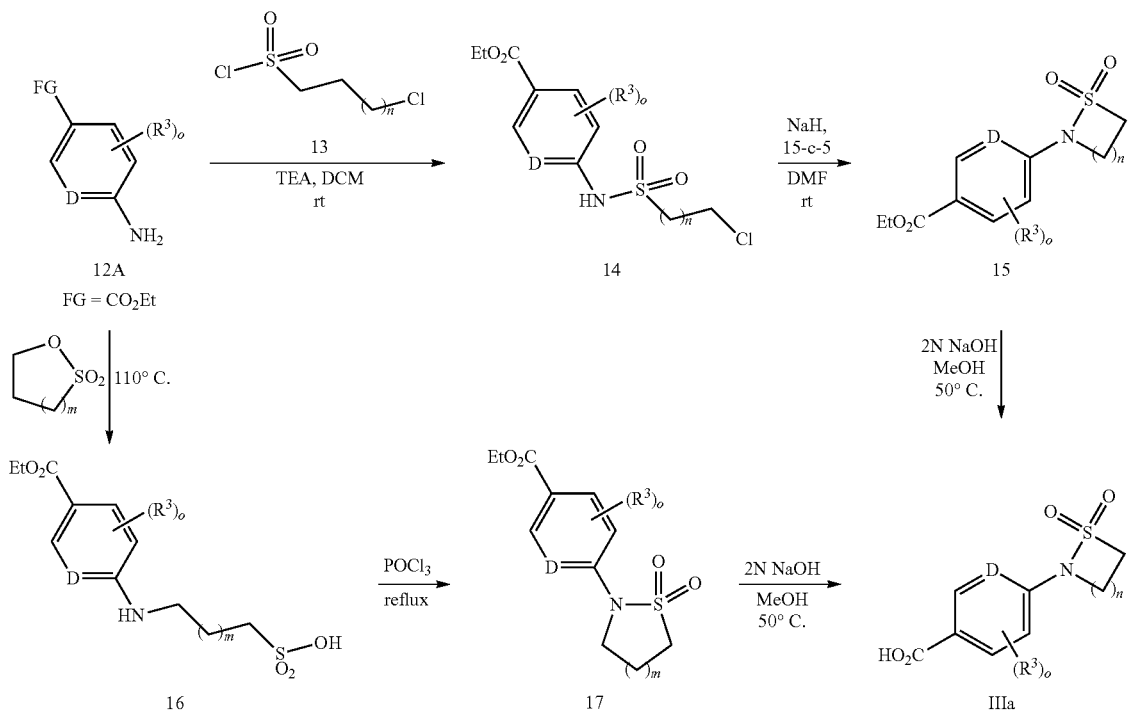

n = 1, 2 or 3
m = 1 or 2

The strategies described in Scheme 6 were adapted to other anilines 12B (FG=NO₂), 12C (FG=OMe) and 12D (FG=SMe). In the final steps, either reduction of the nitro group or removal of methyl group via the use of boron tribromide could afford the desired IIIb-d.

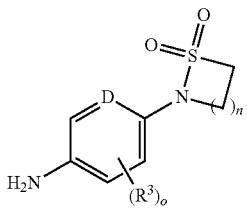

IIIb

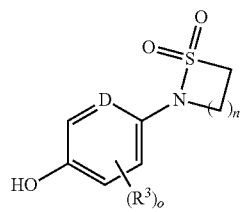

IIIc

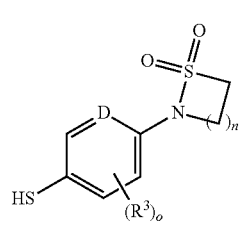

IIId

Alternatively, another type of general methods (Steinhuebel D. et al. *Tetrahedron Lett.* 2004, 45, 3305-3307) is described in Scheme 7 to prepare the benzoic acid ester appended by a cyclic sulfonamide ring. Palladium acetate-catalyzed cross coupling of compound 18 with a variety of aromatic bromides 19 using Buchwald-Hartwig's amination conditions could generally provide the desirable IIIa in good yields. This method served as a general strategy for preparation of acids in the formular (III).

Scheme 7

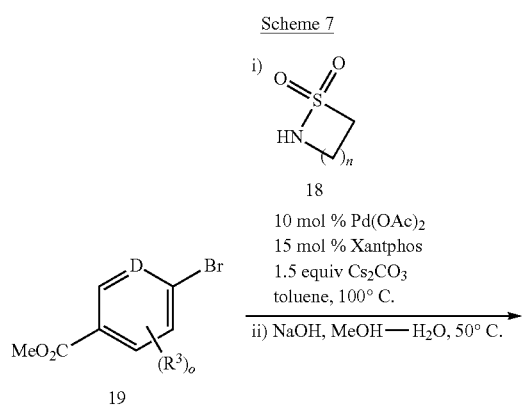

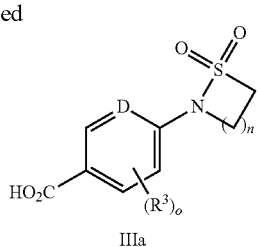

IIIa n = 1, 2, 3 or 4

General methods to make sulfonamide-containing benzoic acids in the formula of IIIe were described in Scheme 8. The synthetic routes are referred to a published method (details see in U.S. Pat. No. 3,202,657). Thus, aniline 12 reacted with carbyl sulfate in an aqueous medium in the presence of an acid-binding agent. Treatment of the potassium sulfate intermediate 20 with excess formaldehyde in formic acid could afford the 1,4,3-oxathiazinane 4,4-dioxide intermediate 21. Further saponification using aqueous NaOH solution afforded the desired acid product IIIe.

Scheme 8

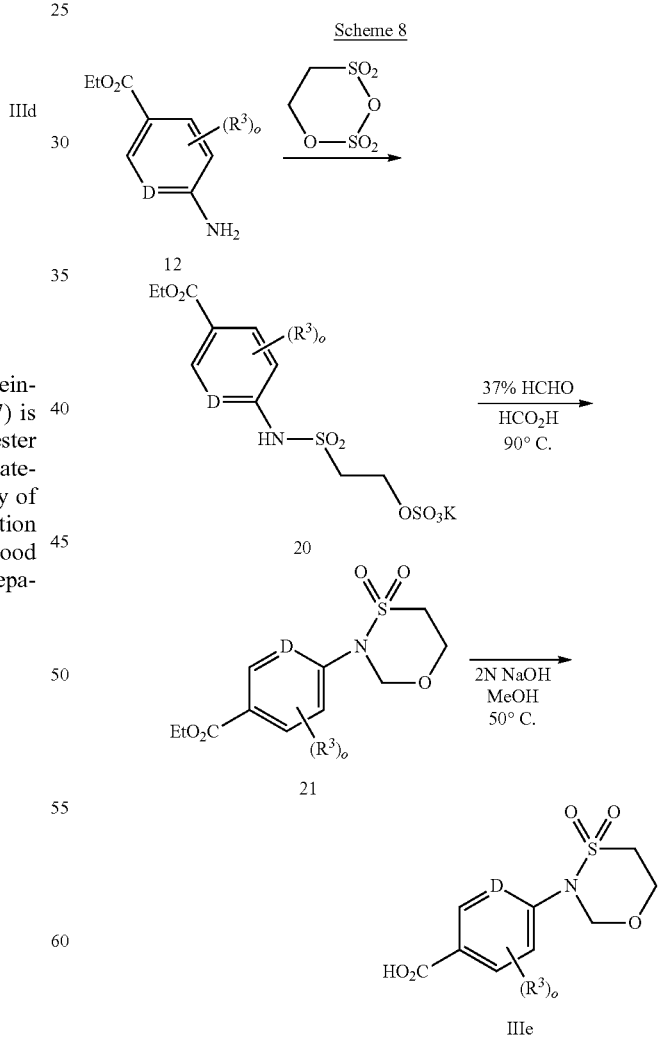

General methods to make cyclic sulfonamide containing benzoic acids in the formula of IIIf were described in Scheme 9 (a) EP1571154 A1; b) Borcard F. et al. Bioorg. Med. Chem. Lett. 2010, 20, 5353-5356). Benzyl group protected aminoethanol 22 was reacted with chloromethanesulfonyl chloride in the presence of diisopropylethyl amine in THF at room temperature to form an alcohol intermediate 23. Further treatment of the alcohol with cesium carbonate in N,N'-dimethylformamide at elevated temperature could furnish an 1,3,4-oxathiazinane 3,3-dioxide intermediate 24. Under hydrogenolysis conditions the benzyl protecting group was further removed to afford 1,3,4-oxathiazinane 3,3-dioxide 25. SNAr displacement of a phenyl fluoride intermediate 26 with 1,3,4-oxathiazinane 3,3-dioxide in the presence of cesium carbonate formed an ester intermediate 27 that further underwent alkaline hydrolysis and consequently formed the desired product IIIf.

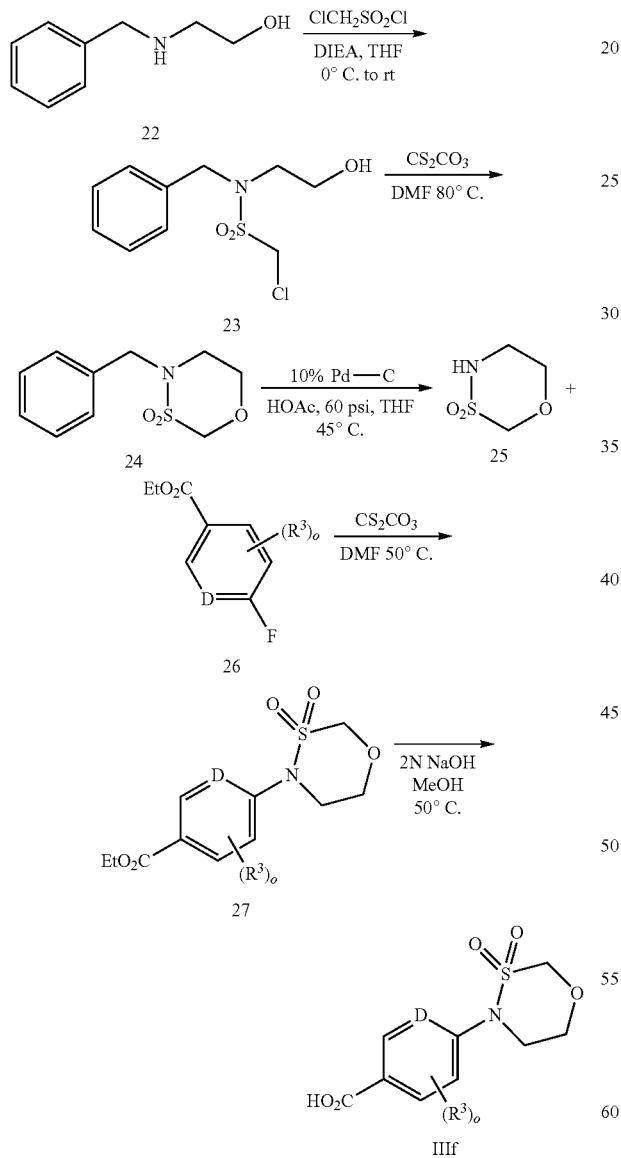

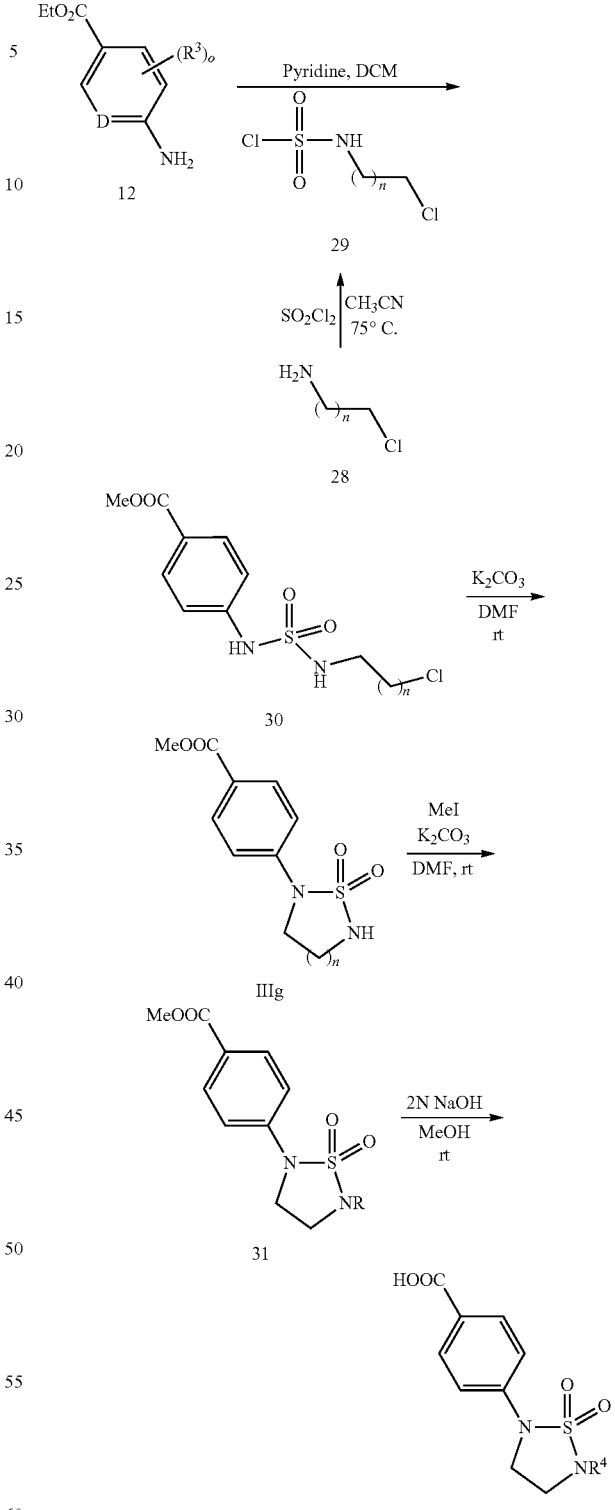

General methods to make cyclic sulfonamide containing benzoic acids in the formula of IIIg or IIIh were described in Scheme 10 and referred to published patent procedures (PCT/US2005/024881).

General methods to make cyclic sulfonamide containing phenyl sulfonyl chlorides in the formula of IIIi and IIIj were described in Scheme 11. Follow a similar protocol in literature (Fortin S.; Wei L.; et al. J. Med. Chem. 2011, 54, 4559-4580), the cyclic sulfamide containing intermediates 33 or 34 were charged with chlorosulfonic acid at 0° C. in carbon tetrachloride to afford the desired aryl sulfonyl chlorides.

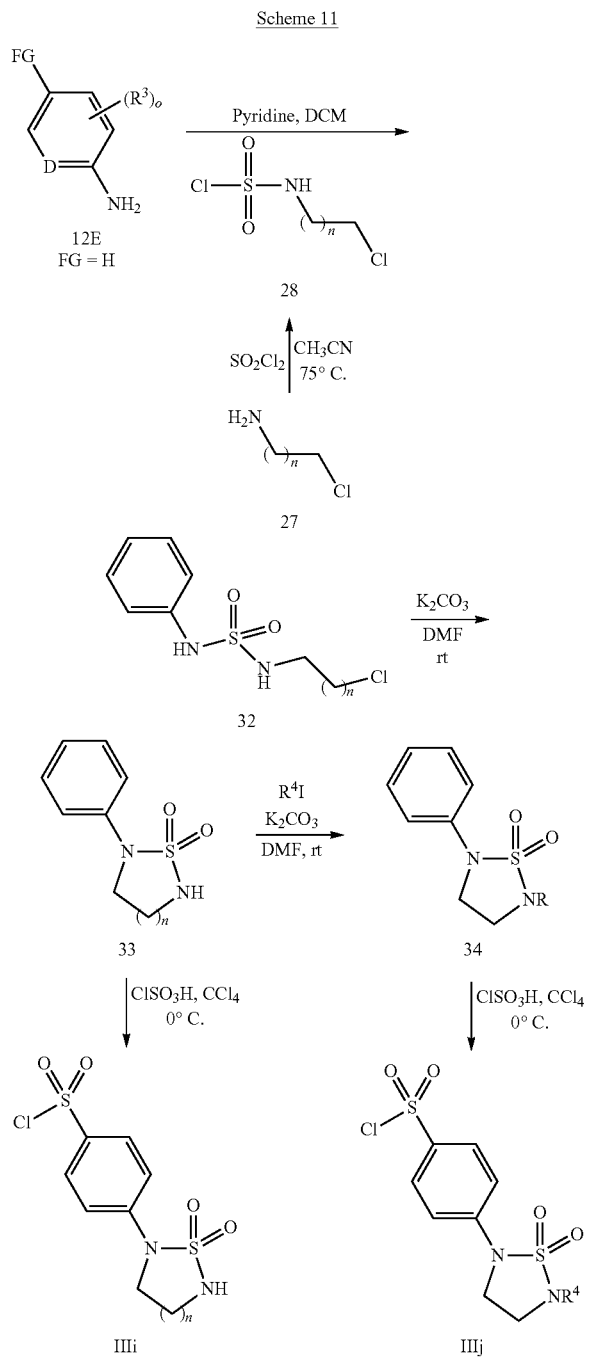

Scheme 11

The present invention provides compositions of matter that are formulations of one or more active drugs and a pharmaceutically-acceptable carrier. In this regard, the invention provides a composition for administration to a mammalian subject, which may include a compound of formula (I), or its pharmaceutically acceptable salts.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N+(C1-4 alkyl)4 salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

The pharmaceutically acceptable compositions of this invention may be orally administered in any orally acceptable dosage form including, but not limited to, capsules, tablets, troches, elixirs, suspensions, syrups, wafers, chewing gums, aqueous suspensions or solutions.

The oral compositions may contain additional ingredients such as: a binder such as microcrystalline cellulose, gum tragacanth or gelatin; an excipient such as starch or lactose, a disintegrating agent such as alginic acid, corn starch and the like; a lubricant such as magnesium stearate; a glidant such as colloidal silicon dioxide; and a sweetening agent such as sucrose or saccharin or flavoring agent such as peppermint, methyl salicylate, or orange flavoring. When the dosage unit form is a capsule, it may additionally contain a liquid carrier such as a fatty oil. Other dosage unit forms may contain other various materials which modify the physical form of the dosage unit, such as, for example, a coating. Thus, tablets or pills may be coated with sugar, shellac, or other enteric coating agents. A syrup may contain, in addition to the active ingredients, sucrose as a sweetening agent and certain preservatives, dyes and colorings and flavors. Materials used in preparing these various compositions should be pharmaceutically or veterinarally pure and non-toxic in the amounts used.

For the purposes of parenteral therapeutic administration, the active ingredient may be incorporated into a solution or suspension. The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The pharmaceutical forms suitable for injectable use include sterile solutions, dispersions, emulsions, and sterile powders. The final form should be stable under conditions of manufacture and storage. Furthermore, the final pharmaceutical form should be protected against contamination and should, therefore, be able to inhibit the growth of microorganisms such as bacteria or fungi. A single intravenous or intraperitoneal dose can be administered. Alternatively, a slow long-term infusion or multiple short-term daily infusions may be utilized, typically lasting from 1 to 8 days. Alternate day dosing or dosing once every several days may also be utilized.

Sterile, injectable solutions may be prepared by incorporating a compound in the required amount into one or more appropriate solvents to which other ingredients, listed above or known to those skilled in the art, may be added as required. Sterile injectable solutions may be prepared by incorporating the compound in the required amount in the appropriate solvent with various other ingredients as required. Sterilizing procedures, such as filtration, may then follow. Typically, dispersions are made by incorporating the compound into a sterile vehicle which also contains the dispersion medium and the required other ingredients as indicated above. In the case of a sterile powder, the preferred methods include vacuum drying or freeze drying to which any required ingredients are added.

Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer. In all cases, the final form, as noted, must be sterile and should also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

U.S. Pat. Nos. 5,916,596, 6,506,405 and 6,537,579 teach the preparation of nanoparticles from the biocompatible polymers, such as albumin. Thus, in accordance with the present invention, there are provided methods for the formation of nanoparticles of the present invention by a solvent evaporation technique from an oil-in-water emulsion prepared under conditions of high shear forces (e.g., sonication, high pressure homogenization, or the like).

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

In accordance with the invention, the compounds of the invention inhibit the hedgehog signaling and may be used to treat cancers associated with aberrant hedgehog signaling, cellular proliferation or hyperproliferation, such as cancers which include but are not limited to tumors of the nasal cavity, paranasal sinuses, nasopharynx, oral cavity, oropharynx, larynx, hypopharynx, salivary glands, and paragangliomas. The compounds of the invention may also be used to treat cancers of the liver and biliary tree (particularly hepatocellular carcinoma), intestinal cancers, particularly colorectal cancer, ovarian cancer, small cell and non-small cell lung cancer, breast cancer, sarcomas (including fibrosarcoma, malignant fibrous histiocytoma, embryonal rhabdomysocarcoma, leiomysosarcoma, neurofibrosarcoma, osteosarcoma, synovial sarcoma, liposarcoma, and alveolar soft part sarcoma), neoplasms of the central nervous systems (particularly brain cancer), and lymphomas (including Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma).

The compounds and methods of the present invention, either when administered alone or in combination with other agents (e.g., chemotherapeutic agents or protein therapeutic agents described below) are also useful in treating a variety of disorders, including but not limited to, for example: stroke, cardiovascular disease, myocardial infarction, congestive heart failure, cardiomyopathy, myocarditis, ischemic heart disease, coronary artery disease, cardiogenic shock, vascular shock, pulmonary hypertension, pulmonary edema (including cardiogenic pulmonary edema), pleural effusions, rheumatoid arthritis, diabetic retinopathy, retinitis pigmentosa, and retinopathies, including diabetic retinopathy and retinopathy of prematurity, inflammatory diseases, restenosis, asthma, acute or adult respiratory distress syndrome (ARDS), lupus, vascular leakage, protection from ischemic or reperfusion injury such as ischemic or reperfusion injury incurred during organ transplantation, transplantation tolerance induction; ischemic or reperfusion injury following angioplasty; arthritis (such as rheumatoid arthritis, psoriatic arthritis or osteoarthritis); multiple sclerosis; inflammatory bowel disease, including ulcerative colitis and Crohn's disease; lupus (systemic lupus erythematosis); graft vs. host diseases; T-cell mediated hypersensitivity diseases, including contact hypersensitivity, delayed-type hypersensitivity, and gluten-sensitive enteropathy (Celiac disease); Type 1 diabetes; psoriasis; contact dermatitis (including that due to poison ivy); Hashimoto's thyroiditis; Sjogren's syndrome; Autoimmune Hyperthyroidism, such as Graves' disease; Addison's disease (autoimmune disease of the adrenal glands); autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers, including those where kineses such as Src-family kineses are activated or overexpressed, such as colon carcinoma and thymoma, or cancers where kinase activity facilitates tumor growth or survival; glomerulonephritis, serum sickness; uticaria; allergic diseases such as respiratory allergies (asthma, hayfever, allergic rhinitis) or skin allergies; mycosis fungoides; acute inflammatory responses (such as acute or adult respiratory distress syndrome and ischemialreperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; morphea; peripheral limb ischemia and ischemic limb disease; bone disease such as osteoporosis, osteomalacia, hyperparathyroidism, Paget's disease, and renal osteodystrophy; vascular leak syndromes, including vascular leak syndromes induced by chemotherapies or immunomodulators such as IL-2; spinal cord and brain injury or trauma; glaucoma; retinal diseases, including macular degeneration; vitreoretinal disease; pancreatitis; vasculatides, including vasculitis, Kawasaki disease, thromboangiitis obliterans, Wegener s granulomatosis, and Behcet's disease; scleroderma; preeclampsia; thalassemia; Kaposi's sarcoma; von Hippel Lindau disease; and the like.

The invention also provides methods of treating a mammal afflicted with the above diseases and conditions. The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

In one aspect, the invention compounds are administered in combination with chemotherapeutic agent, an anti-inflammatory agent, antihistamines, chemotherapeutic agent, immunomodulator, therapeutic antibody or a protein kinase inhibitor, e.g., a tyrosine kinase inhibitor, to a subject in need of such treatment.

The method includes administering one or more of the inventive compounds to the afflicted mammal. The method may further include the administration of a second active agent, such as a cytotoxic agent, including alkylating agents, tumor necrosis factors, intercalators, microtubulin inhibitors, and topoisomerase inhibitors. The second active agent may be co-administered in the same composition or in a second composition. Examples of suitable second active agents include, but are not limited to, a cytotoxic drug such as Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-a; Interferon Gamma-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safmgol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride;

Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; and Zorubicin Hydrochloride.

In accordance with the invention, the compounds and compositions may be used at sub-cytotoxic levels in combination with other agents in order to achieve highly selective activity in the treatment of non-neoplastic disorders, such as heart disease, stroke and neurodegenerative diseases (Whitesell et al., Curr. Cancer Drug Targets 2003, 3(5), 349-58).

The exemplary therapeutical agents that may be administered in combination with invention compounds include EGFR inhibitors, such as gefitinib, erlotinib, and cetuximab. Her2 inhibitors include canertinib, EKB-569, and GW-572016. Also included are Src inhibitors, dasatinib, as well as Casodex (bicalutamide), Tamoxifen, MEK-1 kinase inhibitors, MARK kinase inhibitors, PI3 inhibitors, and PDGF inhibitors, such as imatinib, Hsp90 inhibitors, such as 17-AAG and 17-DMAG. Also included are anti-angiogenic and antivascular agents which, by interrupting blood flow to solid tumors, render cancer cells quiescent by depriving them of nutrition. Castration, which also renders androgen dependent carcinomas non-proliferative, may also be utilized. Also included are IGF1R inhibitors, inhibitors of non-receptor and receptor tyrosine kineses, and inhibitors of integrin.

The pharmaceutical composition and method of the present invention may further combine other protein therapeutic agents such as cytokines, immunomodulatory agents and antibodies. As used herein the term "cytokine" encompasses chemokines, interleukins, lymphokines, monokines, colony stimulating factors, and receptor associated proteins, and functional fragments thereof. As used herein, the term "functional fragment" refers to a polypeptide or peptide which possesses biological function or activity that is identified through a defined functional assay. The cytokines include endothelial monocyte activating polypeptide II (EMAP-II), granulocyte-macrophage-CSF (GM-CSF), granulocyte-CSF (G-CSF), macrophage-CSF (M-CSF), IL-1, IL-2, IL-3, IL-4, IL-5, IL-6, IL-12, and IL-13, interferons, and the like and which is associated with a particular biologic, morphologic, or phenotypic alteration in a cell or cell mechanism.

Other therapeutic agents for the combinatory therapy include cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and for gpn39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HM:G CoA reductase inhibitors (lovastatin and simvastatin), non-steroidal antiinflammatory drugs (NSAIDs) such as ibuprofen and cyclooxygenase inhibitors such as rofecoxib, steroids such as prednisone or dexamethasone, gold compounds, antiproliferative agents such as methotrexate, FK506 (tacrolimus, Prograf), mycophenolate mofetil, cytotoxic drugs such as azathioprine and cyclophosphamide, TNF-a inhibitors such as tenidap, anti-TNF antibodies or soluble TNF receptor, and rapamycin (sirolimus or Rapamune) or derivatives thereof.

When other therapeutic agents are employed in combination with the compounds of the present invention they may be used for example in amounts as noted in the Physician Desk Reference (PDR) or as otherwise determined by one having ordinary skill in the art.

EXAMPLES

The following examples are provided to further illustrate the present invention but, of course, should not be construed as in any way limiting its scope.

All experiments were performed under anhydrous conditions (i.e. dry solvents) in an atmosphere of argon, except where stated, using oven-dried apparatus and employing standard techniques in handling air-sensitive materials.

Analytical thin layer chromatography (TLC) was carried out on Merck Kiesel gel 60 F254 plates with visualization by ultraviolet and/or anisaldehyde, potassium permanganate or phosphomolybdic acid dips.

NMR spectra: 1H Nuclear magnetic resonance spectra were recorded at 400 MHz. Data are presented as follows: chemical shift, multiplicity (s=singlet, d=doublet, t=triplet, q=quartet, qn=quintet, dd=doublet of doublets, m=multiplet, bs=broad singlet), coupling constant (J/Hz) and integration. Coupling constants were taken and calculated directly from the spectra and are uncorrected.

LC/mass spectra: Electrospray (ES+) ionization was used. The protonated parent ion (M+H) or parent sodium ion (M+Na) or fragment of highest mass is quoted. Analytical gradient consisted of 10% ACN in water ramping up to 100% ACN over 5 minutes unless otherwise stated.

General Procedure for Parallel Synthesis—Acid Chloride Couplings I. A flame-dried 100 mL round-bottomed flask was equipped with a magnetic stirrer and was charged with the carboxylic acid (see individual entries). The flask was then sealed with a rubber septum and filled with a nitrogen atmosphere by needle. Then, dry THF (10 mL) was added by syringe, and the resulting mixture was placed under sonication until a uniformly smooth, white suspension had formed. Then thionyl chloride (see individual entries) was added by syringe, and the suspension was stirred overnight at r.t. and under argon atmosphere. After overnight the mixture was concentrated to dryness via rotary evaporation. The resulting solid was further dried by the addition of toluene (4 mL), and re-concentration to dryness via rotary evaporation. The solid was then re-suspended in dry dichloromethane (10 mL).

Separately, a reaction tube (18×150) was charged with the aniline (see individual entries) and dry pyridine (2.0 mL). After dissolution of the aniline, the acid chloride (2.0 mL of suspension in dichloromethane; 1.6 equiv of acid chloride) was added to the reaction mixture by syringe. The resulting homogeneous solution was analyzed by LC-MS after 1 hr to judge its level of conversion.

The mixture was then extracted twice with saturated aqueous sodium bicarbonate, and the organic layer was dried (sodium sulfate) and then concentrated by Genevac. The product was then further purified by crystallization and/or chromatography (eluent: CH2Cl2/methanol gradient), as needed (see individual entries).

General Procedure for Parallel Synthesis—Amide Couplings II. A reaction tube (24×150) was charged with carboxylic acid (0.25 mmol), a cross-shaped magnetic stirrer, and a solution of HATU in DMF (2 mL of 0.13 M solution; 97 mg of HATU, 0.26 mmol). The mixture was stirred for about 5 min, then DIEA (105 µL, 0.60 mmol) and a solution of 4-chloro-3-(isoquinolin-1-yl)aniline in DMF (1 mL of 0.20 M solution; 50 mg of aniline, 0.20 mmol) was added. The reaction tubes were then loaded into a Mettler Toledo parallel synthesis apparatus, which was placed on top of a stir plate and also placed under nitrogen gas flow. The reaction mixtures were then stirred at r.t. for 1 to 2 days (see individual entries).

The reaction mixtures were then diluted with ethyl acetate (ca. 3 mL) and saturated aqueous sodium bicarbonated (ca. 4 mL) was added, and the resulting mixture was stirred for 5 min ensuring efficient mixing. The biphasic mixtures were then allowed to separate into two layers, and the organic layer was pipetted into a test tube (18×150).

The organic mixtures were then concentrated by Gene-Vac, and directly purified via silica chromatography (eluent: CH2Cl2/methanol gradient) to afford the individual products.

General procedures for coupling of aryl halides with cyclic sulfonamides. A Schlenk flask was charged with cyclic sulfonamide (1.3 equiv), palladium acetate (10% mmol), Xantphos (15% mmol) and cesium carbonate (1.5 equiv). Toluene was added, followed by methyl 2-bromobenzoate (1 equiv). The flask was then capped with a septum. The flask was evacuated and refilled with nitrogen, this procedure was repeated a total of three times. The flask was placed into a 100° C. oil bath for 3 h and then cooled to room temperature and diluted with dichloromethane (20 mL). The slurry was filtered through a pad of solkafloc and the pad washed with additional dichloromethane (20 mL). The volatiles were removed and the crude material was chromatographed on silica gel (Methylene chloride/ethyl acetate) to afford the product as a white solid.

Example 1

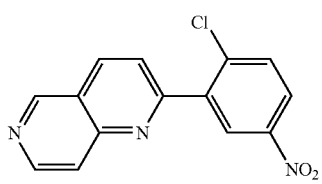 [SMILES: O=[N+]([O-])c1ccc(Cl)c(-c2ccc3cnccc3n2)c1]

4-aminonicotinaldehyde (100 mg, 0.41 mmol) and 1-(2-chloro-5-nitrophenyl)ethanone (168 mg, 0.41 mmol) were put into ethanol (1 mL), and then added NaOH (6 mg, 0.01 mmol) at room temperature. The solution was heated to 70° C. and stirred at this temperature for overnight. The reaction mixture was concentrated under reduced pressure. The residue was purified by flash column chromatography on silica gel to yield the desired product (180 mg, 80% yield) as a white solid. $^1$H NMR (400 MHz, DMSO-$d_6$): δ 9.50 (s, 1H), 8.71 (d, J=5.2 Hz, 1H), 8.63 (d, J=8.4 Hz, 1H), 8.53 (d, J=2.8 Hz, 1H), 8.40-8.37 (m, 1H), 8.16 (d, J=8.8 Hz, 1H), 8.04-8.02 (m, 1H), 7.99-7.97 (m, 1H). MS (ESI): Calcd. for $C_{14}H_8ClN_3O_2$: 285. found 286 (M+H)$^+$.

Example 2

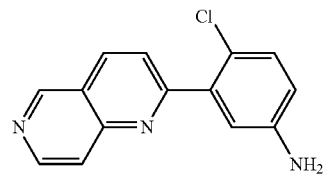 [SMILES: Nc1ccc(Cl)c(-c2ccc3cnccc3n2)c1]

A mixture of 2-(2-chloro-5-nitrophenyl)-1,6-naphthyridine (18 mg, 0.06 mmol) and tin (II) chloride dihydrate (70 mg, 0.31 mmol) in ethanol (8 mL) was heated at 70° C. for 2 hrs. The reaction mixture was cooled down and then poured into ice-water followed by neutralization with saturated NaHCO3 solution. The mixture was filtered through a pad of celite and washed with EtOAc. The filtrate was extracted with EtOAc and the combined extracts were washed with brine, dried over anhydrous Na2SO4 and then concentrated under reduced pressure. The residue was purified by flash column chromatography on silica gel (hexanes/EtOAc, 10:1) to yield the desired product. MS (ESI): Calcd. For C14H10ClN3: 255. found 256 (M+H)+.

Example 3

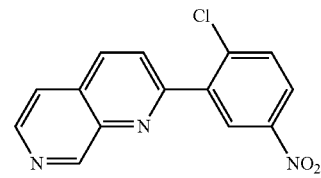 [SMILES: O=[N+]([O-])c1ccc(Cl)c(-c2ccc3ccncc3n2)c1]

3-aminonicotinaldehyde (50 mg, 0.41 mmol) and 1-(2-chloro-5-nitrophenyl)ethanone (82 mg, 0.41 mmol) were put into ethanol (1 mL), and then added NaOH (0.3 mg, 0.01 mmol) at room temperature. The solution was heated to 70° C. and stirred at this temperature for overnight. The reaction mixture was concentrated under reduced pressure. The residue was purified by flash column chromatography on silica gel to yield the desired product (38 mg, 33% yield) as a white solid. $^1$H NMR (400 MHz, DMSO-$d_6$): δ 9.50 (s, 1H), 8.71 (d, J=5.2 Hz, 1H), 8.63 (d, J=8.4 Hz, 1H), 8.53 (d, J=2.8 Hz, 1H), 8.40-8.37 (m, 1H), 8.16 (d, J=8.8 Hz, 1H), 8.04-8.02 (m, 1H), 7.99-7.97 (m, 1H). MS (ESI): Calcd. for $C_{14}H_8ClN_3O_2$: 285. found 286 (M+H)$^+$.

Example 4

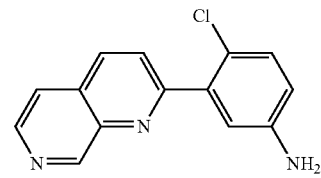

A mixture of 2-(2-chloro-5-nitrophenyl)-1,7-naphthyridine (35 mg, 0.12 mmol) and tin (II) chloride dihydrate (138 mg, 0.61 mmol) in ethanol (5 mL) was heated at 70° C. for 4 hrs. The reaction mixture was cooled down and then poured into ice-water followed by neutralization with saturated NaHCO₃ solution. The mixture was filtered through a pad of celite and washed with DCM. The filtrate was extracted with DCM and the combined extracts were washed with brine, dried over anhydrous Na₂SO₄ and then concentrated under reduced pressure to yield the desired product (25 mg). MS (ESI): Calcd. for $C_{14}H_{10}ClN_3$: 255. found 256 $(M+H)^+$.

Example 5

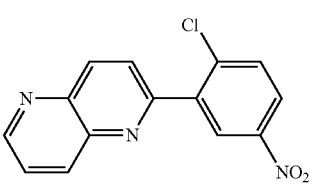 [SMILES: O=[N+]([O-])c1ccc(Cl)c(-c2ccc3ncccc3n2)c1]

A solution of 3-Amino-2-formylpyridine (100 mg, 0.82 mmol)) and 2'-Chloro-5'-nitroacetophenone (163 mg, 0.82 mmol) in EtOH (5 mL) was added with stirring to a suspension of NaOH (6 mg, 0.16 mmol) in EtOH (1 mL) at room temperature, and then stirred at room temperature for 10 mins. A lots of solid precipitated out of the solution, TLC (Hexanes/EtOAc, 1/1) indicated that there was intermediate produced, and then continued to stir at room temperature for overnight. The mixture was concentrated, the residue was purified on column (hexane-EtOAc, from 1:0 to 1:1) to obtain 2-(2-chloro-5-nitrophenyl)-1,5-naphthyridine (130 mg, 56%) as an off-white solid. ¹H NMR (400 MHz, DMSO-d₆): δ 9.10-9.09 (m, 1H), 8.61 (d, J=0.4 Hz, 1H), 8.55-8.52 (m, 2H), 8.37 (dd, J=2.8, 8.8 Hz, 2H), 8.16 (d, J=8.8 Hz, 1H), 7.97 (d, J=8.8 Hz, 1H), 7.87 (dd, J=8.4, 4.4 Hz, 1H). MS (ESI): Calcd. for $C_{14}H_8ClN_3O_2$: 285. found 286 $(M+H)^+$.

Example 6

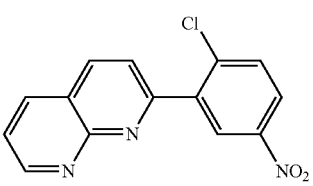 [SMILES: O=[N+]([O-])c1ccc(Cl)c(-c2ccc3cccnc3n2)c1]

A solution of 2-Amino-3-formylpyridine (100 mg, 0.82 mmol) and 2'-Chloro-5'-nitroacetophenone (163 mg, 0.82 mmol) in EtOH (5 mL) was added with stirring to a suspension of NaOH (6 mg, 0.16 mmol) in EtOH (1 mL) at room temperature, and then stirred at room temperature for 10 min. A lots of solid precipitated out of the solution, TLC (Hexanes/EtOAc=1/1) showed there was intermediate produced, and then continued to stir at room temperature for overnight. The reaction mixture was filtered and the crude solid was washed with ethanol and water to obtain compound 2-(2-chloro-5-nitrophenyl)-1,8-naphthyridine (120 mg) as an off-white solid. The mother liquid was concentrated and the residue was purified on column (hexane-EtOAc, from 1:0 to 1:1) to obtain 2-(2-chloro-5-nitrophenyl)-1,8-naphthyridine (80 mg) as an off-white solid. These two fractions were combined to yield totally 2-(2-chloro-5-nitrophenyl)-1,8-naphthyridine (200 mg, yield 86%) as an off-white solid. 1H NMR (400 MHz, DMSO-d6): δ 9.18 (dd, J=4.0 and 2.0 Hz, 1H), 8.67 (d, J=8.4 Hz, 1H), 8.59 (dd, J=8.4, 2.0 Hz, 1H), 8.53 (dd, J=2.8, 0.4 Hz, 1H), 8.38 (dd, J=8.8 and 2.8 Hz, 1H), 8.04 (d, J=8.4 Hz, 1H), 7.98 (dd, J=8.8, 0.4 Hz, 1H), 7.74 (dd, J=8.4, 4.4 Hz, 1H). MS (ESI): Calcd. for C14H8ClN3O2: 285. found 286 $(M+H)^+$.

Example 7

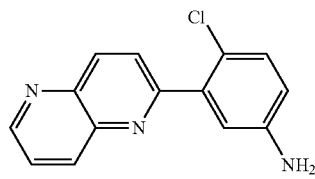

A mixture of 2-(2-chloro-5-nitrophenyl)-1,5-naphthyridine (130 mg, 0.46 mmol) and tin (II) chloride dehydrate (515 mg, 2.28 mmol) in ethanol (10 mL) was heated at 70° C. for 2 hrs. The reaction mixture was cooled down and then poured into ice-water followed by neutralization with saturated NaHCO₃ solution, adjusted the PH ~9 (If necessarily added additional 1N NaOH solution to adjust the PH). Added 100 mL DCM and shake violently until two layer came out clearly, and then, the mixture was filtered through a pad of celite and washed with DCM for 3 times. The filtrate was extracted with DCM and the combined extracts were washed with brine, dried over anhydrous Na₂SO₄ and then concentrated under reduced pressure to yield 4-chloro-3-(1,5-naphthyridin-2-yl)aniline (100 mg, yield 86%) as a yellow solid. MS (ESI): Calcd. for $C_{14}H_{10}ClN_3$: 255. found 256 $(M+H)^+$.

Example 8

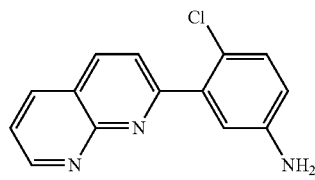

A mixture of 2-(2-chloro-5-nitrophenyl)-1,8-naphthyridine (200 mg, 0.70 mmol) and tin (II) chloride dehydrate (790 mg, 3.50 mmol) in ethanol (20 mL) was heated at 70° C. for 2 hr. The reaction mixture was cooled down and then poured into ice-water followed by neutralization with saturated NaHCO₃ solution, adjusted the PH ~9 (If necessarily added additional 1N NaOH solution to adjust the PH). Added 100 mL DCM and shake violently until two layer came out clearly, and then, the mixture was filtered through a pad of celite and washed with DCM for 3 times. The filtrate was extracted with DCM and the combined extracts were washed with brine, dried over anhydrous Na₂SO₄ and then concentrated under reduced pressure to yield 4-chloro-3-(1,8-naphthyridin-2-yl)aniline (163 mg, yield 92%) as a yellow solid. ¹H NMR (400 MHz, DMSO-d₆): δ 9.18 (dd, J=4.4, 2.0 Hz, 1H), 8.53-8.51 (m, 2H), 7.84 (d, J=8.4 Hz, 1H), 7.67 (dd, J=8.0, 4.4 Hz, 1H), 7.22 (d, J=8.4 Hz, 1H), 6.90 (dd, J=2.8, 0.4 Hz, 1H), 6.70 (dd, J=8.8, 2.8 Hz, 1H), 5.46 (brs, 2H). MS (ESI): Calcd. for $C_{14}H_{10}ClN_3$: 255. found 256 (M+H)$^+$.

Example 9

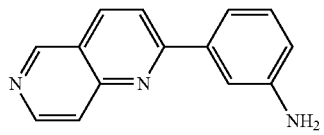

A mixture of 2-(5-nitrophenyl)-1,6-naphthyridine (23 mg, 0.09 mmol) and tin (II) chloride dihydrate (101 mg, 0.45 mmol) in ethanol (8 mL) was heated at 70° C. for 2 hrs. The reaction mixture was cooled down and then poured into ice-water followed by neutralization with saturated NaHCO$_3$ solution. The mixture was filtered through a pad of celite and washed with EtOAc. The filtrate was extracted with EtOAc and the combined extracts were washed with brine, dried over anhydrous Na$_2$SO$_4$ and then concentrated under reduced pressure. The residue was purified by flash column chromatography on silica gel (Hexanes/EtOAc, 10:1) to yield the desired product. MS (ESI): Calcd. For $C_{14}H_{11}N_3$: 221. found 222(M+H)$^+$.

Example 10

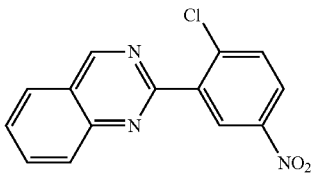

2-Chloroquinazoline (150 mg, 0.91 mmol), 2-chloro-5-nitrophenylboronic acid (239 mg, 1.18 mmol), Pd$_2$dba$_3$ (21 mg, 0.023 mmol), PCy$_3$ (26 mg, 0.093 mmol) were loaded into a microwave vial equipped with a stirbar. The vial was capped with a Teflon septum and purged with argon (by needle) for 5 min. Then 2.0 mL 1,4-dioxane and 1.0 mL of 1.27 M K$_3$PO$_4$ (aq.) were added via syringe and the solution was further degassed with argon for 5 min. The vial was then subjected to microwave irradiation for 40 mins at 100° C. The reaction mixture was then concentrated, adsorbed onto silica gel, and purified via silica chromatography (eluent: ethyl acetate in hexanes) to afford the product as a white crystalline solid (38 mg, 15%) along with recovered 2-chloroquinazoline (52 mg, 35%). $^1$H-NMR (400 MHz, d$_6$-DMSO): δ 9.82 (s, 1H), 8.68 (d, J=2.8 Hz, 1H), 8.37 (dd, J=2.9, 8.8 Hz, 2H), 8.29 (d, J=8.1 Hz, 1H), 8.14-8.13 (m, 1H), 7.96 (d, J=8.8 Hz, 1H), 7.88 (ddd, J=3.4, 4.6, 8.1 Hz, 1H).

Example 11

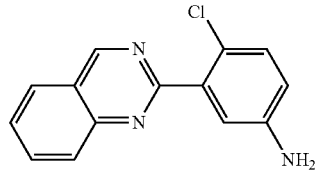 [SMILES: O=[N+]([O-])c1ccc(Cl)c(-c2ncc3ccccc3n2)c1]

2-chloro-5-nitrobenzaldehyde (44 mg, 0.23 mmol) was added to a solution of 2-aminobenzaldehyde 0-phenyl oxime (50 mg, 0.23 mmol) in toluene containing anhydrous ZnCl2 (0.5 M in toluene, 0.15 mL) and eminPF6 (63 mg, 0.25 mmol) in a microwave vessel (2~5 mL), the vessel was sealed and subjected to microwave irradiation for 30 mins at 160° C. in a biotage irritation system, and then poured into NaHCO$_3$ and extrated with ethyl acetate, dried on hydrous Na$_2$SO$_4$ and then removed the solvents, purified on column to obtain a white solid as the crude product.

Crude intermediate 2-(2-chloro-5-nitrophenyl)quinazoline (90 mg, 0.31 mmol) and tin (II) chloride dehydrate (355 mg, 1.57 mmol) in ethanol (5 mL) was heated at 70° C. for 2 hrs. The reaction mixture was cooled down and then poured into ice-water followed by neutralization with saturated NaHCO$_3$ solution. The mixture was filtered through a pad of celite and washed with DCM. The filtrate was extracted with DCM and the combined extracts were washed with brine, dried over anhydrous Na$_2$SO$_4$ and then concentrated under reduced pressure to yield the desired compound (26.6 mg) as a yellow solid. $^1$H NMR (400 MHz, CDCl$_3$): δ 9.70 (s, 1H), 8.22-8.20 (m, 1H), 8.07-8.04 (m, 2H), 7.82-7.78 (m, 1H), 7.19 (d, J=8.4 Hz, 1H), 7.00 (d, J=2.8 hz, 1H), 6.68 (dd, J=8.8, 2.8 Hz, 1H), 5.41 (brs, 2H). MS (ESI): Calcd. for C14H10ClN3: 255. found 256 (M+H)$^+$.

Example 12

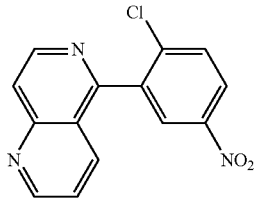

A suspension of 5-bromo-1,6-naphthyridine (4.62 g, 22.10 mmol) and (2-chloro-5-nitrophenyl)boronic acid (11.57 g, 2.6 eq.) in a mixture of toluene (172 mL) and ethanol (22 mL) was charged with an aqueous LiOH solution (2 N, 33 mL, 2.78 g, 3 eq.). The mixture was stirred under vacuum for 5 mins and purged with argon. Under an atmosphere of argon, bistriphenylchloride palladium(II) chloride (1.27 g, 5% mmol) was added quickly to the reaction mixture. The resulting mixture was put on vaccum-purge cycle for three times and stirred under argon in an oil bath (90° C.). 3.5 hours later TLC results indicated a full conversion of 5-bromo-1,6-naphthyridine. The oil bath was removed and the reaction mixture was cooled at room temperature. Ethyl acetate (150 mL) was added to extract the mixture. The organic phase wash washed with copious amount of saturated aqueous sodium bicarbonate solution followed by brine. The organic phase was dried over anhydrous sodium sulfate, filtered and concentrated in vacuo. The crude product was charged with 30 mL of chilled hexanes and 1 mL of ethyl ether. The mixture was stirred at room temperature for 36 hrs. The supernatant solution was decanted off and the desired product was obtained as a light yellow powder (5.12 g, 81.1%).

Example 13

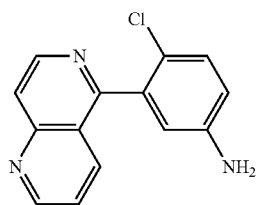 [SMILES: Nc1ccc(Cl)c(-c2nccc3ncccc23)c1]

5-(2-chloro-5-nitrophenyl)-1,6-naphthyridine (81 mg, 0.28 mmol) and tin (II) chloride dehydrate (319 mg, 1.42 mmol) in ethanol (10 mL) was heated at 70° C. for 2 hrs. The reaction mixture was cooled down and then poured into ice-water followed by neutralization with saturated NaHCO$_3$ solution. The mixture was filtered through a pad of celite and washed with DCM. The filtrate was extracted with DCM and the combined extracts were washed with brine, dried over anhydrous Na$_2$SO$_4$ and then concentrated under reduced pressure to yield the desired product (76 mg) as a yellow solid. MS (ESI): Calcd. for C14H10ClN3: 255. found 256 (M+H)$^+$.

Example 14

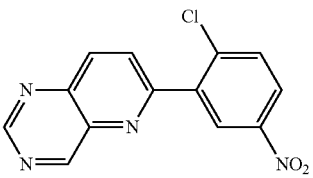

A solution of 5-aminopyrimidine-4-carbaldehyde (100 mg, 0.81 mmol)) and 2'-Chloro-5'-nitroacetophenone (162 mg, 0.81 mmol) in EtOH (5 mL) was added with stirring to a suspension of NaOH (6 mg, 0.16 mmol) in EtOH (1 mL) at room temperature, and then stirred at room temperature for overnight. The reaction mixture was concentrated and the residue was purified on column (hexanes-EtOAc, from 1:0 to 1:1) to obtain 6-(2-chloro-5-nitrophenyl)pyrido[3,2-d]pyrimidine (200 mg, yield 85.8%) as a yellow solid. MS (ESI): Calcd. for C13H7ClN4O2: 286. found 287 (M+H)$^+$.

Example 15

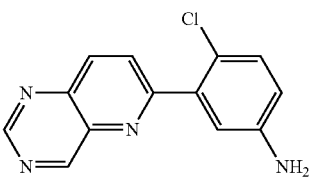

A mixture of 6-(2-chloro-5-nitrophenyl)pyrido[3,2-d]pyrimidine (180 mg, 0.63 mmol) and tin (II) chloride dehydrate (426 mg, 1.89 mmol) in ethanol (10 mL) was heated at 70° C. for overnight. The reaction mixture was cooled down and then poured into ice-water followed by neutralization with saturated NaHCO$_3$ solution, adjusted the PH ~9 (If necessarily added additional 1N NaOH solution to adjust the PH). Added 100 mL DCM and shake violently until two layer came out clearly, and then, the mixture was filtered through a pad of celite and washed with DCM for 3 times. The filtrate was extracted with DCM and the combined extracts were washed with brine, dried over anhydrous Na$_2$SO$_4$ and then concentrated under reduced pressure to yield the compound 4-chloro-3-(pyrido[3,2-d]pyrimidin-6-yl)aniline (142 mg, 87.9%) as a brown solid. MS (ESI): Calcd. for C13H9ClN4: 256. found 257 (M+H)$^+$.

Example 16

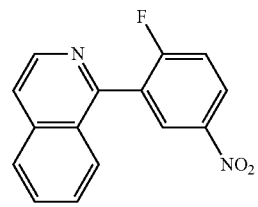 [SMILES: O=[N+]([O-])c1ccc(F)c(-c2nccc3ccccc23)c1]

(2-fluoro-5-nitrophenyl)boronic acid (535 mg, 2.89 mmol), 2-chloroisoquinoline (395 mg, 2.41 mmol), LiOH (203 mg, 4.83 mmol) and Pd(PPh$_3$)$_4$ (139 mg, 0.12 mmol) were put into mixture solvents of toluene (20 mL) and ethanol (2 mL). Degassed the whole solution and then sealed the tube. Heated in the microwave at 60° C. for 4.5 hrs and then removed the solvents and the residue was purified by flash column chromatography on silica gel to obtain 1-(2-fluoro-5-nitrophenyl)isoquinoline (186 mg, yield 27.5%) as a yellow solid. MS (ESI): Calcd. for C15H9FN2O2: 268. found 269 (M+H)$^+$.

Example 17

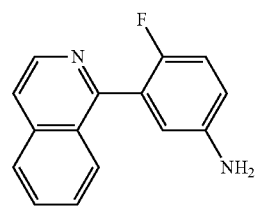

A mixture of 1-(2-fluoro-5-nitrophenyl)isoquinoline (180 mg, 0.67 mmol) and tin (II) chloride dehydrate (455 mg, 2.01 mmol) in ethanol (10 mL) was heated at 70° C. for overnight. The reaction mixture was cooled down and then poured into ice-water followed by neutralization with saturated NaHCO3 solution, adjusted the PH ~9 (If necessarily added additional 1N NaOH solution to adjust the PH). Added 100 mL DCM and shake violently until two layer came out clearly, and then, the mixture was filtered through a pad of celite and washed with DCM for 3 times. The filtrate was extracted with DCM and the combined extracts were washed with brine, dried over anhydrous Na2SO4 and then concentrated under reduced pressure to yield 4-fluoro-3-(isoquinolin-1-yl)aniline (129 mg, 80.6%) as a brown solid. MS (ESI): Calcd. for C15H11FN2: 238. found 239 (M+H)+.

Example 18

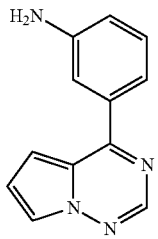 [SMILES: Nc1cccc(-c2ncnn3cccc23)c1]

A mixture of 4 4-(3-nitrophenyl)pyrrolo[2,1-f][1,2,4]triazine (100 mg, 0.416 mmol) and tin (II) chloride dihydrate (395 mg, 2.08 mmol) in ethanol (18 mL) was heated at 70° C. for 2 hrs. The reaction mixture was cooled down and then poured into ice-water followed by neutralization with saturated NaHCO3 solution. The mixture was filtered through a pad of celite and washed with EtOAc. The filtrate was extracted with EtOAc and the combined extracts were washed with brine, dried over anhydrous Na2SO4 and then concentrated under reduced pressure. The residue was purified by flash column chromatography on silica gel (hexanes/EtOAc, 10:1 to) to yield the desired compound (85 mg, 98%). MS (ESI): Calcd. For C12H10N4: 210. found 211 (M+H)+.

Example 19

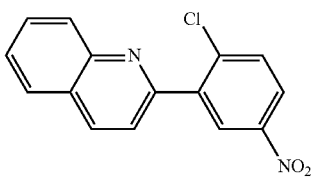 [SMILES: O=[N+]([O-])c1ccc(Cl)c(-c2ccc3ccccc3n2)c1]

A mixture of 2-bromoquinoline (360 mg, 1.73 mmol), 2-chloro-5-nitrophenylboronic acid (418 mg, 2.08 mmol), Pd(PPh3)4 (100 mg, 0.087 mmol) and 2M K2CO3 solution (1.73 mL, 3.46 mmol) in toluene (20.0 mL) and ethanol (1.5 mL) was refluxed for 6 hrs. The reaction mixture was cooled down and water was added. The resulting mixture was extracted with EtOAc and the combined extracts were washed with brine, dried over anhydrous Na2SO4 and then concentrated under reduced pressure. The residue was purified by flash column chromatography on silica gel (hexanes/EtOAc, 10:1 to 10:5) to yield the desired compound (100 mg, 20% yield) as a white solid. $^1$H NMR (400 MHz, DMSO-d$_6$): δ 8.55 (d, J=8.4 Hz, 1H), 8.48 (d, J=2.8 Hz, 1H), 8.35 (dd, J=2.8, 8.8 Hz, 1H), 8.11 (m, 2H), 7.95 (d, J=8.8 Hz, 1H), 7.90 (d, J=8.4 Hz, 1H), 7.86 (ddd, J=1.6, 6.8, 8.4 Hz, 1H), 7.71 (dd, J=1.2, 6.8, 8.4 Hz, 1H). MS (ESI): Calcd. for C$_{15}$H$_{10}$ClN$_2$O$_2$: 285. found 285 (M+H)$^+$.

Example 20

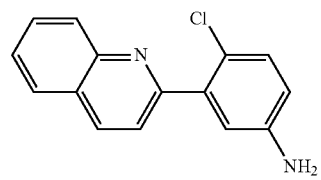

A mixture of 2-(2-chloro-5-nitrophenyl)quinoline (440 mg, 1.55 mmol) and tin (II) chloride dihydrate (1.57 g, 6.98 mmol) in ethanol (31.0 mL) was heated at 70° C. for 2 hr. The reaction mixture was cooled down and then poured into ice-water followed by neutralization with saturated NaHCO3 solution. The mixture was filtered through a pad of celite and washed with EtOAc. The filtrate was extracted with EtOAc and the combined extracts were washed with brine, dried over anhydrous Na2SO4 and then concentrated under reduced pressure to yield the desired compound (370 mg, 94% yield) as a yellow solid. $^1$H NMR (400 MHz, DMSO-d$_6$): δ 8.41 (d, J=8.4 Hz, 1H), 8.03 (m, 2H), 7.80 (ddd, J=1.6, 6.8, 8.4 Hz, 1H), 7.72 (d, J=8.4 Hz, 1H), 7.64 (ddd, J=1.2, 6.8, 8.0 Hz, 1H), 7.20 (d, J=8.4 Hz, 1H), 6.87 (d, J=2.8 Hz, 1H), 6.68 (dd, J=2.8, 8.4 Hz, 1H), 5.42 (s, 2H). MS (ESI): Calcd. for C$_{15}$H$_{12}$ClN$_2$: 255. found 255 (M+H)$^+$.

Example 21

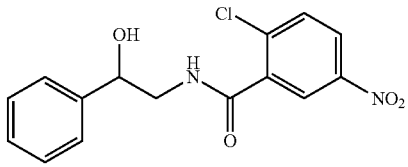 [SMILES: O=C(NCC(O)c1ccccc1)c1cc([N+](=O)[O-])ccc1Cl]

A solution of 2-chloro-5-nitrobenzoyl chloride (11.70 g, 53.2 mmol) in DCM (66.0 mL) was added dropwise to a solution of 2-amino-1-phenylethanol (7.30 g, 53.2 mmol) in DCM (200 mL) containing triethylamine (7.40 mL, 53.2 mmol) at 0° C. The reaction mixture was stirred at 0° C. for 1 hr. The reaction was quenched with saturated NaHCO3 solution and the organic layer was separated. The organic layer was washed with brine, dried over anhydrous Na2SO4 and then concentrated under reduced pressure. The crude residue was recrystallized from hexanes/EtOAc to yield the desired compound (15.29 g, 90% yield) as a white solid. $^1$H NMR (400 MHz, CDCl$_3$): δ 8.46 (d, J=2.8 Hz, 1H), 8.21 (dd, J=2.8, 8.8 Hz, 1H), 7.59 (d, J=8.8 Hz, 1H), 7.44-7.31 (m, 5H), 6.65 (br s, 1H), 5.01 (m, 1H), 3.97 (m, 1H), 3.56 (m 1H), 2.68 (d, J=2.8 Hz, 1H). MS (ESI): Calcd. for C$_{15}$H$_{13}$ClN$_2$O$_4$Na 343. found 343 (M+Na)$^+$.

Example 22

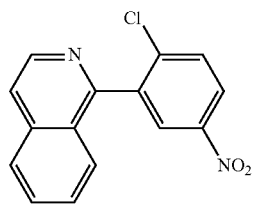

A mixture of 2-chloro-N-(2-hydroxy-2-phenylethyl)-5-nitrobenzamide (3.40 g, 10.60 mmol) with POCl₃ (11.86 mL, 127.2 mmol) and P₂O₅ (17.0 g, 119.8 mmol) in toluene/xylene (265 mL, 1:1) was refluxed for 2 d. The reaction mixture was cooled down and then poured into ice-water followed by neutralization with 10% NaOH solution. The mixture was extracted with EtOAc and the combined extracts were washed with brine, dried over anhydrous Na₂SO₄ and then concentrated under reduced pressure. The residue was purified by flash column chromatography on silica gel (hexane/EtOAc 95:5 to 90:10) followed by recrystallization from hexane/EtOAc to yield the compound XS343 (850 mg, 28%) as yellow crystals. ¹H NMR (400 MHz, CDCl₃): δ 8.66 (d, J=5.6 Hz, 1H), 8.38 (d, J=2.8 Hz, 1H), 8.32 (dd, J=2.8, 8.8 Hz, 1H), 7.95 (m, 1H), 7.80 (d, J=5.6 Hz, 1H), 7.77-7.73 (m, 2H), 7.57 (m, 2H). MS (ESI): Calcd. for $C_{15}H_{10}ClN_2O_2$: 285. found 285 (M+H)⁺.

Example 23

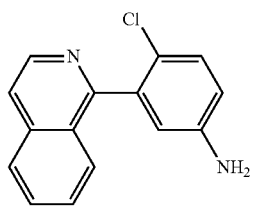 [SMILES: O=[N+]([O-])c1ccc(Cl)c(-c2nccc3ccccc23)c1]

A mixture of 1-(2-chloro-5-nitrophenyl)isoquinoline (785 mg, 2.76 mmol) and tin (II) chloride dehydrate (2.93 g, 12.97 mmol) in ethanol (36.8 mL) was heated at 70° C. for 1.5 hrs. The reaction mixture was cooled down and then poured into ice-water followed by neutralization with saturated NaHCO₃ solution. The mixture was filtered through a pad of celite and washed with EtOAc. The filtrate was extracted with EtOAc and the combined extracts were washed with brine, dried over anhydrous Na₂SO₄ and then concentrated under reduced pressure to yield the desired compound (650 mg, 92%) as a yellow solid. ¹H NMR (400 MHz, CDCl₃): δ 8.61 (d, J=5.6 Hz, 1H), 7.88 (d, J=8.0 Hz, 1H), 7.75-7.67 (m, 3H), 7.53 (m, 1H), 7.29 (dd, J=0.8, 8.0 Hz, 1H), 6.76 (m, 2H), 3.76 (br s, 2H). MS (ESI): Calcd. for $C_{15}H_{12}ClN_2$: 255. found 255 (M+H)⁺.

Example 24

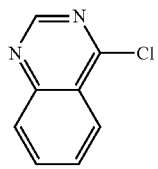

A mixture of 4-hydroxyquinazoline (1.20 g, 8.21 mmol) in SOCl₂ (27.4 mL) containing DMF (2 drops) was refluxed for 2 h. SOCl₂ was removed under reduced pressure and the residue was dissolved in DCM. The solution was washed with saturated NaHCO₃ solution and brine, respectively, dried over anhydrous Na₂SO₄ and then concentrated under reduced pressure to yield the compound (1.19 g, 88% yield) as white solid. ¹H NMR (400 MHz, CDCl₃): δ 9.06 (s, 1H), 8.29 (m, 1H), 8.09 (m, 1H), 7.98 (m, 1H), 7.75 (m, 1H). MS (ESI): Calcd. for $C_8H_6ClN_2$: 165. found 165 (M+H)⁺.

Example 25

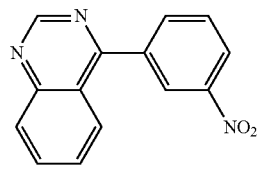

A mixture of 4-chloroquinazoline (658 mg, 4.0 mmol), 3-nitrophenylboronic acid (935 mg, 5.6 mmol), Pd(PPh₃)₄ (231 mg, 0.2 mmol) and 2M K₂CO₃ solution (4.0 mL, 8.0 mmol) in toluene (30.0 mL) and ethanol (2.0 mL) was refluxed for 6 h. The reaction mixture was cooled down and water was added. The resulting mixture was extracted with EtOAc and the combined extracts were washed with brine, dried over anhydrous Na₂SO₄ and then concentrated under reduced pressure. The residue was purified by flash column chromatography on silica gel (hexane/EtOAc 10:1 to 1:1) to yield the desired compound (771 mg, 77% yield) as a pale yellow solid. ¹H NMR (400 MHz, CDCl₃): δ 9.43 (s, 1H), 8.69 (m, 1H), 8.45 (ddd, J=1.0, 2.4, 8.4 Hz, 1H), 8.17 (m, 2H), 8.05 (ddd, J=0.8, 1.2, 2.0 Hz, 1H), 7.99 (m, 1H), 7.80 (m, 1H), 7.69 (m, 1H). MS (ESI): Calcd. for $C_{14}H_{10}N_3O_2$: 252. found 252 (M+H)⁺.

Example 26

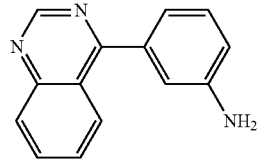 [SMILES: Nc1cccc(-c2ncnc3ccccc23)c1]

A mixture of 4-(3-nitrophenyl)quinazoline (700 mg, 2.79 mmol) and tin (II) chloride dihydrate (2.83 g, 12.56 mmol) in ethanol (37.2 mL) was heated at 70° C. for 1.5 hr. The reaction mixture was cooled down and then poured into ice-water followed by neutralization with saturated NaHCO₃ solution. The mixture was filtered through a pad of celite and washed with EtOAc. The filtrate was extracted with EtOAc and the combined extracts were washed with brine, dried over anhydrous Na₂SO₄ and then concentrated under reduced pressure to yield the compound (600 mg, 97%) as a yellow solid. ¹H NMR (400 MHz, CDCl₃): δ 9.36 (s, 1H), 8.19 (m, 1H), 8.10 (d, J=8.4 Hz, 1H), 7.91 (m, 1H), 7.60 (m, 1H), 7.34 (t, J=8.0 Hz, 1H), 7.12 (m, 1H), 7.09 (t, J=2.0 Hz, 1H), 6.88 (ddd, J=1.2, 2.4, 8.0 Hz, 1H), 3.85 (s, 2H). MS (ESI): Calcd. for $C_{14}H_{12}N_3$: 222. found 222 (M+H)⁺.

Example 27

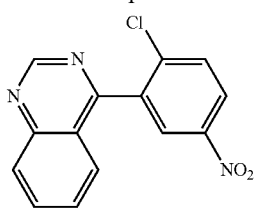

A mixture of 4-chloroquinazoline (497 mg, 3.02 mmol), 3-nitrophenylboronic acid (852 mg, 4.23 mmol), Pd(PPh$_3$)$_4$ (175 mg, 0.15 mmol) and 2M K$_2$CO$_3$ solution (3.02 mL, 6.04 mmol) in toluene (30.0 mL) and ethanol (2.0 mL) was refluxed for 7 h. The reaction mixture was cooled down and water was added. The resulting mixture was extracted with EtOAc and the combined extracts were washed with brine, dried over anhydrous Na$_2$SO$_4$ and then concentrated under reduced pressure. The residue was purified by flash column chromatography on silica gel (hexanes/EtOAc, 10:1 to 1:1) to yield the compound (125 mg, 14% yield) as a pale yellow solid. $^1$H NMR (400 MHz, DMSO-d$_6$): δ 9.46 (s, 1H), 8.51 (d, J=2.4 Hz, 1H), 8.47 (dd, J=2.8, 8.8 Hz, 1H), 8.17 (d, J=8.4 Hz, 1H), 8.10 (m, 1H), 8.03 (dd, J=0.4, 8.8 Hz, 1H), 7.75 (m, 1H), 7.68 (m, 1H). MS (ESI): Calcd. for C$_{14}$H$_9$ClN$_3$O$_2$: 286. found 286 (M+H)$^+$.

Example 28

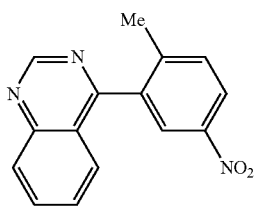 [SMILES: Cc1ccc([N+](=O)[O-])cc1-c1ncnc2ccccc12]

A mixture of 4-chloroquinazoline (600 mg, 3.65 mmol), 2-methyl-5-nitrophenylboronic acid (925 mg, 5.11 mmol), Pd(PPh$_3$)$_4$ (211 mg, 0.18 mmol) and 2M K$_2$CO$_3$ solution (3.65 mL, 7.30 mmol) in toluene (30.0 mL) and ethanol (2.0 mL) was refluxed for 6 h. The reaction mixture was cooled down and water was added. The resulting mixture was extracted with EtOAc and the combined extracts were washed with brine, dried over anhydrous Na$_2$SO$_4$ and then concentrated under reduced pressure. The residue was purified by flash column chromatography on silica gel (hexanes/EtOAc, 10:1) to yield the desired compound (840 mg, 87% yield) as an off-white solid. $^1$H NMR (400 MHz, DMSO-d$_6$): δ 9.42 (s, 1H), 8.36 (ddd, J=0.4, 2.4, 8.4 Hz, 1H), 8.26 (d, J=2.8 Hz, 1H), 8.15 (m, 1H), 8.08 (ddd, J=1.6, 6.8, 8.4 Hz, 1H), 7.76 (m, 1H), 7.72 (m, 1H), 7.65 (dq, J=0.8, 8.4 Hz, 1H), 2.18 (s, 3H). MS (ESI): Calcd. for C$_{15}$H$_{12}$N$_3$O$_2$: 266. found 266 (M+H)$^+$.

Example 29

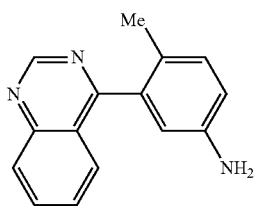

A mixture of 4-(2-methyl-5-nitrophenyl)quinazoline (770 mg, 2.90 mmol) and tin (II) chloride dihydrate (2.62 g, 11.60 mmol) in ethanol (38.7 mL) was heated at 70° C. for 2 hrs. The reaction mixture was cooled down and then poured into ice-water followed by neutralization with saturated NaHCO$_3$ solution. The mixture was filtered through a pad of celite and washed with EtOAc. The filtrate was extracted with EtOAc and the combined extracts were washed with brine, dried over anhydrous Na$_2$SO$_4$ and then concentrated under reduced pressure. The residue was purified by flash column chromatography on silica gel (hexanes/EtOAc, 10:1 to) to yield the desired compound (513 mg, 75% yield) as a yellow solid. $^1$H NMR (400 MHz, DMSO-d$_6$): δ 9.34 (s, 1H), 8.08 (m, 1H), 8.02 (ddd, J=2.4, 5.6, 8.0 Hz, 1H), 7.69 (m, 2H), 7.06 (d, J=8.0 Hz, 1H), 6.69 (dd, J=2.4, 8.0 Hz, 1H), 6.54 (d, J=2.4 Hz, 1H), 5.09 (s, 2H), 1.85 (s, 3H). MS (ESI): Calcd. for C$_{15}$H$_{14}$N$_3$: 236. found 236 (M+H)$^+$.

Example 30

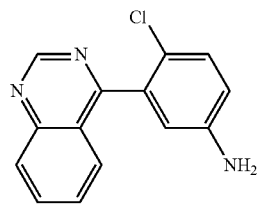 [SMILES: Nc1ccc(Cl)c(-c2ncnc3ccccc23)c1]

A mixture of 4-(2-chloro-5-nitrophenyl)quinazoline (395 mg, 1.38 mmol) and tin (II) chloride dihydrate (1.40 g, 6.21 mmol) in ethanol (27.6 mL) was heated at 70° C. for 3 hr. The reaction mixture was cooled down and then poured into ice-water followed by neutralization with saturated NaHCO$_3$ solution. The mixture was filtered through a pad of celite and washed with EtOAc. The filtrate was extracted with EtOAc and the combined extracts were washed with brine, dried over anhydrous Na$_2$SO$_4$ and then concentrated under reduced pressure to yield the compound (345 mg, 98%) as a yellow solid. $^1$H NMR (400 MHz, DMSO-d$_6$): δ 9.37 (s, 1H), 8.10 (m, 1H), 8.04 (ddd, J=1.6, 6.8, 8.4 Hz, 1H), 7.73 (ddd, J=1.2, 6.4, 8.4 Hz, 1H), 7.66 (m, 1H), 7.27 (d, J=8.4 Hz, 1H), 6.77 (dd, J=2.8, 8.8 Hz, 1H), 6.67 (d, J=2.8 Hz, 1H), 5.51 (s, 2H). MS (ESI): Calcd. for C$_{14}$H$_{11}$ClN$_3$: 256. found 256 (M+H)$^+$.

Example 31

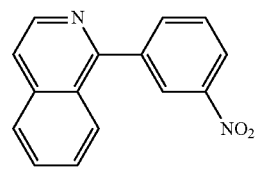

A mixture of 1-chloroisoquinoline (1.0 g, 6.11 mmol), 3-nitrophenylboronic acid (1.22 g, 7.33 mmol), Pd(PPh$_3$)$_4$ (353 mg, 0.31 mmol) and 2M K$_2$CO$_3$ solution (6.11 mL, 12.22 mmol) in toluene (50.0 mL) and ethanol (3.0 mL) was refluxed for 6 h. The reaction mixture was cooled down and water was added. The resulting mixture was extracted with EtOAc and the combined extracts were washed with brine, dried over anhydrous Na$_2$SO$_4$ and then concentrated under reduced pressure. The residue was purified by flash column chromatography on silica gel (hexane/EtOAc 10:1 to 1:1) to yield the compound (830 mg, 54% yield) as a white solid. $^1$H NMR (400 MHz, DMSO-d$_6$): δ 8.65 (d, J=5.6 Hz, 1H), 8.47 (t, J=1.8 Hz, 1H), 8.40 (ddd, J=0.8, 2.4, 8.4 Hz, 1H), 8.17 (ddd, J=0.8, 1.6, 8.0 Hz, 1H), 8.11 (d, J=8.0 Hz, 1H), 8.04 (m, 1H), 7.95 (dd, J=0.8, 5.6 Hz, 1H), 7.88 (d, J=7.6 Hz, 1H), 7.85 (m, 1H), 7.70 (ddd, J=1.2, 6.8, 8.4 Hz, 1H). MS (ESI): Calcd. for C$_{15}$H$_{11}$N$_2$O$_2$: 251. found 251 (M+H)$^+$.

Example 32

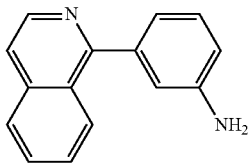 [SMILES: O=[N+]([O-])c1cccc(-c2nccc3ccccc23)c1]

A mixture of 1-(3-nitrophenyl)isoquinoline (790 mg, 3.16 mmol) and tin (II) chloride dihydrate (3.18 g, 14.22 mmol) in ethanol (62.6 mL) was heated at 70° C. for 2 hr. The reaction mixture was cooled down and then poured into ice-water followed by neutralization with saturated NaHCO$_3$ solution. The mixture was filtered through a pad of celite and washed with EtOAc. The filtrate was extracted with EtOAc and the combined extracts were washed with brine, dried over anhydrous Na$_2$SO$_4$ and then concentrated under reduced pressure to yield the compound (690 mg, 99% yield) as a yellow solid. $^1$H NMR (400 MHz, DMSO-d$_6$): δ 8.53 (d, J=6.0 Hz, 1H), 8.08 (dd, J=0.8, 8.4 Hz, 1H), 8.02 (d, J=8.4 Hz, 1H), 7.78 (m, 2H), 7.63 (ddd, J=1.2, 6.8, 8.4 Hz, 1H), 7.18 (t, J=7.8 Hz, 1H), 6.86 (t, J=1.8 Hz, 1H), 6.75 (m, 1H), 6.71 (ddd, J=0.8, 2.4, 8.0 Hz, 1H), 5.24 (s, 2H). MS (ESI): Calcd. for C$_{16}$H$_{13}$N$_2$: 221. found 221 (M+H)$^+$.

Example 33

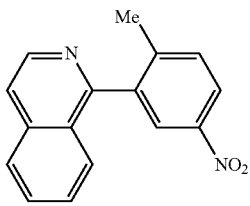 [SMILES: Cc1ccc([N+](=O)[O-])cc1-c1nccc2ccccc12]

A mixture of 1-chloroisoquinoline (750 mg, 4.58 mmol), 2-methyl-5-nitrophenylboronic acid (995 mg, 5.50 mmol), Pd(PPh$_3$)$_4$ (265 mg, 0.23 mmol) and 2M K$_2$CO$_3$ solution (4.58 mL, 9.16 mmol) in toluene (50.0 mL) and ethanol (3.0 mL) was refluxed for 6 hrs. The reaction mixture was cooled down and water was added. The resulting mixture was extracted with EtOAc and the combined extracts were washed with brine, dried over anhydrous Na$_2$SO$_4$ and then concentrated under reduced pressure. The residue was purified by flash column chromatography on silica gel (hexanes/EtOAc, 10:1 to 1:1) to yield the compound (1.15 g, 95% yield) as a white solid. $^1$H NMR (400 MHz, DMSO-d$_6$): δ 8.63 (d, J=5.6 Hz, 1H), 8.31 (dd, J=2.4, 8.4 Hz, 1H), 8.12 (d, J=2.0 Hz, 1H), 8.10 (d, J=7.2 Hz, 1H), 7.96 (dd, J=0.8, 6.0 Hz, 1H), 7.83 (ddd, J=1.2, 6.8, 8.4 Hz, 1H), 7.72 (dd, J=0.4, 8.4 Hz, 1H), 7.63 (ddd, J=1.2, 6.8, 8.4 Hz, 1H), 7.55 (dd, J=0.8, 8.4 Hz, 1H), 2.10 (s, 3H). MS (ESI): Calcd. for C$_{16}$H$_{13}$N$_2$O$_2$: 265. found 265 (M+H)$^+$.

Example 34

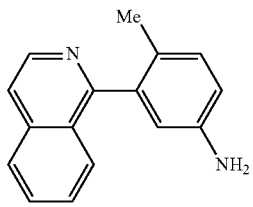 [SMILES: Cc1ccc(N)cc1-c1nccc2ccccc12]

A mixture of 1-(2-methyl-5-nitrophenyl)isoquinoline (1.14 g, 4.31 mmol) and tin (II) chloride dihydrate (4.38 g, 19.40 mmol) in ethanol (86.2 mL) was heated at 70° C. for 2 hrs. The reaction mixture was cooled down and then poured into ice-water followed by neutralization with saturated NaHCO$_3$ solution. The mixture was filtered through a pad of celite and washed with EtOAc. The filtrate was extracted with EtOAc and the combined extracts were washed with brine, dried over anhydrous Na$_2$SO$_4$ and then concentrated under reduced pressure to yield the compound (910 mg, 90%) as a yellow solid. $^1$H NMR (400 MHz, DMSO-d$_6$): δ 8.54 (d, J=5.6 Hz, 1H), 8.02 (d, J=8.4 Hz, 1H), 7.81 (d, J=5.6 Hz, 1H), 7.76 (ddd, J=2.4, 5.6, 8.0 Hz, 1H), 7.59 (m, 2H), 7.01 (d, J=8.0 Hz, 1H), 6.63 (dd, J=2.4, 8.0 Hz, 1H), 6.49 (d, J=2.4 Hz, 1H), 4.99 (s, 2H), 1.77 (s, 3H). MS (ESI): Calcd. for C$_{16}$H$_{15}$N$_2$: 235. found 235 (M+H)$^+$.

Example 35

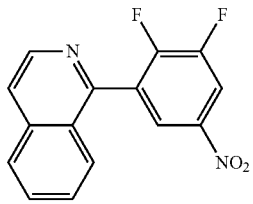 [SMILES: O=[N+]([O-])c1cc(F)c(F)c(-c2nccc3ccccc23)c1]

A mixture of 3-chloro isoquinoline (100 mg, 0.64 mmol), 2,3-difluora-5-nitrophenylboronic acid (162 mg, 0.77 mmol) and Pd(PPh$_3$)$_4$ (36 mg, 0.03 mmol) in toluene (4.0 mL) and ethanol (0.5 mL) was stirred at room temperature for 15 min while solution was degassed by argon. Then 2 N LiOH solutions (0.7 mL) were added and reaction was microwaved at 60° C. for 2 h. The reaction mixture was cooled down and water was added. The resulting mixture was extracted with EtOAc and the combined extracts were washed with brine, dried over anhydrous Na$_2$SO$_4$ and then concentrated under reduced pressure. The resulting crude product was purified by Teledyne-Isco flash system by using Hexane/EtOAc, 0 to 15% of ethyl acetatel in hexanes to provide the desired product as a light yellow solid (15 mg, 9%).

Example 36

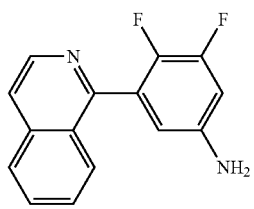 [SMILES: Nc1cc(F)c(F)c(-c2nccc3ccccc23)c1]

A mixture of 3,4-difluoro-5-(isoquinolin-1-yl)aniline (38) (30 mg, 1.56 mmol) and tin (II) chloride dihydrate (112 mg, 7.02 mmol) in ethanol (4.0 mL) was heated at 70° C. for 1.5 hrs. The reaction mixture was cooled down and then poured into ice-water followed by neutralization with saturated NaHCO$_3$ solution. The mixture was filtered through a pad of celite and washed with EtOAc. The filtrate was extracted with EtOAc and the combined extracts were washed with brine, dried over anhydrous Na$_2$SO$_4$ and then concentrated under reduced pressure to provide the desired product as a yellow solid (30 mg, 99%).

Example 37

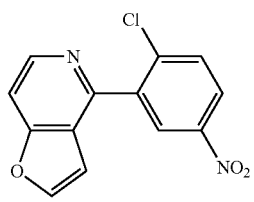 [SMILES: O=[N+]([O-])c1ccc(Cl)c(-c2nccc3occc23)c1]

1.4 M aq. potassium phosphate (2.0 mL) was added to a solution of potassium (2-chloro-5-nitrophenyl)trifluoroborate (240 mg, 0.91 mmol), 4-chlorofuro[3,2-c]pyridine (100 mg, 0.65 mmol), 1.4 M aq. potassium phosphate (2.0 mL), and Pd(PPh$_3$)$_4$ (150 mg, 0.13 mmol) in toluene (10 mL). The mixture was degassed with argon and then heated to 110° C. for ca. 15 hrs. Then the mixture was concentrated and purified by silica chromatography (eluent: methanol in dichloromethane) to afford the compound 4-(2-chloro-5-nitrophenyl)furo[3,2-c]pyridine (30 mg, 17%) as a white, crystalline solid. MS (ESI): Calcd. for C13H7ClN2O3: 274. found 275 (M+H)$^+$.

Example 38

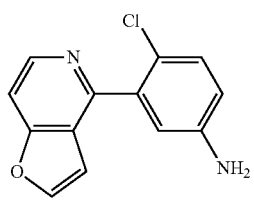

A solution of chloro-5-nitrophenyl)furo[3,2-c]pyridine (20 mg, 0.07 mmol) and tin (II) chloride dihydrate (82 mg, 0.36 mmol) in ethanol (25 mL) was heated at 75° C. under a nitrogen atmosphere for ca. 15 hrs. Then the saturated aq. sodium bicarbonate (2 mL) was added and the mixture was concentrated and purified by silica chromatography (eluent: methanol in dichloromethane) to afford the compound 4-chloro-3-(furo[3,2-c]pyridin-4-yl)aniline (9.2 mg, 51%) as a yellow residue. MS (ESI): Calcd. for C13H9ClN2O: 244. found 245 (M+H)$^+$.

Example 39

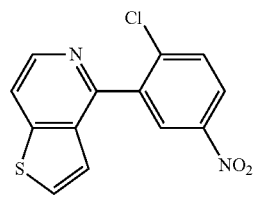 [SMILES: O=[N+]([O-])c1ccc(Cl)c(-c2nccc3sccc23)c1]

2.0 M aq. lithium hydroxide (1.0 mL) was added to a solution of (2-chloro-5-nitrophenyl)boronic acid (297 mg, 1.47 mmol), 4-chlorothieno[3,2-c]pyridine (125 mg, 0.74 mmol), and Pd(PPh3)4 (85 mg, 0.07 mmol) in toluene (12 mL). The mixture was degassed with argon and then heated to 90° C. for ca. 15 hrs. Then the mixture was concentrated and purified by silica chromatography (eluent: methanol in dichloromethane) to afford the compound 4-(2-chloro-5-nitrophenyl)thieno[3,2-c]pyridine (14 mg, 7%) as a white solid. MS (ESI): Calcd. for C13H7ClN2O2S: 290. found 291 (M+H)$^+$.

Example 40

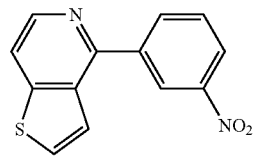 [SMILES: O=[N+]([O-])c1cccc(-c2nccc3sccc23)c1]

4-Chlorothieno[3,2-c]pyridine (173 mg, 1.02 mmol), (3-nitrophenyl)boronic acid (255 mg, 1.53 mmol), Pd(PPh$_3$)$_4$ (177 mg, 0.15 mmol), and saturated aqueous K$_3$PO$_4$ (2.0 mL) and toluene (ca. 10 mL) were stirred together in a round-bottomed flask equipped with a reflux condenser. Argon gas was then bubbled through the reaction mixture for ca. 20 min, and the reaction was submerged into an oil bath preheated to 95° C. Degassing with argon was continued for another 20 min. The reaction mixture was stirred at 95° C. overnight. The next day, the crude reaction mixture was adsorbed onto silica gel and purified via silica chromatography (eluent: CH$_2$Cl$_2$/methanol gradient), to afford the product as a fluffy white solid (110 mg, 42%). LC-MS (ESI): calculated for C13H8N2O2S: 256.0. found: 257.0 (M+H)$^+$.

Example 41

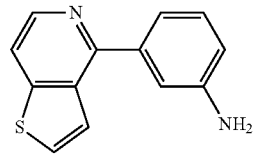

4-(3-Nitrophenyl)thieno[3,2-c]pyridine (110 mg, 0.429 mmol) and $SnCl_2 \cdot 2H_2O$ (480 mg, 2.13 mmol) were stirred into ethanol (ca. 20 mL), and warmed to reflux overnight, under a nitrogen atmosphere. The next day, the mixture was basified with saturated aqueous $NaHCO_3$ (as tested with pH paper), and then concentrated and adsorbed onto silica gel, and then purified via silica chromatography (eluent: $CH_2Cl_2$/methanol gradient) to afford the product as a clear yellow oil (94 mg, 97%). LC-MS (ESI): calculated for C13H10N2S: 226.1. found: 227.0 $(M+H)^+$.

Example 42

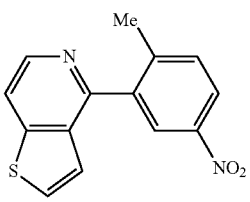 [SMILES: Cc1ccc([N+](=O)[O-])cc1-c1nccc2sccc12]

To a mixture of 4-chlorothieno[3,2-c]pyridine (434 mg, 2.65 mmol), (2-methyl-5-nitrophenyl)boronic acid (556 mg, 3.07 mmol), and $Pd(PPh_3)_4$ (296 mg, 0.256 mmol) in 9:1 toluene/ethanol was added 2M aq. $K_2CO_3$ (2.0 mL). The mixture was degassed with argon and then heated to 90° C. for ca. 15 hrs. The next day, the reaction mixture was concentrated and purified via silica chromatography (eluent: $CH_2Cl_2$/methanol gradient), to afford the product 4-(2-methyl-5-nitrophenyl)thieno[3,2-c]pyridine as a fluffy white solid (480 mg, 69%). MS (ESI): Calcd. for C14H10N2O2S: 270. found 271 $(M+H)^+$.

Example 43

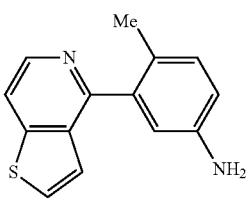

A solution of 4-(2-methyl-5-nitrophenyl)thieno[3,2-c]pyridine (480 mg, 1.78 mmol) and tin (II) chloride dihydrate (1.8 mg, 8.0 mmol) in ethanol (50 mL) was heated at 70° C. under a nitrogen atmosphere for 3 hrs. Then saturated aqueous sodium bicarbonated (ca. 20 mL) was added to the mixture, which was then concentrated and purified by silica chromatography (eluent: $CH_2Cl_2$/methanol gradient) to afford the compound 4-methyl-3-(thieno[3,2-c]pyridin-4-yl)aniline as a brownish solid which was directly carried forward to the next synthetic step. MS (ESI): Calcd. for C14H12N2S: 240. found 241 $(M+H)^+$.

Example 44

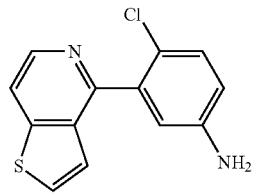 [SMILES: Nc1ccc(Cl)c(-c2nccc3sccc23)c1]

A solution of 4-(2-chloro-5-nitrophenyl)thieno[3,2-c]pyridine (12 mg, 0.04 mmol) and tin (II) chloride dihydrate (47 mg, 0.21 mmol) in ethanol (ca. 10 mL) was heated at 70° C. under a nitrogen atmosphere for ca. 15 hrs. Then the mixture was concentrated and purified by silica chromatography (eluent: methanol in dichloromethane) to afford the compound 4-chloro-3-(thieno[3,2-c]pyridin-4-yl)aniline (13 mg, >100%) as a brown oil. MS (ESI): Calcd. for C13H9ClN2S: 260. found 261 $(M+H)^+$.

Example 45

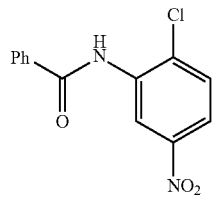

A mixture of 2-chloro-5-nitroaniline (2.5 g, 15 mmol), benzoyl chloride (1.85 mL, 15.9 mmol), and triethylamine (2.02 mL, 29.0 mmol) in THF (50 mL) was stirred at room temperature for ca. 15 hrs. EtOAc was added and the mixture was washed with aq $NaHCO_3$ solution. The organic layer was dried over anhydrous $Na_2SO_4$ and concentrated under reduced pressure. The resulting residue was purified by crystallization from hexanes/EtOAc to yield the desired compound N-(2-chloro-5-nitrophenyl)benzamide (3.14 g, 78%) as a white, fibrous crystalline solid. $^1$H-NMR (400 MHz, $d_6$-DMSO): δ 10.36 (s, 1H), 8.58-8.57 (m, 1H), 8.15-8.01 (m, 3H), 7.88 (d, J=8.8 Hz, 1H), 7.66-7.56 (m, 3H); MS (ESI): Calcd. for C13H9ClN2O3: 276. found: 277 $(M+H)^+$.

Example 46

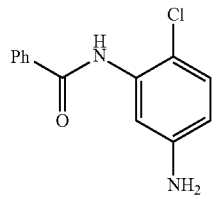 [SMILES: Nc1ccc(Cl)c(NC(=O)c2ccccc2)c1]

A mixture of N-(2-chloro-5-nitrophenyl)benzamide (1.15 g, 4.16 mmol) and tin (II) chloride dihydrate (3.29 g, 14.60 mmol) in ethanol (100 mL) was stirred at 70° C. for 3 hrs. The reaction mixture was allowed to cool to room temperature, DCM was added, and the mixture was washed with aq. NaHCO₃ and brine, respectively. The organic layer was then dried over anhydrous Na₂SO₄ and concentrated under reduced pressure. The resulting residue was purified by flash column chromatography on silica gel (DCM/MeOH) to yield the desired compound N-(5-amino-2-chlorophenyl)benzamide (0.82 g, 80%) as an off-white solid. ¹H-NMR (400 MHz, d₆-DMSO): δ 9.71 (s, 1H), 7.97-7.94 (m, 2H), 7.59-7.57 (m, 1H), 7.54-7.50 (m, 2H), 7.12 (d, J=8.4 Hz, 1H), 6.85 (d, J=2.4 Hz, 1 h), 6.48-6.45 (m, 1H); MS (ESI): Calcd. for C13H11ClN2O: 246. found: 247 (M+H)⁺.

Example 47

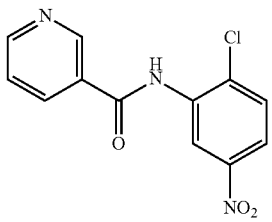

A mixture of 2-chloro-5-nitroaniline (2.55 g, 14.8 mmol), nicotinic acid (2.00 g, 16.2 mmol), HATU (6.19 g, 16.3 mmol), and DIEA (10.3 mL, 59.2 mmol) in DMF (10.0 mL) was stirred at room temperature for 24 hrs. EtOAc was added and the mixture was washed with aq NaHCO₃ solution and brine, respectively. The organic layer was dried over Na₂SO₄, and concentrated under vacuum whereupon the desired product N-(2-chloro-5-nitrophenyl)nicotinamide crystallized (1.61 g, 39%) as an off-white crystalline solid. ¹H-NMR (400 MHz, d₆-DMSO): δ 10.66 (br s, 1H), 9.17-9.16 (m, 1H), 8.81-8.79 (m, 1H), 8.60 (d, J=2.8 Hz, 1H), 8.36-8.33 (m, 1H), 8.14-8.11 (m, 1H), 7.88 (d, J=9.2 Hz, 1H), 7.62-7.58 (m, 1H); MS (ESI): Calcd. for C12H8ClN3O3: 277. found: 278 (M+H)⁺.

Example 48

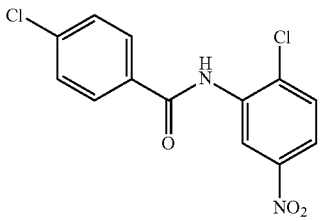 [SMILES: O=C(Nc1cc([N+](=O)[O-])ccc1Cl)c1ccc(Cl)cc1]

A mixture of 2-chloro-5-nitroaniline (2.50 g, 14.5 mmol), 4-chlorobenzoyl chloride (2.04 mL, 15.9 mmol), and TEA (5.05 mL, 36.3 mmol) in THF (100 mL) was stirred at room temperature for 24 hrs. EtOAc was added and the mixture was washed with aq NaHCO₃ solution and brine, respectively. The organic layer was dried over anhydrous Na₂SO₄ and crystallized out of EtOAc/hexanes. The crystals were collected by filtration under reduced pressure and washed with minimal EtOAc. The supernatant liquid was concentrated under reduced pressure, and the resulting residue was purified by flash column chromatography on silica gel (EtOAc/hexanes) to yield additional desired compound 4-chloro-N-(2-chloro-5-nitrophenyl)benzamide (668 mg, 15%) as an off-white crystalline solid. ¹H-NMR (400 MHz, d₆-DMSO): δ 10.47 (s, 1H), 8.56 (d, J=2.8 Hz, 1H), 8.14-8.11 (m, 1H), 8.04-8.01 (m, 2H), 7.87 (d, J=8.8 Hz, 1H), 7.66-7.64 (m, 2H); MS (ESI): Calcd. for C13H8Cl2N2O3: 310. found: 311 (M+H)⁺.

Example 49

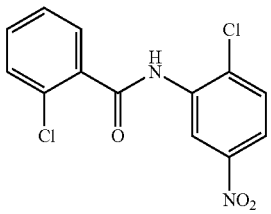 [SMILES: O=C(Nc1cc([N+](=O)[O-])ccc1Cl)c1ccccc1Cl]

A mixture of 2-chloro-5-nitroaniline (2.50 g, 14.5 mmol) and 2-chlorobenzoyl chloride (3.05 mL, 17.4 mmol) in pyridine (10 mL) was stirred at room temperature for 17 hrs. EtOAc was added and the mixture was washed with aq NaHCO₃ solution and brine, respectively. The organic layer was dried over anhydrous Na₂SO₄ and crystallized out of EtOAc/hexanes. The crystals were collected by filtration under reduced pressure and washed with minimal EtOAc to yield additional desired compound 2-chloro-N-(2-chloro-5-nitrophenyl)benzamide (3.31 g, 73% yield) as an off-white crystalline solid. ¹H-NMR (400 MHz, d₆-DMSO): δ 10.61 (s, 1H), 8.67 (s, 1H), 8.13-8.11 (m, 1H), 7.87 (d, J=8.8 Hz, 1H), 7.70-7.47 (m, 4H); MS (ESI): Calcd. for C13H8Cl2N2O3: 310. found: 311 (M+H)⁺.

Example 50

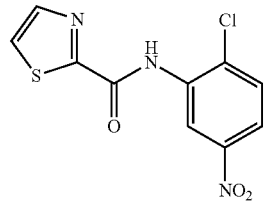 [SMILES: O=C(Nc1cc([N+](=O)[O-])ccc1Cl)c1nccs1]

A mixture of thiazole-2-carboxylic acid (978 mg, 7.57 mmol), 2-chloro-5-nitroaniline (1.19 g, 6.89 mmol), HATU (4.45 g, 11.7 mmol), and DIEA (4.80 mL, 27.6 mmol) in DMF (50 mL) was stirred at room temperature for 20 hrs. EtOAc was added and the mixture was washed with aq NaHCO₃. The organic layer was dried over anhydrous Na₂SO₄ and crystallized out of EtOAc/hexanes. The crystals were collected by filtration under reduced pressure and washed with minimal EtOAc. The supernatant liquid was concentrated under reduced pressure, and the resulting residue was purified by flash column chromatography on silica gel (EtOAc/hexanes) to yield additional desired compound N-(2-chloro-5-nitrophenyl)thiazole-2-carboxamide (912 mg, 47%) as an off-white crystalline solid. ¹H-NMR (400 MHz, d₆-DMSO): δ 10.43 (s, 1H), 8.88 (d, J=2.8 Hz, 1H), 8.24 (d, J=2.8 Hz, 1H), 8.18 (d, J=3.2 Hz, 1H), 8.13-8.10 (m, 1H), 7.91 (d, J=9.2 Hz, 1H); MS (ESI): Calcd. for C10H6ClN3O3S: 283. found: 284 (M+H)⁺.

Example 51

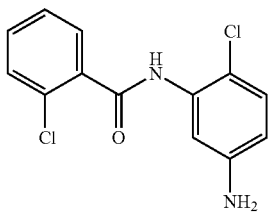

A mixture of 2-chloro-N-(2-chloro-5-nitrophenyl)benzamide (2.08 g, 6.69 mmol) and tin (II) chloride dihydrate (5.28 g, 23.4 mmol) in ethanol (50 mL) was stirred at 70° C. for 17 hrs. The reaction mixture was allowed to cool to room temperature, EtOAc was added, and the mixture was washed with aq. NaHCO$_3$ and brine, respectively. The organic layer was dried over anhydrous Na$_2$SO$_4$ and crystallized out of EtOAc/hexanes. The crystals were collected by filtration under reduced pressure and washed with minimal EtOAc. The supernatant liquid was concentrated under reduced pressure, and the resulting residue was purified by flash column chromatography on silica gel (EtOAc/hexanes) to yield additional desired compound N-(5-amino-2-chlorophenyl)-2-chlorobenzamide (1.64 g, 87% yield) as an off-white solid. $^1$H-NMR (400 MHz, d$_6$-DMSO): δ 9.85 (s, 1H), 7.57-7.43 (m, 4H), 7.10 (d, J=8.4 Hz, 1H), 6.92 (s, 1H), 6.47-6.44 (m, 1H), 5.35 (br s, 2H); MS (ESI): Calcd. for C13H10Cl2N2O: 280. found: 281 (M+H)$^+$.

Example 52

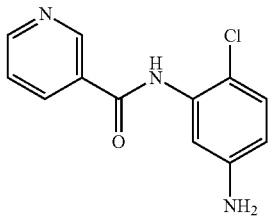

A mixture of N-(2-chloro-5-nitrophenyl)nicotinamide (1.68 g, 6.05 mmol) and tin (II) chloride dihydrate (4.78 g, 21.2 mmol) in ethanol (70 mL) was stirred at 60° C. for 17 hrs. The reaction mixture was allowed to cool to room temperature, DCM was added, and the mixture was washed with aq. NaHCO$_3$ and brine, respectively. The organic layer was then dried over anhydrous Na$_2$SO$_4$ and concentrated under reduced pressure. The resulting residue was purified by flash column chromatography on silica gel (EtOAc/hexanes) to yield the desired compound N-(5-amino-2-chlorophenyl)nicotinamide (760 mg, 51%) as an off-white solid. $^1$H-NMR (400 MHz, d$_6$-DMSO): δ 9.99 (s, 1H), 9.10 (t, J=1.6 Hz, 1H), 8.77-8.76 (m, 1H), 8.30-8.27 (m, 1H), 7.58-7.55 (m, 1H), 7.13 (d, J=8.4 Hz, 1H), 6.81 (d, J=2.8 Hz, 1H), 6.50-6.48 (m, 1H), 5.35 (br s, 2H); MS (ESI): Calcd. for C12H10ClN3O: 247. found: 248 (M+H)$^+$.

Example 53

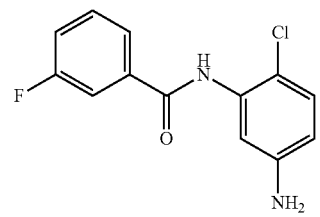 [SMILES: Nc1ccc(Cl)c(NC(=O)c2cccc(F)c2)c1]

A mixture of N-(2-chloro-5-nitrophenyl)-3-fluorobenzamide (1.52 g, 5.16 mmol) and tin (II) chloride dihydrate (4.07 g, 18.1 mmol) in ethanol (50 mL) was stirred at 70° C. for 19 hrs. The reaction mixture was allowed to cool to room temperature, DCM was added, and the mixture was washed with 2 M aq. NaOH and brine, respectively. The organic layer was concentrated under reduced pressure, and the resulting residue was purified by flash column chromatography on silica gel (EtOAc/hexanes) to yield additional desired compound N-(5-amino-2-chlorophenyl)-3-fluorobenzamide (454 mg, 33%) as an off-white solid. $^1$H-NMR (400 MHz, d$_6$-DMSO): δ 9.86 (s, 1H), 9.83-7.11 (m, 4H), 7.12 (d, J=8.4 Hz, 1H), 6.79 (d, J=2.4 Hz, 1H) 6.50-6.47 (m, 1H), 5.34 (br s, 2H); MS (ESI): Calcd. for C13H10ClFN2O: 264. found: 265 (M+H)$^+$.

Example 54

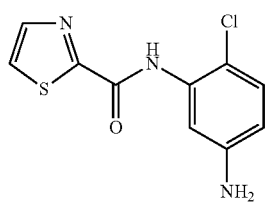 [SMILES: Nc1ccc(Cl)c(NC(=O)c2nccs2)c1]

A mixture of N-(2-chloro-5-nitrophenyl)thiazole-2-carboxamide (871 mg, 3.07 mmol) and tin (II) chloride dihydrate (3.11 g, 13.8 mmol) in ethanol (50 mL) was stirred at 70° C. for 2 hrs. The reaction mixture was allowed to cool to room temperature, DCM was added, and the mixture was washed with aq. NaHCO$_3$ and brine, respectively. The organic layer was concentrated under reduced pressure, and the resulting residue was purified by flash column chromatography on silica gel (EtOAc/hexanes) to yield the desired compound N-(5-amino-2-chlorophenyl)thiazole-2-carboxamide (590 mg, 76%) as a yellow solid. $^1$H-NMR (400 MHz, d$_6$-DMSO): δ 9.83 (s, 1H), 8.17-8.11 (m, 2H), 7.38 (d, J=2.8 Hz, 1H), 7.14 (d, J=8.4 Hz, 1H), 6.44-6.41 (m, 1H), 5.44 (br s, 2H). MS (ESI): Calcd. for C10H8ClN3OS: 253. found: 254 (M+H)$^+$.

Example 55

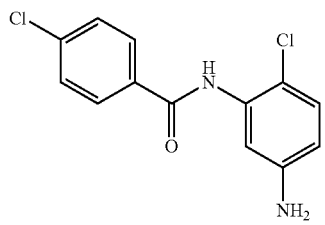 [SMILES: Nc1ccc(Cl)c(NC(=O)c2ccc(Cl)cc2)c1]

A mixture of 4-chloro-N-(2-chloro-5-nitrophenyl)benzamide (650 mg, 2.09 mmol) and tin (II) chloride dihydrate (1.89 g, 8.38 mmol) in ethanol (50 mL) was stirred at 50° C. for 17 h. The reaction mixture was allowed to cool to room temperature, DCM was added, and the mixture was washed with 2 M aq. NaOH and brine, respectively. The organic layer was concentrated under reduced pressure, and the resulting residue was purified by flash column chromatography on silica gel (EtOAc/hexanes) to yield the desired compound N-(5-amino-2-chlorophenyl)-4-chlorobenzamide (0.49 g, 83%) as a white solid. $^1$H-NMR (400 MHz, d$_6$-DMSO): δ 9.83 (s, 1H), 7.98-7.96 (m, 2H), 7.61-7.59 (m, 2H), 7.12 (d, J=8.8 Hz, 1H), 6.80 (d, J=2.8 Hz, 1H), 6.49-6.46 (m, 1H), 5.33 (br s, 2H); MS (ESI): Calcd. for C13H11Cl2N2O (M+H)$^+$: 281. found: 281.

Example 56

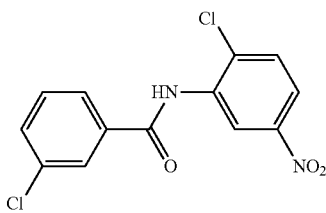

To a solution of 2-chloro-5-nitroaniline (5.71 g, 33.06 mmol) in 50 mL of anhydrous pyridine was added m-chlorobenzoyl chloride (5.79 g, 1.2 equiv.) at room temperature. After the completion of addition, a piece of DMAP was added to the mixture. The reaction was stirred at room temperature for 24 hrs and quenched with saturated aqueous sodium bicarbonate. A mixture of ethyl acetate (150 mL) and ethyl ether (30 mL) was added to extract the mixture. The organic phase was washed with brine and dried over anhydrous sodium sulfate, filtered and concentrated in vacuo to afford the product as a pale yellow powder (10.4 g, 100%). Both $^1$H-NMR and TLC indicated the product was pure enough for further reactions. $^1$H-NMR (400 MHz, CDCl3): δ 10.50 (s, 1H), 8.52 (dd, J=1.6, 2.8 Hz, 1H), 8.14 (dd, J=1.6, 2.8 Hz, 1H), 8.12 (dd, J=1.6, 2.8 Hz, 1H), 8.03 (t, J=2.0 Hz, 1H), 7.94 (dd, J=1.0, 7.8 Hz, 1H), 7.86 (dd, J=1.6, 9.0 HZ, 1H), 7.72-7.58 (m, 2H). ESI-MS: calcd for C13H9Cl2N2O3 (M+H)$^+$: 311. found: 311.

Example 57

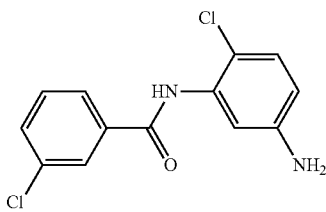 [SMILES: Nc1ccc(Cl)c(NC(=O)c2cccc(Cl)c2)c1]

To a suspension of 3-chloro-N-(2-chloro-5-nitrophenyl) benzamide (5.18 g, 16.66 mmol) in 80 mL of absolute ethanol was added tin(II) chloride hydrate (18.8 g, 5 eq.) at room temperature. The reaction mixture was stirred at 78° C. for 3.5 hrs, upon which the TLC indicated the full conversion of starting material. The reaction mixture was concentrated on rotavapor to remove most of ethanol. Ethyl acetate (100 mL) and saturated aqueous sodium bicarbonate solution (50 mL) were added to partition the mixture. The resulting suspension was filtered and the filtrate was concentrated to dryness to afford the desired product as a pale grayish powder (4.45 g, 95.0%). $^1$H-NMR (400 MHz, CDCl3): δ 9.89 (s, 1H), 7.97 (s, 1H), 7.89 (s, J=3.6 Hz, 1H), 7.65 (d, J=8.0 Hz, 1H), 7.55 (dd, J=6.8, 9.0 Hz, 1H), 7.11 (dd, J=2.4, 8.4 Hz, 1H), 6.76 (d, J=2.4 Hz, 1H), 6.46 (dd, J=2.6, 8.6 Hz, 1H), 5.32 (s, 2H). ESI-MS: calcd for C13H11Cl2N2O (M+H)$^+$: 281. found: 281.

Example 58

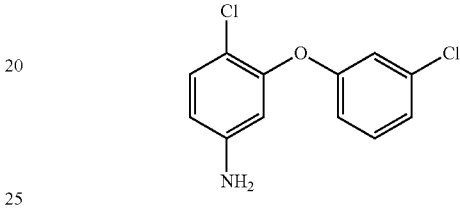

To a mixture of 1-chloro-3-iodobenzene (5.18 g, 21.72 mmol) and 5-amino-2-chlorophenol (5.33 g, 1.71 equiv) and 2-picolinic acid (535 mg, 20 mol %) in 60 mL of anhydrous DMSO was charged sequentially with potassium phosphate (9.2 g, 2 equiv) and copper(I) iodide (414 mg, 10 mol %) under argon atmosphere. The resulting mixture was stirred in an oil bath of 89° C. for 24 hrs, upon which TLC indicated a full conversion of the starting material. The reaction mixture was cooled down to room temperature and charged with water (50 mL) and 150 mL of ethyl acetate. The layers were separated and the organic phase was washed with brine (80 mL) and dried over anhydrous sodium sulfate. Upon filtration the organic phase was concentrated in vacuo to dryness. The residue was purified via silica gel column chromatography (ethyl acetate in hexanes, 0-40%) to afford the desired product as a brownish oil. $^1$H-NMR (400 MHz, CDCl3): δ 7.22 (d, J=7.2 Hz, 2H), 7.21 (t, J=1.6 Hz, 1H), 7.05 (d, J=8.0 Hz, 1H), 7.04 (d, J=8.0 Hz, 1H), 6.84 (d, J=6.0 Hz, 1H), 6.39 (t, J=2.0 Hz, 1H), 4.11 (dd, J=1.2, 7.2 Hz, 2H). MS (ESI): Calcd. For C12H10Cl2NO (M+H)$^+$: 254. found: 254.

Example 59

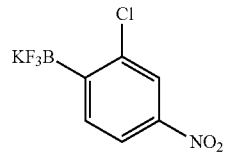

2-Chloro-4-nitrophenylboronic acid (2.50 g, 12.4 mmol), potassium hydrogen fluoride (2.42 g, 31.0 mmol), methanol (4.0 mL), and water (8.0 mL) were stirred together in a 50-mL plastic vial at room temperature for 2 hrs. Over that time, the mixture became a smooth white gel. Then 20 mL of additional methanol was stirred into the mixture, and the mixture was allowed to sit, without stirring, for an additional 2 hrs. The mixture was then filtered (filter paper) and washed with methanol. The solid residue was taken up into acetone (ca. 20 mL), gently heated, and filtered again (filter paper). The supernatant fluid was diluted with an equal volume of diethyl ether, and stored in the freezer overnight. The next day product was collected as a white crystalline solid (2.52 g, 77%).

Example 60

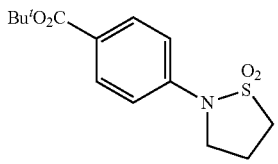

A mixture of tert-butyl 4-aminobenzoate (3.0 g, 16 mmol) and 3-chloropropane-1-sulfonyl chloride (5.3 g, 30 mmol) in pyridine (ca. 10 mL) was stirred at room temperature for 1 hr. The mixture was then concentrated and purified by chromatography (eluent: methanol in dichloromethane) to afford the intermediate tert-butyl 4-(3-chloropropylsulfonamido)benzoate as a brown oil, which was then dissolved into dry THF (150 mL). To this mixture was added a 1:1 w/w solution of sodium hydroxide in water (30 mL), and tetrabutylammonium iodide (290 mg, 0.79 mmol), and the mixture was stirred at room temperature for 22 h. The mixture was then partitioned between ethyl acetate and water (ca. 100 mL each), and the organic layer was concentrated and purified by silica chromatography (eluent: ethyl acetate in hexanes) to afford the product tert-butyl 4-(1,1-dioxidoisothiazolidin-2-yl)benzoate (670 mg, 14%) as a white solid. $^1$H-NMR (400 MHz, d$_6$-DMSO): δ 7.89 (d, J=8.8 Hz, 2H), 7.24 (d, J=8.8 Hz, 2H), 3.80 (t, J=6.4 Hz, 2H), 3.58 (t, J=7.2 Hz, 2H), 1.54 (s, 9H); MS (ESI): Calcd. for C14H19NO4S (M+H)$^+$: 298. found: 298.

Example 61

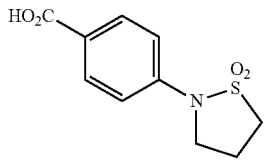

To a mixture of tert-butyl 4-(1,1-dioxidoisothiazolidin-2-yl)benzoate (670 mg, 2.25 mmol) in dichloromethane (10 mL) was added trifluoroacetic acid (1.0 mL), and the mixture was stirred at room temperature for ca. 15 hrs. Then the mixture was concentrated, and the resulting solid was further purified by crystallization out of ethanol and ethyl acetate to afford the product 4-(1,1-dioxidoisothiazolidin-2-yl)benzoic acid (393 mg, 72%) as a yellow powder. $^1$H-NMR (400 MHz, d$_6$-DMSO): δ 12.75 (br s, 1H), 7.93 (d, J=8.8 Hz, 2H), 7.25 (d, J=8.8 Hz, 2H), 3.81 (t, J=6.4 Hz, 2H), 3.58 (t, J=7.2 Hz, 2H), 2.43 (p, J=7.6 Hz, 2H); MS (ESI): Calcd. for C10H11NO4S (M+H)$^+$: 242. found: 242.

Example 62

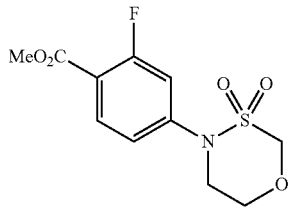 [SMILES: COC(=O)c1ccc(N2CCOCS2(=O)=O)cc1F]

A mixture of methyl 4-bromo-2-fluorobenzoate (1.06 g, 4.56 mmol), 1,3,4-oxathiazinane 3,3-dioxide (750 mg, 5.47 mmol), palladium acetate (102 mg, 0.45 mmol), xantphos (396 g, 0.68 mmol), and cesium carbonate (2.23 g, 6.84 mmol) in dioxane (15 mL) was degassed with argon and stirred at 95° C. for 2 hrs. EtOAc was added and the mixture was washed with water and brine, respectively. The organic layer was dried over anhydrous Na$_2$SO$_4$ and concentrated under reduced pressure whereupon the desired compound precipitated. EtOAc was added, and the precipitate was collected by filtration under reduced pressure and washed with additional EtOAc. The supernatant liquid was concentrated under reduced pressure, and the resulting residue was purified by flash column chromatography on silica gel (DCM/MeOH) to yield additional desired compound methyl 4-(3,3-dioxido-1,3,4-oxathiazinan-4-yl)-2-fluorobenzoate (1.15 g, 87%) as an off-white crystalline solid. $^1$H-NMR (400 MHz, d$_6$-DMSO): δ 7.94-7.90 (m, 1H), 7.36-7.30 (m, 2H), 5.04 (s, 2H), 4.08-405 (m, 2H), 4.01-3.98 (m, 2H), 3.85 (m, 3H); MS (ESI): Calcd. for C11H13FNO5S (M+H)$^+$: 290. found: 290.

Example 63

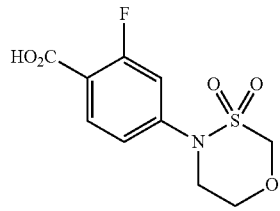 [SMILES: O=C(O)c1ccc(N2CCOCS2(=O)=O)cc1F]

To a mixture of methyl 4-(3,3-dioxido-1,3,4-oxathiazinan-4-yl)-2-fluorobenzoate (992 mg, 3.43 mmol) in 1:1 THF/MeOH (40 mL) was added aq 2M NaOH (8.5 mL, 17 mmol). The mixture was stirred at room temperature for 10 minutes. Then aq 2M HCl (30 mL) was added, and the mixture was concentrated under reduced pressure whereupon a precipitate formed. The precipitate was collected and washed with DCM and water to yield the desired compound 4-(3,3-dioxido-1,3,4-oxathiazinan-4-yl)-2-fluorobenzoic acid (750 mg, 79%) as an off-white crystalline solid. $^1$H-NMR (400 MHz, d$_6$-DMSO): δ 13.27 (br s, 1H), 7.91-7.87 (m, 1H), 7.32-7.26 (m, 2H), 5.03 (s, 2H), 4.07-4.04 (m, 2H), 4.00-3.67 (m, 2H); MS (ESI): Weak signal.

Example 64

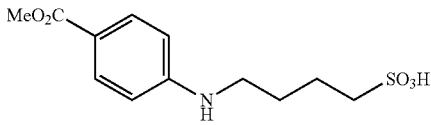 [SMILES: COC(=O)c1ccc(NCCCCS(=O)(=O)O)cc1]

A mixture of methyl 4-aminobenzoate (7.95 g, 52.6 mmol) and 1,2-oxathiane 2,2-dioxide (6.75 g, 49.6 mmol) was heated at 100-110° C. for 2.5 hrs. The mixture was cooled at room temperature and the desired product was obtained as orange viscous solid. Without work-up, the crude product was directly used for the following step as described in Example 65. LC-MS (ESI): Calcd. For $C_{12}H_{18}NO_5S$: 288 (M+H)$^+$. found: 288.

Example 65

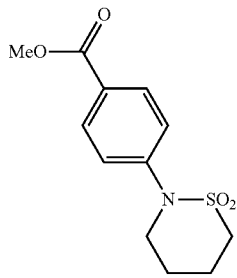 [SMILES: COC(=O)c1ccc(N2CCCCS2(=O)=O)cc1]

Crude 4-((4-(methoxycarbonyl)phenyl)amino)butane-1-sulfonic acid (5.0 g, 17.42 mmol) was charged dropwise with POCl$_3$ (20 mL) and the mixture was refluxed for 6 hrs. Upon cooling, the mixture was carefully decanted into ice water. The resulting solution was neutralized with chilled 4N NaOH and the pH was adjusted to be around 8. The faint yellow precipitate was filtered, washed with copious amount of cold water, air-dried to afford the desired methyl 4-(1,1-dioxido-1,2-thiazinan-2-yl)benzoate as a yellow solid (4.6 g, 97.8%). $^1$H-NMR (400 MHz, CDCl$_3$): δ 8.04-8.01 (m, 2H), 7.40-7.37 (m, 2H), 3.91 (s, 3H), 3.80 (d, J=5.6 Hz, 2H), 3.23-3.19 (m, 2H), 2.35-2.33 (m, 2H), 1.93-1.91 (m, 2H). LC-MS (ESI): Calcd. For $C_{12}H_{16}NO_4S$: 270 (M+H)$^+$. found: 270.

Example 66

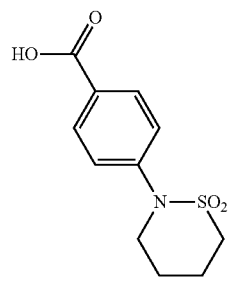 [SMILES: O=C(O)c1ccc(N2CCCCS2(=O)=O)cc1]

Methyl 4-(1,1-dioxido-1,2-thiazinan-2-yl)benzoate (4.6 g, 17.0 mmol) was suspended in a mixture of 20 mL of methanol and 10 mL of 1N NaOH. The mixture was stirred at 50° C. for several hours and concentrated to dryness on rotavapor. The residue was charged with aqueous 1N HCl solution (25 mL) until the pH of the mixture reached ~5. The suspension was slowly stirred in an ice-water bath for 20 min and filtered under vacuum. The residue was washed quickly with cold water (10 mL×2) and dried in vacuo to afford the desired product (3.75 g, 86%) as a faint yellow solid. $^1$H-NMR (400 MHz, d$_6$-DMSO): δ 7.91 (t, J=7.2 Hz, 2H), 7.38 (t, J=7.2 Hz, 2H), 3.71 (t, J=5.2 Hz, 2H), 3.29 (t, J=6.0 Hz, 2H), 2.14 (t, J=4.8 Hz, 2H), 1.80 (t, J=4.8 Hz, 2H); LC-MS (ESI): Calcd. For $C_{11}H_{14}NO_4S$ (M+H)$^+$: 256. found: 256.

Example 67

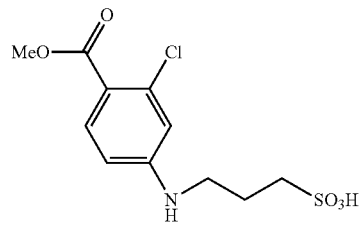 [SMILES: COC(=O)c1ccc(NCCCS(=O)(=O)O)cc1Cl]

A mixture of methyl 4-aminobenzoate (5.23 g, 28.2 mmol) and 1,2-oxathiane 2,2-dioxide (3.44 g, 28.2 mmol) was heated at 100-110° C. for 4.5 hrs. The mixture was cooled at room temperature and the desired product was obtained as brownish solid. Without work-up, the crude product was directly used for the following step as described in Example 68. LC-MS (ESI): Calcd. For $C_{11}H_{15}NO_5SCl$: 308 (M+H)$^+$. found: 308.

Example 68

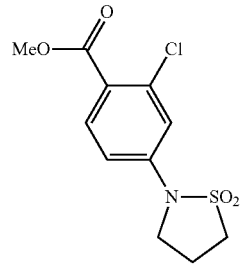 [SMILES: COC(=O)c1ccc(N2CCCS2(=O)=O)cc1Cl]

Crude 3-((3-chloro-4-(methoxycarbonyl)phenyl)amino)propane-1-sulfonic acid obtained above was charged dropwise with POCl$_3$ (6 mL) and the mixture was refluxed for 5 hrs. Upon cooling, the mixture was carefully decanted into ice water. The resulting solution was neutralized with chilled 4N NaOH and the pH was adjusted to be around 8. Ethyl acetate (100 mL) was added tp extract the mixture. The organic layer was separated and washed with water (50 mL) and brine (50 mL). The solution was dried over anhydrous sodium sulfate and concentrated in vacuo. The residue was purified via silica gel column chromatography (ethyl acetate in hexanes, 0 to 44%) to afford the desired product as a yellow foam (916 mg, 27.5%). $^1$H-NMR (400 MHz, CDCl3): δ 7.91 (dd, J=1.6, 8.4 Hz, 1H), 7.26-7.20 (m, 3H), 3.81 (t, J=6.4 Hz, 2H), 3.42 (t, J=7.2 Hz, 2H), 2.59 (t, J=7.2 Hz, 2H). MS (ESI): Calcd. For $C_{11}H_{13}NClO_4S$ (M+H)$^+$: 290. found: 290.

Example 69

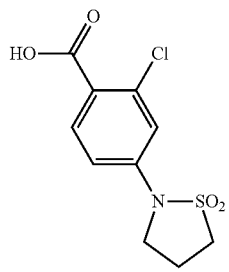 [SMILES: O=C(O)c1ccc(N2CCCS2(=O)=O)cc1Cl]

To a solution of methyl 2-chloro-4-(1,1-dioxidoisothiazolidin-2-yl)benzoate (2.04 g, 7.06 mmol) in a mixture of THF (6 mL), MeOH (6 mL) and water (2 mL) was charged with lithium hydroxide (1.48 g, 5 equiv.) at room temperature. The mixture was stirred for 8 hrs and TLC indicated the full conversion of starting material. 1N aqueous HCl solution was added to adjust the pH to be around 5. Ethyl acetate (100 mL) was added and the organic layer was washed with brine and further dried over anhydrous sodium sulfate. Upon filtration, the solution was concentrated to give the desired product as a yellow solid (1.7 g, 87.3%). $^1$H NMR (400 MHz) δ (ppm): 7.90 (d, J=8.8 Hz, 1H), 7.32 (t, J=1.0 Hz, 1H), 7.22-7.19 (m, 1H), 3.80 (t, J=7.2 Hz, 2H), 3.58 (t, J=7.4 Hz, 2H), 2.41 (t, J=7.2 Hz, 2H). ESI-MS: calcd for $C_{10}H_{11}NClO_4S$ (M+H)$^+$: 276. found: 276.

Example 70

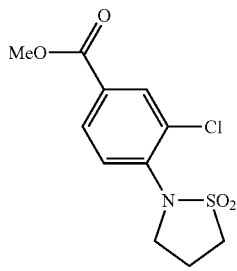 [SMILES: COC(=O)c1ccc(N2CCCS2(=O)=O)c(Cl)c1]

A mixture of methyl 4-amino-3-chlorobenzoate (4.2 g, 22.63 mmol) and 1,2-oxathiane 2,2-dioxide (2.76 g, 22.63 mmol) was heated at 100-110° C. for 20 hrs. The mixture was cooled at room temperature and the desired product was obtained as brownish solid. Without work-up, the crude product was directly used for the following step.

The viscous oil obtained above was charged cautiously with 10 mL of POCl3 at room temperature. The mixture was refluxed for 6 hrs and cooled down to room temperature and was further quenched with ice-water. 1N NaOH was added to adjust the pH of the suspension to be around 8. Ethyl acetate (120 mL) was added to extract the mixture. The organic phase was washed with saturated aqueous NaHCO3 followed by brine. The organic phase was dried over anhydrous Na2SO4, filtered through a cotton pad and concentrated on rotavapor to dryness. The residue was purified via silica gel column chromatography (ethyl acetate in hexanes, 0 to 50%) to furnish the desired product as a yellow solid (4.08 g, 97.1%). $^1$H-NMR (400 MHz, CDCl3): δ 8.03 (t, J=1.0 Hz, 1H), 7.97-7.94 (m, 1H), 7.72 (d, J=8.4 Hz, 1H), 3.75 (t, J=6.8 Hz, 2H), 2.48 (t, J=6.8 Hz, 2H). ESI-MS: calcd for C11H13ClNO4S (M+H)$^+$: 290. found: 290.

Example 71

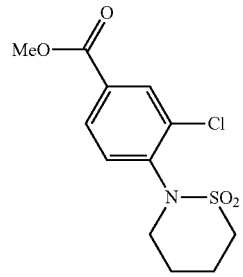 [SMILES: COC(=O)c1ccc(N2CCCCS2(=O)=O)c(Cl)c1]

A mixture of methyl 4-amino-3-chlorobenzoate (881 mg, 4.75 mmol) and 1,2-oxathiane 2,2-dioxide (646 mg, 1 equiv) was heated at 100-110° C. for 10 hrs. The mixture was cooled at room temperature and the desired product was obtained as brownish solid. Without work-up, the crude product was directly used for the following step.

The viscous oil obtained above was charged cautiously with 5 mL of POCl3 at room temperature. The mixture was refluxed for 6 hrs and cooled down to room temperature and was further quenched with ice-water. 1N NaOH was added to adjust the pH of the suspension to be around 8. Ethyl acetate (60 mL) was added to extract the mixture. The organic phase was washed with saturated aqueous NaHCO3 followed by brine. The organic phase was dried over anhydrous Na2SO4, filtered through a cotton pad and concentrated on rotavapor to dryness. The residue was purified via silica gel column chromatography (ethyl acetate in hexanes, 0 to 50%) to furnish the desired product as a yellow solid (411 mg, 28.5% in two steps). 1H-NMR (400 MHz, CDCl3): δ 8.02 (d, J=1.6 Hz, 1H), 7.93 (dd, J=1.2, 5.2 Hz, 1H), 7.69 (d, J=8.4 Hz, 1H), 3.59 (t, J=5.2 Hz, 2H), 3.58 (s, 3H), 2.19 (t, J=5.6 Hz, 2H), 2.03-1.97 (m, 4H). ESI-MS: calcd for C12H15ClNO4S (M+H)+: 304. found: 304.

Example 72

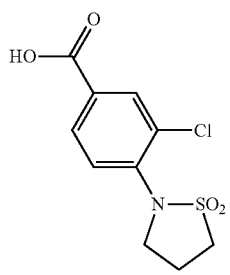 [SMILES: O=C(O)c1ccc(N2CCCS2(=O)=O)c(Cl)c1]

To a solution of methyl 3-chloro-4-(1,1-dioxidoisothiazolidin-2-yl)benzoate (4.06 g, 14.01 mmol) in a mixture of THF (9 mL), MeOH (9 mL) and water (3 mL) was charged with lithium hydroxide (2.94 g, 5 equiv.) at room temperature. The mixture was stirred for 20 hrs and TLC indicated the full conversion of starting material. 1N aqueous HCl solution was added to adjust the pH to be around 5. Ethyl acetate (100 mL) was added and the organic layer was washed with brine and further dried over anhydrous sodium sulfate. Upon filtration, the solution was concentrated to give the desired product as a yellow solid (3.24 g, 83.8%). $^1$H NMR (400 MHz) δ (ppm): 7.99 (d, J=2.0 Hz, 1H), 7.93 (dd, J=2.2, 8.4 Hz, 1H), 7.69 (d, J=8.4 Hz, 1H), 3.74 (t, J=6.4 Hz, 2H), 3.42 (t, J=6.4 Hz, 2H), 2.48-2.43 (m, 2H). ESI-MS: calcd for C10H11NClO4S (M+H)$^+$: 276. found: 276.

Example 73

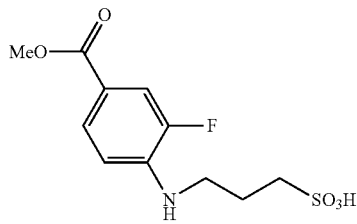 [SMILES: COC(=O)c1ccc(NCCCS(=O)(=O)O)c(F)c1]

A mixture of methyl 4-amino-3-fluorobenzoate (5 g, 40.94 mmol) and 1,2-oxathiane 2,2-dioxide (4.76 g, 1 equiv) was heated at 120° C. for 2 hrs. The mixture was cooled at room temperature and the desired product was obtained as light brownish solid. Without work-up, the crude product was directly used for the following step. LC-MS (ESI): Calcd. For C11H15FNO5S: 292 (M+H)$^+$. found: 292.

Example 74

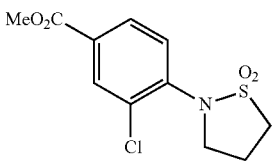 [SMILES: COC(=O)c1ccc(N2CCCS2(=O)=O)c(Cl)c1]

A mixture of methyl 4-amino-3-chlorobenzoate (4.20 g, 22.63 mmol) and 1,2-oxathiane 2,2-dioxide (2.76 g, 22.63 mmol) was heated at 100-110° C. for 20 hrs. The mixture was cooled at room temperature and the desired product was obtained as brownish solid. Without work-up, the crude product was directly used for the following step. The viscous oil obtained above was charged cautiously with 10 mL of POCl$_3$ at room temperature. The mixture was refluxed for 6 hrs and cooled down to room temperature and was further quenched with ice-water. 1N NaOH was added to adjust the pH of the suspension to be around 8. Ethyl acetate (120 mL) was added to extract the mixture. The organic phase was washed with saturated aqueous NaHCO$_3$ followed by brine. The organic phase was dried over anhydrous Na$_2$SO$_4$, filtered through a cotton pad and concentrated on rotavapor to dryness. The residue was purified via silica gel column chromatography (ethyl acetate in hexanes, 0 to 50%) to furnish the desired product as a yellow solid (4.08 g, 97.1%). $^1$H-NMR (400 MHz, CDCl3): δ 8.03 (t, J=1.0 Hz, 1H), 7.97-7.94 (m, 1H), 7.72 (d, J=8.4 Hz, 1H), 3.75 (t, J=6.8 Hz, 2H), 2.48 (t, J=6.8 Hz, 2H).

Example 75

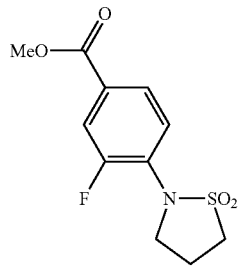 [SMILES: COC(=O)c1ccc(N2CCCS2(=O)=O)c(F)c1]

Crude 3-((2-fluoro-4-(methoxycarbonyl)phenyl)amino) propane-1-sulfonic acid obtained above was charged dropwise with POCl$_3$ (15 mL) and the mixture was refluxed for 6 hrs. Upon cooling, the mixture was carefully decanted into ice water. The resulting solution was neutralized with chilled 4N NaOH and the pH was adjusted to be around 8. Ethyl acetate (120 mL) was added tp extract the mixture. The organic layer was separated and washed with water (50 mL) and brine (50 mL). The solution was dried over anhydrous sodium sulfate and concentrated in vacuo. The residue was suspended into a mixture of hexanes and ethyl ether (10:1) and the mixture was stirred at room temperature for 24 hrs. The suspension was filtered and the desired product was obtained as a light brownish powder (4.2 g, 37.5%). $^1$H-NMR (400 MHz, CDCl3): δ 7.82-7.75 (m, 2H), 7.57-7.51 (m, 1H), 3.84 (s, 3H), 3.91-3.72 (m, 1H), 3.47 (t, J=5.6 Hz, 2H), 2.45 (t, J=5.8 Hz, 2H). Calcd. For C11H13FNO4S (M+H)$^+$: 274. found: 274.

Example 76

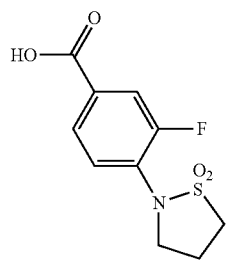 [SMILES: O=C(O)c1ccc(N2CCCS2(=O)=O)c(F)c1]

A solution of methyl 4-(1,1-dioxidoisothiazolidin-2-yl)-3-fluorobenzoate (3.4 g, 12.44 mmol) in a mixture of THF (12 mL), MeOH (12 mL) and water (4 mL) was charged with lithium hydroxide (2.6 g, 5 equiv.) at room temperature. The mixture was stirred for 22 hrs and TLC indicated the full conversion of starting material. 1N aqueous HCl solution was added to adjust the pH to be around 4. Ethyl acetate (30 mL) was added and the organic layer was washed with brine and further dried over anhydrous sodium sulfate. Upon filtration, the solution was concentrated to give the desired product as a gray solid (1.3 g, 40.3%). $^1$H NMR (400 MHz) δ (ppm): 13.20-13.16 (brs, 1H, OH), 7.79-7.71 (m, 2H), 7.52 (t, J=7.6 Hz, 1H), 3.84 (t, J=6.8 Hz, 2H), 3.45 (d, J=0.8 Hz, 2H), 2.49-2.44 (m, 2H). ESI-MS: calcd for C10H11FNO4S (M+H)$^+$: 260. found: 260.

Example 77

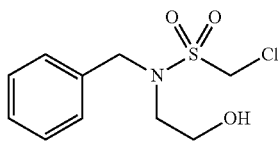 [SMILES: O=S(=O)(CCl)N(CCO)Cc1ccccc1]

To a solution of DIEA (11.2 mL, 120 mmol) and 2-(benzylamino)ethanol (5.0 g, 33.00 mmol) in dry THF (180 mL) cooled to 0° C. under nitrogen atmosphere was added chloromethanesulfonyl chloride (4.9 g, 33.00 mmol). The mixture was then removed from the cold bath and stirred at r.t. for ca. 15 hrs. It was then concentrated, partitioned between ethyl acetate and water, and the organic layer was dried over sodium sulfate and concentrated in vacuo to afford the product N-benzyl-1-chloro-N-(2-hydroxyethyl)methanesulfonamide as a yellow oil (7.8 g, 89%). $^1$H-NMR (400 MHz, $d_6$-DMSO): δ 7.41-7.30 (m, 5H), 5.14 (s, 2H), 4.89 (t, J=4.8 Hz, 1H), 4.52 (s, 2H), 3.43 (q, J=5.2 Hz, 2H), 3.23 (t, J=6.0 Hz, 2H).

Example 78

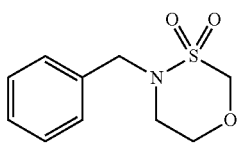 [SMILES: O=S1(=O)COCCN1Cc1ccccc1]

To a solution of 2-(benzylamino)ethanol (20.72 g, 137 mmol) and 47.6 mL of DIEA in 500 mL of anhydrous THF at 0° C. was added dropwise a solution of chloromethanesulfonyl chloride (20.38 g, 137 mmol) in 100 mL of THF. The slow addition was completed over 2 hrs and the resulting mixture was stirred at room temperature for 21 hrs and TLC indicated the completion of the reaction. The mixture was concentrated on rotavapor to dryness. 120 mL of ethyl acetate and 100 mL of water were added to partition. The organic layer was washed with brine and the dried over anhydrous sodium sulfate. The extract was filtered and concentrated on rotavapor and the crude product was obtained as an orange oil.

The above-obtained compound was charged with 400 mL of anhydrous DMF and 89 g of cesium carbonate. The mixture was heated at 80° C. for 24 hrs and cooled down at room temperature. To the mixture was added ethyl acetate (150 mL) and water (100 mL). The organic layer was further washed with brine (80 mL) and dried over anhydrous sodium sulfate. The extract was filtered and concentrated on rotavapor to dryness. The residue was dried on vacuum line for 10 hrs until the trapped DMF was removed. To the solid residue was added 50 mL of absolute ethanol and instantly a white solid was precipitated from the solution. The suspension was stirred for 30 mins and filtered under vacuum to collect the desired product as an off-white powder (14.21 g, 2 steps, 45.6%). 1H NMR (400 MHz) δ (ppm): 7.36-7.32 (m, 5H), 4.82 (s, 2H), 4.29 (s, 2H), 3.79 (t, J=4.4 Hz, 2H), 3.33 (t, J=4.4 Hz, 2H).

Example 79

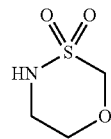

To a solution of 4-benzyl-1,3,4-oxathiazinane 3,3-dioxide (1.74 g, 7.66 mmol) in a mixture of ethyl acetate (50 mL) and absolute ethanol (50 mL) was added 1 mL of acetic acid. The solution was vacuumed and purged with argon for a minute and charged with 20% palladium(II) hydroxide (100 mg). The reaction mixture was shaked on a hydrogenation apparatus under hydrogen pressure of 60 psi for 21 hrs, upon which TLC indicated the full conversion of starting material. The hydrogen source was removed and the reaction mixture was filtered via bed of celite. The filtrate was concentrated on rotavapor to dryness and the desired product was obtained as a white powder (1.04 g, 100%). 1H NMR (400 MHz) δ (ppm): 7.16 (d, J=2.0 Hz, 1H), 4.65 (d, J=4.4 Hz, 2H), 3.65 (d, J=4.4 Hz, 2H), 3.29 (d, J=4.4 Hz, 2H).

Example 80

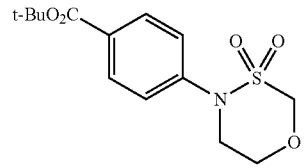

A mixture of 1,3,4-oxathiazinane 3,3-dioxide (70 mg, 1.30 mmol), tert-butyl 4-bromobenzoate (100 mg, 0.39 mmol), palladium acetate (9 mg, 0.04 mmol), Xantphos (34 mg, 0.06 mmol), and cesium carbonate (192 mg, 0.59 mmol) in dioxane (1.0 mL) in a microwave vial was degassed with argon and subjected to microwave irradiation: 100° C. for 2 hrs. The mixture was then partitioned between ethyl acetate and water, and the organic layer was dried (sodium sulfate), concentrated, and purified via silica chromatography (eluent: methanol in dichloromethane) to afford the product tert-butyl 4-(3,3-dioxido-1,3,4-oxathiazinan-4-yl)benzoate (121 mg, 98%) as a white solid. 1H-NMR (400 MHz, d6-DMSO): δ 7.93-7.91 (m, 2H), 7.46-7.44 (m, 2H), 5.00 (s, 2H), 4.08-4.06 (m, 2H), 3.94-3.92 (m, 2H).

Example 81

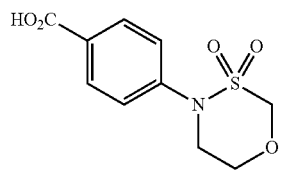 [SMILES: O=C(O)c1ccc(N2CCOCS2(=O)=O)cc1]

A mixture of tert-butyl 4-(3,3-dioxido-1,3,4-oxathiazinan-4-yl)benzoate (492 mg, 1.57 mmol) in 15% TFA in dichloromethane (ca. 20 mL) was stirred at r.t. for ca. 2 hrs.

The mixture was then concentrated and redissolved in dichloromethane whereupon product crystallized and was collected by filtration to obtain 4-(3,3-dioxido-1,3,4-oxathiazinan-4-yl)benzoic acid (218 mg, 55%) as a white crystalline solid. 1H-NMR (400 MHz, d6-DMSO): δ 13.07 (br s, 1H), 7.96 (d, J=9.2 Hz, 2H), 7.45 (d, J=8.8 Hz, 2H), 5.02 (s, 2H), 4.08-4.06 (m, 2H), 3.95-3.93 (m, 2H).

Example 82

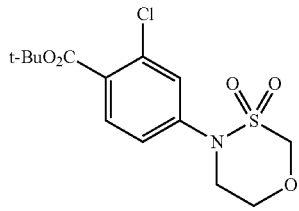

A mixture of 1,3,4-oxathiazinane 3,3-dioxide (190 mg, 1.39 mmol), tert-butyl 4-bromo-2-chlorobenzoate (404 mg, 1.39 mmol), palladium acetate (31 mg, 0.14 mmol), Xantphos (121 mg, 0.21 mmol), and cesium carbonate (679 mg, 2.08 mmol) in dioxane (5.0 mL) in a microwave vial was degassed with argon and subjected to microwave irradiation: 100° C. for 2 hrs. The mixture was then partitioned between ethyl acetate and water, and the organic layer was dried over sodium sulfate, concentrated, and purified via silica chromatography (eluent: methanol in dichloromethane) to afford the product tert-butyl 2-chloro-4-(3,3-dioxido-1,3,4-oxathiazinan-4-yl)benzoate (367 mg, 76%) as a white solid. $^1$H-NMR (400 MHz, d$_6$-DMSO): δ 7.75 (d, J=8.4 Hz, 1H), 7.50 (d, J=2.0 Hz, 1H), 7.39 (dd, J=2.4, 8.4 Hz, 1H), 5.04 (s, 2H), 4.07-4.06 (m, 2H), 3.97-3.94 (m, 2H), 1.54 (s, 9H).

Example 83

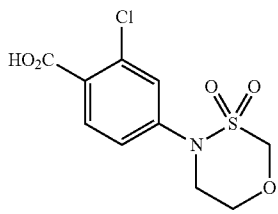 [SMILES: O=C(O)c1ccc(N2CCOCS2(=O)=O)cc1Cl]

A mixture of tert-butyl 2-chloro-4-(3,3-dioxido-1,3,4-oxathiazinan-4-yl)benzoate (353 mg, 1.01 mmol) in 15% TFA in dichloromethane (ca. 20 mL) was stirred at r.t. for ca. 2 hrs. The mixture was then concentrated and redissolved in dichloromethane whereupon product crystallized and was collected by filtration to obtain 2-chloro-4-(3,3-dioxido-1,3,4-oxathiazinan-4-yl)benzoic acid (158 mg, 54%) as a white crystalline solid. $^1$H-NMR (400 MHz, d$_6$-DMSO): δ 13.40 (br s, 1H), 7.86-7.84 (m, 1H), 7.50 (s, 1H), 7.42-7.39 (m, 1H), 5.04 (s, 2H), 4.07-4.06 (m, 2H), 3.97-3.96 (m, 2H).

Example 84

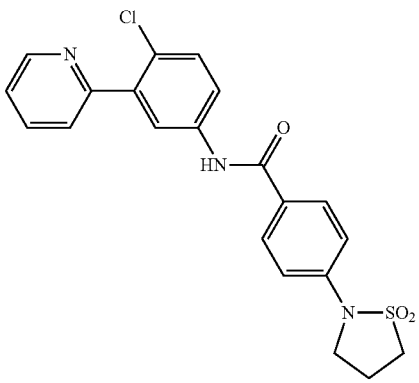 [SMILES: O=C(Nc1ccc(Cl)c(-c2ccccn2)c1)c1ccc(N2CCCS2(=O)=O)cc1]

A solution of 4-(5-methyl-1,3,4-oxadiazol-2-yl)benzoic acid (56 mg, 0.27 mmol), DIEA (94 uL, 2 eq) and HATU (123 mg, 1.2 eq) in 1.7 mL of anhydrous DMF was charged with a solution of 4-chloro-3-(pyridin-2-yl)aniline (56 mg, 1 eq) in 0.4 mL of anhydrous DMF at room temperature. The reaction mixture was stirred at room temperature for 24 hrs and TLC indicated the completion of the reaction. Ethyl acetate (5 mL) and saturated aqueous sodium bicarbonate (2 mL) were added to partition the mixture. The mixture was filtered and the filtrate was transferred to a separatory funnel. The organic phase was washed with additional 2 mL of brine and dried over anhydrous sodium sulfate. After filtration, the solution was concentrated on rotavapor to dryness. The crude product was charged with 1 mL of chilled methylene chloride. Hexanes was added dropwise to the solution until cloudy suspension started to form. Two drops of methylene chloride was added back to achieve a clear solution. The resulting solution stood still at room temperature for several hours. The solid recrystallized from the mother liquid was collected and washed quickly with cold methylene chloride and further dried in vacuo. The desired product was obtained as a yellow powder (30 mg, 28.4%). The remained mother liquid was concentrated to dryness and stored in freezer. $^1$H NMR (400 MHz) δ (ppm): 10.51 (dd, J=2.8, 3.8 Hz, 1H), 8.61 (d, J=6.0 Hz, 1H), 8.08-7.55 (m, 11H), 3.85 (d, J=6.4 HZ, 2H), 3.45 (d, J=6.0 Hz, 2H), 2.49 (t, J=2.0 Hz, 2H). ESI-MS: calcd for C21H19ClN3O3S (M+H)$^+$: 428. found: 428.

Example 85

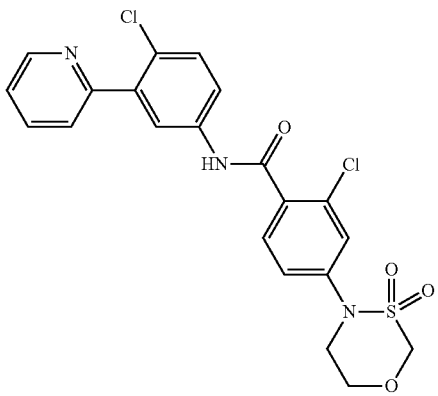 [SMILES: O=C(Nc1ccc(Cl)c(-c2ccccn2)c1)c1ccc(N2CCOCS2(=O)=O)cc1Cl]

A mixture of 2-chloro-4-(3,3-dioxido-1,3,4-oxathiazinan-4-yl)benzoic acid (40 mg, 0.14 mmol), 4-chloro-3-(pyridin-2-yl)aniline (30 mg, 0.12 mmol), HATU (68 mg, 0.18 mmol), and DIEA (90 μL, 0.51 mmol) in DMF (2.0 mL) was stirred at room temperature for ca. 15 h. EtOAc was added and the mixture was washed with aq NaHCO₃ solution. The organic layer was concentrated under reduced pressure and the resulting residue was purified by flash column chromatography on silica gel (DCM/MeOH) and concentrated under reduced pressure. The residue was dissolved into EtOAc and washed with 2M aq HCl solution. The organic layer was dried over anhydrous Na₂SO₄ and concentrated under reduced pressure to yield the desired compound 2-chloro-N-(4-chloro-3-(pyridin-2-yl)phenyl)-4-(3,3-dioxido-1,3,4-oxathiazinan-4-yl)benzamide (15 mg, 23%) as an off-white solid. ¹H-NMR (400 MHz, d₆-DMSO): δ 10.77 (s, 1H), 8.70-8.68 (m, 1H), 8.00 (d, J=2.8 Hz, 1H), 7.92-7.90 (m, 1H), 7.74-7.64 (m, 3H), 7.56-7.41 (m, 5H), 5.02 (s, 2H), 4.08-4.03 (m, 2H), 3.94-3.90 (m, 2H); MS (ESI): Calcd. for C21H17Cl2N3O4S: 477. found: 478 (M+H).

Example 86

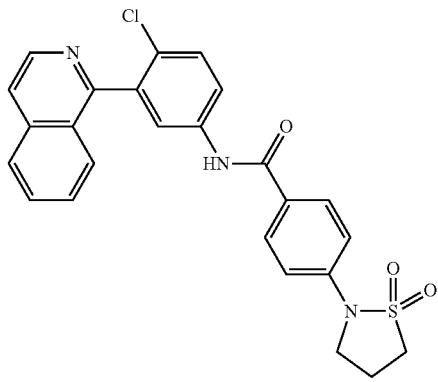 [SMILES: O=C(Nc1ccc(Cl)c(-c2nccc3ccccc23)c1)c1ccc(N2CCCS2(=O)=O)cc1]

This product was prepared according to the 'General Procedure for Parallel Synthesis—Amide Couplings I' with 4-(1,1-dioxidoisothiazolidin-2-yl)benzoic acid (59 mg, 0.25 mmol). The reaction mixture was amber colored and homogeneous. Purification via silica chromatography (eluent: CH₂Cl₂/methanol gradient) afforded product as a clear resin (6 mg, 6%). ¹H-NMR (400 MHz, CDCl₃): δ 8.53 (d, J=6.0 Hz, 1H), 8.16 (s, 1H), 8.01-7.99 (m, 1H), 7.95 (d, J=8.4 Hz, 1H), 7.88-7.52 (m, 10H), 7.29-7.27 (m, 1H), 3.83 (t, J=6.4 Hz, 2H), 3.42 (t, J=7.6 Hz, 2H), 2.58 (p, J=6.8 Hz, 2H); LC-MS (ESI): calculated for C25H20ClN3O3S: 477.1. found: 478.2 (M+H).

Example 87

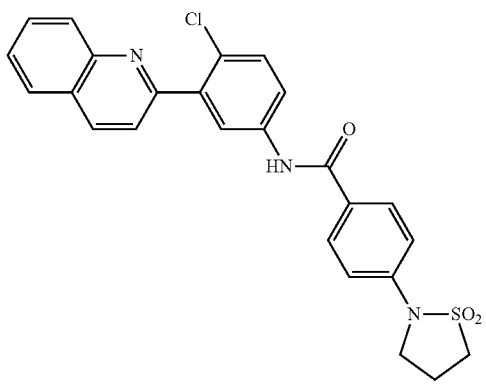 [SMILES: O=C(Nc1ccc(Cl)c(-c2ccc3ccccc3n2)c1)c1ccc(N2CCCS2(=O)=O)cc1]

To a solution of 4-(1,1-dioxidoisothiazolindin-2-yl)benzoic acid (76 mg, 0.32 mmol) in tetrahydrofuran (2.5 mL) was added thionyl chloride (0.28 mL, 3.93 mmol) and stirred under argon for 24 hours. The solvent was removed and toluene (2 mL) was added then removed again under vacuum. A solution of 4-chloro-3-(quinolin-2-yl)aniline (50 mg, 0.2 mmol) in pyridine (2 mL) was added under ice-bath and stirred for 10 min. The mixture was then allowed to equilibrate to room temperature and continued to stir for 30 min then quenched with sat. NaHCO₃. Extracted with ethyl acetate (4 mL) and washed with sat. NaHCO₃. The combined organic extracts were dried over anhydrous Na₂SO₄ and concentrated. To the crude oil was added dichloromethane (8 mL) and sonicated, then the precipitated solid was collected by filtration to give the desired product (65 mg, 69%) as a beige solid. ¹H-NMR (400 MHz, d₆-DMSO): δ 10.40 (s, 1H), 8.47 (d, 1H, J=8.4 Hz), 8.12 (m, 1H), 8.04 (m, 2H), 7.99 (m, 3H), 7.81 (m, 2H), 7.66 (m, 1H), 7.58 (dd, 1H, J=8.8, 1.6 Hz), 7.28 (m, 2H), 3.81 (m, 2H), 3.56 (m, 2H), 2.42 (m, 2H). MS (ESI): Calcd. for C25H20ClN3O3S: 477. found: 478 (M+H).

Example 88

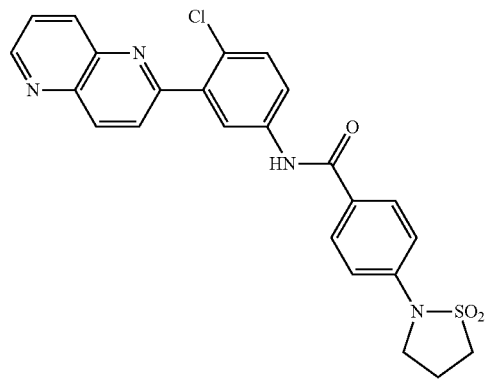 [SMILES: O=C(Nc1ccc(Cl)c(-c2ccc3ncccc3n2)c1)c1ccc(N2CCCS2(=O)=O)cc1]

To a solution of 4-(1,1-dioxidoisothiazolindin-2-yl)benzoic acid (76 mg, 0.32 mmol) in tetrahydrofuran (2.5 mL) was added thionyl chloride (0.28 mL, 3.93 mmol) and stirred under argon for 24 hours. The solvent was removed and toluene (2 mL) was added then removed again under vacuum. A solution of 4-chloro-3-(1,5-naphthyridin-2-yl)aniline (50 mg, 0.2 mmol) in pyridine (2 mL) was added under ice-bath and stirred for 10 min. The mixture was then allowed to equilibrate to room temperature and continued to stir for 30 min then quenched with sat. NaHCO₃. Extracted with ethyl acetate (4 mL) and washed with sat. NaHCO₃. The combined organic extracts were dried over anhydrous Na₂SO₄ and concentrated. To the crude oil was added dichloromethane (8 mL) and sonicated, then the precipitated solid was collected by filtration to give the desired product (48 mg, 51%) as a beige solid. ¹H-NMR (400 MHz, d₆-DMSO): δ 10.37 (s, 1H), 9.00 (m, 1H), 8.48 (d, 1H, J=8.8 Hz), 8.43 (m, 1H), 8.10 (dd, 1H, J=2.4, 0.4 Hz), 8.01 (dd, 1H, J=8.8, 0.8 Hz), 7.93 (m, 3H), 7.80 (dd, 1H, J=4.8, 0.4 Hz), 7.56 (dd, 1H, J=8.8, 0.4 Hz), 7.23 (m, 2H), 3.77 (m, 2H), 3.52 (m, 2H), 2.37 (m, 2H). MS (ESI): Calcd. for C24H19ClN4O3S: 457. found: 458 (M+H).

Example 89

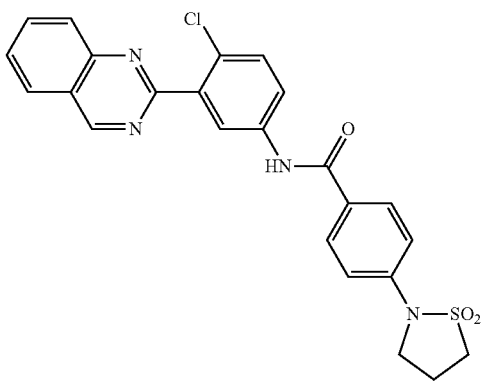 [SMILES: O=C(Nc1ccc(Cl)c(-c2ncc3ccccc3n2)c1)c1ccc(N2CCCS2(=O)=O)cc1]

To a solution of 4-(1,1-dioxidoisothiazolindin-2-yl)benzoic acid (0.076 g, 0.31 mmol) in tetrahydrofuran (2.5 mL) was added thionyl chloride (0.28 mL, 3.93 mmol) and stirred under argon for 24 hours. The solvent was removed and toluene (2 mL) was added then removed again under vacuum. A solution of 4-chloro-3-(quinazolin-2-yl)aniline (0.050 g, 0.20 mmol) in pyridine (2 mL) was added under ice-bath and stirred for 10 min. The mixture was then allowed to equilibrate to room temperature and continued to stir for 30 min then quenched with sat. NaHCO$_3$. Extracted with ethyl acetate (4 mL) and washed with sat. NaHCO$_3$. The combined organic extracts were dried over anhydrous Na$_2$SO$_4$ and concentrated. To the crude oil was added dichloromethane (8 mL) and sonicated, then the precipitated solid was collected by filtration to give the desired product (0.066 g, 70%) as a beige solid. $^1$H-NMR (400 MHz, d$_6$-DMSO): δ 10.42 (s, 1H), 9.75 (s, 1H), 8.29 (d, 1H, J=2.4 Hz), 8.23 (m, 1H), 8.08 (m, 2H), 7.99 (m, 3H), 7.82 (m, 1H), 7.58 (d, 1H, J=8.8 Hz), 7.28 (m, 2H), 3.81 (m, 2H), 3.57 (m, 2H), 2.42 (m, 2H). MS (ESI): Calcd. for C$_{24}$H$_{19}$ClN$_4$O$_3$S: 457. found: 458 (M+H).

Example 90

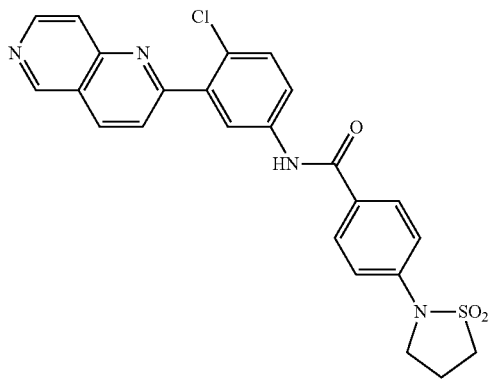 [SMILES: O=C(Nc1ccc(Cl)c(-c2ccc3cnccc3n2)c1)c1ccc(N2CCCS2(=O)=O)cc1]

To a solution of 4-(1,1-dioxidoisothiazolindin-2-yl)benzoic acid (0.076 g, 0.31 mmol) in tetrahydrofuran (2.5 mL) was added thionyl chloride (0.28 mL, 3.93 mmol) and stirred under argon for 24 hours. The solvent was removed and toluene (2 mL) was added then removed again under vacuum. A solution of 4-chloro-3-(1,6-naphthyridin-2-yl) aniline (0.050 g, 0.20 mmol) in pyridine (2 mL) was added under ice-bath and stirred for 10 min. The mixture was then allowed to equilibrate to room temperature and continued to stir for 30 min then quenched with sat. NaHCO$_3$. Extracted with ethyl acetate (4 mL) and washed with sat. NaHCO$_3$. The combined organic extracts were dried over anhydrous Na$_2$SO$_4$ and concentrated. To the crude oil was added dichloromethane (8 mL) and sonicated, then the precipitated solid was collected by filtration to give the desired product (0.032 g, 34%) as a beige solid. $^1$H-NMR (400 MHz, d$_6$-DMSO): δ 10.42 (s, 1H), 9.47 (s, 1H), 8.78 (d, 1H, J=5.6 Hz), 8.68 (d, 1H, J=8.4 Hz), 8.14 (dd, 1H, J=2.4, 0.8 Hz), 7.98 (m, 5H), 7.61 (dd, 1H, J=8.8, 0.8 Hz), 7.28 (m, 2H), 3.81 (m, 2H), 3.56 (m, 2H), 2.42 (m, 2H). MS (ESI): Calcd. for C$_{24}$H$_{20}$ClN$_4$O$_3$S: 458 (M+H). found: 458.

Example 91

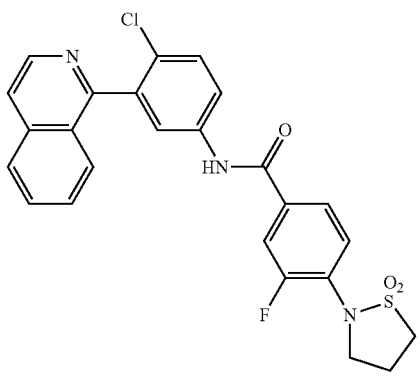 [SMILES: O=C(Nc1ccc(Cl)c(-c2nccc3ccccc23)c1)c1ccc(N2CCCS2(=O)=O)c(F)c1]

A solution of 4-(1,1-dioxidoisothiazolidin-2-yl)-3-fluorobenzoic acid (89 mg, 0.33 mmol), DIEA (115 μL, 2 eq) and HATU (160 mg, 1.2 eq) in 2.5 mL of anhydrous DMF was charged with a solution of 4-chloro-3-(1,6-naphthyridin-5-yl)aniline (82 mg, 1 eq) in 0.5 mL of anhydrous DMF at room temperature. The reaction mixture was stirred at room temperature for 24 hrs and TLC indicated the completion of the reaction. Ethyl acetate (25 mL) and saturated aqueous sodium bicarbonate (10 mL) were added to partition the mixture. The mixture was filtered and the filtrate was transferred to a separatory funnel. The organic phase was washed with additional 10 mL of brine and dried over anhydrous sodium sulfate. After filtration, the solution was concentrated on rotavapor to dryness. The crude product was charged with 1 mL of chilled methylene chloride. Hexanes was added dropwise to the solution until cloudy suspension started to form. Two drops of methylene chloride was added back to achieve a clear solution. The resulting solution stood still at room temperature for several hours. The solid recrystallized from the mother liquid was collected and washed quickly with cold methylene chloride and further dried in vacuo. The desired product was obtained as a brownish powder (38 mg, 23.2%). $^1$H NMR (400 MHz) δ (ppm): 10.51 (dd, J=2.6, 3.8 Hz, 1H), 8.61 (d, J=6.0 Hz, 1H), 8.08 (s, 1H), 7.95-7.58 (m, 10H), 3.85 (d, J=6.4 Hz, 2H), 3.46 (d, J=6.0 Hz, 2H), 2.50 (t, J=2.0 Hz, 2H). ESI-MS: calcd for C25H20ClFN3O3S (M+H): 496. found: 496.

Example 92

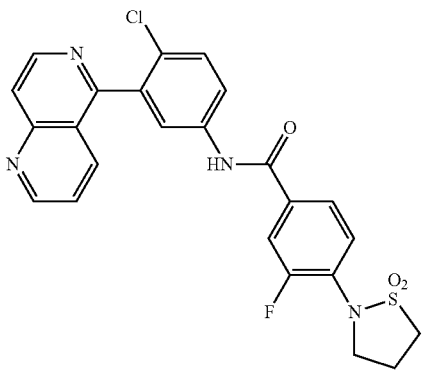 [SMILES: O=C(Nc1ccc(Cl)c(-c2nccc3ncccc23)c1)c1ccc(N2CCCS2(=O)=O)c(F)c1]

A solution of 4-(1,1-dioxidoisothiazolidin-2-yl)-3-fluorobenzoic acid (89 mg, 0.33 mmol), DIEA (115 uL, 2 eq) and HATU (160 mg, 1.2 eq) in 2.5 mL of anhydrous DMF was charged with a solution of 4-chloro-3-(1,6-naphthyridin-5-yl)aniline (83 mg, 1 eq) in 0.5 mL of anhydrous DMF at room temperature. The reaction mixture was stirred at room temperature for 24 hrs and TLC indicated the completion of the reaction. Ethyl acetate (25 mL) and saturated aqueous sodium bicarbonate (10 mL) were added to partition the mixture. The mixture was filtered and the filtrate was transferred to a separatory funnel. The organic phase was washed with additional 10 mL of brine and dried over anhydrous sodium sulfate. After filtration, the solution was concentrated on rotavapor to dryness. The crude product was charged with 1 mL of chilled methylene chloride. Hexanes was added dropwise to the solution until cloudy suspension started to form. Two drops of methylene chloride was added back to achieve a clear solution. The resulting solution stood still at room temperature for several hours. The solid recrystallized from the mother liquid was collected and washed quickly with cold methylene chloride and further dried in vacuo. The desired product was obtained as a brownish powder (42 mg, 25.6%). $^1$H NMR (400 MHz) δ (ppm): 10.53 (s, 1H), 9.16 (t, J=2.2 Hz, 1H), 8.84 (d, J=6.0 Hz, 1H), 8.02-7.54 (m, 10H), 3.84 (t, J=6.4 Hz, 2H), 3.45 (t, J=6.4 Hz, 2H), 2.49-2.44 (m, 2H). ESI-MS: calcd for $C_{24}H_{19}ClFN_4O_3S$ (M+H): 497. found: 497.

Example 93

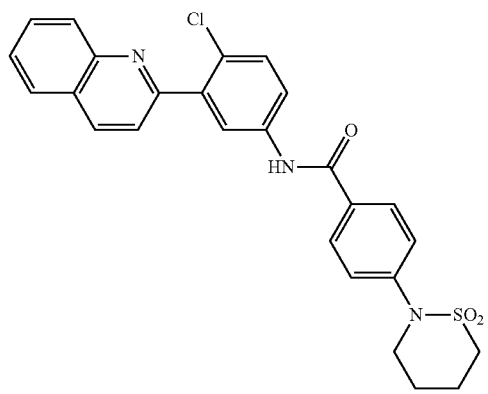

To a solution of 4-(1,1-dioxo-1lamba"6"-[1,2]thiazina-2-yl)benzoic acid (0.060 g, 0.31 mmol) in tetrahydrofuran (2.5 mL) was added thionyl chloride (0.28 mL, 3.93 mmol) and stirred under argon for 24 hours. The solvent was removed and toluene (2 mL) was added then removed again under vacuum. A solution of 4-chloro-3-(quinolin-2-yl)aniline (0.050 g, 0.20 mmol) in pyridine (2 mL) was added under ice-bath and stirred for 10 min. The mixture was then allowed to equilibrate to room temperature and continued to stir for 30 min then quenched with sat. NaHCO$_3$. Extracted with ethyl acetate (4 mL) and washed with sat. NaHCO$_3$. The combined organic extracts were dried over anhydrous Na$_2$SO$_4$ and concentrated. To the crude oil was added dichloromethane (8 mL) and sonicated, then the precipitated solid was collected by filtration to give the desired product (0.07 g, 73%) as an off-white solid. $^1$H-NMR (400 MHz, d$_6$-DMSO): δ 10.51 (s, 1H), 8.47 (d, 1H, J=8.4 Hz), 8.12 (d, 1H, J=2.4 Hz), 8.06 (m, 2H), 7.97 (m, 3H), 7.81 (m, 2H), 7.66 (m, 1H), 7.59 (d, 1H, J=8.8 Hz), 7.44 (m, 2H), 3.73 (m, 2H), 3.31 (m, 2H), 2.16 (m, 2H), 1.81 (m, 2H). MS (ESI): Calcd. for $C_{26}H_{22}ClN_3O_3S$: 492. found: 493 (M+H).

Example 94

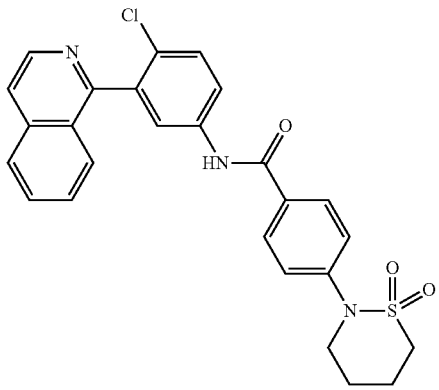

This product was prepared according to the 'General Procedure for Parallel Synthesis—Amide Couplings I' with 4-(1,1-dioxido-1,2-thiazinan-2-yl)benzoic acid (63 mg, 0.25 mmol). The reaction mixture was amber colored and homogeneous. Purification via silica chromatography (eluent: CH$_2$Cl$_2$/methanol gradient) afforded product as a clear resin (101 mg, ca. 100%). $^1$H-NMR (400 MHz, d$_6$-DMSO): δ 10.49 (s, 1H), 8.62 (d, J=5.6 Hz, 1H), 8.09 (d, J=8.4 Hz, 1H), 8.00-7.94 (m, 4H), 7.84-7.80 (m, 1H), 7.67-7.44 (m, 5H), 3.74 (t, J=5.6 Hz, 2H), 3.34-3.31 (m, 2H, masked), 2.18-2.15 (m, 2H), 1.84-1.81 (m, 2H); LC-MS (ESI): calculated for $C_{26}H_{22}ClN_3O_3S$: 491. found: 492 (M+H).

Example 95

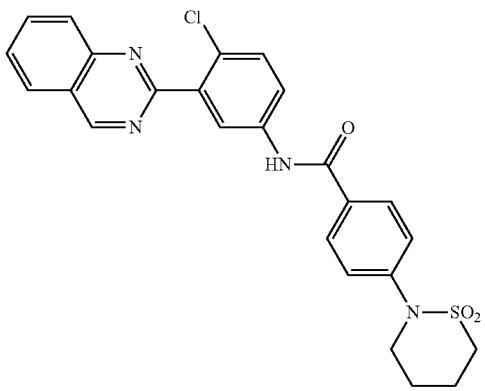 [SMILES: O=C(Nc1ccc(Cl)c(-c2ccc3ccccc3n2)c1)c1ccc(N2CCCCS2(=O)=O)cc1]

To a solution of 4-(1,1-dioxo-1lamba"6"-[1,2]thiazina-2-yl)benzoic acid (0.06 g, 0.31 mmol) in tetrahydrofuran (2.5 mL) was added thionyl chloride (0.28 mL, 3.93 mmol) and stirred under argon for 24 hours. The solvent was removed and toluene (2 mL) was added then removed again under vacuum. A solution of 4-chloro-3-(quinazolin-2-yl)aniline (0.05 g, 0.2 mmol) in pyridine (2 mL) was added at 0° C. and stirred for 10 min. The mixture was then allowed to equilibrate to room temperature and continued to stir for 30 min then quenched with sat. NaHCO3. Extracted with ethyl acetate (4 mL) and washed with sat. NaHCO3. The combined organic extracts were dried over anhydrous Na2SO4 and concentrated. To the crude oil was added dichloromethane (8 mL) and sonicated, then the precipitated solid was collected by filtration to give the desired product (89 mg, 92%) as an off-white solid. 1H-NMR (400 MHz, d6-DMSO): δ 10.52 (s, 1H), 9.75 (s, 1H), 8.30 (d, 1H, J=2.4 Hz), 8.23 (dd, 1H, J=8.4, 0.8 Hz), 8.08 (m, 2H), 7.96 (m, 3H), 7.82 (m, 1H), 7.59 (d, 1H, J=8.8 Hz), 7.44 (m, 2H), 3.73 (m, 2H), 3.32 (m, 2H), 2.15 (m, 2H), 1.81 (m, 2H). MS (ESI): Calcd. for $C_{25}H_{23}ClN_4O_3S$: 493. found: 494 (M+H).

Example 96

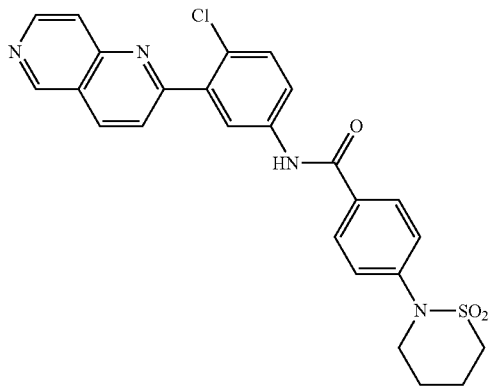 [SMILES: O=C(Nc1ccc(Cl)c(-c2ccc3cnccc3n2)c1)c1ccc(N2CCCCS2(=O)=O)cc1]

To a solution of 4-(1,1-dioxo-1lamba"6"-[1,2]thiazina-2-yl)benzoic acid (0.060 g, 0.31 mmol) in tetrahydrofuran (2.5 mL) was added thionyl chloride (0.28 mL, 3.93 mmol) and stirred under argon for 24 hrs. The solvent was removed and toluene (2 mL) was added then removed again under vacuum. A solution of 4-chloro-3-(1,6-naphthyridin-2-yl)aniline (0.050 g, 0.2 mmol) in pyridine (2 mL) was added under ice-bath and stirred for 10 min. The mixture was then allowed to equilibrate to room temperature and continued to stir for 30 min. Extracted with ethyl acetate (4 mL) and washed with sat. NaHCO3. The combined organic extracts were dried over anhydrous Na2SO4 and concentrated. To the crude oil was added dichloromethane (8 mL) and sonicated, then the precipitated solid was collected by filtration to give the desired product (0.046 g, 48%) as a beige solid. 1H-NMR (400 MHz, d6-DMSO): δ 10.53 (s, 1H), 9.47 (s, 1H), 8.78 (d, 1H, J=6.4 Hz), 8.68 (d, 1H, J=8.8 Hz), 8.15 (d, 1H, J=2.4 Hz), 7.98 (m, 5H), 7.62 (d, 1H, J=8.8 Hz), 7.44 (d, 1H, J=8.0 Hz), 3.73 (m, 2H), 3.31 (m, 2H), 2.15 (m, 2H), 1.81 (m, 2H). MS (ESI): Calcd. for $C_{25}H_{23}ClN_4O_3S$: 493. found: 494 (M+H).

Example 97

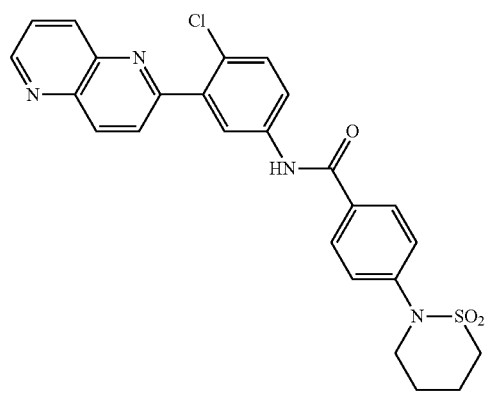

To a solution of 4-(1,1-dioxo-1lamba"6"-[1,2]thiazina-2-yl)benzoic acid (0.060 g, 0.31 mmol) in tetrahydrofuran (2.5 mL) was added thionyl chloride (0.28 mL, 3.93 mmol) and stirred under argon for 24 hrs. The solvent was removed and toluene (2 mL) was added then removed again under vacuum. A solution of 4-chloro-3-(1,5-naphthyridin-2-yl)aniline (0.050 g, 0.20 mmol) in pyridine (2 mL) was added under ice-bath and stirred for 10 min. The mixture was then allowed to equilibrate to room temperature and continued to stir for 30 min. Extracted with ethyl acetate (4 mL) and washed with sat. NaHCO3. The combined organic extracts were dried over anhydrous Na2SO4 and concentrated. To the crude oil was added dichloromethane (8 mL) and sonicated, then the precipitated solid was collected by filtration to give the desired product (0.058 g, 59%) as a beige solid. 1H-NMR (400 MHz, d6-DMSO): δ 10.52 (s, 1H), 9.05 (m, 1H), 8.53 (d, 1H, J=8.8 Hz), 8.48 (m, 1H), 8.16 (d, 1H, J=2.4 Hz), 8.05 (d, 1H, J=8.8 Hz), 7.97 (m, 3H), 7.84 (dd, 1H, J=8.8, 4.4 Hz), 7.61 (d, 1H, J=8.8 Hz), 7.44 (m, 2H), 3.73 (m, 2H), 3.31 (m, 2H), 2.15 (m, 2H), 1.81 (m, 2H). MS (ESI): Calcd. for $C_{25}H_{23}ClN_4O_3S$: 493. found: 494 (M+H).

Example 98

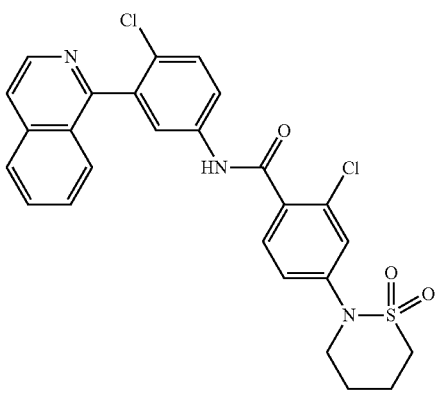 [SMILES: O=C(Nc1ccc(Cl)c(-c2nccc3ccccc23)c1)c1ccc(N2CCCCS2(=O)=O)cc1Cl]

This product was prepared according to the 'General Procedure for Parallel Synthesis—Amide Couplings I' with 2-chloro-4-(1,1-dioxido-1,2-thiazinan-2-yl)benzoic acid (71 mg, 0.25 mmol). The reaction mixture was amber colored and homogeneous. Purification via silica chromatography afforded product as a clear, glassy solid (132 mg, >100%). $^1$H-NMR (400 MHz, d$_6$-DMSO): δ 10.83 (s, 1H), 8.61 (d, J=5.7 Hz, 1H), 8.09 (d, J=8.2 Hz, 1H), 7.95-7.80 (m, 5H), 7.67-7.56 (m, 4H), 7.49-7.35 (m, 3H), 3.83-3.71 (m, 2H), 3.36-3.33 (m, 2H), 2.19-2.13 (m, 2H), 1.85-1.80 (m, 2H). LC-MS (ESI): calculated for C26H21Cl2N3O3S: 525. found: 527 (M+H).

Example 99

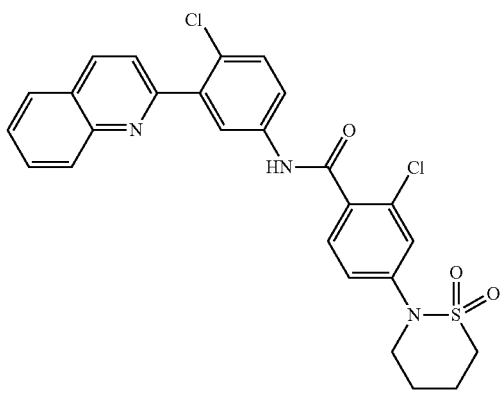 [SMILES: O=C(Nc1ccc(Cl)c(-c2ccc3ccccc3n2)c1)c1ccc(N2CCCCS2(=O)=O)cc1Cl]

This product was prepared according to the 'General Procedure for Parallel Synthesis—Amide Couplings II' with 2-chloro-4-(1,1-dioxido-1,2-thiazinan-2-yl)benzoic acid (49 mg, 0.17 mmol) and 4-chloro-3-(quinolin-2-yl)aniline (50 mg, 0.20 mmol). The reaction mixture was brown colored and heterogeneous. After the first day of stirring at r.t. about 90% conversion was observed by LC-MS. Purification via silica chromatography (eluent: CH$_2$Cl$_2$/methanol gradient) to yield product as a clear resin (17 mg, 19%). $^1$H-NMR (400 MHz, d$_6$-DMSO): δ 10.81 (s, 1H), 8.47 (d, J=8.0 Hz, 1H), 8.08-8.04 (m, 2H), 7.83-7.77 (m 2H), 7.83-7.59 (m, 6H), 7.48-7.38 (m, 2H), 3.71 (t, J=6.0 Hz, 2H), 3.34 (t, J=5.6 Hz, 2H), 2.16-2.13 (m 2H), 1.82-1.80 (m, 2H); LC-MS (ESI): calculated for C26H21Cl2N3O3S: 525.1. found: 526.1 (M+H).

Example 100

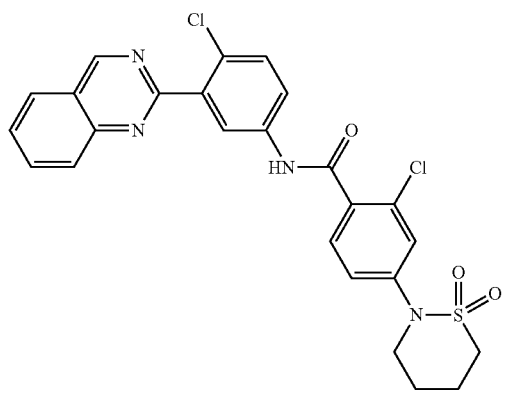 [SMILES: O=C(Nc1ccc(Cl)c(-c2ncc3ccccc3n2)c1)c1ccc(N2CCCCS2(=O)=O)cc1Cl]

This product was prepared according to the 'General Procedure for Parallel Synthesis—Amide Couplings II' with 2-chloro-4-(1,1-dioxido-1,2-thiazinan-2-yl)benzoic acid (49 mg, 0.17 mmol) and 4-chloro-3-(quinazolin-2-yl)aniline (51 mg, 0.20 mmol). The reaction mixture was brown colored and heterogeneous. After the first day of stirring at r.t. about 85% conversion was observed by LC-MS. Purification via silica chromatography (eluent: CH$_2$Cl$_2$/methanol gradient) to yield product as an oil, yellow resin (17 mg, 19%); $^1$H-NMR (400 MHz, d$_6$-DMSO): δ 10.84 (s, 1H), 9.77 (s, 1H), 8.28-8.09 (m, 2H), 8.10-8.09 (m, 2H), 7.86-7.81 (m, 2H), 7.66-7.40 (m, 4H), 3.73 (t, J=5.6 Hz, 2H), 3.37-3.34 (m, 2H), 2.18-2.15 (m, 2H), 1.84-1.82 (m, 2H); LC-MS (ESI): calculated for C25H20Cl2N4O3S: 526.1. found: 527.1 (M+H).

Example 101

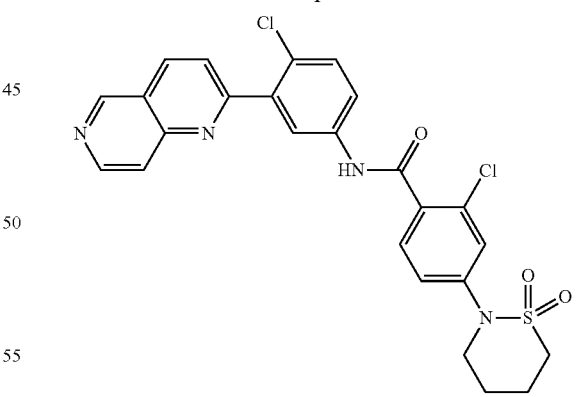

This product was prepared according to the 'General Procedure for Parallel Synthesis—Acid Chloride Couplings I' with an acid chloride stock solution prepared using 2-chloro-4-(1,1-dioxido-1,2-thiazinan-2-yl)benzoic acid (200 mg, 0.69 mmol) and thionyl chloride (1.01 mL; 0.14 mmol). A portion of the acid chloride suspension (2.0 mL of a 8.5 mL suspension; ca. 0.16 mmol acid chloride per portion) was added to 4-chloro-3-(1,6-naphthyridin-2-yl) aniline (26 mg, 0.10 mmol), and after 1 h the reaction was extracted and concentrated as described in the General Procedure. The mixture was further purified by chromatography (eluent: CH$_2$Cl$_2$/methanol gradient) and then product was crystallized out of cold dichloromethane as a yellow solid (19 mg, 35%). $^1$H-NMR (400 MHz, d$_6$-DMSO): δ 10.86 (s, 1H), 9.49 (s, 1H), 8.80 (d, J=5.6 Hz, 1H), 8.70 (d, J=8.8 Hz, 1H), 8.13 (d, J=2.8 Hz, 1H), 7.99-7.83 (m, 3H), 7.65-7.40 (m, 4H), 3.70 (t, J=5.6 Hz, 2H), 3.35 (t, J=6.0 Hz, 2H), 2.20-2.14 (m, 2H), 1.86-1.80 (m, 2H); LC-MS (ESI): calculated for C25H20Cl2N4O3S: 526.1. found: 527.1 (M+H).

Example 102

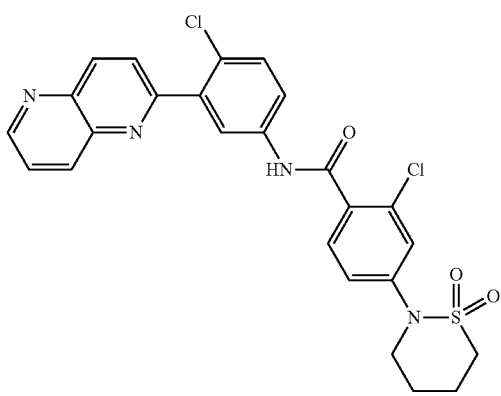 [SMILES: O=C(Nc1ccc(Cl)c(-c2ccc3ncccc3n2)c1)c1ccc(N2CCCCS2(=O)=O)cc1Cl]

This product was prepared according to the 'General Procedure for Parallel Synthesis—Acid Chloride Couplings I' with an acid chloride stock solution prepared using 2-chloro-4-(1,1-dioxido-1,2-thiazinan-2-yl)benzoic acid (200 mg, 0.69 mmol) and thionyl chloride (1.01 mL; 0.14 mmol). A portion of the acid chloride suspension (2.0 mL of a 8.5 mL suspension; ca. 0.16 mmol acid chloride per portion) was added to 4-chloro-3-(1,5-naphthyridin-2-yl)aniline (24 mg, 0.09 mmol), and after 1 h the reaction was extracted and concentrated as described in the General Procedure. The mixture was further purified by chromatography (eluent: CH$_2$Cl$_2$/methanol gradient) affording the product as a yellow residue (31 mg, 62%). $^1$H-NMR (400 MHz, d$_6$-DMSO): δ 10.85 (s, 1H), 9.07 (dd, J=1.6, 4.0 Hz, 1H), 8.56-8.49 (m, 2H), 8.14 (d, J=2.4 Hz, 1H), 8.06 (d, J=8.8 Hz, 1H), 7.87-7.40 (m, 6H), 3.73 (t, J=5.2 Hz, 2H), 3.36 (t, J=5.2 Hz, 2H), 2.18-2.15 (m, 2H), 1.84-1.81 (m, 2H); LC-MS (ESI): calculated for C25H20Cl2N4O3S: 526.1. found: 527.1 (M+H).

Example 103

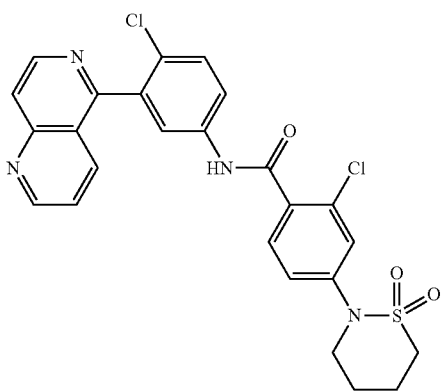 [SMILES: O=C(Nc1ccc(Cl)c(-c2nccc3ncccc23)c1)c1ccc(N2CCCCS2(=O)=O)cc1Cl]

This product was prepared according to the 'General Procedure for Parallel Synthesis—Acid Chloride Couplings I' with an acid chloride stock solution prepared using 2-chloro-4-(1,1-dioxido-1,2-thiazinan-2-yl)benzoic acid (200 mg, 0.690 mmol) and thionyl chloride (1.01 mL; 0.14 mmol). A portion of the acid chloride suspension (2.0 mL of a 8.5 mL suspension; ca. 0.16 mmol acid chloride per portion) was added to 4-chloro-3-(1,6-naphthyridin-5-yl)aniline (26 mg, 0.10 mmol), and after 1 h the reaction was extracted and concentrated as described in the General Procedure. The mixture was further purified by chromatography (eluent: CH$_2$Cl$_2$/methanol gradient) affording the product as a yellow solid (38 mg, 71%). $^1$H-NMR (400 MHz, d$_6$-DMSO): δ 10.86 (s, 1H), 9.18-9.17 (m, 1H), 8.85 (d, J=6.0 Hz, 1H), 8.03-7.85 (m, 4H), 7.70-7.64 (m, 3H), 7.49 (d, J=2.0 Hz, 1H), 7.42-7.39 (m, 1H), 3.72 (t, J=5.6 Hz, 2H), 3.35 (t, J=6.0 Hz, 2H), 2.19-2.13 (m, 2H), 1.85-1.79 (m, 2H). LC-MS (ESI): calculated for C25H20Cl2N4O3S: 526.1. found: 527.1 (M+H).

Example 104

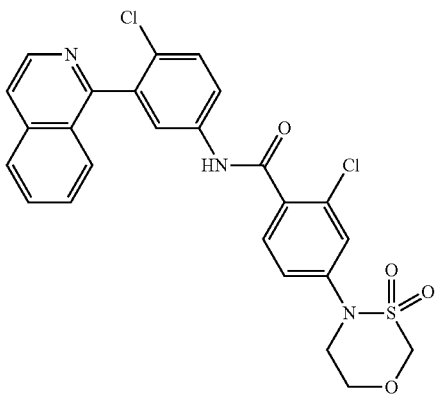 [SMILES: O=C(Nc1ccc(Cl)c(-c2nccc3ccccc23)c1)c1ccc(N2CCOCS2(=O)=O)cc1Cl]

A mixture of 2-chloro-4-(3,3-dioxido-1,3,4-oxathiazinan-4-yl)benzoic acid (64 mg, 0.22 mmol), 4-chloro-3-(isoquinolin-1-yl)aniline (47 mg, 0.18 mmol), HATU (103 mg, 0.27 mmol), and DIEA (130 μL, 1.36 mmol) in DMF (ca. 3 mL) was stirred at r.t. for ca. 15 hrs. Then the mixture was partitioned between ethyl acetate and sat. aq. sodium bicarbonate, and the organic layer was collected and dried (sodium sulfate) and further purified by silica chromatography (eluent: methanol in dichloromethane), and further purified by crystallization out of 1:1 hexanes/dichloromethane to afford the product 2-chloro-N-(4-chloro-3-(isoquinolin-1-yl)phenyl)-4-(3,3-dioxido-1,3,4-oxathiazinan-4-yl) benzamide (8.1 mg, yield: 9%) as a white solid. $^1$H-NMR (400 MHz, d$_6$-DMSO): δ 10.84 (s, 1H), 8.61 (d, J=5.6 Hz, 1H), 8.09 (d, J=8.0 Hz, 1H), 7.94 (d, J=5.6 Hz, 1H), 7.90 (d, J=2.4 Hz, 1H), 7.87-7.80 (m, 3H), 7.68-7.57 (m, 4H), 7.54 (d, J=2.0 Hz, 1H), 7.45-7.42 (m, 1H), 5.03 (s, 2H), 4.09-4.06 (m, 2H), 3.94-3.92 (m, 2H); MS (ESI): Calcd. for C25H19Cl2N3O4S: 527. found: 528 (M+H).

Example 105

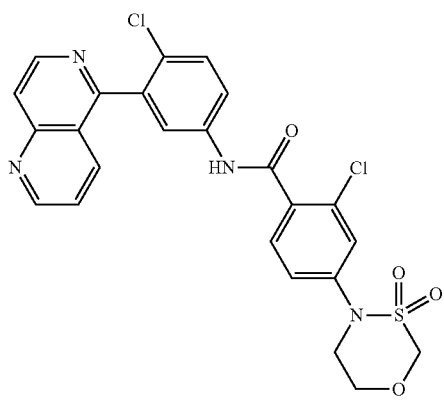 [SMILES: O=C(Nc1ccc(Cl)c(-c2nccc3ncccc23)c1)c1ccc(N2CCOCS2(=O)=O)cc1Cl]

A mixture of 2-chloro-4-(3,3-dioxido-1,3,4-oxathiazinan-4-yl)benzoic acid (34 mg, 0.12 mmol), 4-chloro-3-(1,6-naphthyridin-5-yl)aniline (25 mg, 0.10 mmol), HATU (55 mg, 0.14 mmol), and DIEA (70 μL, 0.40 mmol) in DMF (ca. 3 mL) was stirred at r.t. for ca. 15 h. Then the mixture was partitioned between ethyl acetate and sat. aq. sodium bicarbonate, whereupon product crystallized out to 2-chloro-N-(4-chloro-3-(1,6-naphthyridin-5-yl)phenyl)-4-(3,3-dioxido-1,3,4-oxathiazinan-4-yl)benzamide (7.5 mg, yield: 15%) as an off-white solid. $^1$H-NMR (400 MHz, d$_6$-DMSO): δ 10.91 (s, 1H), 9.18-9.17 (m, 1H), 8.85 (d, J=5.6 Hz, 1H), 8.04-8.00 (m, 2H), 7.95 (d, J=2.4 Hz, 1H), 7.88-7.85 (m, 1H), 7.70-7.66 (m, 3H), 7.55 (d, J=2.0 Hz, 1H), 7.45-7.42 (m, 1H), 5.04 (s, 2H), 4.09-4.06 (m, 2H), 3.95-3.92 (m, 2H); MS (ESI): Calcd. for C24H18Cl2N4O4S: 528. found: 529 (M+H).

Example 106

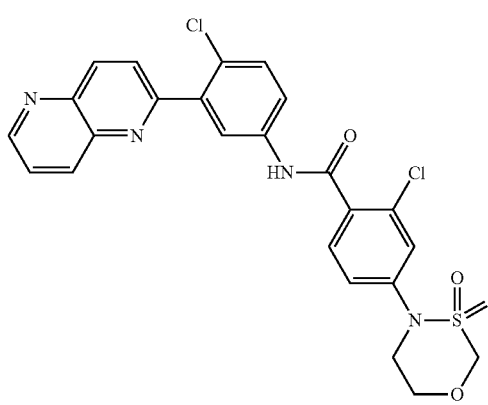

A mixture of 2-chloro-4-(3,3-dioxido-1,3,4-oxathiazinan-4-yl)benzoic acid (40 mg, 0.14 mmol), 4-chloro-3-(1,5-naphthyridin-2-yl)aniline (32 mg, 0.13 mmol), HATU (71 mg, 0.19 mmol), and DIEA (87 μL, 0.50 mmol) in DMF (2.0 mL) was stirred at room temperature for ca. 15 h. EtOAc was added and the mixture was washed with aq NaHCO$_3$ solution and 2M aq HCl, respectively. The organic layer was concentrated under reduced pressure and the resulting residue was purified by flash column chromatography on silica gel (DCM/MeOH) to yield the desired compound 2-chloro-N-(4-chloro-3-(1,5-naphthyridin-2-yl)phenyl)-4-(3,3-dioxido-1,3,4-oxathiazinan-4-yl)benzamide (20 mg, 30%) as an orange solid. $^1$H-NMR (400 MHz, d$_6$-DMSO): δ 10.80 (s, 1H), 9.02-9.01 (m, 1H), 8.50-8.45 (m, 2H), 8.08 (d, J=2.4 Hz, 1H), 8.01 (d, J=8.8 Hz, 1H), 7.82-7.75 (m, 2H), 7.62-7.56 (m, 2H), 7.48 (d, J=2.0 Hz, 1H), 7.39-7.37 (m, 1H), 4.97 (s, 2H), 4.03-4.00 (m, 2H), 3.89-3.87 (m, 2H); MS (ESI): Calcd. for C24H18Cl2N4O4S: 528. found: 529 (M+H).

Example 107

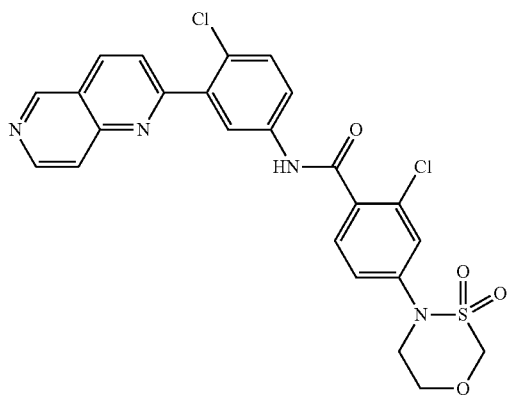 [SMILES: O=C(Nc1ccc(Cl)c(-c2ccc3cnccc3n2)c1)c1ccc(N2CCOCS2(=O)=O)cc1Cl]

A mixture of 2-chloro-4-(3,3-dioxido-1,3,4-oxathiazinan-4-yl)benzoic acid (40 mg, 0.14 mmol), 4-chloro-3-(1,6-naphthyridin-2-yl)aniline (32 mg, 0.13 mmol), HATU (71 mg, 0.19 mmol), and DIEA (87 μL, 0.50 mmol) in DMF (2.0 mL) was stirred at room temperature for ca. 15 h. EtOAc was added and the mixture was washed with aq NaHCO$_3$ solution and 2M aq HCl solution, respectively. The organic layer was concentrated under reduced pressure and the resulting residue was purified by flash column chromatography on silica gel (DCM/MeOH) to yield the desired compound 2-chloro-N-(4-chloro-3-(1,6-naphthyridin-2-yl)phenyl)-4-(3,3-dioxido-1,3,4-oxathiazinan-4-yl)benzamide (20 mg, 31%) as an off-white solid. $^1$H-NMR (400 MHz, d$_6$-DMSO): δ 10.87 (s, 1H), 9.49 (d, J=0.8 Hz, 1H), 8.80 (d, J=6.0 Hz, 1H), 8.72-8.69 (m, 1H), 8.12 (d, J=2.4 Hz, 1H), 7.99-7.97 (m, 2H), 7.86-7.83 (m, 1H), 7.69-7.63 (m, 2H), 7.55 (d, J=2.0 Hz, 1H), 7.46-7.43 (m, 1H), 5.04 (s, 2H), 4.09-4.07 (m, 2H), 3.95-3.93 (m, 2H); MS (ESI): Calcd. for C24H18Cl2N4O4S: 528. found: 529 (M+H).

Example 108

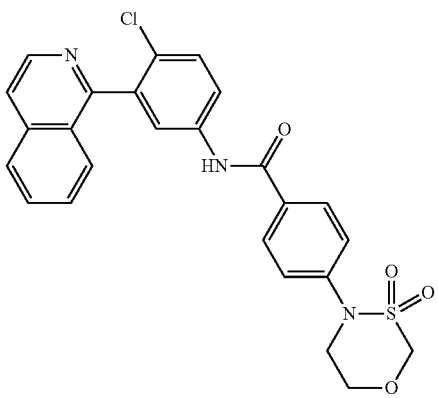 [SMILES: O=C(Nc1ccc(Cl)c(-c2nccc3ccccc23)c1)c1ccc(N2CCOCS2(=O)=O)cc1]

A mixture of 4-(3,3-dioxido-1,3,4-oxathiazinan-4-yl)benzoic acid (51 mg, 0.20 mmol), 4-chloro-3-(isoquinolin-1-yl)aniline (50 mg, 0.20 mmol), HATU (114 mg, 0.30 mmol), and DIEA (140 μL, 0.80 mmol) in DMF (2.0 mL) was stirred at r.t. for ca. 15 h. Then the mixture was partitioned between ethyl acetate and sat. aq. sodium bicarbonate, the organic layer was separated and cooled, whereupon product crystallized out to give N-(4-chloro-3-(isoquinolin-1-yl)phenyl)-4-(3,3-dioxido-1,3,4-oxathiazinan-4-yl)benzamide (38.7 mg, 39%) as an off-white solid. $^1$H-NMR (400 MHz, d$_6$-DMSO): δ 10.54 (s, 1H), 8.62 (d, J=5.6 Hz, 1H), 8.09 (d, J=8.0 Hz, 1H), 8.00-7.94 (m, 5H), 7.84-7.80 (m, 1H), 7.67-7.63 (m, 2H), 7.60-7.58 (m, 2H), 7.50-7.48 (m, 2H), 5.02 (s, 2H), 4.09-4.07 (m, 2H), 3.95-3.93 (m, 2H); MS (ESI): Calcd. for C25H20ClN3O4S: 493. found: 494 (M+H).

Example 109

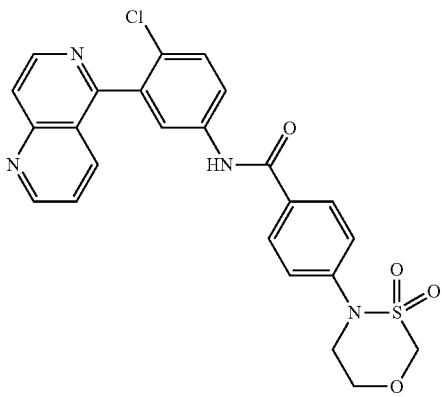 [SMILES: O=C(Nc1ccc(Cl)c(-c2nccc3ncccc23)c1)c1ccc(N2CCOCS2(=O)=O)cc1]

A mixture of 4-(3,3-dioxido-1,3,4-oxathiazinan-4-yl)benzoic acid (31 mg, 0.12 mmol), 4-chloro-3-(1,6-naphthyridin-5-yl)aniline (26 mg, 0.10 mmol), HATU (57 mg, 0.15 mmol), and DIEA (70 μL, 0.40 mmol) in DMF (2.0 mL) was stirred at r.t. for ca. 15 hrs. Then the mixture was partitioned between ethyl acetate and sat. aq. sodium bicarbonate, the organic layer was separated and cooled, whereupon product crystallized out to give N-(4-chloro-3-(1,6-naphthyridin-5-yl)phenyl)-4-(3,3-dioxido-1,3,4-oxathiazinan-4-yl)benzamide (33.3 mg, 34%) as a white solid. $^1$H-NMR (400 MHz, d$_6$-DMSO): δ 10.57 (s, 1H), 9.19-9.17 (m, 1H), 8.86 (d, J=6.0 Hz, 1H), 8.04-7.97 (m, 6H), 7.70-7.66 (m, 2H), 7.49 (d, J=8.8 Hz, 2H), 5.02 (s, 2H), 4.09-4.07 (m, 2H), 3.95-3.93 (m, 2H); MS (ESI): Calcd. for C24H19ClN4O4S: 494. found: 495 (M+H).

Example 110

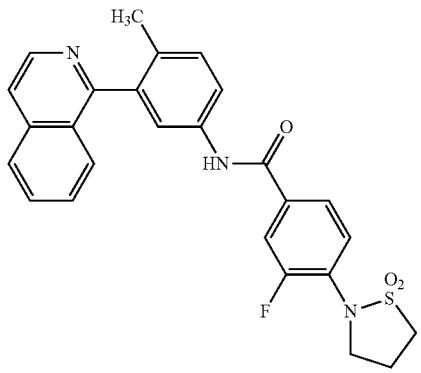 [SMILES: Cc1ccc(NC(=O)c2ccc(N3CCCS3(=O)=O)c(F)c2)cc1-c1nccc2ccccc12]

A solution of 4-(1,1-dioxidoisothiazolidin-2-yl)-3-fluorobenzoic acid (62 mg, 0.23 mmol), DIEA (80 uL, 2 eq) and HATU (105 mg, 1.2 eq) in 2.5 mL of anhydrous DMF was charged with a solution of 3-(isoquinolin-1-yl)-4-methylaniline (54 mg, 1 eq) in 0.5 mL of anhydrous DMF at room temperature. The reaction mixture was stirred at room temperature for 24 hrs and TLC indicated the completion of the reaction. Ethyl acetate (25 mL) and saturated aqueous sodium bicarbonate (10 mL) were added to partition the mixture. The mixture was filtered and the filtrate was transferred to a separatory funnel. The organic phase was washed with additional 10 mL of brine and dried over anhydrous sodium sulfate. After filtration, the solution was concentrated on rotavapor to dryness. The crude product was charged with 1 mL of chilled methylene chloride. Hexanes was added dropwise to the solution until cloudy suspension started to form. Two drops of methylene chloride was added back to achieve a clear solution. The resulting solution stood still at room temperature for several hours. The solid recrystallized from the mother liquid was collected and washed quickly with cold methylene chloride and further dried in vacuo. The desired product was obtained as a yellow powder (65 mg, 68%). $^1$H NMR (400 MHz) δ (ppm): 10.31 (s, 1H), 8.58 (d, J=4.4 Hz, 1H), 8.05 (d, J=8.4 Hz, 1H), 7.93-7.54 (m, 10H), 7.37 (d, J=8.0 Hz, 1H), 3.44 (t, J=6.4 Hz, 2H), 2.72-2.67 (m, 2H), 1.94 (s, 3H). ESI-MS: calcd for C26H23FN3O3S (M+H): 476. found: 476.

Example 111

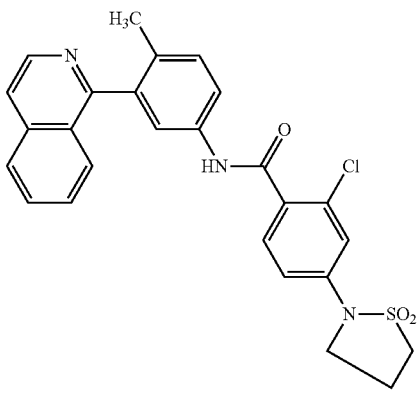 [SMILES: Cc1ccc(NC(=O)c2ccc(N3CCCS3(=O)=O)cc2Cl)cc1-c1nccc2ccccc12]

A solution of 4-(1,1-dioxidoisothiazolidin-2-yl)-3-fluorobenzoic acid (60 mg, 0.22 mmol), DIEA (80 uL, 2 eq) and HATU (100 mg, 1.2 eq) in 2.5 mL of anhydrous DMF was charged with a solution of 3-(isoquinolin-1-yl)-4-methylaniline (52 mg, 1 eq) in 0.5 mL of anhydrous DMF at room temperature. The reaction mixture was stirred at room temperature for 24 hrs and TLC indicated the completion of the reaction. Ethyl acetate (25 mL) and saturated aqueous sodium bicarbonate (10 mL) were added to partition the mixture. The mixture was filtered and the filtrate was transferred to a separatory funnel. The organic phase was washed with additional 10 mL of brine and dried over anhydrous sodium sulfate. After filtration, the solution was concentrated on rotavapor to dryness. The crude product was charged with 1 mL of chilled methylene chloride. Hexanes was added dropwise to the solution until cloudy suspension started to form. Two drops of methylene chloride was added back to achieve a clear solution. The resulting solution stood still at room temperature for several hours. The solid recrys-

Example 112

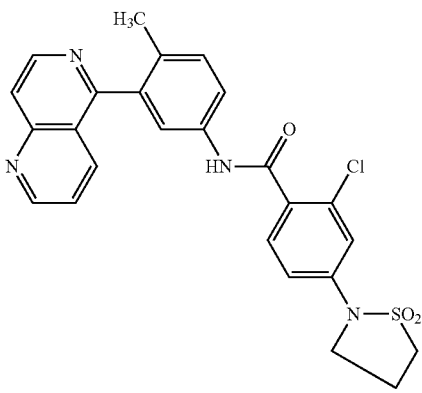 [SMILES: Cc1ccc(NC(=O)c2ccc(N3CCCS3(=O)=O)cc2Cl)cc1-c1nccc2ncccc12]

A solution of 4-(1,1-dioxidoisothiazolidin-2-yl)-3-fluorobenzoic acid (592 mg, 2.15 mmol), DIEA (748 uL, 2 eq) and HATU (981 mg, 1.2 eq) in 10 mL of anhydrous DMF was charged with 4-chloro-3-(1,6-naphthyridin-5-yl)aniline (549 mg, 1 eq) portion-wise at room temperature. The reaction mixture was stirred at room temperature for 36 hrs and TLC indicated the completion of the reaction. Ethyl acetate (60 mL) and saturated aqueous sodium bicarbonate (20 mL) were added to partition the mixture. The mixture was filtered and the filtrate was transferred to a separatory funnel. The organic phase was washed with additional 20 mL of brine and dried over anhydrous sodium sulfate. After filtration, the solution was concentrated on rotavapor to dryness. The crude product was dried on vacuum lines for 20 hrs and charged with 5 mL of chilled methylene chloride. Hexanes was added dropwise to the solution until cloudy suspension started to form. Few drops of methylene chloride was added back to achieve a clear solution. The resulting solution stood still at room temperature for several hours. The solid recrystallized from the mother liquid was collected and washed quickly with cold methylene chloride and further dried in vacuo. The desired product was obtained as a yellow powder (687 mg, 62.4%). The mother liquid containing the desired product was concentrated to dryness and stored at −5° C. $^1$H NMR (400 MHz) δ (ppm): 10.77 (s, 1H), 9.16 (t, J=2.0 Hz, 1H), 8.84 (dd, J=1.4, 6.2 Hz, 1H), 8.02-7.23 (m, 9H), 3.79 (t, J=6.4 Hz, 2H), 3.58 (t, J=6.4 Hz, 2H), 2.41 (t, J=6.4 Hz, 2H); ESI-MS: calcd for C24H19Cl2N4O3S (M+H): 513. found: 513.

Example 113

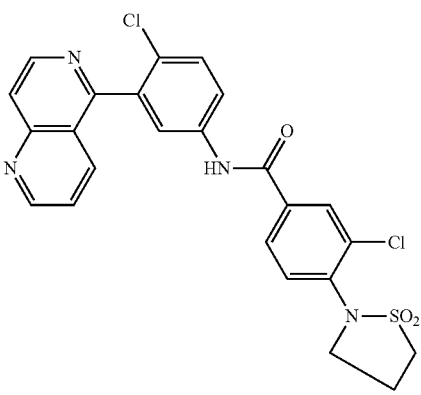 [SMILES: O=C(Nc1ccc(Cl)c(-c2nccc3ncccc23)c1)c1ccc(N2CCCS2(=O)=O)c(Cl)c1]

A solution of 3-chloro-4-(1,1-dioxidoisothiazolidin-2-yl) benzoic acid (94 mg, 0.34 mmol), DIEA (118 uL, 2 eq) and HATU (129 mg, 1.2 eq) in 4 mL of anhydrous DMF was charged with 4-chloro-3-(1,6-naphthyridin-5-yl)aniline (87 mg, 1 eq) portion-wise at room temperature. The reaction mixture was stirred at room temperature for 24 hrs and TLC indicated the completion of the reaction. Ethyl acetate (60 mL) and saturated aqueous sodium bicarbonate (20 mL) were added to partition the mixture. The mixture was filtered and the filtrate was transferred to a separatory funnel. The organic phase was washed with additional 20 mL of brine and dried over anhydrous sodium sulfate. After filtration, the solution was concentrated on rotavapor to dryness. The crude product was dried on vacuum lines for 20 hrs and charged with 5 mL of chilled methylene chloride. Hexanes was added dropwise to the solution until cloudy suspension started to form. Few drops of methylene chloride was added back to achieve a clear solution. The resulting solution stood still at room temperature for several hours. The solid recrystallized from the mother liquid was collected and washed quickly with cold methylene chloride and further dried in vacuo. The desired product was obtained as an off-white powder (48 mg, 27.6%). The mother liquid containing the desired product was concentrated to dryness and stored at −5° C. $^1$H NMR (400 MHz) δ (ppm): 10.62 (d, J=2.4 Hz, 1H), 9.16 (d, J=0.8 Hz, 1H), 8.84 (t, J=2.6 Hz, 1H), 8.13-7.96 (m, 6H), 7.68-7.66 (m, 3H), 3.77-3.74 (m, 2H), 3.43 (d, J=2.8 Hz, 2H), 2.48 (d, J=1.2 Hz, 2H); ESI-MS: calcd for C24H19Cl2N4O3S (M+H): 513. found: 513.

Example 114

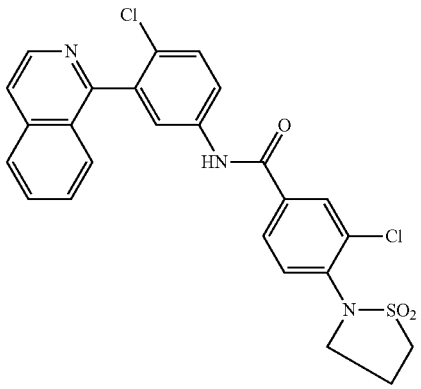 [SMILES: O=C(Nc1ccc(Cl)c(-c2nccc3ccccc23)c1)c1ccc(N2CCCS2(=O)=O)c(Cl)c1]

(Previous example continuation at top of page 353:)
tallized from the mother liquid was collected and washed quickly with cold methylene chloride and further dried in vacuo. The desired product was obtained as a yellow powder (70 mg, 64.8%). $^1$H NMR (400 MHz) δ (ppm): 10.47 (s, 1H), 8.57 (d, J=5.6 Hz, 1H), 8.04 (d, J=8.0 Hz, 1H), 7.88-7.34 (m, 8H), 7.26-7.22 (m, 3H), 3.78 (t, J=6.4 Hz, 2H), 3.56 (t, J=6.4 Hz, 2H), 2.41 (t, J=6.8 Hz, 2H). ESI-MS: calcd for C26H23ClN3O3S (M+H): 492. found: 492.

A solution of 3-chloro-4-(1,1-dioxidoisothiazolidin-2-yl)benzoic acid (74 mg, 0.27 mmol), DIEA (94 uL, 2 eq) and HATU (103 mg, 1.2 eq) in 4 mL of anhydrous DMF was charged with 4-chloro-3-(1,6-naphthyridin-5-yl)aniline (69 mg, 1 eq) portion-wise at room temperature. The reaction mixture was stirred at room temperature for 24 hrs and TLC indicated the completion of the reaction. Ethyl acetate (60 mL) and saturated aqueous sodium bicarbonate (20 mL) were added to partition the mixture. The mixture was filtered and the filtrate was transferred to a separatory funnel. The organic phase was washed with additional 20 mL of brine and dried over anhydrous sodium sulfate. After filtration, the solution was concentrated on rotavapor to dryness. The crude product was dried on vacuum lines for 20 hrs and charged with 5 mL of chilled methylene chloride. Hexanes was added dropwise to the solution until cloudy suspension started to form. Few drops of methylene chloride was added back to achieve a clear solution. The resulting solution stood still at room temperature for several hours. The solid recrystallized from the mother liquid was collected and washed quickly with cold methylene chloride and further dried in vacuo. The desired product was obtained as a yellow powder (31 mg, 22.5%). The mother liquid containing the desired product was concentrated to dryness and stored at −5° C. $^1$H NMR (400 MHz) δ (ppm): 10.59 (s, 1H), 8.59 (d, J=5.6 Hz, 1H), 8.12-7.58 (m, 10H), 3.74 (t, J=6.8 Hz, 2H), 3.42 (t, J=7.2 Hz, 2H), 2.49-2.46 (m, 2H); ESI-MS: calcd for C25H20Cl2N3O3S (M+H): 512. found: 512.

Example 115

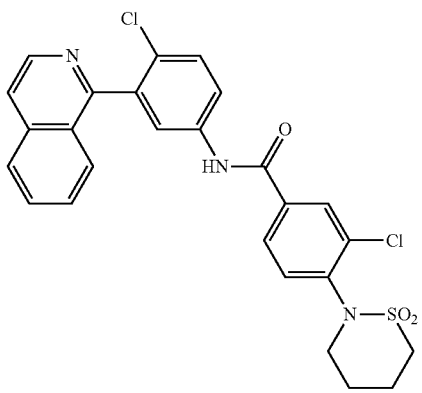 [SMILES: O=C(Nc1ccc(Cl)c(-c2nccc3ccccc23)c1)c1ccc(N2CCCCS2(=O)=O)c(Cl)c1]

A solution of 3-chloro-4-(1,1-dioxido-1,2-thiazinan-2-yl)benzoic acid (68 mg, 0.24 mmol), DIEA (83 uL, 2 eq) and HATU (110 mg, 1.2 eq) in 4 mL of anhydrous DMF was charged with 4-chloro-3-(isoquinolin-1-yl)aniline (62 mg, 1 eq) portion-wise at room temperature. The reaction mixture was stirred at room temperature for 20 hrs and TLC indicated the completion of the reaction. Ethyl acetate (60 mL) and saturated aqueous sodium bicarbonate (20 mL) were added to partition the mixture. The mixture was filtered and the filtrate was transferred to a separatory funnel. The organic phase was washed with additional 20 mL of brine and dried over anhydrous sodium sulfate. After filtration, the solution was concentrated on rotavapor to dryness. The crude product was dried on vacuum lines for 20 hrs and charged with 5 mL of chilled methylene chloride. Hexanes was added dropwise to the solution until cloudy suspension started to form. Few drops of methylene chloride was added back to achieve a clear solution. The resulting solution stood still at room temperature for several hours. The solid recrystallized from the mother liquid was collected and washed quickly with cold methylene chloride and further dried in vacuo. The desired product was obtained as a brownish powder (42 mg, 33.2%). The mother liquid containing the desired product was concentrated to dryness and stored at −5° C. $^1$H NMR (400 MHz) δ (ppm): 10.60 (s, 1H), 8.59 (d, J=5.6 Hz, 1H), 8.11-7.58 (m, 12H), 3.59 (t, J=4.8 Hz, 2H), 2.20 (t, J=4.4 Hz, 2H), 1.80 (t, J=3.2 Hz, 2H); ESI-MS: calcd for Chemical Formula: C26H22Cl2N3O3S (M+H): 526. found: 526.

Example 116

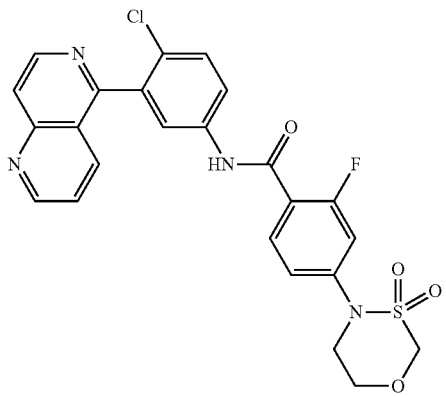

A mixture of 4-(3,3-dioxido-1,3,4-oxathiazinan-4-yl)-2-fluorobenzoic acid (40 mg, 0.15 mmol), 4-chloro-3-(1,6-naphthyridin-5-yl)aniline (31 mg, 0.12 mmol), HATU (78 mg, 0.21 mmol), and DIEA (84 µL, 0.88 mmol) in DMF (1.5 mL) was stirred at room temperature for 24 h. EtOAc was added and the mixture was washed with aq NaHCO$_3$. The organic layer was concentrated under reduced pressure and the resulting residue was purified by flash column chromatography on silica gel (DCM/MeOH) to yield the desired compound N-(4-chloro-3-(1,6-naphthyridin-5-yl)phenyl)-4-(3,3-dioxido-1,3,4-oxathiazinan-4-yl)-2-fluorobenzamide (60 mg, 96%) as a glassy, yellow solid. $^1$H-NMR (400 MHz, d$_6$-DMSO): δ 10.74 (s, 1H), 9.18-9.17 (m, 1H), 8.85 (d, J=6.0 Hz, 1H), 8.04-7.88 (m, 4H), 7.74-7.66 (m, 3H), 7.38-7.30 (m, 2H), 5.03 (s, 2H), 4.09-4.06 (m, 2H), 3.97-3.94 (m, 2H); MS (ESI): Calcd. for C24H18ClFN4O4S: 512. found: 513 (M+H).

Example 117

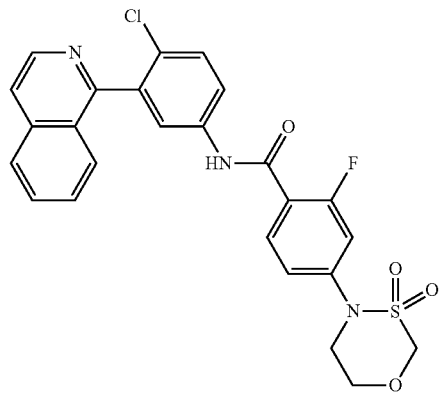

A mixture of 4-(3,3-dioxido-1,3,4-oxathiazinan-4-yl)-2-fluorobenzoic acid (40 mg, 0.15 mmol), 4-chloro-3-(isoquinolin-1-yl)aniline (31 mg, 0.12 mmol), HATU (78 mg, 0.21 mmol), and DIEA (84 μL, 0.88 mmol) in DMF (1.5 mL) was stirred at room temperature for 24 h. EtOAc was added and the mixture was washed with aq NaHCO$_3$ solution and 2M aq HCl, respectively. The organic layer was concentrated under reduced pressure and the resulting residue was purified by flash column chromatography on silica gel (DCM/MeOH) to yield the desired compound N-(4-chloro-3-(isoquinolin-1-yl)phenyl)-4-(3,3-dioxido-1,3,4-oxathiazinan-4-yl)-2-fluorobenzamide (47 mg, 76%) as a glassy, yellow solid. $^1$H-NMR (400 MHz, d$_6$-DMSO): δ 10.71 (s, 1H), 8.61 (d, J=5.6 Hz, 1H), 8.08 (d, J=8.4 Hz, 1H), 7.95-7.80 (m, 4H), 7.74-7.57 (m, 4H), 7.38-7.30 (m, 3H), 5.03 (s, 2H), 4.09-4.06 (m, 2H), 3.96-3.80 (m, 2H); MS (ESI): Calcd. for C25H19ClFN3O4S: 511. found: 512 (M+H).

Example 118

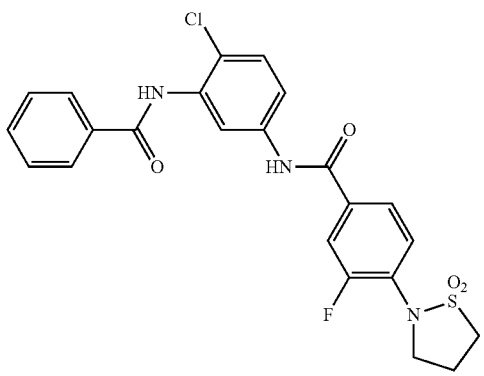 [SMILES: O=C(Nc1ccc(Cl)c(NC(=O)c2ccccc2)c1)c1ccc(N2CCCS2(=O)=O)c(F)c1]

A solution of 4-(1,1-dioxidoisothiazolidin-2-yl)-3-fluorobenzoic acid (48 mg, 0.19 mmol), DIEA (66 uL, 2 eq) and HATU (87 mg, 1.2 eq) in 4 mL of anhydrous DMF was charged with a solution of N-(5-amino-2-chlorophenyl)benzamide (47 mg, 1 eq) in 1 mL of anhydrous DMF at room temperature. The reaction mixture was stirred at room temperature for 20 hrs and TLC indicated the completion of the reaction. Ethyl acetate (40 mL) and saturated aqueous sodium bicarbonate (20 mL) were added to partition the mixture. The mixture was filtered and the filtrate was transferred to a separatory funnel. The organic phase was washed with additional 10 mL of brine and dried over anhydrous sodium sulfate. After filtration, the solution was concentrated on rotavapor to dryness. The crude product was charged with 1 mL of chilled methylene chloride. Hexanes was added dropwise to the solution until cloudy suspension started to form. Two drops of methylene chloride was added back to achieve a clear solution. The resulting solution stood still at room temperature for several hours. The solid recrystallized from the mother liquid was collected and washed quickly with cold methylene chloride and further dried in vacuo. The first-batch desired product was obtained as a yellow powder (49 mg, 52.9%). The mother liquid was stored in a refrigerator. $^1$H NMR (400 MHz) δ (ppm): 10.47 (s, 1H), 10.33 (s, 1H), 9.13 (t, J=1.0 Hz, 1H), 8.76 (d, J=4.8 Hz, 1H), 8.31 (t, J=5.2 Hz, 1H), 8.08 (d, J=1.6 Hz, 1H), 7.91-7.53 (m, 7H), 3.85 (t, J=6.4 Hz, 2H), 3.47-3.44 (m, 2H), 2.45 (t, J=6.4 Hz, 2H). ESI-MS: calcd for C23H20ClFN3O4S (M+H): 488. found: 488.

Example 119

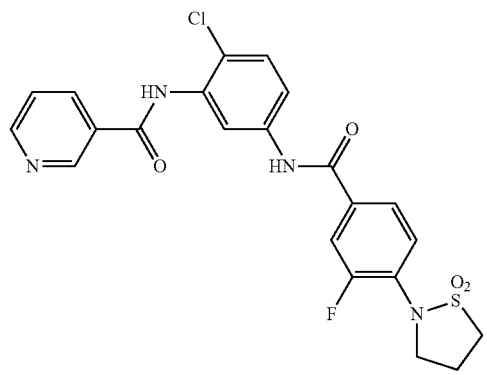 [SMILES: O=C(Nc1ccc(Cl)c(NC(=O)c2cccnc2)c1)c1ccc(N2CCCS2(=O)=O)c(F)c1]

A solution of 4-(1,1-dioxidoisothiazolidin-2-yl)-3-fluorobenzoic acid (53 mg, 0.20 mmol), DIEA (70 uL, 2 eq) and HATU (91 mg, 1.2 eq) in 4 mL of anhydrous DMF was charged with a solution of N-(5-amino-2-chlorophenyl)nicotinamide (50 mg, 1 eq) in 1 mL of anhydrous DMF at room temperature. The reaction mixture was stirred at room temperature for 20 hrs and TLC indicated the completion of the reaction. Ethyl acetate (40 mL) and saturated aqueous sodium bicarbonate (10 mL) were added to partition the mixture. The mixture was filtered and the filtrate was transferred to a separatory funnel. The organic phase was washed with additional 10 mL of brine and dried over anhydrous sodium sulfate. After filtration, the solution was concentrated on rotavapor to dryness. The crude product was charged with 1 mL of chilled methylene chloride. Hexanes was added dropwise to the solution until cloudy suspension started to form. Two drops of methylene chloride was added back to achieve a clear solution. The resulting solution stood still at room temperature for several hours. The solid recrystallized from the mother liquid was collected and washed quickly with cold methylene chloride and further dried in vacuo. The first-batch desired product was obtained as a yellow powder (46 mg, 47.1%). The mother liquid was stored in a refrigerator. $^1$H NMR (400 MHz) δ (ppm): 10.46 (s, 1H), 10.06 (s, 1H), 8.08 (d, J=1.6 Hz, 1H), 7.98 (d, J=8.4 Hz, 1H), 7.86-7.51 (m, 8H), 3.85 (t, J=6.4 Hz, 2H), 3.45 (t, J=7.2 Hz, 2H), 2.48-2.43 (m, 2H). ESI-MS: calcd for C22H19ClFN4O4S (M+H): 489. found: 489.

Example 120

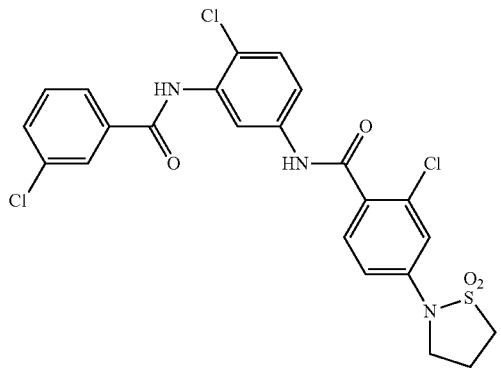 [SMILES: O=C(Nc1cc(NC(=O)c2ccc(N3CCCS3(=O)=O)cc2Cl)ccc1Cl)c1cccc(Cl)c1]

A solution of 2-chloro-4-(1,1-dioxidoisothiazolidin-2-yl)benzoic acid (67 mg, 0.24 mmol), DIEA (84 uL, 2 eq) and HATU (110 mg, 1.2 eq) in 2.5 mL of anhydrous DMF was charged with a solution of N-(5-amino-2-chlorophenyl)-3-chlorobenzamide (68 mg, 1 eq) in 0.5 mL of anhydrous DMF at room temperature. The reaction mixture was stirred at room temperature for 24 hrs and TLC indicated the completion of the reaction. Ethyl acetate (25 mL) and saturated aqueous sodium bicarbonate (10 mL) were added to partition the mixture. The mixture was filtered and the filtrate was transferred to a separatory funnel. The organic phase was washed with additional 10 mL of brine and dried over anhydrous sodium sulfate. After filtration, the solution was concentrated on rotavapor to dryness. The crude product was charged with 1 mL of chilled methylene chloride. Hexanes was added dropwise to the solution until cloudy suspension started to form. Two drops of methylene chloride was added back to achieve a clear solution. The resulting solution stood still at room temperature for several hours. The solid recrystallized from the mother liquid was collected and washed quickly with cold methylene chloride and further dried in vacuo. The desired product was obtained as a yellow powder (61 mg, 47.3%). $^1$H NMR (400 MHz) δ (ppm): 10.65 (s, 1H), 10.25 (s, 1H), 8.01-7.93 (m, 3H), 7.69-7.50 (m, 5H), 7.29-7.24 (m, 2H), 3.80 (t, J=6.4 Hz, 2H), 3.59-3.56 (m, 2H), 2.49-2.44 (m, 2H). ESI-MS: calcd for C23H19Cl3N3O4S (M+H): 538. found: 538.

Example 121

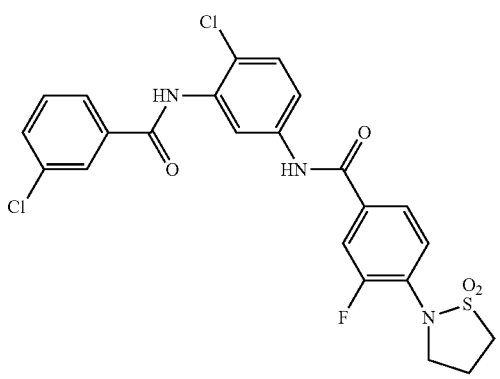

A solution of 4-(1,1-dioxidoisothiazolidin-2-yl)-3-fluorobenzoic acid (62 mg, 0.23 mmol), DIEA (84 uL, 2 eq) and HATU (110 mg, 1.2 eq) in 2.5 mL of anhydrous DMF was charged with a solution of N-(5-amino-2-chlorophenyl)-3-chlorobenzamide (68 mg, 1 eq) in 0.5 mL of anhydrous DMF at room temperature. The reaction mixture was stirred at room temperature for 24 hrs and TLC indicated the completion of the reaction. Ethyl acetate (25 mL) and saturated aqueous sodium bicarbonate (10 mL) were added to partition the mixture. The mixture was filtered and the filtrate was transferred to a separatory funnel. The organic phase was washed with additional 10 mL of brine and dried over anhydrous sodium sulfate. After filtration, the solution was concentrated on rotavapor to dryness. The crude product was purified via silica gel column chromatography (Ethyl acetate in hexanes, 0-50%) to yield the desired product as a light yellow powder (60 mg, 49.9%). $^1$H NMR (400 MHz) δ (ppm): ESI-MS: calcd for C23H19Cl2FN3O4S (M+H): 523. found: 523.

Example 122

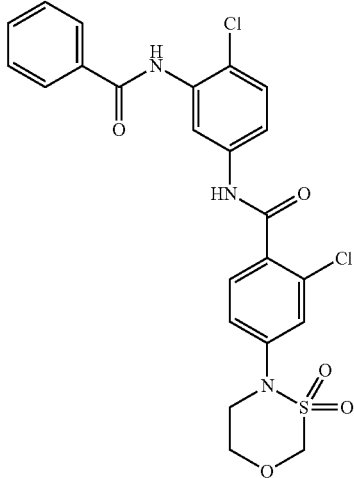 [SMILES: O=C(Nc1cc(NC(=O)c2ccc(N3CCOCS3(=O)=O)cc2Cl)ccc1Cl)c1ccccc1]

A mixture of 2-chloro-4-(3,3-dioxido-1,3,4-oxathiazinan-4-yl)benzoic acid (60 mg, 0.21 mmol), N-(5-amino-2-chlorophenyl)benzamide (42 mg, 0.17 mmol), HATU (65 mg, 0.17 mmol), and DIEA (119 μL, 0.68 mmol) in DMF (1.5 mL) was stirred at room temperature for 17 hrs. EtOAc was added and the mixture was washed with aq NaHCO$_3$. The organic layer was concentrated under reduced pressure and the resulting residue was purified by flash column chromatography on silica gel (DCM/MeOH) and further purified by crystallization out of DCM/hexanes to yield the desired compound N-(3-benzamido-4-chlorophenyl)-2-chloro-4-(3,3-dioxido-1,3,4-oxathiazinan-4-yl)benzamide (30 mg, 34%) as an off-white crystalline solid. $^1$H-NMR (400 MHz, d$_6$-DMSO): δ 10.77 (s, 1H), 10.09 (s, 1H), 8.04-7.98 (m, 3H), 7.68-7.43 (m, 8H), 5.04 (s, 2H), 4.10-4.07 (m, 2H), 3.95-3.93 (m, 2H); MS (ESI): Calcd. for C23H19Cl2N3O5S: 519. found: 542 (M+Na).

Example 123

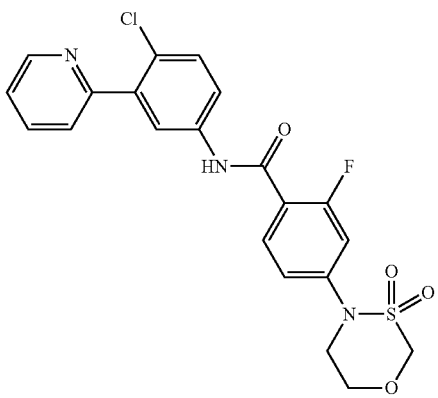 [SMILES: O=C(Nc1ccc(Cl)c(-c2ccccn2)c1)c1ccc(N2CCOCS2(=O)=O)cc1F]

A mixture of 4-(3,3-dioxido-1,3,4-oxathiazinan-4-yl)-2-fluorobenzoic acid (56 mg, 0.21 mmol), 4-chloro-3-(pyridin-2-yl)aniline (35 mg, 0.17 mmol), HATU (110 mg, 0.29 mmol), and DIEA (118 µL, 0.68 mmol) in DMF (1.5 mL) was stirred at room temperature for 24 hrs. EtOAc was added and the mixture was washed with aq NaHCO₃. The organic layer was concentrated under reduced pressure and the resulting residue was purified by flash column chromatography on silica gel (DCM/MeOH) and was further purified by crystallization from hexanes/EtOAc to yield the desired compound N-(4-chloro-3-(pyridin-2-yl)phenyl)-4-(3,3-dioxido-1,3,4-oxathiazinan-4-yl)-2-fluorobenzamide (54 mg, 69%) as an off-white solid. $^1$H-NMR (400 MHz, d₆-DMSO): δ 10.66 (s, 1H), 8.72-8.70 (m, 1H), 8.01 (d, J=2.4 Hz, H), 7.94-7.90 (m, 1H), 7.80-7.68 (m, 2H), 7.56 (d, J=8.8 Hz, 1H), 7.46-7.31 (m, 3H), 5.04 (s, 2H), 4.09-4.07 (m, 2H), 3.97-3.95 (m, 2H); MS (ESI): Calcd. for C21H17ClFN3O4S: 461. found: 462 (M+H).

Example 124

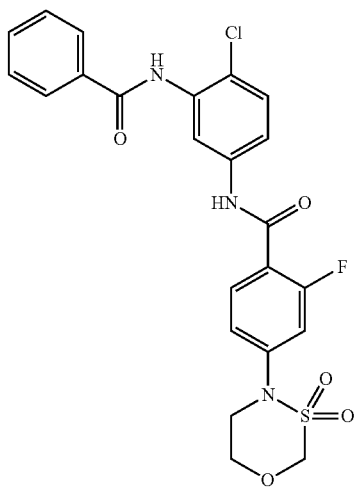 [SMILES: O=C(Nc1cc(NC(=O)c2ccc(N3CCOCS3(=O)=O)cc2F)ccc1Cl)c1ccccc1]

A mixture of 4-(3,3-dioxido-1,3,4-oxathiazinan-4-yl)-2-fluorobenzoic acid (56 mg, 0.21 mmol), N-(5-amino-2-chlorophenyl)benzamide (42 mg, 0.17 mmol), HATU (110 mg, 0.29 mmol), and DIEA (118 µL, 0.68 mmol) in DMF (1.5 mL) was stirred at room temperature for 24 h. EtOAc was added and the mixture was washed with aq NaHCO₃. The organic layer was concentrated under reduced pressure and the resulting residue was purified by flash column chromatography on silica gel (DCM/MeOH) to yield the desired compound N-(3-benzamido-4-chlorophenyl)-4-(3,3-dioxido-1,3,4-oxathiazinan-4-yl)-2-fluorobenzamide (68 mg, 79%) as an off-white crystalline solid. $^1$H-NMR (400 MHz, d₆-DMSO): δ 10.66 (s, 1H), 10.08 (s, 1H), 8.05-7.99 (m, 3H), 7.74-7.52 (m, 6H), 7.36-7.31 (m, 2H), 5.04 (s, 2H), 4.10-4.07 (m, 2H), 3.98-3.95 (m, 2H); MS (ESI): Calcd. for C23H19ClFN3O5S: 503. found: 526 (M+Na).

Example 125

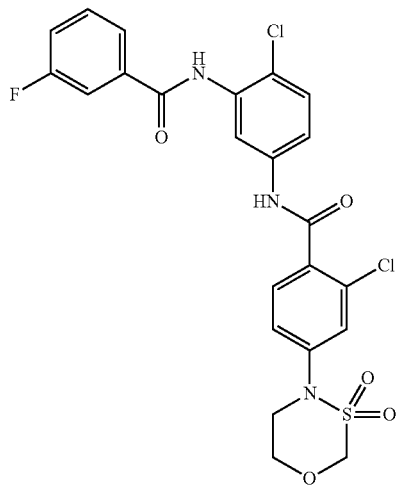 [SMILES: O=C(Nc1cc(NC(=O)c2ccc(N3CCOCS3(=O)=O)cc2Cl)ccc1Cl)c1cccc(F)c1]

A mixture of 2-chloro-4-(3,3-dioxido-1,3,4-oxathiazinan-4-yl)benzoic acid (50 mg, 0.17 mmol), N-(5-amino-2-chlorophenyl)-3-fluorobenzamide (38 mg, 0.14 mmol), HATU (92 mg, 0.24 mmol), and DIEA (100 µL, 0.57 mmol) in DMF (1.5 mL) was stirred at room temperature for 3 days. EtOAc was added and the mixture was washed with aq NaHCO₃. The organic layer was concentrated under reduced pressure and the resulting residue was purified by flash column chromatography on silica gel (EtOAc/hexanes) to yield the desired compound 2-chloro-N-(4-chloro-3-(3-fluorobenzamido)phenyl)-4-(3,3-dioxido-1,3,4-oxathiazinan-4-yl)benzamide (66 mg, 86% yield) as an off-white solid. $^1$H-NMR (400 MHz, d₆-DMSO): δ 10.78 (s, 1H), 10.23 (s, 1H), 8.02 (d, J=2.4 Hz, 1H), 7.86-7.77 (m, 2H), 7.68-7.43 (m, 7H), 5.04 (s, 2H), 4.09-4.07 (m, 2H), 3.95-3.93 (m, 2H); MS (ESI): Calcd. for C23H18Cl2FN3O5S: 537. found: 560 (M+Na).

Example 126

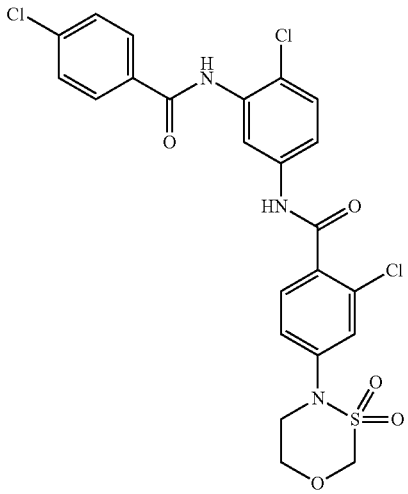 [SMILES: O=C(Nc1cc(NC(=O)c2ccc(N3CCOCS3(=O)=O)cc2Cl)ccc1Cl)c1ccc(Cl)cc1]

A mixture of 2-chloro-4-(3,3-dioxido-1,3,4-oxathiazinan-4-yl)benzoic acid (50 mg, 0.17 mmol), N-(5-amino-2-chlorophenyl)-4-chlorobenzamide (40 mg, 0.14 mmol), HATU (92 mg, 0.24 mmol), and DIEA (100 µL, 0.57 mmol) in DMF (1.5 mL) was stirred at room temperature for 3 days. EtOAc was added and the mixture was washed with aq NaHCO$_3$. The organic layer was concentrated under reduced pressure and the resulting residue was purified by flash column chromatography on silica gel (EtOAc/hexanes) to yield the desired compound 2-chloro-N-(4-chloro-3-(4-chlorobenzamido)phenyl)-4-(3,3-dioxido-1,3,4-oxathiazinan-4-yl)benzamide (68 mg, 85% yield) as an off-white solid. $^1$H-NMR (400 MHz, d$_6$-DMSO): δ 10.77 (s, 1H), 10.20 (s, 1H), 8.03-8.00 (m, 3H), 7.67-7.60 (m, 4H), 7.55-7.52 (m, 2H), 7.45-7.43 (m, 1H), 5.04 (s, 2H), 4.09-4.07 (m, 2H), 3.95-3.93 (m, 2H); MS (ESI): Calcd. for C23H18Cl3N3O5S: 553. found: 576 (M+Na).

Example 127

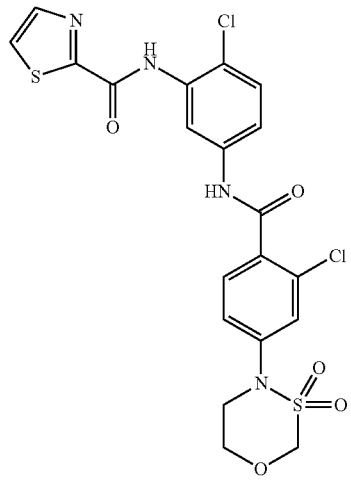 [SMILES: O=C(Nc1cc(NC(=O)c2ccc(N3CCOCS3(=O)=O)cc2Cl)ccc1Cl)c1nccs1]

A mixture of 2-chloro-4-(3,3-dioxido-1,3,4-oxathiazinan-4-yl)benzoic acid (62 mg, 0.17 mmol), N-(5-amino-2-chlorophenyl)thiazole-2-carboxamide (36 mg, 0.14 mmol), HATU (92 mg, 0.24 mmol), and DIEA (100 µL, 0.57 mmol) in DMF (1.5 mL) was stirred at room temperature for 3 days. EtOAc was added and the mixture was washed with aq NaHCO$_3$. The organic layer was concentrated under reduced pressure and the resulting residue was purified by flash column chromatography on silica gel (EtOAc/hexanes) to yield the desired compound N-(2-chloro-5-(2-chloro-4-(3,3-dioxido-1,3,4-oxathiazinan-4-yl)benzamido)phenyl)thiazole-2-carboxamide (65 mg, 78% yield) as an off-white solid. $^1$H-NMR (400 MHz, d$_6$-DMSO): δ 10.82 (s, 1H), 10.19 (s, 1H), 8.44 (d, J=2.4 Hz, 1H), 8.20-8.14 (m, 2H), 7.68-7.43 (m, 5H), 5.04 (s, 2H), 4.10-4.07 (m, 2H), 3.96-3.93 (m, 2H); MS (ESI): Calcd. for C20H16Cl2N4O5S2: 526. found: 549 (M+Na).

Example 128

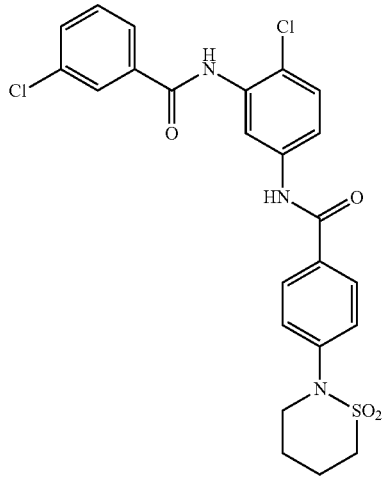 [SMILES: O=C(Nc1ccc(Cl)c(NC(=O)c2cccc(Cl)c2)c1)c1ccc(N2CCCCS2(=O)=O)cc1]

A solution of 4-(1,1-dioxido-1,2-thiazinan-2-yl)benzoic acid (73 mg, 0.29 mmol), DIEA (101 uL, 2 eq) and COMU (149 mg, 1.2 eq) in 4 mL of anhydrous DMF was charged with a solution of N-(5-amino-2-chlorophenyl)-3-chlorobenzamide (81 mg, 1 eq) in 1 mL of anhydrous DMF at room temperature. The reaction mixture was stirred at room temperature for 24 hrs and TLC indicated the completion of the reaction. Ethyl acetate (25 mL) and saturated aqueous sodium bicarbonate (10 mL) were added to partition the mixture. The mixture was filtered and the filtrate was transferred to a separatory funnel. The organic phase was washed with additional 10 mL of brine and dried over anhydrous sodium sulfate. After filtration, the solution was concentrated on rotavapor to dryness. The crude product was purified via silica gel column chromatography (Ethyl acetate in hexanes, 0-50%) to yield the desired product as a light yellow powder (17 mg, 11.3%). $^1$H NMR (400 MHz) δ (ppm): 10.44 (s, 1H), 10.24 (s, 1H), 8.06-7.94 (m, 5H), 7.73-7.43 (m, 6H), 3.73 (t, J=5.2 Hz, 2H), 2.17-2.15 (m, 2H), 1.82 (dd, J=1.2, 6.0 Hz, 2H). ESI-MS: calcd for C24H22Cl2N3O4S (M+H): 518. found: 518.

Example 129

A solution of 4-(1,1-dioxidoisothiazolidin-2-yl)benzoic acid (64 mg, 0.24 mmol), DIEA (94 uL, 2 eq) and HATU (123 mg, 1.2 eq) in 2.5 mL of anhydrous DMF was charged with a solution of N-(5-amino-2-chlorophenyl)-3-chlorobenzamide (75 mg, 1 eq) in 0.5 mL of anhydrous DMF at room temperature. The reaction mixture was stirred at room temperature for 24 hrs and TLC indicated the completion of the reaction. Ethyl acetate (25 mL) and saturated aqueous sodium bicarbonate (10 mL) were added to partition the mixture. The mixture was filtered and the filtrate was transferred to a separatory funnel. The organic phase was washed with additional 10 mL of brine and dried over anhydrous sodium sulfate. After filtration, the solution was concentrated on rotavapor to dryness. The crude product was recrystallized from a chilled mixture of dichloromethane and hexanes to yield the desired product as a yellow powder (52 mg, 38.1%). The mother liquid was concentrated and stored in refrigerator. $^1$H NMR (400 MHz) δ (ppm): 10.34 (d, J=2.4 Hz, 1H), 10.22 (d, J=2.4 Hz, 1H), 8.05-7.97 (m, 4H), 7.74-7.49 (m, 3H), 7.29-7.26 (m, 2H), 3.83 (t, J=3.2 Hz, 2H), 3.80 (t, J=3.2 Hz, 2H), 2.47 (t, J=1.8 Hz, 2H). ESI-MS: calcd for C23H20Cl2N3O4S (M+H): 504. found: 504.

Example 130

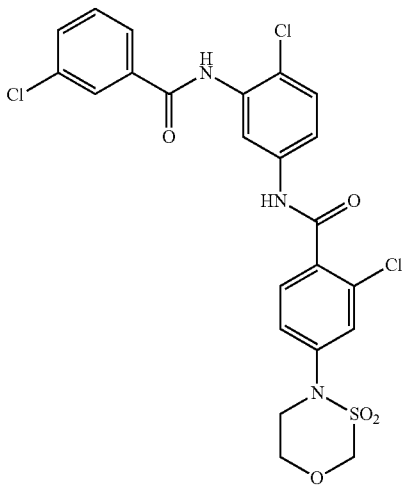 [SMILES: O=C(Nc1cc(NC(=O)c2ccc(N3CCOCS3(=O)=O)cc2Cl)ccc1Cl)c1cccc(Cl)c1]

A solution of 2-chloro-4-(3,3-dioxido-1,3,4-oxathiazinan-4-yl)benzoic acid (65 mg, 0.22 mmol), DIEA (2 eq) and HATU (100 mg, 1.2 eq) in 4 mL of anhydrous DMF was charged with a solution of N-(5-amino-2-chlorophenyl)-3-chlorobenzamide (62 mg, 1 eq) in 1 mL of anhydrous DMF at room temperature. The reaction mixture was stirred at room temperature for 24 hrs and TLC indicated the completion of the reaction. Ethyl acetate (25 mL) and saturated aqueous sodium bicarbonate (10 mL) were added to partition the mixture. The mixture was filtered and the filtrate was transferred to a separatory funnel. The organic phase was washed with additional 10 mL of brine and dried over anhydrous sodium sulfate. After filtration, the solution was concentrated on rotavapor to dryness. The crude product was purified via silica gel column chromatography (Ethyl acetate in hexanes, 0-50%) to yield the desired product as a white powder (30 mg, 24.6%). $^1$H NMR (400 MHz) δ (ppm): 10.77 (s, 1H), 10.26 (s, 1H), 10.01-7.92 (m, 3H), 7.69-7.42 (m, 7H), 4.07 (t, J=4.4 Hz, 2H), 3.93 (t, J=4.4 Hz, 2H), 2.48 (d, J=1.6 Hz, 2H). ESI-MS: calcd for C23H19Cl3N3O5S (M+H): 554. found: 554.

Example 131

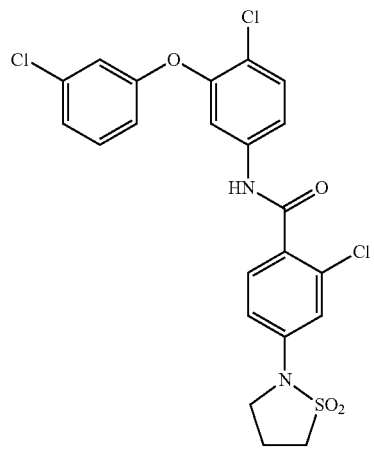 [SMILES: O=C(Nc1ccc(Cl)c(Oc2cccc(Cl)c2)c1)c1ccc(N2CCCS2(=O)=O)cc1Cl]

A solution of 4-(1,1-dioxidoisothiazolidin-2-yl)-3-fluorobenzoic acid (52 mg, 0.19 mmol), DIEA (87 uL, 2 eq) and HATU (87 mg, 1.2 eq) in 2.5 mL of anhydrous DMF was charged with a solution of 4-chloro-3-(3-chlorophenoxy) aniline (48 mg, 1 eq) in 0.5 mL of anhydrous DMF at room temperature. The reaction mixture was stirred at room temperature for 24 hrs and TLC indicated the completion of the reaction. Ethyl acetate (25 mL) and saturated aqueous sodium bicarbonate (10 mL) were added to partition the mixture. The mixture was filtered and the filtrate was transferred to a separatory funnel. The organic phase was washed with additional 10 mL of brine and dried over anhydrous sodium sulfate. After filtration, the solution was concentrated on rotavapor to dryness. The crude product was purified via silica gel column chromatography (Ethyl acetate in hexanes, 0-50%) to yield the desired product as a white foam (55 mg, 56.6%). $^1$H NMR (400 MHz) δ (ppm): 10.21 (s, 1H), 8.65-8.45 (m, 1H), 7.94-6.95 (m, 8H), 3.79 (d, J=6.4 Hz, 2H), 3.57-3.54 (m, 2H), 2.40 (dd, J=1.6, 4.0 Hz, 2H). ESI-MS: calcd for C22H18Cl3N2O4S (M+H): 511. found: 511.

Example 132

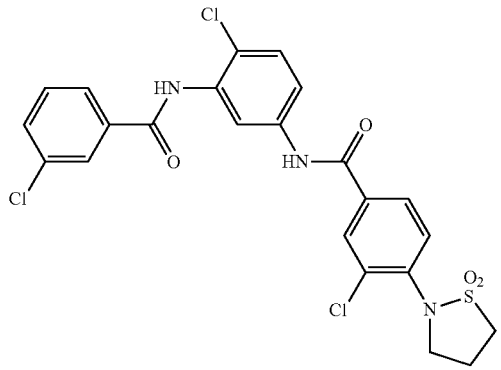 [SMILES: O=C(Nc1ccc(Cl)c(NC(=O)c2cccc(Cl)c2)c1)c1ccc(N2CCCS2(=O)=O)c(Cl)c1]

A solution of 3-chloro-4-(1,1-dioxidoisothiazolidin-2-yl) benzoic acid (71 mg, 0.25 mmol), DIEA (87 uL, 2 eq) and HATU (114 mg, 1.2 eq) in 10 mL of anhydrous DMF was charged with a solution of N-(5-amino-2-chlorophenyl)-3-chlorobenzamide (69 mg, 1 eq) in 1.5 mL of anhydrous DMF at room temperature. The reaction mixture was stirred at room temperature for 24 hrs and TLC indicated the completion of the reaction. Ethyl acetate (60 mL) and saturated aqueous sodium bicarbonate (20 mL) were added to partition the mixture. The mixture was filtered and the filtrate was transferred to a separatory funnel. The organic phase was washed with additional 10 mL of brine and dried over anhydrous sodium sulfate. After filtration, the solution was concentrated on rotavapor to dryness. The crude product was purified via silica gel column chromatography (ethyl acetate in hexanes, 0 to 50%) to yield the desired product as a yellow oil (110 mg, 81.9%). $^1$H NMR (400 MHz) δ (ppm): 10.54 (d, J=3.2 Hz, 1H), 10.24 (d, J=2.0 Hz, 1H), 8.13-7.93 (m, 5H), 7.73-7.53 (m, 5H), 3.77-3.74 (m, 1H), 3.42 (t, J=3.6 Hz, 2H), 1.96 (t, J=3.2 Hz, 2H). ESI-MS: calcd for Chemical Formula: C23H19Cl3N3O4S (M+H): 538. found: 538.

Example 133

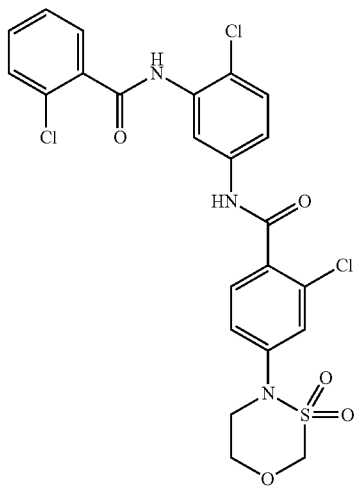 [SMILES: O=C(Nc1ccc(Cl)c(NC(=O)c2ccccc2Cl)c1)c1ccc(N2CCOCS2(=O)=O)cc1Cl]

A mixture of 2-chloro-4-(3,3-dioxido-1,3,4-oxathiazinan-4-yl)benzoic acid (53 mg, 0.18 mmol), N-(5-amino-2-chlorophenyl)-2-chlorobenzamide (46 mg, 0.15 mmol), HATU (130 mg, 0.34 mmol), and DIEA (110 μL, 0.60 mmol) in DMF (1.5 mL) was stirred at room temperature for 1 day. EtOAc was added and the mixture was washed with aq NaHCO$_3$. The organic layer was concentrated under reduced pressure and the resulting residue was purified by flash column chromatography on silica gel (EtOAc/hexanes) to yield the desired compound 2-chloro-N-(4-chloro-3-(2-chlorobenzamido)phenyl)-4-(3,3-dioxido-1,3,4-oxathiazinan-4-yl)benzamide (65 mg, 78% yield) as an off-white solid. $^1$H-NMR (400 MHz, d$_6$-DMSO): δ 10.78 (s, 1H), 10.23 (s, 1H), 8.10 (s, 1H), 7.68-7.43 (m, 9H), 5.04 (s, 2H), 4.10-4.07 (m, 2H), 3.96-3.93 (m, 2H); MS (ESI): Calcd. for C23H18Cl3N3O5S: 553. found: 576 (M+Na).

Example 134

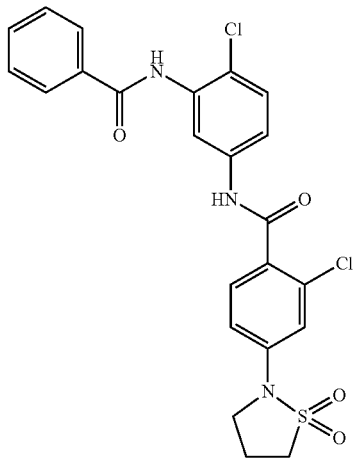 [SMILES: O=C(Nc1cc(NC(=O)c2ccc(N3CCCS3(=O)=O)cc2Cl)ccc1Cl)c1ccccc1]

A mixture 2-chloro-4-(1,1-dioxidoisothiazolidin-2-yl) benzoic acid (60 mg, 0.21 mmol), N-(5-amino-2-chlorophenyl)benzamide (42 mg, 0.17 mmol), HATU (65 mg, 0.17 mmol), and DIEA (119 μL, 0.68 mmol) in DMF (1.5 mL) was stirred at room temperature for 17 h. EtOAc was added and the mixture was washed with aq NaHCO$_3$. The organic layer was concentrated under reduced pressure and the resulting residue was purified by flash column chromatography on silica gel (DCM/MeOH) and further purified by crystallization out of DCM/hexanes to yield the desired compound N-(3-benzamido-4-chlorophenyl)-2-chloro-4-(3,3-dioxido-1,3,4-oxathiazinan-4-yl)benzamide (30 mg, 34% yield) as an off-white crystalline solid. $^1$H-NMR (400 MHz, d$_6$-DMSO): δ 10.77 (s, 1H), 10.09 (s, 1H), 8.04-7.98 (m, 3H), 7.68-7.43 (m, 8H), 5.04 (s, 2H), 4.10-4.07 (m, 2H), 3.95-3.93 (m, 2H); MS (ESI): Calcd. for C23H19ClFN3O5S: 503. found: 526 (M+Na).

Example 135

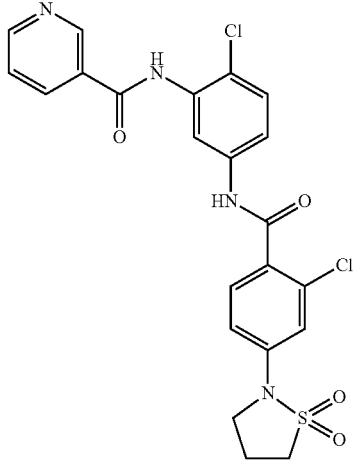 [SMILES: O=C(Nc1cc(NC(=O)c2ccc(N3CCCS3(=O)=O)cc2Cl)ccc1Cl)c1cccnc1]

A mixture of 2-chloro-4-(1,1-dioxidoisothiazolidin-2-yl) benzoic acid (44 mg, 0.16 mmol), N-(5-amino-2-chlorophenyl)nicotinamide (33 mg, 0.14 mmol), HATU (98 mg, 0.23 mmol), and DIEA (94 µL, 0.54 mmol) in DMF (1.5 mL) was stirred at room temperature for 17 h. EtOAc was added and the mixture was washed with aq NaHCO₃. The organic layer was concentrated under reduced pressure and the resulting residue was purified by flash column chromatography on silica gel (DCM/MeOH) to yield the desired compound N-(2-chloro-5-(2-chloro-4-(1,1-dioxidoisothiazolidin-2-yl)benzamido)phenyl) nicotinamide (14 mg, 34%) as an off-white crystalline solid. $^1$H-NMR (400 MHz, d$_6$-DMSO): δ 10.67 (s, 1H), 10.35 (s, 1H), 9.14 (d, J=1.6 Hz, 1H), 8.80-8.78 (m, 1H), 8.34-8.31 (m, 1H), 8.05 (d, J=2.4 Hz, 1H), 7.65-7.53 (m, 4H), 7.31-7.25 (m, 2H), 3.83-3.80 (m, 2H), 3.61-3.58 (m, 2H), 2.47-2.40 (m, 2H); MS (ESI): Calcd. for C22H18Cl2N4O4S: 504. found: 505 (M+H).

Example 136

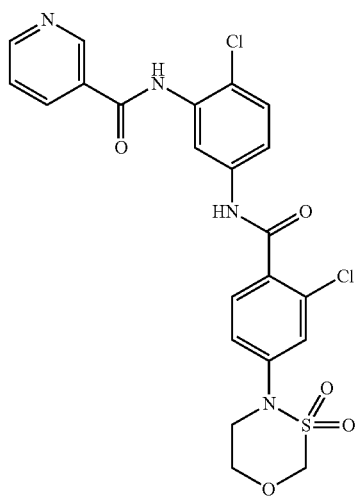 [SMILES: O=C(Nc1cc(NC(=O)c2ccc(N3CCOCS3(=O)=O)cc2Cl)ccc1Cl)c1cccnc1]

A mixture of 2-chloro-4-(3,3-dioxido-1,3,4-oxathiazinan-4-yl)benzoic acid (70 mg, 0.24 mmol), N-(5-amino-2-chlorophenyl)nicotinamide (50 mg, 0.20 mmol), HATU (129 mg, 0.339 mmol), and DIPEA (94 µL, 0.54 mmol) in DMF (1.5 mL) was stirred at room temperature for 17 h. EtOAc was added and the mixture was washed with aq NaHCO₃. The organic layer was concentrated under reduced pressure and the resulting residue was purified by flash column chromatography on silica gel (DCM/MeOH) to yield the desired compound N-(2-chloro-5-(2-chloro-4-(1,1-dioxidoisothiazolidin-2-yl)benzamido)phenyl) nicotinamide (54 mg, 51%) as an off-white crystalline solid. $^1$H-NMR (400 MHz, d$_6$-DMSO): δ 10.79 (s, 1H), 10.36 (s, 1H), 9.15-9.14 (m, 1H), 8.80-8.78 (m, 1H), 8.34-8.31 (m, 1H), 8.06 (d, J=2.4 Hz, 1H), 7.68-7.54 (m, 5H), 7.46-7.43 (m, 1H), 5.04 (s, 2H), 4.10-4.07 (m, 2H), 3.96-3.93 (m, 2H); MS (ESI): Calcd. for C22H18Cl2N4O5S: 520. found: 521 (M+H).

Example 137

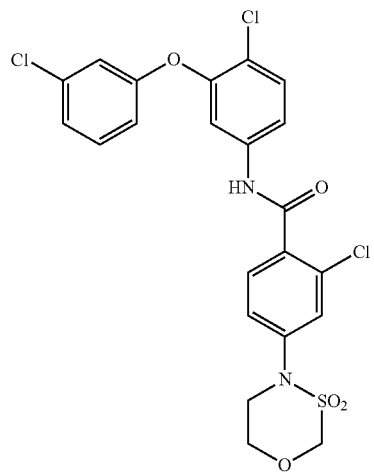 [SMILES: O=C(Nc1ccc(Cl)c(Oc2cccc(Cl)c2)c1)c1ccc(N2CCOCS2(=O)=O)cc1Cl]

A solution of 2-chloro-4-(1,1-dioxido-1,2-thiazinan-2-yl)benzoic acid (56 mg, 0.19 mmol), DIEA (87 uL, 2 eq) and HATU (87 mg, 1.2 eq) in 2.5 mL of anhydrous DMF was charged with a solution of 4-chloro-3-(3-chlorophenoxy)aniline (48 mg, 1 eq) in 0.5 mL of anhydrous DMF at room temperature. The reaction mixture was stirred at room temperature for 24 hrs and TLC indicated the completion of the reaction. Ethyl acetate (25 mL) and saturated aqueous sodium bicarbonate (10 mL) were added to partition the mixture. The mixture was filtered and the filtrate was transferred to a separatory funnel. The organic phase was washed with additional 10 mL of brine and dried over anhydrous sodium sulfate. After filtration, the solution was concentrated on rotavapor to dryness. The crude product was purified via silica gel column chromatography (Ethyl acetate in hexanes, 0-50%) to yield the desired product as a white foam (55 mg, 55.2%). $^1$H NMR (400 MHz) δ (ppm): 10.75 (s, 1H), 7.63-7.22 (m, 7H), 7.23 (t, J=1.0 Hz, 1H), 7.21 (t, J=1.0 Hz, 1H), 7.08 (t, J=2.2 Hz, 1H), 4.06-4.04 (m, 2H), 3.91 (t, J=4.4 Hz, 2H), 1.99 (s, 2H). ESI-MS: calcd for C22H18Cl3N2O5S (M+H): 527. found: 527.

Example 138

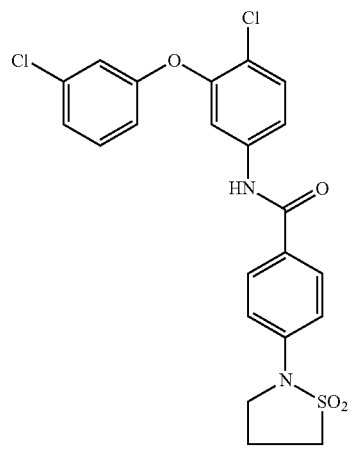 [SMILES: O=C(Nc1ccc(Cl)c(Oc2cccc(Cl)c2)c1)c1ccc(N2CCCS2(=O)=O)cc1]

A solution of 4-(1,1-dioxidoisothiazolidin-2-yl)benzoic acid (62 mg, 0.26 mmol), DIEA (90 uL, 2 eq) and HATU (119 mg, 1.2 eq) in 2.5 mL of anhydrous DMF was charged with a solution of 4-chloro-3-(3-chlorophenoxy)aniline (66 mg, 1 eq) in 0.5 mL of anhydrous DMF at room temperature. The reaction mixture was stirred at room temperature for 24 hrs and TLC indicated the completion of the reaction. Ethyl acetate (40 mL) and saturated aqueous sodium bicarbonate (10 mL) were added to partition the mixture. The mixture was filtered and the filtrate was transferred to a separatory funnel. The organic phase was washed with additional 10 mL of brine and dried over anhydrous sodium sulfate. After filtration, the solution was concentrated on rotavapor to dryness. The crude product was recrystallized from a mixture of DCM and hexanes to yield the desired product as an off white powder (35 mg, 28.2%). The mother liquid was stored in refrigerator. $^1$H NMR (400 MHz) δ (ppm): 10.32 (s, 1H), 7.93 (d, J=7.6 Hz, 1H), 7.70-7.66 (m, 2H), 7.56 (d, J=8.4 Hz, 1H), 7.44 (t, J=6.8 Hz, 1H), 7.42-7.08 (m, 6H), 3.79 (t, J=6.4 Hz, 2H), 3.57-3.54 (m, 2H), 2.41 (t, J=6.8 Hz, 2H). ESI-MS: calcd for C22H19Cl2N2O4S (M+H): 477. found: 477.

Example 139

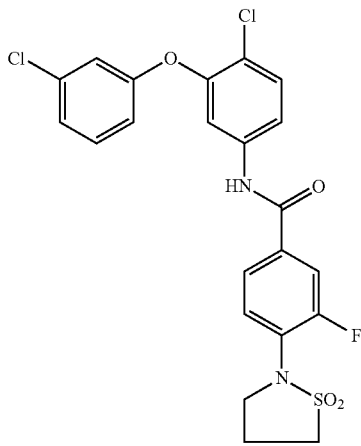 [SMILES: O=C(Nc1ccc(Cl)c(Oc2cccc(Cl)c2)c1)c1ccc(N2CCCS2(=O)=O)c(F)c1]

A solution of 4-(1,1-dioxidoisothiazolidin-2-yl)-3-fluorobenzoic acid (49 mg, 0.19 mmol), DIEA (66 uL, 2 eq) and HATU (87 mg, 1.2 eq) in 2.5 mL of anhydrous DMF was charged with a solution of 4-chloro-3-(3-chlorophenoxy)aniline (48 mg, 1 eq) in 0.5 mL of anhydrous DMF at room temperature. The reaction mixture was stirred at room temperature for 24 hrs and TLC indicated the completion of the reaction. Ethyl acetate (40 mL) and saturated aqueous sodium bicarbonate (10 mL) were added to partition the mixture. The mixture was filtered and the filtrate was transferred to a separatory funnel. The organic phase was washed with additional 10 mL of brine and dried over anhydrous sodium sulfate. After filtration, the solution was concentrated on rotavapor to dryness. The crude product was recrystallized from a mixture of DCM and hexanes to yield the desired product as an off white powder (9 mg, 9.6%). The mother liquid was stored in a refrigerator. $^1$H NMR (400 MHz) δ (ppm): 10.43 (s, 1H), 7.85-7.51 (m, 6H), 7.42 (t, J=8.0 Hz, 1H), 7.24-6.95 (m, 3H), 3.83 (t, J=6.4 Hz, 2H), 3.44 (t, J=7.2 Hz, 2H), 2.42 (t, J=6.4 Hz, 2H). ESI-MS: calcd for C22H18Cl2FN2O4S (M+H): 495. found: 495.

Example 140

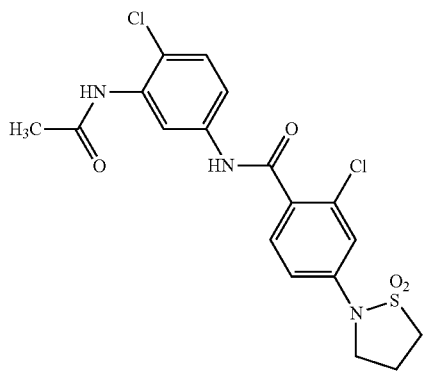 [SMILES: CC(=O)Nc1cc(NC(=O)c2ccc(N3CCCS3(=O)=O)cc2Cl)ccc1Cl]

A solution of 2-chloro-4-(1,1-dioxidoisothiazolidin-2-yl)benzoic acid (63 mg, 0.23 mmol), DIEA (90 uL, 2 eq) and HATU (87 mg, 1.2 eq) in 4 mL of anhydrous DMF was charged with a solution of N-(5-amino-2-chlorophenyl)acetamide (56 mg, 1 eq) in 1 mL of anhydrous DMF at room temperature. The reaction mixture was stirred at room temperature for 20 hrs and TLC indicated the completion of the reaction. Ethyl acetate (40 mL) and saturated aqueous sodium bicarbonate (20 mL) were added to partition the mixture. The mixture was filtered and the filtrate was transferred to a separatory funnel. The organic phase was washed with additional 10 mL of brine and dried over anhydrous sodium sulfate. After filtration, the solution was concentrated on rotavapor to dryness. The crude product was charged with 1 mL of chilled methylene chloride. Hexanes was added dropwise to the solution until cloudy suspension started to form. Two drops of methylene chloride was added back to achieve a clear solution. The resulting solution stood still at room temperature for several hours. The solid recrystallized from the mother liquid was collected and washed quickly with cold methylene chloride and further dried in vacuo. The first-batch desired product was obtained as a yellow powder (28 mg, 27.6%). The mother liquid was stored in a refrigerator. $^1$H NMR (400 MHz) δ (ppm): 10.28 (s, 1H), 9.48 (s, 1H), 8.13 (s, 1H), 7.96 (d, J=8.8 Hz, 1H), 7.63 (dd, J=2.4, 8.8 Hz, 1H), 7.42 (d, J=8.8 Hz, 1H), 7.26 (d, J=8.4 Hz, 1H), 3.81 (t, J=6.4 Hz, 2H), 3.56 (t, J=7.2 Hz, 2H), 2.42 (t, J=6.8 Hz, 2H), 2.08 (s, 3H). ESI-MS: calcd for C18H18Cl2N3O4S (M+H)$^+$: 442. found: 442.

Example 141

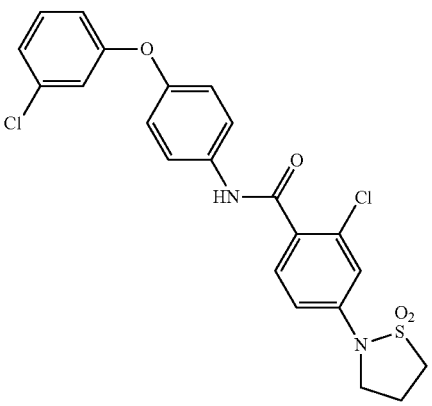 [SMILES: O=C(Nc1ccc(Oc2cccc(Cl)c2)cc1)c1ccc(N2CCCS2(=O)=O)cc1Cl]

A solution of 2-chloro-4-(1,1-dioxidoisothiazolidin-2-yl) benzoic acid (63 mg, 0.23 mmol), DIEA (90 uL, 2 eq) and HATU (87 mg, 1.2 eq) in 4 mL of anhydrous DMF was charged with a solution of N-(5-amino-2-chlorophenyl)acetamide (57 mg, 1 eq) in 1 mL of anhydrous DMF at room temperature. The reaction mixture was stirred at room temperature for 20 hrs and TLC indicated the completion of the reaction. Ethyl acetate (40 mL) and saturated aqueous sodium bicarbonate (20 mL) were added to partition the mixture. The mixture was filtered and the filtrate was transferred to a separatory funnel. The organic phase was washed with additional 10 mL of brine and dried over anhydrous sodium sulfate. After filtration, the solution was concentrated on rotavapor to dryness. The crude product was charged with 1 mL of chilled methylene chloride. Hexanes was added dropwise to the solution until cloudy suspension started to form. Two drops of methylene chloride was added back to achieve a clear solution. The resulting solution stood still at room temperature for several hours. The solid recrystallized from the mother liquid was collected and washed quickly with cold methylene chloride and further dried in vacuo. The first-batch desired product was obtained as a pale grayish flake (55 mg, 50.2%). The mother liquid was stored in a refrigerator. $^1$H NMR (400 MHz) δ (ppm): 10.35 (s, 1H), 7.97 (d, J=7.2 Hz, 1H), 7.81-7.59 (m, 2H), 7.36 (d, J=8.4 Hz, 1H), 7.29-6.92 (m, 7H), 3.80 (d, J=2.8 Hz, 2H), 3.58-3.56 (m, 2H), 2.48 (d, J=1.6 Hz, 2H). ESI-MS: calcd for C22H19Cl2N2O4S (M+H): 477. found: 477.

Example 142

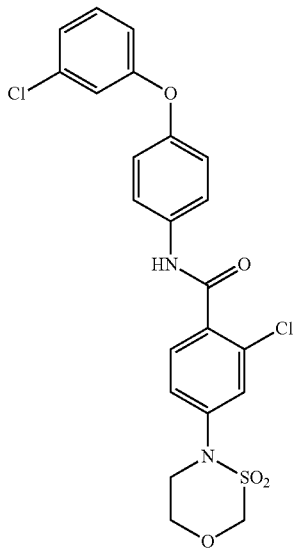 [SMILES: O=C(Nc1ccc(Oc2cccc(Cl)c2)cc1)c1ccc(N2CCOCS2(=O)=O)cc1Cl]

A solution of 2-chloro-4-(1,1-dioxido-1,2-thiazinan-2-yl) benzoic acid (48 mg, 0.16 mmol), DIEA (56 uL, 2 eq) and HATU (73 mg, 1.2 eq) in 2.5 mL of anhydrous DMF was charged with a solution of 4-chloro-3-(3-chlorophenoxy) aniline (35 mg, 1 eq) in 0.5 mL of anhydrous DMF at room temperature. The reaction mixture was stirred at room temperature for 24 hrs and TLC indicated the completion of the reaction. Ethyl acetate (25 mL) and saturated aqueous sodium bicarbonate (10 mL) were added to partition the mixture. The mixture was filtered and the filtrate was transferred to a separatory funnel. The organic phase was washed with additional 10 mL of brine and dried over anhydrous sodium sulfate. After filtration, the solution was concentrated on rotavapor to dryness. The crude product was purified via silica gel column chromatography (Ethyl acetate in hexanes, 0-40%) to yield the desired product as a white foam (70 mg, 88.9%). $^1$H NMR (400 MHz) δ (ppm): 10.61 (s, 1H), 7.74 (d, J=8.4 Hz, 2H), 7.63 (d, J=8.4 Hz, 1H), 7.52 (d, J=1.6 Hz, 1H), 7.43-7.41 (1H), 7.37 (t, J=8.2 Hz, 2H), 7.16 (t, J=1.0 Hz, 1H), 7.14-6.91 (m, 3H), 5.03 (s, 2H), 3.92 (t, J=4.4 Hz, 2H), 3.92 (t, J=4.4 Hz, 2H). ESI-MS: calcd for C22H19Cl2N2O5S (M+H): 493. found: 493.

Example 143

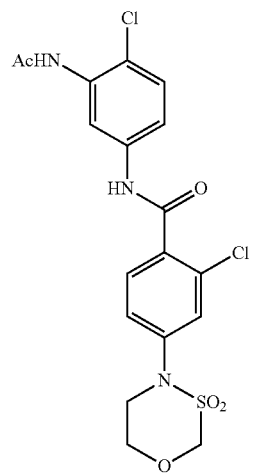 [SMILES: CC(=O)Nc1cc(NC(=O)c2ccc(N3CCOCS3(=O)=O)cc2Cl)ccc1Cl]

A solution of 2-chloro-4-(1,1-dioxido-1,2-thiazinan-2-yl) benzoic acid (52 mg, 0.18 mmol), DIEA (63 uL, 2 eq) and HATU (82 mg, 1.2 eq) in 2.5 mL of anhydrous DMF was charged with a solution of N-(5-amino-2-chlorophenyl)acetamide (33 mg, 1 eq) in 0.5 mL of anhydrous DMF at room temperature. The reaction mixture was stirred at room temperature for 24 hrs and TLC indicated the completion of the reaction. Ethyl acetate (25 mL) and saturated aqueous sodium bicarbonate (10 mL) were added to partition the mixture. The mixture was filtered and the filtrate was transferred to a separatory funnel. The organic phase was washed with additional 10 mL of brine and dried over anhydrous sodium sulfate. After filtration, the solution was concentrated on rotavapor to dryness. The crude product was purified via silica gel column chromatography (Ethyl acetate in hexanes, 0-60%) to yield the desired product as a colorless oil (65 mg, 79.0%). $^1$H NMR (400 MHz) δ (ppm): 10.69 (s, 1H), 9.51 (s, 1H), 8.07 (s, 1H), 7.62-7.39 (m, 5H), 5.00 (s, 2H), 4.06 (t, J=4.4 Hz, 2H), 3.90 (t, J=4.0 Hz, 2H), 2.48 (d, J=1.2 Hz, 3H). ESI-MS: calcd for C18H18Cl2N3O5S (M+H): 458. found: 458.2.

The invention also encompasses pharmaceutical compositions comprising any one or more of the compounds disclosed herein and said compounds in the form of pharmaceutically acceptable salts, hydrates, solvates, crystal forms and individual steroisomers thereof (e.g, diastereomers, enantamers), and a in a composition with a pharmaceutically acceptable carrier. These include, but are not limited to, wherein the inventive compounds are formulated into a composition in a neutral or salt form.

"Pharmaceutically acceptable salts" include the acid addition salts (formed with the free amino groups of the protein) and which are formed with inorganic acids such as, for example, hydrochloric or phosphoric acids, or such as organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, and procaine and the like.

"Salts" are chemical combinations of two ionizable components (e.g., when dissolved in water), one acidic and the other basic with respect to one another. If in a salt form, a drug can be either the acidic or the basic component.

"Pharmaceutically acceptable salts" include any salt form of the compound wherein the salt is safe for animal ingestion (e.g., nontoxic to humans when taken orally). Exemplary such salts that can be used in accordance with the invention include, but are not limited to, 2-hydroxyethanesulfonate, 2-naphthalenesulfonate, 3-hydroxy-2-naphthoate, 3-phenylpropionate, acetate, adipate, alginate, amsonate, aspartate, benzenesulfonate, benzoate, besylate, bicarbonate, bisulfate, bitartrate, borate, butyrate, calcium edetate, camphorate, camphorsulfonate, camsylate, carbonate, citrate, clavulariate, cyclopentanepropionate, digluconate, dodecylsulfate, edetate, edisylate, estolate, esylate, ethanesulfonate, finnarate, gluceptate, glucoheptanoate, gluconate, glutamate, glycerophosphate, glycollylarsanilate, hemisulfate, heptanoate, hexafluorophosphate, hexanoate, hexylresorcinate, hydrabamine, hydrobromide, hydrochloride, hydroiodide, hydroxynaphthoate, iodide, isothionate, lactate, lactobionate, laurate, laurylsulphonate, malate, maleate, mandelate, mesylate, methanesulfonate, methylbromide, methylnitrate, methylsulfate, mucate, naphthylate, napsylate, nicotinate, nitrate, N-methylglucamine ammonium salt, oleate, oxalate, palmitate, pamoate, pantothenate, pectinate, persulfate, phosphate, phosphateldiphosphate, picrate, pivalate, polygalacturonate, propionate, p-toluenesulfonate, saccharate, salicylate, stearate, subacetate, succinate, sulfate, sulfosaliculate, suramate, tannate, tartrate, teoclate, thiocyanate, tosylate, triethiodide, undecanoate, and valerate salts, and the like (see also S. M. Berge et al., Pharmaceutical Salts, *J. Pharm. Scis.*, 1977, 66:1-18; P. L. Gould, Salt selection for basic drugs, *Int'l J. Pharms.* 1986, 33:201-17.)

"Solvates" are compositions which, during the process of crystallization of a compound from solution, trap molecules of the solvent in the forming lattice.

"Hydrates" are solvates wherein the solvent was water.

"Crystal" forms are solid compostions wherein the molecules making up the composition are packed in a repeating lattice structure. When more than one lattice pattern is possible for compostions made up the same molecules, the different compositions are called "polymorphs."

"Diastereomers" are stereoisomers that are not related as object and mirror image, but still differ is in the arrangement in three-dimensional space about one tetrahedral, sp3-hybridized carbon.

An "enantiomer" is one of two stereoisomers that are mirror images of each other, but are non-superposable (not identical).

"Pharmaceutically acceptable carrier" is any excipient which is non-toxic and aids in a drug's function (see also, Rowe R C et al., Handbook of Pharmaceutical Excipients, 5$^{th}$ ed., 2006.)

Example 144

Hedgehog signalling inhibition assays. The following table 2 represents the average $EC_{50}$ values for particular compounds of the inventions. Gli-bla NIH3T3 cells (7500 cells/well) were plated the day prior to the assay in a 384-well and 96-format in complete growth medium. On the day of the assay, growth medium was replaced with assay medium containing 0.5% FCS and cells were treated with new compound at the indicated concentrations for 0.5 hours before mShh was added at $EC_{50}$ (400 ng/ml) to all treated cells. Cells were stimulated with mShh for 24 hours and then loaded with LiveBLAzer™-FRET B/G Substrate for 3 hours. Emission values at 460 nm and 530 nm were obtained using a standard fluorescence plate reader and the 460/530 Ratios plotted for each treatment (n=4 for each data point).

TABLE 1

| compound | $EC_{50}$ (μM) | compound | $EC_{50}$ (μM) |
| --- | --- | --- | --- |
| 84 | <0.01 | 85 | <0.01 |
| 86 | 28 | 87 | 3 |
| 88 | 10 | 89 | 14 |
| 90 | 12 | 91 | 17 |
| 92 | 13 | 93 | 0.01 |
| 94 | <0.01 | 95 | <0.01 |
| 96 | <0.01 | 97 | <0.01 |
| 98 | <0.01 | 99 | <0.01 |
| 100 | <0.01 | 101 | <0.01 |
| 102 | <0.01 | 103 | <0.01 |
| 104 | <0.01 | 105 | <0.01 |
| 106 | <0.01 | 107 | <0.01 |
| 108 | 11 | 109 | <0.01 |
| 110 | 21 | 111 | <0.01 |
| 112 | <0.01 | 113 | <0.01 |
| 114 | <0.01 | 115 | <0.01 |
| 116 | <0.01 | 117 | 16 |
| 118 | <0.01 | 119 | <0.01 |
| 120 | <0.01 | 121 | <0.01 |
| 122 | <0.01 | 123 | <0.01 |
| 124 | <0.01 | 125 | <0.01 |
| 126 | <0.01 | 127 | <0.01 |
| 128 | <0.01 | 129 | <0.01 |
| 130 | <0.01 | 131 | <0.01 |
| 132 | <0.01 | 133 | <0.01 |
| 134 | <0.01 | 135 | <0.01 |
| 136 | <0.01 | 137 | <0.01 |
| 138 | <0.01 | 139 | <0.01 |
| 140 | 1 | 141 | <0.01 |
| 142 | <0.01 | 143 | <0.01 |

Example 145

The compound of Example 120 above (also known as NTW-3729) showed strong kinase inhibition and was further analyzed.

This example studies the effect of NTW-3729 on the Hedgehog pathway. The inappropriate activation of this pathway can result in tumorigenesis (Hunter, T. *Cell* 1997, 88, 333-346).

Biological testing of NTW-3729 utilized two assays: Gli-Bla reporter assay in NIH 3T3-cells (see Zlokarnik, G., et al, Quantitation of Transcription and Clonal Selection of Single Living Cells with Beta-Lactamase as Reporter, *Science* 1998, 279: 84-88; Kunapuli P. et al. Development of an Intact Cell Reporter Gene Beta-lactamase Assay for G Protein-coupled Receptors, *Analytical Biochem.* (2003), 314: 16-29; Xing, H., Pollok, B., et al, A Fluorescent Reporter Assay For The Detection of Ligands Acting Through Gli Protein coupled Receptors, *J. Receptor & Signal Transduction Research*, 2000, 20:189-210) and the SMO BOOIPY-CYC binding assay done using HEK293H cells (Fan, Q et al., Tumor shrinkage by cyclopamine tartrate through inhibiting hedgehog signaling, *Chin. J. Cancer,* 2011, 30(7):472-81).

Figure 2:
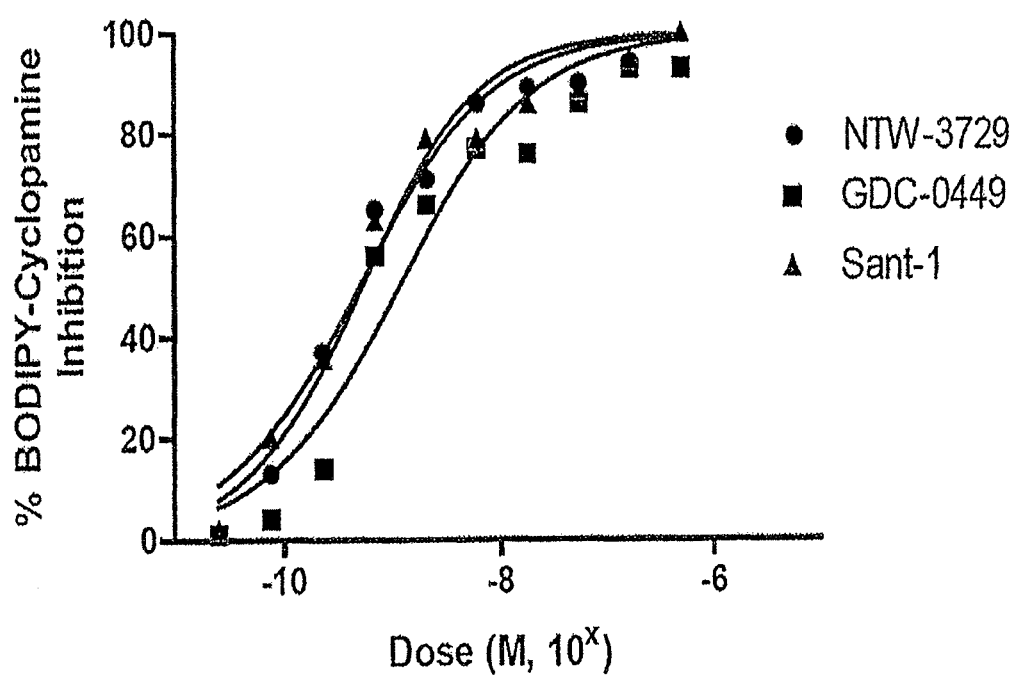
FIG. 2 depicts a dose response curve for NTW-3729 and positive control (GDC-0449, Sant-1) inhibitors of the SMO-BODIPY-CYC assay.

Using the Gli-Bla assay, NTW-3729 was confirmed to be a hedgehog pathway antagonist showing 3 orders of magnitude greater potency than either GDC-0449 or Sant-I. NTW-3729 showed approximately equivalent potency to Sant-I, but a 5-fold increase in potency over GOC-0449. FIG. 1 depicts a dose response curve for NTW-3729 and positive control inhibitors (GDC-0449, Sant-1) of the Gli-Bla reporter assay. FIG. 2 depicts a dose response curve for NTW-3729 and positive control (GDC-0449, Sant-1) inhibitors of the SMO-BODIPY-CYC assay.

The Biological testing results are summarized in Table 2.

TABLE 2

| compound | Gli-Bla reporter assay ($EC_{50}$, nM) | BODIPY-CYC binding assay ($EC_{50}$, nM) |
| --- | --- | --- |
| NTW-3729 | 0.005 | 0.773 |
| GDC-0449 | 7 | 4 |
| Sant-1 | 5 | 0.592 |

These results confirm that NTW-3729 is a strong inhibitor of Hedgehog pathway signal transduction.

Example 146

This example looks at NTW-3729's activity in murine model tumor systems.

Mouse models of cancer have been increasingly used qualify new anticancer drugs for study in human clinical trials. Of such models, the most used include transplantable murine tumors grown in syngeneic hosts and xenografts of human tumors grown in immunodeficient mice. (for further a discussion see, e.g., Sausville E A, Burger A M, Contributions of human tumor xenografts to anticancer drug development, *Cancer Res.* 2006, Apr. 1; 66(7):3351-4, discussion 3354.)

The Hedgehog pathway is involved in a wide range of cancers (Evangelista M et al., hedgehog signaling pathway in cancer, *Clin. Cancer Res.*, 2006 Oct. 15; 12 (20 Pt 1):5924-8). For example, Medulloblastoma (MB), a tumor of the cerebellum, is the most frequent childhood brain tumor. Multiple genes are causally involved in MB including PATCHED1 (PTCH1). The Patched1 (Ptc1) protein is a receptor for Sonic hedgehog (Shh). Purkinje cell-derived Shh stimulates mitosis of the granule cell precursors that are likely the cell type of origin in MB. Ptc1 attenuates the effects of the Shh signaling. Mutations in PTCH1 may lead to persistent granule cell precursors susceptible to further genetic or environmental events that cause MB. Accordingly, murine models for MB have been developed. Mice heterozygous for patched1 (ptc1) mutations, like heterozygous PTCH1 humans, have a high rate of MB (for the mice ~14%) and other tumors. In addition, it has recently determined that mice who are heterozygous for patched1 (ptc1) mutations and also have mutations in both copies of p53 have a 95% incidence of MB.

Figure 3:
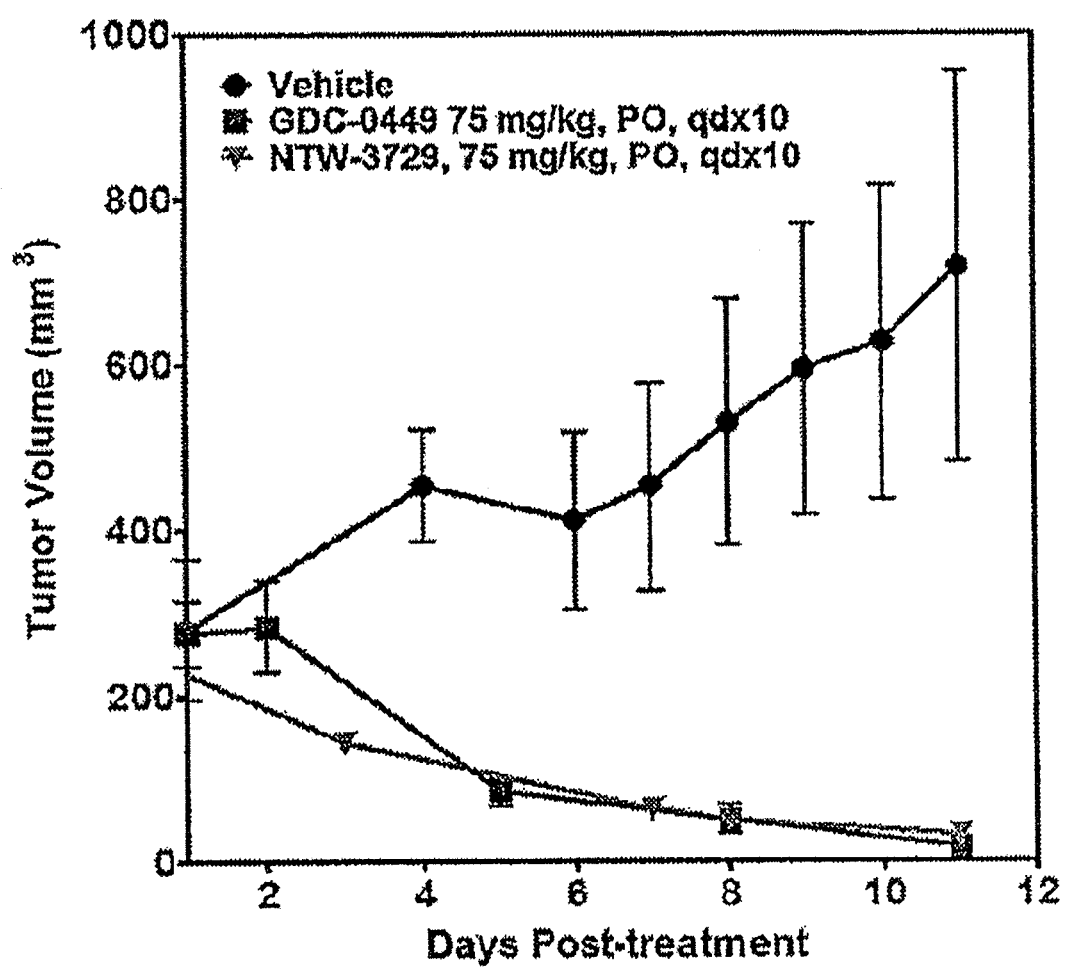
Figure 4:
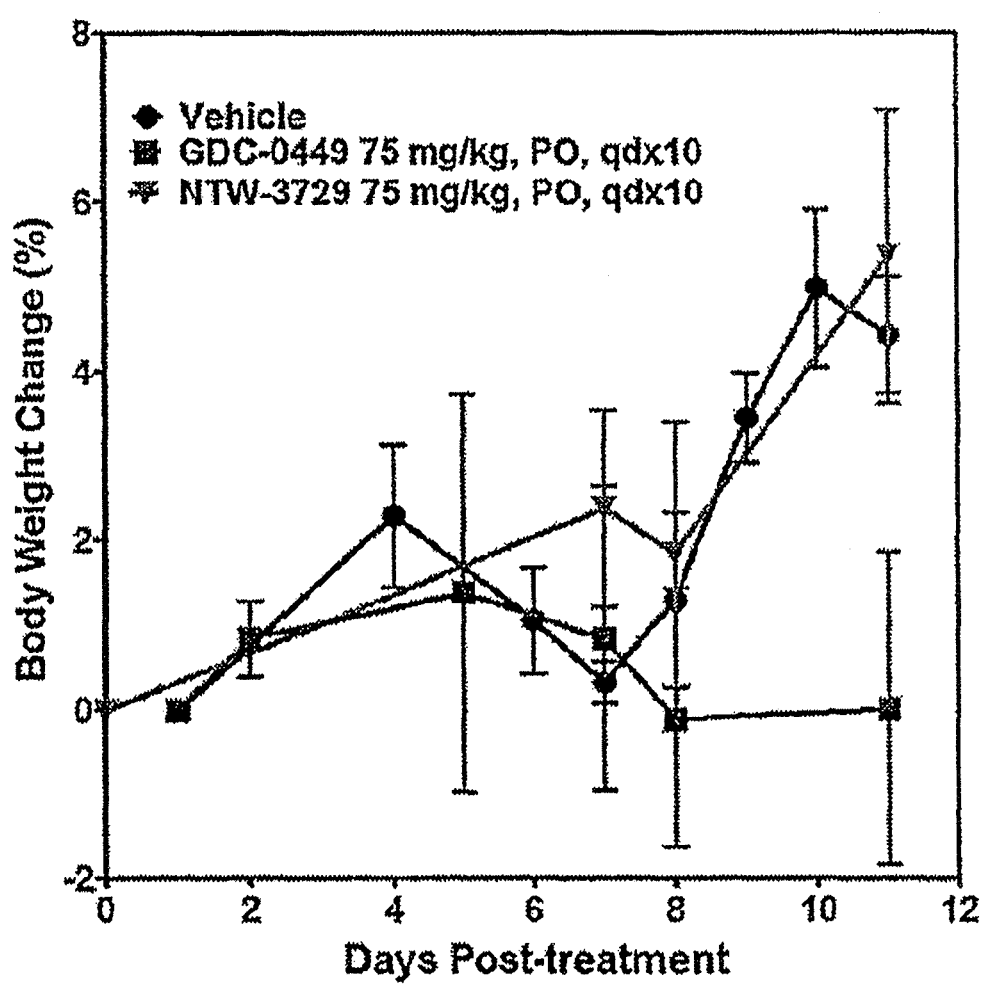
FIG. 4 depicts the weight change time course for Ptch$^{+/-}$p53$^{-/-}$ treated with NTW-3729, Vehicle (negative control), and GDC-0449 (positive control) in Ptch$^{+/-}$p53$^{-/-}$ mice.
Figure 5:
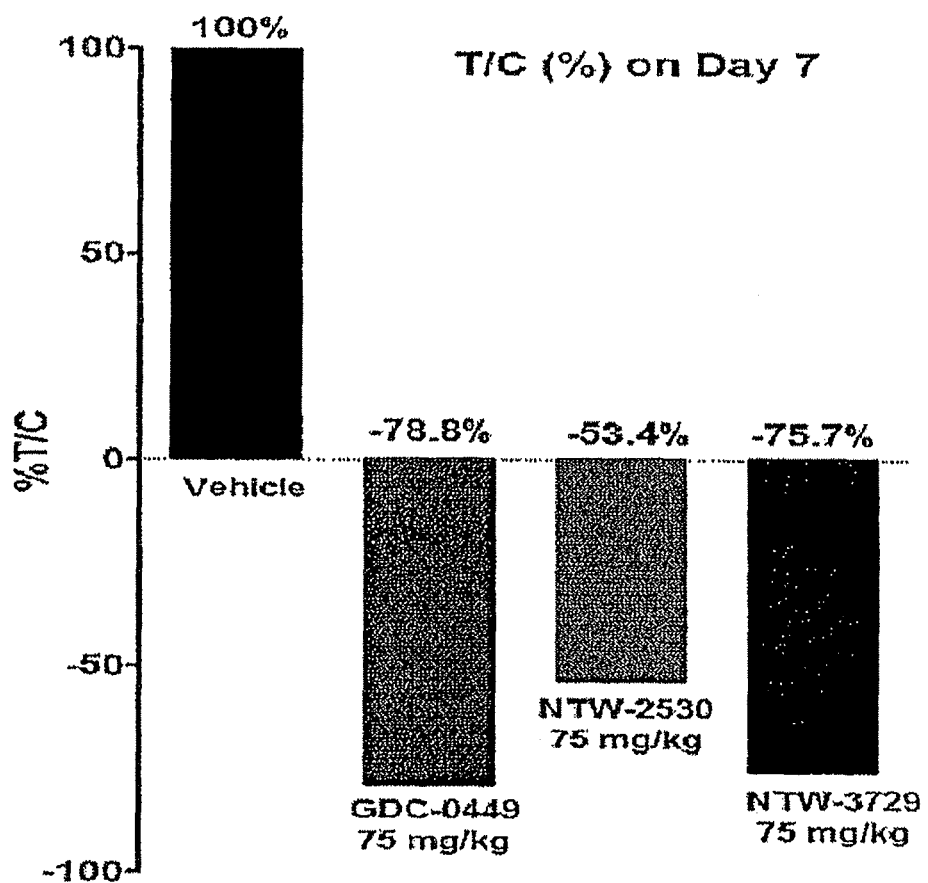
FIG. 5 depicts relative tumor size at day 7 for NTW-3729, Vehicle (negative control), and GDC-0449 (positive control) treated Ptch$^{+/-}$p53$^{-/-}$ mice.
Figure 6:
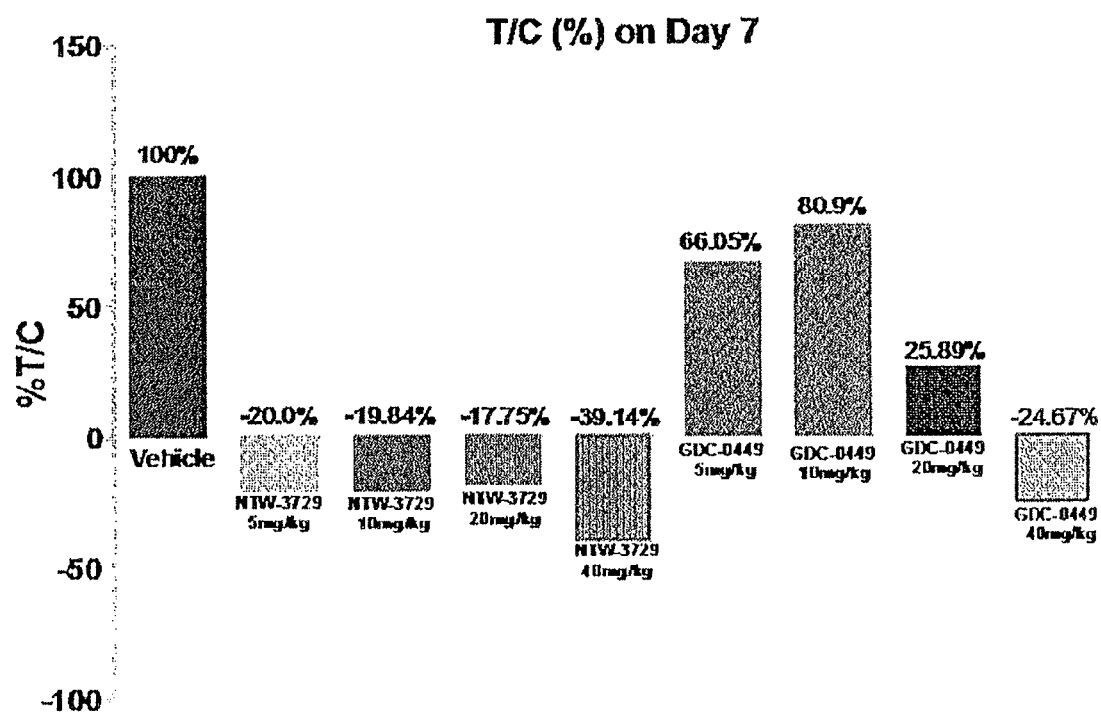
FIG. 6 is another depiction of the the relative tumor size at day 7 for NTW-3729, Vehicle (negative control), and GDC-0449 (positive control) in Ptch$^{+/-}$p53$^{-/-}$ mice.
Figure 7:
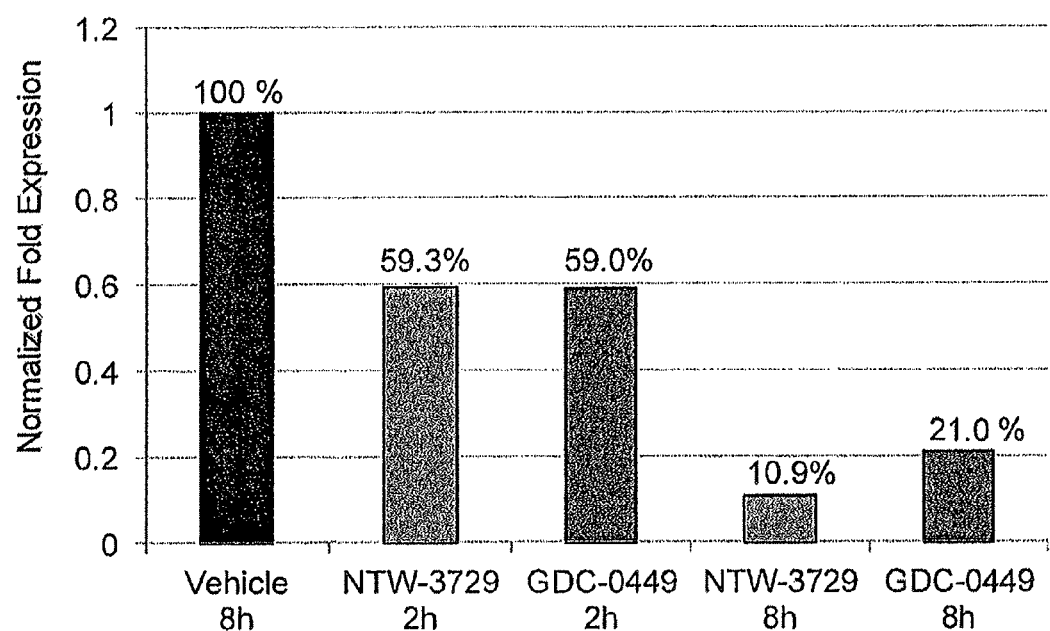
FIG. 7 depicts the time course of gli mRNA suppression in mice treated with NTW-3729, Vehicle (negative control), and GDC-0449 (positive control).

NTW-3729 has anti-tumor activity in $Ptch^{+/-}p53^{-/-}$ mice (FIG. 3). (To control for tumor size reductions due to an agent's general toxicity, mouse weight is monitored along with tumor size (FIG. 4).) FIG. 5 demonstrates that the degree of NTW-3729's of anti-tumor activity in $Ptch^{+/-}p53^{-/-}$ mice is greater than that of GDC-0449. FIG. 6 also compares NTW-3729 anti-tumor activity to that of GDC-0449 in $Ptch^{+/-}p53^{-/-}$ mice and FIG. 7, presents RT-PCR results to compare the time courses of Gli RNA suppression by NTW-3729 to that of GDC-0449. These studies teach that NTW-3729 is highly active against MB formation in $Ptch^{+/-}p53^{-/-}$ mice. From this data those of skill in the art would readily precieve NTW-3729's utility in the treatment of other cancers that are caused by abnormalities in the Hedgehog pathway.

Figure 8:
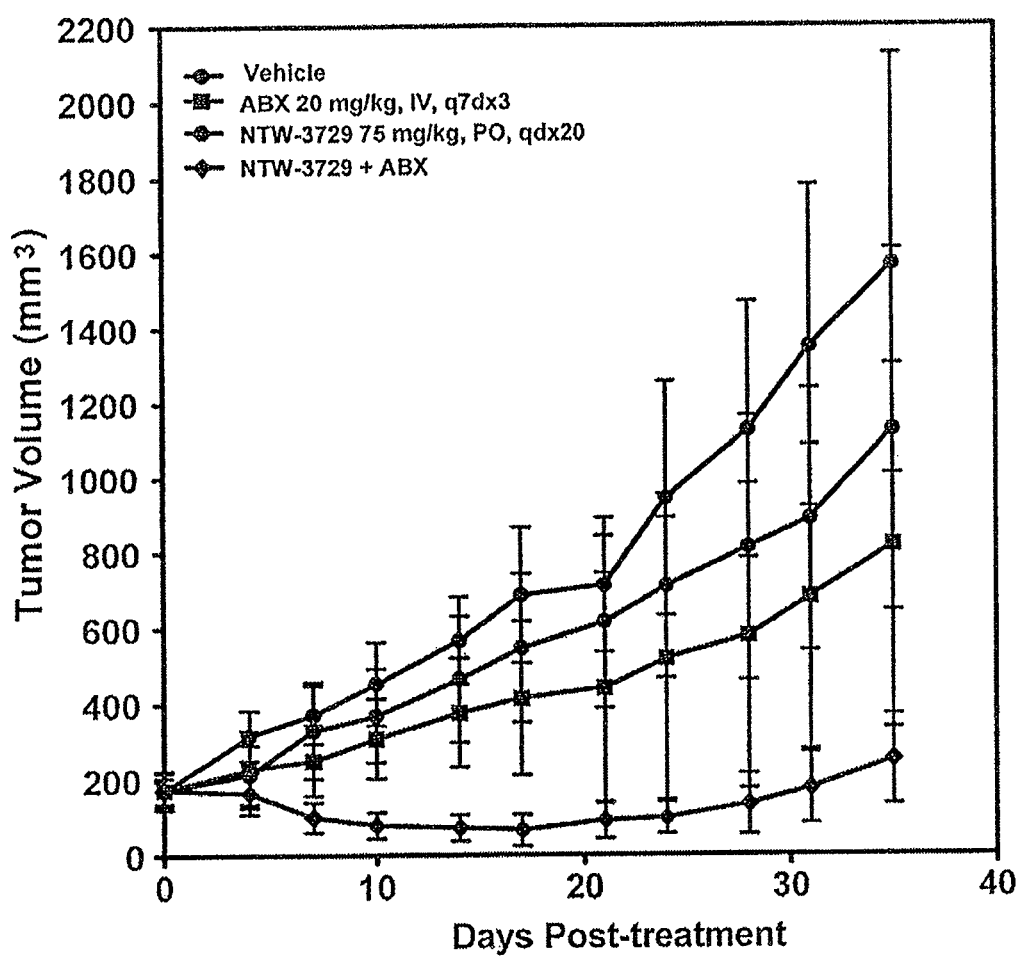
FIG. 8 depicts the tumor size time course in pancreatic carcinoma xenografts (MIAPaCa-2 cells) treated with NTW-3729 alone or in combination with Abraxane® (Vehicle is a negative control).
Figure 9:
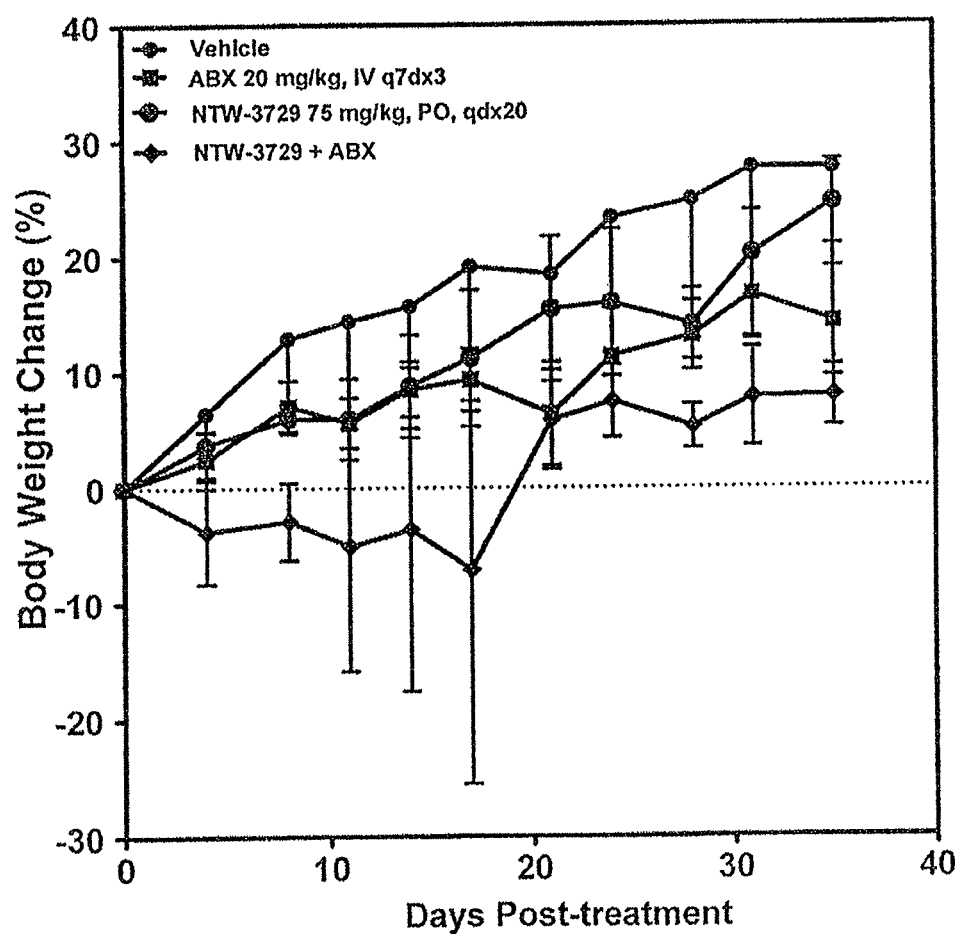
FIG. 9 depicts the weight change time course in pancreatic carcinoma xenografts (MIAPaCa-2 cells) treated with NTW-3729 alone or in combination with Abraxane® ("Vehicle" is a negative control).
Figure 10:
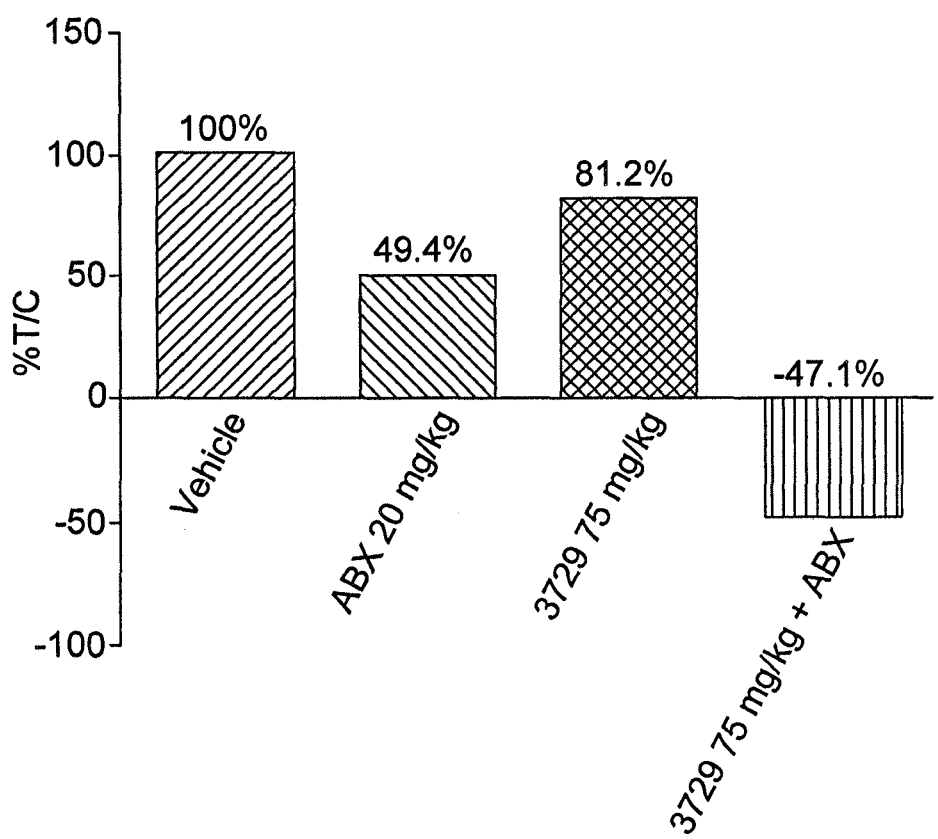
FIG. 10 demonstrates the synergistic effect on tumor growth at 21 days seen with NTW-3729/Abraxane® combination therapy in pancreatic carcinoma xenografts (MIAPaCa-2 cells), Vehicle (negative control), and GDC-0449 (positive control)).

Next, the inventors analyzed MTW-3729 activity in other mouse models of human cancer. FIG. 8 depicts the tumor size time course in pancreatic carcinoma xenografts (MIAPaCa-2 cells) treated with NTW-3729 alone or in combination with nanoparticulate albumin bound paclitaxel (Abraxane®) (Vehicle is a negative control). FIG. 9 depicts the weight change time course in pancreatic carcinoma xenografts (MIAPaCa-2 cells) treated with NTW-3729 alone or in combination with Abraxane (Vehicle is a negative control). FIG. 10 demonstrates that combination therapy using NTW-3729 and Abraxane® results in synergistic anti-tumor activity in pancreatic carcinoma xenografts (MIAPaCa-2 cells) (Vehicle is a negative control).

Figure 11:
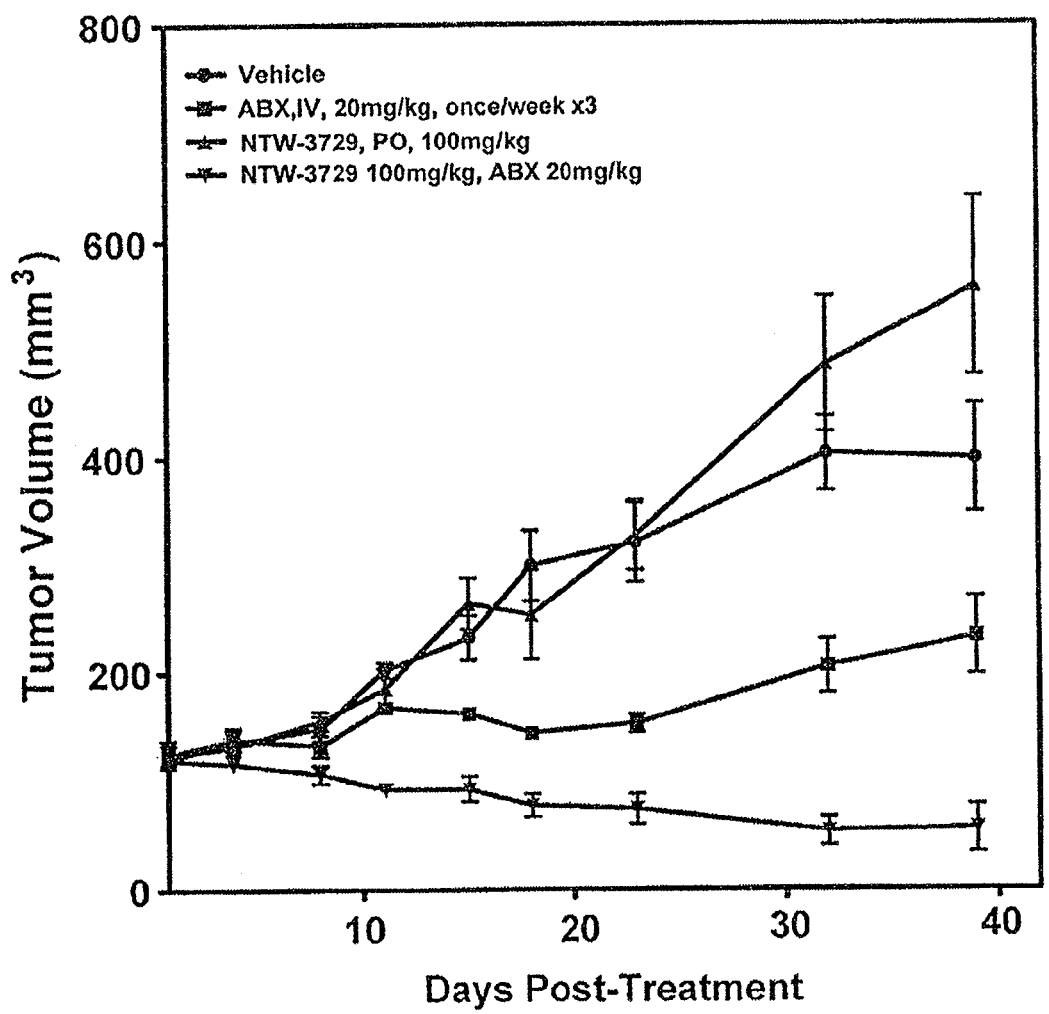
FIG. 11 depicts the tumor size time course in lung carcinoma xenografts (A594 cells) treated with NTW-3729 alone or in combination with nanoparticulate albumin bound paclitaxel (Abraxane®) (Vehicle is a negative control).
Figure 12:
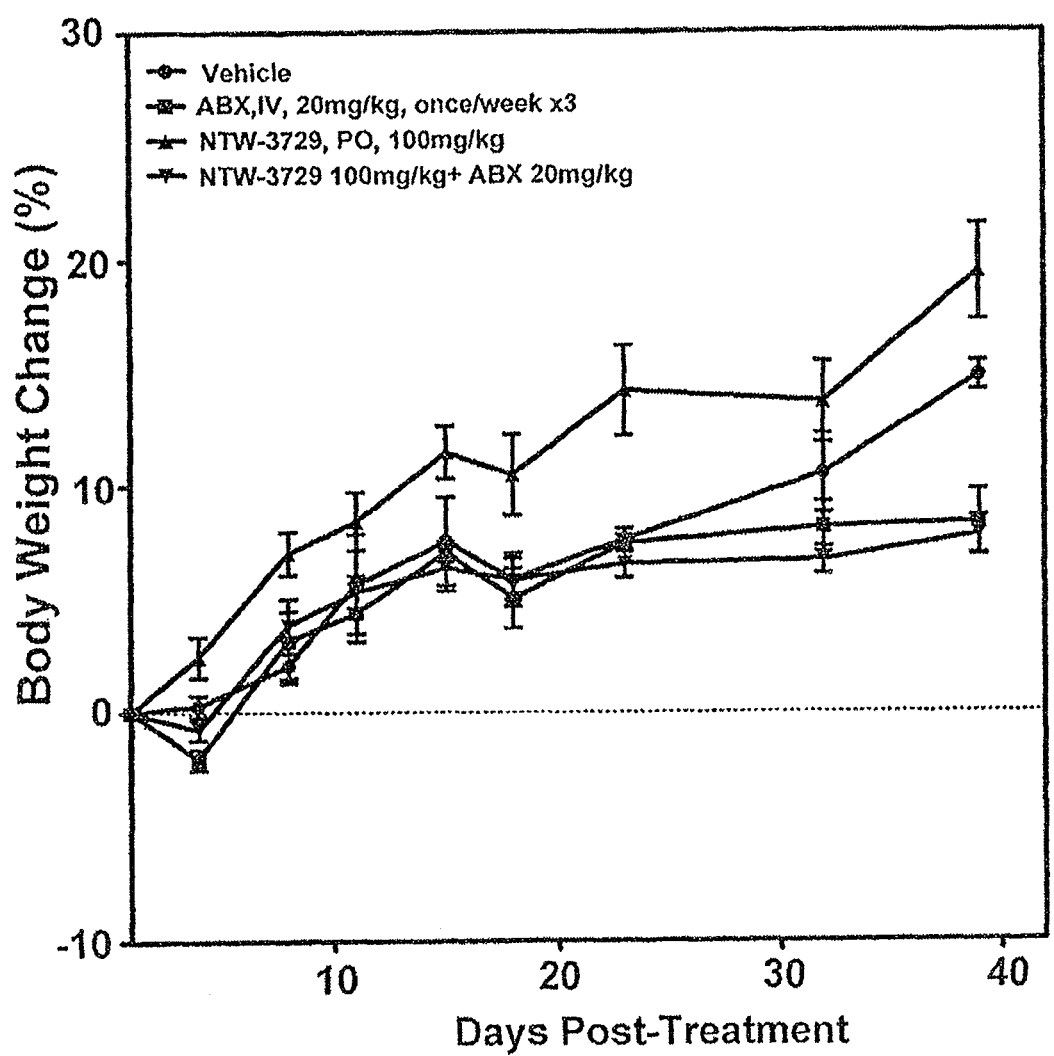
FIG. 12 depicts the weight change time course in lung carcinoma xenografts (A594 cells) treated treated with NTW-3729 alone or in combination with Abraxane® (Vehicle is a negative control).
Figure 13:
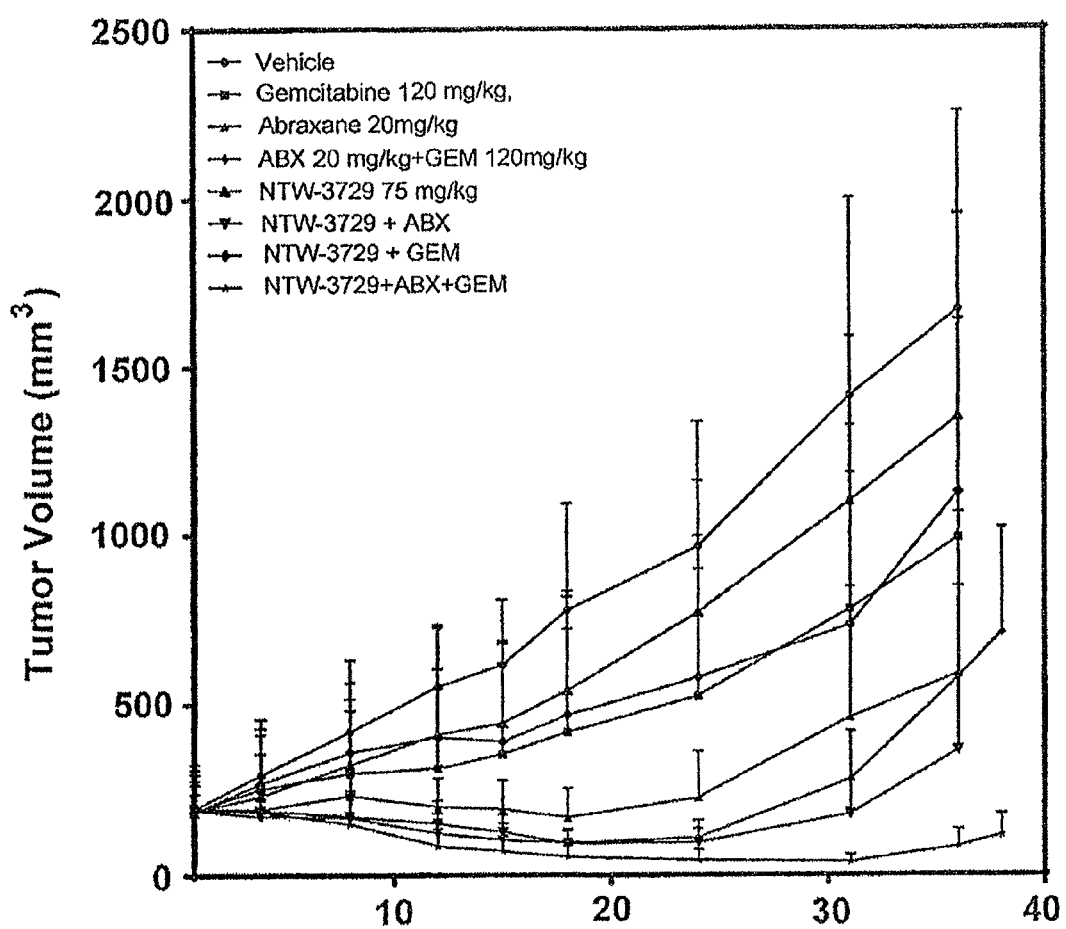
FIG. 13 depicts the tumor size time course in pancreatic carcinoma xenografts (Panc-1 cells) treated with NTW-3729 alone or in combination with Abraxane® and/or Gemcitabine (Vehicle is a negative control).
Figure 14:
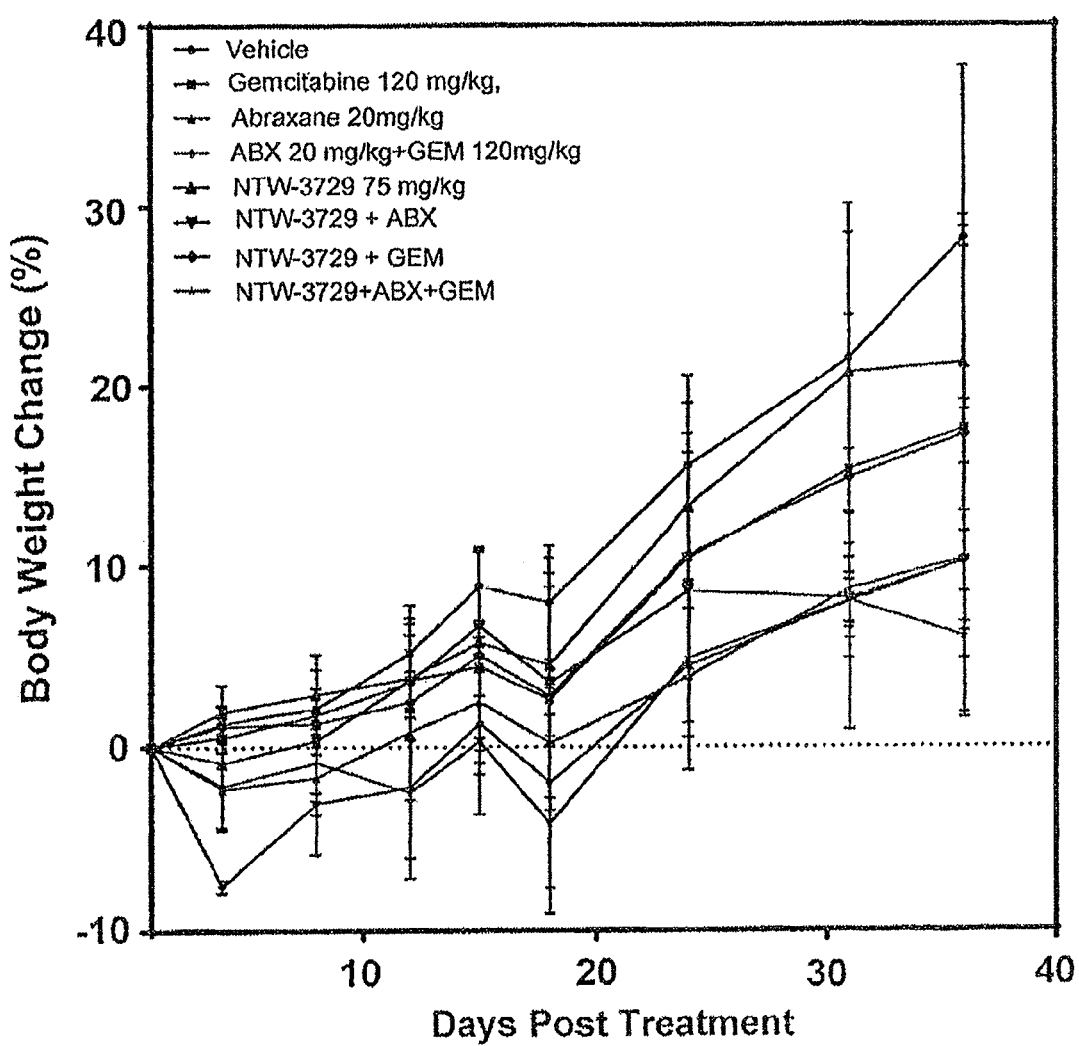
FIG. 14 depicts the weight change time course in pancreatic carcinoma xenografts (Panc-1 cells) treated with NTW-3729 alone or in combination with Abraxane® and/or Gemcitabine (Vehicle is a negative control).

FIG. 11 depicts the tumor size time course in lung carcinoma xenografts (A594 cells) treated with NTW-3729 alone or in combination with Abraxane® (Vehicle is a negative control). FIG. 12 depicts the weight change time course in lung carcinoma xenografts (A594 cells) treated treated with NTW-3729 alone or in combination with Abraxane® (Vehicle is a negative control). Returning to pancreatic tumors, FIG. 13 depicts the tumor size time course in pancreatic carcinoma xenografts (Panc-1 cells) treated with NTW-3729 alone or in combination with Abraxane and/or Gemcitabine (Vehicle is a negative control). FIG. 14 depicts the weight change time course in pancreatic carcinoma xenografts (Panc-1 cells) treated with NTW-3729 alone or in combination with Abraxane® and/or Gemcitabine (Vehicle is a negative control). FIG. 15 depicts the relative tumor size in pancreatic carcinoma xenografts (Panc-1 cells) treated with NTW-3729 alone or in combination with Abraxane® and/or Gemcitabine (Vehicle is a negative control). After 24 days both the NTW-3729/Abraxane® and the NTW-3729/Gemcitabine combinations showed synergistic anti-tumor activity.

These studies indicate that NTW3729 has potential as a broad spectrum kinase inhibitor and an effective anticancer drug.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound with the structure:

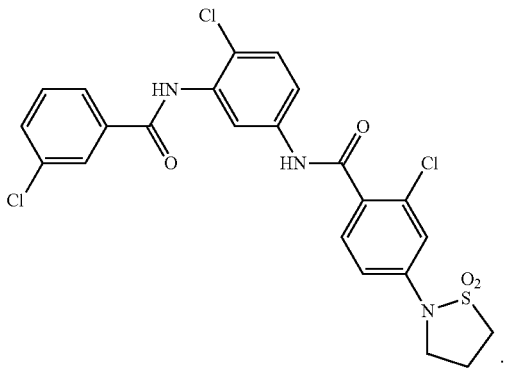 [SMILES: O=C(Nc1cc(NC(=O)c2ccc(N3CCCS3(=O)=O)cc2Cl)ccc1Cl)c1cccc(Cl)c1]

* * * * *